US012473289B2

(12) United States Patent
Allen et al.

(10) Patent No.: US 12,473,289 B2
(45) Date of Patent: Nov. 18, 2025

(54) HETEROCYCLIC COMPOUNDS AS DELTA-5 DESATURASE INHIBITORS AND METHODS OF USE

(71) Applicant: Amgen Inc., Thousand Oaks, CA (US)

(72) Inventors: Jennifer R. Allen, Newbury Park, CA (US); Albert Amegadzie, Moorpark, CA (US); Matthew P. Bourbeau, Woodland Hills, CA (US); Ning Chen, Thousand Oaks, CA (US); Clifford Goodman, Calabasas, CA (US); Giulia Lattanzi, Verona (IT); Iain Lingard, Verona (IT); Qingyian Liu, Camarillo, CA (US); Jonathan D. Low, Reseda, CA (US); Vu Van Ma, Oak Park, CA (US); Ana E. Minatti, Los Angeles, CA (US); Alfonso Pozzan, Verona (IT); Corey Reeves, Los Angeles, CA (US); Aaron C. Siegmund, Ventura, CA (US); Sabrina Tassini, Verona (IT); Federica Tonelli, Verona (IT); Mary Walton Cabrera, Pacifica, CA (US)

(73) Assignee: AMGEN INC., Thousand Oaks, CA (US)

( * ) Notice: Subject to any disclaimer, the term of this patent is extended or adjusted under 35 U.S.C. 154(b) by 116 days.

(21) Appl. No.: 17/103,350

(22) Filed: Nov. 24, 2020

(65) Prior Publication Data

US 2021/0171529 A1 Jun. 10, 2021

Related U.S. Application Data

(60) Provisional application No. 62/939,819, filed on Nov. 25, 2019.

(51) Int. Cl.

| | |
|---|---|
| ***C07D 487/04*** | (2006.01) |
| ***A61P 3/04*** | (2006.01) |
| ***C07D 471/04*** | (2006.01) |
| ***C07D 498/04*** | (2006.01) |

(52) U.S. Cl.

CPC .............. *C07D 487/04* (2013.01); *A61P 3/04* (2018.01); *C07D 471/04* (2013.01); *C07D 498/04* (2013.01); *C07B 2200/05* (2013.01)

(58) Field of Classification Search

CPC ............................ C07D 487/04; C07D 471/04

See application file for complete search history.

(56) References Cited

U.S. PATENT DOCUMENTS

| | | | | |
|---|---|---|---|---|
| 3,558,618 | A | 1/1971 | Trepanier | |
| 7,799,795 | B2 | 9/2010 | Bergeron | |
| 8,349,846 | B2 | 1/2013 | Lingam | |
| 8,754,089 | B2 | 6/2014 | Cushing | |
| 8,952,012 | B2 | 2/2015 | Chicco | |
| 2005/0256157 | A1 | 11/2005 | Gesner | |
| 2005/0261307 | A1 | 11/2005 | Cai | |
| 2008/0194616 | A1 * | 8/2008 | Liu | A61P 5/14 546/121 |
| 2013/0072457 | A1 | 3/2013 | Saxty | |
| 2015/0322090 | A1 | 11/2015 | Campbell | |
| 2016/0376289 | A1 | 12/2016 | Okuyama | |

FOREIGN PATENT DOCUMENTS

| | | | |
|---|---|---|---|
| GB | 2307177 | A | 5/1997 |
| RU | 2603770 | A | 6/2016 |
| WO | 199207468 | W | 5/1992 |
| WO | 199323398 | W | 11/1993 |
| WO | 2007002701 | A2 | 1/2007 |
| WO | 2008097991 | A1 | 8/2008 |
| WO | 2009109987 | A2 | 9/2009 |
| WO | 2010045371 | A1 | 4/2010 |
| WO | 2010049269 | A1 | 5/2010 |
| WO | 2010151735 | A2 | 12/2010 |
| WO | 2011008487 | A1 | 1/2011 |
| WO | 2011085990 | A1 | 7/2011 |
| WO | 2012011591 | A1 | 1/2012 |

(Continued)

OTHER PUBLICATIONS

Aurora Fine Chemicals (Registry No. 1190021-33-0, available on Oct. 25, 2009).*

(Continued)

*Primary Examiner* — Susanna Moore

(74) *Attorney, Agent, or Firm* — Mark Metzke

(57) ABSTRACT

The present disclosure provides compounds useful for the inhibition of Delta-5 Desaturase ("D5D"). The compounds have a general Formula 1:

I

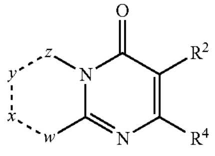

wherein the variables of Formula I are defined herein. This disclosure also provides pharmaceutical compositions comprising the compounds, uses of the compounds, and compositions for treatment of, for example, a metabolic or cardiovascular disorder. Further, the disclosure provides intermediates useful in the synthesis of compounds of Formula I.

10 Claims, 1 Drawing Sheet

(56) References Cited

FOREIGN PATENT DOCUMENTS

| | | | |
|---|---|---|---|
| WO | 2012011592 | A1 | 1/2012 |
| WO | 2013144860 | A1 | 10/2013 |
| WO | 2015062984 | A1 | 5/2015 |
| WO | 2016054491 | A1 | 4/2016 |
| WO | 2017112678 | A1 | 6/2017 |
| WO | 2017122722 | A1 | 7/2017 |
| WO | 2017214269 | A1 | 12/2017 |

OTHER PUBLICATIONS

Baugh, SD. et al., “Design, synthesis, and in vivo activity of novel inhibitors of delta-5 desaturase for the treatment of metabolic syndrome”, Bioorg. Med. Chem. Lett. 25(18):3836-3839 (2015).
Chen, X. et al., “Discovery of potent and specific CXCR3 antagonists”, Bioorganic & Medicinal Chemistry Letters (2012), 22(1), 357-362.
Chopra, M. et al., “A global response to a global problem: the epidemic of overnutrition”, Bull. World Health Organ. 80:952-958 (2002).
Del Turco, et al. “A novel 2,3-diphenyl-4H-pyrido[1,2-a]pyrimidin 4-one derivative inhibits endothelial cell dysfunction and smooth muscle cell proliferation/activation”, European Journal of Medicinal Chemistry (2014), 72, 102-109.
Del Turco, et al. “Synthetic analogues of flavonoids with improved activity against platelet activation and aggregation as novel prototypes of food supplements”, Food Chemistry (2015), 175, 494-499.
Di Marzo V and Matias I, “Endocannabinoid control of food intake and energy balance”, Nat. Neurosci. 8(5):585-589 (2005).
Djerrari, et al., “L’acide dehydracetique, précurseur de nouvelles pyridopyrimidines”, thiazolopyrimidines et pyridones; vol. 5, No. 3., p. 177-183, 2002.
Dupuis, J., New genetic loci implicated in fasting glucose homeostasis and their impact on type 2 diabetes risk, Nat. Genet. 42(2):105-116 (2010).
El Otmani, et al., “Synthesis and HIV effect of pyrazolyl(isoxazolyl)pyrido[1,2-a]pyrimidines”, Journal Marocain de Chimie Heterocyclique (2005), 4(1), 26-38.
Elotmani, B.; et al, “2-Methyl-3-(3-methyl-1H-pyrazol-5-yl)pyrido[1,2-a]pyrimidin-4-one, Acta Crystallographica”, Section E: Structure Reports Online (2002), 58(4), o388-o389.
Fumagalli, M. et al., Greenlandic Inuit show genetic signatures of diet and climate adaptation, Science 349(6254):1343-1347 (2015).
Guchhait, Sankar K. et al. “A nitrile-stabilized ammonium ylide as a masked C—C=N synthon in heterocyclization with amidine-imine: 3-component assembly to fused pyrimidine scaffolds”, Chemical Communications (Cambridge, United Kingdom) (2017), 53(51), 6941-6944.
Haidar, Y.M. and Cosman B.C., Obesity epidemiology, Clin. Colon Rectal Surg. 24:205-210 (2011).
Harizi, H. et al., Arachidonic-acid-derived eicosanoids: roles in biology and immunopathology, Trends Mol. Med. 14(10):461-469 (2008).
Huang, “Dane On the Value of Homology Models for Virtual Screening: Discovering hCXCR3 Antagonists by Pharmacophore-Based and Structure-Based Approaches”, Journal of Chemical Information and Modeling (2012), 52(5), 1356-1366.
Jadhav, Sunil B. et al. “Pyrido[1,2-a]pyrimidin-4-ones: Ligand-based Design, Synthesis, and Evaluation as an Anti-Inflammatory Agent”, Journal of Heterocyclic Chemistry (2017), 54(6), 3299-3313.
Kabri, Youssef, “One-pot chemoselective bis(Suzuki-Miyaura cross-coupling): efficient access to 3,9-bis[(hetero)aryl]-4H-pyrido[1,2-a]pyrimidin-4-one derivatives under microwave irradiation”, European Journal of Organic Chemistry (2012), 2012(28), 5595-5604.
Kabri, Youssef, et al. “Efficient and original microwave-assisted Suzuki-Miyaura cross-coupling reaction in the 4H-pyrido[1,2-a]pyrimidin-4-one series”, Synthesis (2011), (19), 3115-3122.
Kroger J. and Schulze M.B., Recent insights into the relation of delta5 desaturase and delta6 desaturase activity to the development of type 2 diabetes, Curr. Opin. Lipidol. 23(1):4-10 (2012).
Liang, Yu-Feng; Manganese-Catalyzed Carbonylative Annulations for Redox-Neutral Late-Stage Diversification, Angewandte Chemie, International Edition (2018), 57(19), 5384-5388.
Malki, Fatiha, et al. Extraction and recrystallization of mesoionic pyrimidinium betaines, International Journal of Chemical Engineering and Applications (2014), 5(2), 151-154.
Mendis S. et al., World Health Organization (WHO) and International Society of Hypertension (ISH) risk prediction charts: assessment of cardiovascular risk for prevention and control of cardiovascular disease in low and middle-income countries, J. Hypertens. 25:1578-1582 (2007).
Merino, D.M. et al., Genetic variation in lipid desaturases and its impact on the development of human disease, Lipids Health Dis. 9:63 (2010).
Merino, D.M. et al., Polymorphisms in FADS1 and FADS2 alter desaturase activity in young Caucasian and Asian adults, Mol. Genet. Metab. 103(2):171-178 (2011).
Miyahisa, I. et al., T-3364366 Targets the Desaturase Domain of Delta-5 Desaturase with Nanomolar Potency and a Multihour Residence Time, ACS Med. Chem. Lett. 7(9):868-872 (2016).
Monteiro, C.A. et al., Socioeconomic status and obesity in adult populations of developing countries: a review. Bull. World Health Organ. 82:940-946 (2004).
Obukowicz, M.G. et al., Novel, selective delta6 or delta5 fatty acid desaturase inhibitors as antiinflammatory agents in mice, J. Pharmacol. Exp. Ther. 287(1):157-166 (1998).
Powell, D.R. et al., Fatty acid desaturase 1 knockout mice are lean with improved glycemic control and decreased development of atheromatous plaque, Diabetes Metab. Syndr. Obes. 9:185-199 (2016).
Reilly, Regina M. et al. Analgesic potential of TRPV3 antagonists, Current Topics in Medicinal Chemistry (Sharjah, United Arab Emirates) (2011), 11(17), 2210-2215.
Tosi, F. et al., Delta-5 and delta-6 desaturases: crucial enzymes in polyunsaturated fatty acid-related pathways with pleiotropic influences in health and disease, Adv. Exp. Med. Biol. 824:61-81 (2014).
Wilen, et al., Strategies in optical resolutions, Tetrahedron 33:2725-2769, 1977.
Willer, C.J. et al., Discovery and refinement of loci associated with lipid levels, Nat. Genet. 45(11):1274-1283 (2013).
Written Opinion of the International Search Authority for PCT/US2020/062011, mail date: Mar. 17, 2021.
Yashiro, H. et al., A Novel Selective Inhibitor of Delta-5 Desaturase Lowers Insulin Resistance and Reduces Body Weight in Diet-Induced Obese C57BL/6J Mice, PLoS One 11(11):e0166198 (2016).
Yoshida, Ken-ichi, et al., “MexAB-OprM specific efflux pump inhibitors in Pseudomonas aeruginosa. Part 5: Carbon-substituted analogues at the C-2 position”, Bioorganic & Medicinal Chemistry (2006), 14(6), 1993-2004.
Missaoui, B.E. et al. Novel Synthesis Method of Pyrimidine and Pyrazole Derivatives, Asian journal of chemistry 27(2) 671-673 (2015).
Tovey, Pharmaceutical Formulation: The Science and Technology of Dosage Forms (Drug Discovery), first edition, Royal Society of Chemistry, 2018.

* cited by examiner

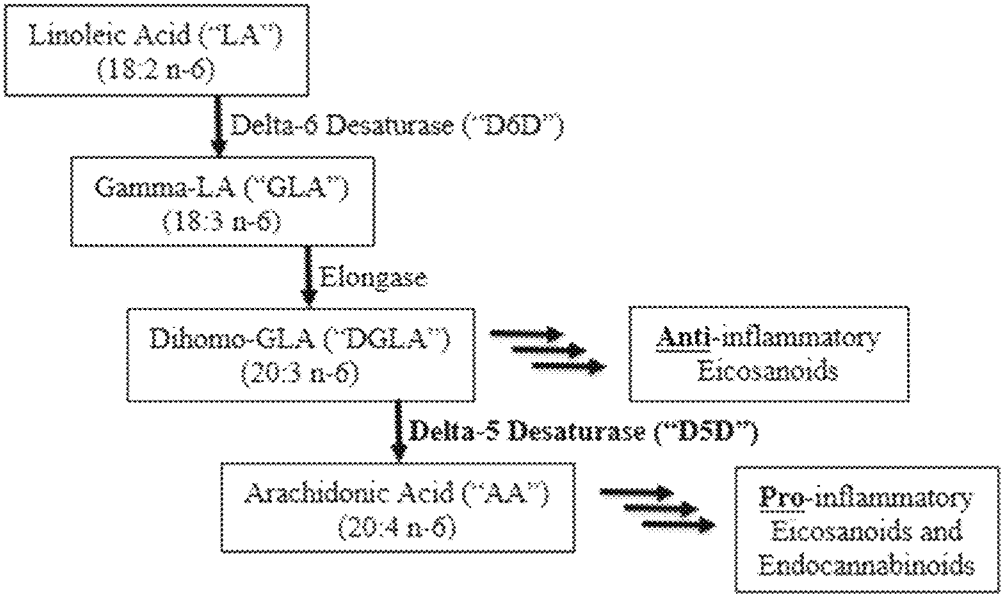
Linoleic Acid ("LA")
(18:2 n-6)
Delta-6 Desaturase ("D6D")
Gamma-LA ("GLA")
(18:3 n-6)
Elongase
Dihomo-GLA ("DGLA")
(20:3 n-6)
Anti-inflammatory
Eicosanoids
Delta-5 Desaturase ("D5D")
Arachidonic Acid ("AA")
(20:4 n-6)
Pro-inflammatory
Eicosanoids and
Endocannabinoids

HETEROCYCLIC COMPOUNDS AS DELTA-5 DESATURASE INHIBITORS AND METHODS OF USE

CROSS-REFERENCE TO RELATED APPLICATION

This application claims benefit of U.S. Provisional Patent Application No. 62/939,819, filed Nov. 25, 2019, which is incorporated by reference in its entirety.

FIELD

The present disclosure provides compounds useful for the inhibition of Delta-5 Desaturase ("D5D"). This disclosure also provides pharmaceutical compositions comprising the compounds, uses of the compounds, and compositions for treatment of, for example, a metabolic or cardiovascular disorder. Further, the disclosure provides intermediates useful in the synthesis of compounds of Formula I.

BACKGROUND

Polyunsaturated fatty acids ("PUFAs") exert important physiological functions in the human body. Kroeger J and Schulze M B, 2012, page 4. PUFAs serve as sources of energy and structural components of cell membranes. Id. PUFAs also regulate genes and are biosynthetic precursors of other physiologically relevant biomolecules, such as eicosanoids and endocannabinoids. Id. Di Marzo V and Matias I, 2005, page 585.

Eicosanoids are signaling molecules that have multiple functions and regulate, among other things, the human inflammatory response. Harizi H et al., 2008. Endocannabinoids (N-arachidonoyl ethanolamine (anandamide) and 2-arachidonoyl glycerol (2-AG) are endogenous ligands for the cannabinoid receptors which have been established to have a role in food intake and energy balance. Di Marzo V and Matias 1, 2005, page 585. Yashiro H et al., 2016, page 2/18. Obukowicz M G et al., 1998, page 158. Di Marzo V and Matias I, 2005, page 585.

The pertinent part of the metabolic pathway of a certain PUFA, linoleic acid ("LA"), which leads, among other things, to the formation of anti- and pro-inflammatory eicosanoids and endocannabinoids, is shown in FIG. 1.

The desaturase enzymes, which catalyze certain steps in the conversion of LA in AA are delta-6-desaturase ("D6D;" encoded by the gene Fatty Acid Desaturase 2 ("FADS2")) and delta-5-desaturase ("D5D;" encoded by the gene Fatty Acid Desaturase 1 ("FADS1")). Yashiro H et al., 2016, page 2/18. Selectively inhibiting D5D activity reduces the amount of AA generated, while increasing the amount of DGLA. Such a pharmacological intervention reduces downstream generation of, for example, pro-inflammatory eicosanoids and endocannabinoids and leads to build-up of anti-inflammatory eicosanoids, both of which may overall ameliorate inflammation-related conditions and may improve energy balance. Yashiro H et al., 2016, page 3/18. Di Marzo V and Matias I, 2005, page 585. This is especially relevant in subjects with high intake of LA, for example, humans exposed to Western-style diets. Yashiro H et al., 2016, page 3/18.

The FADS1-3 locus has been associated with many metabolic traits in human genome-wide association studies including fasting glucose, plasma lipids, and body weight. Fumagalli M et al., 2015. Willer C J et al., 2013. Dupuis J et al., 2010. An increase or elevation of each metabolic trait is associated with the FADS1-3 locus is also associated with an increase in the activity of D5D as estimated by AA:DGLA ratios. Fumagalli M et al., 2015. Merino D M et al., 2011.

In addition to human genetic evidence supporting a role of FADS1/D5D in metabolic disorders, FADS1 knock out ("KO") mice also show a phenotype with protection from diet-induced obesity including low body fat content, improved glycemic control, and decreased circulating lipid levels. Powell D R et al., 2016, page 197. In addition, the FADS1 KO mice are resistant to the development of arterial atheromatous plaque. Id.

Desaturase enzyme activity has been linked to a variety of diseases, in particular metabolic and cardiovascular diseases, such as obesity, diabetes, nonalcoholic steatohepatitis ("NASH"), dyslipidemia, and coronary artery disease. Tosi F et al., 2014; Kroeger J and Schulze M B, 2012; and Merino D M et al., 2010. Therefore, the pharmacological inhibition of D5D is a target of interest for treating metabolic, cardiovascular and other diseases. Powell D R et al., 2016, page 197.

Despite some progress in the area of small molecule therapeutics (for example, Miyahisa I et al., 2016; Yashiro H et al., 2016; and Baugh S D et al., 2015), a need for inhibitors of D5D, which may be suitable for use as therapeutic agents, remains in view of the significant continuing societal burden caused by, for example, metabolic and cardiovascular diseases (for example, Haidar Y M and Cosman B C, 2011; Mendis S et al., 2007; Chopra M et al., 2002; and Monteiro C A et al., 2004).

SUMMARY

First, provided herein is A compound of Formula I

I

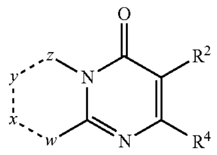

or a tautomer thereof, or a pharmaceutically acceptable salt of said compound or said tautomer, wherein

1)

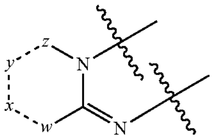

is

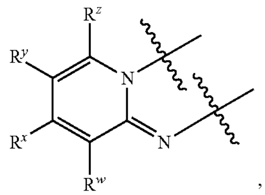

, wherein optionally one of $CR^w$, $CR^x$, $CR^y$, and $CR^z$ is N;

2)

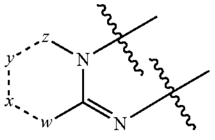

is

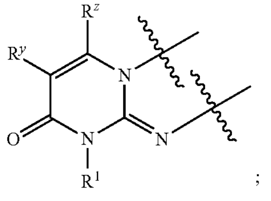

; or

-continued

3)

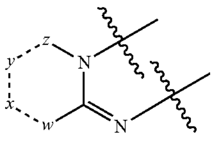

is

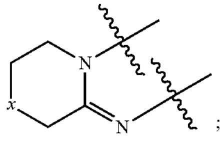

;

wherein $R^w$ is H, halogen, —CN, —CO($C_{1-4}$alkyl), —S(O)$_n$($C_{1-4}$ alkyl), —COOH, —COO($C_{1-4}$-alkyl), —$CONH_2$, —CONH($C_{1-4}$alkyl), —CO(di$C_{1-4}$alkylamino), —$NH_2$, $C_{1-4}$alkylamino, di$C_{1-4}$alkylamino, —NH($COC_{1-4}$alkyl), —N($C_{1-4}$alkyl)C(═O)F, $C_{1-4}$alkyl, $C_{1-4}$deuteroalkyl, $C_{3-5}$cycloalkyl, $C_{3-4}$heterocycloalkyl, $C_{2-4}$alkenyl, $C_{1-4}$deuteroalkoxy, or 5-membered heteroaryl; wherein the $C_{1-4}$alkyl and $C_{3-4}$heterocycloalkyl groups are optionally substituted with 1 to 4 substituents independently selected from halogen, —OH, —CN, $C_{1-4}$alkoxy, $C_{1-4}$alkyl, —$NH_2$, $C_{1-4}$alkylamino, di$C_{1-4}$alkylamino, and —S(O)$_n$($C_{1-4}$alkyl);

$R^y$ is H, F, Cl, —OH, —CN, —CO($C_{1-4}$alkyl), —S(O)$_n$($C_{1-4}$alkyl), —COOH, —COO($C_{1-4}$alkyl), —$CONH_2$, —CONH($C_{1-4}$alkyl), —CO(di$C_{1-4}$alkylamino), —$NH_2$, $C_{1-4}$-alkylamino, di$C_{1-4}$alkylamino, —NH($COC_{1-4}$alkyl), —N($C_{1-4}$alkyl)C(═O)F, $C_{1-4}$alkyl, $C_{1-4}$deuteroalkyl, $C_{3-5}$ cycloalkyl, $C_{3-4}$heterocycloalkyl, $C_{2-4}$alkenyl, $C_{1-4}$alkoxy, $C_{1-4}$deuteroalkoxy, or 5-membered heteroaryl; wherein the $C_{1-4}$alkyl, $C_{3-4}$heterocycloalkyl, and $C_{1-4}$alkoxy groups are optionally substituted with 1 to 4 substituents independently selected from halogen, —OH, —CN, $C_{1-4}$alkoxy, $C_{1-4}$alkyl, —$NH_2$, $C_{1-4}$alkylamino, di$C_{1-4}$alkylamino, and —S(O)$_n$($C_{1-4}$alkyl);

$R^x$ and $R^z$ are independently H, halogen, —OH, —CN, —CO($C_{1-4}$alkyl), —S(O)$_n$($C_{1-4}$ alkyl), —COOH, —COO($C_{1-4}$alkyl), —$CONH_2$, —CONH($C_{1-4}$-alkyl), —CO(di$C_{1-4}$alkylamino), —$NH_2$, $C_{1-4}$alkylamino, di$C_{1-4}$alkylamino, —NH($COC_{1-4}$alkyl), —N($C_{1-4}$alkyl)C(═O)F, $C_{1-4}$alkyl, $C_{1-4}$deuteroalkyl, $C_{3-5}$cycloalkyl, $C_{3-4}$heterocycloalkyl, $C_{2-4}$alkenyl, $C_{1-4}$alkoxy, $C_{1-4}$deuteroalkoxy, or 5-membered heteroaryl; wherein the $C_{1-4}$alkyl, $C_{3-4}$heterocycloalkyl, and $C_{1-4}$alkoxy groups are optionally substituted with 1 to 4 substituents independently selected from halogen, —OH, —CN, $C_{1-4}$alkoxy, $C_{1-4}$alkyl, —$NH_2$, $C_{1-4}$alkylamino, di$C_{1-4}$alkylamino, and —S(O)$_n$($C_{1-4}$alkyl);

$R^1$ is H, $C_{1-4}$alkyl, $C_{1-4}$haloalkyl, or $C_{1-4}$deuteroalkyl;

x is 0, NH, or N($C_{1-4}$alkyl);

$R^2$ is

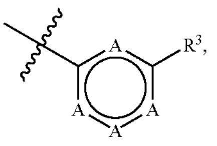

,

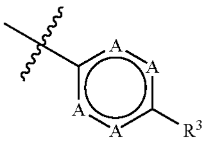

,

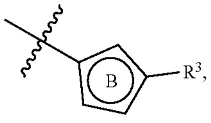

or 2-benzofuranyl, wherein

A is independently CH or N, and wherein

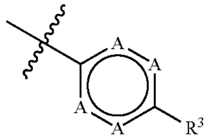

is not

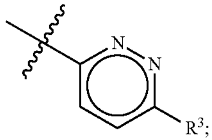

and

B is a 5-membered heteroaryl containing one heteroatom selected from N, S, and O and optionally one or two further N atoms, wherein i) B is attached via a C atom to the bicyclic core and $R^3$ is attached via an N atom; or ii) B is attached via an N atom to the bicyclic core and $R^3$ is attached via a C atom; or iii) B is attached via a C atom to the bicyclic core and $R^3$ is attached via a C atom;

and wherein the

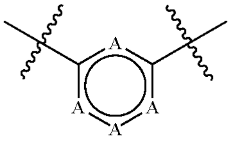

,

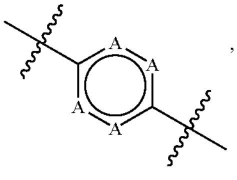

, or

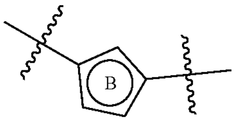

portion of $R^2$ or the 2-benzofuranyl is further optionally substituted with one or two independently selected substituents $R^{3'}$;

$R^3$ is $CH_2CN$, $C_{2-6}$alkyl, $C_{3-5}$cycloalkyl, $C_{1-3}$alkoxy, $C_{1-6}$alkylamino, di$C_{1-6}$alkylamino, —S(O)$_n$($C_{1-6}$alkyl), —$CH_2$($C_{3-5}$cycloalkyl), —$OCH_2$($C_{3-5}$cycloalkyl), —$NHCH_2$($C_{3-5}$cycloalkyl), —S(O)$_n$$CH_2$($C_{3-5}$cycloalkyl), —$CH_2$($C_{3-5}$heterocycloalkyl), or phenyl; wherein the $C_{2-6}$alkyl, $C_{3-5}$cycloalkyl, $C_{1-3}$alkoxy, $C_{1-6}$alkylamino, di$C_{1-6}$alkylamino, —S(O)$_n$($C_{1-5}$alkyl), —$CH_2$($C_{3-5}$cycloalkyl), —$OCH_2$($C_{3-5}$cycloalkyl), —$NHCH_2$($C_{3-5}$cycloalkyl), and —S(O)$_n$$CH_2$($C_{3-5}$ cycloalkyl) groups are optionally substituted with 1-9 halogen atoms and are optionally substituted with —CN and wherein the phenyl is optionally substituted with 1-3 substituents selected from halogen, $C_{1-4}$alkyl, $C_{1-4}$haloalkyl, $C_{1-4}$alkoxy, and $C_{1-4}$haloalkoxy;

$R^{3'}$ independently is halogen, $C_{1-4}$alkyl, $C_{1-4}$haloalkyl, $C_{1-4}$alkoxy, or $C_{1-4}$haloalkoxy;

$R^4$ is $C_{1-3}$alkyl, $C_{1-4}$haloalkyl, $C_{1-4}$alkoxy, $C_{1-4}$haloalkoxy, $C_{3-5}$cycloalkyl, or $C_{3-5}$cyclohaloalkyl; and n is 0, 1, or 2.

Second, provided herein is a pharmaceutical composition comprising a compound of Formula I, or a tautomer thereof, or a pharmaceutically acceptable salt of said compound or said tautomer, and a pharmaceutically acceptable excipient.

Third, provided herein is a compound of Formula 1, or a tautomer thereof, or a pharmaceutically acceptable salt of said compound or said tautomer, or the pharmaceutical composition as described hereinabove for use in reducing the body weight of a subject or for use in reducing the body-mass-index of a subject.

Fourth, provided herein is a compound of Formula I, or a tautomer thereof, or a pharmaceutically acceptable salt of said compound or said tautomer, or the pharmaceutical composition as described hereinabove for use in treating a metabolic disorder or for use in treating a cardiovascular disorder.

Fifth, provided herein is a compound of Formula I, or a tautomer thereof, or a pharmaceutically acceptable salt of said compound or said tautomer, or the pharmaceutical composition as described hereinabove for use in treating a metabolic disorder or for use in treating diabetes, obesity, dyslipidemia, or non-alcoholic steatohepatitis (NASH).

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

BRIEF DESCRIPTION OF THE DRAWINGS

FIG. 1 provides a scheme showing the pertinent part of the metabolic pathway of a LA, which leads, among other things, to the formation of anti- and pro-inflammatory eicosanoids and endocannabinoids.

DETAILED DESCRIPTION

Provided herein as Embodiment 1 is a compound of Formula I

I

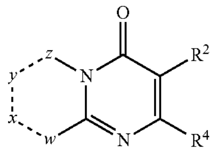

or a tautomer thereof, or a pharmaceutically acceptable salt of said compound or said tautomer, wherein

1)

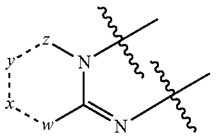 is 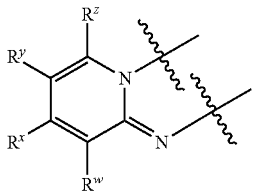, wherein optionally one of $CR^w$, $CR^x$, $CR^y$, and $CR^z$ is N;

2)

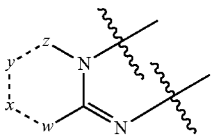 is 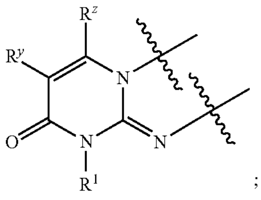; or

-continued

3)

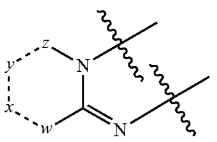 is 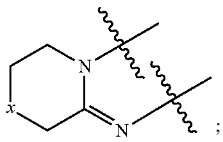;

wherein $R^w$ is H, halogen, —CN, —CO($C_{1-4}$alkyl), —S(O)$_n$($C_{1-4}$ alkyl), —COOH, —COO($C_{1-4}$alkyl), —$CONH_2$, —CONH($C_{1-4}$alkyl), —CO(di$C_{1-4}$alkylamino), —$NH_2$, $C_{1-4}$alkylamino, di$C_{1-4}$alkylamino, —NH($COC_{1-4}$alkyl), —N($C_{1-4}$alkyl)C(═O)F, $C_{1-4}$alkyl, $C_{1-4}$deuteroalkyl, $C_{3-5}$ cycloalkyl, $C_{3-4}$heterocycloalkyl, $C_{2-4}$alkenyl, $C_{1-4}$deuteroalkoxy, or 5-membered heteroaryl; wherein the $C_{1-4}$alkyl and $C_{3-4}$heterocycloalkyl groups are optionally substituted with 1 to 4 substituents independently selected from halogen, —OH, —CN, $C_{1-4}$alkoxy, $C_{1-4}$alkyl, —$NH_2$, $C_{1-4}$alkylamino, di$C_{1-4}$alkylamino, and —S(O)$_n$($C_{1-4}$alkyl);

$R^y$ is H, F, Cl, —OH, —CN, —CO($C_{1-4}$alkyl), —S(O)$_n$($C_{1-4}$alkyl), —COOH, —COO($C_{1-4}$alkyl), —$CONH_2$, —CONH($C_{1-4}$alkyl), —CO(di$C_{1-4}$alkylamino), —$NH_2$, $C_{1-4}$alkylamino, di$C_{1-4}$alkylamino, —NH($COC_{1-4}$alkyl), —N($C_{1-4}$alkyl)C(═O)F, $C_{1-4}$alkyl, $C_{1-4}$deuteroalkyl, $C_{3-5}$cycloalkyl, $C_{3-4}$heterocycloalkyl, $C_{2-4}$alkenyl, $C_{1-4}$alkoxy, $C_{1-4}$deuteroalkoxy, or 5-membered heteroaryl; wherein the $C_{1-4}$alkyl, $C_{3-4}$heterocycloalkyl, and $C_{1-4}$alkoxy groups are optionally substituted with 1 to 4 substituents independently selected from halogen, —OH, —CN, $C_{1-4}$alkoxy, $C_{1-4}$alkyl, —$NH_2$, $C_{1-4}$alkylamino, di$C_{1-4}$alkylamino, and —S(O)$_n$($C_{1-4}$alkyl);

$R^x$ and $R^z$ are independently H, halogen, —OH, —CN, —CO($C_{1-4}$alkyl), —S(O)$_n$($C_{1-4}$alkyl), —COOH, —COO($C_{1-4}$alkyl), —$CONH_2$, —CONH($C_{1-4}$alkyl), —CO(di$C_{1-4}$alkylamino), —$NH_2$, $C_{1-4}$alkylamino, di$C_{1-4}$alkylamino, —NH($COC_{1-4}$alkyl), —N($C_{1-4}$alkyl)C(═O)F, $C_{1-4}$alkyl, $C_{1-4}$deuteroalkyl, $C_{3-5}$cycloalkyl, $C_{3-4}$heterocycloalkyl, $C_{2-4}$alkenyl, $C_{1-4}$alkoxy, $C_{1-4}$deuteroalkoxy, or 5-membered heteroaryl; wherein the $C_4$alkyl, $C_{3-4}$heterocycloalkyl, and $C_{1-4}$alkoxy groups are optionally substituted with 1 to 4 substituents independently selected from halogen, —OH, —CN, $C_{1-4}$alkoxy, $C_{1-4}$alkyl, —$NH_2$, $C_{1-4}$alkylamino, di$C_{1-4}$alkylamino, and —S(O)$_n$($C_{1-4}$alkyl);

$R^1$ is H, $C_{1-4}$alkyl, $C_{1-4}$haloalkyl, or $C_{1-4}$deuteroalkyl;

x is O, NH, or N($C_{1-4}$alkyl);

$R^2$ is

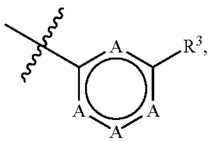, 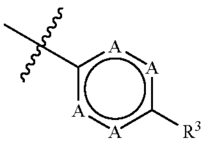, 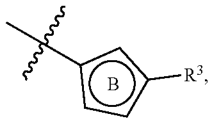, or 2-benzofuranyl, wherein

A is independently CH or N, and wherein

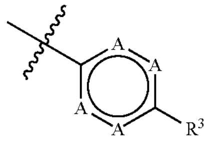

is not

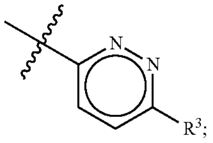

and

B is a 5-membered heteroaryl containing one heteroatom selected from N, S, and 0 and optionally one or two further N atoms, wherein i) B is attached via a C atom to the bicyclic core and $R^3$ is attached via an N atom; or ii) B is attached via an N atom to the bicyclic core and $R^3$ is attached via a C atom; or iii) B is attached via a C atom to the bicyclic core and $R^3$ is attached via a C atom;

and wherein the

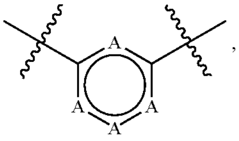

,

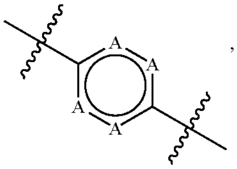

, or

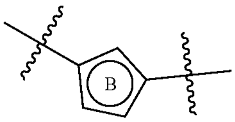

portion of $R^2$ or the 2-benzofuranyl is further optionally substituted with one or two independently selected substituents $R^{3'}$;

$R^3$ is $CH_2CN$, $C_{2-6}$alkyl, $C_{3-5}$cycloalkyl, $C_{1-3}$alkoxy, $C_{1-6}$alkylamino, di$C_{1-6}$alkylamino, —$S(O)_n(C_{1-6}$alkyl), —$CH_2(C_{3-5}$cycloalkyl), —$OCH_2(C_{3-5}$cycloalkyl), —$NHCH_2(C_{3-5}$cycloalkyl), —$S(O)_nCH_2(C_{3-5}$cycloalkyl), —$CH_2(C_{3-5}$heterocycloalkyl), or phenyl; wherein the $C_{2-6}$alkyl, $C_{3-5}$cycloalkyl, $C_{1-3}$alkoxy, $C_{1-6}$alkylamino, di$C_{1-6}$alkylamino, —$S(O)_n(C_{1-6}$alkyl), —$CH_2(C_{3-5}$cycloalkyl), —$OCH_2(C_{3-5}$cycloalkyl), —$NHCH_2(C_{3-5}$cycloalkyl), and —$S(O)_nCH_2$ ($C_{3-5}$ cycloalkyl) groups are optionally substituted with 1-9 halogen atoms and are optionally substituted with —CN and wherein the phenyl is optionally substituted with 1-3 substituents selected from halogen, $C_{1-4}$alkyl, $C_{1-4}$haloalkyl, $C_{1-4}$alkoxy, and $C_{1-4}$haloalkoxy;

$R^{3'}$ independently is halogen, $C_{1-4}$alkyl, $C_{1-4}$haloalkyl, $C_{1-4}$alkoxy, or $C_{1-4}$haloalkoxy;

$R^4$ is $C_{1-3}$alkyl, $C_{1-4}$haloalkyl, $C_{1-4}$alkoxy, $C_{1-4}$haloalkoxy, $C_{3-5}$cycloalkyl, or $C_{3-5}$cyclohaloalkyl; and n is 0, 1, or 2.

Provided herein as Embodiment 2 is the compound according to Embodiment 1, or a tautomer thereof, or a pharmaceutically acceptable salt of said compound or said tautomer, wherein the compound is not 3-[2-(2,2,2-trifluoroethoxy)pyrimidin-5-yl]-2-(trifluoromethyl)-4H,6H,7H,9H-pyrimido[2,1-c][1,4]oxazin-4-one;

7-(azetidin-1-yl)-3-[1-(2,2,3,3,3-pentafluoropropyl)-1H-pyrazol-4-yl]-2-(trifluoromethyl)-4H-pyrido[1,2-a]pyrimidin-4-one;

7-[(dimethylamino)methyl]-3-[1-(2,2,3,3,3-pentafluoropropyl)-1H-pyrazol-4-yl]-2-(trifluoromethyl)-4H-pyrido[1,2-a]pyrimidin-4-one;

7-chloro-3-[2-(2,2,2-trifluoroethoxy)pyrimidin-5-yl]-2-(trifluoromethyl)-4H-pyrido[1,2-a]pyrimidin-4-one;

7-cyclopropyl-3-[2-(2,2,2-trifluoroethoxy)pyrimidin-5-yl]-2-(trifluoromethyl)-4H-pyrido[1,2-a]pyrimidin-4-one;

7-fluoro-3-[2-(2,2,2-trifluoroethoxy)pyrimidin-5-yl]-2-(trifluoromethyl)-4H-pyrido[1,2-a]pyrimidin-4-one;

7-methoxy-3-[1-(2,2,3,3,3-pentafluoropropyl)-1H-pyrazol-4-yl]-2-(trifluoromethyl)-4H-pyrimido[1,2-b]pyridazin-4-one;

7-methoxy-3-[2-(2,2,2-trifluoroethoxy)pyrimidin-5-yl]-2-(trifluoromethyl)-4H-pyrimido[1,2-b]pyridazin-4-one;

7-methyl-3-[2-(2,2,2-trifluoroethoxy)pyrimidin-5-yl]-2-(trifluoromethyl)-4H-pyrazino[1,2-a]pyrimidin-4-one;

7-methyl-3-[2-(2,2,2-trifluoroethoxy)pyrimidin-5-yl]-2-(trifluoromethyl)-4H-pyrimido[1,2-b]pyridazin-4-one;

8-methoxy-3-[1-(2,2,3,3,3-pentafluoropropyl)-1H-1,2,4-triazol-3-yl]-2-(trifluoromethyl)-4H-pyrido[1,2-a]pyrimidin-4-one;

8-methoxy-3-[3-(2,2,2-trifluoroethoxy)phenyl]-2-(trifluoromethyl)-4H-pyrido[1,2-a]pyrimidin-4-one; or methyl 4-oxo-3-[1-(2,2,3,3,3-pentafluoropropyl)-1H-pyrazol-4-yl]-2-(trifluoromethyl)-4H-pyrido[1,2-a]pyrimidine-7-carboxylate.

Provided herein as Embodiment 3 is the compound according to Embodiment I or Embodiment 2, or a tautomer thereof, or a pharmaceutically acceptable salt of said compound or said tautomer, wherein the compound of Formula I is a compound of Formula IA

IA

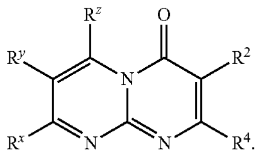

Provided herein as Embodiment 4 is the compound according to Embodiment 1 or Embodiment 2, or a tautomer thereof, or a pharmaceutically acceptable salt of said compound or said tautomer, wherein the compound of Formula I is a compound of Formula IB

IB

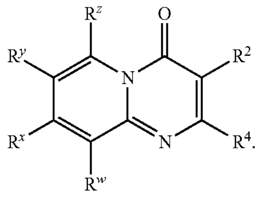

Provided herein as Embodiment 5 is the compound according to Embodiment I or Embodiment 2, or a tautomer thereof, or a pharmaceutically acceptable salt of said compound or said tautomer, wherein the compound of Formula I is a compound of Formula IC

IC

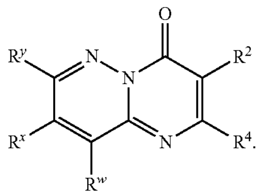

Provided herein as Embodiment 6 is the compound according to any one of Embodiments 1, 2, 4, and 5, or a tautomer thereof, or a pharmaceutically acceptable salt of said compound or said tautomer, wherein $R^w$ is H, halogen, —CN, —CO($C_{1-4}$alkyl), —S(O)$_n$($C_{1-4}$ alkyl), —$CONH_2$, —$NH_2$, $C_{1-4}$alkylamino, di$C_{1-4}$alkylamino, —NH($COC_{1-4}$alkyl), —N($C_{1-4}$alkyl)C(═O)F, $C_{1-4}$alkyl, $C_{1-4}$deuteroalkyl, $C_{3-5}$cycloalkyl, $C_{2-4}$alkenyl, $C_{1-4}$deuteroalkoxy, or 5-membered heteroaryl;

wherein the $C_{1-4}$alkyl group is optionally substituted with 1 to 4 substituents independently selected from halogen, —OH, —CN, $C_{1-4}$alkoxy, —$NH_2$, and di$C_{1-4}$alkylamino.

Provided herein as Embodiment 7 is the compound according to any one of Embodiments 1, 2, 4, and 5, or a tautomer thereof, or a pharmaceutically acceptable salt of said compound or said tautomer, wherein $R^w$ is H, halogen, —CN, —$CONH_2$, —$NH_2$, $C_{1-4}$alkylamino, di$C_{1-4}$alkylamino, or $C_{1-4}$deuteroalkoxyl; wherein the $C_{1-4}$alkyl group is optionally substituted with 1 to 4 substituents independently selected from halogen, —OH, $C_{1-4}$alkoxy, —$NH_2$, and di$C_{1-4}$alkylamino.

Provided herein as Embodiment 8 is the compound according to any one of Embodiments 1, 2, 4, and 5, or a tautomer thereof, or a pharmaceutically acceptable salt of said compound or said tautomer, wherein $R^w$ is H, F, Cl, —CN, —COMe, —SMe, —$CONH_2$, —$NH_2$, —NHMe, —$N(CH_3)_2$, —NH($COCH_3$), —N($CH_3$)C(═O)F, methyl, ethyl, —$CD_3$, cyclopropyl, —CH═$CH_2$, —$OCD_3$, or 1,3-oxazol-2-yl; wherein the methyl group is optionally substituted with 1 to 3 substituents independently selected from F, Cl, —OH, —CN, methoxy, —$NH_2$, and —$N(CH_3)_2$.

Provided herein as Embodiment 9 is the compound according to any one of Embodiments 1, 2, 4, and 5, or a tautomer thereof, or a pharmaceutically acceptable salt of said compound or said tautomer, wherein $R^w$ is H, F, Cl, —CN, —$CONH_2$, —$NH_2$, —NHMe, or —$OCD_3$; wherein the methyl group is optionally substituted with 1 to 3 substituents independently selected from F, —OH, methoxy, —$NH_2$, and —$N(CH_3)_2$.

Provided herein as Embodiment 10 is the compound according to any one of Embodiments 1, 2, 4, and 5, or a tautomer thereof, or a pharmaceutically acceptable salt of said compound or said tautomer, wherein $R^w$ is H, halogen, or $C_{1-4}$alkyl.

Provided herein as Embodiment 11 is the compound according to any one of Embodiments 1, 2, 4, and 5, or a tautomer thereof, or a pharmaceutically acceptable salt of said compound or said tautomer, wherein $R^w$ is H, F, Cl, or methyl.

Provided herein as Embodiment 12 is the compound according to any one of Embodiments 1, 2, 4, and 5, or a tautomer thereof, or a pharmaceutically acceptable salt of said compound or said tautomer, wherein $R^w$ is H.

Provided herein as Embodiment 13 is the compound according to any one of Embodiments 1-12, or a tautomer thereof, or a pharmaceutically acceptable salt of said compound or said tautomer, wherein $R^x$ is H, halogen, —OH, —CN, —CO($C_{1-4}$alkyl), —S(O)$_n$($C_{1-4}$alkyl), —$CONH_2$, —$NH_2$, $C_{1-4}$alkylamino, di$C_{1-4}$alkylamino, —NH($COC_{1-4}$ alkyl), —N($C_{1-4}$alkyl)C(═O)F, $C_{1-4}$alkyl, $C_{1-4}$deuteroalkyl, $C_{3-5}$cycloalkyl, $C_{2-4}$alkenyl, $C_{1-4}$alkoxy, $C_{1-4}$deuteroalkoxy, or 5-membered heteroaryl; wherein the $C_{1-4}$alkyl and $C_{1-4}$alkoxy groups are optionally substituted with 1 to 4 substituents independently selected from halogen, —OH, —CN, $C_{1-4}$alkoxy, —$NH_2$, and di$C_{1-4}$alkylamino.

Provided herein as Embodiment 14 is the compound according to any one of Embodiments 1-12, or a tautomer thereof, or a pharmaceutically acceptable salt of said compound or said tautomer, wherein $R^x$ is H, halogen, —OH, —CN, —$CONH_2$, —$NH_2$, $C_{1-4}$alkylamino, di$C_{1-4}$alkylamino, $C_{1-4}$alkoxy, or $C_{1-4}$deuteroalkoxyl; wherein the $C_{1-4}$alkyl and $C_{1-4}$alkoxy groups are optionally substituted with 1 to 4 substituents independently selected from halogen, —OH, $C_{1-4}$alkoxy, —$NH_2$, and di$C_{1-4}$alkylamino.

Provided herein as Embodiment 15 is the compound according to any one of Embodiments 1-12, or a tautomer thereof, or a pharmaceutically acceptable salt of said compound or said tautomer, wherein $R^x$ is H, F, Cl, —OH, —CN, —COMe, —SMe, —$CONH_2$, —$NH_2$, —NHMe, —$N(CH_3)_2$, —NH ($COCH_3$), —N($CH_3$)C(═O)F, methyl, ethyl, —$CD_3$, cyclopropyl, —CH═$CH_2$, methoxy, ethoxy, —$OCD_3$, or 1,3-oxazol-2-yl; wherein the methyl and methoxy groups are optionally substituted with 1 to 3 substituents independently selected from F, Cl, —OH, —CN, methoxy, —$NH_2$, and —$N(CH_3)_2$.

Provided herein as Embodiment 16 is the compound according to any one of Embodiments 1-12, or a tautomer thereof, or a pharmaceutically acceptable salt of said compound or said tautomer, wherein $R^x$ is H, F, Cl, —OH, —CN, —$CONH_2$, —$NH_2$, —NHMe, methoxy, ethoxy, or —$OCD_3$; wherein the methyl and methoxy groups are optionally substituted with 1 to 3 substituents independently selected from F, —OH, methoxy, —$NH_2$, and —$N(CH_3)_2$.

Provided herein as Embodiment 17 is the compound according to any one of Embodiments 1-12, or a tautomer thereof, or a pharmaceutically acceptable salt of said compound or said tautomer, wherein $R^x$ is H, halogen, —OH, —CN, —CO($C_{1-4}$alkyl), —S(O)$_n$ ($C_{1-4}$alkyl), —$CONH_2$, —$NH_2$, $C_{1-4}$alkylamino, di$C_{1-4}$alkylamino, —NH($COC_{1-4}$alkyl), —N($C_{1-4}$alkyl)C(═O)F, $C_{1-4}$alkyl, $C_{3-5}$cycloalkyl, $C_{2-4}$alkenyl, $C_{1-4}$alkoxy, $C_{1-4}$deuteroalkoxy, or 5-membered heteroaryl; wherein the $C_{1-4}$alkyl and $C_{1-4}$alkoxy groups are optionally substituted with 1 to 4 substituents independently selected from halogen, —OH, —CN, $C_{1-4}$alkoxy, —$NH_2$, and di$C_{1-4}$alkylamino.

Provided herein as Embodiment 18 is the compound according to any one of Embodiments 1-12, or a tautomer thereof, or a pharmaceutically acceptable salt of said compound or said tautomer, wherein $R^x$ is H, halogen, —OH, —CN, —$CONH_2$, —$NH_2$, $C_{1-4}$alkylamino, di$C_{1-4}$alkylamino, $C_{1-4}$alkyl, $C_{1-4}$alkoxy, or $C_{1-4}$deuteroalkoxy; wherein the $C_{1-4}$alkyl and $C_{1-4}$alkoxy groups are optionally substituted with 1 to 4 substituents independently selected from halogen, —OH, $C_{1-4}$alkoxy, —$NH_2$, and di$C_{1-4}$alkylamino.

Provided herein as Embodiment 19 is the compound according to any one of Embodiments 1-12, or a tautomer thereof, or a pharmaceutically acceptable salt of said compound or said tautomer, wherein $R^x$ is H, —CN, —$NH_2$, $C_{1-4}$alkoxy, or $C_{1-4}$deuteroalkoxy.

Provided herein as Embodiment 20 is the compound according to any one of Embodiments 1-12, or a tautomer thereof, or a pharmaceutically acceptable salt of said compound or said tautomer, wherein $R^x$ is H, F, Cl, —OH, —CN, —COMe, —SMe, —$CONH_2$, —$NH_2$, —NHMe, —$NH(CH_3)_2$, —NH($COCH_3$), —$N(CH_3)C(=O)F$, methyl, ethyl, cyclopropyl, —$CH=CH_2$, methoxy, ethoxy, —$OCD_3$ or 1,3-oxazol-2-yl; wherein the methyl and methoxy groups are optionally substituted with 1 to 4 substituents independently selected from F, Cl, —OH, —CN, methoxy, —$NH_2$, and —$N(CH_3)_2$.

Provided herein as Embodiment 21 is the compound according to any one of Embodiments 1-12, or a tautomer thereof, or a pharmaceutically acceptable salt of said compound or said tautomer, wherein $R^x$ is H, F, Cl, —OH, —CN, —$CONH_2$, —$NH_2$, —NHMe, methyl, methoxy, ethoxy, or —$OCD_3$; wherein the methyl and methoxy groups are optionally substituted with 1 to 4 substituents independently selected from F, —OH, methoxy, —$NH_2$, and —$N(CH_3)_2$.

Provided herein as Embodiment 22 is the compound according to any one of Embodiments 1-12, or a tautomer thereof, or a pharmaceutically acceptable salt of said compound or said tautomer, wherein $R^x$ is H, —CN, —$NH_2$, methoxy, or —$OCD_3$.

Provided herein as Embodiment 23 is the compound according to any one of Embodiments 1-22, or a tautomer thereof, or a pharmaceutically acceptable salt of said compound or said tautomer, wherein $R^y$ is H, F, Cl, —OH, —CN, —CO($C_{1-4}$alkyl), —$S(O)_n$ ($C_{1-4}$alkyl), —$CONH_2$, —$NH_2$, $C_{1-4}$alkylamino, di$C_{1-4}$ alkylamino, —NH(CO$C_{1-4}$alkyl), —N($C_{1-4}$alkyl)C(=O)F, $C_{1-4}$alkyl, $C_{1-4}$deuteroalkyl, $C_{3-5}$cycloalkyl, $C_{2-4}$alkenyl, $C_{1-4}$alkoxy, $C_{1-4}$deuteroalkoxy, or 5-membered heteroaryl; wherein the $C_{1-4}$alkyl and $C_{1-4}$alkoxy groups are optionally substituted with 1 to 4 substituents independently selected from halogen, —OH, —CN, $C_{1-4}$alkoxy, —$NH_2$, and di$C_{1-4}$alkylamino.

Provided herein as Embodiment 24 is the compound according to any one of Embodiments 1-22, or a tautomer thereof, or a pharmaceutically acceptable salt of said compound or said tautomer, wherein $R^y$ is H, F, Cl, —OH, —CN, —$CONH_2$, —$NH_2$, $C_{1-4}$alkylamino, di$C_{1-4}$alkylamino, $C_{1-4}$alkoxy, or $C_{1-4}$deuteroalkoxyl; wherein the $C_{1-4}$alkyl and $C_{1-4}$alkoxy groups are optionally substituted with 1 to 4 substituents independently selected from halogen, —OH, $C_{1-4}$alkoxy, —$NH_2$, and di$C_{1-4}$alkylamino.

Provided herein as Embodiment 25 is the compound according to any one of Embodiments 1-22, or a tautomer thereof, or a pharmaceutically acceptable salt of said compound or said tautomer, wherein $R^y$ is H, F, Cl, —OH, —CN, —COMe, —SMe, —$CONH_2$, —$NH_2$, —NHMe, —$N(CH_3)_2$, —NH($COCH_3$), —$N(CH_3)C(=O)F$, methyl, ethyl, —$CD_3$, cyclopropyl, —$CH=CH_2$, methoxy, ethoxy, —$OCD_3$, or 1,3-oxazol-2-yl; wherein the methyl and methoxy groups are optionally substituted with 1 to 3 substituents independently selected from F, Cl, —OH, —CN, methoxy, —$NH_2$, and —$N(CH_3)_2$.

Provided herein as Embodiment 26 is the compound according to any one of Embodiments 1-22, or a tautomer thereof, or a pharmaceutically acceptable salt of said compound or said tautomer, wherein $R^y$ is H, F, Cl, —OH, —CN, —$CONH_2$, —$NH_2$, —NHMe, methoxy, ethoxy, or —$OCD_3$; wherein the methyl and methoxy groups are optionally substituted with 1 to 3 substituents independently selected from F, —OH, methoxy, —$NH_2$, and —$N(CH_3)_2$.

Provided herein as Embodiment 27 is the compound according to any one of Embodiments 1-22, or a tautomer thereof, or a pharmaceutically acceptable salt of said compound or said tautomer, wherein $R^y$ is H, F, Cl, —CN, —COO($C_{1-4}$alkyl), $C_{1-4}$alkyl, $C_{3-5}$cycloalkyl, $C_{3-4}$heterocycloalkyl, or $C_{1-4}$alkoxy; wherein the $C_{1-4}$alkyl group is optionally substituted with 1 to 4 substituents independently selected from $C_{1-4}$alkoxy and di$C_{1-4}$alkylamino.

Provided herein as Embodiment 28 is the compound according to any one of Embodiments 1-22, or a tautomer thereof, or a pharmaceutically acceptable salt of said compound or said tautomer, wherein $R^y$ is H, F, Cl, —CN, —COOMe, methyl, cyclopropyl, azetidinyl, or methoxy; wherein the methyl group is optionally substituted with 1 to 3 substituents independently selected from methoxy and dimethylamino.

Provided herein as Embodiment 29 is the compound according to any one of Embodiments 1-22, or a tautomer thereof, or a pharmaceutically acceptable salt of said compound or said tautomer, wherein $R^y$ is H or Cl.

Provided herein as Embodiment 30 is the compound according to any one of Embodiments 1-4 and 6-29, or a tautomer thereof, or a pharmaceutically acceptable salt of said compound or said tautomer, wherein $R^z$ is H, halogen, —OH, —CN, —CO($C_{1-4}$alkyl), —$S(O)_n$ ($C_{1-4}$alkyl), —$CONH_2$, —$NH_2$, $C_{1-4}$alkylamino, di$C_{1-4}$alkylamino, —NH(CO$C_{1-4}$alkyl), —N($C_{1-4}$alkyl)C(=O)F, $C_{1-4}$alkyl, $C_{1-4}$deuteroalkyl, $C_{3-5}$cycloalkyl, $C_{2-4}$alkenyl, $C_{1-4}$alkoxy, $C_{1-4}$deuteroalkoxy, or 5-membered heteroaryl; wherein the $C_{1-4}$alkyl and $C_{1-4}$alkoxy groups are optionally substituted with 1 to 4 substituents independently selected from halogen, —OH, —CN, $C_{1-4}$alkoxy, —$NH_2$, and di$C_{1-4}$alkylamino.

Provided herein as Embodiment 31 is the compound according to any one of Embodiments 1-4 and 6-29, or a tautomer thereof, or a pharmaceutically acceptable salt of said compound or said tautomer, wherein $R^z$ is H, halogen, —OH, —CN, —$CONH_2$, —$NH_2$, $C_{1-4}$alkylamino, di$C_{1-4}$alkylamino, $C_{1-4}$alkoxy, or $C_{1-4}$deuteroalkoxyl; wherein the $C_{1-4}$alkyl and $C_{1-4}$alkoxy groups are optionally substituted with 1 to 4 substituents independently selected from halogen, —OH, $C_{1-4}$alkoxy, —$NH_2$, and di$C_{1-4}$alkylamino.

Provided herein as Embodiment 32 is the compound according to any one of Embodiments 1-4 and 6-29, or a tautomer thereof, or a pharmaceutically acceptable salt of said compound or said tautomer, wherein $R^z$ is H, F, Cl, —OH, —CN, —COMe, —SMe, —$CONH_2$, —$NH_2$, —NHMe, —$N(CH_3)_2$, —NH($COCH_3$), —$N(CH_3)C$(═O)F, methyl, ethyl, —$CD_3$, cyclopropyl, —CH═$CH_2$, methoxy, ethoxy, —$OCD_3$, or 1,3-oxazol-2-yl; wherein the methyl and methoxy groups are optionally substituted with 1 to 3 substituents independently selected from F, Cl, —OH, —CN, methoxy, —$NH_2$, and —$N(CH_3)_2$.

Provided herein as Embodiment 33 is the compound according to any one of Embodiments 1-4 and 6-29, or a tautomer thereof, or a pharmaceutically acceptable salt of said compound or said tautomer, wherein $R^z$ is H, F, Cl, —OH, —CN, —$CONH_2$, —$NH_2$, —NHMe, methoxy, ethoxy, or —$OCD_3$; wherein the methyl and methoxy groups are optionally substituted with 1 to 3 substituents independently selected from F, —OH, methoxy, —$NH_2$, and —$N(CH_3)_2$.

Provided herein as Embodiment 34 is the compound according to any one of Embodiments 1-4 and 6-29, or a tautomer thereof, or a pharmaceutically acceptable salt of said compound or said tautomer, wherein $R^z$ is H or $C_{1-4}$alkyl.

Provided herein as Embodiment 35 is the compound according to any one of Embodiments 1-4 and 6-29, or a tautomer thereof, or a pharmaceutically acceptable salt of said compound or said tautomer, wherein $R^z$ is H or methyl.

Provided herein as Embodiment 36 is the compound according to any one of Embodiments 1-4 and 6-29, or a tautomer thereof, or a pharmaceutically acceptable salt of said compound or said tautomer, wherein $R^z$ is H.

Provided herein as Embodiment 37 is the compound according to Embodiment 1 or Embodiment 2, or a tautomer thereof, or a pharmaceutically acceptable salt of said compound or said tautomer, wherein the compound of Formula I is a compound of Formula ID

ID

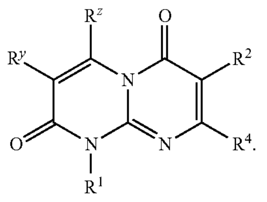

Provided herein as Embodiment 38 is the compound according to Embodiment 37, or a tautomer thereof, or a pharmaceutically acceptable salt of said compound or said tautomer, wherein $R^y$ is H, F, Cl, —OH, —CN, —CO($C_{1-4}$alkyl), —$S(O)_n$($C_{1-4}$alkyl), —$CONH_2$, —$NH_2$, $C_{1-4}$alkylamino, di$C_{1-4}$ alkylamino, —NH($COC_{1-4}$alkyl), —N($C_{1-4}$alkyl)C(═O)F, $C_{1-4}$alkyl, $C_{1-4}$deuteroalkyl, $C_{3-5}$cycloalkyl, $C_{2-4}$alkenyl, $C_{1-4}$alkoxy, $C_{1-4}$deuteroalkoxy, or 5-membered heteroaryl; wherein the $C_{1-4}$alkyl and $C_{1-4}$alkoxy groups are optionally substituted with 1 to 4 substituents independently selected from halogen, —OH, —CN, $C_{1-4}$alkoxy, —$NH_2$, and di$C_{1-4}$alkylamino.

Provided herein as Embodiment 39 is the compound according to Embodiment 37, or a tautomer thereof, or a pharmaceutically acceptable salt of said compound or said tautomer, wherein $R^y$ is H, F, Cl, —OH, —CN, —$CONH_2$, —$NH_2$, $C_{1-4}$alkylamino, di$C_{1-4}$alkylamino, $C_{1-4}$alkoxy, or $C_{1-4}$deuteroalkoxyl; wherein the $C_{1-4}$alkyl and $C_{1-4}$alkoxy groups are optionally substituted with 1 to 4 substituents independently selected from halogen, —OH, $C_{1-4}$alkoxy, —$NH_2$, and di$C_{1-4}$alkylamino.

Provided herein as Embodiment 40 is the compound according to Embodiment 37, or a tautomer thereof, or a pharmaceutically acceptable salt of said compound or said tautomer, wherein $R^y$ is H, F, Cl, —OH, —CN, —COMe, —SMe, —$CONH_2$, —$NH_2$, —NHMe, —$N(CH_3)_2$, —NH($COCH_3$), —$N(CH_3)C$(═O)F, methyl, ethyl, —$CD_3$, cyclopropyl, —CH═$CH_2$, methoxy, ethoxy, —$OCD_3$, or 1,3-oxazol-2-yl; wherein the methyl and methoxy groups are optionally substituted with 1 to 3 substituents independently selected from F, Cl, —OH, —CN, methoxy, —$NH_2$, and —$N(CH_3)_2$.

Provided herein as Embodiment 41 is the compound according to Embodiment 37, or a tautomer thereof, or a pharmaceutically acceptable salt of said compound or said tautomer, wherein $R^y$ is H, F, Cl, —OH, —CN, —$CONH_2$, —$NH_2$, —NHMe, methoxy, ethoxy, or —$OCD_3$; wherein the methyl and methoxy groups are optionally substituted with 1 to 3 substituents independently selected from F, —OH, methoxy, —$NH_2$, and —$N(CH_3)_2$.

Provided herein as Embodiment 42 is the compound according to Embodiment 37, or a tautomer thereof, or a pharmaceutically acceptable salt of said compound or said tautomer, wherein $R^y$ is H, F, Cl, —CN, —COO($C_{1-4}$alkyl), $C_{1-4}$alkyl, $C_{3-5}$cycloalkyl, $C_{3-4}$heterocycloalkyl, or $C_{1-4}$alkoxy; wherein the $C_{1-4}$alkyl group is optionally substituted with 1 to 4 substituents independently selected from $C_{1-4}$alkoxy and di$C_{1-4}$alkylamino.

Provided herein as Embodiment 43 is the compound according to Embodiment 37, or a tautomer thereof, or a pharmaceutically acceptable salt of said compound or said tautomer, wherein $R^y$ is H, F, Cl, —CN, —COOMe, methyl, cyclopropyl, azetidinyl, or methoxy; wherein the methyl group is optionally substituted with 1 to 3 substituents independently selected from methoxy and dimethylamino.

Provided herein as Embodiment 44 is the compound according to Embodiment 37, or a tautomer thereof, or a pharmaceutically acceptable salt of said compound or said tautomer, wherein $R^y$ is H or Cl.

Provided herein as Embodiment 45 is the compound according to any one of Embodiments 37-44, or a tautomer thereof, or a pharmaceutically acceptable salt of said compound or said tautomer, wherein $R^z$ is H, halogen, —OH, —CN, —CO($C_{1-4}$alkyl), —$S(O)_n$ ($C_{1-4}$alkyl), —$CONH_2$, —$NH_2$, $C_{1-4}$alkylamino, di$C_{1-4}$alkylamino, —NH($COC_{1-4}$alkyl), —N($C_{1-4}$alkyl)C(═O)F, $C_{1-4}$alkyl, $C_{1-4}$deuteroalkyl, $C_{3-5}$cycloalkyl, $C_{2-4}$alkenyl, $C_{1-4}$alkoxy, $C_{1-4}$deuteroalkoxy, or 5-membered heteroaryl; wherein the $C_{1-4}$alkyl and $C_{1-4}$alkoxy groups are optionally substituted with 1 to 4 substituents independently selected from halogen, —OH, —CN, $C_{1-4}$alkoxy, —$NH_2$, and di$C_{1-4}$alkylamino.

Provided herein as Embodiment 46 is the compound according to any one of Embodiments 37-44, or a tautomer thereof, or a pharmaceutically acceptable salt of said compound or said tautomer, wherein $R^z$ is H, halogen, —OH, —CN, —$CONH_2$, —$NH_2$, $C_{1-4}$alkylamino, di$C_{1-4}$alkylamino, $C_{1-4}$ alkoxy, or $C_{1-4}$deuteroalkoxyl; wherein the $C_{1-4}$alkyl and $C_{1-4}$alkoxy groups are optionally substituted with 1 to 4 substituents independently selected from halogen, —OH, $C_{1-4}$alkoxy, —$NH_2$, and di$C_{1-4}$alkylamino.

Provided herein as Embodiment 47 is the compound according to any one of Embodiments 37-44, or a tautomer thereof, or a pharmaceutically acceptable salt of said compound or said tautomer, wherein $R^z$ is H, F, Cl, —OH, —CN, —COMe, —SMe, —$CONH_2$, —$NH_2$, —NHMe, —$N(CH_3)_2$, —NH($COCH_3$), —$N(CH_3)C(=O)F$, methyl, ethyl, —$CD_3$, cyclopropyl, —$CH=CH_2$, methoxy, ethoxy, —$OCD_3$, or 1,3-oxazol-2-yl; wherein the methyl and methoxy groups are optionally substituted with 1 to 3 substituents independently selected from F, Cl, —OH, —CN, methoxy, —$NH_2$, and —$N(CH_3)_2$.

Provided herein as Embodiment 48 is the compound according to any one of Embodiments 37-44, or a tautomer thereof, or a pharmaceutically acceptable salt of said compound or said tautomer, wherein $R^z$ is H, F, Cl, —OH, —CN, —$CONH_2$, —$NH_2$, —NHMe, methoxy, ethoxy, or —$OCD_3$;

wherein the methyl and methoxy groups are optionally substituted with 1 to 3 substituents independently selected from F, —OH, methoxy, —$NH_2$, and —$N(CH_3)_2$.

Provided herein as Embodiment 49 is the compound according to any one of Embodiments 37-44, or a tautomer thereof, or a pharmaceutically acceptable salt of said compound or said tautomer, wherein $R^z$ is H, halogen, or $C_{1-4}$alkyl Provided herein as Embodiment 50 is the compound according to any one of Embodiments 37-44, or a tautomer thereof, or a pharmaceutically acceptable salt of said compound or said tautomer, wherein $R^z$ is H, F, Cl, or methyl.

Provided herein as Embodiment 51 is the compound according to any one of Embodiments 37-44, or a tautomer thereof, or a pharmaceutically acceptable salt of said compound or said tautomer, wherein $R^z$ is H.

Provided herein as Embodiment 52 is the compound according to any one of Embodiments 37-51, or a tautomer thereof, or a pharmaceutically acceptable salt of said compound or said tautomer, wherein $R^1$ is H, methyl, $CH_2F$, or $CD_3$.

Provided herein as Embodiment 53 is the compound according to any one of Embodiments 37-51, or a tautomer thereof, or a pharmaceutically acceptable salt of said compound or said tautomer, wherein $R^1$ is H.

Provided herein as Embodiment 54 is the compound according to Embodiment 1 or Embodiment 2, or a tautomer thereof, or a pharmaceutically acceptable salt of said compound or said tautomer, wherein the compound of Formula I is a compound of Formula IE

IE

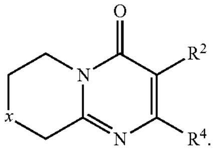

Provided herein as Embodiment 55 is the compound according to Embodiment 54, or a tautomer thereof, or a pharmaceutically acceptable salt of said compound or said tautomer, wherein x is O.

Provided herein as Embodiment 56 is the compound according to Embodiment 54, or a tautomer thereof, or a pharmaceutically acceptable salt of said compound or said tautomer, wherein x is NH.

Provided herein as Embodiment 57 is the compound according to Embodiment 54, or a tautomer thereof, or a pharmaceutically acceptable salt of said compound or said tautomer, wherein x is N($C_{1-4}$alkyl).

Provided herein as Embodiment 58 is the compound according to Embodiment 54, or a tautomer thereof, or a pharmaceutically acceptable salt of said compound or said tautomer, wherein x is $NCH_3$.

Provided herein as Embodiment 59 is the compound according to any one of Embodiments 1-58, or a tautomer thereof, or a pharmaceutically acceptable salt of said compound or said tautomer, wherein $R^2$ is

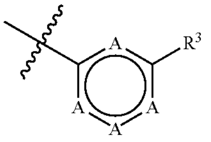

or

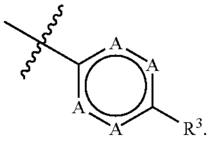

Provided herein as Embodiment 60 is the compound according to any one of Embodiments 1-58, or a tautomer thereof, or a pharmaceutically acceptable salt of said compound or said tautomer, wherein $R^2$ is

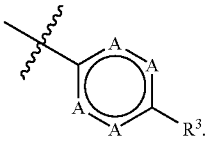

Provided herein as Embodiment 61 is the compound according to any one of Embodiments 1-58, or a tautomer thereof, or a pharmaceutically acceptable salt of said compound or said tautomer, wherein $R^2$ is

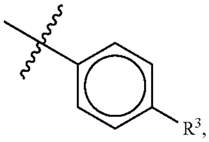

,

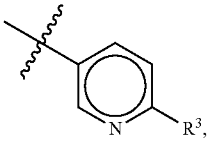

,

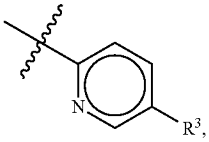

, or

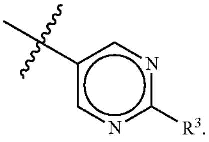

Provided herein as Embodiment 62 is the compound according to any one of Embodiments 1-58, or a tautomer thereof, or a pharmaceutically acceptable salt of said compound or said tautomer, wherein $R^2$ is

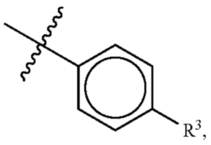
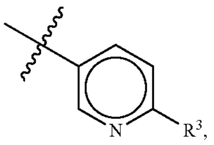
or
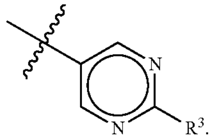

Provided herein as Embodiment 63 is the compound according to any one of Embodiments 1-58, or a tautomer thereof, or a pharmaceutically acceptable salt of said compound or said tautomer, wherein $R^2$ is

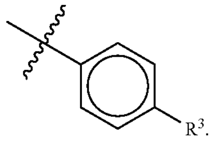

Provided herein as Embodiment 64 is the compound according to any one of Embodiments 1-58, or a tautomer thereof, or a pharmaceutically acceptable salt of said compound or said tautomer, wherein $R^2$ is

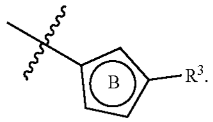

Provided herein as Embodiment 65 is the compound according to any one of Embodiments 1-58, or a tautomer thereof, or a pharmaceutically acceptable salt of said compound or said tautomer, wherein $R^2$ is

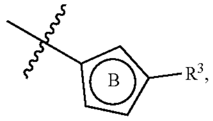

wherein B is a 5-membered heteroaryl containing two N atoms.

Provided herein as Embodiment 66 is the compound according to any one of Embodiments 1-58, 64, and 65, or a tautomer thereof, or a pharmaceutically acceptable salt of said compound or said tautomer, wherein B is attached via a C atom to the bicyclic core and $R^3$ is attached via an N atom.

Provided herein as Embodiment 67 is the compound according to any one of Embodiments 1-58, 64, and 65, or a tautomer thereof, or a pharmaceutically acceptable salt of said compound or said tautomer, wherein B is attached via an N atom to the bicyclic core and $R^3$ is attached via a C atom;

Provided herein as Embodiment 68 is the compound according to any one of Embodiments 1-58, 64, and 65, or a tautomer thereof, or a pharmaceutically acceptable salt of said compound or said tautomer, wherein B is attached via a C atom to the bicyclic core and $R^3$ is attached via a C atom.

Provided herein as Embodiment 69 is the compound according to any one of Embodiments 1-58, or a tautomer thereof, or a pharmaceutically acceptable salt of said compound or said tautomer, wherein $R^2$ is

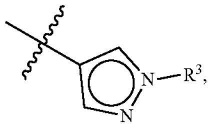
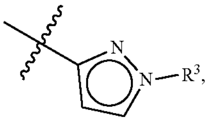
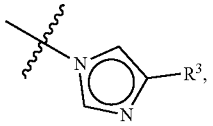
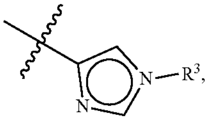
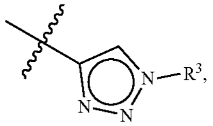
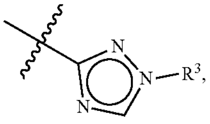
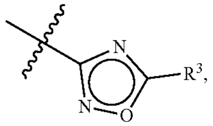
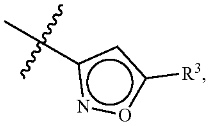
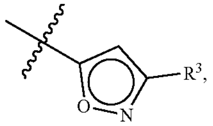
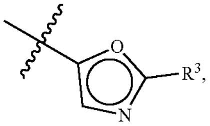
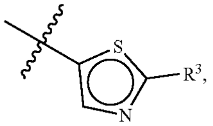
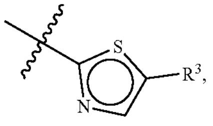
or
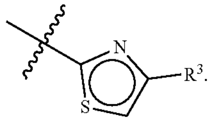

Provided herein as Embodiment 70 is the compound according to any one of Embodiments 1-58, or a tautomer thereof, or a pharmaceutically acceptable salt of said compound or said tautomer, wherein $R^2$ is

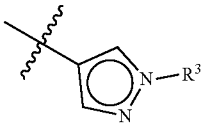
or
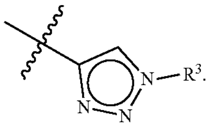

Provided herein as Embodiment 71 is the compound according to any one of Embodiments 1-58, or a tautomer thereof, or a pharmaceutically acceptable salt of said compound or said tautomer, wherein $R^2$ is 2-benzofuranyl.

Provided herein as Embodiment 72 is the compound according to any one of Embodiments 1-71, or a tautomer thereof, or a pharmaceutically acceptable salt of said compound or said tautomer, wherein the

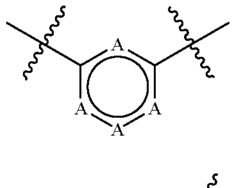
,
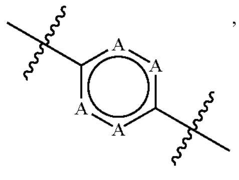
, or
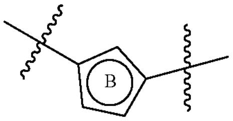

portion of $R^2$ or the 2-benzofuranyl is further optionally substituted with one substituent $R^{3'}$.

Provided herein as Embodiment 73 is the compound according to any one of Embodiments 1-71, or a tautomer thereof, or a pharmaceutically acceptable salt of said compound or said tautomer, wherein the

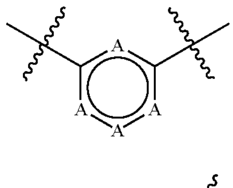
,
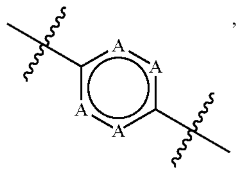
, or
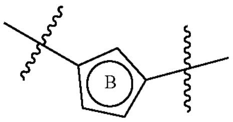

portion of $R^3$ or the 2-benzofuranyl is not further substituted with one or two independently selected substituents $R^{3'}$.

Provided herein as Embodiment 74 is the compound according to any one of Embodiments 1-70, 72, and 73, or a tautomer thereof, or a pharmaceutically acceptable salt of said compound or said tautomer, wherein $R^3$ is $C_{2-6}$alkyl, $C_{1-3}$alkoxy, —$CH_2$($C_{3-5}$cycloalkyl), —$OCH_2$($C_{3-5}$cycloalkyl), or phenyl; wherein the $C_{2-6}$alkyl, $C_{1-3}$alkoxy, —$CH_2$($C_{3-5}$cycloalkyl), and —$OCH_2$($C_{3-5}$cycloalkyl) groups are optionally substituted with 1 to 5 halogen atoms and are optionally substituted with —CN and wherein the phenyl is optionally substituted with one halogen substituent.

Provided herein as Embodiment 75 is the compound according to any one of Embodiments 1-70, 72, and 73, or a tautomer thereof, or a pharmaceutically acceptable salt of said compound or said tautomer, wherein $R^3$ is $C_{2-6}$alkyl, $C_{1-3}$alkoxy, or —$OCH_2$($C_{3-5}$cycloalkyl); wherein the $C_{2-6}$alkyl, $C_{1-3}$alkoxy, and —$OCH_2$($C_{3-5}$cycloalkyl) groups are optionally substituted with 1 to 5 halogen atoms and are optionally substituted with —CN.

Provided herein as Embodiment 76 is the compound according to any one of Embodiments 1-70, 72, and 73, or a tautomer thereof, or a pharmaceutically acceptable salt of said compound or said tautomer, wherein $R^3$ is $C_{2-6}$alkyl or $C_{1-3}$alkoxy; wherein the $C_{2-6}$alkyl and $C_{1-3}$alkoxy groups are optionally substituted with 3-5 halogen atoms.

Provided herein as Embodiment 77 is the compound according to any one of Embodiments 1-70, 72, and 73, or a tautomer thereof, or a pharmaceutically acceptable salt of said compound or said tautomer, wherein $R^3$ is 2,2,2-trifluoroethyl, propyl, 2,2-difluoropropyl, 3,3,3-trifluoropropyl, 4,4,4-trifluorobutyl, 2,2,3,3,3-pentafluoropropyl, —$OCH_2CN$, —$OC(CH_3)_2CN$, difluoromethoxy, trifluoromethoxy, —$OCH(CN)CH_3$, 2-fluoroethoxy, 2,2,-difluoroethoxy, 2,2,2-trifluoroethoxy, 2,2-difluoropropoxy, 2,2,3,3-tetrafluoropropoxy, 2,2,3,3,3-pentafluoropropoxy, cyclopropylmethyl, (2,2-difluorocyclopropyl)methyl, (3,3-difluorocyclobutyl)methyl, cyclopropylmethoxy, (2,2-difluorocyclopropyl)methoxy, phenyl, 3-fluorophenyl, or 4-fluorophenyl.

Provided herein as Embodiment 78 is the compound according to any one of Embodiments 1-70, 72, and 73, or a tautomer thereof, or a pharmaceutically acceptable salt of said compound or said tautomer, wherein $R^3$ is 2,2-difluoropropyl, 4,4,4-trifluorobutyl, 2,2,3,3,3-pentafluoropropyl, —$OC(CH_3)_2CN$, trifluoromethoxy, —$OCH(CN)CH_3$, 2-fluoroethoxy, 2,2,-difluoroethoxy, 2,2,2-trifluoroethoxy, 2,2-difluoropropoxy, cyclopropylmethoxy, or (2,2-difluorocyclopropyl)methoxy.

Provided herein as Embodiment 79 is the compound according to any one of Embodiments 1-70, 72, and 73, or a tautomer thereof, or a pharmaceutically acceptable salt of said compound or said tautomer, wherein $R^3$ is 2,2,3,3,3-pentafluoropropyl or 2,2,2-trifluoroethoxy.

Provided herein as Embodiment 80 is the compound according to any one of Embodiments 1-72 and 74-79, or a tautomer thereof, or a pharmaceutically acceptable salt of said compound or said tautomer, wherein $R^{3'}$ independently is halogen or $C_{1-4}$alkyl.

Provided herein as Embodiment 81 is the compound according to any one of Embodiments 1-72 and 74-79, or a tautomer thereof, or a pharmaceutically acceptable salt of said compound or said tautomer, wherein $R^{3'}$ is F or methyl.

Provided herein as Embodiment 82 is the compound according to any one of Embodiments 1-81, or a tautomer thereof, or a pharmaceutically acceptable salt of said compound or said tautomer, wherein $R^4$ is $C_{1-3}$alkyl, $C_{1-4}$haloalkyl, $C_{1-4}$alkoxy, or $C_{3-5}$cycloalkyl.

Provided herein as Embodiment 83 is the compound according to any one of Embodiments 1-81, or a tautomer thereof, or a pharmaceutically acceptable salt of said compound or said tautomer, wherein $R^4$ is $C_{1-3}$haloalkyl.

Provided herein as Embodiment 84 is the compound according to any one of Embodiments 1-81, or a tautomer thereof, or a pharmaceutically acceptable salt of said compound or said tautomer, wherein $R^4$ is methyl, ethyl, fluoromethyl, difluoromethyl, trifluoromethyl, methoxy, ethoxy, or cyclopropyl.

Provided herein as Embodiment 85 is the compound according to any one of Embodiments 1-81, or a tautomer thereof, or a pharmaceutically acceptable salt of said compound or said tautomer, wherein $R^4$ is ethyl, fluoromethyl, difluoromethyl, trifluoromethyl, methoxy, ethoxy, or cyclopropyl.

Provided herein as Embodiment 86 is the compound according to any one of Embodiments 1-81, or a tautomer thereof, or a pharmaceutically acceptable salt of said compound or said tautomer, wherein $R^4$ is trifluoromethyl.

Provided herein as Embodiment 87 is the compound according to any one of Embodiments 1-86, or a tautomer thereof, or a pharmaceutically acceptable salt of said compound or said tautomer, wherein n is 0.

Provided herein as Embodiment 88 is the compound according to any one of Embodiments 1-86, or a tautomer thereof, or a pharmaceutically acceptable salt of said compound or said tautomer, wherein n is 1.

Provided herein as Embodiment 89 is the compound according to any one of Embodiments 1-86, or a tautomer thereof, or a pharmaceutically acceptable salt of said compound or said tautomer, wherein n is 2.

Provided herein as Embodiment 90 is the compound according to Embodiment 1, or a tautomer thereof, or a pharmaceutically acceptable salt of said compound or said tautomer, wherein the compound is (2R)-2-(4-(8-methoxy-4-oxo-2-(trifluoromethyl)-4H-pyrido[1,2-a]pyrimidin-3-yl)phenoxy)propanenitrile;

(2R)-2-(4-(8-methoxy-4-oxo-2-(trifluoromethyl)-4H-pyrimido[1,2-a]pyrimidin-3-yl)phenoxy)propanenitrile;

(2S)-2-(4-(8-methoxy-4-oxo-2-(trifluoromethyl)-4H-pyrido[1,2-a]pyrimidin-3-yl)phenoxy)propanenitrile;

(2S)-2-(4-(8-methoxy-4-oxo-2-(trifluoromethyl)-4H-pyrimido[1,2-a]pyrimidin-3-yl)phenoxy)propanenitrile;

(4-(8-methoxy-4-oxo-2-(trifluoromethyl)-4H-pyrido[1,2-a]pyrimidin-3-yl)-1H-pyrazol-1-yl)acetonitrile;

(4-(8-methoxy-4-oxo-2-(trifluoromethyl)-4H-pyrido[1,2-a]pyrimidin-3-yl)phenoxy)acetonitrile;

(4-(8-methoxy-4-oxo-2-(trifluoromethyl)-4H-pyrido[1,2-a]pyrimidin-3-yl)phenyl)acetonitrile;

(4-(8-methoxy-4-oxo-2-(trifluoromethyl)-4H-pyrimido[1,2-a]pyrimidin-3-yl)phenoxy)acetonitrile;

(4-oxo-3-(1-(2,2,3,3,3-pentafluoropropyl)-1H-pyrazol-4-yl)-2-(trifluoromethyl)-4H-pyrido[1,2-a]pyrimidin-8-yl)acetonitrile;

1-(chloromethyl)-7-[1-(2,2,3,3,3-pentafluoropropyl)-1H-pyrazol-4-yl]-8-(trifluoromethyl)-1H,2H,6H-pyrimido[1,2-a][1,3]diazine-2,6-dione;

1-(fluoromethyl)-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione;

1-(methyl-$d_3$)-7-(4-(2,2,2-trifluoroethoxy)phenyl)-8-(trifluoromethyl)-2H-pyrimido[1,2-a]pyrimidine-2,6(1H)-dione;

1-methyl-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione;

2-(4-(8-methoxy-4-oxo-2-(trifluoromethyl)-4H-pyrido[1,2-a]pyrimidin-3-yl)phenoxy)-2-methylpropanenitrile;

2-(4-(8-methoxy-4-oxo-2-(trifluoromethyl)-4H-pyrido[1,2-a]pyrimidin-3-yl)phenoxy)propanenitrile;

2-(4-(8-methoxy-4-oxo-2-(trifluoromethyl)-4H-pyrimido[1,2-a]pyrimidin-3-yl)phenoxy)propanenitrile;

2-(difluoromethyl)-3-(3-fluoro-4-(2,2,2-trifluoroethoxy)phenyl)-8-methoxy-4H-pyrido[1,2-a]pyrimidin-4-one;

2-(difluoromethyl)-4-oxo-3-(1-(2,2,3,3,3-pentafluoropropyl)-1H-pyrazol-4-yl)-4H-pyrido[1,2-a]pyrimidine-8-carbonitrile;

2-(difluoromethyl)-8-methoxy-3-(1-(3,3,3-trifluoropropyl)-1H-pyrazol-4-yl)-4H-pyrido[1,2-a]pyrimidin-4-one;

2-(difluoromethyl)-8-methoxy-3-(1-(4,4,4-trifluorobutyl)-1H-pyrazol-4-yl)-4H-pyrido[1,2-a]pyrimidin-4-one;

2-(difluoromethyl)-8-methoxy-3-(4-(2,2,2-trifluoroethoxy)phenyl)-4H-pyrido[1,2-a]pyrimidin-4-one;

2-(difluoromethyl)-8-methoxy-3-(6-(2,2,2-trifluoroethoxy)-3-pyridinyl)-4H-pyrido[1,2-a]pyrimidin-4-one;

2-(fluoromethyl)-4-oxo-3-(1-(2,2,3,3,3-pentafluoropropyl)-1H-pyrazol-4-yl)-4H-pyrido[1,2-a]pyrimidine-8-carbonitrile;

2-(fluoromethyl)-8-methoxy-3-(4-(2,2,2-trifluoroethoxy)phenyl)-4H-pyrido[1,2-a]pyrimidin-4-one;

2-(trifluoromethyl)-3-[1-(3,3,3-trifluoropropyl)-1H-pyrazol-4-yl]-4H,6H,7H,9H-pyrimido[2,1-c][1,4]oxazin-4-one;

2,8-dimethoxy-3-(4-(2,2,2-trifluoroethoxy)phenyl)-4H-pyrido[1,2-a]pyrimidin-4-one;

2-cyclopropyl-8-methoxy-3-(4-(2,2,2-trifluoroethoxy)phenyl)-4H-pyrido[1,2-a]pyrimidin-4-one;

2-ethoxy-8-methoxy-3-(4-(2,2,2-trifluoroethoxy)phenyl)-4H-pyrido[1,2-a]pyrimidin-4-one;

2-ethoxy-8-methoxy-3-[1-(2,2,3,3,3-pentafluoropropyl)-1H-pyrazol-4-yl]-4H-pyrido[1,2-a]pyrimidin-4-one;

2-ethyl-8-methoxy-3-(1-(2,2,3,3,3-pentafluoropropyl)-1H-pyrazol-4-yl)-4H-pyrido[1,2-a]pyrimidin-4-one;

2-ethyl-8-methoxy-3-(4-(2,2,2-trifluoroethoxy)phenyl)-4H-pyrido[1,2-a]pyrimidin-4-one;

2-ethyl-8-methoxy-3-(6-(2,2,2-trifluoroethoxy)-3-pyridinyl)-4H-pyrido[1,2-a]pyrimidin-4-one;

3-(1-(2,2,3,3,3-pentafluoropropyl)-1H-pyrazol-4-yl)-2-(trifluoromethyl)-4H-pyrido[1,2-a]pyrimidine-4,8(1H)-dione;

3-(1-(2,2-difluoropropyl)-1H-pyrazol-4-yl)-8-methoxy-2-(trifluoromethyl)-4H-pyrido[1,2-a]pyrimidin-4-one;

3-(1-(3-fluorophenyl)-1H-pyrazol-4-yl)-8-methoxy-2-(trifluoromethyl)-4H-pyrido[1,2-a]pyrimidin-4-one;

3-(1-(4-fluorophenyl)-1H-pyrazol-4-yl)-2-(trifluoromethyl)-4H-pyrido[1,2-a]pyrimidin-4-one;

3-(1-(4-fluorophenyl)-1H-pyrazol-4-yl)-8-methoxy-2-(trifluoromethyl)-4H-pyrido[1,2-a]pyrimidin-4-one;

3-(1-{[(1R)-2,2-difluorocyclopropyl]methyl}-1H-pyrazol-4-yl)-8-methoxy-2-(trifluoromethyl)-4H-pyrido[1,2-a]pyrimidin-4-one;

3-(1-{[(1S)-2,2-difluorocyclopropyl]methyl}-1H-pyrazol-4-yl)-8-methoxy-2-(trifluoromethyl)-4H-pyrido[1,2-a]pyrimidin-4-one;

3-(1-benzofuran-2-yl)-8-methoxy-2-(trifluoromethyl)-4H-pyrido[1,2-a]pyrimidin-4-one;

3-(1-cyclopropyl-1H-pyrazol-4-yl)-2-(trifluoromethyl)-4H-pyrido[1,2-a]pyrimidin-4-one;

3-(1-cyclopropyl-1H-pyrazol-4-yl)-8-methoxy-2-(trifluoromethyl)-4H-pyrido[1,2-a]pyrimidin-4-one;

3-(1-phenyl-1H-pyrazol-4-yl)-2-(trifluoromethyl)-4H-pyrido[1,2-a]pyrimidin-4-one;

3-(1-propyl-1H-pyrazol-4-yl)-2-(trifluoromethyl)-4H-pyrido[1,2-a]pyrimidin-4-one;

3-(2-chloro-4-(2,2,2-trifluoroethoxy)phenyl)-8-methoxy-2-(trifluoromethyl)-4H-pyrido[1,2-a]pyrimidin-4-one;

3-(2-fluoro-4-(2,2,2-trifluoroethoxy)phenyl)-2-(trifluoromethyl)-4H-pyrido[1,2-a]pyrimidin-4-one;

3-(2-fluoro-4-(2,2,2-trifluoroethoxy)phenyl)-8-methoxy-2-(trifluoromethyl)-4H-pyrido[1,2-a]pyrimidin-4-one;

3-(2-fluoro-4-(2,2,2-trifluoroethoxy)phenyl)-8-methoxy-2-(trifluoromethyl)-4H-pyrimido[1,2-a]pyrimidin-4-one;

3-(2-fluoro-4-(trifluoromethoxy)phenyl)-8-methoxy-2-(trifluoromethyl)-4H-pyrido[1,2-a]pyrimidin-4-one;

3-(2-fluoro-6-(2,2,2-trifluoroethoxy)-3-pyridinyl)-8-methoxy-2-(trifluoromethyl)-4H-pyrido[1,2-a]pyrimidin-4-one;
3-(3-chloro-4-(2,2,2-trifluoroethoxy)phenyl)-2-(trifluoromethyl)-4H-pyrido[1,2-a]pyrimidin-4-one;
3-(3-fluoro-4-(2,2,2-trifluoroethoxy)phenyl)-8-methoxy-2-(trifluoromethyl)-4H-pyrido[1,2-a]pyrimidin-4-one;
3-(3-fluoro-4-(2,2,2-trifluoroethoxy)phenyl)-8-methoxy-2-(trifluoromethyl)-4H-pyrimido[1,2-a]pyrimidin-4-one;
3-(4-(((1R)-2,2-difluorocyclopropyl)methoxy)phenyl)-8-methoxy-2-(trifluoromethyl)-4H-pyrido[1,2-a]pyrimidin-4-one;
3-(4-(((1S)-2,2-difluorocyclopropyl)methoxy)phenyl)-8-methoxy-2-(trifluoromethyl)-4H-pyrido[1,2-a]pyrimidin-4-one;
3-(4-((2,2-difluorocyclopropyl)methoxy)phenyl)-8-methoxy-2-(trifluoromethyl)-4H-pyrido[1,2-a]pyrimidin-4-one;
3-(4-(2,2,2-trifluoroethoxy)phenyl)-2-(trifluoromethyl)-4H-pyrido[1,2-a]pyrimidin-4-one;
3-(4-(2,2,2-trifluoroethoxy)phenyl)-2-(trifluoromethyl)-4H-pyrido[1,2-a]pyrimidine-4,8(1H)-dione;
3-(4-(2,2,2-trifluoroethoxy)phenyl)-2,8-bis(trifluoromethyl)-4H-pyrido[1,2-a]pyrimidin-4-one;
3-(4-(2,2-difluoroethoxy)-2-fluorophenyl)-8-methoxy-2-(trifluoromethyl)-4H-pyrido[1,2-a]pyrimidin-4-one;
3-(4-(2,2-difluoroethoxy)phenyl)-8-(methyloxy-$d_3$)-2-(trifluoromethyl)-4H-pyrido[1,2-a]pyrimidin-4-one;
3-(4-(2,2-difluoroethoxy)phenyl)-8-methoxy-2-(trifluoromethyl)-4H-pyrido[1,2-a]pyrimidin-4-one;
3-(4-(2,2-difluoropropoxy)phenyl)-8-methoxy-2-(trifluoromethyl)-4H-pyrido[1,2-a]pyrimidin-4-one;
3-(4-(2-fluoroethoxy)phenyl)-8-(methyloxy-$d_3$)-2-(trifluoromethyl)-4H-pyrido[1,2-a]pyrimidin-4-one;
3-(4-(2-fluoroethoxy)phenyl)-8-(methyloxy-$d_3$)-2-(trifluoromethyl)-4H-pyrimido[1,2-a]pyrimidin-4-one;
3-(4-(2-fluoroethoxy)phenyl)-8-methoxy-2-(trifluoromethyl)-4H-pyrido[1,2-a]pyrimidin-4-one;
3-(4-(2-fluoroethoxy)phenyl)-8-methoxy-2-(trifluoromethyl)-4H-pyrimido[1,2-a]pyrimidin-4-one;
3-(4-(8-methoxy-4-oxo-2-(trifluoromethyl)-4H-pyrido[1,2-a]pyrimidin-3-yl)-1H-pyrazol-1-yl)propanenitrile;
3-(4-(8-methoxy-4-oxo-2-(trifluoromethyl)-4H-pyrido[1,2-a]pyrimidin-3-yl)phenyl)propanenitrile;
3-(4-(cyclopropylmethoxy)-2-fluorophenyl)-8-methoxy-2-(trifluoromethyl)-4H-pyrido[1,2-a]pyrimidin-4-one;
3-(4-(cyclopropylmethoxy)phenyl)-8-(methyloxy-$d_3$)-2-(trifluoromethyl)-4H-pyrido[1,2-a]pyrimidin-4-one;
3-(4-(cyclopropylmethoxy)phenyl)-8-methoxy-2-(trifluoromethyl)-4H-pyrido[1,2-a]pyrimidin-4-one;
3-(4-(cyclopropylmethoxy)phenyl)-8-methoxy-2-(trifluoromethyl)-4H-pyrimido[1,2-a]pyrimidin-4-one;
3-(4-(difluoromethoxy)phenyl)-8-methoxy-2-(trifluoromethyl)-4H-pyrido[1,2-a]pyrimidin-4-one;
3-(5-(2,2,2-trifluoroethoxy)-2-pyridinyl)-2-(trifluoromethyl)-4H-pyrido[1,2-a]pyrimidin-4-one;
3-(5-fluoro-6-(2,2,2-trifluoroethoxy)-3-pyridinyl)-8-methoxy-2-(trifluoromethyl)-4H-pyrido[1,2-a]pyrimidin-4-one;
3-(6-(2,2,2-trifluoroethoxy)-3-pyridinyl)-2-(trifluoromethyl)-4H-pyrido[1,2-a]pyrimidin-4-one;
3-[1-(2,2,3,3,3-pentafluoropropyl)-1H-pyrazol-4-yl]-2-(trifluoromethyl)-4H,6H,7H,9H-pyrimido[2,1-c][1,4]oxazin-4-one;
3-[1-(2,2,3,3,3-pentafluoropropyl)-1H-pyrazol-4-yl]-2-(trifluoromethyl)-4H-pyrazino[1,2-a]pyrimidin-4-one;
3-[1-(2,2,3,3,3-pentafluoropropyl)-1H-pyrazol-4-yl]-2-(trifluoromethyl)-4H-pyrido[1,2-a]pyrimidin-4-one;
3-[1-(cyclopropylmethyl)-1H-pyrazol-4-yl]-8-methoxy-2-(trifluoromethyl)-4H-pyrido[1,2-a]pyrimidin-4-one;
3-[1-(cyclopropylmethyl)-1H-pyrazol-4-yl]-8-methyl-2-(trifluoromethyl)-4H-pyrimido[1,2-b]pyridazin-4-one;
3-[5-iodo-1-(2,2,3,3,3-pentafluoropropyl)-1H-1,2,3-triazol-4-yl]-8-methoxy-2-(trifluoromethyl)-4H-pyrido[1,2-a]pyrimidin-4-one;
3-{1-[(2,2-difluorocyclopropyl)methyl]-1H-pyrazol-4-yl}-7-fluoro-8-methoxy-2-(trifluoromethyl)-4H-pyrido[1,2-a]pyrimidin-4-one;
3-{1-[(2,2-difluorocyclopropyl)methyl]-1H-pyrazol-4-yl}-8-methoxy-2-(trifluoromethyl)-4H-pyrido[1,2-a]pyrimidin-4-one;
3-{1-[(2,2-difluorocyclopropyl)methyl]-1H-pyrazol-4-yl}-8-methyl-2-(trifluoromethyl)-4H-pyrimido[1,2-b]pyridazin-4-one;
3-{1-[(3,3-difluorocyclobutyl)methyl]-1H-pyrazol-4-yl}-8-methoxy-2-(trifluoromethyl)-4H-pyrido[1,2-a]pyrimidin-4-one;
3-{1-[(3,3-difluorocyclobutyl)methyl]-1H-pyrazol-4-yl}-8-methoxy-2-(trifluoromethyl)-4H-pyrimido[1,2-b]pyridazin-4-one;
3-{1-[(3,3-difluorocyclobutyl)methyl]-1H-pyrazol-4-yl}-8-methyl-2-(trifluoromethyl)-4H-pyrimido[1,2-b]pyridazin-4-one;
3-fluoro-1-methyl-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione;
4-oxo-3-(1-(2,2,3,3,3-pentafluoropropyl)-1H-pyrazol-4-yl)-2-(trifluoromethyl)-4H-pyrido[1,2-a]pyrimidine-8-carbonitrile;
4-oxo-3-(1-(2,2,3,3,3-pentafluoropropyl)-1H-pyrazol-4-yl)-2-(trifluoromethyl)-4H-pyrido[1,2-a]pyrimidine-8-carboxylic acid;
4-oxo-3-(4-(2,2,2-trifluoroethoxy)phenyl)-2-(trifluoromethyl)-4H-pyrido[1,2-a]pyrimidine-8-carbonitrile;
4-oxo-3-(4-(2,2,2-trifluoroethoxy)phenyl)-2-(trifluoromethyl)-4H-pyrido[1,2-a]pyrimidine-8-carboxamide;
4-oxo-3-(4-(2,2,2-trifluoroethoxy)phenyl)-2-(trifluoromethyl)-4H-pyrido[1,2-a]pyrimidine-8-carboxylic acid;
4-oxo-3-[1-(2,2,3,3,3-pentafluoropropyl)-1H-pyrazol-4-yl]-2-(trifluoromethyl)-4H-pyrido[1,2-a]pyrimidine-7-carbonitrile;
7-(1-(2,2,3,3,3-pentafluoropropyl)-1H-pyrazol-4-yl)-8-(trifluoromethyl)-2H-pyrimido[1,2-a]pyrimidine-2,6(1H)-dione;
7-(3-fluoro-4-(2,2,2-trifluoroethoxy)phenyl)-8-(trifluoromethyl)-2H-pyrimido[1,2-a]pyrimidine-2,6(1H)-dione;
7-(4-(2,2,2-trifluoroethoxy)phenyl)-8-(trifluoromethyl)-2H-pyrimido[1,2-a]pyrimidine-2,6(1H)-dione;
7-(4-(2-fluoroethoxy)phenyl)-8-(trifluoromethyl)-2H-pyrimido[1,2-a]pyrimidine-2,6(1H)-dione;
7-(methoxymethyl)-3-[1-(2,2,3,3,3-pentafluoropropyl)-1H-pyrazol-4-yl]-2-(trifluoromethyl)-4H-pyrido[1,2-a]pyrimidin-4-one;
7,8-dimethyl-2-(trifluoromethyl)-3-[1-(3,3,3-trifluoropropyl)-1H-pyrazol-4-yl]-4H-pyrimido[1,2-b]pyridazin-4-one;
7,8-dimethyl-3-[1-(2,2,3,3,3-pentafluoropropyl)-1H-pyrazol-4-yl]-2-(trifluoromethyl)-4H-pyrimido[1,2-b]pyridazin-4-one;
7,9-dimethyl-3-[1-(2,2,3,3,3-pentafluoropropyl)-1H-pyrazol-4-yl]-2-(trifluoromethyl)-4H-pyrazino[1,2-a]pyrimidin-4-one;

7-chloro-2-(trifluoromethyl)-3-[1-(3,3,3-trifluoropropyl)-1H-pyrazol-4-yl]-4H-pyrido[1,2-a]pyrimidin-4-one;
7-chloro-3-[1-(2,2,3,3,3-pentafluoropropyl)-1H-pyrazol-4-yl]-2-(trifluoromethyl)-4H-pyrazino[1,2-a]pyrimidin-4-one;
7-chloro-3-[1-(2,2,3,3,3-pentafluoropropyl)-1H-pyrazol-4-yl]-2-(trifluoromethyl)-4H-pyrido[1,2-a]pyrimidin-4-one;
7-chloro-8-methoxy-2-(trifluoromethyl)-3-[1-(3,3,3-trifluoropropyl)-1H-pyrazol-4-yl]-4H-pyrido[1,2-a]pyrimidin-4-one;
7-chloro-8-methoxy-3-[1-(2,2,3,3,3-pentafluoropropyl)-1H-pyrazol-4-yl]-2-(trifluoromethyl)-4H-[1,3]diazino[1,2-a]pyrimidin-4-one;
7-chloro-8-methoxy-3-[1-(2,2,3,3,3-pentafluoropropyl)-1H-pyrazol-4-yl]-2-(trifluoromethyl)-4H-pyrido[1,2-a]pyrimidin-4-one;
7-chloro-8-methyl-2-(trifluoromethyl)-3-[1-(3,3,3-trifluoropropyl)-1H-pyrazol-4-yl]-4H-pyrido[1,2-a]pyrimidin-4-one;
7-chloro-8-methyl-3-[1-(2,2,3,3,3-pentafluoropropyl)-1H-pyrazol-4-yl]-2-(trifluoromethyl)-4H-pyrido[1,2-a]pyrimidin-4-one;
7-chloro-8-methyl-3-[4-(2,2,2-trifluoroethoxy)phenyl]-2-(trifluoromethyl)-4H-pyrido[1,2-a]pyrimidin-4-one;
7-cyclopropyl-2-(trifluoromethyl)-3-[1-(3,3,3-trifluoropropyl)-1H-pyrazol-4-yl]-4H-pyrido[1,2-a]pyrimidin-4-one;
7-cyclopropyl-3-[1-(2,2,3,3,3-pentafluoropropyl)-1H-pyrazol-4-yl]-2-(trifluoromethyl)-4H-pyrido[1,2-a]pyrimidin-4-one;
7-fluoro-2-(trifluoromethyl)-3-[1-(3,3,3-trifluoropropyl)-1H-pyrazol-4-yl]-4H-pyrido[1,2-a]pyrimidin-4-one;
7-fluoro-3-[1-(2,2,3,3,3-pentafluoropropyl)-1H-pyrazol-4-yl]-2-(trifluoromethyl)-4H-pyrido[1,2-a]pyrimidin-4-one;
7-fluoro-8-hydroxy-3-[1-(2,2,3,3,3-pentafluoropropyl)-1H-pyrazol-4-yl]-2-(trifluoromethyl)-4H-pyrido[1,2-a]pyrimidin-4-one;
7-fluoro-8-methoxy-2-(trifluoromethyl)-3-[1-(3,3,3-trifluoropropyl)-1H-pyrazol-4-yl]-4H-pyrido[1,2-a]pyrimidin-4-one;
7-fluoro-8-methoxy-3-[1-(2,2,3,3,3-pentafluoropropyl)-1H-pyrazol-4-yl]-2-(trifluoromethyl)-4H-[1,3]diazino[1,2-a]pyrimidin-4-one;
7-fluoro-8-methoxy-3-[1-(2,2,3,3,3-pentafluoropropyl)-1H-pyrazol-4-yl]-2-(trifluoromethyl)-4H-pyrido[1,2-a]pyrimidin-4-one;
7-fluoro-8-methoxy-3-[4-(2,2,2-trifluoroethoxy)phenyl]-2-(trifluoromethyl)-4H-pyrido[1,2-a]pyrimidin-4-one;
7-fluoro-8-methyl-3-[1-(2,2,3,3,3-pentafluoropropyl)-1H-pyrazol-4-yl]-2-(trifluoromethyl)-4H-pyrido[1,2-a]pyrimidin-4-one;
7-methoxy-3-[1-(2,2,3,3,3-pentafluoropropyl)-1H-pyrazol-4-yl]-2-(trifluoromethyl)-4H-[1,3]diazino[1,2-a]pyrimidin-4-one;
7-methoxy-3-[1-(2,2,3,3,3-pentafluoropropyl)-1H-pyrazol-4-yl]-2-(trifluoromethyl)-4H-pyrazino[1,2-a]pyrimidin-4-one;
7-methoxy-3-[1-(2,2,3,3,3-pentafluoropropyl)-1H-pyrazol-4-yl]-2-(trifluoromethyl)-4H-pyrido[1,2-a]pyrimidin-4-one;
7-methyl-2-(trifluoromethyl)-3-[1-(3,3,3-trifluoropropyl)-1H-pyrazol-4-yl]-4H-pyrimido[1,2-b]pyridazin-4-one;
7-methyl-3-[1-(2,2,3,3,3-pentafluoropropyl)-1H-pyrazol-4-yl]-2-(trifluoromethyl)-4H-[1,3]diazino[1,2-a]pyrimidin-4-one;
7-methyl-3-[1-(2,2,3,3,3-pentafluoropropyl)-1H-pyrazol-4-yl]-2-(trifluoromethyl)-4H-pyrazino[1,2-a]pyrimidin-4-one;
7-methyl-3-[1-(2,2,3,3,3-pentafluoropropyl)-1H-pyrazol-4-yl]-2-(trifluoromethyl)-4H-pyrido[1,2-a]pyrimidin-4-one;
7-methyl-3-[1-(2,2,3,3,3-pentafluoropropyl)-1H-pyrazol-4-yl]-2-(trifluoromethyl)-4H-pyrimido[1,2-b]pyridazin-4-one;
8-((1R)-1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one;
8-((1R)-1-hydroxyethyl)-3-(4-(2,2,2-trifluoroethoxy)phenyl)-2-(trifluoromethyl)-4H-pyrido[1,2-a]pyrimidin-4-one;
8-((1S)-1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one;
8-((1S)-1-hydroxyethyl)-3-(4-(2,2,2-trifluoroethoxy)phenyl)-2-(trifluoromethyl)-4H-pyrido[1,2-a]pyrimidin-4-one;
8-((dimethylamino)methyl)-3-(1-(2,2,3,3,3-pentafluoropropyl)-1H-pyrazol-4-yl)-2-(trifluoromethyl)-4H-pyrido[1,2-a]pyrimidin-4-one;
8-(methyloxy-$d_3$)-2-(trifluoromethyl)-3-(1-(3,3,3-trifluoropropyl)-1H-pyrazol-4-yl)-4H-pyrido[1,2-a]pyrimidin-4-one;
8-((methylsulfanyl)methoxy)-3-(4-(2,2,2-trifluoroethoxy)phenyl)-2-(trifluoromethyl)-4H-pyrido[1,2-a]pyrimidin-4-one;
8-((R)-ethylsulfinyl)-3-(4-(2,2,2-trifluoroethoxy)phenyl)-2-(trifluoromethyl)-4H-pyrido[1,2-a]pyrimidin-4-one;
8-((R)-methylsulfinyl)-3-(1-(2,2,3,3,3-pentafluoropropyl)-1H-pyrazol-4-yl)-2-(trifluoromethyl)-4H-pyrido[1,2-a]pyrimidin-4-one;
8-((R)-methylsulfinyl)-3-(4-(2,2,2-trifluoroethoxy)phenyl)-2-(trifluoromethyl)-4H-pyrido[1,2-a]pyrimidin-4-one;
8-((S)-ethylsulfinyl)-3-(4-(2,2,2-trifluoroethoxy)phenyl)-2-(trifluoromethyl)-4H-pyrido[1,2-a]pyrimidin-4-one;
8-((S)-methylsulfinyl)-3-(1-(2,2,3,3,3-pentafluoropropyl)-1H-pyrazol-4-yl)-2-(trifluoromethyl)-4H-pyrido[1,2-a]pyrimidin-4-one;
8-((S)-methylsulfinyl)-3-(4-(2,2,2-trifluoroethoxy)phenyl)-2-(trifluoromethyl)-4H-pyrido[1,2-a]pyrimidin-4-one;
8-(1,3-oxazol-2-yl)-3-(4-(2,2,2-trifluoroethoxy)phenyl)-2-(trifluoromethyl)-4H-pyrido[1,2-a]pyrimidin-4-one;
8-(1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one;
8-(1-hydroxyethyl)-3-(4-(2,2,2-trifluoroethoxy)phenyl)-2-(trifluoromethyl)-4H-pyrido[1,2-a]pyrimidin-4-one;
8-(2-hydroxypropan-2-yl)-3-[1-(2,2,3,3,3-pentafluoropropyl)-1H-pyrazol-4-yl]-2-(trifluoromethyl)-4H-pyrido[1,2-a]pyrimidin-4-one;
8-(2-methyl-2-oxetanyl)-3-(4-(2,2,2-trifluoroethoxy)phenyl)-2-(trifluoromethyl)-4H-pyrido[1,2-a]pyrimidin-4-one;
8-(2-propanyl)-3-(4-(2,2,2-trifluoroethoxy)phenyl)-2-(trifluoromethyl)-4H-pyrido[1,2-a]pyrimidin-4-one;
8-(3-azetidinyl)-3-(4-(2,2,2-trifluoroethoxy)phenyl)-2-(trifluoromethyl)-4H-pyrido[1,2-a]pyrimidin-4-one;
8-(aminomethyl)-3-(1-(2,2,3,3,3-pentafluoropropyl)-1H-pyrazol-4-yl)-2-(trifluoromethyl)-4H-pyrido[1,2-a]pyrimidin-4-one;
8-(1-azetidinyl)-3-(1-(2,2,3,3,3-pentafluoropropyl)-1H-pyrazol-4-yl)-2-(trifluoromethyl)-4H-pyrido[1,2-a]pyrimidin-4-one;

8-(chloromethoxy)-3-[1-(2,2,3,3,3-pentafluoropropyl)-1H-pyrazol-4-yl]-2-(trifluoromethyl)-4H-pyrido[1,2-a]pyrimidin-4-one;
8-(chloromethoxy)-3-[1-(2,2,3,3,3-pentafluoropropyl)-1H-pyrazol-4-yl]-2-(trifluoromethyl)-4H-pyrimido[1,2-b]pyridazin-4-one;
8-(difluoromethoxy)-3-(4-(2,2,2-trifluoroethoxy)phenyl)-2-(trifluoromethyl)-4H-pyrido[1,2-a]pyrimidin-4-one;
8-(difluoromethyl)-3-(4-(2,2,2-trifluoroethoxy)phenyl)-2-(trifluoromethyl)-4H-pyrido[1,2-a]pyrimidin-4-one;
8-(dimethylamino)-3-(1-(2,2,3,3,3-pentafluoropropyl)-1H-pyrazol-4-yl)-2-(trifluoromethyl)-4H-pyrido[1,2-a]pyrimidin-4-one;
8-(dimethylamino)-3-(4-(2,2,2-trifluoroethoxy)phenyl)-2-(trifluoromethyl)-4H-pyrido[1,2-a]pyrimidin-4-one;
8-(ethylsulfinyl)-3-(4-(2,2,2-trifluoroethoxy)phenyl)-2-(trifluoromethyl)-4H-pyrido[1,2-a]pyrimidin-4-one;
8-(fluoromethoxy)-2-(trifluoromethyl)-3-(1-(3,3,3-trifluoropropyl)-1H-pyrazol-4-yl)-4H-pyrido[1,2-a]pyrimidin-4-one;
8-(fluoromethoxy)-3-(4-(2,2,2-trifluoroethoxy)phenyl)-2-(trifluoromethyl)-4H-pyrido[1,2-a]pyrimidin-4-one;
8-(fluoromethoxy)-3-[1-(2,2,3,3,3-pentafluoropropyl)-1H-pyrazol-4-yl]-2-(trifluoromethyl)-4H-pyrido[1,2-a]pyrimidin-4-one;
8-(fluoromethoxy)-3-[1-(2,2,3,3,3-pentafluoropropyl)-1H-pyrazol-4-yl]-2-(trifluoromethyl)-4H-pyrimido[1,2-b]pyridazin-4-one;
8-(fluoromethyl)-3-(1-(2,2,3,3,3-pentafluoropropyl)-1H-pyrazol-4-yl)-2-(trifluoromethyl)-4H-pyrido[1,2-a]pyrimidin-4-one;
8-(fluoromethyl)-3-(4-(2,2,2-trifluoroethoxy)phenyl)-2-(trifluoromethyl)-4H-pyrido[1,2-a]pyrimidin-4-one;
8-(hydroxymethyl)-3-(1-(2,2,3,3,3-pentafluoropropyl)-1H-pyrazol-4-yl)-2-(trifluoromethyl)-4H-pyrido[1,2-a]pyrimidin-4-one;
8-(hydroxymethyl)-3-(4-(2,2,2-trifluoroethoxy)phenyl)-2-(trifluoromethyl)-4H-pyrido[1,2-a]pyrimidin-4-one;
8-(methoxymethyl)-3-[1-(2,2,3,3,3-pentafluoropropyl)-1H-pyrazol-4-yl]-2-(trifluoromethyl)-4H-pyrido[1,2-a]pyrimidin-4-one;
8-(methylamino)-3-(1-(2,2,3,3,3-pentafluoropropyl)-1H-pyrazol-4-yl)-2-(trifluoromethyl)-4H-pyrido[1,2-a]pyrimidin-4-one;
8-(methylamino)-3-(4-(2,2,2-trifluoroethoxy)phenyl)-2-(trifluoromethyl)-4H-pyrido[1,2-a]pyrimidin-4-one;
8-(methylamino)-3-(4-(2,2,2-trifluoroethoxy)phenyl)-2-(trifluoromethyl)-4H-pyrimido[1,2-a]pyrimidin-4-one;
8-(methyl-$d_3$)-3-(4-(2,2,2-trifluoroethoxy)phenyl)-2-(trifluoromethyl)-4H-pyrido[1,2-a]pyrimidin-4-one;
8-(methyloxy-$d_3$)-3-(1-(2,2,3,3,3-pentafluoropropyl)-1H-pyrazol-4-yl)-2-(trifluoromethyl)-4H-pyrido[1,2-a]pyrimidin-4-one;
8-(methyloxy-$d_3$)-3-(1-(2,2,3,3,3-pentafluoropropyl)-1H-pyrazol-4-yl)-2-(trifluoromethyl)-4H-pyrimido[1,2-a]pyrimidin-4-one;
8-(methyloxy-$d_3$)-3-(1-(4,4,4-trifluorobutyl)-1H-pyrazol-4-yl)-2-(trifluoromethyl)-4H-pyrido[1,2-a]pyrimidin-4-one;
8-(methyloxy-$d_3$)-3-(4-(2,2,2-trifluoroethoxy)phenyl)-2-(trifluoromethyl)-4H-pyrido[1,2-a]pyrimidin-4-one;
8-(methyloxy-$d_3$)-3-(4-(2,2,2-trifluoroethoxy)phenyl)-2-(trifluoromethyl)-4H-pyrimido[1,2-a]pyrimidin-4-one;
8-(methyloxy-$d_3$)-3-(6-(2,2,2-trifluoroethoxy)-3-pyridinyl)-2-(trifluoromethyl)-4H-pyrido[1,2-a]pyrimidin-4-one;
8-(methylsulfanyl)-3-(1-(2,2,3,3,3-pentafluoropropyl)-1H-pyrazol-4-yl)-2-(trifluoromethyl)-4H-pyrido[1,2-a]pyrimidin-4-one;
8-(methylsulfanyl)-3-(4-(2,2,2-trifluoroethoxy)phenyl)-2-(trifluoromethyl)-4H-pyrido[1,2-a]pyrimidin-4-one;
8-(methylsulfinyl)-3-(1-(2,2,3,3,3-pentafluoropropyl)-1H-pyrazol-4-yl)-2-(trifluoromethyl)-4H-pyrido[1,2-a]pyrimidin-4-one;
8-(methylsulfinyl)-3-(4-(2,2,2-trifluoroethoxy)phenyl)-2-(trifluoromethyl)-4H-pyrido[1,2-a]pyrimidin-4-one;
8-(methylsulfonyl)-3-(4-(2,2,2-trifluoroethoxy)phenyl)-2-(trifluoromethyl)-4H-pyrido[1,2-a]pyrimidin-4-one;
8-acetyl-3-(4-(2,2,2-trifluoroethoxy)phenyl)-2-(trifluoromethyl)-4H-pyrido[1,2-a]pyrimidin-4-one;
8-amino-3-(1-(2,2,3,3,3-pentafluoropropyl)-1H-pyrazol-4-yl)-2-(trifluoromethyl)-4H-pyrido[1,2-a]pyrimidin-4-one;
8-amino-3-(4-(2,2,2-trifluoroethoxy)phenyl)-2-(trifluoromethyl)-4H-pyrido[1,2-a]pyrimidin-4-one;
8-amino-3-(4-(2,2,2-trifluoroethoxy)phenyl)-2-(trifluoromethyl)-4H-pyrimido[1,2-a]pyrimidin-4-one;
8-chloro-3-(1-(2,2,3,3,3-pentafluoropropyl)-1H-pyrazol-4-yl)-2-(trifluoromethyl)-4H-pyrido[1,2-a]pyrimidin-4-one;
8-chloro-3-(4-(2,2,2-trifluoroethoxy)phenyl)-2-(trifluoromethyl)-4H-pyrido[1,2-a]pyrimidin-4-one;
8-cyclopropyl-3-(4-(2,2,2-trifluoroethoxy)phenyl)-2-(trifluoromethyl)-4H-pyrido[1,2-a]pyrimidin-4-one;
8-cyclopropyl-3-(1-(2,2,3,3,3-pentafluoropropyl)-1H-pyrazol-4-yl)-2-(trifluoromethyl)-4H-pyrido[1,2-a]pyrimidin-4-one;
8-ethenyl-3-(4-(2,2,2-trifluoroethoxy)phenyl)-2-(trifluoromethyl)-4H-pyrido[1,2-a]pyrimidin-4-one;
8-ethoxy-3-(4-(2,2,2-trifluoroethoxy)phenyl)-2-(trifluoromethyl)-4H-pyrido[1,2-a]pyrimidin-4-one;
8-ethyl-3-(4-(2,2,2-trifluoroethoxy)phenyl)-2-(trifluoromethyl)-4H-pyrido[1,2-a]pyrimidin-4-one;
8-fluoro-3-(4-(2,2,2-trifluoroethoxy)phenyl)-2-(trifluoromethyl)-4H-pyrido[1,2-a]pyrimidin-4-one;
8-hydroxy-3-[1-(2,2,3,3,3-pentafluoropropyl)-1H-pyrazol-4-yl]-2-(trifluoromethyl)-4H-pyrimido[1,2-b]pyridazin-4-one;
8-methoxy-2-(trifluoromethyl)-3-(1-(3-(trifluoromethyl)phenyl)-1H-pyrazol-4-yl)-4H-pyrido[1,2-a]pyrimidin-4-one;
8-methoxy-2-(trifluoromethyl)-3-(1-(3,3,3-trifluoropropyl)-1H-imidazol-4-yl)-4H-pyrido[1,2-a]pyrimidin-4-one;
8-methoxy-2-(trifluoromethyl)-3-(1-(3,3,3-trifluoropropyl)-1H-pyrazol-4-yl)-4H-pyrido[1,2-a]pyrimidin-4-one;
8-methoxy-2-(trifluoromethyl)-3-(1-(3,3,3-trifluoropropyl)-1H-pyrazol-4-yl)-4H-pyrimido[1,2-a]pyrimidin-4-one;
8-methoxy-2-(trifluoromethyl)-3-(1-(4-(trifluoromethyl)phenyl)-1H-pyrazol-4-yl)-4H-pyrido[1,2-a]pyrimidin-4-one;
8-methoxy-2-(trifluoromethyl)-3-(4-(3,3,3-trifluoropropyl)phenyl)-4H-pyrido[1,2-a]pyrimidin-4-one;
8-methoxy-2-(trifluoromethyl)-3-[1-(3,3,3-trifluoropropyl)-1H-pyrazol-4-yl]-4H-pyrimido[1,2-b]pyridazin-4-one;
8-methoxy-2-(trifluoromethyl)-3-[3-(3,3,3-trifluoropropyl)-1,2-oxazol-5-yl]-4H-pyrido[1,2-a]pyrimidin-4-one;
8-methoxy-2-(trifluoromethyl)-3-[4-(3,3,3-trifluoropropyl)-1H-imidazol-1-yl]-4H-pyrido[1,2-a]pyrimidin-4-one;
8-methoxy-2-(trifluoromethyl)-3-[5-(3,3,3-trifluoropropyl)-1,3-thiazol-2-yl]-4H-pyrido[1,2-a]pyrimidin-4-one;
8-methoxy-2-methyl-3-(4-(2,2,2-trifluoroethoxy)phenyl)-4H-pyrido[1,2-a]pyrimidin-4-one;

8-methoxy-3-(1-(2,2,2-trifluoroethyl)-1H-pyrazol-4-yl)-2-(trifluoromethyl)-4H-pyrido[1,2-a]pyrimidin-4-one;

8-methoxy-3-(1-(2,2,3,3,3-pentafluoropropyl)-1H-pyrazol-4-yl)-2-(trifluoromethyl)-4H-pyrido[1,2-a]pyrimidin-4-one;

8-methoxy-3-(1-(2,2,3,3,3-pentafluoropropyl)-1H-pyrazol-4-yl)-2-(trifluoromethyl)-4H-pyrimido[1,2-a]pyrimidin-4-one;

8-methoxy-3-(1-(4,4,4-trifluorobutyl)-1H-pyrazol-4-yl)-2-(trifluoromethyl)-4H-pyrido[1,2-a]pyrimidin-4-one;

8-methoxy-3-(1-(4,4,4-trifluorobutyl)-1H-pyrazol-4-yl)-2-(trifluoromethyl)-4H-pyrimido[1,2-a]pyrimidin-4-one;

8-methoxy-3-(1-phenyl-1H-pyrazol-3-yl)-2-(trifluoromethyl)-4H-pyrido[1,2-a]pyrimidin-4-one;

8-methoxy-3-(1-phenyl-1H-pyrazol-4-yl)-2-(trifluoromethyl)-4H-pyrido[1,2-a]pyrimidin-4-one;

8-methoxy-3-(1-propyl-1H-pyrazol-4-yl)-2-(trifluoromethyl)-4H-pyrido[1,2-a]pyrimidin-4-one;

8-methoxy-3-(2-methyl-4-(2,2,2-trifluoroethoxy)phenyl)-2-(trifluoromethyl)-4H-pyrido[1,2-a]pyrimidin-4-one;

8-methoxy-3-(2-phenyl-1,3-oxazol-5-yl)-2-(trifluoromethyl)-4H-pyrido[1,2-a]pyrimidin-4-one;

8-methoxy-3-(3-phenyl-1,2-oxazol-5-yl)-2-(trifluoromethyl)-4H-pyrido[1,2-a]pyrimidin-4-one;

8-methoxy-3-(4-(2,2,2-trifluoroethoxy)-2-(trifluoromethyl)phenyl)-2-(trifluoromethyl)-4H-pyrido[1,2-a]pyrimidin-4-one;

8-methoxy-3-(4-(2,2,2-trifluoroethoxy)phenyl)-2-(trifluoromethyl)-4H-pyrido[1,2-a]pyrimidin-4-one;

8-methoxy-3-(4-(2,2,2-trifluoroethoxy)phenyl)-2-(trifluoromethyl)-4H-pyrimido[1,2-a]pyrimidin-4-one;

8-methoxy-3-(4-(2,2,3,3,3-pentafluoropropoxy)phenyl)-2-(trifluoromethyl)-4H-pyrido[1,2-a]pyrimidin-4-one;

8-methoxy-3-(4-(2,2,3,3-tetrafluoropropoxy)phenyl)-2-(trifluoromethyl)-4H-pyrido[1,2-a]pyrimidin-4-one;

8-methoxy-3-(4-(trifluoromethoxy)phenyl)-2-(trifluoromethyl)-4H-pyrido[1,2-a]pyrimidin-4-one;

8-methoxy-3-(4-(trifluoromethoxy)phenyl)-2-(trifluoromethyl)-4H-pyrimido[1,2-a]pyrimidin-4-one;

8-methoxy-3-(4-propylphenyl)-2-(trifluoromethyl)-4H-pyrido[1,2-a]pyrimidin-4-one;

8-methoxy-3-(5-propyl-1,2-oxazol-3-yl)-2-(trifluoromethyl)-4H-pyrido[1,2-a]pyrimidin-4-one;

8-methoxy-3-(6-(2,2,2-trifluoroethoxy)-3-pyridinyl)-2-(trifluoromethyl)-4H-pyrido[1,2-a]pyrimidin-4-one;

8-methoxy-3-(6-(2,2,2-trifluoroethoxy)-3-pyridinyl)-2-(trifluoromethyl)-4H-pyrimido[1,2-a]pyrimidin-4-one;

8-methoxy-3-(6-propyl-3-pyridinyl)-2-(trifluoromethyl)-4H-pyrido[1,2-a]pyrimidin-4-one;

8-methoxy-3-[1-(2,2,3,3,3-pentafluoropropyl)-1H-1,2,3-triazol-4-yl]-2-(trifluoromethyl)-4H-pyrido[1,2-a]pyrimidin-4-one;

8-methoxy-3-[1-(2,2,3,3,3-pentafluoropropyl)-1H-pyrazol-3-yl]-2-(trifluoromethyl)-4H-pyrido[1,2-a]pyrimidin-4-one;

8-methoxy-3-[1-(2,2,3,3,3-pentafluoropropyl)-1H-pyrazol-4-yl]-2-(trifluoromethyl)-4H-[1,3]diazino[1,6-a]pyrimidin-4-one;

8-methoxy-3-[1-(2,2,3,3,3-pentafluoropropyl)-1H-pyrazol-4-yl]-2-(trifluoromethyl)-4H-pyrimido[1,2-b]pyridazin-4-one;

8-methoxy-3-[2-(2,2,2-trifluoroethoxy)-1,3-thiazol-5-yl]-2-(trifluoromethyl)-4H-pyrido[1,2-a]pyrimidin-4-one;

8-methoxy-3-[2-(2,2,2-trifluoroethoxy)pyrimidin-5-yl]-2-(trifluoromethyl)-4H-[1,3]diazino[1,2-a]pyrimidin-4-one;

8-methoxy-3-[2-(2,2,2-trifluoroethoxy)pyrimidin-5-yl]-2-(trifluoromethyl)-4H-pyrido[1,2-a]pyrimidin-4-one;

8-methoxy-3-[2-(2,2,2-trifluoroethoxy)pyrimidin-5-yl]-2-(trifluoromethyl)-4H-pyrimido[1,2-b]pyridazin-4-one;

8-methoxy-3-[2-(2,2,3,3,3-pentafluoropropoxy)pyrimidin-5-yl]-2-(trifluoromethyl)-4H-pyrido[1,2-a]pyrimidin-4-one;

8-methoxy-3-[3-(2,2,3,3,3-pentafluoropropyl)-1,2-oxazol-5-yl]-2-(trifluoromethyl)-4H-pyrido[1,2-a]pyrimidin-4-one;

8-methoxy-3-[4-(2,2,2-trifluoroethoxy)-1,3-thiazol-2-yl]-2-(trifluoromethyl)-4H-pyrido[1,2-a]pyrimidin-4-one;

8-methoxy-3-[5-(2,2,2-trifluoroethoxy)-1,3-thiazol-2-yl]-2-(trifluoromethyl)-4H-pyrido[1,2-a]pyrimidin-4-one;

8-methoxy-3-{1-[(oxetan-3-yl)methyl]-1H-pyrazol-4-yl}-2-(trifluoromethyl)-4H-pyrido[1,2-a]pyrimidin-4-one;

8-methoxy-6-methyl-3-[1-(2,2,3,3,3-pentafluoropropyl)-1H-pyrazol-4-yl]-2-(trifluoromethyl)-4H-pyrido[1,2-a]pyrimidin-4-one;

8-methyl-2-(trifluoromethyl)-3-[1-(3,3,3-trifluoropropyl)-1H-pyrazol-4-yl]-4H-pyrimido[1,2-b]pyridazin-4-one;

8-methyl-2-(trifluoromethyl)-3-[5-(3,3,3-trifluoropropyl)-1,2,4-oxadiazol-3-yl]-4H-pyrido[1,2-a]pyrimidin-4-one;

8-methyl-3-(4-(2,2,2-trifluoroethoxy)phenyl)-2-(trifluoromethyl)-4H-pyrido[1,2-a]pyrimidin-4-one;

8-methyl-3-[1-(2,2,3,3,3-pentafluoropropyl)-1H-pyrazol-4-yl]-2-(trifluoromethyl)-4H,6H,7H,8H,9H-pyrimido[1,2-a]pyrazin-4-one;

8-methyl-3-[1-(2,2,3,3,3-pentafluoropropyl)-1H-pyrazol-4-yl]-2-(trifluoromethyl)-4H-pyrimido[1,2-b]pyridazin-4-one;

8-methyl-3-[2-(2,2,2-trifluoroethoxy)pyrimidin-5-yl]-2-(trifluoromethyl)-4H-pyrimido[1,2-b]pyridazin-4-one;

8-methyl-3-[4-(2,2,2-trifluoroethoxy)phenyl]-2-(trifluoromethyl)-4H-pyrimido[1,2-b]pyridazin-4-one;

9-chloro-8-methoxy-3-[1-(2,2,3,3,3-pentafluoropropyl)-1H-pyrazol-4-yl]-2-(trifluoromethyl)-4H-pyrido[1,2-a]pyrimidin-4-one;

9-fluoro-8-methoxy-3-[1-(2,2,3,3,3-pentafluoropropyl)-1H-pyrazol-4-yl]-2-(trifluoromethyl)-4H-pyrido[1,2-a]pyrimidin-4-one;

9-methyl-3-[1-(2,2,3,3,3-pentafluoropropyl)-1H-pyrazol-4-yl]-2-(trifluoromethyl)-4H-pyrazino[1,2-a]pyrimidin-4-one;

methyl 4-oxo-3-(4-(2,2,2-trifluoroethoxy)phenyl)-2-(trifluoromethyl)-4H-pyrido[1,2-a]pyrimidine-8-carboxylate;

methyl(4-oxo-3-(1-(2,2,3,3,3-pentafluoropropyl)-1H-pyrazol-4-yl)-2-(trifluoromethyl)-4H-pyrido[1,2-a]pyrimidin-8-yl)carbamyl fluoride;

N-(4-oxo-3-(1-(2,2,3,3,3-pentafluoropropyl)-1H-pyrazol-4-yl)-2-(trifluoromethyl)-4H-pyrido[1,2-a]pyrimidin-8-yl)acetamide;

N-(4-oxo-3-(4-(2,2,2-trifluoroethoxy)phenyl)-2-(trifluoromethyl)-4H-pyrido[1,2-a]pyrimidin-8-yl)acetamide;

N,N-dimethyl-4-oxo-3-(4-(2,2,2-trifluoroethoxy)phenyl)-2-(trifluoromethyl)-4H-pyrido[1,2-a]pyrimidine-8-carboxamide;

N-ethyl-4-oxo-3-(4-(2,2,2-trifluoroethoxy)phenyl)-2-(trifluoromethyl)-4H-pyrido[1,2-a]pyrimidine-8-carboxamide;

N-methyl-4-oxo-3-(1-(2,2,3,3,3-pentafluoropropyl)-1H-pyrazol-4-yl)-2-(trifluoromethyl)-4H-pyrido[1,2-a]pyrimidine-8-carboxamide; or N-methyl-4-oxo-3-(4-(2,2,2-trifluoroethoxy)phenyl)-2-(trifluoromethyl)-4H-pyrido[1,2-a]pyrimidine-8-carboxamide.

Provided herein as Embodiment 91 is the compound according to Embodiment 1, or a tautomer thereof, or a pharmaceutically acceptable salt of said compound or said tautomer, wherein the compound is (2R)-2-(4-(8-methoxy-4-oxo-2-(trifluoromethyl)-4H-pyrimido[1,2-a]pyrimidin-3-yl)phenoxy)propanenitrile;

(2S)-2-(4-(8-methoxy-4-oxo-2-(trifluoromethyl)-4H-pyrido[1,2-a]pyrimidin-3-yl)phenoxy)propanenitrile;

2-(4-(8-methoxy-4-oxo-2-(trifluoromethyl)-4H-pyrido[1,2-a]pyrimidin-3-yl)phenoxy)-2-methylpropanenitrile;

2-(difluoromethyl)-8-methoxy-3-(4-(2,2,2-trifluoroethoxy)phenyl)-4H-pyrido[1,2-a]pyrimidin-4-one;

2-(fluoromethyl)-8-methoxy-3-(4-(2,2,2-trifluoroethoxy)phenyl)-4H-pyrido[1,2-a]pyrimidin-4-one;

2,8-dimethoxy-3-(4-(2,2,2-trifluoroethoxy)phenyl)-4H-pyrido[1,2-a]pyrimidin-4-one;

2-cyclopropyl-8-methoxy-3-(4-(2,2,2-trifluoroethoxy)phenyl)-4H-pyrido[1,2-a]pyrimidin-4-one;

2-ethoxy-8-methoxy-3-(4-(2,2,2-trifluoroethoxy)phenyl)-4H-pyrido[1,2-a]pyrimidin-4-one;

2-ethyl-8-methoxy-3-(4-(2,2,2-trifluoroethoxy)phenyl)-4H-pyrido[1,2-a]pyrimidin-4-one;

3-(1-(2,2,3,3,3-pentafluoropropyl)-1H-pyrazol-4-yl)-2-(trifluoromethyl)-4H-pyrido[1,2-a]pyrimidine-4,8(1H)-dione;

3-(1-(2,2-difluoropropyl)-1H-pyrazol-4-yl)-8-methoxy-2-(trifluoromethyl)-4H-pyrido[1,2-a]pyrimidin-4-one;

3-(2-fluoro-4-(2,2,2-trifluoroethoxy)phenyl)-8-methoxy-2-(trifluoromethyl)-4H-pyrido[1,2-a]pyrimidin-4-one;

3-(2-fluoro-4-(trifluoromethoxy)phenyl)-8-methoxy-2-(trifluoromethyl)-4H-pyrido[1,2-a]pyrimidin-4-one;

3-(3-fluoro-4-(2,2,2-trifluoroethoxy)phenyl)-8-methoxy-2-(trifluoromethyl)-4H-pyrido[1,2-a]pyrimidin-4-one;

3-(3-fluoro-4-(2,2,2-trifluoroethoxy)phenyl)-8-methoxy-2-(trifluoromethyl)-4H-pyrimido[1,2-a]pyrimidin-4-one;

3-(4-((2,2-difluorocyclopropyl)methoxy)phenyl)-8-methoxy-2-(trifluoromethyl)-4H-pyrido[1,2-a]pyrimidin-4-one;

3-(4-(2,2,2-trifluoroethoxy)phenyl)-2-(trifluoromethyl)-4H-pyrido[1,2-a]pyrimidin-4-one;

3-(4-(2,2,2-trifluoroethoxy)phenyl)-2-(trifluoromethyl)-4H-pyrido[1,2-a]pyrimidine-4,8(1H)-dione;

3-(4-(2,2-difluoroethoxy)-2-fluorophenyl)-8-methoxy-2-(trifluoromethyl)-4H-pyrido[1,2-a]pyrimidin-4-one;

3-(4-(2,2-difluoroethoxy)phenyl)-8-methoxy-2-(trifluoromethyl)-4H-pyrido[1,2-a]pyrimidin-4-one;

3-(4-(2,2-difluoropropoxy)phenyl)-8-methoxy-2-(trifluoromethyl)-4H-pyrido[1,2-a]pyrimidin-4-one;

3-(4-(2-fluoroethoxy)phenyl)-8-methoxy-2-(trifluoromethyl)-4H-pyrido[1,2-a]pyrimidin-4-one;

3-(4-(cyclopropylmethoxy)phenyl)-8-methoxy-2-(trifluoromethyl)-4H-pyrido[1,2-a]pyrimidin-4-one;

4-oxo-3-(1-(2,2,3,3,3-pentafluoropropyl)-1H-pyrazol-4-yl)-2-(trifluoromethyl)-4H-pyrido[1,2-a]pyrimidine-8-carbonitrile;

4-oxo-3-(4-(2,2,2-trifluoroethoxy)phenyl)-2-(trifluoromethyl)-4H-pyrido[1,2-a]pyrimidine-8-carboxamide;

7-(1-(2,2,3,3,3-pentafluoropropyl)-1H-pyrazol-4-yl)-8-(trifluoromethyl)-2H-pyrimido[1,2-a]pyrimidine-2,6(1H)-dione;

7-chloro-3-[1-(2,2,3,3,3-pentafluoropropyl)-1H-pyrazol-4-yl]-2-(trifluoromethyl)-4H-pyrido[1,2-a]pyrimidin-4-one;

7-chloro-8-methoxy-3-[1-(2,2,3,3,3-pentafluoropropyl)-1H-pyrazol-4-yl]-2-(trifluoromethyl)-4H-[1,3]diazino[1,2-a]pyrimidin-4-one;

7-fluoro-8-methoxy-3-[1-(2,2,3,3,3-pentafluoropropyl)-1H-pyrazol-4-yl]-2-(trifluoromethyl)-4H-pyrido[1,2-a]pyrimidin-4-one;

8-((1R)-1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one;

8-((1S)-1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one;

8-((dimethylamino)methyl)-3-(1-(2,2,3,3,3-pentafluoropropyl)-1H-pyrazol-4-yl)-2-(trifluoromethyl)-4H-pyrido[1,2-a]pyrimidin-4-one;

8-(aminomethyl)-3-(1-(2,2,3,3,3-pentafluoropropyl)-1H-pyrazol-4-yl)-2-(trifluoromethyl)-4H-pyrido[1,2-a]pyrimidin-4-one;

8-(dimethylamino)-3-(1-(2,2,3,3,3-pentafluoropropyl)-1H-pyrazol-4-yl)-2-(trifluoromethyl)-4H-pyrido[1,2-a]pyrimidin-4-one;

8-(fluoromethoxy)-3-[1-(2,2,3,3,3-pentafluoropropyl)-1H-pyrazol-4-yl]-2-(trifluoromethyl)-4H-pyrido[1,2-a]pyrimidin-4-one;

8-(fluoromethyl)-3-(4-(2,2,2-trifluoroethoxy)phenyl)-2-(trifluoromethyl)-4H-pyrido[1,2-a]pyrimidin-4-one;

8-(hydroxymethyl)-3-(1-(2,2,3,3,3-pentafluoropropyl)-1H-pyrazol-4-yl)-2-(trifluoromethyl)-4H-pyrido[1,2-a]pyrimidin-4-one;

8-(hydroxymethyl)-3-(4-(2,2,2-trifluoroethoxy)phenyl)-2-(trifluoromethyl)-4H-pyrido[1,2-a]pyrimidin-4-one;

8-(methoxymethyl)-3-[1-(2,2,3,3,3-pentafluoropropyl)-1H-pyrazol-4-yl]-2-(trifluoromethyl)-4H-pyrido[1,2-a]pyrimidin-4-one;

8-(methylamino)-3-(1-(2,2,3,3,3-pentafluoropropyl)-1H-pyrazol-4-yl)-2-(trifluoromethyl)-4H-pyrido[1,2-a]pyrimidin-4-one;

8-(methylamino)-3-(4-(2,2,2-trifluoroethoxy)phenyl)-2-(trifluoromethyl)-4H-pyrido[1,2-a]pyrimidin-4-one;

8-(methyloxy-$d_3$)-3-(1-(2,2,3,3,3-pentafluoropropyl)-1H-pyrazol-4-yl)-2-(trifluoromethyl)-4H-pyrido[1,2-a]pyrimidin-4-one;

8-(methyloxy-$d_3$)-3-(1-(2,2,3,3,3-pentafluoropropyl)-1H-pyrazol-4-yl)-2-(trifluoromethyl)-4H-pyrimido[1,2-a]pyrimidin-4-one;

8-(methyloxy-$d_3$)-3-(4-(2,2,2-trifluoroethoxy)phenyl)-2-(trifluoromethyl)-4H-pyrido[1,2-a]pyrimidin-4-one;

8-(methyloxy-$d_3$)-3-(4-(2,2,2-trifluoroethoxy)phenyl)-2-(trifluoromethyl)-4H-pyrimido[1,2-a]pyrimidin-4-one;

8-amino-3-(1-(2,2,3,3,3-pentafluoropropyl)-1H-pyrazol-4-yl)-2-(trifluoromethyl)-4H-pyrido[1,2-a]pyrimidin-4-one;

8-amino-3-(4-(2,2,2-trifluoroethoxy)phenyl)-2-(trifluoromethyl)-4H-pyrido[1,2-a]pyrimidin-4-one;

8-amino-3-(4-(2,2,2-trifluoroethoxy)phenyl)-2-(trifluoromethyl)-4H-pyrimido[1,2-a]pyrimidin-4-one;

8-chloro-3-(1-(2,2,3,3,3-pentafluoropropyl)-1H-pyrazol-4-yl)-2-(trifluoromethyl)-4H-pyrido[1,2-a]pyrimidin-4-one;

8-ethoxy-3-(4-(2,2,2-trifluoroethoxy)phenyl)-2-(trifluoromethyl)-4H-pyrido[1,2-a]pyrimidin-4-one;

8-methoxy-2-(trifluoromethyl)-3-(1-(3,3,3-trifluoropropyl)-1H-pyrazol-4-yl)-4H-pyrido[1,2-a]pyrimidin-4-one;

8-methoxy-3-(1-(2,2,3,3,3-pentafluoropropyl)-1H-pyrazol-4-yl)-2-(trifluoromethyl)-4H-pyrido[1,2-a]pyrimidin-4-one;

8-methoxy-3-(1-(2,2,3,3,3-pentafluoropropyl)-1H-pyrazol-4-yl)-2-(trifluoromethyl)-4H-pyrimido[1,2-a]pyrimidin-4-one;

8-methoxy-3-(1-(4,4,4-trifluorobutyl)-1H-pyrazol-4-yl)-2-(trifluoromethyl)-4H-pyrido[1,2-a]pyrimidin-4-one;

8-methoxy-3-(2-methyl-4-(2,2,2-trifluoroethoxy)phenyl)-2-(trifluoromethyl)-4H-pyrido[1,2-a]pyrimidin-4-one;

8-methoxy-3-(4-(2,2,2-trifluoroethoxy)phenyl)-2-(trifluoromethyl)-4H-pyrido[1,2-a]pyrimidin-4-one;

8-methoxy-3-(4-(2,2,2-trifluoroethoxy)phenyl)-2-(trifluoromethyl)-4H-pyrimido[1,2-a]pyrimidin-4-one;

8-methoxy-3-(4-(trifluoromethoxy)phenyl)-2-(trifluoromethyl)-4H-pyrimido[1,2-a]pyrimidin-4-one;

8-methoxy-3-(6-(2,2,2-trifluoroethoxy)-3-pyridinyl)-2-(trifluoromethyl)-4H-pyrido[1,2-a]pyrimidin-4-one;

8-methoxy-3-[1-(2,2,3,3,3-pentafluoropropyl)-1H-1,2,3-triazol-4-yl]-2-(trifluoromethyl)-4H-pyrido[1,2-a]pyrimidin-4-one;

8-methoxy-3-[1-(2,2,3,3,3-pentafluoropropyl)-1H-pyrazol-4-yl]-2-(trifluoromethyl)-4H-pyrimido[1,2-b]pyridazin-4-one;

8-methoxy-3-[2-(2,2,2-trifluoroethoxy)pyrimidin-5-yl]-2-(trifluoromethyl)-4H-pyrido[1,2-a]pyrimidin-4-one; or 8-methoxy-3-[2-(2,2,2-trifluoroethoxy)pyrimidin-5-yl]-2-(trifluoromethyl)-4H-pyrimido[1,2-b]pyridazin-4-one.

Provided herein as Embodiment 92 is the compound according to Embodiment 1, or a tautomer thereof, or a pharmaceutically acceptable salt of said compound or said tautomer, wherein the compound is 4-oxo-3-(1-(2,2,3,3,3-pentafluoropropyl)-1H-pyrazol-4-yl)-2-(trifluoromethyl)-4H-pyrido[1,2-a]pyrimidine-8-carbonitrile;

8-(methyloxy-$d_3$)-3-(1-(2,2,3,3,3-pentafluoropropyl)-1H-pyrazol-4-yl)-2-(trifluoromethyl)-4H-pyrido[1,2-a]pyrimidin-4-one;

8-amino-3-(4-(2,2,2-trifluoroethoxy)phenyl)-2-(trifluoromethyl)-4H-pyrido[1,2-a]pyrimidin-4-one;

8-methoxy-3-(1-(2,2,3,3,3-pentafluoropropyl)-1H-pyrazol-4-yl)-2-(trifluoromethyl)-4H-pyrido[1,2-a]pyrimidin-4-one;

8-methoxy-3-(1-(2,2,3,3,3-pentafluoropropyl)-1H-pyrazol-4-yl)-2-(trifluoromethyl)-4H-pyrimido[1,2-a]pyrimidin-4-one; or 8-methoxy-3-(4-(2,2,2-trifluoroethoxy)phenyl)-2-(trifluoromethyl)-4H-pyrido[1,2-a]pyrimidin-4-one.

Provided herein as Embodiment 93 is the compound according to Embodiment 1, or a pharmaceutically acceptable salt thereof, wherein the compound is

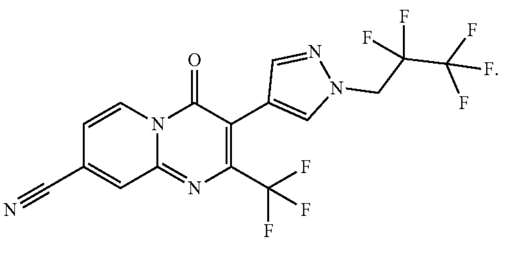 [SMILES: N#Cc1ccn2c(=O)c(-c3cnn(CC(F)(F)C(F)(F)F)c3)c(C(F)(F)F)nc2c1]

Provided herein as Embodiment 94 is the compound according to Embodiment 1, or a tautomer thereof, or a pharmaceutically acceptable salt of said compound or said tautomer, wherein the compound is

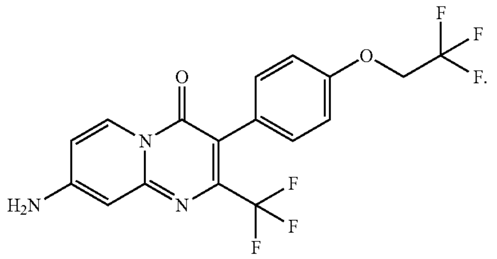 [SMILES: Nc1ccn2c(=O)c(-c3ccc(OCC(F)(F)F)cc3)c(C(F)(F)F)nc2c1]

Provided herein as Embodiment 95 is the compound according to Embodiment 1, or a pharmaceutically acceptable salt thereof, wherein the compound is

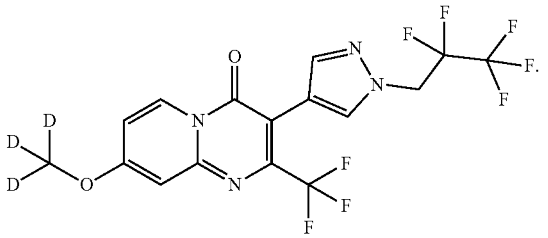 [SMILES: [2H]C([2H])([2H])Oc1ccn2c(=O)c(-c3cnn(CC(F)(F)C(F)(F)F)c3)c(C(F)(F)F)nc2c1]

Provided herein as Embodiment 96 is the compound according to Embodiment 1, or a pharmaceutically acceptable salt thereof, wherein the compound is

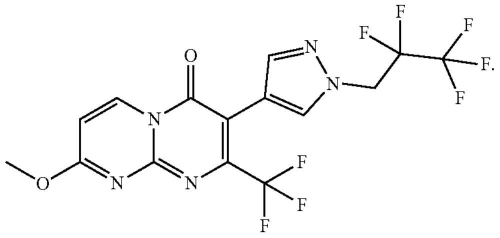 [SMILES: COc1ccn2c(=O)c(-c3cnn(CC(F)(F)C(F)(F)F)c3)c(C(F)(F)F)nc2n1]

Provided herein as Embodiment 97 is the compound according to Embodiment 1, or a pharmaceutically acceptable salt thereof, wherein the compound is

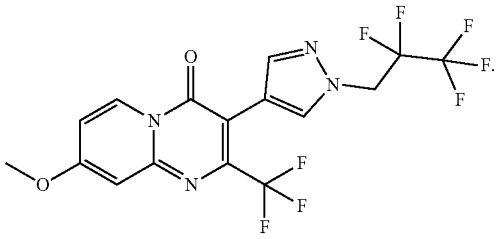 [SMILES: COc1ccn2c(=O)c(-c3cnn(CC(F)(F)C(F)(F)F)c3)c(C(F)(F)F)nc2c1]

Provided herein as Embodiment 98 is the compound according to Embodiment 1, or a pharmaceutically acceptable salt thereof, wherein the compound is

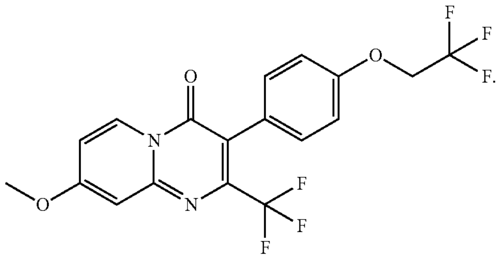 [SMILES: COc1ccn2c(=O)c(-c3ccc(OCC(F)(F)F)cc3)c(C(F)(F)F)nc2c1]

The foregoing merely summarizes certain aspects of this disclosure and is not intended, nor should it be construed, as limiting the disclosure in any way.

Formulation and Route of Administration

While it may be possible to administer a compound disclosed herein alone in the uses described, the compound administered normally will be present as an active ingredient in a pharmaceutical composition. Thus, in one embodiment, provided herein is a pharmaceutical composition comprising a compound disclosed herein in combination with one or more pharmaceutically acceptable excipients, such as diluents, carriers, adjuvants and the like, and, if desired, other active ingredients. See, e.g., Remington: The Science and Practice of Pharmacy, Volume I and Volume II, twenty-second edition, edited by Loyd V. Allen Jr., Philadelphia, PA, Pharmaceutical Press, 2012; Pharmaceutical Dosage Forms (Vol. 1-3), Liberman et al., Eds., Marcel Dekker, New York, NY, 1992; Handbook of Pharmaceutical Excipients (3rd Ed.), edited by Arthur H. Kibbe, American Pharmaceutical Association, Washington, 2000; Pharmaceutical Formulation: The Science and Technology of Dosage Forms (Drug Discovery), first edition, edited by GD Tovey, Royal Society of Chemistry, 2018. In one embodiment, a pharmaceutical composition comprises a therapeutically effective amount of a compound disclosed herein.

The compound(s) disclosed herein may be administered by any suitable route in the form of a pharmaceutical composition adapted to such a route and in a dose effective for the treatment intended. The compounds and compositions presented herein may, for example, be administered orally, mucosally, topically, transdermally, rectally, pulmonarily, parentally, intranasally, intravascularly, intravenously, intraarterial, intraperitoneally, intrathecally, subcutaneously, sublingually, intramuscularly, intrasternally, vaginally or by infusion techniques, in dosage unit formulations containing conventional pharmaceutically acceptable excipients.

The pharmaceutical composition may be in the form of, for example, a tablet, chewable tablet, minitablet, caplet, pill, bead, hard capsule, soft capsule, gelatin capsule, granule, powder, lozenge, patch, cream, gel, sachet, microneedle array, syrup, flavored syrup, juice, drop, injectable solution, emulsion, microemulsion, ointment, aerosol, aqueous suspension, or oily suspension. The pharmaceutical composition is typically made in the form of a dosage unit containing a particular amount of the active ingredient.

Provided herein as Embodiment 99 is a pharmaceutical composition comprising the compound according to any one of Embodiments 1-98, or a tautomer thereof, or a pharmaceutically acceptable salt of said compound or said tautomer, and a pharmaceutically acceptable excipient.

Provided herein as Embodiment 100 is a compound according to any one of Embodiments 1-98, or a tautomer thereof, or a pharmaceutically acceptable salt of said compound or said tautomer, or the pharmaceutical composition according to Embodiment 99 for use as a medicament.

Further, this disclosure encompasses pharmaceutical compositions comprising mixtures of any of the compounds disclosed herein and one or more other active agents disclosed herein.

Methods of Use

As discussed herein (see, section entitled "Definitions"), the compounds described herein are to be understood to include all stereoisomers, tautomers, or pharmaceutically acceptable salts of any of the foregoing or solvates of any of the foregoing. Accordingly, the scope of the methods and uses provided in the instant disclosure is to be understood to encompass also methods and uses employing all such forms.

Besides being useful for human treatment, the compounds provided herein may be useful for veterinary treatment of companion animals, exotic animals and farm animals, including mammals, rodents, and the like. For example, animals including horses, dogs, and cats may be treated with compounds provided herein.

Provided herein as Embodiment 101 is a compound according to any one of Embodiments 1-98, or a tautomer thereof, or a pharmaceutically acceptable salt of said compound or said tautomer, or the pharmaceutical composition according to Embodiment 99 for use in reducing the body weight.

Provided herein as Embodiment 102 is a compound according to any one of Embodiments 1-98, or a tautomer thereof, or a pharmaceutically acceptable salt of said compound or said tautomer, or the pharmaceutical composition according to Embodiment 99 for use in reducing the body-mass-index of a subject.

Provided herein as Embodiment 103 is a compound according to any one of Embodiments 1-98, or a tautomer thereof, or a pharmaceutically acceptable salt of said compound or said tautomer, or the pharmaceutical composition according to Embodiment 99 for use in treating a metabolic disorder.

Provided herein as Embodiment 104 is a compound according to any one of Embodiments 1-98, or a tautomer thereof, or a pharmaceutically acceptable salt of said compound or said tautomer, or the pharmaceutical composition according to Embodiment 99 for use in treating a cardiovascular disorder.

Provided herein as Embodiment 105 is a compound according to any one of Embodiments 1-98, or a tautomer thereof, or a pharmaceutically acceptable salt of said compound or said tautomer, or the pharmaceutical composition according to Embodiment 99 for use in treating diabetes.

Provided herein as Embodiment 106 is a compound according to any one of Embodiments 1-98, or a tautomer thereof, or a pharmaceutically acceptable salt of said compound or said tautomer, or the pharmaceutical composition according to Embodiment 99 for use in treating obesity.

Provided herein as Embodiment 107 is a compound according to any one of Embodiments 1-98, or a tautomer thereof, or a pharmaceutically acceptable salt of said compound or said tautomer, or the pharmaceutical composition according to Embodiment 99 for use in treating dyslipidemia.

Provided herein as Embodiment 108 is a compound according to any one of Embodiments 1-98, or a tautomer thereof, or a pharmaceutically acceptable salt of said compound or said tautomer, or the pharmaceutical composition according to Embodiment 99 for use in treating non-alcoholic steatohepatitis (NASH).

Provided herein as Embodiment 109 is a use of the compound according to any one of Embodiments 1-98, or a tautomer thereof, or a pharmaceutically acceptable salt of said compound or said tautomer, or the pharmaceutical composition according to Embodiment 99 in the preparation of a medicament for reducing the body weight or the body-mass-index of a subject.

Provided herein as Embodiment 110 is a use of the compound according to any one of Embodiments 1-98, or a tautomer thereof, or a pharmaceutically acceptable salt of said compound or said tautomer, or the pharmaceutical composition according to Embodiment 99 in the preparation of a medicament for treating a metabolic or a cardiovascular disorder.

Provided herein as Embodiment 111 is a use of the compound according to any one of Embodiments 1-98, or a tautomer thereof, or a pharmaceutically acceptable salt of said compound or said tautomer, or the pharmaceutical composition according to Embodiment 99 in the preparation of a medicament for treating diabetes, obesity, dyslipidemia, or non-alcoholic steatohepatitis (NASH).

Provided herein as Embodiment 112 is a method of reducing the body weight or the body-mass-index of a subject in need thereof, the method comprising administering to the subject a therapeutically effective amount of the compound according to any one of Embodiments 1-98, or a tautomer thereof, or a pharmaceutically acceptable salt of said compound or said tautomer.

Provided herein as Embodiment 113 is a method of treating a metabolic or cardiovascular disorder in a subject in need thereof, the method comprising administering to the subject a therapeutically effective amount of the compound according to any one of Embodiments 1-98, or a tautomer thereof, or a pharmaceutically acceptable salt of said compound or said tautomer.

Provided herein as Embodiment 114 is a method of treating diabetes, obesity, dyslipidemia, or non-alcoholic steatohepatitis (NASH) in a subject in need thereof, the method comprising administering to the subject a therapeutically effective amount of the compound according to any one of Embodiments 1-98, or a tautomer thereof, or a pharmaceutically acceptable salt of said compound or said tautomer.

Provided herein as a further embodiment is a method of reducing the waist-to-hip ratio (WHR) of a subject in need thereof, the method comprising administering to the subject a therapeutically effective amount of the compound according to any one of Embodiments 1-98, or a tautomer thereof, or a pharmaceutically acceptable salt of said compound or said tautomer. Provided herein as a further embodiment is use of the compound according to any one of Embodiments 1-98, or a tautomer thereof, or a pharmaceutically acceptable salt of said compound or said tautomer, or the pharmaceutical composition according to Embodiment 99 in the preparation of a medicament for reducing the waist-to-hip ratio (WHR) of a subject. Provided herein as a further embodiment is a compound according to any one of Embodiments 1-98, or a tautomer thereof, or a pharmaceutically acceptable salt of said compound or said tautomer, or the pharmaceutical composition according to Embodiment 99 for use in reducing the waist-to-hip ratio (WHR) of a subject.

Provided herein as a further embodiment is a method of lowering blood glucose in a subject in need thereof, the method comprising administering a therapeutically effective amount of the compound according to any one of Embodiments 1-98, or a tautomer thereof, or a pharmaceutically acceptable salt of said compound or said tautomer, or the pharmaceutical composition according to embodiment 99. In some embodiments, the method lowers blood glucose 10% or greater. In some embodiments, the method lowers blood glucose 15% or greater. In some embodiments, the method lowers blood glucose 20% or greater. In some embodiments, the method lowers blood glucose 25% or greater. In some embodiments, the method lowers blood glucose while having minimal effect on food intake/appetite. In some embodiments, the method lowers blood glucose while having no effect on food intake/appetite.

Provided herein as a further embodiment is a method of lowering insulin in a subject in need thereof, the method comprising administering a therapeutically effective amount of the compound according to any one of Embodiments 1-98, or a tautomer thereof, or a pharmaceutically acceptable salt of said compound or said tautomer, or the pharmaceutical composition according to embodiment 99. In some embodiments, the method lowers insulin 50% or greater. In some embodiments, the method lowers insulin 60% or greater. In some embodiments, the method lowers insulin 70% or greater. In some embodiments, the method lowers insulin 80% or greater. In some embodiments, the method lowers blood insulin 85% or greater. In some embodiments, the method lowers insulin 86% or greater. In some embodiments, the method lowers insulin 87% or greater. In some embodiments, the method lowers insulin 88% or greater. In some embodiments, the method lowers insulin 89% or greater. In some embodiments, the method lowers insulin 90% or greater. In some embodiments, the method lowers insulin 91% or greater. In some embodiments, the method lowers insulin while having minimal effect on food intake/appetite. In some embodiments, the method lowers insulin while having no effect on food intake/appetite.

Provided herein as a further embodiment is a method of lowering cholesterol in a subject in need thereof, the method comprising administering a therapeutically effective amount of the compound according to any one of Embodiments 1-98, or a tautomer thereof, or a pharmaceutically acceptable salt of said compound or said tautomer, or the pharmaceutical composition according to embodiment 99. In some embodiments, the method lowers cholesterol 10% or greater. In some embodiments, the method lowers cholesterol 15% or greater. In some embodiments, the method lowers cholesterol 20% or greater. In some embodiments, the method lowers cholesterol 30% or greater. In some embodiments, the method lowers cholesterol 31% or greater. In some embodiments, the method lowers cholesterol 32% or greater. In some embodiments, the method lowers cholesterol 33% or greater. In some embodiments, the method lowers cholesterol 34% or greater. In some embodiments, the method lowers cholesterol 35% or greater. In some embodiments, the method lowers blood cholesterol 36% or greater. In some embodiments, the method lowers cholesterol 37% or greater. In some embodiments, the method lowers cholesterol 38% or greater. In some embodiments, the method lowers cholesterol 39% or greater. In some embodiments, the method lowers cholesterol while having minimal effect on food intake/appetite. In some embodiments, the method lowers cholesterol while having no effect on food intake/appetite.

Provided herein as a further embodiment is a method of lowering LDL in a subject in need thereof, the method comprising administering a therapeutically effective amount of the compound according to any one of Embodiments 1-98, or a tautomer thereof, or a pharmaceutically acceptable salt of said compound or said tautomer, or the pharmaceutical composition according to embodiment 99. In some embodiments, the method lowers low-density lipoproteins (LDL) 10% or greater. In some embodiments, the method lowers LDL 20% or greater. In some embodiments, the method lowers LDL 21% or greater. In some embodiments, the method lowers LDL 22% or greater. In some embodiments, the method lowers LDL 23% or greater. In some embodiments, the method lowers LDL 24% or greater. In some embodiments, the method lowers LDL 25% or greater. In some embodiments, the method lowers LDL 26% or greater. In some embodiments, the method lowers blood LDL 27% or greater. In some embodiments, the method lowers LDL while having minimal effect on food intake/appetite. In some embodiments, the method lowers LDL while having no effect on food intake/appetite.

Provided herein as a further embodiment is a method of lowering triglycerides in a subject in need thereof, the method comprising administering a therapeutically effective amount of the compound according to any one of Embodiments 1-98, or a tautomer thereof, or a pharmaceutically acceptable salt of said compound or said tautomer, or the pharmaceutical composition according to embodiment 99. In some embodiments, the method lowers triglycerides 30% or greater. In some embodiments, the method lowers triglycerides 40% or greater. In some embodiments, the method lowers triglycerides 50% or greater. In some embodiments, the method lowers triglycerides 51% or greater. In some embodiments, the method lowers triglycerides 52% or greater. In some embodiments, the method lowers triglycerides 53% or greater. In some embodiments, the method lowers triglycerides 54% or greater. In some embodiments, the method lowers triglycerides 55% or greater. In some embodiments, the method lowers blood triglycerides 56% or greater. In some embodiments, the method lowers triglycerides 57% or greater. In some embodiments, the method lowers triglycerides while having minimal effect on food intake/appetite. In some embodiments, the method lowers triglycerides while having no effect on food intake/appetite Provided herein as a further embodiment is a method of lowering fat mass in a subject in need thereof, the method comprising administering a therapeutically effective amount of the compound according to any one of Embodiments 1-98, or a tautomer thereof, or a pharmaceutically acceptable salt of said compound or said tautomer, or the pharmaceutical composition according to embodiment 99. In some embodiments, the method lowers fat mass of a subject 30% or greater. In some embodiments, the method lowers fat mass of a subject 40% or greater. In some embodiments, the method lowers fat mass of a subject 45% or greater. In some embodiments, the method lowers fat mass of a subject 50% or greater. In some embodiments, the method lowers fat mass of a subject 55% or greater. In some embodiments, the method lowers blood fat mass of a subject 60% or greater. In some embodiments, the method lowers fat mass of a subject 65% or greater. In some embodiments, the method lowers fat mass of a subject 70% or greater. In some embodiments, the method lowers fat mass of a subject 75% or greater. In some embodiments, the method lowers fat mass of a subject while having minimal effect on food intake/appetite. In some embodiments, the method lowers fat mass of a subject while having no effect on food intake/appetite.

Provided herein as a further embodiment is a method of raising adiponectin in a subject in need thereof, the method comprising administering a therapeutically effective amount of the compound according to any one of Embodiments 1-98, or a tautomer thereof, or a pharmaceutically acceptable salt of said compound or said tautomer, or the pharmaceutical composition according to embodiment 99.

Provided herein as a further embodiment is a method of lowering leptin in a subject in need thereof, the method comprising administering a therapeutically effective amount of the compound according to any one of Embodiments 1-98, or a tautomer thereof, or a pharmaceutically acceptable salt of said compound or said tautomer, or the pharmaceutical composition according to embodiment 99.

Provided herein as a further embodiment is a method of lowering resisten in a subject in need thereof, the method comprising administering a therapeutically effective amount of the compound according to any one of Embodiments 1-98, or a tautomer thereof, or a pharmaceutically acceptable salt of said compound or said tautomer, or the pharmaceutical composition according to embodiment 99.

Combinations

Provided herein is a further embodiment is a pharmaceutical composition comprising a compound according to any one of Embodiments 1-98 and one or more other active agents. In some embodiments, the one or more active agents include but are not limited to a source of omega-3 fatty acids. In some embodiments, the one or more active agents include but are not limited to omega-3 fatty acid supplements. In some embodiments, the one or more active agents include but are not limited to omega-3-carboxylic acids (e.g., Epanova®), omega-3-acid ethyl esters (e.g., Lovaza® or Omtryg®) or icosapent ethyl (e.g., Vascepa®).

Provided herein as a further embodiment is a method of treating diabetes, obesity, dyslipidemia, or non-alcoholic steatohepatitis (NASH) in a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents. In some embodiments, the one or more active agents include but are not limited to a source of omega-3 fatty acids. In some embodiments, the one or more active agents include but are not limited to omega-3 fatty acid supplements. In some embodiments, the one or more active agents include but are not limited to omega-3-carboxylic acids (e.g., Epanova®), omega-3-acid ethyl esters (e.g., Lovaza® or Omtryg®) or icosapent ethyl (e.g., Vascepa®).

Provided herein as a further embodiment is a method of reducing body weight or the body-mass-index of a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents. In some embodiments, the one or more active agents include but are not limited to a source of omega-3 fatty acids. In some embodiments, the one or more active agents include but are not limited to omega-3 fatty acid supplements. In some embodiments, the one or more active agents include but are not limited to omega-3-carboxylic acids (e.g., Epanova®), omega-3-acid ethyl esters (e.g., Lovaza® or Omtryg®) or icosapent ethyl (e.g., Vascepa®).

Provided herein as a further embodiment is a method of treating a metabolic or cardiovascular disorder in a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents. In some embodiments, the one or more active agents include but are not limited to a source of omega-3 fatty acids. In some embodiments, the one or more active agents include but are not limited to omega-3 fatty acid supplements. In some embodiments, the one or more active agents include but are not limited to omega-3-carboxylic acids (e.g., Epanova®), omega-3-acid ethyl esters (e.g., Lovaza® or Omtryg®) or icosapent ethyl (e.g., Vascepa®).

Provided herein as a further embodiment is a method of reducing the waist-to-hip ratio (WHR) of a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents.

Provided herein as a further embodiment is a method of lowering blood glucose in a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents.

Provided herein as a further embodiment is a method of lowering insulin in a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents.

Provided herein as a further embodiment is a method of lowering cholesterol in a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents.

Provided herein as a further embodiment is a method of lowering LDL in a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents.

Provided herein as a further embodiment is a method of lowering triglycerides in a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents.

Provided herein as a further embodiment is a method of lowering fat mass in a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents.

Provided herein as a further embodiment is a method of raising adiponectin in a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents.

Provided herein as a further embodiment is a method of lowering leptin in a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents.

Provided herein as a further embodiment is a method of lowering resisten in a subject in need thereof, the method comprising administering a combination of a therapeutically effective amount of the compound according to any one of Embodiments 1-98, or a tautomer thereof, or a pharmaceutically acceptable salt of said compound or said tautomer in combination with one or more other active agents.

In some embodiments, the one or more active agents of the combinations described herein or methods utilizing these combinations described herein include but are not limited to omega-3-carboxylic acids (e.g., Epanova®), omega-3-acid ethyl esters (e.g., Lovaza® or Omtryg®) or icosapent ethyl (e.g., Vascepa®).

Definitions

The following definitions are provided to assist in understanding the scope of this disclosure.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound.

Stereoisomers

The compounds of the present disclosure may contain, for example, double bonds, one or more asymmetric carbon atoms, and bonds with a hindered rotation, and therefore, may exist as stereoisomers, such as double-bond isomers (i.e., geometric isomers (E/Z)), enantiomers, diastereomers, and atropoisomers. Accordingly, the scope of the instant disclosure is to be understood to encompass all possible stereoisomers of the illustrated compounds including the stereoisomerically pure form (for example, geometrically pure, enantiomerically pure, diastereomerically pure, and atropoisomerically pure) and stereoisomeric mixtures (for example, mixtures of geometric isomers, enantiomers, diastereomers, and atropoisomers, or mixtures of any of the foregoing) of any chemical structures disclosed herein (in whole or in part), unless the stereochemistry is specifically identified.

If the stereochemistry of a structure or a portion of a structure is not indicated with, for example, bold or dashed lines, the structure or portion of the structure is to be interpreted as encompassing all stereoisomers of it. If the stereochemistry of a structure or a portion of a structure is indicated with, for example, bold or dashed lines, the structure or portion of the structure is to be interpreted as encompassing only the stereoisomer indicated. A bond drawn with a wavy line indicates that both stereoisomers are encompassed. This is not to be confused with a wavy line drawn perpendicular to a bond which indicates the point of attachment of a group to the rest of the molecule.

The term "stereoisomer" or "stereoisomerically pure" compound as used herein refers to one stereoisomer (for example, geometric isomer, enantiomer, diastereomer and atropoisomer) of a compound that is substantially free of other stereoisomers of that compound. For example, a stereoisomerically pure compound having one chiral center will be substantially free of the mirror image enantiomer of the compound and a stereoisomerically pure compound having two chiral centers will be substantially free of other enantiomers or diastereomers of the compound. A typical stereoisomerically pure compound comprises greater than about 80% by weight of one stereoisomer of the compound and equal or less than about 20% by weight of other stereoisomers of the compound, greater than about 90% by weight of one stereoisomer of the compound and equal or less than about 10% by weight of the other stereoisomers of the compound, greater than about 95% by weight of one stereoisomer of the compound and equal or less than about 5% by weight of the other stereoisomers of the compound, or greater than about 97% by weight of one stereoisomer of the compound and equal or less than about 3% by weight of the other stereoisomers of the compound.

This disclosure also encompasses the pharmaceutical compositions comprising stereoisomerically pure forms and the use of stereoisomerically pure forms of any compounds disclosed herein. Further, this disclosure also encompasses pharmaceutical compositions comprising mixtures of stereoisomers of any compounds disclosed herein and the use of said pharmaceutical compositions or mixtures of stereoisomers. These stereoisomers or mixtures thereof may be synthesized in accordance with methods well known in the art and methods disclosed herein. Mixtures of stereoisomers may be resolved using standard techniques, such as chiral columns or chiral resolving agents. See, for example, Jacques et al., Enantiomers, Racemates and Resolutions (Wiley-Interscience, New York, 1981); Wilen et al., *Tetrahedron* 33:2725; Eliel, Stereochemistry of Carbon Compounds (McGraw-Hill, NY, 1962); and Wilen, Tables of Resolving Agents and Optical Resolutions, page 268 (Eliel, Ed., Univ. of Notre Dame Press, Notre Dame, IN, 1972).

Tautomers

As known by those skilled in the art, certain compounds disclosed herein may exist in one or more tautomeric forms. Because one chemical structure may only be used to represent one tautomeric form, it will be understood that for convenience, referral to a compound of a given structural formula includes other tautomers of said structural formula. For example, the following is illustrative of tautomers of the compounds of Formula I, wherein w, y and z are $CR^w$, $CR^y$, and $CR^z$, respectively, and x is COH:

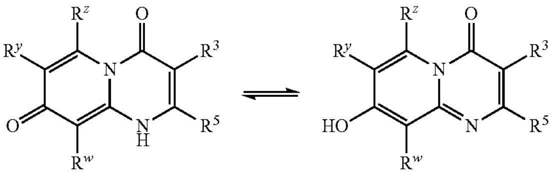

Accordingly, the scope of the instant disclosure is to be understood to encompass all tautomeric forms of the compounds disclosed herein.

Isotopically-Labelled Compounds

Further, the scope of the present disclosure includes all pharmaceutically acceptable isotopically-labelled compounds of the compounds disclosed herein, such as the compounds of Formula I, wherein one or more atoms are replaced by atoms having the same atomic number, but an atomic mass or mass number different from the atomic mass or mass number usually found in nature. Examples of isotopes suitable for inclusion in the compounds disclosed herein include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of Formula I, for example, those incorporating a radioactive isotope, are useful in drug and/or substrate tissue distribution studies. The radioactive isotopes tritium (3H) and carbon-14 (14C) are particularly useful for this purpose in view of their ease of incorporation and ready means of detection. Substitution with isotopes such as deuterium (2H or D) may afford certain therapeutic advantages resulting from greater metabolic stability, for example, increased in vivo half-life or reduced dosage requirements, and hence may be advantageous in some circumstances. Substitution with positron emitting isotopes, such as $^{11}C$, $^{18}F$, $^{15}O$ and $^{3}N$, can be useful in Positron Emission Topography (PET) studies, for example, for examining target occupancy. Isotopically-labelled compounds of the compounds disclosed herein can generally be prepared by conventional techniques known to those skilled in the art or by processes analogous to those described in the accompanying General Synthetic Schemes and Examples using an appropriate isotopically-labelled reagent in place of the non-labelled reagent previously employed.

Solvates

As discussed above, the compounds disclosed herein and the stereoisomers, tautomers, and isotopically-labelled forms thereof or a pharmaceutically acceptable salt of any of the foregoing may exist in solvated or unsolvated forms.

The term "solvate" as used herein refers to a molecular complex comprising a compound or a pharmaceutically acceptable salt thereof as described herein and a stoichiometric or non-stoichiometric amount of one or more pharmaceutically acceptable solvent molecules. If the solvent is water, the solvate is referred to as a "hydrate."

Accordingly, the scope of the instant disclosure is to be understood to encompass all solvents of the compounds disclosed herein and the stereoisomers, tautomers and isotopically-labelled forms thereof or a pharmaceutically acceptable salt of any of the foregoing.

Miscellaneous Definitions

This section will define additional terms used to describe the scope of the compounds, compositions and uses disclosed herein.

The terms "$C_{1-3}$alkyl," "$C_{1-4}$alkyl," "$C_{2-6}$alkyl," and "$C_{1-6}$ alkyl" as used herein refer to a straight or branched chain hydrocarbon containing from 1 to 3, 1 to 4, 2 to 6, and 1 to 6 carbon atoms, respectively. Representative examples of $C_{1-3}$alkyl, $C_{1-4}$alkyl, $C_{2-6}$alkyl, or $C_{1-6}$alkyl include, but are not limited to, methyl, ethyl, n-propyl, iso-propyl, n-butyl, sec-butyl, iso-butyl, tert-butyl, pentyl and hexyl.

The term "$C_{2-4}$alkenyl" as used herein refers to a saturated hydrocarbon containing 2 to 4 carbon atoms having at least one carbon-carbon double bond. Alkenyl groups include both straight and branched moieties. Representative examples of $C_{2-4}$alkenyl include, but are not limited to, 1-propenyl, 2-propenyl, 2-methyl-2-propenyl, and butenyl.

The terms "$C_{1-4}$alkylamino" or "$C_{1-6}$alkylamino" as used herein refer to —NHR*, wherein R* represents a $C_{1-4}$alkyl and $C_{1-6}$alkyl, respectively, as defined herein. Representative examples of $C_{1-4}$alkylamino or $C_{1-6}$alkylamino include, but are not limited to, $—NHCH_3$, $—NHCH_2CH_3$, $—NHCH_2CH_2CH_3$, and $—NHCH(CH_3)_2$.

The term "$C_{3-5}$cycloalkyl" as used herein refers to a saturated carbocyclic molecule wherein the cyclic framework has 3 to 6 carbons. Representative examples of $C_{3-5}$cycloalkyl include, but are not limited to cyclopropyl and cyclobutyl.

The term "deutero" as used herein as a prefix to another term for a chemical group refers to a modification of the chemical group, wherein one or more hydrogen atoms are substituted with deuterium ("D," "d," or "$^2$H"). For example, the term "$C_{1-4}$deuteroalkyl" refers to a $C_{1-4}$alkyl as defined herein, wherein one or more hydrogen atoms are substituted with D. Representative examples of $C_{1-4}$deuteroalkyl include, but are not limited to, $—CH_2D$, $—CHD_2$, $—CD_3$, $—CH_2CD_3$, $—CDHCD_3$, $—CD_2CD_3$, $—CH(CD_3)_2$, $—CD(CHD_2)_2$, and $—CH(CH_2D)(CD_3)$.

The terms "di$C_{1-4}$alkylamino" or "di$C_{1-6}$alkylamino" as used herein refer to —NR*R**, wherein R* and R** independently represent a $C_{1-4}$alkyl and $C_{1-6}$alkyl, respectively, as defined herein. Representative examples of di$C_{1-4}$ alkylamino or di$C_{1-6}$alkylamino include, but are not limited to, $—N(CH_3)_2$, $—N(CH_2CH_3)_2$, $—N(CH_3)(CH_2CH_3)$, $—N(CH_2CH_2CH_3)_2$, and $—N(CH(CH_3)_2)_2$.

The term "$C_{1-4}$alkoxy" or "$C_{1-3}$alkoxy" as used herein refers to $—OR^{\#}$, wherein $R^{\#}$ represents a $C_{1-4}$alkyl group or $C_{1-3}$alkyl group, respectively, as defined herein. Representative examples of $C_{1-4}$alkoxy or $C_{1-3}$alkoxy include, but are not limited to, methoxy, ethoxy, propoxy, iso-propoxy, and butoxy.

The term "halogen" as used herein refers to —F, —Cl, —Br, or —I.

The term "halo" as used herein as a prefix to another term for a chemical group refers to a modification of the chemical group, wherein one or more hydrogen atoms are substituted with a halogen as defined herein. The halogen is independently selected at each occurrence. For example, the term "$C_{1-4}$haloalkyl" refers to a $C_{1-4}$alkyl as defined herein, wherein one or more hydrogen atoms are substituted with a halogen. Representative examples of $C_{1-4}$haloalkyl include, but are not limited to, $—CH_2F$, $—CHF_2$, $—CF_3$, —CHFCl, $—CH_2CF_3$, $—CFHCF_3$, $—CF_2CF_3$, $—CH(CF_3)_2$, $—CF(CHF_2)_2$, and $—CH(CH_2F)(CF_3)$.

The term "5-membered heteroaryl" as used herein refers to a 5-membered carbon ring with two double bonds containing one ring heteroatom selected from N, S, and O and optionally one or two further ring N atoms instead of the one or more ring carbon atom(s). Representative examples of a 5-membered heteroaryl include, but are not limited to, furyl, imidazolyl, isoxazolyl, isothiazolyl, oxadiazolyl, and oxazolyl.

The term "$C_{3-5}$heterocycloalkyl" or "$C_{3-4}$heterocycloalkyl" as used herein refers to a saturated carbocyclic molecule wherein the cyclic framework has 3 to 5 carbons or 3 to 4 carbons and wherein one carbon atom is substituted with a heteroatom selected from N, O, and S. Representative examples of $C_{3-5}$heterocycloalkyl or $C_{3-4}$heterocycloalkyl include, but are not limited to aziridnyl, azetidinyl, oxetanyl, and pyrrolidinyl.

The term "pharmaceutically acceptable" as used herein refers to generally recognized for use in subjects, particularly in humans.

The term "pharmaceutically acceptable salt" as used herein refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, for example, an alkali metal ion, an alkaline earth ion, or an aluminum ion; or coordinates with an organic base such as ethanolamine, diethanolamine, triethanolamine, N-methylglucamine, dicyclohexylamine, and the like. Additional examples of such salts can be found in Berge et al., *J. Pharm. Sci.* 66(1):1-19 (1977). See also Stahl et al., Pharmaceutical Salts: Properties, Selection, and Use, $2^{nd}$ Revised Edition (2011).

The term "pharmaceutically acceptable excipient" as used herein refers to a broad range of ingredients that may be combined with a compound or salt disclosed herein to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

The term "subject" as used herein refers to humans and mammals, including, but not limited to, primates, cows, sheep, goats, horses, dogs, cats, rabbits, rats, and mice. In one embodiment the subject is a human.

The term "therapeutically effective amount" as used herein refers to that amount of a compound disclosed herein that will elicit the biological or medical response of a tissue, a system, or subject that is being sought by a researcher, veterinarian, medical doctor or other clinician.

The term "body-mass-index" ("BMI") as used herein may be calculated, for example, by determining a subject's weight in kilograms and dividing it by the square of height in meters. See, e.g., https://www.cdc.gov/healthyweight/assessing/bmi/index.html (last accessed Nov. 4, 2019). The BMI is an indicator of the amount of body fat in a subject, such as a human. The BMI is used as a screening tool to identify whether a subject is at a healthy weight or responds to weight loss treatment.

Synthetic Procedures

The compounds provided herein can be synthesized according to the procedures described in this and the following sections. The synthetic methods described herein are merely exemplary, and the compounds disclosed herein may also be synthesized by alternate routes utilizing alternative synthetic strategies, as appreciated by persons of ordinary skill in the art. It should be appreciated that the general synthetic procedures and specific examples provided herein are illustrative only and should not be construed as limiting the scope of the present disclosure in any manner.

All starting materials are either commercially available, for example, from Sigma-Aldrich Chemical Company, Inc., St. Louis, MO, USA, or known in the art and may be synthesized by employing known procedures using ordinary skill. Starting material may also be synthesized via the procedures disclosed herein.

As can be appreciated by the skilled artisan, the representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

Purification methods for the compounds described herein are known in the art and include, for example, crystallization, chromatography (for example, liquid and gas phase), extraction, distillation, trituration, and reverse phase HPLC.

The disclosure further encompasses "intermediate" compounds, including structures produced from the synthetic procedures described, whether isolated or generated in-situ and not isolated, prior to obtaining the finally desired compound. These intermediates are included in the scope of this disclosure. Exemplary embodiments of such intermediate compounds are set forth below.

Provided herein as Embodiment 115 is a compound, wherein the compound is

N-(3-iodo-4-oxo-2-(trifluoromethyl)-4H-pyrido[1,2-a]pyrimidin-8-yl)acetamide;

8-bromo-3-iodo-2-(trifluoromethyl)-4H-pyrido[1,2-a]pyrimidin-4-one;

8-bromo-2-(trifluoromethyl)-4H-pyrido[1,2-a]pyrimidin-4-one;

8-hydroxy-2-(trifluoromethyl)-4H-pyrido[1,2-a]pyrimidin-4-one;

4-oxo-2-(trifluoromethyl)-4H-pyrido[1,2-a]pyrimidine-8-carbonitrile;

3-Iodo-4-oxo-2-(trifluoromethyl)-4H-pyrido[1,2-a]pyrimidine-8-carbonitrile;

3-bromo-8-methoxy-2-(trifluoromethyl)pyrimido[1,2-a]pyrimidin-4-one;

8-methoxy-2-(trifluoromethyl)-4H-pyrimido[1,2-a]pyrimidin-4-one; or 1-(2,2,3,3,3-pentafluoropropyl)-4-(4,4,5,5-tetramethyl-1,3,2-dioxaborolan-2-yl)-1H-pyrazole.

EXAMPLES

This section provides specific examples of compounds of Formula I and methods of making the same.

LIST OF ABBREVIATIONS

TABLE 1

| | |
|---|---|
| AcOH | acetic acid |
| AIBN | Azobisisobutyronitrile |
| aq or aq, | aqueous |
| BOC or Boc | tert-butyloxycarbonyl |
| $Cu(OTf)_2$ | Copper trifluoromethanesulfonate |
| Cy | Cyclohexane |
| DAST | Diethylaminosulfur trifluoride |
| DCE | 1,2-dichloroethane |
| DABCO | 1,4-diazabicyclo[2.2.2]octane |
| DIBAL-H | Diisobutylaluminum hydride |
| DCM | dichloromethane |
| DIAD | Diisopropyl azodiformate |
| DMA | N,N-dimethylacetamide |
| DMAP | 4-dimethylaminopyridine |
| DME | 1,2-dimethoxyethane |
| DMF | N,N-dimethylformamide |
| DMSO | dimethyl sulfoxide |
| DMP | Dess-Martin Periodinane |
| Dppf, DPPF or dppf | 1,1'-bis(diphenylphosphino)ferrocene |
| eq or eq, or equiv. | equivalent |
| ESI or ES | electrospray ionization |
| Et | ethyl |
| $Et_2O$ | diethyl ether |
| EtOAc | ethyl acetate |
| g | gram(s) |
| h | hour(s) |
| HATU | (1-[Bis(dimethylamino)methylene]-1H-1,2,3-triazolo[4,5-b]pyridinium 3-oxide hexafluorophosphate |
| HBTU | N,N,N',N'-tetramethyl-O-(1H-benzotriazol-1-yl)uronium hexafluorophosphate, O-(benzotriazol-1-yl)-N,N,N',N'-tetramethyluronium hexafluorophosphate |
| HPLC | high pressure liquid chromatography |
| iPr | isopropyl |
| iPr2NEt or DIPEA | N-ethyl diisopropylamine (Hünig's base) |
| KHMDS | potassium hexamethyldisilazide |
| KOAc | potassium acetate |
| LC MS, LCMS, LC-MS or LC/MS | liquid chromatography mass spectroscopy |
| LG | leaving group (e.g., halogen, mesylate, triflate) |
| LHMDS or LiHMDS | lithium hexamethyldisilazide |
| m/z | mass divided by charge |
| mCPBA | meta-chloroperoxybenzoic acid |
| Me | methyl |
| MeCN | acetonitrile |
| MeOH | methanol |
| Met | metal species for cross-coupling (e.g., MgX, ZnX, SnR3, SiR3, B(OR)2) |

TABLE 1-continued

| | |
|---|---|
| μm | micrometer |
| μL or μl | microliter |
| mg | milligrams |
| min | minutes |
| mL or ml | milliliters |
| MS | mass spectra |
| NaHMDS | sodium hexamethyldisilazide |
| NBS | N-bromosuccinimide |
| n-BuLi | n-butyllithium |
| NIS | N-iodosuccinimide |
| NBS | N-bromosuccinimide |
| NCS | N-chlorosuccinimide |
| NMP | N-Methyl-2-pyrrolidone |
| NMR | nuclear magnetic resonance |
| Pd-118, $Pd(dtbpf)Cl_2$ | 1,1'-bis(di-tert-butylphosphino)ferrocene]-dichloropalladium(II) dichloride |
| $Pd_2(dba)_3$ | tris(dibenzylideneacetone)dipalladium(0) |
| $Pd(dppf)Cl_2$ | [1,1'-bis(diphenylphosphino)ferrocene]-dichloropalladium(II) |
| $Pd(dppf)Cl_2$•DCM | [1,1'-bis(diphenylphosphino)ferrocene]-dichloropalladium(II), complex with dichloromethane |
| $Pd(PPh_3)_4$ | tetrakis(triphenylphosphine)palladium(0) |
| Ph | phenyl |
| PPA | Polyphosphoric acid |
| PR or PG or Prot. group | protecting group |
| rbf | round-bottomed flask |
| RP HPLC | reverse phase high pressure liquid chromatography |
| RT or rt or r.t. | room temperature |
| sat. or satd. | saturated |
| SCX | Strong Cation Exchange |
| SFC | supercritical fluid chromatography |
| SIPr | 1,3-Bis(2,6-diisopropylphenyl)imidazolidene |
| SPhos | 2-dicyclohexylphosphino-2',6'-dimethoxybiphenyl |
| SPhos Palladacycle or SPhos Palladacycle G1 | (2-Dicyclohexylphosphino-2',6'-dimethoxy-1,1'-biphenyl)[2-(2-aminoethylphenyl)]palladium(II) chloride methyl-t-butylether adduct |
| Sphos Palladacycle G3 | (2-dicyclohexylphosphino-2',6'-dimethoxybiphenyl) [2-(2'-amino-1,1'-biphenyl)]palladium(II) methanesulfonate |
| TBAF | tetra-n-butylammonium fluoride |
| TBTU | N,N,N',N'-tetramethyl-O-(benzotriazol-1-yl)uronium tetrafluoroborate |
| tBuBrettPhos Palladcycle G3 | Methanesulfonato(2-(di-t-butylphosphino)-3,6-dimethoxy-2',4',6'-tri-i-propyl-1-1'-biphenyl)(2'-amino-1,1'-biphenyl-2-yl)palladium(II) |
| t-BuOH | tert-butanol |
| TEA or Et3N | trimethylamine |
| TFA | trifluoroacetic acid |
| THF | tetrahydrofuran |
| UV | ultraviolet |
| XantPhos | 4,5-Bis(diphenylphosphino)-9,9-dimethylxanthene |

General Analytical and Purification Methods

Provided in this section are descriptions of the general analytical and purification methods used to prepare the specific compounds provided herein.

Chromatography:

Unless otherwise indicated, crude product-containing residues were purified by passing the crude material or concentrate through either a Biotage or Isco brand silica gel column (pre-packed or individually packed with $SiO_2$) or reverse phase flash silica (C18) and eluting the product off the column with a solvent gradient as indicated. For example, a description of (330 g $SiO_2$, 0-40% EtOAc/hexane) means the product was obtained by elution from the column packed with 330 grams of silica, with a solvent gradient of 0% to 40% EtOAc in hexanes.

Preparative HPLC Method:

Where so indicated, the compounds described herein were purified via reverse phase HPLC using one of the following instruments: Shimadzu, Varian, Gilson, Agilent 1260 infinity or Waters Fractionlynx; utilizing one of the following HPLC columns: (a) a Phenomenex Luna or (b) a Gemini column (5 micron or 10 micron, C18, 150×50 mm) or (c) a Waters X-select CSH column (5 micron, C18, 100×30 mm), unless otherwise indicated.

A typical run through the instrument included: eluting at 45 mL/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1H$ NMR spectra were collected on a Bruker NMR Instrument at 300 MHz or 400 or 500 MHz. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an $[M+H]^+$ molecular ion. The molecular ion reported was obtained by electrospray detection method (commonly referred to as an ESI MS) utilizing a PE SCIEX API 150EX MS instrument, an Agilent 1100 series LC/MSD system or a Waters Acquity UPLC/MS. Compounds having an isotopic atom, such as bromine and the like, are generally reported according to the detected isotopic pattern, as appreciated by those skilled in the art.

Compound Names

The compounds disclosed and described herein have been named using the IUPAC naming convention provided with Chem-Draw Professional 15.1.0.144 software, ACD/Labs software version 2015 from Advanced Chemistry Development Inc., or with JChem for Excel 18.22.1.7 from ChemAxon Ltd.

SPECIFIC EXAMPLES

Provided in this section are the procedures to synthesize specific examples of the compounds provided herein. All starting materials are either commercially available from Sigma-Aldrich Chemical Company, Inc., St. Louis, MO, USA, unless otherwise noted, or known in the art and may be synthesized by employing known procedures using ordinary skill.

Synthesis of Intermediates:

Intermediate 1-A

3-Bromo-8-methoxy-2-(trifluoromethyl)-4H-pyrido[1,2-a]pyrimidin-4-one

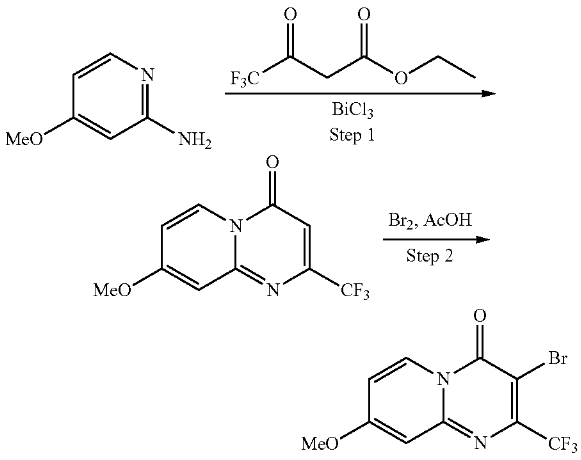

Step 1: 8-Methoxy-2-(trifluoromethyl)-4H-pyrido[1,2-a]pyrimidin-4-one

A reaction mixture of 2-amino-4-methoxypyridine (3.91 g, 31.5 mmol, Oakwood Products, Inc.), ethyl 4,4,4-trifluoroacetoacetate (18.56 ml, 126 mmol), and bismuth(III) trichloride (1.091 ml, 15.75 mmol) was heated to 100° C. for 5 h. The reaction mixture was cooled to rt, diluted with water and extracted with EtOAc. The organic layer was washed with brine, dried over magnesium sulfate and concentrated under reduced pressure. The crude material was purified by silica gel chromatography (eluent: 0-60% EtOAc/heptane) to afford 8-methoxy-2-(trifluoromethyl)-4H-pyrido[1,2-a]pyrimidin-4-one (2.16 g, 8.9 mmol, 28% yield). LC/MS (ESI$^+$) m/z=245.2 [M+H]$^+$.

Step 2: 3-Bromo-8-methoxy-2-(trifluoromethyl)-4H-pyrido[1,2-a]pyrimidin-4-one A solution of bromine (8 μl, 0.16 mmol) in acetic acid (0.5 ml) was added dropwise to a solution of 8-methoxy-2-(trifluoromethyl)-4H-pyrido[1,2-a]pyrimidin-4-one (40 mg, 0.16 mmol) in acetic acid (1.2 ml) at rt. Upon completed addition, the reaction mixture was cooled to 0° C. and diluted with EtOAc (5 mL) and water (2 mL). The organic layer was separated, dried over magnesium sulfate and concentrated under reduced pressure. The crude material was purified silica gel chromatography (eluent: 5-50% EtOAc/heptane) to afford 3-bromo-8-methoxy-2-(trifluoromethyl)-4H-pyrido[1,2-a]pyrimidin-4-one (52 mg g, 0.16 mmol, 98% yield) as a white solid. MS (ESI$^+$) m/z=323.0 [M+H]$^+$. $^1$H NMR (400 MHz, $CDCl_3$) δ 8.97 (d, J=7.82 Hz, 1H) 7.05 (d, J=2.74 Hz, 1H) 6.98 (dd, J=7.92, 2.64 Hz, 1H) 4.02 (s, 3H).

Intermediate 1-B

3-Iodo-8-methoxy-2-(trifluoromethyl)-4H-pyrido[1,2-a]pyrimidin-4-one

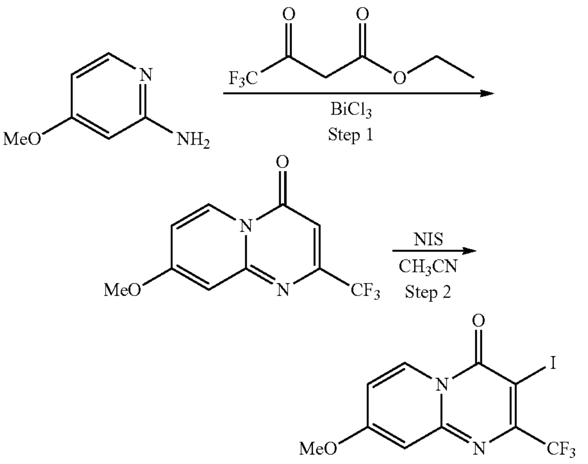

Step 1: 8-Methoxy-2-(trifluoromethyl)-4H-pyrido[1,2-a]pyrimidin-4-one

The title compound was prepared using the procedure described for Intermediate 1-A, Step 1.

Step 2: 3-Iodo-8-methoxy-2-(trifluoromethyl)-4H-pyrido[1,2-a]pyrimidin-4-one To a solution of 8-methoxy-2-(trifluoromethyl)-4H-pyrido[1,2-a]pyrimidin-4-one (0.22 g, 0.89 mmol) in acetonitrile (5 mL) was added N-iodosuccinimide (0.24 g, 1.1 mmol). The reaction mixture was heated to 80° C. for 12 h. The reaction mixture was concentrated in vacuo and the crude residue was purified by silica gel chromatography (eluent: 100% DCM) to give 3-iodo-8-methoxy-2-(trifluoromethyl)-4H-pyrido[1,2-a]pyrimidin-4-one (0.31 g, 0.84 mmol, 94% yield). LC/MS (ESI$^+$) m/z=370.9 [M+H]$^+$, 371.9 [M+2H]$^+$. $^1$H NMR (400 MHz, $CDCl_3$) δ 8.98 (d, J=7.82 Hz, 1H), 7.06 (d, J=2.74 Hz, 1H), 6.97 (dd, J=2.64, 7.92 Hz, 1H), 4.02 (s, 3H). $^{19}$F NMR (376 MHz, $CDCl_3$) δ −67.21 (s, 3F).

Intermediate 1-C

3-Bromo-2-(difluoromethyl)-8-methoxy-pyrido[1,2-a]pyrimidin-4-one

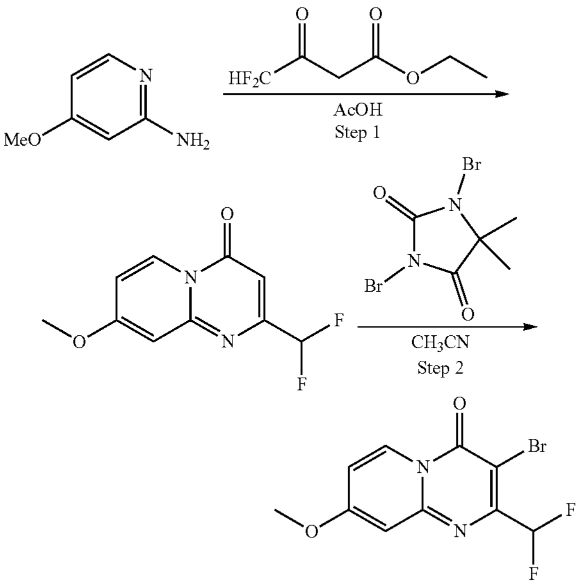

Step 1: 2-(Difluoromethyl)-8-methoxy-4H-pyrido[1,2-a]pyrimidin-4-one

A solution of 4-methoxypyridin-2-amine (3.75 g, 30.2 mmol, Combi-Blocks Inc.) and 4,4-difluoro-3-oxobutanoic acid ethyl ester (7.5 ml, 45 mmol, Combi-Blocks Inc.) in glacial acetic acid (25 ml, 433 mmol) was heated to reflux for 18 h. The reaction mixture was concentrated under reduced pressure and then partitioned between $CH_2Cl_2$(50 mL) and 5 M NaOH (20 mL). The organic layer was extracted with $CH_2Cl_2$ (2×) and the combined organic layers were dried over $Na_2SO_4$. The filtrate was concentrated in vacuo. The crude residue was suspended in DCM (10 mL) and filtered. The filtrate was purified by silica gel chromatography (eluent: 0-35% (3:1 EtOAc/EtOH)/heptane) to afford 2-(difluoromethyl)-8-methoxy-4H-pyrido[1,2-a]pyrimidin-4-one (0.92 g, 4.1 mmol, 14% yield) as a solid. $^1H$ NMR (400 MHz, $CDCl_3$) δ 8.95 (d, J=7.9 Hz, 1H), 6.97 (d, J=2.5 Hz, 1H), 6.88 (dd, J=7.9, 2.70 Hz, 1H), 6.54 (s, 1H), 6.43 (m, 1H), 3.99 (s, 3H).

Step 2: 3-Bromo-2-(difluoromethyl)-8-methoxy-pyrido[1,2-a]pyrimidin-4-one 1,3-Dibromo-5,5-dimethylhydantoin (0.81 g, 2.9 mmol) was added to a stirring suspension of 2-(difluoromethyl)-8-methoxy-4H-pyrido[1,2-a]pyrimidin-4-one (0.92 g, 4.1 mmol) in DMF(7 mL)/DCM (4 mL) at −45° C. under nitrogen atmosphere. After 30 min, the reaction was treated with saturated aqueous $NaHCO_3$ solution (20 mL) and EtOAc (25 mL) and after stirring for 15 min, the resulting precipitate was filtered off. The organic phase of the filtrate was separated, washed with brine (10 mL), and dried over $Na_2SO_4$. The filtrate was concentrated under reduced pressure. The crude material was suspended in DCM (5 mL). The solid as filtered off and dried to obtain 3-bromo-2-(difluoromethyl)-8-methoxy-4H-pyrido[1,2-a]pyrimidin-4-one (0.73 g, 2.4 mmol, 59% yield) as a white solid. LC/MS ($ESI^+$) m/z=305.0 $[M+H]^+$. $^1H$ NMR (400 MHz, $CDCl_3$) δ 8.96 (d, J=7.88 Hz, 1H), 7.07-7.08 (m, 1H), 6.93 (t, J=52 Hz, 1H), 6.95 (d, J=2.7 Hz, 1H), 4.00 (s, 3H).

Intermediate 1-D

Methyl 3-iodo-4-oxo-2-(trifluoromethyl)-4H-pyrido[1,2-a]pyrimidine-8-carboxylate

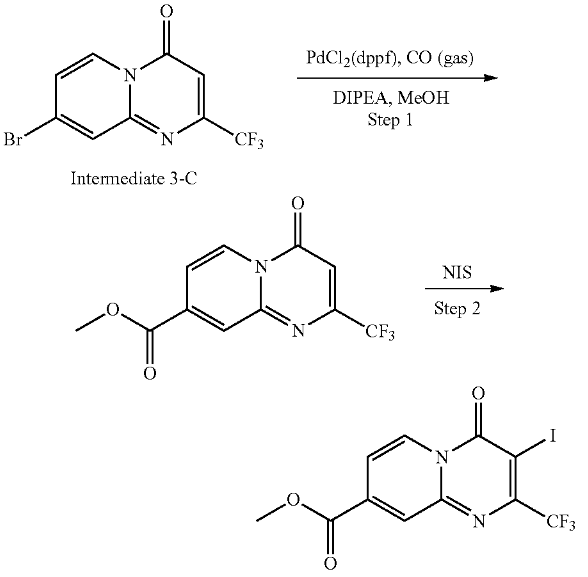

Step 1: Methyl 4-oxo-2-(trifluoromethyl)-4H-pyrido[1,2-a]pyrimidine-8-carboxylate A pressure autoclave was charged with 8-bromo-2-(trifluoromethyl)-4H-pyrido[1,2-a]pyrimidin-4-one (10 g, 34 mmol, Intermediate 3-C), methanol (10 mL), DIPEA (30 mL, 171 mmol) and $Pd(dppf)Cl_2$ (2.5 g, 3.1 mmol). The reaction mixture was heated to 70° C. for 20 h under an atmosphere of carbon monoxide (70 psi pressure). The reaction mixture was cooled to rt and filtered through a pad of celite. The celite pad was washed with dichloromethane (3×50 mL). The combined filtrate was concentrated under reduced pressure. The residue was taken up with water (100 mL) and extracted with DCM (3×100 mL). The combined organic layers were washed with brine (50 mL), dried over $Na_2SO_4$, filtered and concentrated under reduced pressure. The crude material was purified by silica gel chromatography (eluent: 15% ethyl acetate/hexane) to afford methyl 4-oxo-2-(trifluoromethyl)-4H-pyrido[1,2-a]pyrimidine-8-carboxylate (6.7 g, 72% yield) as a pale yellow solid. LC/MS ($ESI^+$) m/z=273.1 $[M+H]^+$. $^1H$ NMR (400 MHz, DMSO-$d_6$) δ 9.07 (d, J=7.4 Hz, 1H), 8.20 (d, J=1.9 Hz, 1H), 7.73 (dd, J=7.2, 1.8 Hz, 1H), 7.00 (s, 1H), 3.96 (s, 3H).

Step 2: Methyl 3-iodo-4-oxo-2-(trifluoromethyl)-4H-pyrido[1,2-a]pyrimidine-8-carboxylate The title compound was prepared using the procedure described for Intermediate 1-B, Step 2 with the following modification: Step 2 was performed with methyl 4-oxo-2-

(trifluoromethyl)-4H-pyrido[1,2-a]pyrimidine-8-carboxylate. LC/MS ($ESI^+$) m/z=398.9 $[M+H]^+$.

Intermediate 1-E 8-(Dimethyl amino)-3-iodo-2-(trifluoromethyl)-4H-pyrido[1,2-a]pyrimidin-4-one

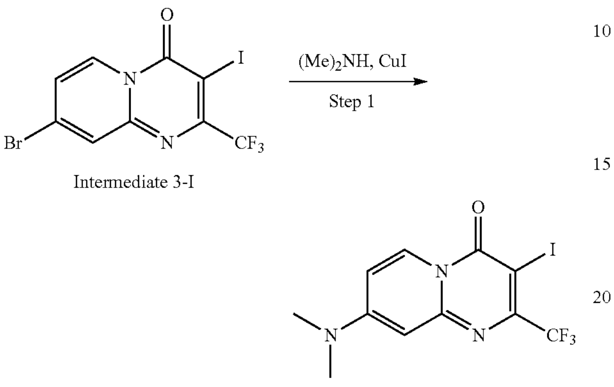

Step 1: 8-(Dimethyl amino)-3-iodo-2-(trifluoromethyl)-4H-pyrido[1,2-a]pyrimidin-4-one A resealable vial was charged with 8-bromo-3-iodo-2-(trifluoromethyl)-4H-pyrido[1,2-a]pyrimidin-4-one (0.5 g, 1.2 mmol, Intermediate 3-I), DMF (5 mL), copper(I) iodide (52 mg, 0.28 mmol) and dimethyl amine (0.66 mL, 1.3 mmol) under nitrogen atmosphere. The reaction mixture was stirred at 80° C. for 3 h. The reaction mixture was cooled to rt, diluted with water and extracted with ethyl acetate (2×30 mL). The combined organic layers were washed with ice cold water (3×20 mL), dried over $Na_2SO_4$ and concentrated under reduced pressure. The crude residue was purified by silica gel chromatography (eluent: 25-30% ethyl acetate/hexane) to provide 8-(dimethyl amino)-3-iodo-2-(trifluoromethyl)-4H-pyrido[1,2-a]pyrimidin-4-one (0.32 g, 0.84 mmol, 70% yield) as a solid. LC/MS ($ESI^+$) m/z=384.1 $[M+H]^+$. $^1H$ NMR (400 MHz, DMSO-$d_6$) δ 8.74 (d, J=8.1 Hz, 1H), 7.20 (dd, J=8.2, 2.9 Hz, 1H), 6.66 (d, J=2.9 Hz, 1H), 3.19 (s, 6H).

Intermediate 1-F

3-Iodo-8-(methylamino)-2-(trifluoromethyl)-4H-pyrido[1,2-a]pyrimidin-4-one

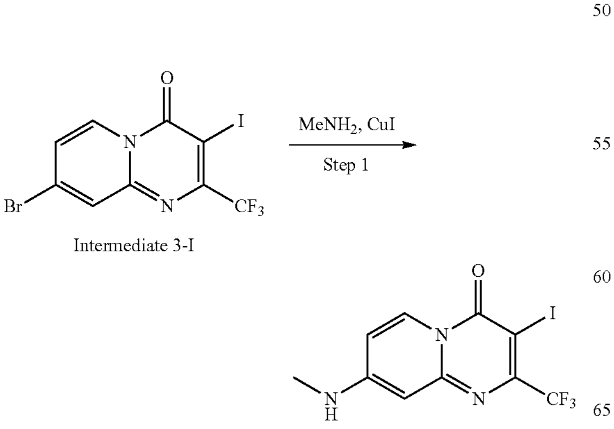

Step 1: 3-Iodo-8-(methylamino)-2-(trifluoromethyl)-4H-pyrido[1,2-a]pyrimidin-4-one The title compound was prepared using the procedure described for Intermediate 1-E, Step 1 with the following modification: Step 1 was performed with methylamine. LC/MS ($ESI^+$) m/z=370.2 $[M+H]^+$. $^1H$ NMR (400 MHz, DMSO-$d_6$) δ 8.67 (d, J=7.8 Hz, 1H), 8.04 (d, J=6.5 Hz, 1H), 6.96-6.84 (m, 1H), 6.48 (s, 1H), 2.87 (d, J=4.8 Hz, 3H).

Intermediate 1-G

8-Acetyl-3-iodo-2-(trifluoromethyl)-4H-pyrido[1,2-a]pyrimidin-4-one

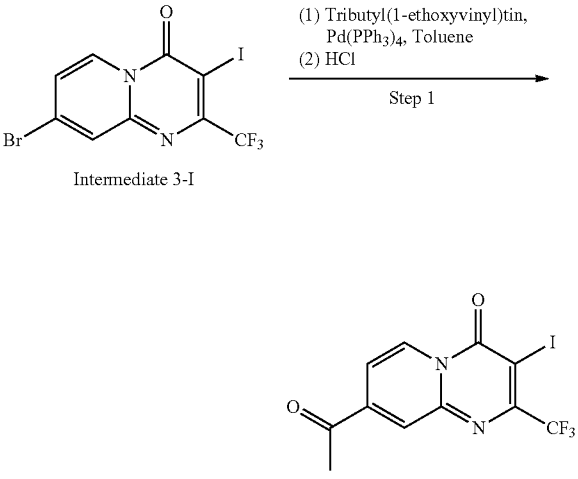

Step 1: 8-Acetyl-3-iodo-2-(trifluoromethyl)-4H-pyrido[1,2-a]pyrimidin-4-one

A pressure tube was charged with 8-bromo-3-iodo-2-(trifluoromethyl)-4H-pyrido[1,2-a]pyrimidin-4-one (2.5 g, 6.0 mmol, Intermediate 3-I), toluene (25 mL) and tributyl (1-ethoxyvinyl)stannane (2.2 g, 6.0 mmol). The reaction mixture was purged with nitrogen for 10 minutes, followed by the addition of $Pd(PPh_3)_4$(0.69 g, 0.6 mmol). The reaction mixture was heated to 105° C. for 1 h. The reaction mixture was cooled to rt and filtered through a pad of celite. The filtrate was concentrated under reduced pressure to get a crude residue, which was dissolved in acetone (35 mL). The solution was cooled to 0° C. and treated with 10% aqueous HCl solution (17 mL). The reaction mixture was warmed to rt and stirred for 30 min. The volatiles were removed under reduced pressure and the remaining residue was diluted with water (20 mL) and extracted with dichloromethane (3×30 mL). The combined organic layers were dried over $Na_2SO_4$ and the filtrate was adsorbed onto a plug of silica gel. Purification by silica gel chromatography (eluent: 0-20% EtOAc/hexane) afforded 8-acetyl-3-iodo-2-(trifluoromethyl)-4H-pyrido[1,2-a]pyrimidin-4-one (700 mg, 31% yield) as yellow solid. LC/MS ($ESI^+$) m/z=382.9 $[M+H]^1H$ NMR (400 MHz, DMSO-$d_6$) δ 9.02 (d, J=7.5 Hz, 1H), 8.43 (d, J=1.9 Hz, 1H), 7.72 (dd, J=7.4, 2.0 Hz, 1H), 2.74 (s, 3H).

Intermediate 1-H

3-Iodo-4-oxo-2-(trifluoromethyl)-4H-pyrido[1,2-a]pyrimidine-8-carbonitrile

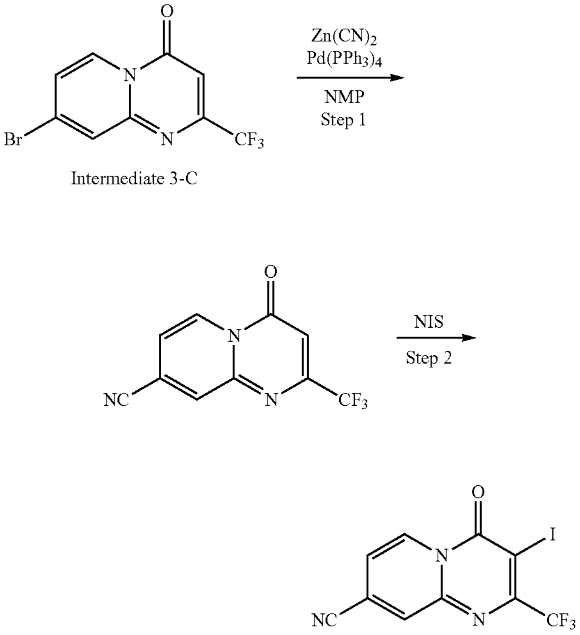

Step 1: 4-Oxo-2-(trifluoromethyl)-4H-pyrido[1,2-a]pyrimidine-8-carbonitrile

A resealable vial was charged with 8-bromo-2-(trifluoromethyl)-4H-pyrido[1,2-a]pyrimidin-4-one (0.3 g, 1.0 mmol, Intermediate 3-C), zinc cyanide (0.12 g, 1.0 mmol), and $Pd(PPh_3)_4$(0.12 g, 0.10 mmol). The vial was evacuated and backfilled with nitrogen. This procedure was repeated 3 times, followed by the addition of NMP (5 ml). The reaction mixture was heated to 90° C. After 18 h, the reaction mixture was partitioned between EtOAc and water. The organic phase was washed with brine, dried over $MgSO_4$, filtered, and adsorbed onto a plug of silica gel. Purification by silica gel chromatography (eluent: 0-10% (3:1 EtOAc/EtOH)/heptane) provided 4-oxo-2-(trifluoromethyl)-4H-pyrido[1,2-a]pyrimidine-8-carbonitrile (0.16 g, 0.66 mmol, 64% yield) as a yellow solid. LC/MS ($ESI^+$) m/z=240.0 $[M+H]^+$. $^1H$ NMR ($CDCl_3$, 400 MHz) δ 9.10 (d, J=7.5 Hz, 1H), 8.10 (s, 1H), 7.28-7.33 (m, 1H), 6.93 (s, 1H).

Step 2: 3-Iodo-4-oxo-2-(trifluoromethyl)-4H-pyrido[1,2-a]pyrimidine-8-carbonitrile The title compound was prepared using the procedure described for Intermediate 1-B, Step 2 with the following modification: Step 2 was performed with 4-oxo-2-(trifluoromethyl)-4H-pyrido[1,2-a]pyrimidine-8-carbonitrile. LC/MS ($ESI^+$) m/z=366.0 $[M+H]^+$. $^1H$ NMR (400 MHz, $CDCl_3$) δ 9.02 (d, J=7.4 Hz, 1H), 8.61 (d, J=1.8 Hz, 1H), 7.73 (dd, J=7.4, 1.9 Hz, 1H).

Intermediate 1-I

7-Chloro-3-iodo-8-methoxy-2-(trifluoromethyl)-4H-pyrido[1,2-a]pyrimidin-4-one

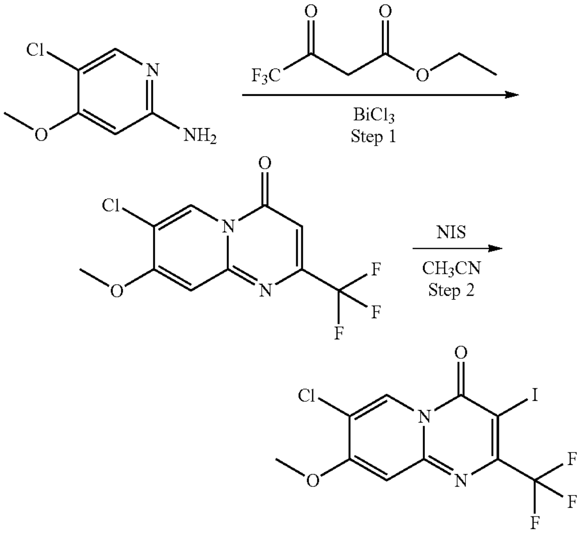

Step 1: 7-Chloro-8-methoxy-2-(trifluoromethyl)-4H-pyrido[1,2-a]pyrimidin-4-one

The title compound was prepared using the procedure described for Intermediate 1-A, Step 1 with the following modification: Step 1 was performed with 5-chloro-4-methoxypyridin-2-amine (prepared according to the procedure described in WO2017/200825A1). LC/MS ($ESI^+$) m/z=279.0 $[M+H]^+$. $^1H$ NMR (400 MHz, DMSO-$d_6$) δ 9.04 (11H, s) 7.47 (1H, s) 6.70 (11H, s) 4.13 (4H, s).

Step 2: 7-Chloro-3-iodo-8-methoxy-2-(trifluoromethyl)-4H-pyrido[1,2-a]pyrimidin-4-one The title compound was prepared using the procedure described for Intermediate 1-B, Step 2 with the following modification: Step 2 was performed with 7-chloro-8-methoxy-2-(trifluoromethyl)-4H-pyrido[1,2-a]pyrimidin-4-one. LC/MS ($ESI^+$) m/z=405.0 [M+H]. $^1H$ NMR (400 MHz, DMSO-$d_6$) δ 9.03 (1H, s) 7.45 (1H, s) 4.13 (3H, s).

Intermediate 1-J 2-(Difluoromethyl)-3-iodo-4-oxo-4H-pyrido[1,2-a]pyrimidine-8-carbonitrile

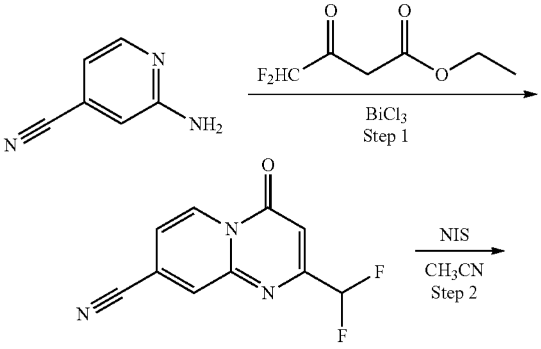

-continued

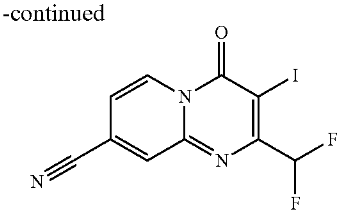

Step 1: 2-(Difluoromethyl)-4-oxo-4H-pyrido[1,2-a]pyrimidine-8-carbonitrile

The title compound was prepared using the procedure described for Intermediate 1-A, Step 1 with the following modification: Step 1 was performed with 2-aminoisonicotinonitrile and 4,4-difluoro-3-oxobutanoic acid ethyl ester (Combi-Blocks Inc).

LC/MS ($ESI^+$) m/z=222.1 $[M+H]^+$. $^1H$ NMR (400 MHz, DMSO-$d_6$) δ 6.77-7.09 (t, 1H) 6.82 (s, 1H) 7.59-7.67 (d, 1H) 8.53 (s, 1H) 8.97-9.07 (d, 1H).

Step 2: 2-(Difluoromethyl)-3-iodo-4-oxo-4H-pyrido[1,2-a]pyrimidine-8-carbonitrile The title compound was prepared using the procedure described for Intermediate 1-B, Step 2 with the following modification: Step 2 was performed with 2-(difluoromethyl)-4-oxo-4H-pyrido[1,2-a]pyrimidine-8-carbonitrile. LC/MS ($ESI^+$) m/z=348.1 [M+H]. $^1H$ NMR (400 MHz, DMSO-$d_6$) δ 6.96-7.29 (t, 1H) 7.67 (dd, 1H) 8.58 (d, 1H) 9.00 (dd, 1H).

Intermediate 1-K

3-Iodo-8-(methylthio)-2-(trifluoromethyl)-4H-pyrido[1,2-a]pyrimidin-4-one

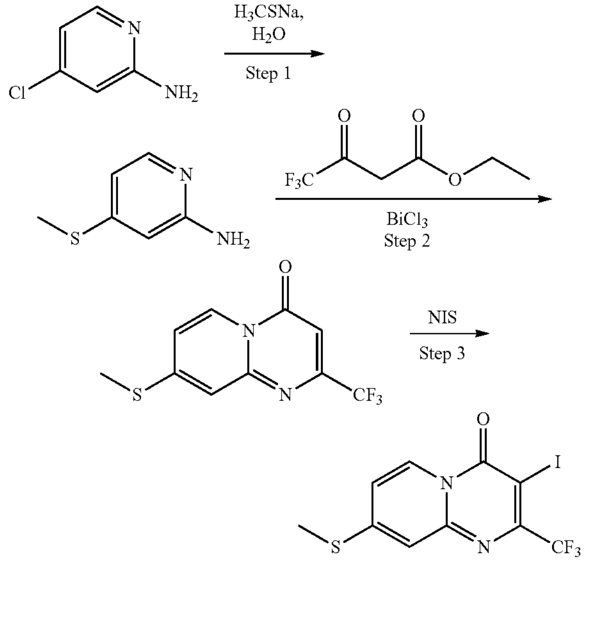

Step 1: 4-(Methylthio)pyridin-2-amine

Sodium thiomethoxide (65.4 g, 933 mmol, Chempure) was added to a solution of 4-chloropyridin-2-amine (20 g, 156 mmol, Combi-Blocks, Inc.) in water (300 mL) at rt. The reaction mixture was stirred at 100° C. for 2 d. The reaction was quenched with water (300 mL) and extracted with EtOAc (2×250 mL). The combined organic layers were washed with brine (250 mL), dried over $Na_2SO_4$, filtered and concentrated under reduced pressure to afford 4-(methylthio)pyridin-2-amine (18.0 g, 83% yield) as a yellow solid. The product was used in next step without further purification. LC/MS ($ESI^+$) m/z=141.1 $[M+H]^+$. $^1H$ NMR (400 MHz, DMSO-$d_6$) δ 7.72 (d, J=5.5 Hz, 1H), 6.36 (dd, J=5.5, 1.7 Hz, 1H), 6.27 (d, J=1.7 Hz, 1H), 5.89 (s, 2H), 2.41 (s, 3H).

Step 2: 8-(Methylthio)-2-(trifluoromethyl)-4H-pyrido[1,2-a]pyrimidin-4-one

The title compound was prepared using the procedure described for Intermediate 1-A, Step 1 with the following modification: Step 1 was performed with 4-(methylthio)pyridin-2-amine. LC/MS ($ESI^+$) m/z=261.1 $[M+H]^+$. $^1H$ NMR (400 MHz, DMSO-$d_6$) δ 8.80 (dd, J=7.6, 1.4 Hz, 1H), 7.49 (d, J=2.1 Hz, 1H), 7.39 (dt, J=7.6, 1.8 Hz, 1H), 6.70 (d, J=1.4 Hz, 1H), 2.69 (d, J=1.6 Hz, 3H).

Step 3: 3-Iodo-8-(methylthio)-2-(trifluoromethyl)-4H-pyrido[1,2-a]pyrimidin-4-one The title compound was prepared using the procedure described for Intermediate 1-B, Step 12 with the following modification: Step 2 was performed with 8-(methylthio)-2-(trifluoromethyl)-4H-pyrido[1,2-a]pyrimidin-4-one. LC/MS ($ESI^+$) m/z=386.9 $[M+H]^+$. $^1H$ NMR (400 MHz, DMSO-$d_6$) δ 8.79 (d, J=7.5 Hz, 1H), 7.48-7.40 (m, 2H), 2.69 (s, 3H).

Intermediate 1-L

N-(3-Iodo-4-oxo-2-(trifluoromethyl)-4H-pyrido[1,2-a]pyrimidin-8-yl)acetamide

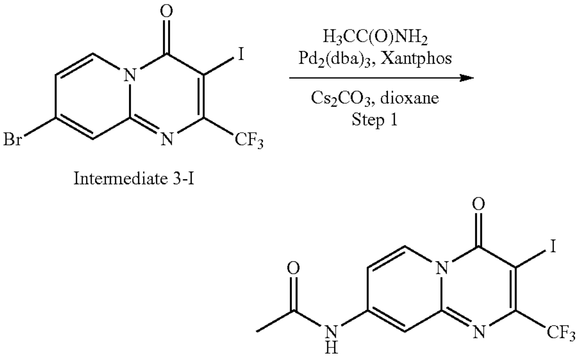

Step 1: N-(3-Iodo-4-oxo-2-(trifluoromethyl)-4H-pyrido[1,2-a]pyrimidin-8-yl)acetamide A resealable vial was charged with 8-bromo-3-iodo-2-(trifluoromethyl)-4H-pyrido[1,2-a]pyrimidin-4-one (0.1 g, 0.239 mmol, Intermediate 3-I), acetamide (19 mg, 0.32 mmol), cesium carbonate (0.16 g, 0.48 mmol), and dioxane (1 mL). The reaction mixture was purged with nitrogen for 10 minutes, followed by addition of $Pd_2(dba)_3$ (11 mg, 0.012 mmol) and Xantphos (7 mg, 0.012 mmol). The reaction mixture was then heated to 80° C. for 5 h. The reaction mixture was cooled to room temperature and concentrated under reduced pressure. The crude residue was purified by silica gel chromatography (eluent: 50-70% ethyl acetate/hexane) to afford N-(3-iodo-4-oxo-2-(trifluoromethyl)-4H-pyrido[1,2-a]pyrimidin-8-yl)acetamide (0.035 g, 0.088 mmol, 37%) as yellow solid. LC/MS (ESI) m/z=397.9 $[M+H]^+$.

Intermediate 1-M

3-Iodo-8-isopropyl-2-(trifluoromethyl)-4H-pyrido[1,2-a]pyrimidin-4-one

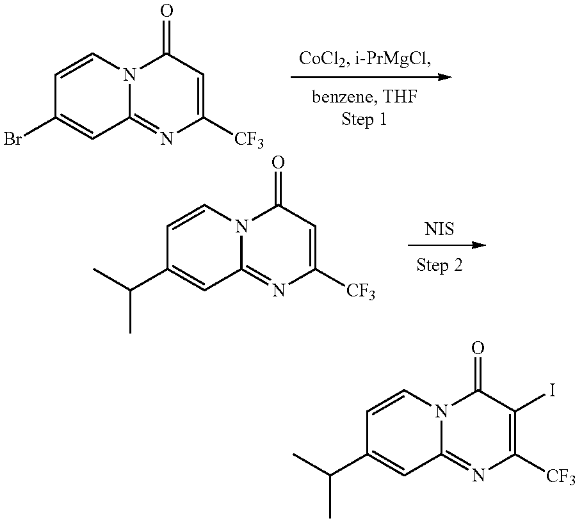

Step 1: 8-Isopropyl-2-(trifluoromethyl)-4H-pyrido[1,2-a]pyrimidin-4-one

Isopropyl magnesium chloride (2M in THF, 4.3 mL, 8.5 mmol,) was added drop wise to a solution of 8-bromo-2-(trifluoromethyl)-4H-pyrido[1,2-a]pyrimidin-4-one (1.0 g, 3.4 mmol, Intermediate 3-C) and $CoCl_2$ (0.22 g, 1.7 mmol) in benzene (10 mL) at rt under nitrogen atmosphere. The reaction mixture was stirred at 80° C. for 3 h. The reaction mixture was diluted with aq. 1.5 N HCl (5 mL) and extracted with ethyl acetate (2×25 mL). The combined organic layers were dried over sodium sulfate, filtered and concentrated under reduced pressure. The crude material was purified by silica gel chromatography (eluent: 0-40% EtOAc/hexane) to provide 8-isopropyl-2-(trifluoromethyl)-4H-pyrido[1,2-a]pyrimidin-4-one (350 mg, 40% yield) as off white solid. LC/MS ($ESI^+$) m/z=257.1 $[M+H]^+$. $^1H$ NMR (400 MHz, DMSO-$d_6$) δ 8.95 (dd, J=7.4, 3.2 Hz, 1H), 7.71-7.66 (m, 1H), 7.50 (dd, J=7.4, 1.9 Hz, 1H), 6.74 (d, J=2.4 Hz, 1H), 3.10 (h, J=6.9 Hz, 1H), 1.28 (d, J=6.9 Hz, 6H).

Step 2: 3-Iodo-8-isopropyl-2-(trifluoromethyl)-4H-pyrido[1,2-a]pyrimidin-4-one

The title compound was prepared using the procedure described for Intermediate 1-B, Step 2 with the following modification: Step 2 was performed with 8-isopropyl-2-(trifluoromethyl)-4H-pyrido[1,2-a]pyrimidin-4-one. LC/MS ($ESI^+$) m/z=383.0 $[M+H]^+$. $^1H$ NMR (400 MHz, DMSO-$d_6$) δ 8.96 (dd, J=7.3, 2.8 Hz, 1H), 7.72 (d, J=2.0 Hz, 1H), 7.56 (dd, J=7.4, 2.0 Hz, 1H), 3.13 (p, J=6.8 Hz, 1H), 1.29 (d, J=6.9 Hz, 6H).

Intermediate 1-N

3-Bromo-8-(methoxy-$d_3$)-2-(trifluoromethyl)-4H-pyrido[1,2-a]pyrimidin-4-one

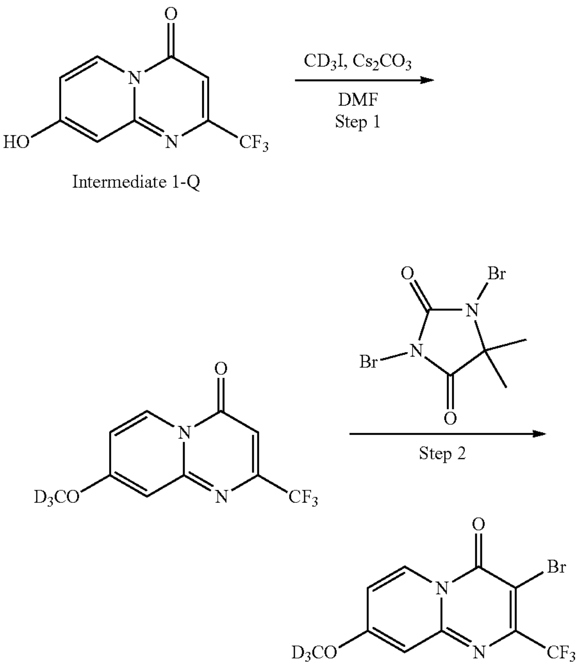

Step 1: 8-(Methoxy-$d_3$)-2-(trifluoromethyl)-4H-pyrido[1,2-a]pyrimidin-4-one

Iodomethane-$d_3$ (0.5 ml, 7.8 mmol) was added to a reaction mixture of 8-hydroxy-2-(trifluoromethyl)-4H-pyrido[1,2-a]pyrimidin-4-one (0.60 g, 2.6 mmol, Intermediate 1-Q) and cesium carbonate (1.3 g, 3.9 mmol) in DMF (14 ml) at 0° C. The reaction mixture was stirred at rt. After 1 h, the reaction mixture was diluted with water and EtOAc. The organic layer was separated, washed with water and brine, dried over $Na_2SO_4$ and concentrated in vacuo. The crude residue was purified by silica gel chromatography (eluent:0-100% EtOAc/heptane) to afford 8-(methoxy-$d_3$)-2-(trifluoromethyl)-4H-pyrido[1,2-a]pyrimidin-4-one as an off-white solid. LC/MS ($ESI^+$) m/z=248.0 $[M+H]^+$. $^1H$ NMR (400 MHz, $CDCl_3$) δ 6.61 (s, 1H) 6.91 (dd, J=7.88, 2.70 Hz, 1H) 7.04 (d, J=2.70 Hz, 1H) 8.96 (d, J=7.88 Hz, 1H).

Step 2: 3-Bromo-8-(methoxy-$d_3$)-2-(trifluoromethyl)-4H-pyrido[1,2-a]pyrimidin-4-one The title compound was prepared using the procedure described for Intermediate 1-C, Step 2 with the following modification: Step 2 was performed with 8-(methoxy-$d_3$)-2-(trifluoromethyl)-4H-pyrido[1,2-a]pyrimidin-4-one. LC/MS ($ESI^+$) m/z=326/328 $[M+H]^+$. $^1H$ NMR (400 MHz, DMSO-$d_6$) δ 7.25 (dd, J=7.88, 2.70 Hz, 1H) 7.31 (d, J=2.70 Hz, 1H) 8.91 (d, J=7.88 Hz, 1H).

Intermediate 1-0

3-Bromo-8-methoxy-2-(trifluoromethyl)pyrimido[1,2-a]pyrimidin-4-one

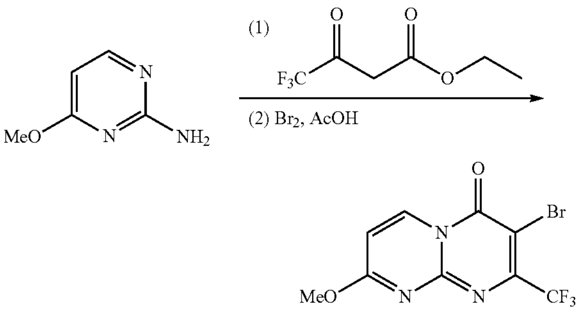

Step 1-1 and Step 1-2: 3-Bromo-8-methoxy-2-(trifluoromethyl)pyrimido[1,2-a]pyrimidin-4-one A reaction mixture of 4-methoxypyrimidin-2-amine (6.0 g, 48 mmol, Ark Pharm) and 4,4,4-trifluoro-3-oxobutanoic acid ethyl ester (26 mL, 144 mmol) in acetic acid (30 mL) was heated to reflux for 18 h. The reaction mixture was cooled to rt and bromine (2.5 mL, 48 mmol) was added dropwise and stirring was continued for at rt for 1 h. The reaction mixture was concentrated in vacuo and the residue was treated with water, satd $NaHCO_3$ solution, and EtOAc. The organic layer was separated and concentrated under reduced pressure. The crude residue was purified silica gel chromatography (eluent: 0-50% EtOAc/heptane to afford 3-bromo-8-methoxy-2-(trifluoromethyl)-4H-pyrimido[1,2-a]pyrimidin-4-one (1.0 g, 3.2 mmol, 7% yield). LC/MS ($ESI^+$) m/z=324.0/326.0 [M+H]+. H NMR (400 MHz, $CDCl_3$) δ 9.07 (d, J=7.63 Hz, 1H), 6.82 (d, J=7.63 Hz, 1H), 4.23 (s, 3H).

Intermediate 1-P

3-Bromo-2-(trifluoromethyl)-4H-pyrido[1,2-a]pyrimidin-4-one

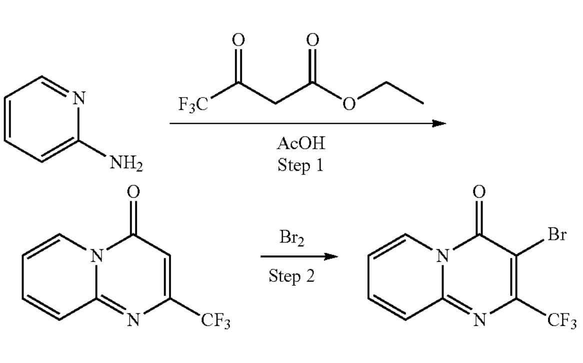

Steps 1 and 2 were performed according to the synthetic procedure described in WO2008097991. LC/MS ($ESI^+$) m/z=295.0 $[M+H]^+$.

Intermediate 1-Q

8-Hydroxy-2-(trifluoromethyl)-4H-pyrido[1,2-a]pyrimidin-4-one

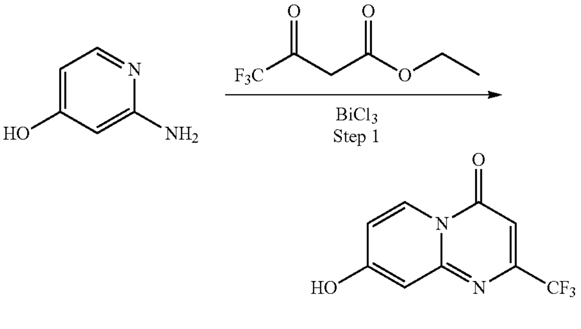

Step 1: 8-Hydroxy-2-(trifluoromethyl)-4H-pyrido[1,2-a]pyrimidin-4-one

The title compound was prepared using the procedure described for Intermediate 1-A, Step 1 with the following modification: Step 1 was performed with 2-aminopyridin-4-ol (Combi-Blocks Inc.). LC/MS (ESI) m/z=231.0 $[M+H]^+$.

Intermediate 1-R

3-Bromo-8-(methoxy-$d_3$)-2-(trifluoromethyl)-4H-pyrimido[1,2-a]pyrimidin-4-one

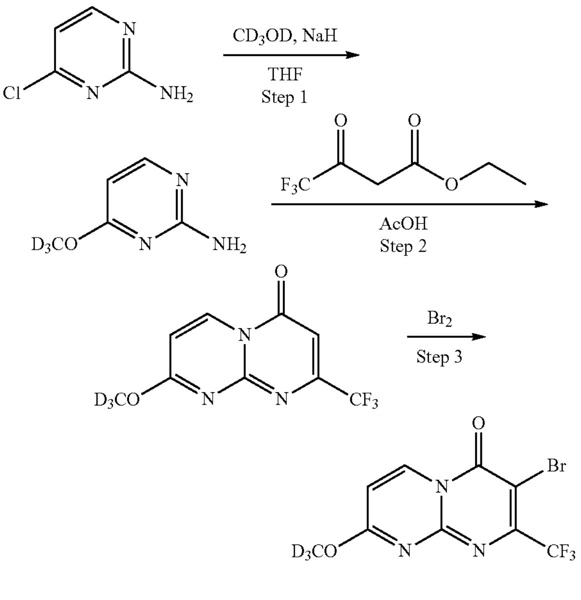

Step 1: 4-(Methoxy-$d_3$)pyrimidin-2-amine

MeOH-$d_4$ (0.41 mL, 10 mmol) was added dropwise to a suspension of sodium hydride (60% in mineral oil, 0.43 g, 10 mmol) in THF. The suspension was stirred for 10 mins and a solution of 2-amino-4-chloropyrimidine (1.0 g, 7.7 mmol, Asta Tech, Inc.) in THF was added slowly. After completed addition the reaction mixture was stirred at rt for 12 h, diluted with water and extracted with EtOAc. The organic phase was concentrated in vacuo to give 4-(methoxy-$d_3$)pyrimidin-2-amine (0.81 g, 6.3 mmol, 82% yield). The crude product was used in the next step without further purification. LC/MS ($ESI^+$) m/z=129.2 $[M+H]^+$.

Step 2: 8-(Methoxy-$d_3$)-2-(trifluoromethyl)-4H-pyrimido[1,2-a]pyrimidin-4-one

The title compound was prepared using the procedure described for Intermediate 1-C, Step 1 with the following modification: Step 1 was performed with 4-(methoxy-$d_3$) pyrimidin-2-amine (0.8 g, 6.3 mmol) and 4,4,4-trifluoro-3-oxobutanoic acid ethyl ester (1.85 mL, 12.6 mmol). LC/MS ($ESI^+$) m/z=249.1 $[M+H]^+$. $^1$H NMR (400 MHz, $CDCl_3$) δ 9.06 (d, J=7.67 Hz, 1H), 6.76 (d, J=7.67 Hz, 1H), 6.71 (s, 1H).

Step 3: 3-Bromo-8-(methoxy-$d_3$)-2-(trifluoromethyl)-4H-pyrimido[1,2-a]pyrimidin-4-one The title compound was prepared using the procedure described for Intermediate 1-A, Step 2 with the following modification: Step 2 was performed with 8-(methoxy-$d_3$)-2-(trifluoromethyl)-4H-pyrimido[1,2-a]pyrimidin-4-one. LC/MS ($ESI^+$) m/z=327.0/329.0 $[M+H]^+$. $^1$H NMR (400 MHz, DMSO-$d_6$) δ 9.06 (d, J=7.67 Hz, 1H), 7.12 (d, J=7.67 Hz, 1H).

Intermediate 1-S

3-Bromo-2-(fluoromethyl)-8-methoxy-4H-pyrido[1,2-a]pyrimidin-4-one

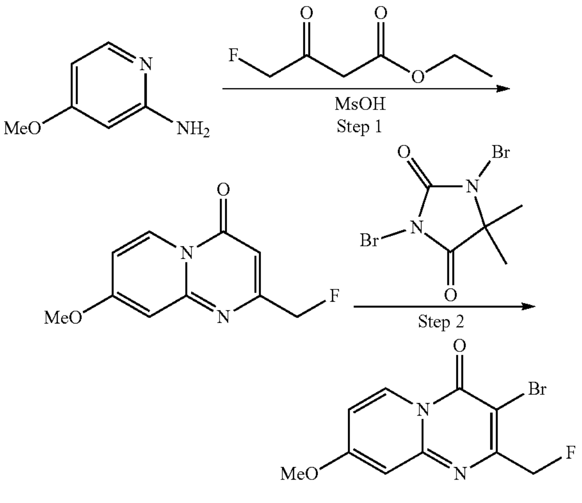

Step 1: 2-(Fluoromethyl)-8-methoxy-4H-pyrido[1,2-a]pyrimidin-4-one

A reaction mixture of 2-amino-4-methoxypyridine (0.5 g, 4.0 mmol, Combi-Blocks, Inc.) and ethyl 4-fluoro-3-oxobutanoate (1.1 g, 7.3 mmol, HCH Pharma) was heated to 120° C. After 20 min, methane sulfonic acid (0.5 ml, 8 mmol) was added. Heating was continued for 1 h. The reaction mixture was cooled to rt and treated with $CH_2Cl_2$ (20 mL) and water (40 mL). The pH was adjusted to pH=14 by dropwise addition of 5M NaOH solution. The organic phase was separated, washed with brine (5 mL), dried over $MgSO_4$, then concentrated under reduced pressure. The crude residue was purified by silica gel chromatography (eluent: 0-40% (3:1 EtOAc/EtOH)/heptane) to afford 2-(fluoromethyl)-8-methoxy-4H-pyrido[1,2-a]pyrimidin-4-one (40 mg, 0.19 mmol, 5% yield) as a white solid. LC/MS ($ESI^+$) m/z=209.1 $[M+H]^+$. $^1$H NMR (400 MHz, $CDCl_3$) δ 8.93 (d, J=7.46 Hz, 1H), 6.77-6.83 (m, 2H), 6.40-6.45 (m, 1H), 5.28 (t, J=46.60 Hz, 3H), 3.96 (s, 3H).

Step 2: 3-Bromo-2-(fluoromethyl)-8-methoxy-4H-pyrido[1,2-a]pyrimidin-4-one

The title compound was prepared using the procedure described for Intermediate 1-C, Step 2 with the following modification: Step 2 was performed with 2-(fluoromethyl)-8-methoxy-4H-pyrido[1,2-a]pyrimidin-4-one. LC/MS ($ESI^+$) m/z=287.0/289.0 $[M+H]^+$. $^1$H NMR (400 MHz, $CDCl_3$) δ 8.95 (d, J=7.88 Hz, 1H), 7.07 (d, J=2.49 Hz, 1H), 6.91 (dd, J=2.49, 7.88 Hz, 1H), 5.53 (d, J=46.65 Hz, 2H), 3.98-4.01 (m, 3H).

Intermediate 1-T

3-Bromo-2-ethyl-8-methoxy-4H-pyrido[1,2-a]pyrimidin-4-one

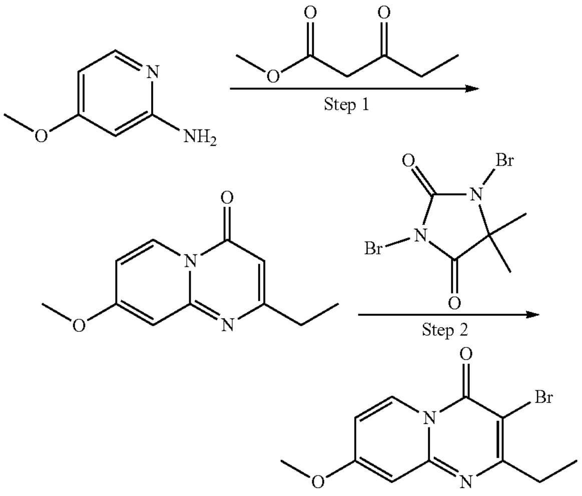

Step 1: 2-Ethyl-8-methoxy-4H-pyrido[1,2-a]pyrimidin-4-one

The title compound was prepared using the procedure described for Intermediate 1-C, Step 1 with the following modification: Step 1 was performed with methyl 3-oxopentanoate (TCI America). LC/MS ($ESI^+$) m/z=205.1 $[M+H]^+$. $^1$H NMR (400 MHz, $CDCl_3$) δ 8.90 (dd, J=8.0, 1.1 Hz, 1H), 6.90-6.85 (m, 1H), 6.77 (ddd, J=7.9, 2.7, 1.1 Hz, 1H), 6.19 (d, J=1.1 Hz, 1H), 3.96 (d, J=1.2 Hz, 3H), 2.67 (qd, J=7.6, 1.1 Hz, 2H), 1.31 (td, J=7.6, 1.2 Hz, 3H).

Step 2: 3-Bromo-2-ethyl-8-methoxy-4H-pyrido[1,2-a]pyrimidin-4-one

The title compound was prepared using the procedure described for Intermediate 1-C, Step 2 with the following modification: Step 2 was performed with 2-ethyl-8-methoxy-4H-pyrido[1,2-a]pyrimidin-4-one. LC/MS ($ESI^+$) m/z=283.0 $[M+H]^+$. $^1$H NMR (400 MHz, $CDCl_3$) δ 8.89 (t, J=7.7 Hz, 1H), 6.86 (dd, J=7.2, 2.8 Hz, 1H), 6.80 (dq, J=7.8, 2.7 Hz, 1H), 3.97 (d, J=4.0 Hz, 3H), 2.91 (p, J=7.4 Hz, 2H), 1.31 (td, J=7.4, 5.2 Hz, 3H).

Intermediate 1-U

3-Bromo-2-cyclopropyl-8-methoxy-4H-pyrido[1,2-a]pyrimidin-4-one

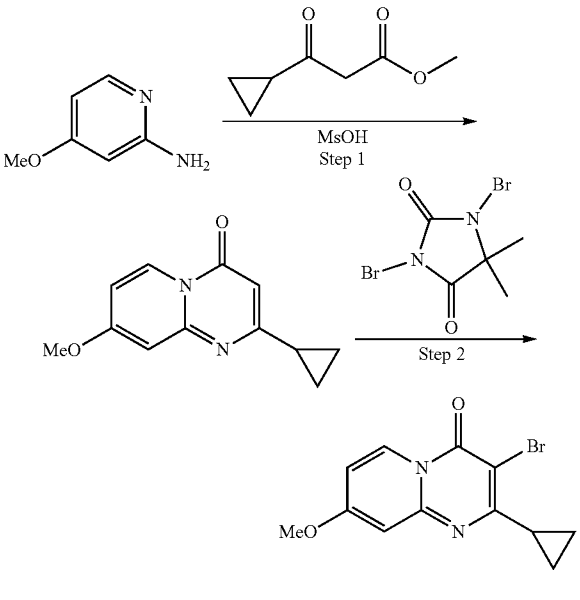

Step 1: 2-Cyclopropyl-8-methoxy-4H-pyrido[1,2-a]pyrimidin-4-one

The title compound was prepared using the procedure described for Intermediate 1-S, Step 1 with the following modification: Step 1 was performed with methyl 3-cyclopropyl-3-oxopropanoate (Accela ChemBio Inc.). LC/MS ($ESI^+$) m/z=217.2 $[M+H]^+$.

Step 2: 3-Bromo-2-cyclopropyl-8-methoxy-4H-pyrido[1,2-a]pyrimidin-4-one

The title compound was prepared using the procedure described for Intermediate 1-C, Step 2 with the following modification: Step 2 was performed with 2-cyclopropyl-8-methoxy-4H-pyrido[1,2-a]pyrimidin-4-one. LC/MS (ESIF) m/z=295.0/297.0 $[M+H]^+$.

Intermediate 1-V

3-Bromo-8-(difluoromethoxy)-2-(trifluoromethyl)-4H-pyrido[1,2-a]pyrimidin-4-one

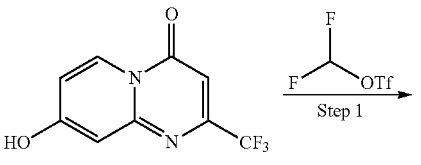

Intermediate 1-Q

-continued

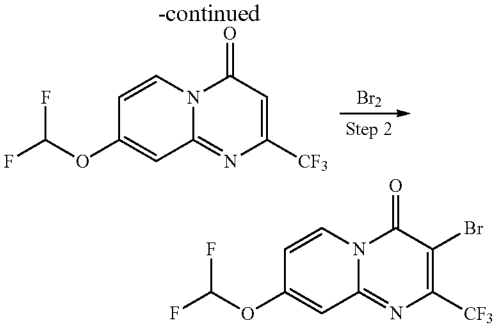

Step 1: 8-(Difluoromethoxy)-2-(trifluoromethyl)-4H-pyrido[1,2-a]pyrimidin-4-one

Difluoromethyl trifluoromethanesulfonate (0.4 g, 2.2 mmol, prepared according to procedure described in Levin et al., Journal of Fluorine Chemistry 130 (2009) 667-670) was added to a suspension of 8-hydroxy-2-(trifluoromethyl)-4H-pyrido[1,2-a]pyrimidin-4-one (0.1 g, 0.4 mmol, Intermediate 1-Q) and potassium hydroxide (0.29 g, 5.2 mmol) in acetonitrile (2 ml). The reaction mixture was stirred for 10 minutes at rt. The reaction was quenched by the addition of saturated ammonium chloride solution. The reaction mixture was diluted with EtOAc and water. The organic phase was separated, washed with brine, dried over magnesium sulfate and concentrated under reduced pressure. The crude residue was dissolved in EtOAc and treated with 1N NaOH. The organic layer was washed with additional 1N NaOH, followed by saturated ammonium chloride and brine. The organic phase was dried over magnesium sulfate and concentrated under reduced pressure to afford 8-(difluoromethoxy)-2-(trifluoromethyl)-4H-pyrido[1,2-a]pyrimidin-4-one (0.1 g, 0.36 mmol) (combined yield). MS ($ESI^+$) m/z=281.0 $[M+H]^+$.

Step 2: 3-Bromo-8-(difluoromethoxy)-2-(trifluoromethyl)-4H-pyrido[1,2-a]pyrimidin-4-one The title compound was prepared using the procedure described for Intermediate 1-A, Step 2 with the following modification: Step 2 was performed with 8-(difluoromethoxy)-2-(trifluoromethyl)-4H-pyrido[1,2-a]pyrimidin-4-one. LC/MS ($ESI^+$) m/z=358.8 $[M+H]^+$. $^1H$ NMR (400 MHz, $CD_2Cl_2$) δ 6.98-7.38 (m, 1H) 7.38-7.42 (m, 1H) 7.80 (d, J=7.67 Hz, 1H) 8.99 (dd, J=7.26, 1.04 Hz, 1H).

Intermediate 1-W

3-Bromo-8-methoxy-2-methyl-4H-pyrido[1,2-a]pyrimidin-4-one

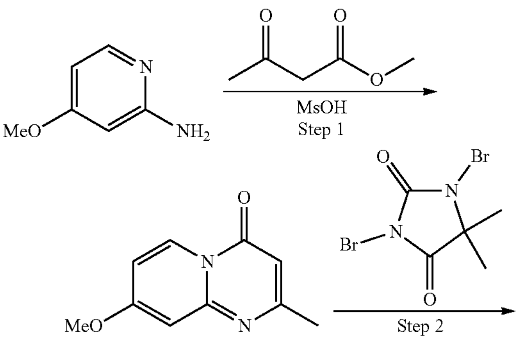

-continued

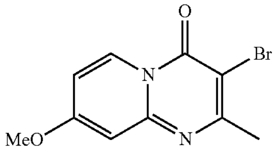

Step 1: 8-Methoxy-2-methyl-4H-pyrido[1,2-a]pyrimidin-4-one

The title compound was prepared using the procedure described for Intermediate 1-C, Step 1 with the following modification: Step 1 was performed with methyl acetoacetate. LC/MS ($ESI^+$) m/z=191.2 $[M+H]^+$.

Step 2: 3-Bromo-8-methoxy-2-methyl-4H-pyrido[1,2-a]pyrimidin-4-one

The title compound was prepared using the procedure described for Intermediate 1-C, Step 2 with the following modification: Step 2 was performed with 8-methoxy-2-methyl-4H-pyrido[1,2-a]pyrimidin-4-one. $^1H$ NMR (400 MHz, $CDCl_3$) δ 8.91 (d, J=7.88 Hz, 1H), 6.86 (d, J=2.49 Hz, 1H), 6.82 (dd, J=7.88, 2.70 Hz, 1H), 3.97 (s, 3H), 2.62 (s, 3H).

Intermediate 1-X

3-Bromo-8-cyclopropyl-2-(trifluoromethyl)-4H-pyrido[1,2-a]pyrimidin-4-one

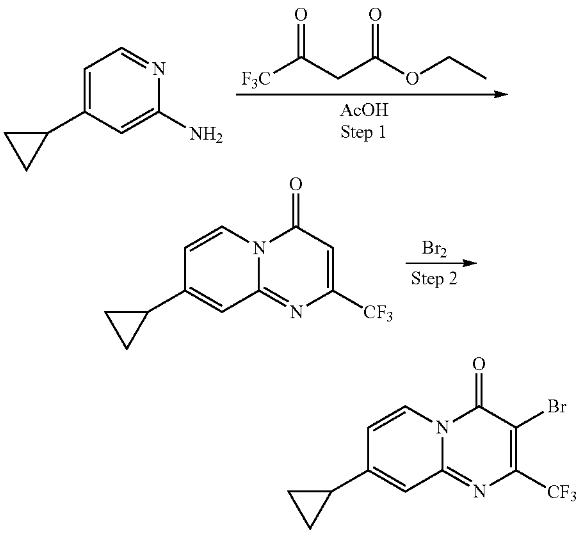

Step 1: 8-Cyclopropyl-2-(trifluoromethyl)-4H-pyrido[1,2-a]pyrimidin-4-one

The title compound was prepared using the procedure described for Intermediate 1-C, Step 1 with the following modification: Step 1 was performed with 4-cyclopropylpyridin-2-amine (ArkPharm). LC/MS ($ESI^+$) m/z=255.1 $[M+H]^+$.

Step 2: 3-Bromo-8-cyclopropyl-2-(trifluoromethyl)-4H-pyrido[1,2-a]pyrimidin-4-one The title compound was prepared using the procedure described for Intermediate 1-A, Step 2 with the following modification: Step 2 was performed with 8-cyclopropyl-2-(trifluoromethyl)-4H-pyrido[1,2-a]pyrimidin-4-one. LC/MS (ESI) m/z=332.9 $[M+H]^+$. $^1H$ NMR ($CDCl_3$, 400 MHz) δ 8.98 (d, J=7.5 Hz, 1H), 7.44 (d, J=1.9 Hz, 1H), 7.02 (dd, J=7.5, 1.9 Hz, 1H), 2.02-2.09 (m, 1H), 1.28-1.35 (m, 2H), 0.96-1.09 (m, 2H).

Intermediate 1-Y

8-Fluoro-3-iodo-2-(trifluoromethyl)-4H-pyrido[1,2-a]pyrimidin-4-one

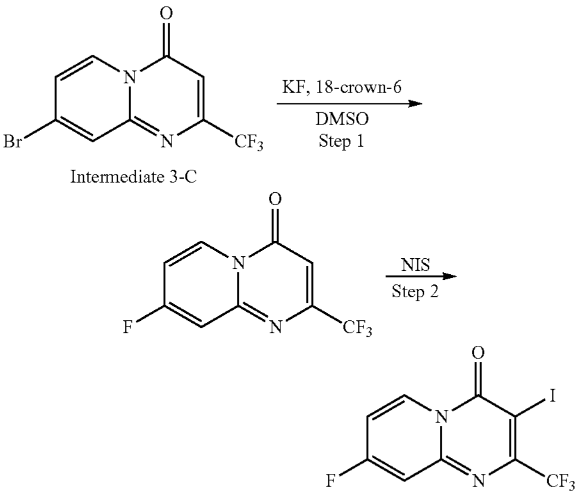

Step 1: 8-Fluoro-2-(trifluoromethyl)-4H-pyrido[1,2-a]pyrimidin-4-one

Potassium fluoride (0.3 g, 5.2 mmol) was added to a solution of 8-bromo-2-(trifluoromethyl)-4H-pyrido[1,2-a]pyrimidin-4-one (0.5 g, 1.7 mmol, Intermediate 3-C) in DMSO (5 mL) under nitrogen atmosphere. 18-Crown-6 (23 mg, 0.085 mmol) was added and the resulting reaction mixture was heated at 100° C. for 6 h. The reaction mixture was cooled to rt and quenched by the addition of ice (10 g). Stirring was continued for 15 min and the resulting precipitate was filtered off. The solid was washed with water (3×5 mL) and dried under reduced pressure to afford 8-fluoro-2-(trifluoromethyl)-4H-pyrido[1,2-a]pyrimidin-4-one (0.3 g, 76% yield). LC/MS ($ESI^+$) m/z=233.1 $[M+H]^+$. $^1H$ NMR (400 MHz, $CDCl_3$) δ 9.15 (dd, J=8.0, 6.2 Hz, 1H), 7.44 (dd, J=8.5, 2.8 Hz, 1H), 7.14 (ddd, J=8.6, 6.2, 2.8 Hz, 1H), 6.77 (s, 1H).

Step 2: 8-Fluoro-3-iodo-2-(trifluoromethyl)-4H-pyrido[1,2-a]pyrimidin-4-one

The title compound was prepared using the procedure described for Intermediate 1-B, Step 2 with the following modification: Step 2 was performed with 8-fluoro-2-(trifluoromethyl)-4H-pyrido[1,2-a]pyrimidin-4-one. LC/MS ($ESI^+$) m/z=359.1 $[M+H]^+$. $^1H$ NMR (400 MHz, DMSO-$d_6$) δ 9.13-9.08 (m, 1H), 7.86 (dd, J=9.2, 2.8 Hz, 1H), 7.63-7.57 (m, 1H).

Intermediate 1-Z

3-Iodo-8-(methyl-$d_3$)-2-(trifluoromethyl)-4H-pyrido[1,2-a]pyrimidin-4-one

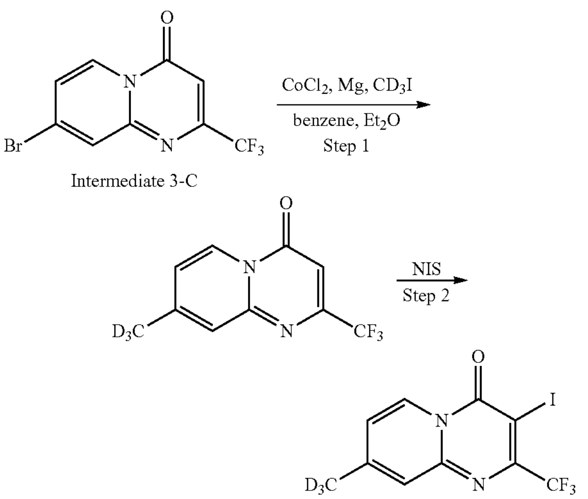

Step 1: 8-(Methyl-$d_3$)-2-(trifluoromethyl)-4H-pyrido[1,2-a]pyrimidin-4-one

Cobalt(II) chloride (0.2 g, 1.5 mmol) was added to a solution of 8-bromo-2-(trifluoromethyl)-4H-pyrido[1,2-a]pyrimidin-4-one (1.0 g, 3.4 mmol, Intermediate 3-C) in benzene (15 mL) at rt under nitrogen atmosphere. A separately prepared solution consisting of magnesium turnings (0.33 g, 13.7 mmol) and trideuteromethyl iodide (0.15 g, 10.2 mmol) in diethyl ether (10 mL), was added dropwise at rt. The reaction mixture was heated to 75° C. for 2 h. The reaction mixture was cooled to room temperature and quenched by addition of aqueous hydrochloric acid (1.5 N, 10 mL). After 10 min, the pH of the reaction mixture was adjusted to pH=8 by addition of $NaHCO_3$, followed by dilution with ethyl acetate (25 mL). The mixture was filtered through a pad of celite and washed with ethyl acetate (3×5 mL). The organic layer was separated, dried over anhydrous $Na_2SO_4$ and concentrated under reduced pressure. The crude material was purified by silica gel chromatography (eluent: 100% DCM) to provide 8-(methyl-$d_3$)-2-(trifluoromethyl)-4H-pyrido[1,2-a]pyrimidin-4-one (0.32 g, 40%) as a yellow solid. LC/MS ($ESI^+$) m/z=232.2 $[M+H]^+$. $^1H$ NMR (400 MHz, $CDCl_3$) δ 9.01 (d, J=7.3 Hz, 1H), 7.62 (d, J=1.8 Hz, 1H), 7.14 (dd, J=7.3, 1.9 Hz, 1H), 6.74 (s, 1H).

Step 2: 3-Iodo-8-(methyl-$d_3$)-2-(trifluoromethyl)-4H-pyrido[1,2-a]pyrimidin-4-one The title compound was prepared using the procedure described for Intermediate 1-B, Step 2 with the following modification: Step 2 was performed with 8-(methyl-$d_3$)-2-(trifluoromethyl)-4H-pyrido[1,2-a]pyrimidin-4-one. LC/MS ($ESI^+$) m/z=358.0 $[M+H]^+$. $^1H$ NMR (400 MHz, $CDCl_3$) δ 9.03 (d, J=7.3 Hz, 1H), 7.64 (d, J=1.9 Hz, 1H), 7.19 (dd, J=7.3, 1.8 Hz, 1H).

Intermediate 2-A 2-(4-((2,2-Difluorocyclopropyl)methoxy)phenyl)-4,4,5,5-tetramethyl-1,3,2-dioxaborolane

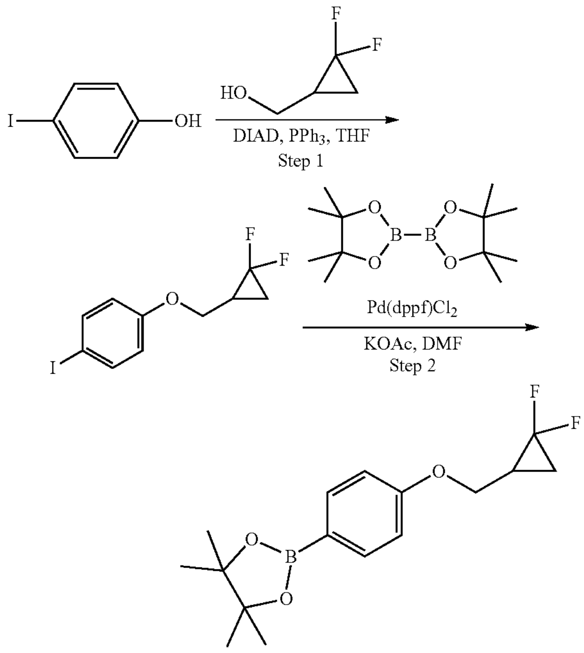

Step 1: 1-((2,2-Difluorocyclopropyl)methoxy)-4-iodobenzene

DIAD (3.6 g, 18 mmol) was added drop-wise to a stirred solution of 4-iodophenol (3.4 g, 15 mmol) and triphenylphosphine (4.7 g, 18 mmol) in tetrahydrofuran (34 mL) under nitrogen atmosphere at 0° C. After 10 min, (2,2-difluorocyclopropyl)methanol (1.5 g, 14 mmol) was added drop-wise and the reaction mixture was allowed to warm to rt and stirred further for 16 h. The reaction was quenched by addition of ice water (100 mL) and extracted with ethyl acetate (2×50 mL). The combined organic layers were dried over $Na_2SO_4$, filtered and concentrated under reduced pressure. The crude material was adsorbed onto a plug of silica gel and purified by silica gel chromatography (eluent: 0-3% of ethyl acetate/hexane) to afford 1-((2,2-difluorocyclopropyl)methoxy)-4-iodobenzene (1.8 g, 5.8 mmol, 42% yield). LC/MS ($ESI^+$) m/z=311.0 $[M+H]^+$. $^1H$ NMR (400 MHz, DMSO-$d_6$) δ 7.62-7.56 (m, 2H), 6.84-6.78 (m, 2H), 4.12 (ddd, J=10.3, 6.6, 3.1 Hz, 1H), 3.95 (ddd, J=10.6, 8.5, 1.8 Hz, 1H), 2.26-2.14 (m, 1H), 1.71 (tdd, J=12.1, 7.9, 4.8 Hz, 1H), 1.50-1.41 (m, 1H).

Step 2: 2-(4-((2,2-Difluorocyclopropyl)methoxy)phenyl)-4,4,5,5-tetramethyl-1,3,2-dioxaborolane A resealable vial was charged with 1-((2,2-difluorocyclopropyl)methoxy)-4-iodobenzene (1.6 g, 5.2 mmol), DMF (10 mL), bis(pinacolato)diboron (1.6 g, 6.2 mmol), and potassium acetate (2.0 g, 21 mmol). The reaction mixture was purged with nitrogen for 15 min and Pd(dppf)$Cl_2$ (0.38 g, 0.52 mmol) was added. The reaction mixture was heated to 90° C. for 16 h. The reaction mixture was filtered through a pad of celite and the filtrate was concentrated under reduced pressure. The crude material was purified by silica gel chromatography (eluent: 0-5% ethyl acetate/hexane) to afford 2-(4-((2,2-Difluorocyclopropyl)methoxy)phenyl)-4,4,5,5-tetramethyl-1,3,2-dioxaborolane (950 mg, 60% yield). $^1H$ NMR (400 MHz, DMSO-$d_6$) δ 7.64-7.59 (m, 2H), 6.97 (dd, J=8.7, 2.6 Hz, 2H), 4.17 (d, J=8.1 Hz, 1H), 4.00 (t, J=9.2 Hz, 1H), 2.25 (s, 1H), 1.74 (d, J=9.1 Hz, 1H), 1.52-1.44 (m, 1H), 1.30-1.27 (m, 12H).

Intermediate 2-B

2-Phenyl-5-(4,4,5,5-tetramethyl-1,3,2-dioxaborolan-2-yl)oxazole

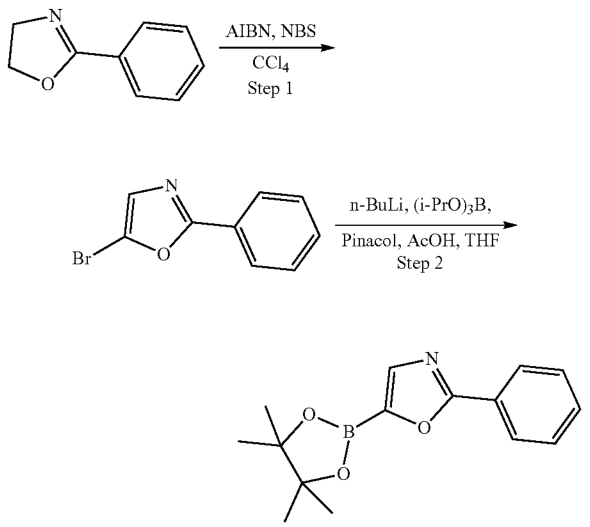

NBS (19 g, 106 mmol) and AIBN (0.67 g, 4.0 mmol, SpectroChem) were added consecutively to a solution of 2-phenyl-4,5-dihydrooxazole (6.0 g, 41 mmol, Arbor) in carbon tetrachloride (60 mL). The reaction mixture was heated to 85° C. for 2 h. The reaction mixture was cooled down to rt and filtered through a pad of celite. The filtrate was concentrated under reduced pressure. The crude material was purified by silica gel chromatography (eluent: 0-5% of ethyl acetate/hexane) to afford 5-bromo-2-phenyloxazol (4.2 g, 46% yield). LC/MS (ESI) m/z=224.0 $[M+H]^+$. $^1H$ NMR (400 MHz, $CDCl_3$) δ 8.05-7.99 (m, 2H), 7.52-7.46 (m, 3H), 7.13 (d, J=1.4 Hz, 1H).

Step 2: 2-Phenyl-5-(4,4,5,5-tetramethyl-1,3,2-dioxaborolan-2-yl)oxazole

N-butyl lithium (1.6 M in hexane, 0.61 mL, 0.982 mmol) was added to a solution of 5-bromo-2-phenyloxazol (200 mg, 0.89 mmol) in tetrahydrofuran (6 mL) at −78° C. under nitrogen atmosphere. The reaction mixture was stirred at −78° C. for 10 min, followed by the addition of triisopropyl borate (201 mg, 1.1 mmol). The reaction mixture was stirred for 30 min at −78° C. and allowed to warm to rt. After 30 min, 2,3-dimethylbutane-2,3-diol (127 mg, 1.1 mmol) and acetic acid (61 μL, 1.1 mmol) were added and stirring was continued at rt for 1 h. The reaction mixture was concentrated under reduced pressure to get a crude residue (400 mg), which was used without further purification.

Intermediate 2-C 2-(4-(2,2-Difluoroethoxy)phenyl)-4,4,5,5-tetramethyl-1,3,2-dioxaborolane

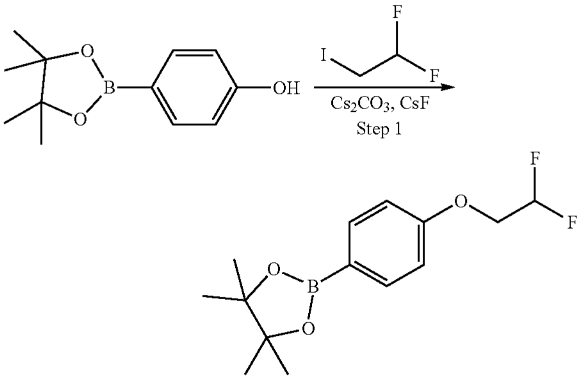

Step 1: 2-(4-(2,2-Difluoroethoxy)phenyl)-4,4,5,5-tetramethyl-1,3,2-dioxaborolane A mixture of 4-hydroxyphenylboronic acid pinacol ester (1.0 g, 4.5 mmol), dimethyl sulfoxide (20 mL), cesium carbonate (2.2 g, 6.8 mmol) and 1,1-difluoro-2-iodoethane (1.2 mL, 13.6 mmol, Matrix) was heated to 75° C. for 2 h. The reaction mixture was diluted with EtOAc and water. The organic phase was separated, dried over $Na_2SO_4$ and concentrated in vacuo. The crude residue was purified by silica gel chromatography (eluent: 0-50% EtOAc/heptane) to obtain 2-(4-(2,2-difluoroethoxy)phenyl)-4,4,5,5-tetramethyl-1,3,2-dioxaborolane (1.18 g, 4.15 mmol, 91% yield). LC/MS ($ESI^+$) m/z=285 $[M+H]^+$. $^1H$ NMR (400 MHz, $CDCl_3$) δ 1.33 (s, 12H) 4.11-4.31 (m, 2H) 5.86-6.27 (m, 1H) 6.91 (d, J=8.71 Hz, 2H) 7.77 (d, J=8.71 Hz, 2H).

Intermediate 2-D 4-(4,4,5,5-Tetramethyl-1,3,2-dioxaborolan-2-yl)-1-(3,3,3-trifluoropropyl)pyrazole

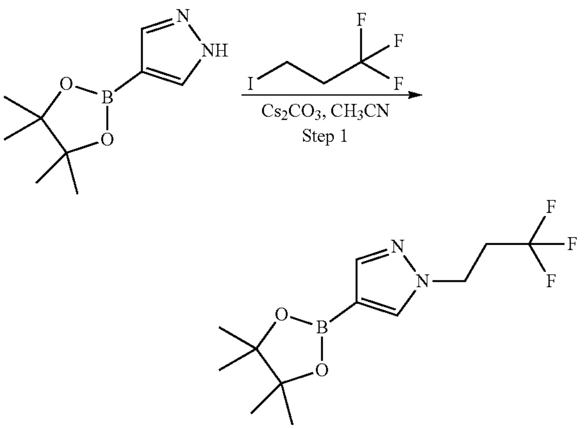

Step 1: 4-(4,4,5,5-Tetramethyl-1,3,2-dioxaborolan-2-yl)-1-(3,3,3-trifluoropropyl)pyrazole A resealable vial was charged with 4-pyrazoleboronic acid pinacol ester (500 mg, 2.6 mmol), acetonitrile (5 mL), cesium carbonate (1.7 g, 5.1 mmol), and 1,1,1-trifluoro-3-iodopropane (604 μl, 5.15 mmol, Oakwood). The reaction mixture was heated to 80° C. for 12 h. The reaction mixture was cooled to rt and filtered with EtOAc through a pad of celite. The filtrate was washed with brine and the organic phase was dried over sodium sulfate. The filtrate was concentrated under reduced pressure. The residue was purified by silica gel chromatography (eluent: 0-60% EtOAc/heptane) to afford 4-(4,4,5,5-tetramethyl-1,3,2-dioxaborolan-2-yl)-1-(3,3,3-trifluoropropyl)-1H-pyrazole (137 mg, 0.47 mmol, 18% yield). $^1$H NMR (400 MHz, $CDCl_3$) δ 1.32 (s, 13H) 2.74 (dt, J=10.37, 7.36 Hz, 2H) 4.37 (t, J=7.36 Hz, 2H) 7.71 (s, 1H) 7.81 (s, 1H).

Intermediate 2-E 4-(4,4,5,5-Tetramethyl-1,3,2-dioxaborolan-2-yl)-1-(4,4,4-trifluorobutyl)pyrazole

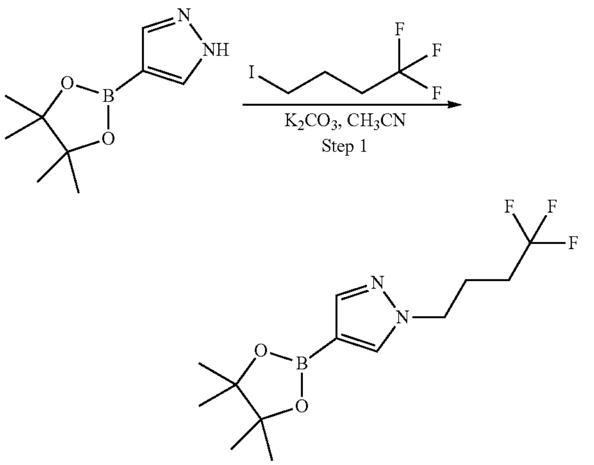

Step 1: 4-(4,4,5,5-Tetramethyl-1,3,2-dioxaborolan-2-yl)-1-(4,4,4-trifluorobutyl)pyrazole A resealable vial was charged with 4-pyrazoleboronic acid pinacol ester (500 mg, 2.58 mmol), acetonitrile (5 ml), potassium carbonate (0.53 g, 3.8 mmol), and 1,1,1-trifluoro-4-iodobutane (0.7 ml, 5.2 mmol, Oakwood). The reaction mixture was heated to 65° C. for 12 h. The reaction mixture was cooled to rt and partitioned between water and EtOAc. The organic phase was dried over sodium sulfate. The filtrate was concentrated under reduced pressure. The residue was purified by silica gel chromatography (eluent: 0-60% EtOAc/heptane) to afford 4-(4,4,5,5-tetramethyl-1,3,2-dioxaborolan-2-yl)-1-(4,4,4-trifluorobutyl)-1H-pyrazole (508 mg, 1.7 mmol, 65% yield). $^1$H NMR (400 MHz, $CDCl_3$) δ 1.33 (s, 13H) 1.99-2.11 (m, 2H) 2.11-2.23 (m, 2H) 4.22 (t, J=6.46 Hz, 2H) 7.69 (s, 1H) 7.81 (s, 1H).

Intermediate 2-F 2-(2-Fluoro-4-(2,2,2-trifluoroethoxy)phenyl)-4,4,5,5-tetramethyl-1,3,2-dioxaborolane

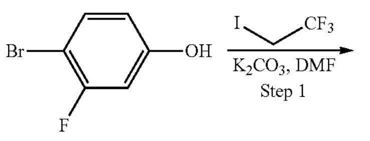

-continued

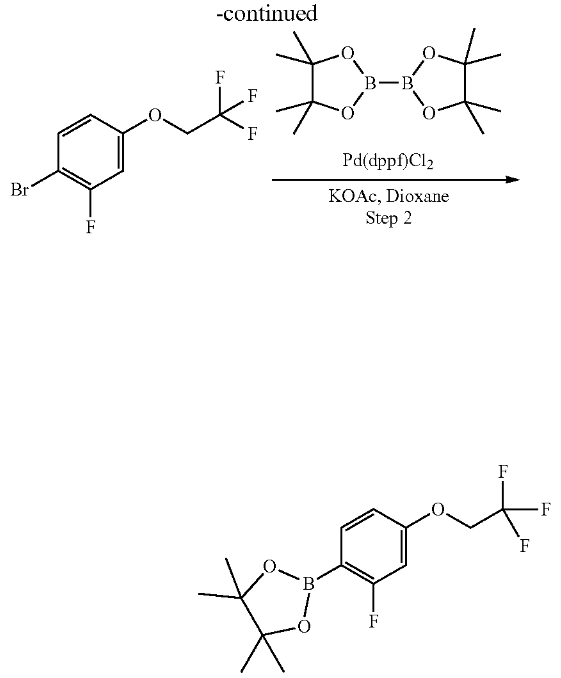

Step 1: 1-Bromo-2-fluoro-4-(2,2,2-trifluoroethoxy)benzene. 2,2,2-Trifluoroethyl iodide (4.6 ml, 47 mmol, Oakwood Products, Inc.) was added to a mixture of 4-bromo-3-fluorophenol (3.0 g, 15 mmol, Apollo Scientific, Ltd.) and potassium carbonate (4.3 g, 31 mmol) in DMF (30 ml). The reaction mixture was heated to 100° C. for 12 h. Additional 2,2,2-trifluoroethyl iodide (1.5 mL) was added and stirring was continued for 12 h. The reaction mixture was cooled rt and filtered with ethyl acetate through a pad of celite. The filtrate was washed with water, and brine and dried over $Na_2SO_4$. The filtrate was concentrated under reduced pressure and the crude residue was purified by silica gel chromatography(eluent: 0-20% ethyl acetate/heptane) to give 1-bromo-2-fluoro-4-(2,2,2-trifluoroethoxy)benzene (3.75 g, 13.7 mmol, 87% yield). $^1$H NMR ($CDCl_3$, 400 MHz): δ=7.48 (dd, J=8.8, 7.8 Hz, 1H), 6.77 (dd, J=9.8, 2.7 Hz, 1H), 6.67 (ddd, J=8.9, 2.9, 1.2 Hz, 1H), 4.34 (q, J=8.0 Hz, 2H).

Step 2: 2-(2-Fluoro-4-(2,2,2-trifluoroethoxy)phenyl)-4,4,5,5-tetramethyl-1,3,2-dioxaborolane A resealable vial was charged with 1-bromo-2-fluoro-4-(2,2,2-trifluoroethoxy)benzene (1.54 g, 5.64 mmol), bis(pinacolato)diboron (2.149 g, 8.46 mmol), potassium acetate (1.9 g, 19 mmol) and 1,4-dioxane (19 ml). The reaction mixture was purged for 5 min with argon, followed by the addition of $Pd(dppf)Cl_2$ (0.46 g, 0.56 mmol, Strem). The reaction mixture was heated to 100° C. for 18 h. The reaction mixture was cooled to rt and filtered with ethyl acetate through a pad of celite. The filtrate was concentrated under reduced pressure and the crude residue was purified by silica gel chromatography (eluent: 0-30% ethyl acetate/heptane) to give 2-(2-fluoro-4-(2,2,2-trifluoroethoxy)phenyl)-4,4,5,5-tetramethyl-1,3,2-dioxaborolane (1.37 g, 4.3 mmol, 76% yield). $^1$H NMR ($CDCl_3$, 400 MHz): δ=7.69 (dd, J=8.3, 7.1 Hz, 1H), 6.72 (dd, J=8.4, 2.3 Hz, 111), 6.61 (dd, J=10.6, 2.3 Hz, 1H), 4.35 (q, J=8.0 Hz, 2H), 1.34 (s, 12H).

Intermediate 2-G 1-(2,2,3,3,3-Pentafluoropropyl)-4-(4,4,5,5-tetramethyl-1,3,2-dioxaborolan-2-yl)-1H-pyrazole

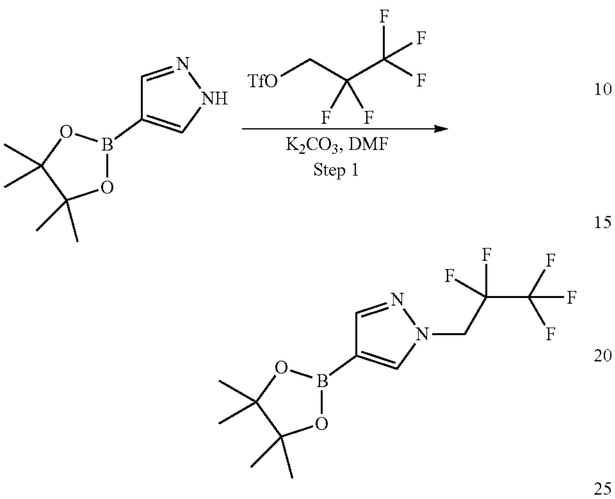

Step 1: 1-(2,2,3,3,3-Pentafluoropropyl)-4-(4,4,5,5-tetramethyl-1,3,2-dioxaborolan-2-yl)-1H-pyrazole A resealable vial was charged 4-pyrazoleboronic acid pinacol ester (0.5 g, 2.6 mmol) potassium carbonate (0.7 g, 5 mmol), DMF (3 ml), and 2,2,3,3,3-pentafluoropropyl trifluoromethanesulfonate (1.0 g, 3.5 mmol, Matrix Scientific). The reaction mixture was heated to 80° C. for 12 h. The reaction mixture was cooled to rt and partitioned between water (70 mL) and EtOAc (70 mL). The organic layer was dried over sodium sulfate, filtered, and adsorbed onto a pad of silica gel. Purification by silica gel chromatography (eluent: 0-60% EtOAc/heptane) afforded 1-(2,2,3,3,3-pentafluoropropyl)-4-(4,4,5,5-tetramethyl-1,3,2-dioxaborolan-2-yl)-1H-pyrazole (289 mg, 0.9 mmol, 34% yield) which was carried forward in the next reaction without further purification. $^1$H NMR (400 MHz, $CDCl_3$) δ 1.32 (s, 16H) 4.75 (t, J=14.10 Hz, 2H) 7.80 (s, 1H) 7.84 (s, 1H).

Intermediate 2-H 3-(4-(4,4,5,5-Tetramethyl-1,3,2-dioxaborolan-2-yl)-1H-pyrazol-1-yl)propanenitrile

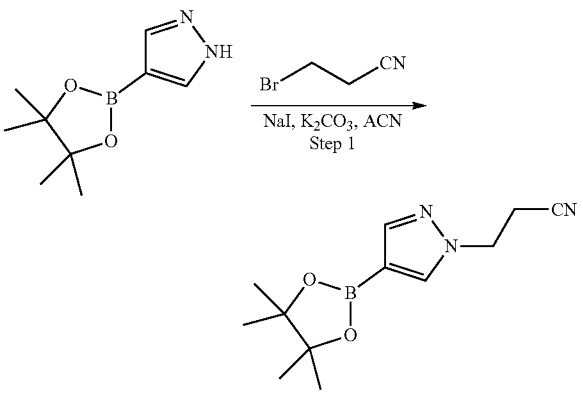

Step 1: 3-(4-(4,4,5,5-Tetramethyl-1,3,2-dioxaborolan-2-yl)-1H-pyrazol-1-yl)propanenitrile 3-Bromo-propionitrile (2.1 g, 15 mmol, Combi-Blocks Inc.), sodium iodide (0.154 g, 1.03 mmol) and potassium carbonate (2.1 g, 15 mmol) were added consecutively to a suspension of 4-(4,4,5,5-tetramethyl-1,3,2-dioxaborolan-2-yl)-1H-pyrazole (2.0 g, 10.3 mmol, 1.0 eq.) in acetonitrile (20 mL). The reaction mixture was heated at 60° C. for 12 h.

The reaction mixture was cooled to room temperature and concentrated under reduced pressure. The residue was partitioned between water and ethyl acetate. The organic layer was washed with brine and dried over $Na_2SO_4$. The filtrate was concentrated under reduced pressure to get the 3-(4-(4,4,5,5-tetramethyl-1,3,2-dioxaborolan-2-yl)-1H-pyrazol-1-yl)propanenitrile (2.5 g, 10.1 mmol, 98% yield) as a yellow liquid which was used for next step without further purification. LC/MS (ESI$^+$) m/z=248.1 [M+H]$^+$. $^1$H NMR (400 MHz, DMSO-$d_6$) δ 8.04 (s, 1H), 7.65 (s, 1H), 4.41 (t, J=6.4 Hz, 2H), 3.07 (t, J=6.4 Hz, 2H), 1.26 (s, 12H).

Intermediate 2-I 2-(4-(4,4,5,5-Tetramethyl-1,3,2-dioxaborolan-2-yl)-1H-pyrazol-1-yl) acetonitrile

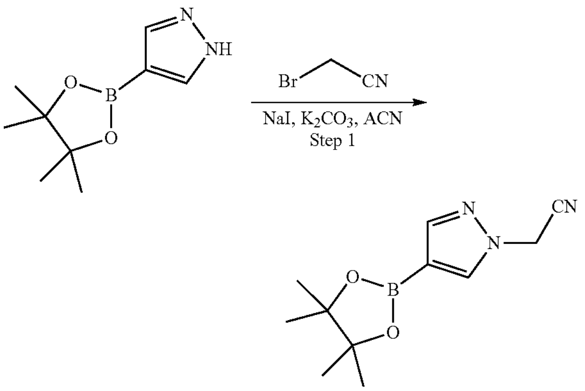

Step 1: 2-(4-(4,4,5,5-Tetramethyl-1,3,2-dioxaborolan-2-yl)-1H-pyrazol-1-yl) acetonitrile The title compound was prepared using the procedure described for Intermediate 2-H, Step 1 with the following modification: Step 1 was performed with 4-(4,4,5,5-tetramethyl-1,3,2-dioxaborolan-2-yl)-1H-pyrazole (2.0 g, 10 mmol, Combi-Blocks Inc.) and 2-bromoacetonitrile (4.95 g, 41.2 mmol, Spectrochem). LC/MS (ESI$^+$) m/z=234.2 [M+H]$^+$. $^1$H NMR (400 MHz, $CDCl_3$) δ 7.85 (s, 2H), 5.10 (s, 2H), 1.33 (s, 12H).

Intermediate 2-J 1-(2,2-Difluoropropyl)-4-(4,4,5,5-tetramethyl-1,3,2-dioxaborolan-2-yl)-1H-pyrazole

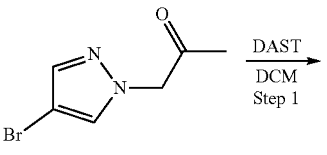

-continued

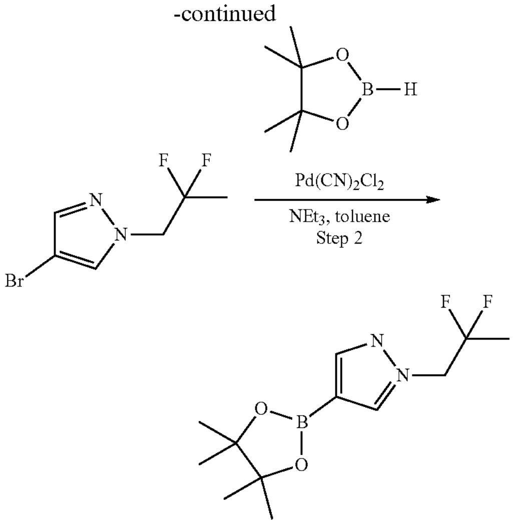

Step 1: 4-Bromo-1-(2,2-difluoropropyl)-1H-pyrazole

A solution of diethylaminosulfur trifluoride (0.84 mL, 6.3 mmol) in DCM (2 mL) was added drop-wise to a solution of 1-(4-bromo-1H-pyrazol-1-yl)propan-2-one (0.33 g, 1.6 mmol, Enamine Ltd) in DCM (10 mL) at −78° C. The reaction mixture was allowed to warm to room temp over the course of 12 h. The reaction mixture was cooled to 0° C. and quenched by the addition of 1 N sodium thiosulfate (20 mL), followed by partitioning between EtOAc and water. The organic extract was washed with brine, dried over sodium sulfate, filtered, and adsorbed onto silica gel. Purification by silica gel chromatography (eluent: 0-100% EtOAc/heptane) afforded 4-bromo-1-(2,2-difluoropropyl)-1H-pyrazole (220 mg, 0.98 mmol, 61% yield) of 4-bromo-1-(2,2-difluoropropyl)-1H-pyrazole. $^{1}H$ NMR (400 MHz, $CDCl_3$) δ 1.57 (t, J=18.66 Hz, 3H) 4.43 (t, J=12.02 Hz, 2H) 7.51 (s, 1H) 7.53 (s, 1H).

Step 2: 1-(2,2-Difluoropropyl)-4-(4,4,5,5-tetramethyl-1,3,2-dioxaborolan-2-yl)-1H-pyrazole A resealable vial was charged with 4-bromo-1-(2,2-difluoropropyl)-1H-pyrazole (0.31 g, 1.4 mmol), bis(acetonitrile)dichloropalladium(II) (11 mg, 0.04 mmol, Strem) and 2-dicyclohexylphosphino-2,6'-dimethoxy-1,1'-biphenyl (51 mg, 0.12 mmol, Strem). The vial was evacuated and backfilled with nitrogen. This procedure was repeated 3 times. Toluene (1.8 ml) was added, followed by pinacolborane (0.24 ml, 1.6 mmol) and triethylamine (0.48 ml, 3.4 mmol). Additional toluene (0.7 ml) was added. The reaction mixture was heated to 90° C. for 12 h. The reaction mixture was filtered through a plug of silica gel and concentrated under pressure. The crude residue was purified by silica gel chromatography (eluent: 0-50% EtOAc/heptane) to afford 1-(2,2-difluoropropyl)-4-(4,4,5,5-tetramethyl-1,3,2-dioxaborolan-2-yl)-1H-pyrazole (164 mg, 0.6 mmol, 44% yield). $^{1}H$ NMR (400 MHz, $CDCl_3$) δ 1.33 (s, 12H) 1.56 (m, 3H) 4.47 (t, J=12.02 Hz, 2H) 7.79 (s, 1H) 7.81 (s, 1H).

Intermediate 2-K 2-(Fluoromethyl)-3-iodo-4-oxo-4H-pyrido[1,2-a]pyrimidine-8-carbonitrile

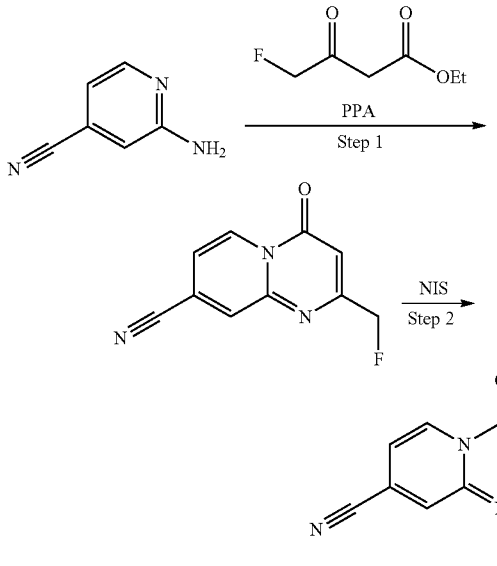

Step 1: 2-(Fluoromethyl)-4-oxo-4H-pyrido[1,2-a]pyrimidine-8-carbonitrile

Polyphosphoric acid (~700 μL) was added to a suspension of ethyl 4-fluoro-3-oxobutanoate (0.4 g, 2.7 mmol, HCH Pharma) and 2-aminopyridine-4-carbonitrile (0.32 mg, 2.7 mmol, Fluorochem). The reaction mixture was heated to 90° C. for 6 h. The reaction mixture was poured into 50 mL of water and extracted with EtOAc (2×). The organic layer was dried, filtered and concentrated under reduced pressure. The residue was dissolved in THF (15 mL) and pyridine (0.3 mL, 4 mmol) was added followed by trifluoroacetic anhydride (370 uL, 2.7 mmol). The resulting mixture was stirred at room temperature for 1 h, then quenched with water and extracted with EtOAc. The organic layer was dried, filtered and concentrated and the residue was purified by silica gel chromatography (eluent: 50% EtOAc/cyclohexane) to give 2-(fluoromethyl)-4-oxopyrido[1,2-a]pyrimidine-8-carbonitrile (290 mg, 1.43 mmol, 53% yield). LC/MS ($ESI^+$) m/z=204.0 $[M+H]^+$. $^{1}H$ NMR (400 MHz, DMSO-$d_6$) δ 5.34-5.61 (d, 2H) 6.55-6.61 (s, 1H) 7.46-7.60 (d, 1H) 8.34-8.43 (s, 1H) 8.93-9.01 (d, 1H).

Step 2: 2-(Fluoromethyl)-3-iodo-4-oxo-4H-pyrido[1,2-a]pyrimidine-8-carbonitrile

The title compound was prepared using the procedure described for Intermediate 1-B, Step 2 with the following modification: Step 2 was performed with 2-(fluoromethyl)-4-oxo-4H-pyrido[1,2-a]pyrimidine-8-carbonitrile. LC/MS ($ESI^+$) m/z=402.1 $[M+H]^+$. $^{1}H$ NMR (400 MHz, DMSO-$d_6$) δ 5.43-5.64 (d, 2H) 7.64 (d, J=7.48, 1H) 8.49-8.54 (s, 1H) 8.96-9.03 (d, 1H).

Intermediate 2-L

(2-Fluoro-4-(2,2,2-trifluoroethoxy)phenyl)boronic acid

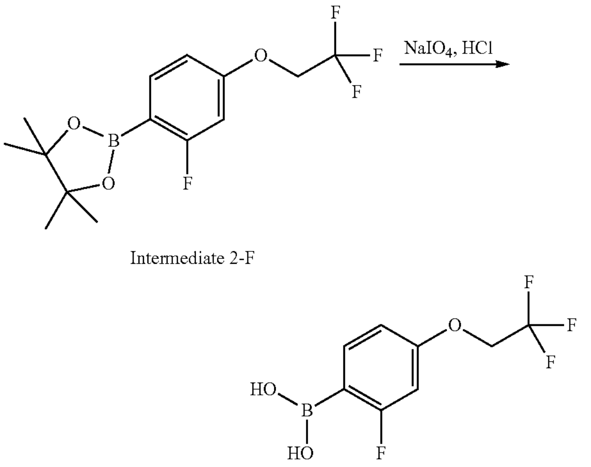

Step 1: (2-Fluoro-4-(2,2,2-trifluoroethoxy)phenyl)boronic acid

Sodium periodate (0.13 ml, 2.3 mmol) was added to a solution of 2-(2-fluoro-4-(2,2,2-trifluoroethoxy)phenyl)-4,4,5,5-tetramethyl-1,3,2-dioxaborolane (0.25 g, 0.78 mmol, Intermediate 2-F) in THF:water concentrated under reduced pressure to afford (2-fluoro-4-(2,2,2-trifluoroethoxy)phenyl) boronic acid. $^1$H NMR (400 MHz, DMSO-$d_6$) δ 8.02 (s, 1H) 7.49-7.81 (m, 1H) 6.76-6.97 (m, 2H) 4.81 (q, J=8.85 Hz, 2H). (1:1, 10 ml) and 1N hydrochloric acid (5 ml). After 20 min, the reaction mixture was partitioned between EtOAc and water. The organic layer was washed with brine, dried over magnesium sulfate and Intermediate 2-M

4-(4,4,5,5-Tetramethyl-1,3,2-dioxaborolan-2-yl)-1-(2,2,2-trifluoroethyl)-1H-pyrazole

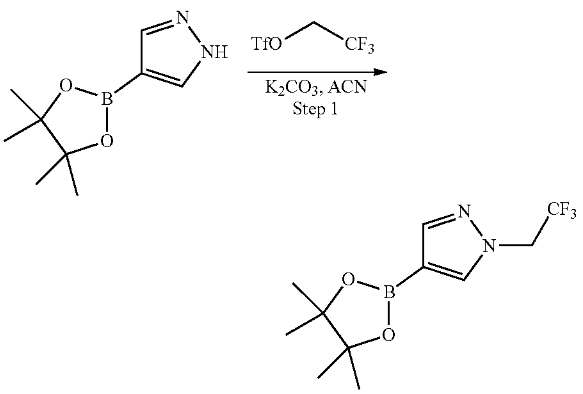

Step 1: 4-(4,4,5,5-Tetramethyl-1,3,2-dioxaborolan-2-yl)-1-(2,2,2-trifluoroethyl)-1H-pyrazole 2,2,2-Trifluoroethyl triflate (0.37 ml, 2.6 mmol, Oakwood Products) was added to a mixture of 4-pyrazoleboronic acid pinacol ester (0.25 g, 1.3 mmol), potassium carbonate (0.27 g, 1.9 mmol), and acetonitrile (2.6 ml). The reaction mixture was heated to 65° C. for 12 h. The reaction mixture cooled to rt and partitioned between water (70 mL) and EtOAc (70 mL). The organic layer was dried over sodium sulfate, filtered, and concentrated under reduced pressure. Purification by silica gel chromatography afforded 4-(4,4,5,5-tetramethyl-1,3,2-dioxaborolan-2-yl)-1-(2,2,2-trifluoroethyl)-1H-pyrazole (133 mg, 0.48 mmol, 37% yield). $^1$H NMR (400 MHz, $CD_2Cl_2$) δ 1.30 (s, 13H) 4.74 (q, J=8.41 Hz, 2H) 7.75 (s, 1H) 7.79 (s, 1H).

Intermediate 2-N

2-(3-Chloro-4-(2,2,2-trifluoroethoxy)phenyl)-4,4,5,5-tetramethyl-1,3,2-dioxaborolane

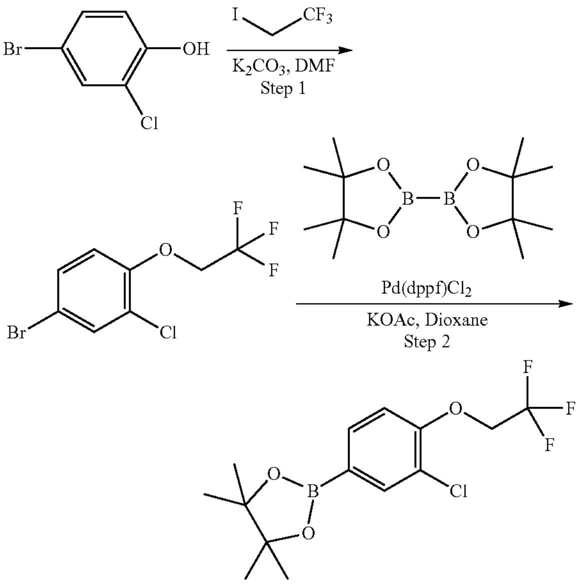

Step 1: 4-Bromo-2-chloro-1-(2,2,2-trifluoroethoxy)benzene 1,1,1-Trifluoro-2-iodoethane (4.2 ml, 43 mmol, Oakwood Products, Inc.) was added to a mixture of 2-chloro-4-bromophenol (3.0 ml, 14 mmol) and potassium carbonate (4.0 g, 29 mmol) in DMF (30 ml). The reaction mixture was heated to 100° C. for 12 h. The reaction mixture was cooled to rt and filtered with EtOAc through a pad of celite. The filtrate was washed with water and brine, dried over $Na_2SO_4$ and concentrated under reduced pressure. The crude residue was purified by silica gel chromatography (eluent: 0-20% ethyl acetate/heptane) to give 4-bromo-2-chloro-1-(2,2,2-trifluoroethoxy)benzene (2.8 g, 9.7 mmol, 67% yield). $^1$H NMR ($CDCl_3$, 400 MHz): δ=7.55 (d, J=2.3 Hz, 1H), 7.36 (dd, J=8.7, 2.4 Hz, 1H), 6.86 (d, J=8.8 Hz, 1H), 4.38 (q, J=8.0 Hz, 2H).

Step 2: 2-(3-Chloro-4-(2,2,2-trifluoroethoxy)phenyl)-4,4,5,5-tetramethyl-1,3,2-dioxaborolane A mixture of 4-bromo-2-chloro-1-(2,2,2-trifluoroethoxy) benzene (1.7 g, 6.0 mmol), bis(pinacolato)diboron (2.3 g, 9.0 mmol), potassium acetate (2.1, 21 mmol) and Pd(dppf) $Cl_2$ (0.49 g, 0.6 mmol, Strem) in dioxane (20 ml) was purged with argon for 5 minutes. The reaction mixture was heated to 110° C. for 12 h. The reaction mixture was cooled tor rt and filtered with EtOAc through a pad of celite. The filtrate was concentrated under reduced pressure and the residue was purified by silica gel chromatography (eluent: 0-20% ethyl acetate/heptane) to give (1.38 g, 4.1 mmol, 68% yield). $^1$H NMR ($CDCl_3$, 400 MHz): δ=7.77 (d, J=1.6 Hz, 1H), 7.59 (dd, J=8.1, 1.5 Hz, 1H), 6.85 (d, J=8.2 Hz, 1H), 4.35 (q, J=8.0 Hz, 2H), 1.26 (s, 12H).

Intermediate 2-O

3-Bromo-2-fluoro-6-(2,2,2-trifluoroethoxy)pyridine

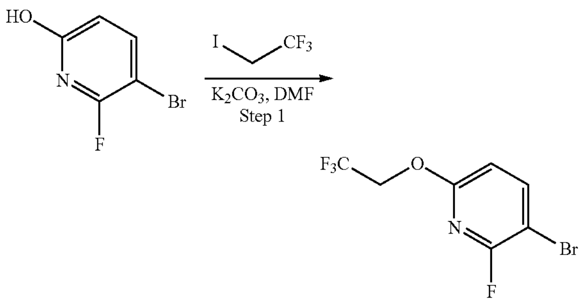

Step 1: 3-Bromo-2-fluoro-6-(2,2,2-trifluoroethoxy)pyridine 1,1,1-Trifluoro-2-iodoethane (0.76 ml, 7.8 mmol, Oakwood Chemical, Estill, SC, USA) was added to a mixture of 3-bromo-2-fluoro-6-hydroxypyridine (500 mg, 2.6 mmol, Combi-Blocks, San Diego, CA, USA) and potassium carbonate (0.72 g, 5.2 mmol) in DMF (5 ml) under argon atmosphere. The reaction mixture was heated to 100° C. for 12 hours. The reaction mixture was cooled to rt and filtered with EtOAc through a pad of celite. The filtrate was washed with water and brine, dried over $Na_2SO_4$ and concentrated under reduced pressure. The crude residue was purified by silica gel chromatography (eluent: 0-10% ethyl acetate/heptane) to give 3-bromo-2-fluoro-6-(2,2,2-trifluoroethoxy)pyridine (0.71 g, 0.91 mmol, 35% yield). LC/MS ($ESI^+$) m/z=274.0 $[M+H]^+$.

Intermediate 2-P

2-Bromo-5-(2,2,2-trifluoroethoxy)pyridine

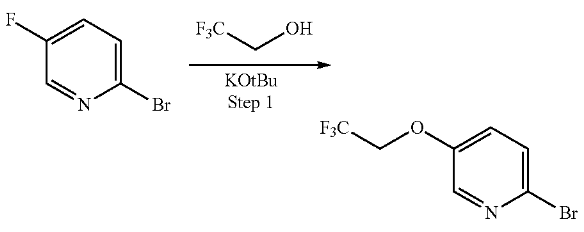

Step 1: 2-Bromo-5-(2,2,2-trifluoroethoxy)pyridine

A resealable vial was charged with 2,2,2-trifluoroethanol (0.42 ml, 5.7 mmol), potassium-tert-butoxide (1M in THF, 5.7 ml, 5.7 mmol), 2-bromo-5-fluoropyridine (1.0 g, 5.68 mmol) and THF (6 ml). The reaction mixture was heated to 70° C. for 60 hours. The reaction mixture was cooled to ambient temperature and partitioned between water and EtOAc. The organic phase was dried over $MgSO_4$ and concentrated in vacuo. The crude residue was purified via silica gel chromatography (eluent: 0-10% EtOAc/heptane) to afford 2-bromo-5-(2,2,2-trifluoroethoxy)pyridine (150 mg, 0.59 mmol, 10% yield) as a solid.

LC/MS ($ESI^+$) m/z=256.0 $[M+H]^+$.

Intermediate 2-Q

5-Bromo-3-fluoro-2-(2,2,2-trifluoroethoxy)pyridine

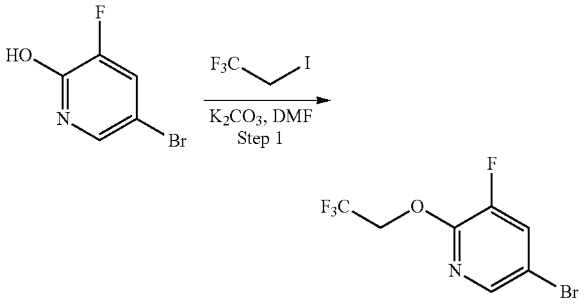

Step 1: 5-Bromo-3-fluoro-2-(2,2,2-trifluoroethoxy)pyridine 1,1,1-Trifluoro-2-iodoethane (2.3 ml, mmol, Oakwood Chemical, Estill, SC, USA) was added to a mixture of 5-bromo-3-fluoropyridin-2-ol (1.5 g, 7.8 mmol, Combi-Blocks, San Diego, CA, USA) and potassium carbonate (2.2 g, 15.6 mmol) in DMF (10 ml) under argon atmosphere. The reaction was heated to 100° C. for 12 h. The reaction mixture was cooled to rt and filtered with EtOAc through a pad of celite. The filtrate was washed with water and brine, dried over $Na_2SO_4$ and concentrated under reduced pressure. The crude residue was purified by silica gel chromatography (eluent: 0-10% ethyl acetate/heptane) to give 5-bromo-3-fluoro-2-(2,2,2-trifluoroethoxy)pyridine (1.28 g, 4.67 mmol, 60% yield). LC/MS ($ESI^+$) m/z=274.0 $[M+H]^+$.

Intermediate 2-R

5-Bromo-2-(2,2,2-trifluoroethoxy)pyridine

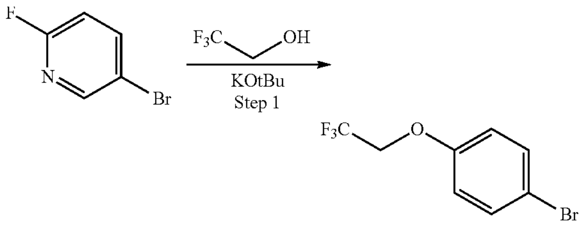

Step 1: 5-Bromo-2-(2,2,2-trifluoroethoxy)pyridine

The title compound was prepared using the procedure described for Intermediate 2-P, Step 1 with the following modification: Step 1 was performed with 5-bromo-2-fluoropyridine. LC/MS ($ESI^+$) m/z=255.8 [M+H]+/258.0 [M+2]+.

Intermediate 2-S (2-Methyl-4-(2,2,2-trifluoroethoxy)phenyl)boronic acid

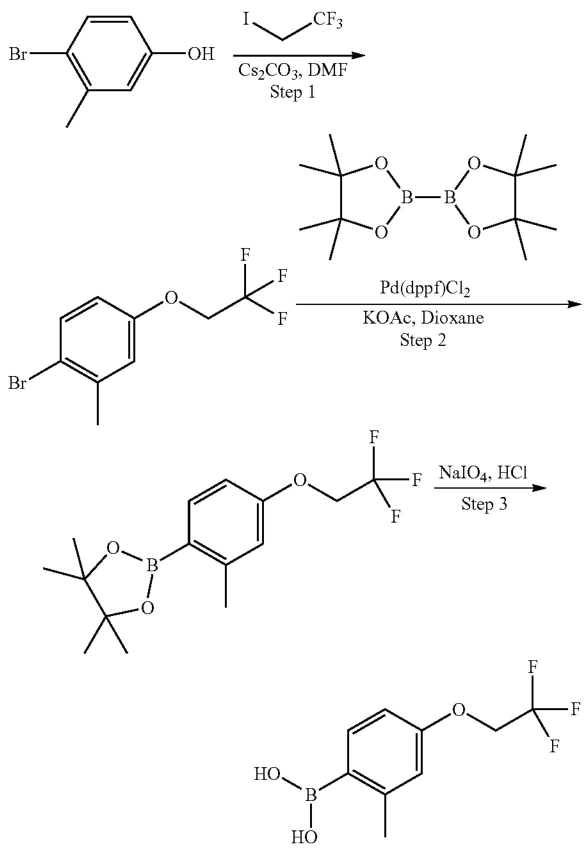

Step 1: 1-Bromo-2-methyl-4-(2,2,2-trifluoroethoxy)benzene

A vial was charged with 4-bromo-3-methylphenol (1 g, 5.4 mmol), 1,1,1-trifluoro-2-iodoethane (4.5 g, 21.4 mmol, Oakwood), DMF (5 ml) and cesium carbonate (3.5 g, 10.7 mmol). The reaction mixture was heated to 60° C. for 48 h. The reaction mixture was cooled to rt and partitioned between EtOAc and water. The organic phase was separated, washed with water and brine, and dried over $MgSO_4$. The filtrate was absorbed onto a pad of silica gel. Purification by silica gel chromatography (eluent: 0-10% (3:1 EtOAc/EtOH)/heptane) provided 1-bromo-2-methyl-4-(2,2,2-trifluoroethoxy)benzene (1.1 g, 4.1 mmol, 76% yield) $^1H$ NMR ($CDCl_3$, 400 MHz) δ 7.37 (d, J=8.7 Hz, 1H), 6.77 (d, J=3.1 Hz, 1H), 6.58 (dd, J=8.7, 3.1 Hz, 1H), 4.24 (q, J=8.2 Hz, 2H), 2.31 (s, 3H).

Step 2: 4,4,5,5-Tetramethyl-2-(2-methyl-4-(2,2,2-trifluoroethoxy)phenyl)-1,3,2-dioxaborolane The title compound was prepared using the procedure described for Intermediate 2-N, Step 2 with the following modification: Step 2 was performed with 1-bromo-2-methyl-4-(2,2,2-trifluoroethoxy)benzene. $^1H$ NMR ($CDCl_3$, 400 MHz) δ 7.74 (br d, J=8.3 Hz, 1H), 6.64-6.79 (m, 2H), 4.29-4.40 (m, 2H), 2.53 (s, 3H), 1.31-1.38 (m, 12H).

Step 3: (2-Methyl-4-(2,2,2-trifluoroethoxy)phenyl)boronic acid

The title compound was prepared using the procedure described for Intermediate 2-L, Step 1 with the following modification: Step 1 was performed with 4,4,5,5-tetramethyl-2-(2-methyl-4-(2,2,2-trifluoroethoxy)phenyl)-1,3,2-dioxaborolane. $^1H$ NMR (DMSO-$d_6$, 400 MHz) δ 7.83 (d, J=9.1 Hz, 1H), 6.76-6.93 (m, 2H), 4.73 (q, J=8.9 Hz, 2H), 2.61-2.65 (m, 3H).

Intermediate 2-T

8-Chloro-3-iodo-2-(trifluoromethyl)-4H-pyrido[1,2-a]pyrimidin-4-one

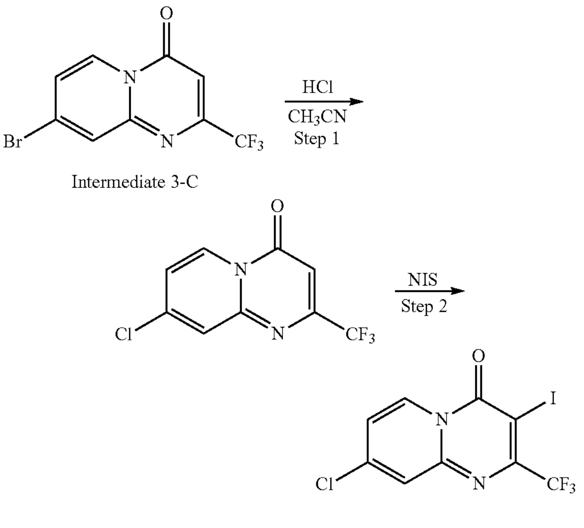

Step 1: 8-Chloro-2-(trifluoromethyl)-4H-pyrido[1,2-a]pyrimidin-4-one

Concentrated hydrochloric acid (37%, 3.4 mL, 41 mmol) was added to a solution of 8-bromo-2-(trifluoromethyl)-4H-pyrido[1,2-a]pyrimidin-4-one (2.0 g, 6.8 mmol, Intermediate 3-C) in acetonitrile (16 mL). The resulting mixture was then subjected to microwave irradiation at 100° C. for 15 mins. The mixture was slowly quenched with saturated $NaHCO_3$ (200 mL) and extracted with EtOAc (2×200 mL). The combined organic extracts were dried over $MgSO_4$ and concentrated under reduced pressure. Purification of the crude residue by silica gel chromatography (eluent: 0%-100% EtOAc/heptane) provided 8-chloro-2-(trifluoromethyl)-4H-pyrido[1,2-a]pyrimidin-4-one. LC/MS (ESI+) m/z=249.1 $[M+H]^+$. $^1H$ NMR (DMSO-$d_6$) δ: 8.97 (d, J=7.7 Hz, 1H), 8.10 (d, J=2.1 Hz, 1H), 7.55 (dd, J=7.7, 2.3 Hz, 1H), 6.87 (s, 1H).

Step 2: 8-Chloro-3-iodo-2-(trifluoromethyl)-4H-pyrido[1,2-a]pyrimidin-4-one

The title compound was prepared using the procedure described for Intermediate 1-B, Step 2 with the following modification: Step 2 was performed with 8-chloro-2-(trifluoromethyl)-4H-pyrido[1,2-a]pyrimidin-4-one. LC/MS ($ESI^+$) m/z=374.9 $[M+H]^+$. $^1H$ NMR (DMSO-$d_6$) δ 8.96 (d, J=7.7 Hz, 1H), 8.10 (d, J=2.1 Hz, 1H), 7.59 (dd, J=7.7, 2.3 Hz, 1H).

Intermediate 2-U

3-Iodo-2-(trifluoromethyl)-8-vinyl-4H-pyrido [1,2-a] pyrimidin-4-one

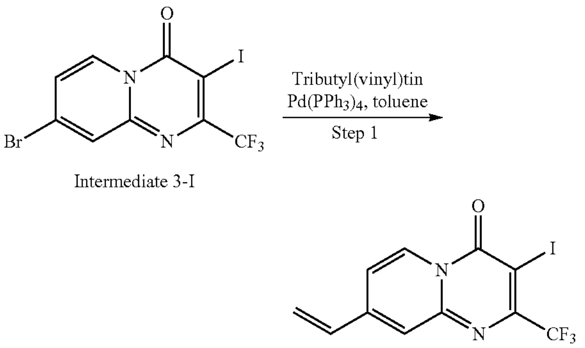

Tributyl(vinyl)tin (0.90 g, 2.86 mmol) was added to a solution of 8-bromo-3-iodo-2-(trifluoromethyl)-4H-pyrido [1,2-a]pyrimidin-4-one (1.0 g, 2.38 mmol, Intermediate 3-I) in toluene (10 mL). The reaction mixture was purged with nitrogen for 10 minutes and $Pd(PPh_3)_4$(276 mg, 0.24 mmol) was added. The reaction mixture was heated to 110° C. for 12 h. The reaction mixture was concentrated under reduced pressure and the crude residue was purified by silica gel chromatography (eluent: 0-10% ethyl acetate/hexane) to afford 3-iodo-2-(trifluoromethyl)-8-vinyl-4H-pyrido [1,2-a] pyrimidin-4-one (400 mg, 46% yield). LC/MS ($ESI^+$) m/z=367.1 $[M+H]^+$. $^1H$ NMR (400 MHz, DMSO-$d_6$) δ 8.93 (d, J=7.5 Hz, 1H), 7.91 (d, J=1.8 Hz, 1H), 7.79 (dd, J=7.6, 1.9 Hz, 1H), 6.96 (dd, J=17.6, 10.9 Hz, 1H), 6.42 (d, J=17.7 Hz, 1H), 5.82 (d, J=10.9 Hz, 1H).

Intermediate 2-V

3-Bromo-8-methyl-2-(trifluoromethyl)-4H-pyrido[1,2-a]pyrimidin-4-one

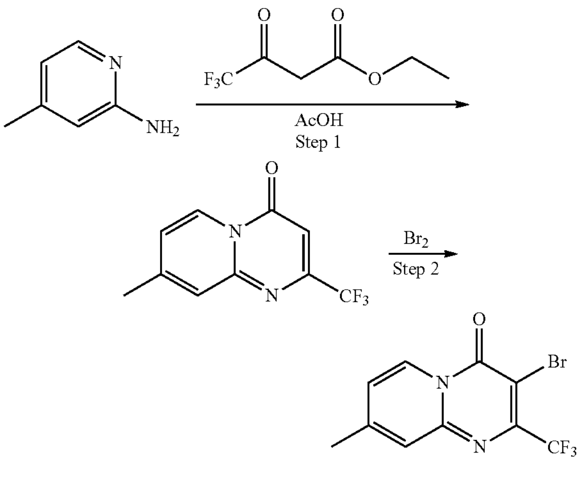

Step 1: 8-Methyl-2-(trifluoromethyl)-4H-pyrido[1,2-a]pyrimidin-4-one

The title compound was prepared using the procedure described for Intermediate 1-O, Step 1-1 with the following modification: Steps 1-1 was performed with 2-amino-4-methylpyridine. LC/MS ($ESI^+$) m/z=229.9 $[M+H]^+$. $^1H$ NMR (400 MHz, $CDCl_3$) δ 8.99 (d, J=7.3 Hz, 1H), 7.60 (s, 11H), 7.14-7.09 (m, 1H), 6.72 (s, 1H), 2.54 (s, 3H).

Step 2: 3-Bromo-8-methyl-2-(trifluoromethyl)-4H-pyrido[1,2-a]pyrimidin-4-one

The title compound was prepared using the procedure described for Intermediate 1-O, Step 1-2 with the following modification: Steps 1-2 was performed with 8-methyl-2-(trifluoromethyl)-4H-pyrido[1,2-a]pyrimidin-4-one. LC/MS ($ESI^+$) m/z=307.0 $[M+H]^+$.

Intermediate 2-W

3-Iodo-2,8-dimethoxy-4H-pyrido[1,2-a]pyrimidin-4-one

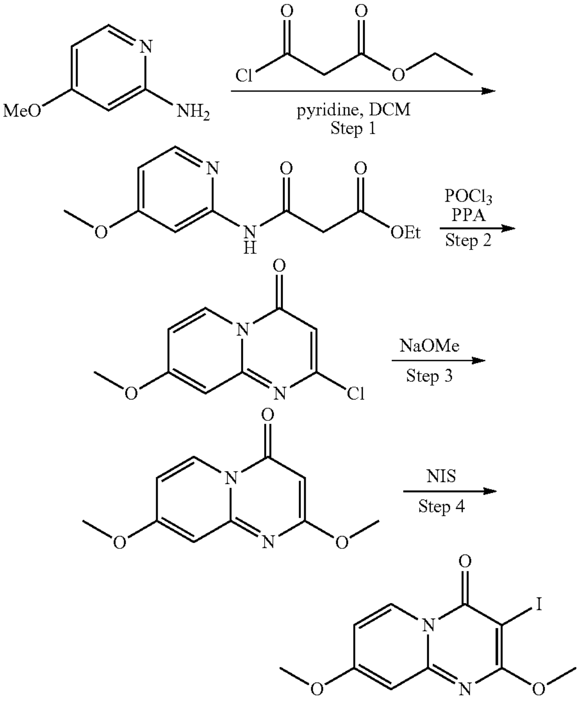

Step 1: Ethyl 3-((4-methoxypyridin-2-yl)amino)-3-oxopropanoate

A solution of ethyl malonyl chloride (3.9 ml, 30 mmol) in DCM (10 mL) was added dropwise to a solution of 2-amino-4-methoxylpyridine (2.5 g, 20 mmol, Combi-Blocks Inc.) in DCM (12 mL) and pyridine (18 ml) at 0° C. The reaction mixture was stirred at 0° C. for 40 min. Water (40 mL) was added and the reaction mixture was stirred vigorously for 3 h at rt. Aqueous, saturated sodium carbonate was added and the organic layer was separated. The aqueous phase was extracted with DCM, the combined organic layers were dried over $Na_2SO_4$ and concentrated in vacuo. The crude material was purified by silica gel chromatography (eluent: 0-25% (3:1 EtOAc/EtOH)/heptane) to provide ethyl 3-((4-methoxypyridin-2-yl)amino)-3-oxopropanoate (1.54 g, 6.5 mmol, 32% yield). $^1$H NMR (400 MHz, $CDCl_3$) δ 9.45 (br s, 1H), 8.09 (d, J=5.80 Hz, 11H), 7.80 (s, 1H), 6.60 (dd, J=2.28, 5.80 Hz, 1H), 4.25 (q, J=7.05 Hz, 2H), 3.86 (s, 3H), 3.47 (s, 2H), 1.31 (t, J=7.15 Hz, 311).

Step 2: 2-Chloro-8-methoxy-4H-pyrido[1,2-a]pyrimidin-4-one

A mixture of ethyl 3-((4-methoxypyridin-2-yl)amino)-3-oxopropanoate (1.0 g, 4.3 mmol), phosphorous oxychloride (1.2 ml, 13.0 mmol), and polyphosphoric acid (0.17 ml, 4.3 mmol) was heated to 130° C. for 16 h. The reaction mixture was cooled to rt, followed by addition of EtOH (4.3 mL). The reaction mixture was further heated at reflux for 30 min, then allowed to cool to rt. The reaction mixture was partitioned between EtOAc and brine. The aqueous layer was back extracted with EtOAc (×2) and the combined organic layers were dried over $Na_2SO_4$. The filtrate was concentrated in vacuo and the residue was suspended in DCM (5 mL). The solid was filtered off and dried to give 2-chloro-8-methoxy-4H-pyrido[1,2-a]pyrimidin-4-one (485 mg, 2.3 mmol, 53% yield) as a solid. LC/MS ($ESI^+$) m/z=211.1 $[M+H]^+$.

Step 3: 2,8-Dimethoxy-4H-pyrido[1,2-a]pyrimidin-4-one

Sodium methoxide (25 wt % in MeOH, 0.33 ml, 1.5 mmol) was added dropwise to a solution of 2-chloro-8-methoxy-4H-pyrido[1,2-a]pyrimidin-4-one (213 mg, 1.0 mmol) in acetonitrile (2 ml). The reaction mixture was stirred at rt for 2 h, followed by partitioning between EtOAc and water. The aqueous layer was extracted with EtOAc and the combined organic layers were dried over $Na_2SO_4$. The filtrate was concentrated to give 2,8-dimethoxy-4H-pyrido[1,2-a]pyrimidin-4-one (172 mg, 0.83 mmol, 82% yield) as an off-white solid. LC/MS ($ESI^+$) m/z=207.2 $[M+H]^+$.

Step 4: 3-Iodo-2,8-dimethoxy-4H-pyrido[1,2-a]pyrimidin-4-one

The title compound was prepared using the procedure described for Intermediate 1-B, Step 2 with the following modification: Steps 2 was performed with 2,8-dimethoxy-4H-pyrido[1,2-a]pyrimidin-4-one. LC/MS ($ESI^+$) m/z=333.0 $[M+H]^+$.

Intermediate 2-X

2-Ethoxy-3-iodo-8-methoxy-4H-pyrido[1,2-a]pyrimidin-4-one

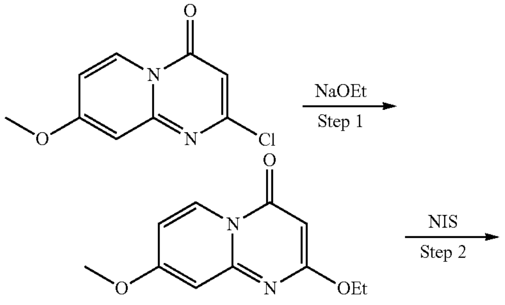

-continued

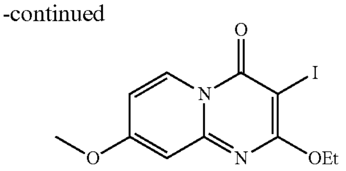

Step 1: 2-Ethoxy-8-methoxy-4H-pyrido[1,2-a]pyrimidin-4-one

Sodium ethoxide (254 mg, 0.78 mmol) was added to a solution of 2-chloro-8-methoxy-4H-pyrido[1,2-a]pyrimidin-4-one (150 mg, 0.71 mmol, prepared according to method described for Intermediate 2-W, Steps 1 and 2) in acetonitrile (2.3 ml). The reaction mixture was stirred at rt for 1 h, followed by partitioning between EtOAc and water. The aqueous layer was extracted with EtOAc and the combined organic layers were dried over $Na_2SO_4$. The filtrate was concentrated and the crude material was purified by silica gel chromatography (eluent: 0%-25% (3:1 EtOAc/EtOH)/heptane) to provide 2-ethoxy-8-methoxy-4H-pyrido[1,2-a]pyrimidin-4-one (85 mg, 0.39 mmol, 54% yield) as a white solid. LC/MS ($ESI^+$) m/z=221.1 $[M+H]^+$.

Step 2: 2-Ethoxy-3-iodo-8-methoxy-4H-pyrido[1,2-a]pyrimidin-4-one

The title compound was prepared using the procedure described for Intermediate 1-B, Step 2 with the following modification: Steps 2 was performed with 2-ethoxy-8-methoxy-4H-pyrido[1,2-a]pyrimidin-4-one. LC/MS (ESI) m/z=347.0 $[M+H]^+$.

Intermediate 2-Y 3-(4-Hydroxy-2-(trifluoromethyl)phenyl)-8-methoxy-2-(trifluoromethyl)-4H-pyrido[1,2-a]pyrimidin-4-one

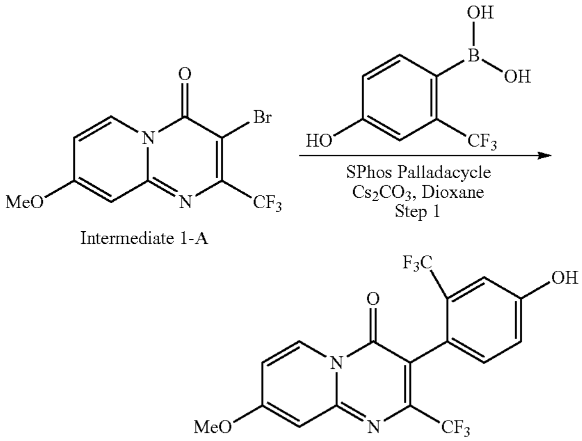

Step 1: 3-(4-Hydroxy-2-(trifluoromethyl)phenyl)-8-methoxy-2-(trifluoromethyl)-4H-pyrido[1,2-a]pyrimidin-4-one The title compound was prepared using the procedure described for Method 4, Step 3 with the following modification: Step 3 was performed with 3-bromo-8-methoxy-2-(trifluoromethyl)-4H-pyrido[1,2-a]pyrimidin-4-one (0.15 g, 0.46 mmol, Intermediate 1-A) and 4-hydroxy-2-(trifluoromethyl)phenylboronic acid (144 mg, 0.7 mmol, Aurum Pharmatech LLC). LC/MS ($ESI^+$) m/z=404.9 $[M+H]^+$. $^1H$ NMR ($DMSO-d_6$, 400 MHz) δ 10.18-10.39 (m, 1H), 8.88 (d, J=7.9 Hz, 1H), 7.31 (d, J=2.7 Hz, 1H), 7.14-7.23 (m, 3H), 7.09 (d, J=8.6 Hz, 1H), 4.05 (s, 3H).

Intermediate 2-Z 3-(2-Chloro-4-hydroxyphenyl)-8-methoxy-2-(trifluoromethyl)-4H-pyrido[1,2-a]pyrimidin-4-one

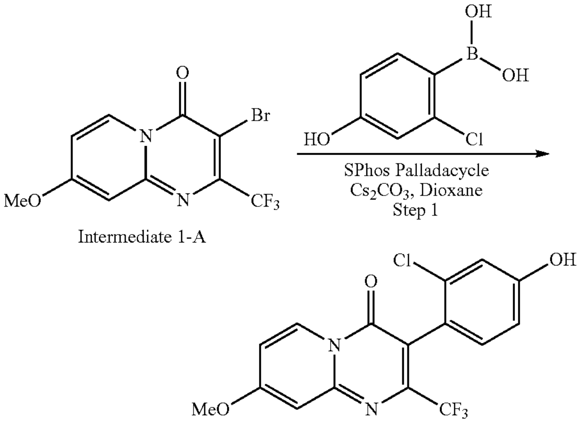

Step 1: 3-(2-Chloro-4-hydroxyphenyl)-8-methoxy-2-(trifluoromethyl)-4H-pyrido[1,2-a]pyrimidin-4-one The title compound was prepared using the procedure described for Method 4, Step 3 with the following modification: Step 3 was performed with 3-bromo-8-methoxy-2-(trifluoromethyl)-4H-pyrido[1,2-a]pyrimidin-4-one (1 g, 3.1 mmol, Intermediate 1-A) and 2-chloro-4-hydroxyphenylboronic acid (800 mg, 4.6 mmol, Combi-Blocks Inc.). LC/MS ($ESI^+$) m/z=371.0 $[M+H]^+$. $^1H$ NMR ($DMSO-d_6$, 400 MHz) δ 10.03 (br s, 1H), 8.89 (d, J=7.9 Hz, 1H), 7.31 (d, J=2.7 Hz, 1H), 7.21 (dd, J=7.9, 2.9 Hz, 1H), 7.12 (d, J=8.3 Hz, 1H), 6.93 (d, J=2.3 Hz, 1H), 6.79 (dd, J=8.3, 2.5 Hz, 1H), 4.04 (s, 3H), 3.30 (s, 3H).

Intermediate 3-A 3-(4-Hydroxyphenyl)-8-methoxy-2-(trifluoromethyl)-4H-pyrido[1,2-a]pyrimidin-4-one

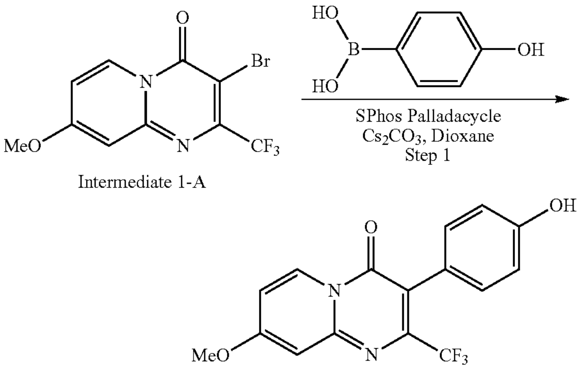

Step 1: 3-(4-Hydroxyphenyl)-8-methoxy-2-(trifluoromethyl)-4H-pyrido[1,2-a]pyrimidin-4-one The title compound was prepared using the procedure described for Method 4, Step 3 with the following modification: Step 3 was performed with 3-bromo-8-methoxy-2-(trifluoromethyl)-4H-pyrido[1,2-a]pyrimidin-4-one (1 g, 3.1 mmol, Intermediate 1-A) and (4-hydroxyphenyl)boronic acid (0.63 g, 4.6 mmol, Combi-Blocks Inc.). LC/MS ($ESI^+$) m/z=337.0 $[M+H]^+$. $^1H$ NMR (400 MHz, $CDCl_3$) δ 8.97 (d, J=7.88 Hz, 1H), 7.14 (d, J=8.29 Hz, 2H), 7.07 (d, J=2.49 Hz, 11H), 6.94 (dd, J=2.70, 7.88 Hz, 1H), 6.79 (d, J=8.50 Hz, 2H), 6.47 (br s, 1H), 4.00 (s, 3H).

Intermediate 3-B 3-(4-Hydroxyphenyl)-8-methoxy-2-(trifluoromethyl)-4H-pyrimido[1,2-a]pyrimidin-4-one

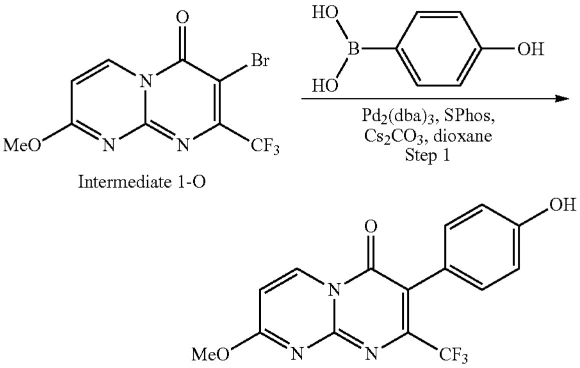

Step 1: 3-(4-Hydroxyphenyl)-8-methoxy-2-(trifluoromethyl)-4H-pyrimido[1,2-a]pyrimidin-4-one The title compound was prepared using the procedure described for Method 1, Step 1 with the following modification: Step 1 was performed with 3-bromo-8-methoxy-2-(trifluoromethyl)pyrimido[1,2-a]pyrimidin-4-one (2.0 g, 6.2 mmol, Intermediate 1-0), (4-hydroxyphenyl)boronic acid (1.0 g, 7.4 mmol, Combi-Blocks Inc.). LC/MS ($ESI^+$) m/z=338.1 $[M+H]^+$. $^1H$ NMR (400 MHz, $DMSO-d_6$) δ 9.60 (s, 1H), 9.01 (d, J=7.7 Hz, 1H), 7.18-7.00 (m, 3H), 6.83-6.78 (m, 2H), 4.10 (s, 3H).

Intermediate 3-C

8-Bromo-2-(trifluoromethyl)-4H-pyrido[1,2-a]pyrimidin-4-one

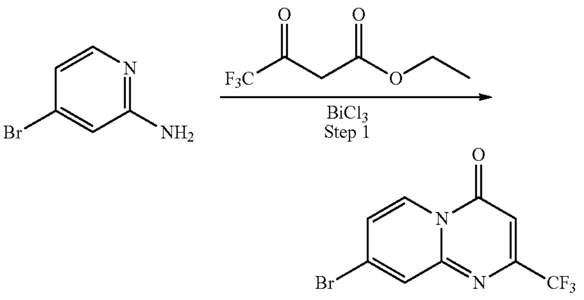

Step 1: 8-Bromo-2-(trifluoromethyl)-4H-pyrido[1,2-a]pyrimidin-4-one

The title compound was prepared using the procedure described for Intermediate 1-A, Step 1 with the following modification: Step 1 was performed with 4-bromopyridin-2-amine (Combi-Blocks Inc.). LC/MS (ESI$^+$) m/z=294.2 $[M+H]^+$. $^1H$ NMR (400 MHz, DMSO-$d_6$) δ 8.88 (d, J=7.6 Hz, 1H), 8.26 (d, J=2.2 Hz, 1H), 7.66 (dd, J=7.6, 2.1 Hz, 1H), 6.89 (s, 1H).

Intermediate 3-D

8-Cyclopropyl-3-iodo-2-(trifluoromethyl)-4H-pyrido[1,2-a]pyrimidin-4-one

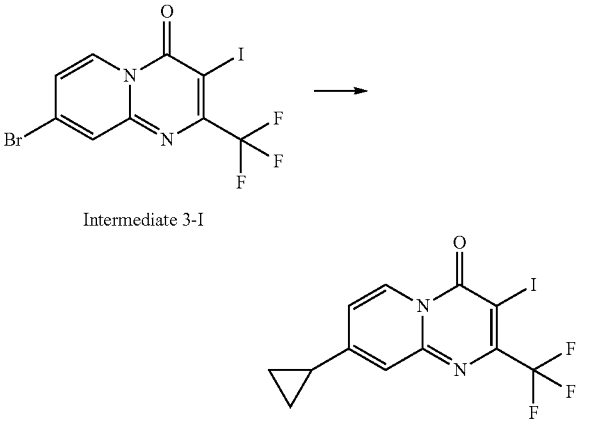

Intermediate 3-I

8-Bromo-3-iodo-2-(trifluoromethyl)pyrido[1,2-a]pyrimidin-4-one (150 mg, 0.36 mmol, Intermediate 3-I), $Pd(PPh_3)_4$(41 mg, 0.04 mmol), cyclopropylboronic acid (61 mg, 0.72 mmol, Fluorochem) and potassium carbonate (100 mg, 0.72 mmol) were suspended in toluene (3 mL). The reaction mixture was heated to 100° C. for 24 h. The reaction mixture was concentrated under reduced pressure and the crude residue was purified by silica gel chromatography (eluent: 0-30% EtOAc/cyclohexane) to give 8-cyclopropyl-3-iodo-2-(trifluoromethyl)pyrido[1,2-a]pyrimidin-4-one (70 mg, 0.18 mmol, 51% yield) as a yellow solid. LC/MS (ESI$^+$) m/z=381.1 $[M+H]^+$. $^1H$ NMR (400 MHz, $CDCl_3$) δ 0.98-1.10 (m, 2H) 1.30-1.41 (m, 2H) 2.01-2.16 (m, 1H) 7.00-7.08 (d, 1H) 7.43-7.51 (s, 1H) 8.96-9.04 (d, 1H).

Intermediate 3-E

8-(Azetidin-1-yl)-3-iodo-2-(trifluoromethyl)-4H-pyrido[1,2-a]pyrimidin-4-one

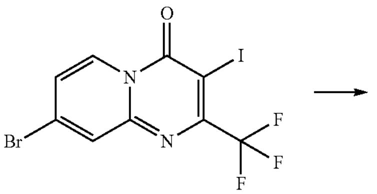

Intermediate 3-I

-continued

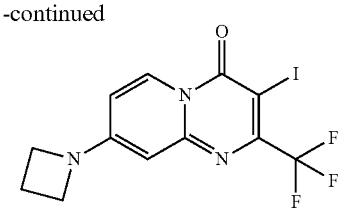

A resealable vial was charged with 8-bromo-3-iodo-2-(trifluoromethyl)pyrido[1,2-a]pyrimidin-4-one (100 mg, 0.24 mmol, Intermediate 3-I), azetidine hydrochloride (25 mg, 0.26 mmol) copper(I)iodide (11 mg, 0.06 mmol), potassium carbonate (40 mg, 0.29 mmol) and DMF (3 mL). The reaction mixture was heated to 80° C. for 1 h. The reaction mixture was diluted with EtOAc and washed with saturated aqueous $NH_4Cl$ and brine. The organic phase was dried and concentrated in vacuo. The crude residue was purified by silica gel chromatography (eluent: 70% EtOAc/cyclohexane) to give 8-(azetidin-1-yl)-3-iodo-2-(trifluoromethyl)pyrido[1,2-a]pyrimidin-4-one (48 mg 0.12 mmol, 51% yield) as a pale yellow solid. LC/MS (ESI$^+$) m/z=396.1 $[M+H]^+$. $^1H$ NMR (400 MHz, $CDCl_3$) δ 2.45-2.71 (m, 2H) 4.06-4.42 (br s, 4H) 6.28-6.39 (d, 1H) 6.39-6.57 (dd, 1H) 8.80-8.97 (d, 1H).

Intermediate 3-F

Methyl 4-oxo-3-(1-(2,2,3,3,3-pentafluoropropyl)-1H-pyrazol-4-yl)-2-(trifluoromethyl)-4H-pyrido[1,2-a]pyrimidine-8-carboxylate

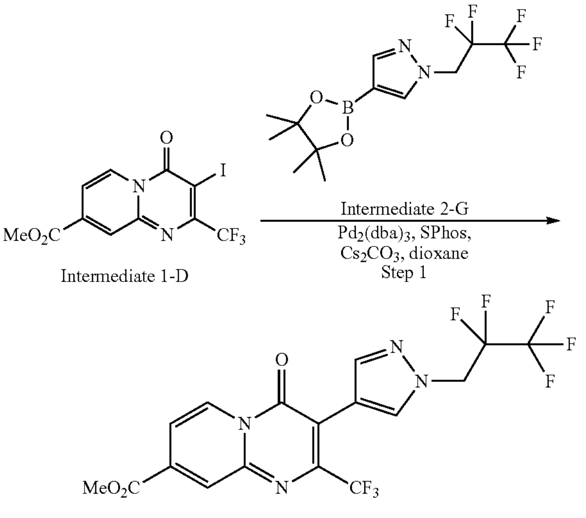

Intermediate 1-D

Step 1: Methyl 4-oxo-3-(1-(2,2,3,3,3-pentafluoropropyl)-1H-pyrazol-4-yl)-2-(trifluoromethyl)-4H-pyrido[1,2-a]pyrimidine-8-carboxylate The title compound was prepared using the procedure described for Method 1, Step 1 with the following modification: Step 1 was performed with methyl 3-iodo-4-oxo-2-(trifluoromethyl)-4H-pyrido[1,2-a]pyrimidine-8-carboxylate (0.47 g, 1.2 mmol, Intermediate 1-D), 1-(2,2,3,3,3-pentafluoropropyl)-4-(4,4,5,5-tetramethyl-1,3,2-dioxaborolan-2-yl)-1H-pyrazole (0.50 g, 1.54 mmol, Intermediate 2-G). LC/MS (ESI$^+$) m/z=471.1 $[M+H]^+$. $^1H$ NMR (400 MHz, $CDCl_3$) δ 9.11 (d, J=7.5 Hz, 1H), 8.46 (s, 1H), 7.98 (s, 1H), 7.91 (s, 1H), 7.74 (dd, J=7.6, 1.8 Hz, 1H), 4.85 (t, J=13.9 Hz, 2H), 4.06 (s, 3H).

Intermediate 3-G 8-(Ethylthio)-3-(4-(2,2,2-trifluoroethoxy)phenyl)-2-(trifluoromethyl)-4H-pyrido[1,2-a]pyrimidin-4-one

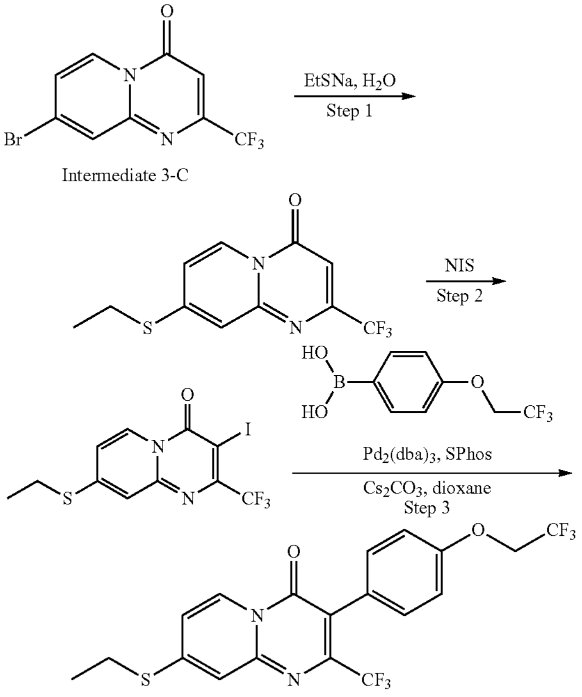

Step 1: 8-(Ethylthio)-2-(trifluoromethyl)-4H-pyrido[1,2-a]pyrimidin-4-one

Sodium ethanethiolate (3.0 g, 36 mmol) was added to a solution of 8-bromo-2-(trifluoromethyl)-4H-pyrido[1,2-a]pyrimidin-4-one (3.0 g, 12 mmol, Intermediate 3-C) and in water (45 mL) at room temperature. The reaction mixture was heated to 100° C. for 48 h. The reaction mixture was cooled to rt and partitioned between water (200 mL) and EtOAc (500 mL). The combined organic layers were washed with brine (250 mL) and dried over sodium sulfate. The filtrate concentrated under reduced pressure to get crude material was purified by silica gel chromatography (eluent: 0-25% ethyl acetate/hexane) to obtain 8-(ethylthio)-2-(trifluoromethyl)-4H-pyrido[1,2-a]pyrimidin-4-one (0.4 g, 1.46 mmol, 12% yield). LC/MS ($ESI^+$) m/z=275.0 $[M+H]^+$. $^1H$ NMR (400 MHz, DMSO-$d_6$) δ 8.81 (d, J=7.6 Hz, 1H), 7.55 (d, J=2.1 Hz, 1H), 7.36 (dd, J=7.6, 2.1 Hz, 1H), 6.69 (s, 1H), 3.26 (t, J=7.4 Hz, 2H), 1.35 (t, J=7.3 Hz, 3H), 1.29-1.20 (m, 1H).

Step 2: 8-(Ethylthio)-3-iodo-2-(trifluoromethyl)-4H-pyrido[1,2-a]pyrimidin-4-one The title compound was prepared using the procedure described for Intermediate 1-B, Step 2 with the following modification: Steps 2 was performed with 8-(ethylthio)-2-(trifluoromethyl)-4H-pyrido[1,2-a]pyrimidin-4-one. LC/MS ($ESI^+$) m/z=401.1 $[M+H]^+$. $^1H$ NMR (400 MHz, DMSO-$d_6$) δ 8.80 (dd, J=7.6, 2.0 Hz, 1H), 7.53 (t, J=2.2 Hz, 1H), 7.41 (dt, J=7.6, 2.2 Hz, 1H), 3.27 (qt, J=7.5, 2.4 Hz, 2H), 1.35 (td, J=7.3, 2.0 Hz, 3H).

Step 3: 8-(Ethylthio)-3-(4-(2,2,2-trifluoroethoxy)phenyl)-2-(trifluoromethyl)-4H-pyrido[1,2-a]pyrimidin-4-one The title compound was prepared using the procedure described for Method 1, Step 1 with the following modification: Step 1 was performed with 8-(ethylthio)-3-iodo-2-(trifluoromethyl)-4H-pyrido[1,2-a]pyrimidin-4-one (0.4 g, 1.0 mmol) and (4-(2,2,2-trifluoroethoxy)phenyl)boronic acid (0.29 g, 1.3 mmol, Combi-Blocks Inc.). LC/MS ($ESI^+$) m/z=449.0 $[M+1]^+$. $^1H$ NMR (400 MHz, DMSO-$d_6$) δ 8.77 (dd, J=7.5, 1.2 Hz, 1H), 7.57-7.51 (m, 1H), 7.38-7.32 (m, 1H), 7.26 (d, J=8.4 Hz, 2H), 7.15-7.09 (m, 2H), 4.82 (q, J=8.9 Hz, 2H), 3.29-3.24 (m, 2H), 1.36 (td, J=7.3, 1.2 Hz, 3H).

Intermediate 3-H

4-Oxo-3-(4-(2,2,2-trifluoroethoxy)phenyl)-2-(trifluoromethyl)-4H-pyrido[1,2-a]pyrimidine-8-carbaldehyde

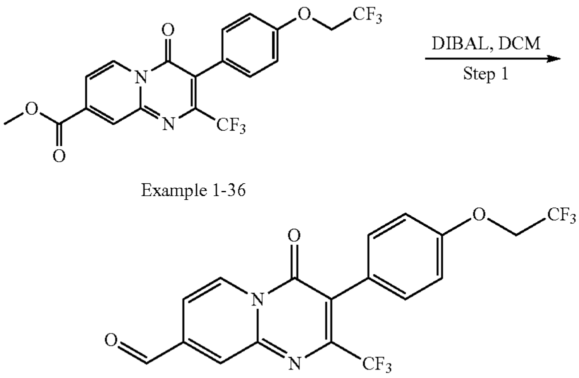

Intermediate 3-H

Step 1: 4-Oxo-3-(4-(2,2,2-trifluoroethoxy)phenyl)-2-(trifluoromethyl)-4H-pyrido[1,2-a]pyrimidine-8-carbaldehyde A solution of DIBAL-H (1M in DCM, 4 mL, 4 mmol) was added dropwise to a solution of methyl 4-oxo-3-[4-(2,2,2-trifluoroethoxy)phenyl]-2-(trifluoromethyl)pyrido[1,2-a]pyrimidine-8-carboxylate (1.5 g, 3.36 mmol, Example 1-36) in dichloromethane (30 mL) at −40° C. Stirring was continued for 5 min, followed by addition of aq. 1N HCl (20 mL). The reaction mixture was extracted with dichloromethane (2×100 mL). The combined organic layers were dried over sodium sulfate, filtered and concentrated under reduced pressure to obtain 4-oxo-3-(4-(2,2,2-trifluoroethoxy)phenyl)-2-(trifluoromethyl)-4H-pyrido[1,2-a]pyrimidine-8-carbaldehyde (0.85 g, 1.3 mmol, 40% yield). The product was used without further purification. LC/MS ($ESI^+$) m/z=417.1 [M+1]*.

Intermediate 3-I

8-Bromo-3-iodo-2-(trifluoromethyl)-4H-pyrido[1,2-a]pyrimidin-4-one

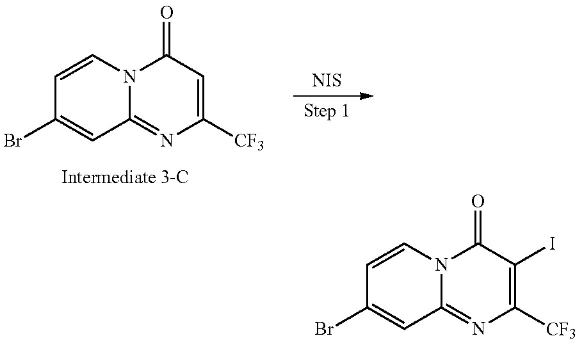

Intermediate 3-C

Step 1: 8-Bromo-3-iodo-2-(trifluoromethyl)-4H-pyrido[1,2-a]pyrimidin-4-one

The title compound was prepared using the procedure described for Intermediate 1-B, Step 2 with the following modification: Step 2 was performed with 8-bromo-2-(trifluoromethyl)pyrido[1,2-a]pyrimidin-4-one. LC/MS (ESI$^+$) m/z=419.0 [M+H]$^+$.

Intermediate 3-J

8-Hydroxy-2-(trifluoromethyl)-3-(1-(3,3,3-trifluoropropyl)-1H-pyrazol-4-yl)-4H-pyrido[1,2-a]pyrimidin-4-one

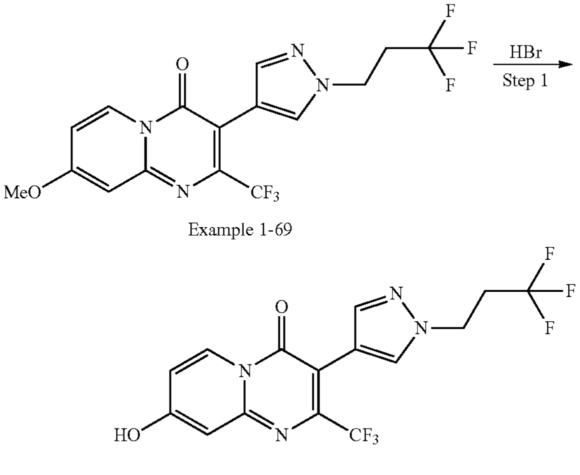

Example 1-69

Step 1: 8-Hydroxy-2-(trifluoromethyl)-3-(1-(3,3,3-trifluoropropyl)-1H-pyrazol-4-yl)-4H-pyrido[1,2-a]pyrimidin-4-one The title compound was prepared using the procedure described for Method 10, Step 1 with the following modification: Step 1 was performed with 8-methoxy-2-(trifluoromethyl)-3-[1-(3,3,3-trifluoropropyl)pyrazol-4-yl]pyrido[1,2-a]pyrimidin-4-one (Example 1-69). LC/MS (ESI$^+$) m/z=393.2 [M+H]$^+$. $^1$H NMR (400 MHz, DMSO-d$_6$) δ 2.82-3.01 (m, 2H) 4.37-4.51 (t, 2H) 6.87-6.96 (s, 1H) 7.02-7.16 (d, 1H) 7.46-7.58 (s, 1H) 7.89-7.96 (s, 1H) 8.85-8.98 (d, 1H) 12.19-12.29 (s, 1H).

Intermediate 3-K

9-Fluoro-3-iodo-8-methoxy-2-(trifluoromethyl)-4H-pyrido[1,2-a]pyrimidin-4-one

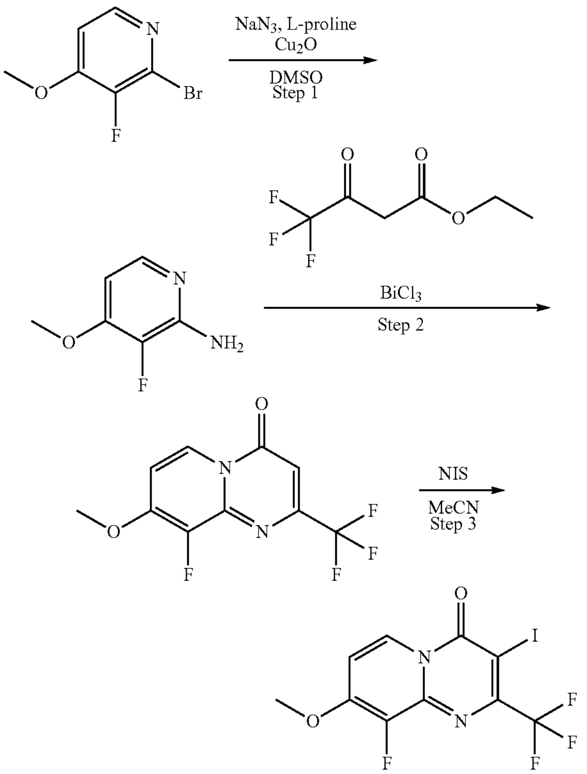

Step 1: 3-Fluoro-4-methoxypyridin-2-amine

A mixture of 2-bromo-3-fluoro-4-methoxypyridine (400 mg, 1.94 mmol), L-proline (224 mg, 1.94 mmol), sodium azide (190 mg, 2.91 mmol) and copper (I) oxide (306 mg, 2.14 mmol) in DMSO (6 mL) was stirred for 10 h at 100° C. The mixture was filtered and the filtrate was directly purified by flash chromatography (C18 cartridge, NH3 0.1% in water: ACN as eluant, from 100% aqueous solution to 8:2) to obtain 3-fluoro-4-methoxypyridin-2-amine as a white solid (185 mg, 1.302 mmol, 67% yield). LC/MS (ESI$^+$) m/z=143.1 [M+H]$^+$.

Step 2: 9-Fluoro-8-methoxy-2-(trifluoromethyl)-4H-pyrido[1,2-a]pyrimidin-4-one

The title compound was prepared using the procedure described for Intermediate 1-A, Step 1 with the following modification: Step 1 was performed with 3-fluoro-4-methoxypyridin-2-amine. LC/MS (ESI$^+$) m/z=263.3 [M+H]$^+$.

Step 3: 9-Fluoro-3-iodo-8-methoxy-2-(trifluoromethyl)-4H-pyrido[1,2-a]pyrimidin-4-one The title compound was prepared using the procedure described for Intermediate 1-B, Step 2 with the following modification: Step 2 was performed with 9-fluoro-8-methoxy-2-(trifluoromethyl)-4H-pyrido[1,2-a]pyrimidin-4-one. LC/MS ($ESI^+$) m/z=388.9 $[M+H]^+$.

Intermediate 3-L

3-Bromo-7-fluoro-8-methoxy-2-(trifluoromethyl)-4H-pyrido[1,2-a]pyrimidin-4-one

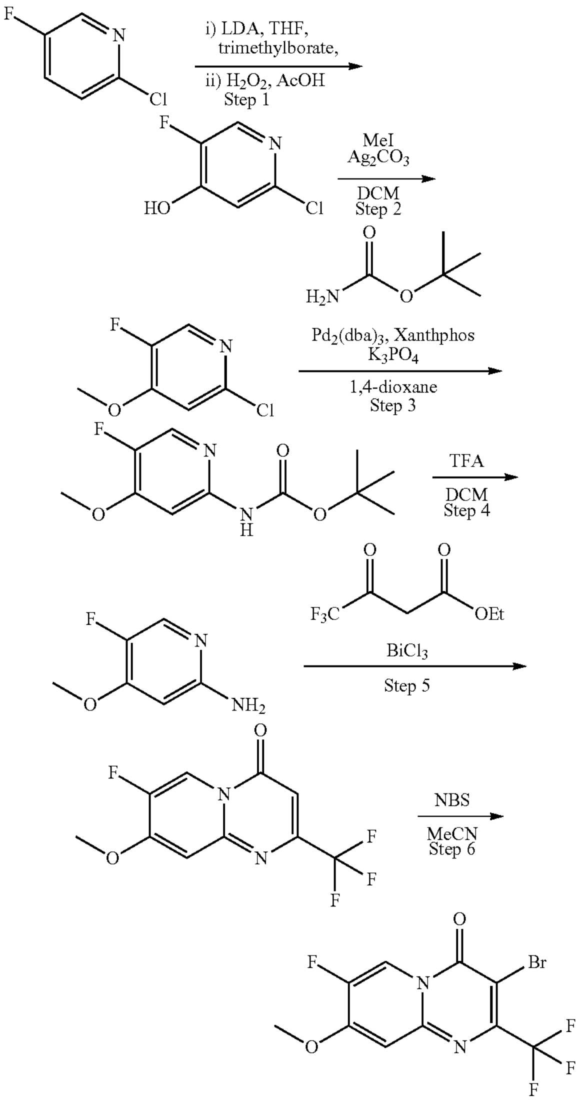

Step 1: 2-chloro-5-fluoropyridin-4-ol

To a solution of 2-chloro-5-fluoropyridine (11.6 mL, 114 mmol) in THF (120 mL) at −78° C. Lithium diisopropylamide (2M in THF, 65 mL, 130 mmol) was added dropwise. The mixture was allowed to warm up at −60° over 3 h then the reaction was cooled to −78° C. and trimethyl borate (25.4 mL, 228 mmol) was slowly added. The temperature was slowly increased to 0° C. and the mixture was stirred for 2 h. Acetic acid (19.6 mL, 342 mmol) was added at the same temperature followed by dropwise addition of hydrogen peroxide (30% in water, 29 mL, 285 mmol) after 20 minutes. The reaction mixture was warmed to r.t. and then stirred overnight. Saturated sodium thiosulfate aqueous solution was added to reaction and the mixture was extracted with EtOAc (×2) and DCM (×2). The aqueous phase was acidified with HCL 6M solution to pH 5/6 and further extracted with EtOAc (×2) and DCM. The combined organic layers were dried over Na2SO4, filtered and concentrated under vacuum. The resulting crude was triturated in DCM and the solid was collected to give 2-chloro-5-fluoropyridin-4-ol as a white solid (15.53 g, 105.3 mmol, 92% yield). LC/MS ($ESI^+$) m/z=148.1/150.1 $[M+H]^+$.

Step 2: 2-chloro-5-fluoro-4-methoxypyridine

To 2-chloro-5-fluoropyridin-4-ol (15.53 g, 105.3 mmol) in DCM (300 mL) was added silver carbonate (62.4 g, 224.64 mmol) and iodomethane (6.99 mL, 112.32 mmol) and the mixture was stirred at r.t. overnight. The mixture was filtered and the residue washed with water (×2). The organics phase was dried over magnesium sulfate and the solvent removed under vacuum. The residue was then purified by flash column chromatography ($SiO_2$, Cy:EtOAc as eluant, from 100% Cy to 7:3) to give 2-chloro-5-fluoro-4-methoxypyridine as a white solid (5.36 g, 33.2 mmol, 32.5% yield). LC/MS ($ESI^+$) m/z=161.9/163.9 $[M+H]^+$.

Step 3: 2-chloro-5-fluoro-4-methoxypyridine

A mixture of 2-chloro-5-fluoro-4-methoxypyridine (5.36 g), carbamic acid tert-butyl ester (4.43 g, 37.8 mmol) and potassium triphosphate (10.17 g, 47.24 mmol) in 1,4-dioxane (200 mL) was degassed for 15 minutes, then $Pd_2dba_3$ (2.88 g, 3.15 mmol) and (5-diphenylphosphino-9,9-dimethyl-4-xanthenyl)-diphenylphosphine (3.64 g, 6.3 mmol) were added and the mixture was stirred at 100° C. for 15 h. The mixture was filtered and the residue concentrated under vacuum. The resulting material was purified by flash chromatography ($Si_2O$, Cy:EtOAc as eluant, from 100% cy to 7:3) to obtain impure tert-butyl N-(5-fluoro-4-methoxypyridin-2-yl)carbamate which was used directly in the following reaction. LC/MS ($ESI^+$) m/z=187.3 $[M-tBu+H]^+$.

Step 4: 5-fluoro-4-methoxypyridin-2-amine

To crude tert-butyl N-(5-fluoro-4-methoxypyridin-2-yl) carbamate (8.3 g) in DCM (70 mL) was added trifluoroacetic acid (10 mL) and the mixture was stirred at r.t. overnight. The mixture was concentrated and the residue loaded into an SCX cartridge, washed with DCM and MeCN and eluted with 10% ammonia in MeCN. The solvent was evaporated to obtain 5-fluoro-4-methoxypyridin-2-amine as a pale orange solid (2.16 g, 15.2 mmol). LC/MS ($ESI^+$) m/z=143.1 $[M+H]^+$.

Step 5: 7-fluoro-8-methoxy-2-(trifluoromethyl) pyrido[1,2-a]pyrimidin-4-one

A mixture of 5-fluoro-4-methoxypyridin-2-amine (2.16 g) 4,4,4-trifluoro-3-oxobutanoic acid ethyl ester (10.33 mL, 70.67 mmol) and bismuth trichloride (0.45 g, 1.41 mmol) was stirred at 120° C. for 24 hours. The mixture was partioned between EtOAc and water and the organic phase was dried over Na2SO4, filtered and concentrated under vacuum. The resulting crude material was purified by flash chromatography ($SiO_2$, DCM:MeOH as eluant, from 100% DCM to 95:5) followed by reverse phase flash chromatography (C18, 0.1% HCOOH solution in water:acetonitrile, from 100% aqueous solution to 1:1) to obtain 7-fluoro-8-methoxy-2-(trifluoromethyl)pyrido[1,2-a]pyrimidin-4-one as a white solid (1.94 g, 7.41 mmol, 52% yield). LC/MS ($ESI^+$) m/z=263.1 $[M+H]^+$.

Step 6: 3-bromo-7-fluoro-8-methoxy-2-(trifluoromethyl)-4H-pyrido[1,2-a]pyrimidin-4-one A mixture of N-bromosuccinimide (1.45 g, 8.16 mmol) and 7-fluoro-8-methoxy-2-(trifluoromethyl)pyrido[1,2-a]pyrimidin-4-one (1.94 g, 7.41 mmol) in MeCN (15 mL) was stirred at 80° C. for 1 h. The mixture was partioned between EtOAc and water and the organic phase was washed with sat. sol. $NaHCO_3$ and sat. sol. $Na_2SO_3$. Then the organic phase was dried over $Na_2SO_4$, filtered and concentrated under vacuum. The crude material was purified by flash chromatography ($SiO_2$, Cy:EtOAc as eluant, from 100% cy to 7:3) to obtain 3-bromo-7-fluoro-8-methoxy-2-(trifluoromethyl)-4H-pyrido[1,2-a]pyrimidin-4-one as a white solid (2.53 g, 7.40 mmol, quantitative yield). LC/MS (ESI) m/z=341.1/343.1 $[M+H]^+$.

Intermediate 3-M

3-Bromo-8-methoxy-2-(trifluoromethyl)-4H-pyrimido[1,2-b]pyridazin-4-one

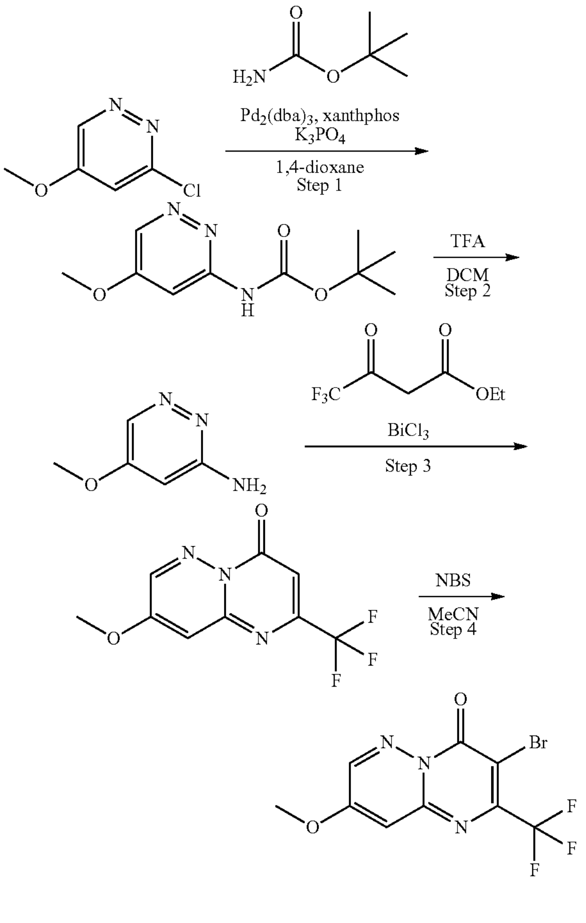

Step 1: tert-butyl N-(5-methoxypyridazin-3-yl)carbamate

A solution of 3-chloro-5-methoxypyridazine (250 mg, 1.73 mmol, Combi-Blocks Inc.), carbamic acid tert-butyl ester (263 mg, 2.25 mmol) and cesium carbonate (794 mg, 2.42 mmol) in 1,4-dioxane (5 mL) was degassed with a flow of nitrogen for 10 minutes then (5-diphenylphosphino-9,9-dimethyl-4-xanthenyl)-diphenylphosphine (150 mg, 0.260 mmol) and palladium(II) diacetate (27 mg, 0.12 mmol) were added. The mixture was heated at 100° C. for 22 hours. The mixture was filtered, diluted with EtOAc and washed with brine twice. The organic phase was dried, filtered and concentrated under vacuum. The resulting material was purified by flash chromatography ($SiO_2$, Cy:EtOAc as eluant, from 100% Cy to 50:50) to give tert-butyl N-(5-methoxypyridazin-3-yl)carbamate as a white solid (160 mg, 0.710 mmol, 41% yield). LC/MS ($ESI^+$) m/z=226.2 $[M+H]^+$. $^1H$ NMR (400 MHz, $CDCl_3$) δ 8.86 (d, J=2.6 Hz, 1H), 8.59 (d, J=2.7 Hz, 1H), 7.75 (d, J=2.7 Hz, 1H), 7.66 (s, 1H), 6.96 (d, J=2.6 Hz, 1H), 3.96 (s, 1H), 3.95 (s, 3H), 1.56 (s, 9H).

Step 2: 5-methoxypyridazin-3-amine

Trifluoroacetic acid (1.07 mL, 14.03 mmol) was added to a solution of tert-butyl N-(5-methoxypyridazin-3-yl)carbamate (158 mg, 0.700 mmol) in DCM (4 mL) at 0° C. The mixture was stirred at room temperature for 3 hours. The mixture was concentrated to give a crude material that was purified by SCX cartridge to obtain 5-methoxypyridazin-3-amine as a white solid. (60 mg, 0.480 mmol, 68% yield). LC/MS ($ESI^+$) m/z=126.2 $[M+H]^+$. $^1H$ NMR (400 MHz, DMSO-$d_6$) δ 8.17 (d, J=2.6 Hz, 1H), 6.22 (d, J=2.7 Hz, 3H), 3.78 (s, 3H).

Step 3: 8-methoxy-2-(trifluoromethyl)-4H-pyrimido[1,2-b]pyridazin-4-one

A mixture of 5-methoxypyridazin-3-amine (85 mg, 0.68 mmol), 4,4,4-trifluoro-3-oxobutanoic acid ethyl ester (1.0 mL, 6.79 mmol) and bismuth trichloride (21 mg, 0.07 mmol) was stirred at 120° C. for 24 h. The mixture was diluted with water and extracted with EtOAc twice. The organic phase was dried over $Na_2SO_4$, filtered and concentrated under vacuum to give a crude material that was purified by flash chromatography ($SiO_2$, Cy:EtOAc as eluant, from 80:20 to 100% EtOAc) to obtain 8-methoxy-2-(trifluoromethyl)-4H-pyrimido[1,2-b]pyridazin-4-one as a pale yellow solid (80 mg, 0.33 mmol, 48% yield). LC/MS ($ESI^+$) m/z=246.1 $[M+H]^+$. $^1H$ NMR (400 MHz, DMSO-$d_6$) δ 8.80 (d, J=2.9 Hz, 11H), 7.58 (d, J=2.9 Hz, 1H), 6.83 (s, 1H), 4.05 (s, 3H).

Step 4: 3-bromo-8-methoxy-2-(trifluoromethyl)-4H-pyrimido[1,2-b]pyridazin-4-one

A mixture of 8-methoxy-2-(trifluoromethyl)pyrimido[1,2-b]pyridazin-4-one (95 mg, 0.390 mmol) and 1-bromopyrrolidine-2,5-dione (103 mg, 0.58 mmol) in MeCN (3 mL) was stirred at room temperature for 18 hours and at 80° C. for 1 hour. The mixture was concentrated, dissolved in DCM and washed subsequently with saturated aqueous $Na_2S_2O_3$ and $NaHCO_3$ solutions and brine. The organic phase was dried and concentrated to give 3-bromo-8-methoxy-2-(trifluoromethyl)-4H-pyrimido[1,2-b]pyridazin-4-one as a yellow solid (112 mg, 0.346 mmol, 89% yield). LC/MS ($ESI^+$) m/z=324.0/326.0 $[M+H]^+$. $^1H$ NMR (400 MHz, DMSO-$d_6$) δ 8.87 (d, J=2.8 Hz, 1H), 7.61 (d, J=2.8 Hz, 1H), 4.06 (s, 3H).

Intermediate 3-N

3-Iodo-2-(trifluoromethyl)-4H-pyrido[1,2-a]pyrimidin-4-one

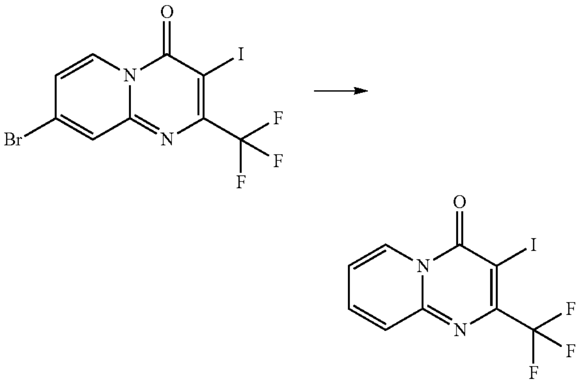

To a suspension of potassium (chloromethyl)trifluoroborate (156 mg, 1 mmol) in methanol (4 mL) was added sodium methoxide (52 mg, 0.95 mmol) and mixture was stirred at 70° C. for 4 h then the solvent evaporated. The resulting crude material was redissolved in 1,4-dioxane (4 mL) and water (1 mL), then cesium carbonate (157 mg, 0.48 mmol), 8-bromo-3-iodo-2-(trifluoromethyl)pyrido[1,2-a]pyrimidin-4-one (Intermediate 3-I, 100 mg, 0.24 mmol) and palladium triphenylphosphine (28 mg, 0.02 mmol) were added and mixture was stirred at 90° C. overnight. After cooling mixture was diluted with EtOAc and washed with water. The organic phase was dried and evaporated and crude was purified by flash chromatography ($SiO_2$, Cy/EtOAc 50:50) affording 3-iodo-2-(trifluoromethyl)-4H-pyrido[1,2-a]pyrimidin-4-one as a yellow solid (62 mg, 0.182 mmol, 77% yield). LC/MS (ESI) m/z=431.0 $[M+H]^+$.

Intermediate 3-0

3-Bromo-7-methoxy-2-(trifluoromethyl)-4H-pyrido[1,2-a]pyrimidin-4-one

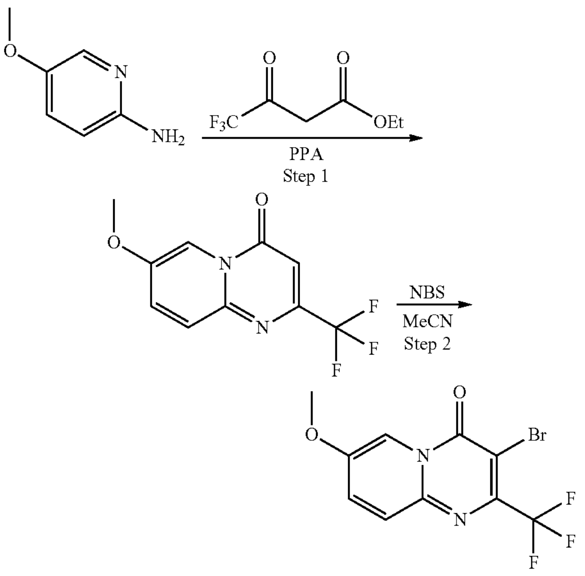

Step 1: 7-methoxy-2-(trifluoromethyl)-4H-pyrido[1,2-a]pyrimidin-4-one

A mixture of 5-methoxypyridin-2-amine (1.0 g, 8.06 mmol, Fluorochem Ltd), 4,4,4-trifluoro-3-oxobutanoic acid ethyl ester (2.36 mL, 16.1 mmol) and polyphosphoric acid (19.3 g, 80.55 mmol) was stirred at 120° C. for 20 h then allowed to cool. The mixture was carefully added to $NaHCO_3$ aq sat sol (80 mL) at 0° C. and pH adjusted to 7. Then the aqueous phase was extracted with AcOEt (3×100 mL). The organic phase was dried over $Na_2SO_4$, filtered and concentrated under vacuum to give a crude material that was purified by flash chromatography ($SiO_2$, Cy:EtOAc from 90:10 to 80:20) to obtain 7-methoxy-2-(trifluoromethyl)-4H-pyrido[1,2-a]pyrimidin-4-one as a pale yellow solid (1.66 g, 6.78 mmol, 84% yield). LC/MS ($ESI^+$) m/z=254.2 $[M+H]^+$. $^1H$ NMR (400 MHz, $CDCl_3$) δ 3.89-4.07 (s, 3H) 6.80 (s, 1H) 7.67 (dd, 1H) 7.78 (d, 1H) 8.62 (d, 1H).

Step 2: 3-bromo-7-methoxy-2-(trifluoromethyl)-4H-pyrido[1,2-a]pyrimidin-4-one

A mixture of obtain 7-methoxy-2-(trifluoromethyl)-4H-pyrido[1,2-a]pyrimidin-4-one (400 mg, 1.64 mmol) and N-bromosuccinimide (321 mg, 1.8 mmol) in MeCN (10 mL) was stirred at room temperature for 5 hours. The mixture was concentrated, dissolved in DCM and washed subsequently with saturated aqueous $Na_2S_2O_3$ and $NaHCO_3$ solutions and brine. The organic phase was dried and the crude was purified by column chromatography ($SiO_2$, Cy:EtOAc from 9:1 to 6:4) to obtain 3-bromo-7-methoxy-2-(trifluoromethyl)-4H-pyrido[1,2-a]pyrimidin-4-one as a white solid (466 mg, 1.44 mmol, 88% yield). LC/MS ($ESI^+$) m/z=323.1/325.1 $[M+H]^+$. $^1H$ NMR (400 MHz, $CDCl_3$) δ 4.02 (s, 3H) 7.70 (dd, 1H) 7.80 (d, 1H) 8.61 (d, J 1H).

Intermediate 3-P

3-Bromo-8-(2-hydroxypropan-2-yl)-2-(trifluoromethyl)-4H-pyrido[1,2-a]pyrimidin-4-one

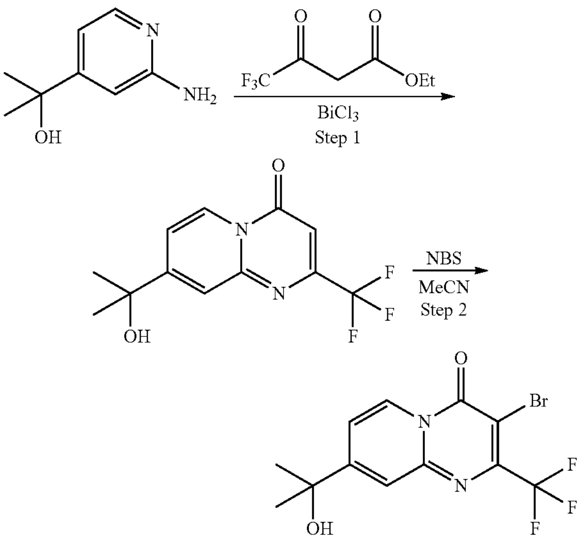

Step 1: 8-(2-hydroxypropan-2-yl)-2-(trifluoromethyl)-4H-pyrido[1,2-a]pyrimidin-4-one A mixture of 2-(2-aminopyridin-4-yl)propan-2-ol (828 mg, 5.44 mmol, Combi-Blocks Inc), 4,4,4-trifluoro-3-oxobutanoic acid ethyl ester (3.98 mL, 27.2 mmol) and bismuth trichloride (172 mg, 0.54 mmol) was stirred at 120° C. for 24 hours. The mixture was diluted with water and extracted with EtOAc twice. The organic phase was dried over $Na_2SO_4$, filtered and concentrated under vacuum to give a crude material that was purified by flash chromatography ($SiO_2$, Cy:EtOAc as eluant, from 80:20 to 100% EtOAc) to obtain 8-(2-hydroxypropan-2-yl)-2-(trifluoromethyl)-4H-pyrido[1,2-a]pyrimidin-4-one (284 mg, 1.04 mmol, 19% yield). LC/MS ($ESI^+$) m/z=273.1 $[M+H]^+$.

Step 2: 3-bromo-8-(2-hydroxypropan-2-yl)-2-(trifluoromethyl)-4H-pyrido[1,2-a]pyrimidin-4-one A mixture of 8-(2-hydroxypropan-2-yl)-2-(trifluoromethyl)-4H-pyrido[1,2-a]pyrimidin-4-one (284 mg, 1.04 mmol) and N-bromosuccinimide (204 mg, 1.15 mmol) in MeCN (5 mL) was stirred at room temperature for 5 hours. The mixture was concentrated, dissolved in DCM and washed subsequently with saturated aqueous $Na_2S2O_3$ and $NaHCO_3$ solutions and brine. The organic phase was dried and concentrated to give 3-bromo-8-(2-hydroxypropan-2-yl)-2-(trifluoromethyl)-4H-pyrido[1,2-a]pyrimidin-4-one as a yellow solid (335 mg, 0.95 mmol, 91% yield). LC/MS ($ESI^+$) m/z=381.1/383.1 $[M+H]^+$. $^1H$ NMR (400 MHz, DMSO-$d_6$) δ 1.51 (s, 6H) 5.66 (s, 1H) 7.67-7.78 (m, 1H) 7.80-7.90 (m, 1H) 8.91-9.08 (m, 1H).

Intermediate 3-Q

3-Bromo-7-chloro-2-(trifluoromethyl)-4H-pyrido[1,2-a]pyrimidin-4-one

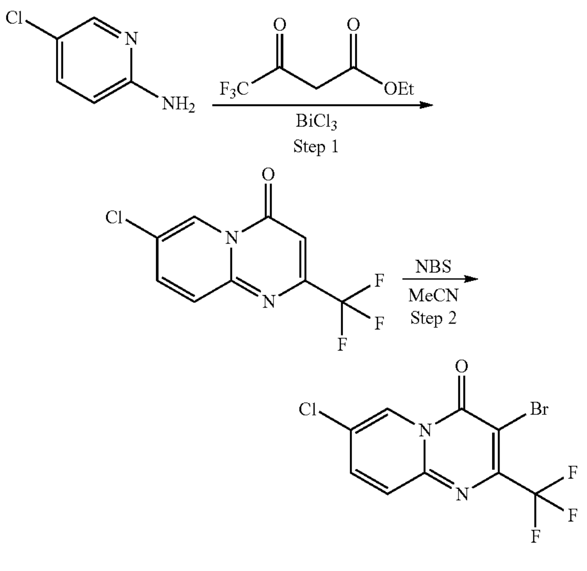

Step 1: 7-chloro-2-(trifluoromethyl)-4H-pyrido[1,2-a]pyrimidin-4-one

A mixture of 2-amino-5-chloropyridine (1250 mg, 9.72 mmol), 4,4,4-trifluoro-3-oxobutanoic acid ethyl ester (2.84 mL, 19.5 mmol) and bismuth trichloride (153 mg, 0.49 mmol) was heated at 120° C. for 18 hours. MeOH was added and the precipitate was filtered under vacuum to obtain 7-chloro-2-(trifluoromethyl)-4H-pyrido[1,2-a]pyrimidin-4-one as a pale yellow solid (753 mg, 3.03 mmol, 31% yield). LC/MS ($ESI^+$) m/z=249.1/251.1 $[M+H]^+$. $^1H$ NMR (400 MHz, DMSO-$d_6$) δ 9.04 (d, J=2.3 Hz, 1H), 8.20 (dd, J=9.5, 2.4 Hz, 1H), 7.92 (dd, J=9.5, 0.7 Hz, 1H), 6.93 (s, 1H).

Step 2: 3-bromo-7-chloro-2-(trifluoromethyl)-4H-pyrido[1,2-a]pyrimidin-4-one

A mixture of 7-chloro-2-(trifluoromethyl)-4H-pyrido[1,2-a]pyrimidin-4-one (753 mg, 3 mmol) and N-bromosuccinimide (800 mg, 4.5 mmol) in MeCN (20 mL) was stirred at 80° C. for 6 hours. The mixture was concentrated, dissolved in DCM and washed subsequently with saturated aqueous $Na_2S2O_3$ and $NaHCO_3$ solutions and brine. The organic phase was dried and concentrated to give 3-bromo-7-chloro-2-(trifluoromethyl)-4H-pyrido[1,2-a]pyrimidin-4-one as a yellow solid (989 mg, 3.02 mmol, quantitative yield). LC/MS ($ESI^+$) m/z=327.0/329.0 $[M+H]^+$. $^1H$ NMR (400 MHz, DMSO-$d_6$) δ 7.96 (d, J=9.46 Hz, 1H) 8.23 (dd, J=9.46, 2.20 Hz, 1H) 9.00-9.12 (m, 1H).

Intermediate 3-R

3-Bromo-8-(methoxymethyl)-2-(trifluoromethyl)-4H-pyrido[1,2-a]pyrimidin-4-one

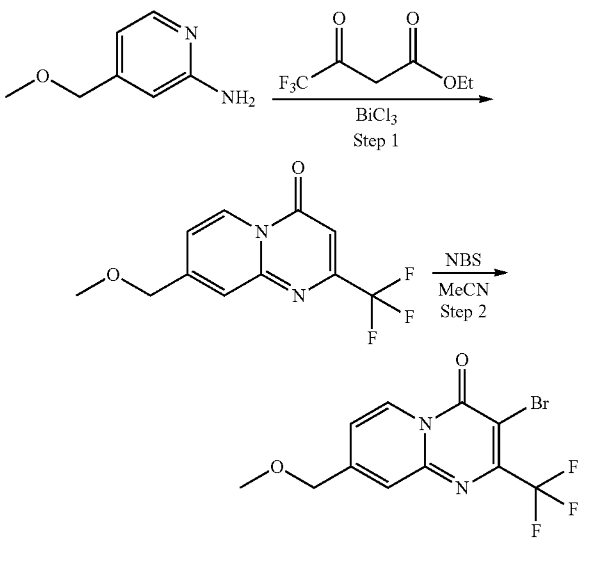

Step 1: 8-(methoxymethyl)-2-(trifluoromethyl)-4H-pyrido[1,2-a]pyrimidin-4-one

A suspension of 4-(methoxymethyl)pyridin-2-amine (100 mg, 0.72 mmol, Enamine Ltd), bismuth(III) chloride (23 mg, 0.07 mmol) and 4,4,4-trifluoro-3-oxobutanoic acid ethyl ester (0.53 mL, 3.62 mmol) was stirred at 120° C. for 48 h. After cooling mixture was diluted with EtOAc and washed with water. The organic phase was dried and evaporated, and crude was purified by flash chromatography ($SiO_2$, Cy/EtOAc 1:1) affording 8-(methoxymethyl)-2-(trifluoromethyl)-4H-pyrido[1,2-a]pyrimidin-4-one (70 mg, 0.27 mmol, 37% yield). $^1$H NMR (400 MHz, $CDCl_3$) δ 9.07 (d, 1H), 7.79 (dq, 1H), 7.26 (dd, 1H), 6.78 (s, 1H), 4.62 (d, 2H), 3.53 (s, 3H).

Step 2: 3-bromo-8-(methoxymethyl)-2-(trifluoromethyl)-4H-pyrido[1,2-a]pyrimidin-4-one 8-(methoxymethyl)-2-(trifluoromethyl)-4H-pyrido[1,2-a]pyrimidin-4-one (70 mg, 0.27 mmol) in MeCN (3 mL) was added N-bromosuccinimide (53 mg, 0.30 mmol) and mixture was stirred at RT for 3 h. The mixture was concentrated, diluted with EtOAc and washed subsequently with $Na_2S_2O_3$ and $NaHCO_3$. The organics were combined, dried and evaporated, affording 3-bromo-8-(methoxymethyl)-2-(trifluoromethyl)-4H-pyrido[1,2-a]pyrimidin-4-one as yellow solid (84 mg, 0.25 mmol, 92% yield). LC/MS ($ESI^+$) m/z=327.0/329.0 $[M+H]^+$. $^1$H NMR (400 MHz, $CDCl_3$) δ 9.09 (dd, 1H), 7.82 (dq, 1H), 7.32 (dd, 1H), 4.62 (d, 2H), 3.54 (s, 3H).

The Intermediates 3-S to 3-AF in Table 2 were prepared analogous to preparation of Intermediate 3-R.

TABLE 2

| Int # | Chemical Structure | Name | Starting Reagents and Conditions | LC/MS ($ESI^+$) m/z |
|---|---|---|---|---|
| 3-S | 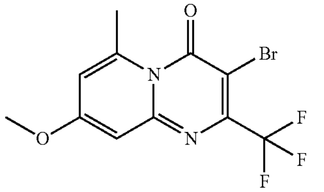 [SMILES: COc1cc(C)n2c(=O)c(Br)c(C(F)(F)F)nc2c1] | 3-bromo-8-methoxy-6-methyl-2-(trifluoromethyl)-4H-pyrido[1,2-a]pyrimidin-4-one | 4-methoxy-6-methylpyridin-2-amine (preparation described in patent application WO2014/153280) | 337.1/ 339.1 $[M + H]^+$ |
| 3-T | 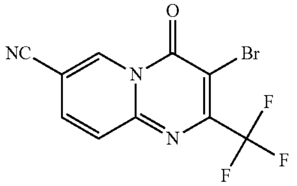 [SMILES: N#Cc1ccc2nc(C(F)(F)F)c(Br)c(=O)n2c1] | 3-bromo-4-oxo-2-(trifluoromethyl)-4H-pyrido[1,2-a]pyrimidine-7-carbonitrile | 6-amino-3-pyridinecarbonitrile | 318.1/ 320.1 $[M + H]^+$ |
| 3-U | 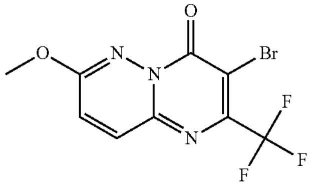 [SMILES: COc1ccc2nc(C(F)(F)F)c(Br)c(=O)n2n1] | 3-bromo-7-methoxy-2-(trifluoromethyl)-4H-pyrimido[1,2-b]pyridazin-4-one | 6-methoxypyridazin-3-amine (preparation described in patent application WO2013/68458) | 324.1/ 326.1 $[M + H]^+$ |
| 3-V | 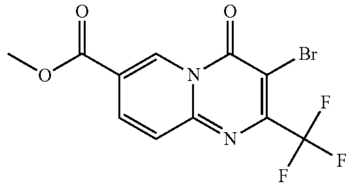 [SMILES: COC(=O)c1ccc2nc(C(F)(F)F)c(Br)c(=O)n2c1] | methyl 3-bromo-4-oxo-2-(trifluoromethyl)-4H-pyrido[1,2-a]pyrimidine-7-carboxylate | 6-amino-3-pyridinecarboxylic acid methyl ester | 351.2/ 353.2 $[M + H]^+$ |
| 3-X | 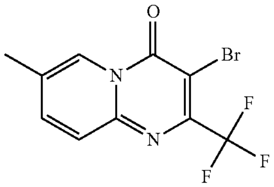 [SMILES: Cc1ccc2nc(C(F)(F)F)c(Br)c(=O)n2c1] | 3-bromo-7-methyl-2-(trifluoromethyl)-4H-pyrido[1,2-a]pyrimidin-4-one | 2-amino-5-methylpyridine | 307.1/ 309.1 $[M + H]^+$ |
| 3-Y | 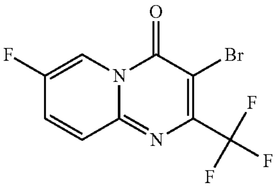 [SMILES: O=c1c(Br)c(C(F)(F)F)nc2ccc(F)cn12] | 3-bromo-7-fluoro-2-(trifluoromethyl)-4H-pyrido[1,2-a]pyrimidin-4-one | 2-amino-5-fluoropyridine | 311.0/ 313.0 $[M + H]^+$ |

TABLE 2-continued

| Int # | Chemical Structure | Name | Starting Reagents and Conditions | LC/MS (ESI+) m/z |
|---|---|---|---|---|
| 3-Z | 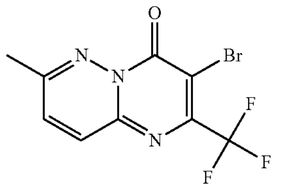 [SMILES: Cc1ccc2nc(C(F)(F)F)c(Br)c(=O)n2n1] | 3-bromo-7-methyl-2-(trifluoromethyl)-4H-pyrimido[1,2-b]pyridazin-4-one | 3-amino-6-methylpyridazine (Apollo Scientific Ltd) | 308.0/ 310.0 $[M + H]^+$ |
| 3-AA | 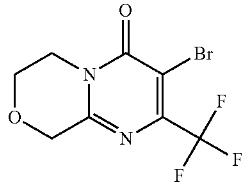 [SMILES: O=c1c(Br)c(C(F)(F)F)nc2n1CCOC2] | 3-bromo-2-(trifluoromethyl)-4H,6H,7H,9H-pyrimido[2,1-c][1,4]oxazin-4-one | morpholin-3-ylideneamine hydrochloride (preparation described in patent application WO2003/93279) | 299.0/ 301.0 $[M + H]^+$ |
| 3-AB | 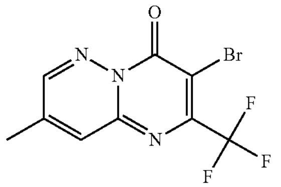 [SMILES: Cc1cnn2c(=O)c(Br)c(C(F)(F)F)nc2c1] | 3-bromo-8-methyl-2-(trifluoromethyl)-4H-pyrimido[1,2-b]pyridazin-4-one | 3-amino-5-methylpyridazine (Apollo Scientific Ltd.) | 307.9/ 309.9 $[M + H]^+$ |
| 3-AC | 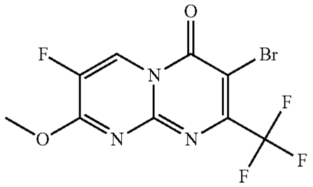 [SMILES: COc1nc2nc(C(F)(F)F)c(Br)c(=O)n2cc1F] | 3-bromo-7-fluoro-8-methoxy-2-(trifluoromethyl)-4H-[1,3]diazino[1,2-a]pyrimidin-4-one | prepared from 2-chloro-5-fluoro-4-methoxypyrimidine (Apollo Scientific Ltd) as described for Intermediate 3-M | 341.9/ 343.9 $[M + H]^+$ |
| 3-AD | 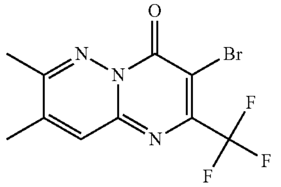 [SMILES: Cc1cc2nc(C(F)(F)F)c(Br)c(=O)n2nc1C] | 3-bromo-7,8-dimethyl-2-(trifluoromethyl)-4H-pyrimido[1,2-b]pyridazin-4-one | 5,6-dimethylpyridazin-3-amine (Enamine Ltd) | 321.9/ 323.9 $[M + H]^+$ |
| 3-AE | 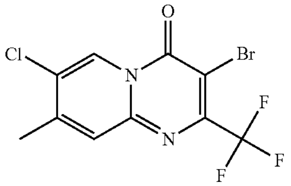 [SMILES: Cc1cc2nc(C(F)(F)F)c(Br)c(=O)n2cc1Cl] | 3-bromo-7-chloro-8-methyl-2-(trifluoromethyl)-4H-pyrido[1,2-a]pyrimidin-4-one | 2-amino-5-chloro-4-picoline (Combi-Blocks Inc.) | 340.9/ 342.9 $[M + H]^+$ |
| 3-AF | 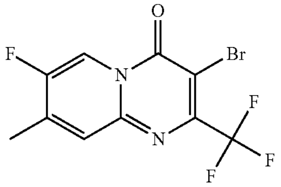 [SMILES: Cc1cc2nc(C(F)(F)F)c(Br)c(=O)n2cc1F] | 3-bromo-7-fluoro-8-methyl-2-(trifluoromethyl)-4H-pyrido[1,2-a]pyrimidin-4-one | 2-Amino-5-fluoro-4-picoline (Combi-Blocks Inc.) | 325.0/ 327.0 $[M + H]^+$ |

Intermediate 4-A

3-Bromo-8-methoxy-2-(trifluoromethyl)-4H-[1,3] diazino[1,6-a]pyrimidin-4-one

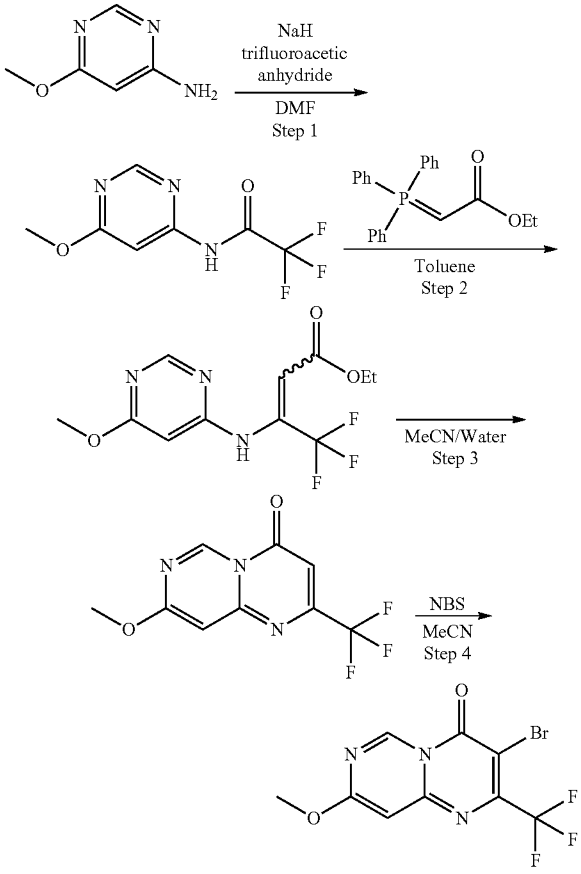

Step 1: 2,2,2-trifluoro-N-(6-methoxypyrimidin-4-yl) acetamide 6-methoxy-4-pyrimidinamine (2.0 g, 15.98 mmol) was dissolved in DMF (106 mL) and sodium hydride (60% in oil, 1.28 g, 31.97 mmol) was added at room temperature. After 1 h, trifluoroacetic anhydride (5.37 g, 25.57 mmol) was added and the mixture was left to react at room temperature for 30 min. The reaction mixture was poured into cold water and extracted with EtOAc. The organic phase was washed with water, brine, dried over $Na_2SO_4$ and evaporated in vacuo. The crude was purified by flash chromatography ($SiO_2$, eluted with cyclohexanes:EtOAc 100:0 to 75:25) to afford 2,2,2-trifluoro-N-(6-methoxypyrimidin-4-yl)acetamide (2.08 g, 9.41 mmol, 59% yield). LC/MS (ESI$^-$) m/z=222.3 $[M+H]^+$. $^1$H NMR (400 MHz, DMSO-$d_6$) δ 3.95 (s, 3H) 7.36 (s, 1H) 8.69 (s, 1H) 12.38 (br s, 1H).

Step 2: Ethyl 4,4,4-trifluoro-3-[(6-methoxypyrimidin-4-yl)amino]but-2-enoate 2,2,2-trifluoro-N-(6-methoxypyrimidin-4-yl)acetamide (2.08 g, 9.41 mmol) was dissolved in toluene (23 mL). (Carbethoxymethylene)triphenylphosphorane (6.55 g, 18.81 mmol) was added and the reaction was left to react at room temperature for 2 h then at 55° C. for 3 h. The solvent was removed in vacuo and the crude was purified by flash chromatography ($SiO_2$, eluted with cyclohexane:EtOAc 100:0 to 80:20) to give ethyl 4,4,4-trifluoro-3-[(6-methoxypyrimidin-4-yl)amino]but-2-enoate (671 mg, 2.30 mmol, 24.5% yield). LC/MS (ESI$^+$) m/z=292.3 $[M+H]^+$. $^1$H NMR (400 MHz, DMSO-$d_6$) δ 1.03 (t, 3H) 3.87 (s, 3H) 3.95 (q, 2H) 6.16 (s, 1H) 6.25 (d, 1H) 8.30 (d, 1H) 9.55 (br s, 1H).

Step 3: 8-methoxy-2-(trifluoromethyl)-4H-[1,3]diazino[1,6-a]pyrimidin-4-one

Ethyl 4,4,4-trifluoro-3-[(6-methoxypyrimidin-4-yl)amino]but-2-enoate (671 mg, 2.30 mmol) was repeatedly evaporated at 60° C. from a mixture of water (70 mL) and MeCN (40 mL). The crude was purified by flash chromatography ($SiO_2$, eluent cyclohexanes:EtOAc 100:0 to 55:45) to afford 8-methoxy-2-(trifluoromethyl)-4H-[1,3]diazino[1,6-a]pyrimidin-4-one (300 mg, 1.22 mmol, 53% yield). LC/MS (ESI$^+$) m/z=246.3 $[M+H]^+$.

Step 4: 3-bromo-8-methoxy-2-(trifluoromethyl)-4H-[1,3]diazino[1,6-a]pyrimidin-4-one A mixture of afford 8-methoxy-2-(trifluoromethyl)-4H-[1,3]diazino[1,6-a]pyrimidin-4-one (300 mg, 1.22 mmol) and N-bromosuccinimide (240 mg, 1.35 mmol) in MeCN (9.5 mL) was stirred at room temperature for 5 hours. The mixture was concentrated, dissolved in EtOAc and washed subsequently with saturated aqueous $Na_2S2O_3$ and $NaHCO_3$ solutions and brine. The organic phase was dried and concentrated to give the crude that was purified by flash chromatography ($SiO_2$, eluant from cyclohexane:EtOAc 100:0 to 50:50) to give 3-bromo-8-methoxy-2-(trifluoromethyl)-4H-[1,3]diazino[1,6-a]pyrimidin-4-one as a yellow solid (153 mg, 0.47 mmol, 39% yield).

LC/MS (ESI$^+$) m/z=324.2/326.2 [M+H]. $^1$H NMR (400 MHz, DMSO-$d_6$) δ 4.07 (s, 3H) 7.13 (m,1H) 9.57-9.64 (in, 1H).

Intermediates 4-B3 to 4-I of Table 3 were prepared analogous to preparation of Intermediate 4-A.

TABLE 3

| Int # | Chemical Structure | Name | Starting Reagents and Conditions | LC/MS (ESI$^+$) m/z |
|---|---|---|---|---|
| 4-B | 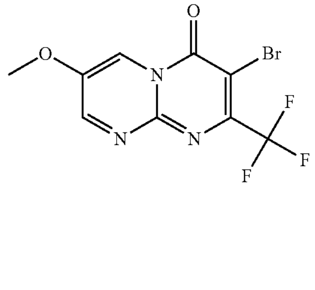 [SMILES: COc1cnc2nc(C(F)(F)F)c(Br)c(=O)n2c1] | 3-bromo-7-methoxy-2-(trifluoromethyl)-4H-[1,3]diazino[1,2-a]pyrimidin-4-one | 2-amino-5-methoxypyrimidine | 324.0/326.0 $[M + H]^+$ |

TABLE 3-continued

| Int # | Chemical Structure | Name | Starting Reagents and Conditions | LC/MS ($ESI^+$) m/z |
|---|---|---|---|---|
| 4-C | 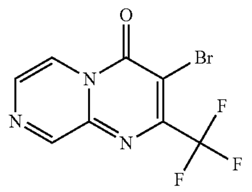 [SMILES: O=c1c(Br)c(C(F)(F)F)nc2cnccn12] | 3-bromo-2-(trifluoromethyl)-4H-pyrazino[1,2-a]pyrimidin-4-one | 2-aminopyrazine | 294.0/296.0 $[M + H]^+$ |
| 4-D | 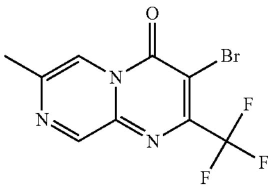 [SMILES: Cc1cn2c(=O)c(Br)c(C(F)(F)F)nc2cn1] | 3-bromo-7-methyl-2-(trifluoromethyl)-4H-pyrazino[1,2-a]pyrimidin-4-one | 2-amino-5-methylpyrazine (Apollo Scientific Ltd) | 308.1/310.1 $[M + H]^+$ |
| 4-E | 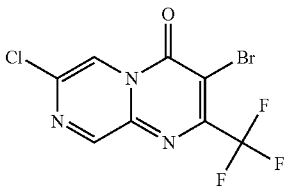 [SMILES: O=c1c(Br)c(C(F)(F)F)nc2cnc(Cl)cn12] | 3-bromo-7-chloro-2-(trifluoromethyl)-4H-pyrazino[1,2-a]pyrimidin-4-one | 2-amino-5-chloropyrazine (Combi-Blocks Inc.) | 328.0/330.0 $[M + H]^+$ |
| 4-F | 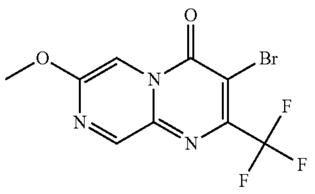 [SMILES: COc1cn2c(=O)c(Br)c(C(F)(F)F)nc2cn1] | 3-bromo-7-methoxy-2-(trifluoromethyl)-4H-pyrazino[1,2-a]pyrimidin-4-one | 2-amino-5-methoxypyrazine (Fluorochem Ltd.) | 323.9/325.9 $[M + H]^+$ |
| 4-G | 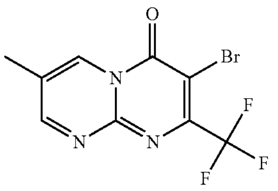 [SMILES: Cc1cnc2nc(C(F)(F)F)c(Br)c(=O)n2c1] | 3-bromo-7-methyl-2-(trifluoromethyl)-4H-[1,3]diazino[1,2-a]pyrimidin-4-one | 2-amino-5-methylpyrimidine (Fluorochem Ltd.); note: Step 3 - Heated to 225° C. in diphenyl ether | 307.9/309.9 $[M + H]^+$ |
| 4-H | 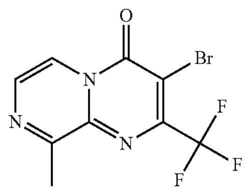 [SMILES: Cc1nccn2c(=O)c(Br)c(C(F)(F)F)nc12] | 3-bromo-9-methyl-2-(trifluoromethyl)-4H-pyrazino[1,2-a]pyrimidin-4-one | 2-amino-3-methylpyrazine (Fluorochem Ltd) | 308.0/310.0 $[M + H]^+$ |
| 4-I | 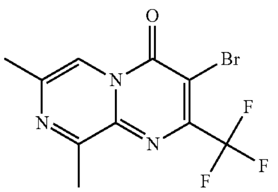 [SMILES: Cc1cn2c(=O)c(Br)c(C(F)(F)F)nc2c(C)n1] | 3-bromo-7,9-dimethyl-2-(trifluoromethyl)-4H-pyrazino[1,2-a]pyrimidin-4-one | 2-amino-3,5-dimethylpyrazine (Combi-Blocks Inc) | 322.0/324.0 $[M + H]^+$ |

Intermediate 4-J

3-Bromo-7-cyclopropyl-2-(trifluoromethyl)-4H-pyrido[1,2-a]pyrimidin-4-one

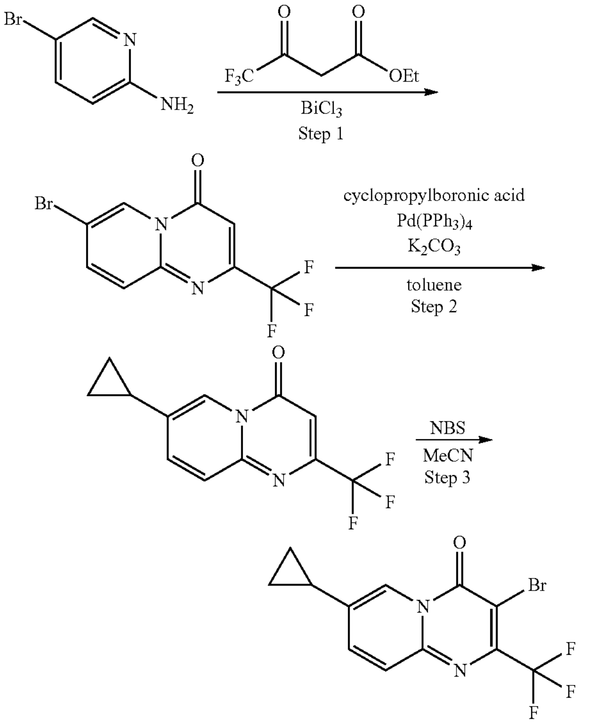

Step 1: 7-bromo-2-(trifluoromethyl)-4H-pyrido[1,2-a]pyrimidin-4-one

A mixture of 5-bromo-2-pyridinamine (1250 mg, 7.23 mmol), 4,4,4-trifluoro-3-oxobutanoic acid ethyl ester (2.11 mL, 14.5 mmol) and bismuth trichloride (114 mg, 0.36 mmol) was heated at 120° C. for 18 hours. The reaction was then cooled down to RT, diluted with a mixture of distilled water/brine and extracted with EtOAc. The organic phase was then washed with brine (x2) and concentrated in vacuo. The mixture was purified by flash chromatography ($SiO_2$, EtOAc:Cy from 3:97 to 25:75) followed by reverse phase flash chromatography (C18, $H_2O$+HCOOH 0.1%: MeCN from 97:3 to 40:60) to afford 7-bromo-2-(trifluoromethyl)-4H-pyrido[1,2-a]pyrimidin-4-one as a white solid (517 mg, 1.76 mmol, 24% yield). LC/MS ($ESI^+$) m/z=293.0/295.0 $[M+H]^+$.

Step 2: 7-Cyclopropyl-2-(trifluoromethyl)-4H-pyrido[1,2-a]pyrimidin-4-one

A mixture of 7-bromo-2-(trifluoromethyl)-4H-pyrido[1,2-a]pyrimidin-4-one (150 mg, 0.51 mmol), palladium triphenylphosphine (592 mg, 0.51 mmol), cyclopropylboronic acid (44 mg, 0.51 mmol) and potassium carbonate (71 mg, 0.51 mmol) was suspended in dry toluene (3 mL) and in a sealable vial. It was degassed with several vacuum/nitrogen cycles and then it was shaken and heated to 100° C. for 18 h. The mixture was cooled to RT, diluted with EtOAc and washed with distilled water and with brine. The organic phase was dried over $Na_2SO_4$ and concentrated in vacuo. The mixture was then purified by flash chromatography ($SiO_2$, EtOAc:Cy from 3:97 to 30:70) to afford 7-cyclopropyl-2-(trifluoromethyl)-4H-pyrido[1,2-a]pyrimidin-4-one as a white solid. (110 mg, 0.43 mmol, 85% yield). LC/MS ($ESI^+$) m/z=255.1 $[M+H]^+$.

Step 3: 3-bromo-7-cyclopropyl-2-(trifluoromethyl)-4H-pyrido[1,2-a]pyrimidin-4-one A mixture of 7-cyclopropyl-2-(trifluoromethyl)pyrido[1,2-a]pyrimidin-4-one (110 mg, 0.43 mmol) and N-bromosuccinimide (85 mg, 0.48 mmol) in MeCN (3 mL) was stirred at room temperature for 1.5 hours. The mixture was diluted with DCM and washed subsequently with saturated aqueous $Na_2S2O_3$ and brine. The mixture was purified by flash chromatography ($SiO_2$ EtOAc:Cy from 3:97 to 25:75) to afford 3-bromo-7-cyclopropyl-2-(trifluoromethyl)-4H-pyrido[1,2-a]pyrimidin-4-one as a white solid (130 mg, 0.39 mmol, 90% yield). LC/MS ($ESI^+$) m/z=333.1/335.1 $[M+H]^+$.

Intermediate 4-K 7-(Azetidin-1-yl)-3-bromo-2-(trifluoromethyl)-4H-pyrido[1,2-a]pyrimidin-4-one

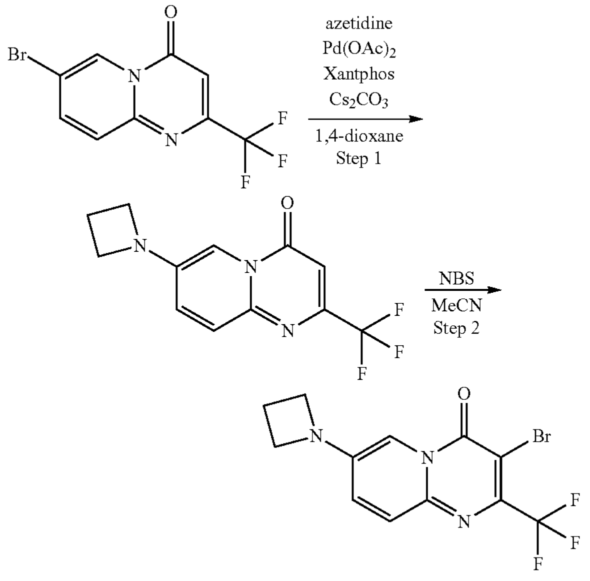

Step 1: 7-(azetidin-1-yl)-2-(trifluoromethyl)-4H-pyrido[1,2-a]pyrimidin-4-one

A screw-capped vial was charged with 7-bromo-2-(trifluoromethyl)-4H-pyrido[1,2-a]pyrimidin-4-one (Intermediate 4-J, Step 1, 60 mg, 0.20 mmol), 1,4-dioxane (3 mL), cesium carbonate (67 mg, 0.20 mmol), azetidine (0.02 mL, 0.25 mmol), (5-diphenylphosphino-9,9-dimethyl-4-xanthenyl)-diphenylphosphine (12 mg, 0.02 mmol), and palladium (II)diacetate (2.3 mg, 0.010 mmol). The mixture was stirred at 100° C. in a screw-capped vial for 4 h then cooled down to rt, diluted with a mixture of water and brine and extracted with EtOAc. The organic phase was dried and evaporated, and the crude was purified by flash chromatography ($SiO_2$, Cy:EtOAc from 95:5 to 60:40) followed by reverse phase flash chromatography (C18, $H_2O$+0.1% HCOOH:MeCN from 97:3 to 50:50) to give 7-(azetidin-1-yl)-2-(trifluoromethyl)pyrido[1,2-a]pyrimidin-4-one as a yellow solid (35 mg, 0.13 mmol, 63% yield). LC/MS (ESI$^+$) m/z=270.1 [M+H]~.

Step 2: 7-(azetidin-1-yl)-3-bromo-2-(trifluoromethyl)-4H-pyrido[1,2-a]pyrimidin-4-one A mixture of 7-(azetidin-1-yl)-2-(trifluoromethyl)-4H-pyrido[1,2-a]pyrimidin-4-one (35 mg, 0.130 mmol) and N-bromosuccinimide (25 mg, 0.140 mmol) in MeCN (2.5 mL) was stirred at room temperature overnight. The mixture was concentrated in vacuo, diluted with EtOAc and washed subsequently with saturated aqueous $Na_2S_2O_3$ and $NaHCO_3$. The organic phase was dried and concentrated in vacuo. The mixture was purified with by reverse phase chromatography (C18, $H_2O$+HCOOH 0.1%: MeCN from 97:3 to 50:50) to obtain 7-(azetidin-1-yl)-3-bromo-2-(trifluoromethyl)-4H-pyrido[1,2-a]pyrimidin-4-one as a yellow solid (18 mg, 0.052 mmol, 40% yield). LC/MS (ESI$^+$) m/z=348.0/350.0 [M+H]$^+$.

Intermediate 4-L

3-Bromo-7-(methoxymethyl)-2-(trifluoromethyl)-4H-pyrido[1,2-a]pyrimidin-4-one

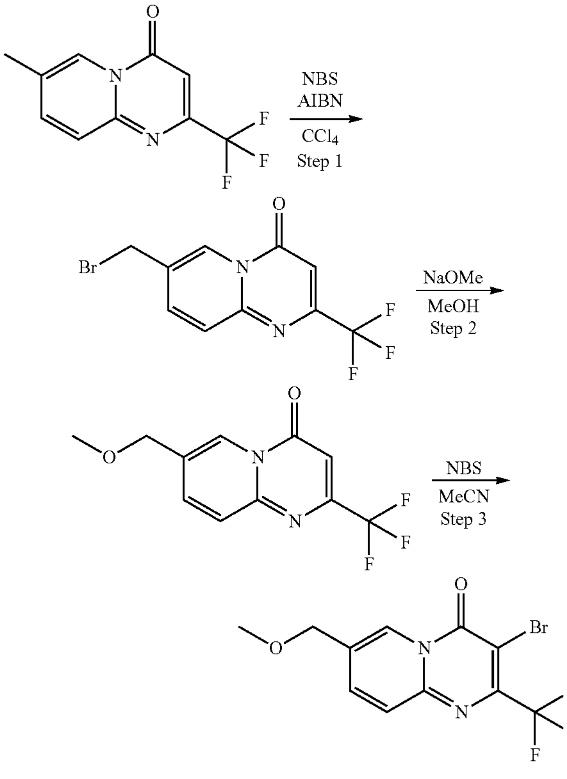

Step 1: 7-(bromomethyl)-2-(trifluoromethyl)-4H-pyrido[1,2-a]pyrimidin-4-one

A suspension of 7-methyl-2-(trifluoromethyl)pyrido[1,2-a]pyrimidin-4-one (Intermediate 3-X, Step 1, 500 mg, 2.19 mmol), N-bromosuccinimide (585 mg, 3.29 mmol) and 2,2'-azobis(2-methylpropionitrile) (36 mg, 0.220 mmol) in carbon tetrachloride (10 mL) was stirred at 80° C. for 7 h. The mixture was evaporated and crude was purified by flash chromatography ($SiO_2$, Cy/EtOAc from 100:0 to 70:30) to give 7-(bromomethyl)-2-(trifluoromethyl)-4H-pyrido[1,2-a]pyrimidin-4-one (130 mg, 0.423 mmol, 19% yield).

LC/MS (ESI$^+$) m/z=307.0/309.0 [M+H]$^+$.

Step 2: 7-(methoxymethyl)-2-(trifluoromethyl)-4H-pyrido[1,2-a]pyrimidin-4-one

To a suspension of 7-(bromomethyl)-2-(trifluoromethyl)-4H-pyrido[1,2-a]pyrimidin-4-one (60 mg, 0.20 mmol) in methanol (4 mL) was added sodium methoxide (11.6 mg, 0.21 mmol) and the mixture was stirred at rt for 3 days. The mixture was evaporated and crude was purified by flash chromatography ($SiO_2$, Cy/EtOAc from 100:0 to 70:30) affording 7-(methoxymethyl)-2-(trifluoromethyl)-4H-pyrido[1,2-a]pyrimidin-4-one as a white solid (34 mg, 0.132 mmol, 67% yield). LC/MS (ESI$^+$) m/z=259.1 [M+H].

Step 3: 3-bromo-7-(methoxymethyl)-2-(trifluoromethyl)-4H-pyrido[1,2-a]pyrimidin-4-one To a solution of 7-(methoxymethyl)-2-(trifluoromethyl)-4H-pyrido[1,2-a]pyrimidin-4-one (34 mg, 0.13 mmol) in MeCN (3 mL) was added N-bromosuccinimide (26 mg, 0.14 mmol) and mixture was stirred at rt for 18 h. The mixture was concentrated, diluted with EtOAc and washed with $Na_2S_2O_3$ and $NaHCO_3$. The organic phases were combined, dried and evaporated affording -bromo-7-(methoxymethyl)-2-(trifluoromethyl)-4H-pyrido[1,2-a]pyrimidin-4-one (35 mg, 0.104 mmol, 79% yield). LC/MS (ESI$^+$) m/z=337.0/339.0 [M+H]$^+$.

Intermediate 4-M

3-Bromo-7-[(dimethylamino)methyl]-2-(trifluoromethyl)-4H-pyrido[1,2-a]pyrimidin-4-one

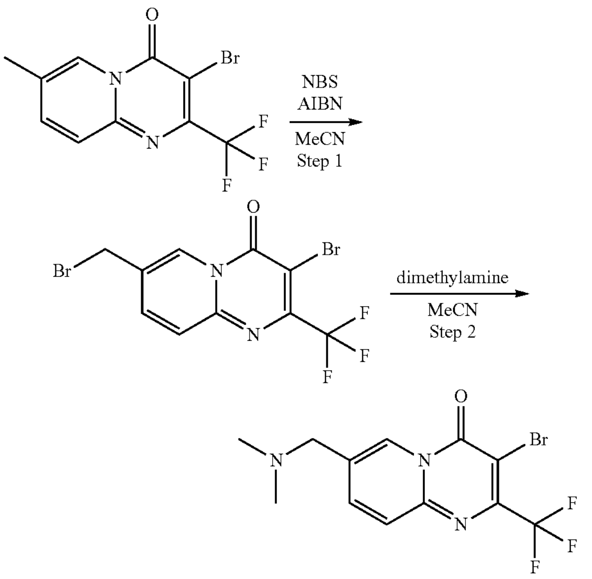

Step 1: 3-bromo-7-[(dimethylamino)methyl]-2-(trifluoromethyl)-4H-pyrido[1,2-a]pyrimidin-4-one A solution of 3-bromo-7-methyl-2-(trifluoromethyl)-4H-pyrido[1,2-a]pyrimidin-4-one (Intermediate 3-X, 30 mg, 0.090 mmol), N-bromosuccinimide (16 mg, 0.090 mmol) and 2,2'-azobis(2-methylpropionitrile) (1.5 mg, 0.010 mmol) in MeCN (3 mL) was shaken at rt for 2 h then warmed to 80° C. and shaken at that temperature for 24 h. The mixture was evaporated and crude was purified by flash chromatography ($SiO_2$, Cy/EtOAc from 100:0 to 70:30) affording 3-bromo-7-(bromomethyl)-2-(trifluoromethyl)-4H-pyrido[1,2-a]pyrimidin-4-one as pale yellow solid (15.5 mg, 0.040 mmol, 46% yield). LC/MS ($ESI^+$) m/z=387.1 $[M+H]^+$.

Step 2: 3-bromo-7-[(dimethylamino)methyl]-2-(trifluoromethyl)-4H-pyrido[1,2-a]pyrimidin-4-one To a solution of 3-bromo-7-(bromomethyl)-2-(trifluoromethyl)-4H-pyrido[1,2-a]pyrimidin-4-one (15 mg, 0.040 mmol) in MeCN (1 mL) was added dimethylamine (2 M in MeOH, 0.05 mL, 0.100 mmol) and the mixture was stirred at rt for 1 h. The mixture was evaporated affording crude 3-bromo-7-[(dimethylamino)methyl]-2-(trifluoromethyl)-4H-pyrido[1,2-a]pyrimidin-4-one which was used directly in the next step. LC/MS ($ESI^+$) m/z=350.2/352.2 [M+H]).

Intermediate 4-N

8-Methoxy-3-(4,4,5,5-tetramethyl-1,3,2-dioxaborolan-2-yl)-2-(trifluoromethyl)-4H-pyrido[1,2-a]pyrimidin-4-one

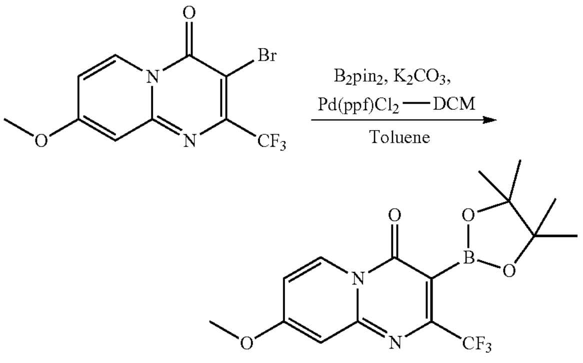

Step 1: 8-methoxy-3-(4,4,5,5-tetramethyl-1,3,2-dioxaborolan-2-yl)-2-(trifluoromethyl)-4H-pyrido[1,2-a]pyrimidin-4-one 3-Bromo-8-methoxy-2-(trifluoromethyl)-4H-pyrido[1,2-a]pyrimidin-4-one (Intermediate 1-A, 0.5 g, 1.55 mmol), bis(pinacolato)diboron (0.51 g, 2.01 mmol), potassium acetate (0.41 g, 4.18 mmol) and [1,1'-bis(diphenylphosphino)ferrocene]dichloropalladium (II) DCM complex (63.4 mg, 0.08 mmol) were combined in a microwave vial in toluene (10.0 mL), and degassed for 10 minutes. The tube was sealed and the reaction stirred at 130° C. for 3 hours under microwave irradiation. After this time, the mixture was diluted with EtOAc, washed with water, dried and eliminated. The residue was purified by flash chromatography ($SiO_2$, cyclohexane:EtOAc) to give 8-methoxy-3-(4,4,5,5-tetramethyl-1,3,2-dioxaborolan-2-yl)-2-(trifluoromethyl)-4H-pyrido[1,2-a]pyrimidin-4-one (30 mg, 0.08 mmol, 5% yield). LC/MS ($ESI^+$) m/z=371.4 $[M+H]^+$.

Intermediate 4-0

3-Bromo-2-ethoxy-8-methoxypyrido[1,2-a]pyrimidin-4-one

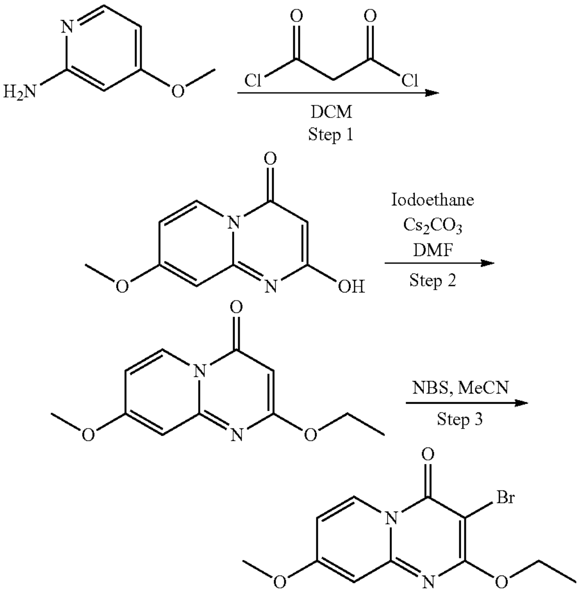

Step 1: 2-hydroxy-8-methoxypyrido[1,2-a]pyrimidin-4-one

4-Methoxy-2-pyridinamine (3.0 g, 24.17 mmol) was dissolved in dry DCM (30 mL) and the solution was cooled to 0° C. Propanedioyl chloride (2.82 mL, 29.0 mmol) was added dropwise under nitrogen atmosphere and the reaction was allowed to stir at room temperature for 48 hours. After this time, the reaction was filtered, washed with DCM, the organic phase dried and evaporated. The crude material was used as such in the following reaction.

Step 2: 2-ethoxy-8-methoxypyrido[1,2-a]pyrimidin-4-one

The crude 2-hydroxy-8-methoxypyrido[1,2-a]pyrimidin-4-one obtained from Step 1, was suspended in DMF (3.0 mL), and cesium carbonate (373 mg, 1.14 mmol) was added. The mixture was degassed and stirred at room temperature for 10 minutes. Iodoethane (0.09 mL, 1.09 mmol) was added, the reaction was stirred at 65° C. overnight. Water was added and the mixture extracted with EtOAc. The organic phase was dried and eliminated. The obtained crude was purified by flash chromatography ($SiO_2$, cyclohexane: EtOAc) to afford 2-ethoxy-8-methoxypyrido[1,2-a]pyrimidin-4-one (102 mg, 0.46 mmol, 44% yield). LC/MS ($ESI^+$) m/z=221.3 $[M+H]^+$.

Step 3: 3-bromo-2-ethoxy-8-methoxypyrido[1,2-a]pyrimidin-4-one

2-Ethoxy-8-methoxypyrido[1,2-a]pyrimidin-4-one (102 mg, 0.46 mmol) was dissolved in MeCN (5.0 mL). N-bromosuccinimide (86.6 mg, 0.49 mmol) was added and the mixture was stirred at room temperature overnight. After this time, the solvent was eliminated and the crude was purified by flash chromatography ($SiO_2$, cyclohexane:E-tOAc) to afford 3-bromo-2-ethoxy-8-methoxypyrido[1,2-a]pyrimidin-4-one (44.0 mg, 0.15 mmol, 31% yield). LC/MS ($ESI^+$) m/z=301.0/302.0 $[M+H]^+$.

Intermediate 4-P

3-Bromo-1-(2,2,3,3,3-pentafluoropropyl)-1,2,4-triazole

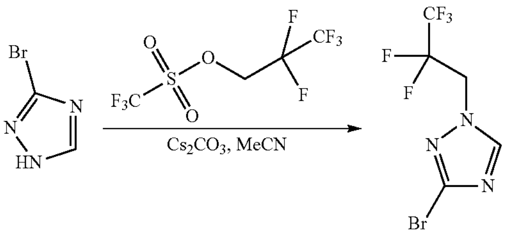

3-Bromo-1H-1,2,4-triazole (500.0 mg, 3.38 mmol), 2,2,3,3,3-pentafluoropropyltriflate (953.3 mg, 3.38 mmol) and cesium carbonate (1.10 g, 3.38 mmol) were suspended in MeCN (20 mL) and stirred at 60° C. for 2 hours. The mixture was concentrated under vacuum, EtOAc was added and the organic phase was washed with water. The solvent was removed to give the product 3-bromo-1-(2,2,3,3,3-pentafluoropropyl)-1,2,4-triazole (865 mg, 3.09 mmol, 91% yield). $^1H$ NMR (500 MHz, DMSO-$d_6$) δ 5.41 (t, J=15.23 Hz, 2H), 8.75 (s, 1H)

Intermediate 4-Q

[2-(2,2,2-Trifluoroethoxy)pyrimidin-5-yl]boronic acid

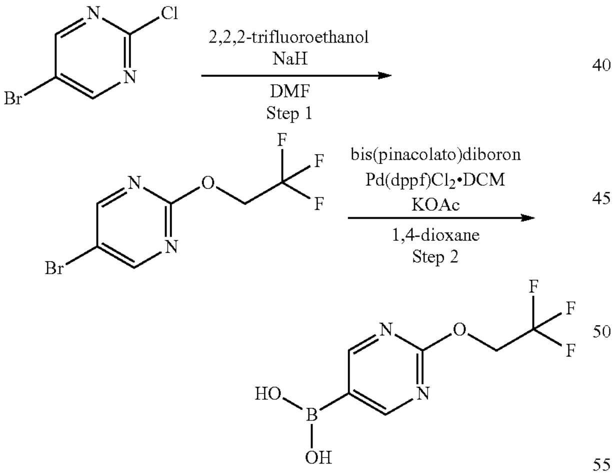

Step 1: 5-bromo-2-(2,2,2-trifluoroethoxy)pyrimidine

To a solution of 2,2,2-trifluoroethanol (0.78 g, 7.75 mmol) in DMF (10 mL) at 0° C. 60% sodium hydride (0.31 g, 7.75 mmol) was added. The mixture was left to reach r.t. in 15 minutes then 5-bromo-2-chloropyrimidine (1.0 g, 5.17 mmol) was added. The mixture was stirred at room temperature for 2 hr. EtOAc and brine were added, phases were separated, organic one was dried over $Na_2SO_4$, filtered and concentrated. The obtained crude was purified by flash-chromatography ($SiO_2$, Cy/EtOAc 95/5) to give 5-bromo-2-(2,2,2-trifluoroethoxy)pyrimidine as a colourless oil. (893 mg, 3.47 mmol, 67% yield). LC/MS ($ESI^+$) m/z=257.1/259.1$[M+H]^+$.

Step 2: [2-(2,2,2-trifluoroethoxy)pyrimidin-5-yl]boronic acid

To a solution of 5-bromo-2-(2,2,2-trifluoroethoxy)pyrimidine (0.89 g, 3.46 mmol) in 1,4-dioxane (10 mL) 4,4,5,5-tetramethyl-2-(4,4,5,5-tetramethyl-1,3,2-dioxaborolan-2-yl)-1,3,2-dioxaborolane (1.32 g, 5.19 mmol), potassium acetate (1030 mg, 10.39 mmol) and [1,1'-Bis(diphenylphosphino)ferrocene]dichloropalladium(II)dichloride, complex with dichloromethane (142 mg, 0.170 mmol) were added. The mixture was degassed for 10 minutes then it was stirred at 90° C. for 3 hr. It was concentrated and purified by flash-chromatography (C18, $H_2O$+0.1% HCOOH/$CH_3CN$ from 1:0 to 1:1) to give [2-(2,2,2-trifluoroethoxy)pyrimidin-5-yl]boronic acid as a white solid (514 mg, 2.32 mmol, 67% yield). $^1H$ NMR (400 MHz, DMSO-$d_6$) δ 4.97-5.00 (m, 1H) 5.06 (q, J=8.95 Hz, 2H) 8.52 (s, 2H) 8.89 (s, 2H).

Intermediate 4-R

[2-(2,2,3,3,3-Pentafluoropropoxy)pyrimidin-5-yl]boronic acid

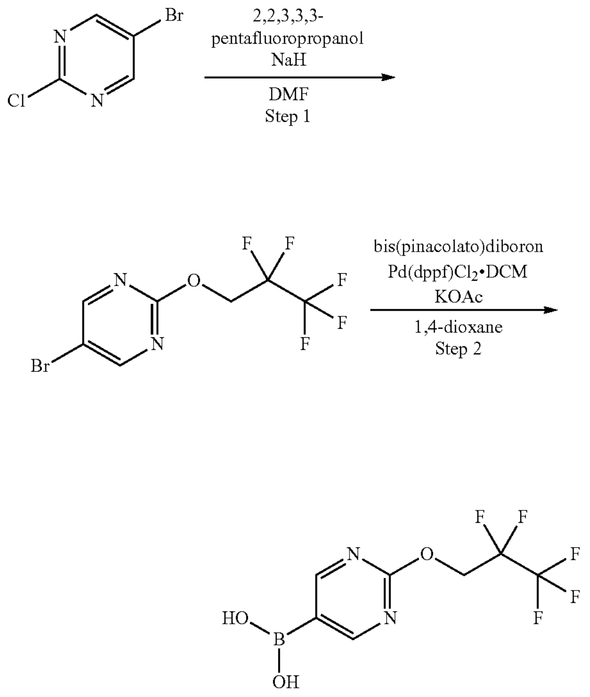

The title compound was prepared using the procedure described for Intermediate 4-Q, Steps 1 and 2 with the following modification: Step 1 was performed with 2,2,3,3,3-pentafluoropropan-1-ol. Step 1 LC/MS ($ESI^+$) m/z=307.1/309.1 $[M+H]^+$. Step 2 LC/MS ($ESI^+$) m/z=273.1$[M+H]^+$. $^1H$ NMR (400 MHz, DMSO-$d_6$) δ 5.16 (t, J=13.20 Hz, 2H) 8.47-8.55 (m, 2H) 8.89 (s, 2H).

Intermediate 4-S

Potassium trifluoro-[1-(2,2,3,3,3-pentafluoropropyl) pyrazol-4-yl]boranuide

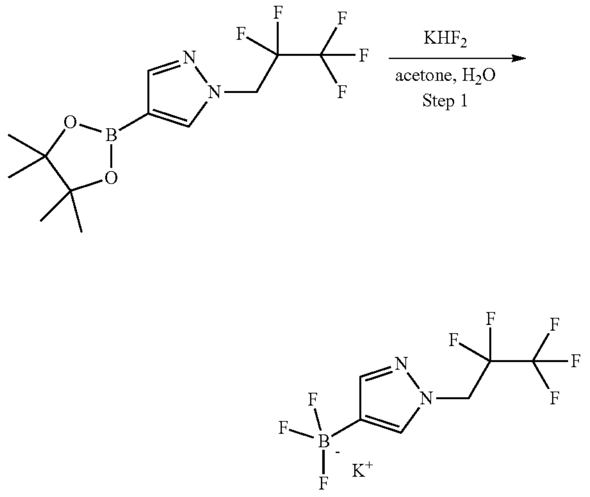

Step 1: Potassium trifluoro-[1-(2,2,3,3,3-pentafluoropropyl)pyrazol-4-yl]boranuide A mixture of 1-(2,2,3,3,3-pentafluoropropyl)-4-(4,4,5,5-tetramethyl-1,3,2-dioxaborolan-2-yl)pyrazole (Intermediate 2-G, 1.0 g, 3.07 mmol) and potassium bifluoride (0.79 g, 10.12 mmol) in acetone (15 mL) and water (5 mL) was stirred at room temperature for 2 h. The solvent was evaporated, the residue suspended in hot acetone (25 mL) and filtered to remove undissolved salts. The solvent was evaporated, residue redisssolved in hot acetone cooled to rt and allowed to stand overnight. The crystallised product was collected, washed with cold acetone and dried under vacuum to give potassium trifluoro-[1-(2,2,3,3,3-pentafluoropropyl) pyrazol-4-yl]boranuide (270 mg, 0.88 mmol, 29% yield). $^1H$ NMR (400 MHz, DMSO-$d_6$) δ 4.98 (t, J=15.30 Hz, 2H), 7.03-7.33 (m, 2H).

Intermediate 4-T

1-[(2,2-Difluorocyclopropyl)methyl]-4-(4,4,5,5-tetramethyl-1,3,2-dioxaborolan-2-yl)pyrazole

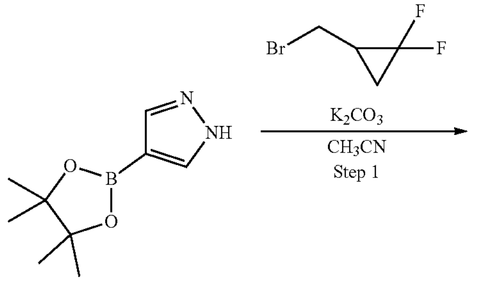

-continued

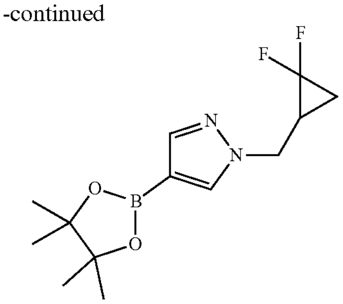

Step 1: 1-[(2,2-difluorocyclopropyl)methyl]-4-(4,4,5,5-tetramethyl-1,3,2-dioxaborolan-2-yl)pyrazole A resealable vial was charged with 4-pyrazoleboronic acid pinacol ester (1 g, 5.15 mmol), potassium carbonate (1.42 g, 10.3 mmol), acetonitrile (20 ml), and 2-(bromomethyl)-1,1-difluorocyclopropane (1.06 g, 6.18 mmol). The reaction mixture was heated at 80° C. for 4 h, then cooled to rt and filtered, washing with MeCN. The filtrate was concentrated under reduced pressure and purified by flash chromatography ($SiO_2$, 0-50% EtOAc/cyclohexane) to afford 1-[(2,2-difluorocyclopropyl)methyl]-4-(4,4,5,5-tetramethyl-1,3,2-dioxaborolan-2-yl)pyrazole (460 mg, 1.62 mmol, 31% yield) as colorless oil. LC/MS ($ESI^+$) m/z=285.2 $[M+H]^+$.

Intermediate 4-U 1-(Cyclopropylmethyl)-4-(4,4,5,5-tetramethyl-1,3,2-dioxaborolan-2-yl)pyrazole

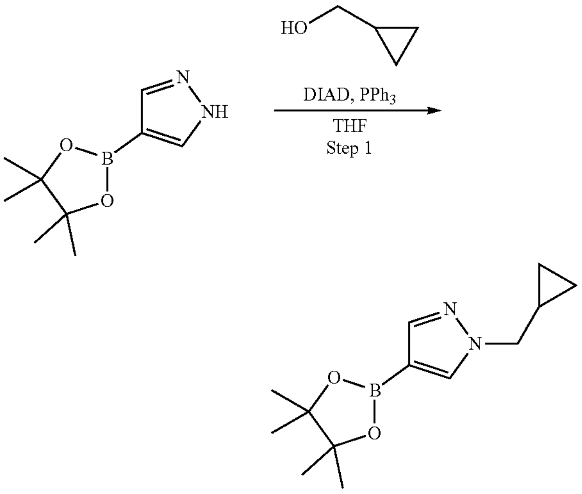

Step 1: 1-(cyclopropylmethyl)-4-(4,4,5,5-tetramethyl-1,3,2-dioxaborolan-2-yl)pyrazole Cyclopropanemethanol (0.89 g, 12.37 mmol) was added dropwise to a stirred solution of 4-pyrazoleboronic acid pinacol ester (2.0 g, 10.31 mmol), triphenylphosphine (2.7 g, 10.31 mmol) and DIAD (2.0 mL, 10.31 mmol) in THF (30 mL) under nitrogen atmosphere at 0° C. The reaction mixture was allowed to warm to rt and stirred for 24 h. The mixture was concentrated under reduced pressure, cyclohexane was added and the resulting precipitate was filtered off. The filtrate was evaporated and the crude was purified by flash chromatography ($SiO_2$, 0-50% EtOAc/cyclohexane) affording 1-(cyclopropylmethyl)-4-(4,4,5,5-tetramethyl-1,3,2-dioxaborolan-2-yl)pyrazole as a white solid (1.78 g, 7.17 mmol, 70% yield). LC/MS (ESI) m/z=249.1 $[M+H]^+$.

Intermediate 4-V

1-[(3,3-Difluorocyclobutyl)methyl]-4-(4,4,5,5-tetramethyl-1,3,2-dioxaborolan-2-yl)pyrazole

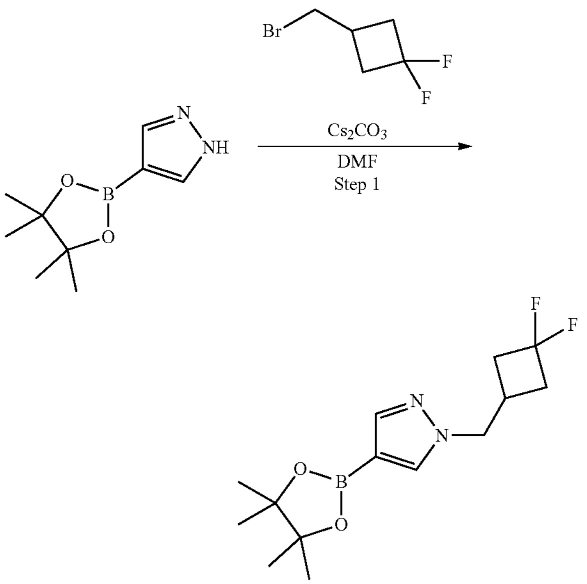

Step 1: 1-[(3,3-difluorocyclobutyl)methyl]-4-(4,4,5,5-tetramethyl-1,3,2-dioxaborolan-2-yl)pyrazole A solution of 3-(bromomethyl)-1,1-difluorocyclobutane (195 mg, 1.05 mmol) in DMF (0.6 mL) was added to a stirred suspension of 4-pyrazoleboronic acid pinacol ester (200 mg, 1.03 mmol) and cesium carbonate (537 mg, 1.65 mmol) in DMF (1.4 ml) at 0° C. The reaction mixture was stirred at rt for 18 h, then filtered, washing with EtOAc. The filtrate was washed with brine (2×), dried over $Na_2SO_4$, filtered and concentrated under reduced pressure to afford 1-[(3,3-difluorocyclobutyl)methyl]-4-(4,4,5,5-tetramethyl-1,3,2-dioxaborolan-2-yl)pyrazole as a colorless oil. (270 mg, 0.9 mmol, 88% yield). LC/MS ($ESI^+$) m/z=299.1 $[M+H]^+$.

Intermediate 4-W 4,4,5,5-Tetramethyl-2-[4-(2,2,2-trifluoroethoxy)phenyl]-1,3,2-dioxaborolane

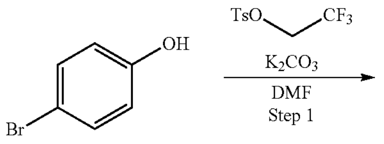

-continued

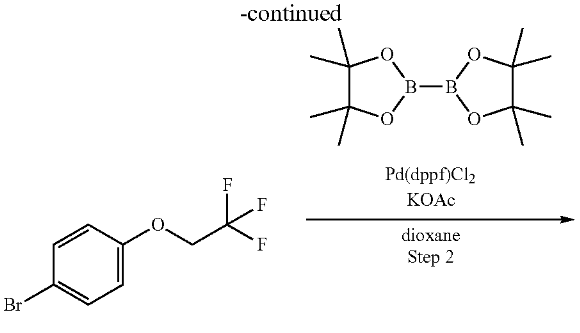

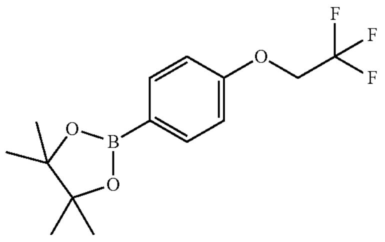

Step 1: 1-bromo-4-(2,2,2-trifluoroethoxy)benzene 4-methylbenzenesulfonic acid 2,2,2-trifluoroethyl ester (14.7 g, 57.9 mmol) was added to a stirred mixture of 4-bromophenol (10 g, 57.8 mmol) and potassium carbonate (39.9 g, 289 mmol) in DMF (80 mL) at 0° C. The reaction mixture was heated at 110° C. for 16 h. After cooling to rt, the mixture was partitioned between water and EtOAc. The organic layer was dried over $Na_2SO_4$, filtered and concentrated under reduced pressure. Purification by flash chromatography ($SiO_2$, 50% EtOAc/cyclohexane) afforded 1-bromo-4-(2,2,2-trifluoroethoxy)benzene (10.9 g, 42.73 mmol, 74% yield). $^1H$ NMR (400 MHz, DMSO-$d_6$) δ 4.78 (q, J=8.88 Hz, 2H), 7.02-7.08 (m, 2H), 7.48-7.56 (m, 2H).

Step 2: 4,4,5,5-tetramethyl-2-[4-(2,2,2-trifluoroethoxy)phenyl]-1,3,2-dioxaborolane A mixture of 1-bromo-4-(2,2,2-trifluoroethoxy)benzene (5.0 g, 19.61 mmol), bis(pinacolato)diboron (5.48 g, 21.57 mmol), potassium acetate (5.77 g, 58.82 mmol) and [1,1'-bis(diphenylphosphino)ferrocene]dichloropalladium(II) (719 mg, 0.98 mmol) in 1,4-dioxane (50 ml) was degassed with nitrogen for 5 min, then heated at 110° C. for 4 h. After cooling to rt, the mixture was filtered with EtOAc through a pad of celite. The filtrate was concentrated under reduced pressure and the residue was purified by flash chromatography ($SiO_2$, 0-3% EtOAc/cyclohexane) to give 4,4,5,5-tetramethyl-2-[4-(2,2,2-trifluoroethoxy)phenyl]-1,3,2-dioxaborolane (2.76 g, 9.13 mmol, 47% yield) as colorless oil. LC/MS ($ESI^+$) m/z=303.1 $[M+H]^+$.

Intermediate 4-X 1-(Oxetan-3-ylmethyl)-4-(4,4,5,5-tetramethyl-1,3,2-dioxaborolan-2-yl)pyrazole

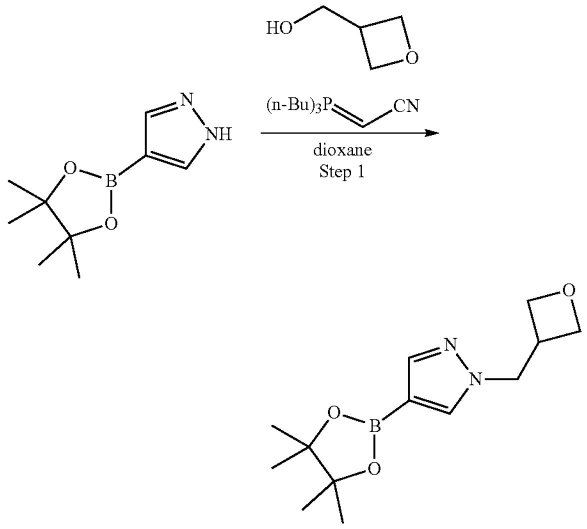

Step 1: 1-(oxetan-3-ylmethyl)-4-(4,4,5,5-tetramethyl-1,3,2-dioxaborolan-2-yl)pyrazole A microwave vial was charged with 4-pyrazoleboronic acid pinacol ester (194 mg, 1 mmol), oxetan-3-ylmethanol (88 mg, 1 mmol), 2-tributylphosphoranylideneacetonitrile (0.52 ml, 2 mmol) and 1,4-dioxane (3 mL). The resulting mixture was subjected to microwave irradiation at 150° C. for 45 min. After cooling to rt, the mixture was partitioned between water and EtOAc. The organic layer was dried over $Na_2SO_4$, filtered and concentrated under reduced pressure. The crude material was purified by flash chromatography ($SiO_2$, 50-90% EtOAc/cyclohexane) obtaining 1-(oxetan-3-ylmethyl)-4-(4,4,5,5-tetramethyl-1,3,2-dioxaborolan-2-yl) pyrazole (270 mg, 1 mmol, 100% yield) as brown oil. LC/MS ($ESI^+$) m/z=265.0 $[M+H]^+$.

Intermediate 4-Y 1-(2,2,3,3,3-Pentafluoropropyl)-3-(4,4,5,5-tetramethyl-1,3,2-dioxaborolan-2-yl)pyrazole

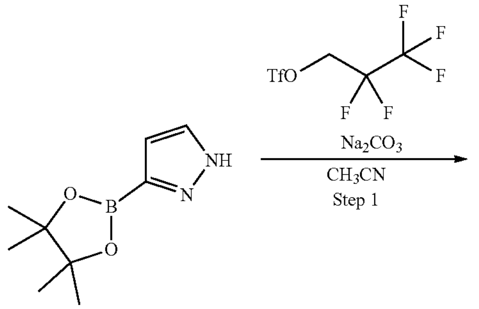

-continued

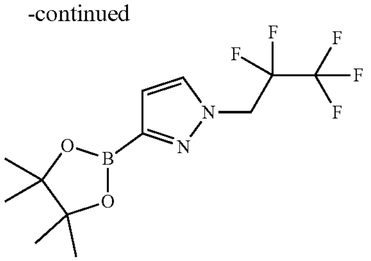

Step 1: 1-(2,2,3,3,3-pentafluoropropyl)-3-(4,4,5,5-tetramethyl-1,3,2-dioxaborolan-2-yl)pyrazole A resealable vial was charged with 3-(4,4,5,5-tetramethyl-1,3,2-dioxaborolan-2-yl)-1H-pyrazole (1.0 g, 5.15 mmol), sodium carbonate (1.09 g, 10.31 mmol), MeCN (5 mL) and 2,2,3,3,3-pentafluoropropyl trifluoromethanesulfonate (1.32 mL, 7.99 mmol). The mixture was heated at 80° C. for 20 h, then cooled to rt and partitioned between water and EtOAc. The organic phases was dried over $Na_2SO_4$, filtered and evaporated under reduced pressure to give 1-(2,2,3,3,3-pentafluoropropyl)-3-(4,4,5,5-tetramethyl-1,3,2-dioxaborolan-2-yl)pyrazole (1 g, 3.07 mmol, 60% yield) which was used in the next reaction without further purification. LC/MS ($ESI^+$) m/z=327.2 $[M+H]^+$.

Intermediate 4-Z

9-Chloro-3-iodo-8-methoxy-2-(trifluoromethyl)-4H-pyrido[1,2-a]pyrimidin-4-one

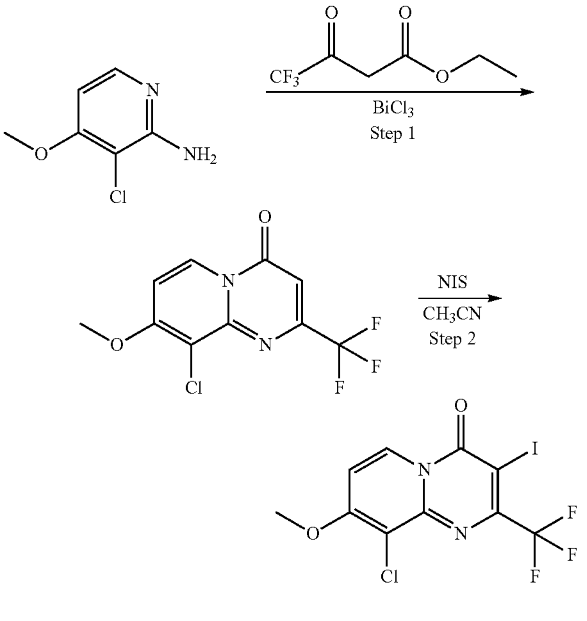

Step 1: 9-Chloro-8-methoxy-2-(trifluoromethyl)-4H-pyrido[1,2-a]pyrimidin-4-one

The title compound was prepared using the procedure described for Intermediate 1-A, Step 1 with the following modification: step 1 was performed with 3-chloro-4-methoxypyridin-2-amine (preparation described in WO2017197555). LC/MS ($ESI^+$) m/z=279.0/281.0 $[M+H]^+$.

Step 2: 9-Chloro-3-iodo-8-methoxy-2-(trifluoromethyl)-4H-pyrido[1,2-a]pyrimidin-4-one The title compound was prepared using the procedure described for Intermediate 1-B, Step 2 with the following modification: Step 2 was performed with 9-chloro-8-methoxy-2-(trifluoromethyl)-4H-pyrido[1,2-a]pyrimidin-4-one. LC/MS ($ESI^+$) m/z=404.9/406.9 $[M+H]^+$.

Synthesis of Examples

Method 1

Example 1-1: 3-(4-(8-Methoxy-4-oxo-2-(trifluoromethyl)-4H-pyrido[1,2-a]pyrimidin-3-yl)phenyl)propanenitrile

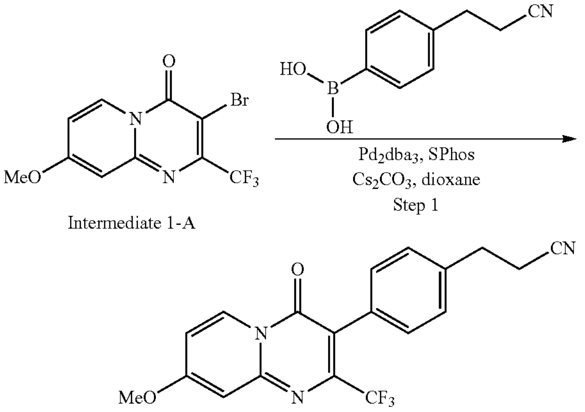

Intermediate 1-A

Step 1: 3-(4-(8-Methoxy-4-oxo-2-(trifluoromethyl)-4H-pyrido[1,2-a]pyrimidin-3-yl)phenyl)propanenitrile A resealable vial with was charged with 3-bromo-8-methoxy-2-(trifluoromethyl)-4H-pyrido[1,2-a]pyrimidin-4-one (Intermediate 1-A, 170 mg, 0.526 mmol), (4-(2-cyanoethyl)phenylboronic acid (138 mg, 0.789 mmol, Combi-Blocks Inc.), tris(dibenzylideneacetone)dipalladium(0) (24 mg, 0.026 mmol), 2-dicyclohexylphosphino-2,6'-dimethoxy-1,1'-biphenyl (22 mg, 0.053 mmol), and cesium carbonate (340 mg, 1.1 mmol). The vial was evacuated and backfilled with nitrogen. This procedure was repeated 3 times, followed by the addition of 1,4-dioxane (850 μl). The reaction mixture was heated to 90° C. and stirred for 12 h. The reaction mixture was quenched with water (2 mL) and diluted with EtOAc (2 mL). The reaction mixture was filtered through a pad of silica gel. The organic phase was separated, washed with brine, dried over magnesium sulfate, filtered, and adsorbed onto silica gel. The crude product was purified by silica gel chromatography (eluent: 0-70% EtOAc/heptane) to provide 3-(4-(8-methoxy-4-oxo-2-(trifluoromethyl)-4H-pyrido[1,2-a]pyrimidin-3-yl)phenyl)propanenitrile as a white solid. LC/MS ($ESI^+$) m/z=374.0 $[M+H]^+$. $^1H$ NMR (400 MHz, $CD_2Cl_2$) δ 2.70 (t, J=7.57 Hz, 2H) 3.03 (t, J=7.46 Hz, 2H) 4.03 (s, 3H) 6.86-7.01 (m, 1H) 7.05 (d, J=2.70 Hz, 1H) 7.23-7.40 (m, 4H) 8.91 (d, J=7.88 Hz, 1H).

Examples 1-2 to 1-88 listed in Table 4 were prepared following the procedure described in Method 1, Step 1, above as follows.

TABLE 4

| Ex. # | Chemical Structure | Name | Reagent and Method Changes |
|---|---|---|---|
| 1-2 | 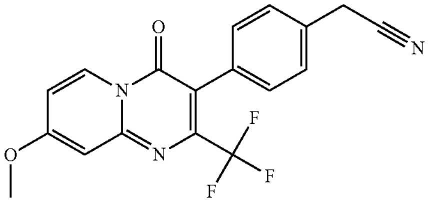 [SMILES: COc1ccn2c(=O)c(-c3ccc(CC#N)cc3)c(C(F)(F)F)nc2c1] | (4-(8-methoxy-4-oxo-2-(trifluoromethyl)-4H-pyrido[1,2-a]pyrimidin-3-yl)phenyl)acetonitrile | (4-(cyanomethyl)phenyl)boronic acid (Combi-Blocks Inc.) |
| 1-3 | 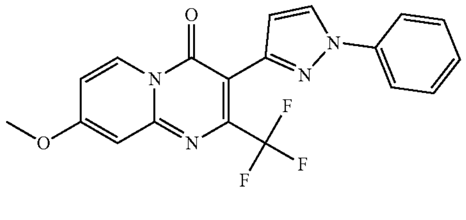 [SMILES: COc1ccn2c(=O)c(-c3ccn(-c4ccccc4)n3)c(C(F)(F)F)nc2c1] | 8-methoxy-3-(1-phenyl-1H-pyrazol-3-yl)-2-(trifluoromethyl)-4H-pyrido[1,2-a]pyrimidin-4-one | 1-Phenyl-3-(4,4,5,5-tetramethyl-1,3,2-dioxaborolan-2-yl)-1H-pyrazole (Essen Scientific) |

TABLE 4-continued

| Ex. # | Chemical Structure | Name | Reagent and Method Changes |
|---|---|---|---|
| 1-4 | 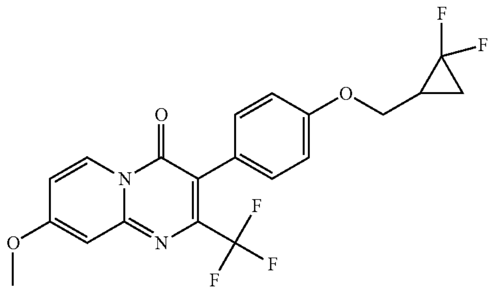 [SMILES: COc1ccn2c(=O)c(-c3ccc(OCC4CC4(F)F)cc3)c(C(F)(F)F)nc2c1] | 3-(4-((2,2-difluorocyclo-propyl)methoxy)phenyl)-8-methoxy-2-(trifluoromethyl)-4H-pyrido[1,2-a]pyrimidin-4-one | 2-[4-[(2,2-difluorocyclo-propyl)methoxy]phenyl]-4,4,5,5-tetramethyl-1,3,2-dioxaborolane (Intermediate 2-A) |
| 1-5 | 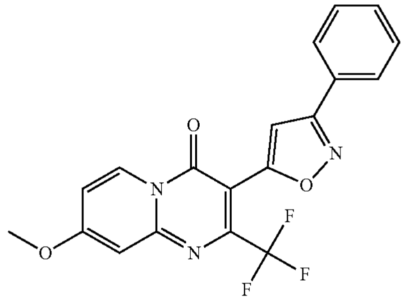 [SMILES: COc1ccn2c(=O)c(-c3cc(-c4ccccc4)no3)c(C(F)(F)F)nc2c1] | 8-methoxy-3-(3-phenyl-1,2-oxazol-5-yl)-2-(trifluoromethyl)-4H-pyrido[1,2-a]pyrimidin-4-one | 3-Phenyl-5-(4,4,5,5-tetramethyl-1,3,2-dioxaborolan-2-yl) isoxazole (Essen Scientific) |
| 1-6 | 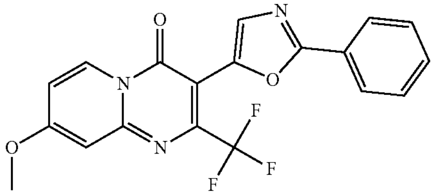 [SMILES: COc1ccn2c(=O)c(-c3cnc(-c4ccccc4)o3)c(C(F)(F)F)nc2c1] | 8-methoxy-3-(2-phenyl-1,3-oxazol-5-yl)-2-(trifluoromethyl)-4H-pyrido[1,2-a]pyrimidin-4-one | 2-phenyl-5-(4,4,5,5-tetramethyl-1,3,2-dioxaborolan-2-yl)oxazole (Intermediate 2-B) |
| 1-7 | 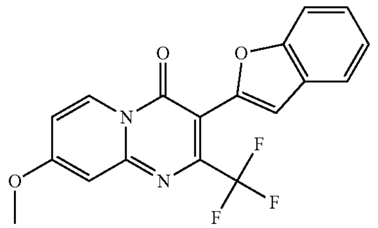 [SMILES: COc1ccn2c(=O)c(-c3cc4ccccc4o3)c(C(F)(F)F)nc2c1] | 3-(1-benzofuran-2-yl)-8-methoxy-2-(trifluoromethyl)-4H-pyrido[1,2-a]pyrimidin-4-one | 3-iodo-8-methoxy-2-(trifluoromethyl)pyrido[1,2-a]pyrimidin-4-one (Intermediate 1-B), benzo[b]furan-2-boronic acid (Alfa Aesar) |
| 1-8 | 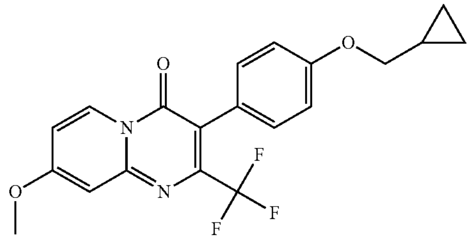 [SMILES: COc1ccn2c(=O)c(-c3ccc(OCC4CC4)cc3)c(C(F)(F)F)nc2c1] | 3-(4-(cyclopropyl-methoxy)phenyl)-8-methoxy-2-(trifluoromethyl)-4H-pyrido[1,2-a]pyrimidin-4-one | 3-iodo-8-methoxy-2-(trifluoromethyl)pyrido[1,2-a]pyrimidin-4-one (Intermediate 1-B), [4-(cyclopropylmethoxy)phe-nyl]boranediol (Combi-Blocks Inc.) |
| 1-9 | 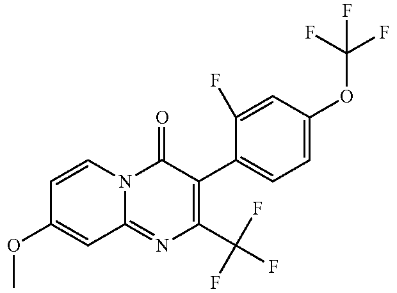 [SMILES: COc1ccn2c(=O)c(-c3ccc(OC(F)(F)F)cc3F)c(C(F)(F)F)nc2c1] | 3-(2-fluoro-4-(trifluoromethoxy)phenyl)-8-methoxy-2-(trifluoromethyl)-4H-pyrido[1,2-a]pyrimidin-4-one | 2-fluoro-4-trifluoromethoxyphenyl-boronic acid (Combi-Blocks Inc.) |

TABLE 4-continued

| Ex. # | Chemical Structure | Name | Reagent and Method Changes |
|---|---|---|---|
| 1-10 | 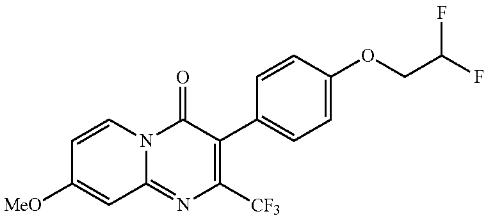 [SMILES: COc1ccn2c(=O)c(-c3ccc(OCC(F)F)cc3)c(C(F)(F)F)nc2c1] | 3-(4-(2,2-difluoroethoxy)phenyl)-8-methoxy-2-(trifluoromethyl)-4H-pyrido[1,2-a]pyrimidin-4-one | 2-(4-(2,2-difluoroethoxy)phenyl)-4,4,5,5-tetramethyl-1,3,2-dioxaborolane (Intermediate 2-C) |
| 1-11 | 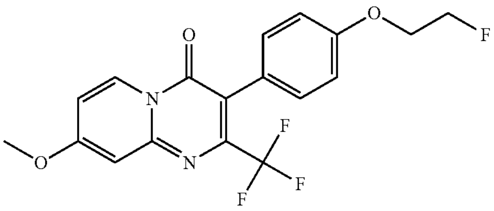 [SMILES: COc1ccn2c(=O)c(-c3ccc(OCCF)cc3)c(C(F)(F)F)nc2c1] | 3-(4-(2-fluoroethoxy)phenyl)-8-methoxy-2-(trifluoromethyl)-4H-pyrido[1,2-a]pyrimidin-4-one | 4-(2-fluoroethoxy)phenylboronic acid (Combi-Blocks Inc.) |
| 1-12 | 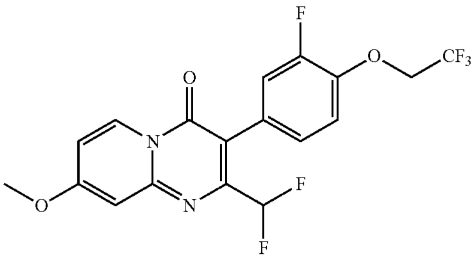 [SMILES: COc1ccn2c(=O)c(-c3ccc(OCC(F)(F)F)c(F)c3)c(C(F)F)nc2c1] | 2-(difluoromethyl)-3-(3-fluoro-4-(2,2,2-trifluoroethoxy)phenyl)-8-methoxy-4H-pyrido[1,2-a]pyrimidin-4-one | 3-bromo-2-(difluoromethyl)-8-methoxy-pyrido[1,2-a]pyrimidin-4-one (Intermediate 1-C); 3-fluoro-4-(2,2,2-trifluoroethoxy)benzene-boronic acid (Combi-Blocks Inc.) |
| 1-13 | 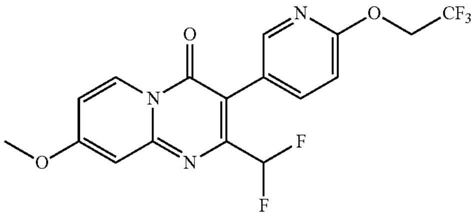 [SMILES: COc1ccn2c(=O)c(-c3ccc(OCC(F)(F)F)nc3)c(C(F)F)nc2c1] | 2-(difluoromethyl)-8-methoxy-3-(6-(2,2,2-trifluoroethoxy)-3-pyridinyl)-4H-pyrido[1,2-a]pyrimidin-4-one | 3-bromo-2-(difluoromethyl)-8-methoxy-pyrido[1,2-a]pyrimidin-4-one (Intermediate 1-C); [6-(2,2,2-trifluoroethoxy)pyridin-3-yl]boronic acid (Combi-Blocks Inc.) |
| 1-14 | 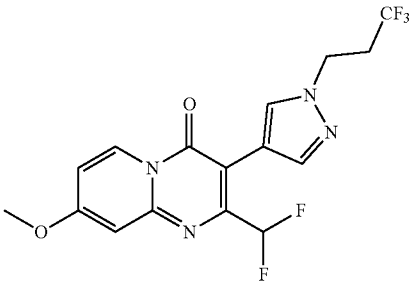 [SMILES: COc1ccn2c(=O)c(-c3cnn(CCC(F)(F)F)c3)c(C(F)F)nc2c1] | 2-(difluoromethyl)-8-methoxy-3-(1-(3,3,3-trifluoropropyl)-1H-pyrazol-4-yl)-4H-pyrido[1,2-a]pyrimidin-4-one | 3-bromo-2-(difluoromethyl)-8-methoxy-pyrido[1,2-a]pyrimidin-4-one (Intermediate 1-C); 4-(4,4,5,5-tetramethyl-1,3,2-dioxaborolan-2-yl)-1-(3,3,3-trifluoropropyl)pyrazole (Intermediate 2-D) |
| 1-15 | 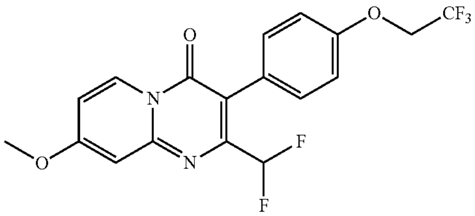 [SMILES: COc1ccn2c(=O)c(-c3ccc(OCC(F)(F)F)cc3)c(C(F)F)nc2c1] | 2-(difluoromethyl)-8-methoxy-3-(4-(2,2,2-trifluoroethoxy)phenyl)-4H-pyrido[1,2-a]pyrimidin-4-one | 3-bromo-2-(difluoromethyl)-8-methoxy-pyrido[1,2-a]pyrimidin-4-one (Intermediate 1-C); 4-(2,2,2-trifluoroethoxy)benzeneboronic acid (Combi-Blocks Inc.) |

TABLE 4-continued

| Ex. # | Chemical Structure | Name | Reagent and Method Changes |
|---|---|---|---|
| 1-16 | 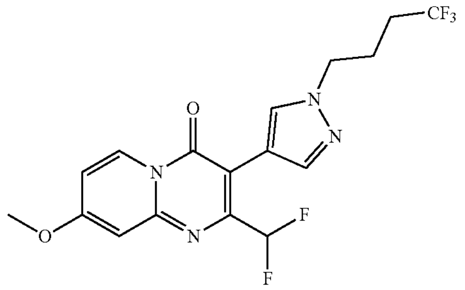 [SMILES: COc1ccn2c(=O)c(-c3cnn(CCCC(F)(F)F)c3)c(C(F)F)nc2c1] | 2-(difluoromethyl)-8-methoxy-3-(1-(4,4,4-trifluorobutyl)-1H-pyrazol-4-yl)-4H-pyrido[1,2-a]pyrimidin-4-one | 3-bromo-2-(difluoromethyl)-8-methoxy-pyrido[1,2-a]pyrimidin-4-one (Intermediate 1-C); 4-(4,4,5,5-tetramethyl-1,3,2-dioxaborolan-2-yl)-1-(4,4,4-trifluorobutyl)-1H-pyrazole (Intermediate 2-E) |
| 1-17 | 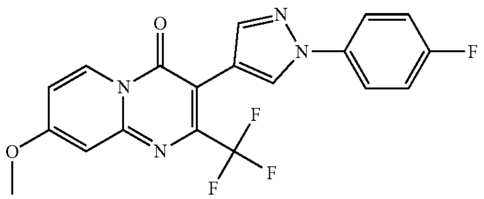 [SMILES: COc1ccn2c(=O)c(-c3cnn(-c4ccc(F)cc4)c3)c(C(F)(F)F)nc2c1] | 3-(1-(4-fluorophenyl)-1H-pyrazol-4-yl)-8-methoxy-2-(trifluoromethyl)-4H-pyrido[1,2-a]pyrimidin-4-one | [1-(4-fluorophenyl)-1h-pyrazol-4-yl]boronic acid (Combi-Blocks Inc.) |
| 1-18 | 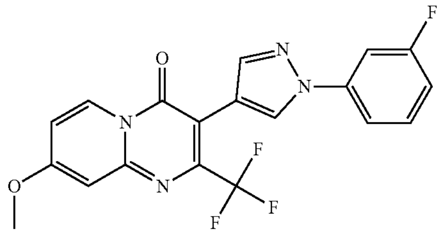 [SMILES: COc1ccn2c(=O)c(-c3cnn(-c4cccc(F)c4)c3)c(C(F)(F)F)nc2c1] | 3-(1-(3-fluorophenyl)-1H-pyrazol-4-yl)-8-methoxy-2-(trifluoromethyl)-4H-pyrido[1,2-a]pyrmidin-4-one | 1-(3-fluorophenyl)-1h-pyrazole-4-boronic acid pinacol ester (Combiphos Catalysts.) |
| 1-19 | 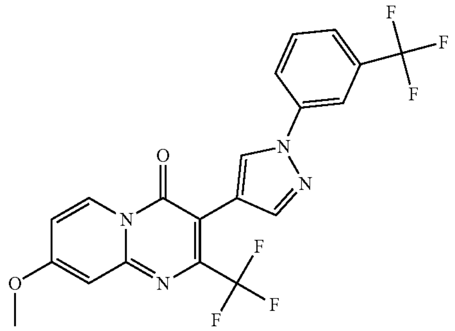 [SMILES: COc1ccn2c(=O)c(-c3cnn(-c4cccc(C(F)(F)F)c4)c3)c(C(F)(F)F)nc2c1] | 8-methoxy-2-(trifluoromethyl)-3-(1-(3-(trifluoromethyl)phenyl)-1H-pyrazol-4-yl)-4H-pyrido[1,2-a]pyrimidin-4-one | (1-[3-(trifluoromethyl)phenyl]-1h-pyrazol-4-yl)boronic acid (Combi-Blocks Inc.) |
| 1-20 | 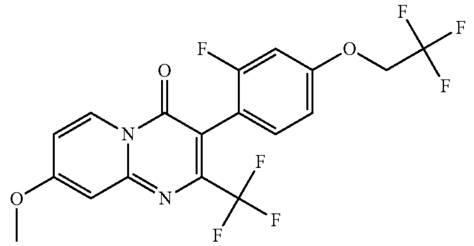 [SMILES: COc1ccn2c(=O)c(-c3ccc(OCC(F)(F)F)cc3F)c(C(F)(F)F)nc2c1] | 3-(2-fluoro-4-(2,2,2-trifluoroethoxy)phenyl)-8-methoxy-2-(trifluoromethyl)-4H-pyrido[1,2-a]pyrimidin-4-one | 2-(2-fluoro-4-(2,2,2-trifluoroethoxy)phenyl)-4,4,5,5-tetramethyl-1,3,2-dioxaborolane (Intermediate 2-F) |
| 1-21 | 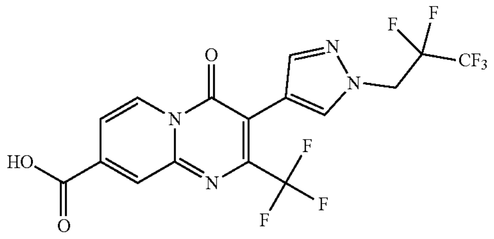 [SMILES: O=C(O)c1ccn2c(=O)c(-c3cnn(CC(F)(F)C(F)(F)F)c3)c(C(F)(F)F)nc2c1] | 4-oxo-3-(1-(2,2,3,3,3-pentafluoropropyl)-1H-pyrazol-4-yl)-2-(trifluoromethyl)-4H-pyrido[1,2-a]pyrimidine-8-carboxylic acid | methyl 3-iodo-4-oxo-2-(trifluoromethyl)-4H-pyrido[1,2-a]pyrimidine-8-carboxylate (Intermediate 1-D); 1-(2,2,3,3,3-pentafluoropropyl)-4-(4,4,5,5-tetramethyl-1,3,2-dioxaborolan-2-yl)-1H-pyrazole (Intermediate 2-G) |

TABLE 4-continued

| Ex. # | Chemical Structure | Name | Reagent and Method Changes |
|---|---|---|---|
| 1-22 | 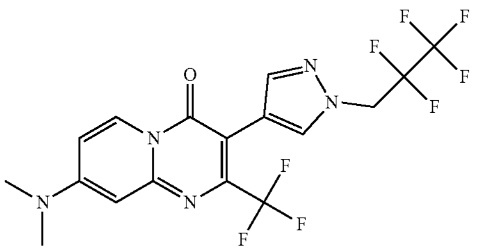 [SMILES: CN(C)c1ccn2c(=O)c(-c3cnn(CC(F)(F)C(F)(F)F)c3)c(C(F)(F)F)nc2c1] | 8-(dimethylamino)-3-(1-(2,2,3,3,3-pentafluoropropyl)-1H-pyrazol-4-yl)-2-(trifluoromethyl)-4H-pyrido[1,2-a]pyrimidin-4-one | 8-(dimethyl amino)-3-iodo-2-(trifluoromethyl)-4H-pyrido[1,2-a] pyrimidin-4-one (Intermediate 1-E), Intermediate 2-G |
| 1-23 | 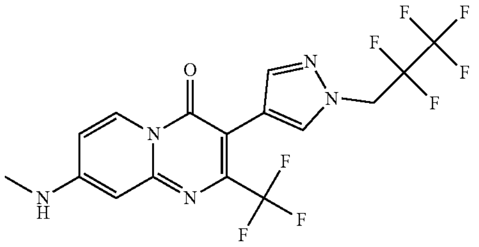 | 8-(methylamino)-3-(1-(2,2,3,3,3-pentafluoropropyl)-1H-pyrazol-4-yl)-2-(trifluoromethyl)-4H-pyrido[1,2-a]pyrimidin-4-one | 3-iodo-8-(methylamino)-2-(trifluoromethyl)-4H-pyrido[1,2-a] pyrimidin-4-one (Intermediate 1-F), Intermediate 2-G |
| 1-24 | 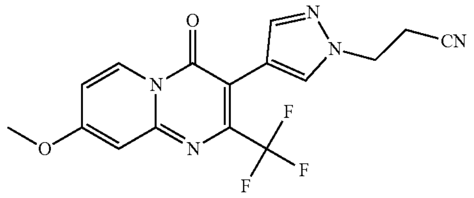 [SMILES: COc1ccn2c(=O)c(-c3cnn(CCC#N)c3)c(C(F)(F)F)nc2c1] | 3-(4-(8-methoxy-4-oxo-2-(trifluoromethyl)-4H-pyrido[1,2-a]pyrimidin-3-yl)-1H-pyrazol-1-yl)propanenitrile | 3-(4-(4,4propanenitrile,5,5-tetramethyl-1,3,2-dioxaborolan-2-yl)-1H-pyrazol-1-yl) (Intermediate 2-H) |
| 1-25 | 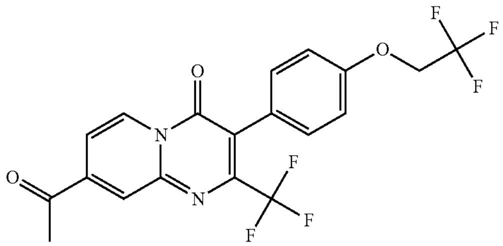 [SMILES: CC(=O)c1ccn2c(=O)c(-c3ccc(OCC(F)(F)F)cc3)c(C(F)(F)F)nc2c1] | 8-acetyl-3-(4-(2,2,2-trifluoroethoxy)phenyl)-2-(trifluoromethyl)-4H-pyrido[1,2-a]pyrimidin-4-one | 8-acetyl-3-iodo-2-(trifluoromethyl)-4H-pyrido[1,2-a]pyrimidin-4-one (Intermediate 1-G); (4-(2,2,2-trifluoroethoxy)phenyl)boronic acid (Combi-Blocks Inc.) |
| 1-26 | 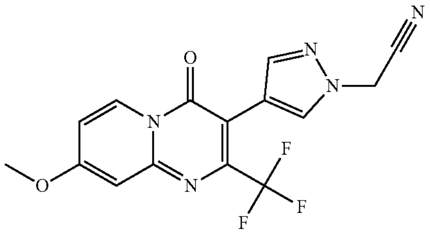 [SMILES: COc1ccn2c(=O)c(-c3cnn(CC#N)c3)c(C(F)(F)F)nc2c1] | (4-(8-methoxy-4-oxo-2-(trifluoromethyl)-4H-pyrido[1,2-a]pyrimidin-3-yl)-1H-pyrazol-1-yl)acetonitrile | 2-(4-(4,4,5,5-tetramethyl-1,3,2-dioxaborolan-2-yl)-1H-pyrazol-1-yl) acetonitrile (Intermediate 2-I) |
| 1-27 | 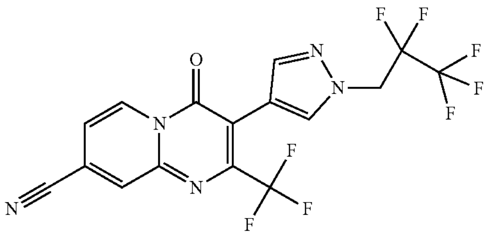 [SMILES: N#Cc1ccn2c(=O)c(-c3cnn(CC(F)(F)C(F)(F)F)c3)c(C(F)(F)F)nc2c1] | 4-oxo-3-(1-(2,2,3,3,3-pentafluoropropyl)-1H-pyrazol-4-yl)-2-(trifluoromethyl)-4H-pyrido[1,2-a]pyrimidine-8-carbonitrile | 3-iodo-4-oxo-2-(trifluoromethyl)-4H-pyrido[1,2-a]pyrimidine-8-carbonitrile (Intermediate 1-H), Intermediate 2-G |

TABLE 4-continued

| Ex. # | Chemical Structure | Name | Reagent and Method Changes |
|---|---|---|---|
| 1-28 | 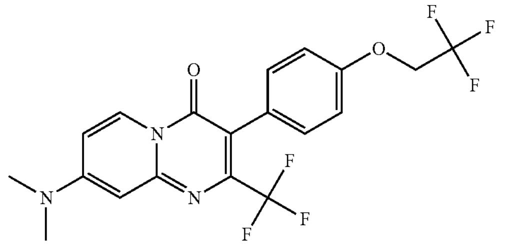 [SMILES: CN(C)c1ccn2c(=O)c(-c3ccc(OCC(F)(F)F)cc3)c(C(F)(F)F)nc2c1] | 8-(dimethylamino)-3-(4-(2,2,2-trifluoroethoxy)phenyl)-2-(trifluoromethyl)-4H-pyrido[1,2-a]pyrimidine-4-one | 8-(dimethylamino)-3-iodo-2-(trifluoromethyl)-4H-pyrido[1,2-a]pyrimidin-4-one (Intermediate 1-E), (4-(2,2,2-trifluoroethoxy)phenyl)boronic acid (Combi-Blocks Inc.) |
| 1-29 | 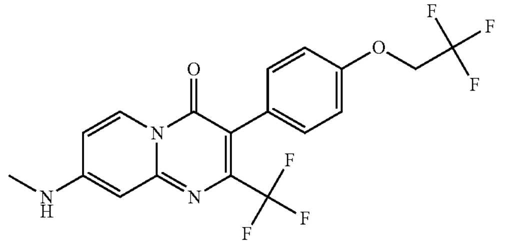 [SMILES: CNc1ccn2c(=O)c(-c3ccc(OCC(F)(F)F)cc3)c(C(F)(F)F)nc2c1] | 8-(methylamino)-3-(4-(2,2,2-trifluoroethoxy)phenyl)-2-(trifluoromethyl)-4H-pyrido[1,2-a]pyrimidin-4-one | 3-iodo-8-(methylamino)-2-(trifluoromethyl)-4H-pyrido[1,2-a]pyrimidin-4-one (Intermediate 1-F), (4-(2,2,2-trifluoroethoxy)phenyl)boronic acid (Combi-Blocks Inc.) |
| 1-30 | 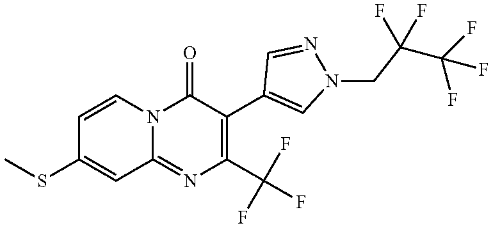 [SMILES: CSc1ccn2c(=O)c(-c3cnn(CC(F)(F)C(F)(F)F)c3)c(C(F)(F)F)nc2c1] | 8-(methylsulfanyl)-3-(1-(2,2,3,3,3-pentafluoropropyl)-1H-pyrazol-4-yl)-2-(trifluoromethyl)-4H-pyrido[1,2-a]pyrimidin-4-one | 3-iodo-8-(methylthio)-2-(trifluoromethyl)-4H-pyrido[1,2-a]pyrimidin-4-one (Intermediate 1-K); Intermediate 2-G |
| 1-31 | 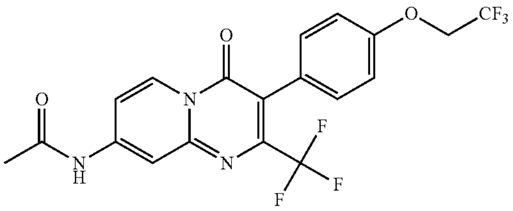 [SMILES: CC(=O)Nc1ccn2c(=O)c(-c3ccc(OCC(F)(F)F)cc3)c(C(F)(F)F)nc2c1] | N-(4-oxo-3-(4-(2,2,2-trifluoroethoxy)phenyl)-2-(trifluoromethyl)-4H-pyrido[1,2-a]pyrimidin-8-yl)acetamide | N-(3-iodo-4-oxo-2-(trifluoromethyl)-4H-pyrido[1,2-a]pyrimidin-8-yl)acetamide (Intermediate 1-L), (4-(2,2,2-trifluoroethoxy)phenyl)boronic acid (Combi-Blocks Inc.) |
| 1-32 | 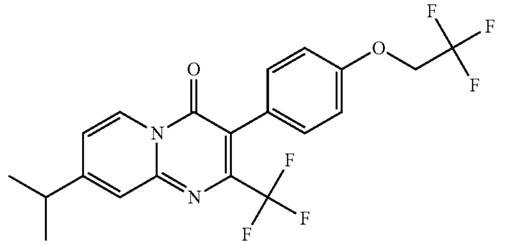 [SMILES: CC(C)c1ccn2c(=O)c(-c3ccc(OCC(F)(F)F)cc3)c(C(F)(F)F)nc2c1] | 8-(2-propanyl)-3-(4-(2,2,2-trifluoroethoxy)phenyl)-2-(trifluoromethyl)-4H-pyrido[1,2-a]pyrimidin-4-one | 3-iodo-8-isopropyl-2-(trifluoromethyl)-4H-pyrido[1,2-a]pyrimidin-4-one (Intermediate 1-M), (4-(2,2,2-trifluoroethoxy)phenyl)boronic acid (Combi-Blocks Inc.) |
| 1-33 | 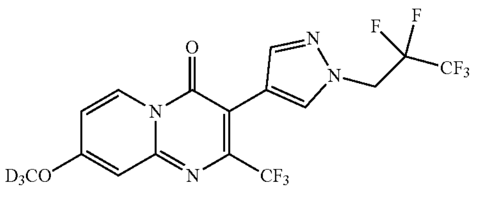 | 8-(methyloxy-$d_3$)-3-(1-(2,2,3,3,3-pentafluoropropyl)-1H-pyrazol-4-yl)-2-(trifluoromethyl)-4H-pyrido[1,2-a]pyrimidin-4-one | 3-bromo-8-(methoxy-$d_3$)-2-(trifluoromethyl)-4H-pyrido[1,2-a]pyrimidin-4-one (Intermediate 1-N), Intermediate 2-G |

TABLE 4-continued

| Ex. # | Chemical Structure | Name | Reagent and Method Changes |
|---|---|---|---|
| 1-34 | 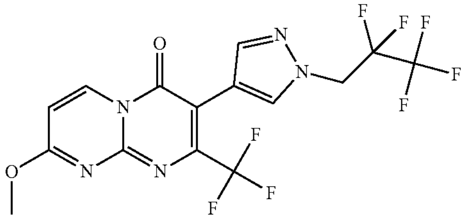 [SMILES: COc1ccn2c(=O)c(-c3cnn(CC(F)(F)C(F)(F)F)c3)c(C(F)(F)F)nc2n1] | 8-methoxy-3-(1-(2,2,3,3,3-pentafluoropropyl)-1H-pyrazol-4-yl)-2-(trifluoromethyl)-4H-pyrimido[1,2-a]pyrimidin-4-one | 3-Bromo-8-methoxy-2-(trifluoromethyl)-4H-pyrimido[1,2-a]pyrimidin-4-one (Intermediate 1-O), Intermediate 2-G |
| 1-35 | 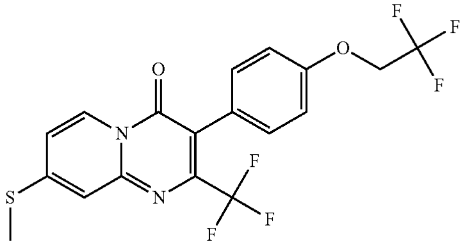 [SMILES: CSc1ccn2c(=O)c(-c3ccc(OCC(F)(F)F)cc3)c(C(F)(F)F)nc2c1] | 8-(methylsulfanyl)-3-(4-(2,2,2-trifluoroethoxy)phenyl)-2-(trifluoromethyl)-4H-pyrido[1,2-a]pyrimidin-4-one | Intermediate 1-K, (4-(2,2,2-trifluoroethoxy)phenyl)boronic acid (Combi-Blocks Inc.) |
| 1-36 | 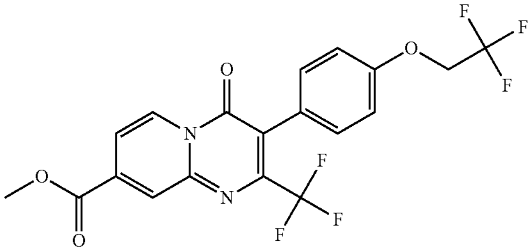 [SMILES: COC(=O)c1ccn2c(=O)c(-c3ccc(OCC(F)(F)F)cc3)c(C(F)(F)F)nc2c1] | methyl 4-oxo-3-(4-(2,2,2-trifluoroethoxy)phenyl)-2-(trifluoromethyl)-4H-pyrido[1,2-a]pyrimidine-8-carboxylate | Intermediate 1-D, (4-(2,2,2-trifluoroethoxy)phenyl)boronic acid (Combi-Blocks Inc.) |
| 1-37 | 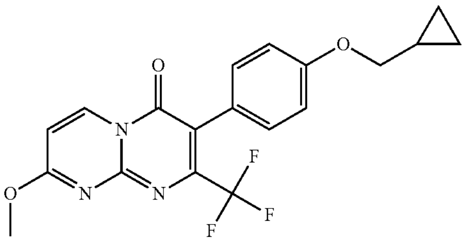 [SMILES: COc1ccn2c(=O)c(-c3ccc(OCC4CC4)cc3)c(C(F)(F)F)nc2n1] | 3-(4-(cyclopropylmethoxy)phenyl)-8-methoxy-2-(trifluoromethyl)-4H-pyrimido[1,2-a]pyrimidin-4-one | Intermediate 1-O, [4-(cyclopropylmethoxy)phenyl]boranediol (Combi-Blocks Inc.) |
| 1-38 | 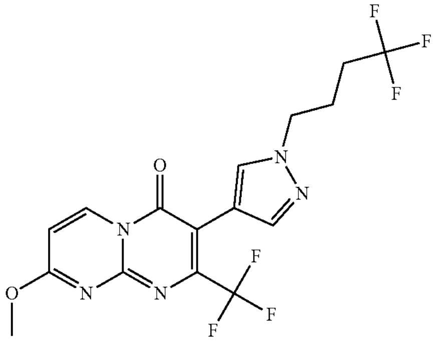 [SMILES: COc1ccn2c(=O)c(-c3cnn(CCCC(F)(F)F)c3)c(C(F)(F)F)nc2n1] | 8-methoxy-3-(1-(4,4,4-trifluorobutyl)-1H-pyrazol-4-yl)-2-(trifluoromethyl)-4H-pyrimido[1,2-a]pyrimidin-4-one | Intermediates 1-O, 2-E |
| 1-39 | 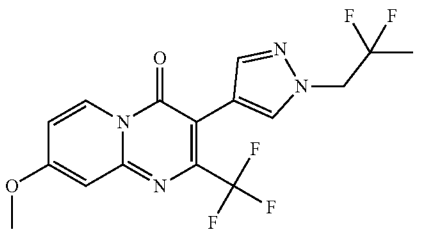 [SMILES: COc1ccn2c(=O)c(-c3cnn(CC(C)(F)F)c3)c(C(F)(F)F)nc2c1] | 3-(1-(2,2-difluoropropyl)-1H-pyrazol-4-yl)-8-methoxy-2-(trifluoromethyl)-4H-pyrido[1,2-a]pyrimidin-4-one | Intermediate 1-A, 1-(2,2-difluoropropyl)-4-(4,4,5,5-tetramethyl-1,3,2-dioxaborolan-2-yl)-1H-pyrazole (Intermediate 2-J) |

TABLE 4-continued

| Ex. # | Chemical Structure | Name | Reagent and Method Changes |
|---|---|---|---|
| 1-40 | 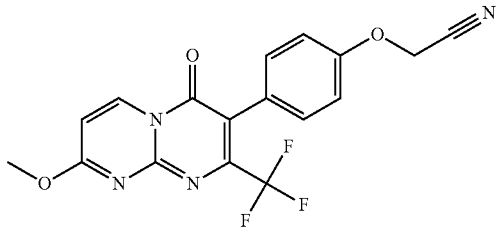 [SMILES: COc1ccn2c(=O)c(-c3ccc(OCC#N)cc3)c(C(F)(F)F)nc2n1] | (4-(8-methoxy-4-oxo-2-(trifluoromethyl)-4H-pyrimido[1,2-a]pyrimidin-3-yl)phenoxy)acetonitrile | Intermediate 1-O, (4-(cyanomethoxy)phenyl)boronic acid (Combi-Blocks Inc.) |
| 1-41 | 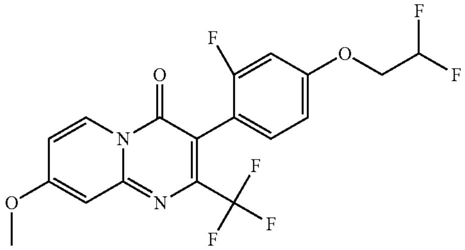 [SMILES: COc1ccn2c(=O)c(-c3ccc(OCC(F)F)cc3F)c(C(F)(F)F)nc2c1] | 3-(4-(2,2-difluoroethoxy)-2-fluorophenyl)-8-methoxy-2-(trifluoromethyl)-4H-pyrido[1,2-a]pyrimidin-4-one | Intermediate 1-B, 2-(4-(2,2-difluoroethoxy)-2-fluorophenyl)-4,4,5,5-tetramethyl-1,3,2-dioxaborolane (Enamine Ltd) |
| 1-42 | 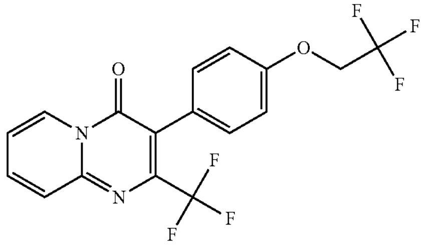 [SMILES: O=c1c(-c2ccc(OCC(F)(F)F)cc2)c(C(F)(F)F)nc2ccccn12] | 3-(4-(2,2,2-trifluoroethoxy)phenyl)-2-(trifluoromethyl)-4H-pyrido[1,2-a]pyrimidin-4-one | 3-bromo-2-(trifluoromethyl)pyrido[1,2-a]pyrimidin-4-one (Intermediate 1-P), 4-(2,2,2-trifluoroethoxy)benzeneboronic acid (Combi-Blocks Inc.) |
| 1-43 | 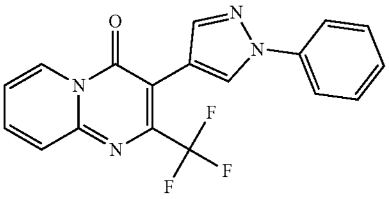 [SMILES: O=c1c(-c2cnn(-c3ccccc3)c2)c(C(F)(F)F)nc2ccccn12] | 3-(1-phenyl-1H-pyrazol-4-yl)-2-(trifluoromethyl)-4H-pyrido[1,2-a]pyrimidin-4-one | Intermediate 1-P, 1-phenyl-4-(4,4,5,5-tetramethyl-1,3,2-dioxaborolan-2-yl)-1H-pyrazole (Combi-Blocks Inc.) |
| 1-44 | 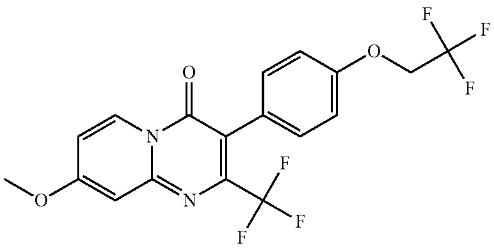 [SMILES: COc1ccn2c(=O)c(-c3ccc(OCC(F)(F)F)cc3)c(C(F)(F)F)nc2c1] | 8-methoxy-3-(4-(2,2,2-trifluoroethoxy)phenyl)-2-(trifluoromethyl)-4H-pyrido[1,2-a]pyrimidin-4-one | Intermediate 1-A, 4-(2,2,2-trifluoroethoxy)benzeneboronic acid (Combi-Blocks Inc.) |
| 1-45 | 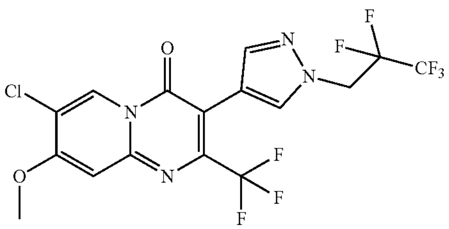 [SMILES: COc1cc2nc(C(F)(F)F)c(-c3cnn(CC(F)(F)C(F)(F)F)c3)c(=O)n2cc1Cl] | 7-chloro-8-methoxy-3-[1-(2,2,3,3,3-pentafluoropropyl)-1H-pyrazol-4-yl]-2-(trifluoromethyl)-4H-pyrido[1,2-a]pyrimidin-4-one | 7-chloro-3-iodo-8-methoxy-2-(trifluoromethyl)-4H-pyrido[1,2-a]pyrimidin-4-one (Intermediate 1-I), Intermediate 2-G |

TABLE 4-continued

| Ex. # | Chemical Structure | Name | Reagent and Method Changes |
|---|---|---|---|
| 1-46 | 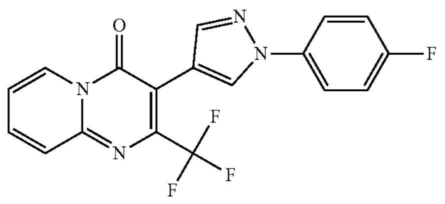 [SMILES: O=c1c(-c2cnn(-c3ccc(F)cc3)c2)c(C(F)(F)F)nc2ccccn12] | 3-(1-(4-fluorophenyl)-1H-pyrazol-4-yl)-2-(trifluoromethyl)-4H-pyrido[1,2-a]pyrimidin-4-one | Intermediate 1-P, [1-(4-fluorophenyl)-1h-pyrazol-4-yl]boronic acid (Combi-Blocks Inc.) |
| 1-47 | 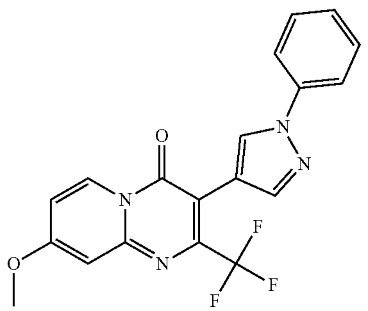 [SMILES: COc1ccn2c(=O)c(-c3cnn(-c4ccccc4)c3)c(C(F)(F)F)nc2c1] | 8-methoxy-3-(1-phenyl-1H-pyrazol-4-yl)-2-(trifluoromethyl)-4H-pyrido[1,2-a]pyrimidin-4-one | Intermediate 1-A, (1-phenyl-1h-pyrazol-4-yl)boronic acid pinacol ester (Combi-Blocks Inc.) |
| 1-48 | 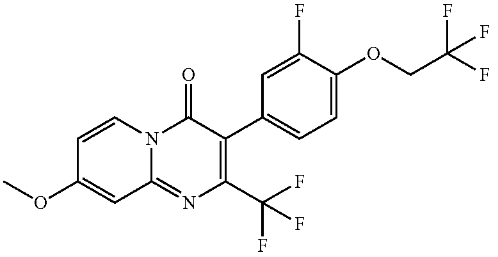 [SMILES: COc1ccn2c(=O)c(-c3ccc(OCC(F)(F)F)c(F)c3)c(C(F)(F)F)nc2c1] | 3-(3-fluoro-4-(2,2,2-trifluoroethoxy)phenyl)-8-methoxy-(trifluoromethyl)-4H-pyrido[1,2-a]pyrimidin-4-one | Intermediates 1-A, 2-F |
| 1-49 | 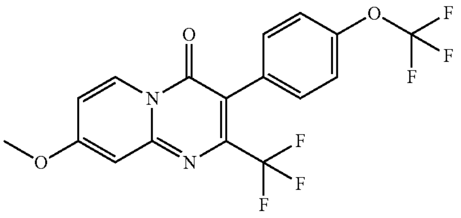 [SMILES: COc1ccn2c(=O)c(-c3ccc(OC(F)(F)F)cc3)c(C(F)(F)F)nc2c1] | 8-methoxy-3-(4-(trifluoromethoxy)phenyl)-2-(trifluoromethyl)-4H-pyrido[1,2-a]pyrimidin-4-one | Intermediate 1-A, 4-(Trifluoromethoxy)benzene-boronic acid (Oakwood Chemical) |
| 1-50 | 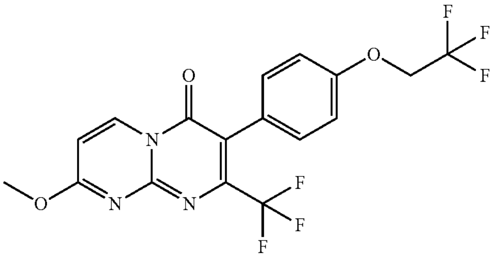 | 8-methoxy-3-(4-(2,2,2-trifluoroethoxy)phenyl)-2-(trifluoromethyl)-4H-pyrimido[1,2-a]pyrimidin-4-one | Intermediate 1-O, 4-(2,2,2-Trifluoroethoxy)benzene-boronic acid (Combi-Blocks Inc.) |
| 1-51 | 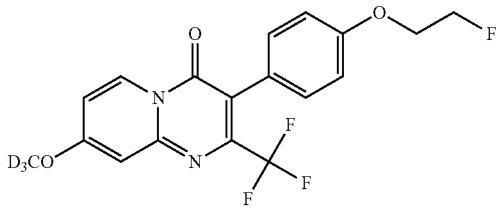 | 3-(4-(2-fluoroethoxy)phenyl)-8-(methyloxy-$d_3$)-2-(trifluoromethyl)-4H-pyrido[1,2-a]pyrimidin-4-one | Intermediate 1-N, (4-(2-Fluoroethoxy)phenyl)boronic acid (Combi-Blocks Inc.) |

TABLE 4-continued

| Ex. # | Chemical Structure | Name | Reagent and Method Changes |
|---|---|---|---|
| 1-52 | 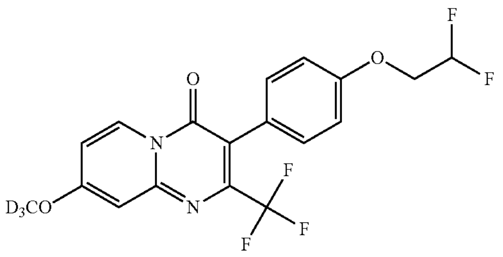 | 3-(4-(2,2-difluoroethoxy)phenyl)-8-(methyloxy-$d_3$)-2-(trifluoromethyl)-4H-pyrido[1,2-a]pyrimidin-4-one | Intermediate 1-N, 2-(4-(2,2-Difluoroethoxy)phenyl)-4,4,5,5-tetramethyl-1,3,2-dioxaborolane (Intermediate 2-C) |
| 1-53 | 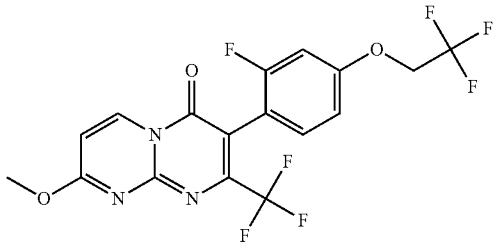 [SMILES: COc1ccn2c(=O)c(-c3ccc(OCC(F)(F)F)cc3F)c(C(F)(F)F)nc2n1] | 3-(2-fluoro-4-(2,2,2-trifluoroethoxy)phenyl)-8-methoxy-2-(trifluoromethyl)-4H-pyrimido[1,2-a]pyrimidin-4-one | Intermediate 1-O, (2-fluoro-4-(2,2,2-trifluoroethoxy)phenyl)boronic acid (Intermediate 2-L) |
| 1-54 | 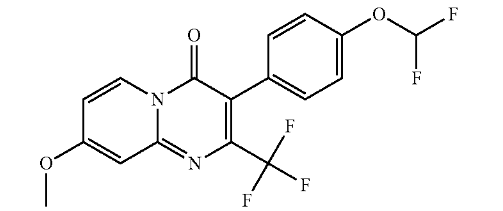 [SMILES: COc1ccn2c(=O)c(-c3ccc(OC(F)F)cc3)c(C(F)(F)F)nc2c1] | 3-(4-(difluoromethoxy)phenyl)-8-methoxy-2-(trifluoromethyl)-4H-pyrido[1,2-a]pyrimidin-4-one | Intermediate 1-B, 4-(difluoromethoxy)phenylboronic acid (Combi-Blocks Inc.) |
| 1-55 | 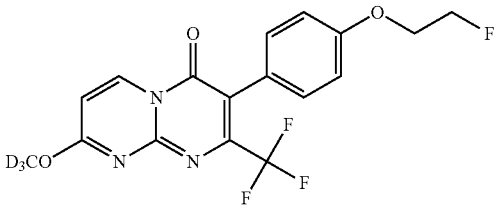 | 3-(4-(2-fluoroethoxy)phenyl)-8-(methyloxy-$d_3$)-2-(trifluoromethyl)-4H-pyrimido[1,2-a]pyrimidin-4-one | 3-Bromo-8-(methoxy-$d_3$)-2-(trifluoromethyl)-4H-pyrimido[1,2-a]pyrimidin-4-one (Intermediate 1-R), 4-(2-fluoroethoxy)phenylboronic acid (Combi-Blocks Inc.) |
| 1-56 | 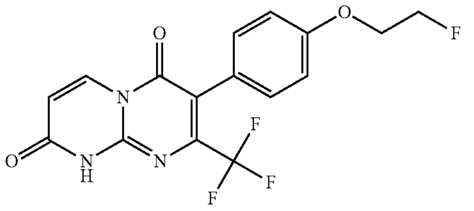 [SMILES: O=c1ccn2c(=O)c(-c3ccc(OCCF)cc3)c(C(F)(F)F)nc2[nH]1] | 7-(4-(2-fluoroethoxy)phenyl)-8-(trifluoromethyl)-2H-pyrimido[1,2-a]pyrimidine-2,6(1H)-dione | Intermediate 1-B, 4-(2-fluoroethoxy)phenylboronic acid (Combi-Blocks Inc.) |
| 1-57 | 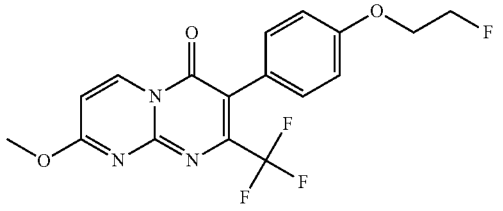 [SMILES: COc1ccn2c(=O)c(-c3ccc(OCCF)cc3)c(C(F)(F)F)nc2n1] | 3-(4-(2-fluoroethoxy)phenyl)-8-methoxy-2-(trifluoromethyl)-4H-pyrimido[1,2-a]pyrimidin-4-one | Intermediate 1-B, 4-(2-fluoroethoxy)phenylboronic acid (Combi-Blocks Inc.) |
| 1-58 | 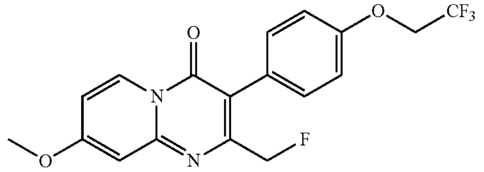 [SMILES: COc1ccn2c(=O)c(-c3ccc(OCC(F)(F)F)cc3)c(CF)nc2c1] | 2-(fluoromethyl)-8-methoxy-3-(4-(2,2,2-trifluoroethoxy)phenyl)-4H-pyrido[1,2-a]pyrimidin-4-one | 3-bromo-2-(fluoromethyl)-8-methoxy-4H-pyrido[1,2-a]pyrimidin-4-one (Intermediate 1-S), 4-(2,2,2-trifluoroethoxy)benzeneboronic acid (Combi-Blocks Inc.) |

TABLE 4-continued

| Ex. # | Chemical Structure | Name | Reagent and Method Changes |
|---|---|---|---|
| 1-59 | 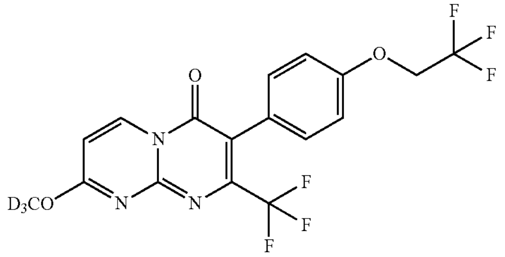 | 8-(methyloxy-$d_3$)-3-(4-(2,2,2-trifluoroethoxy)phenyl)-2-(trifluoromethyl)-4H-pyrimido[1,2-a]pyrimidin-4-one | Intermediate 1-R, 4-(2,2,2-trifluoroethoxy)benzene-boronic acid (Combi-Blocks Inc.) |
| 1-60 | 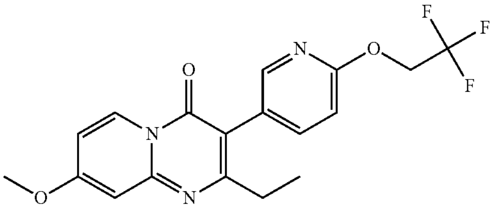 [SMILES: CCc1nc2cc(OC)ccn2c(=O)c1-c1ccc(OCC(F)(F)F)nc1] | 2-ethyl-8-methoxy-3-(6-(2,2,2-trifluoroethoxy)-3-pyridinyl)-4H-pyrido[1,2-a]pyrimidin-4-one | 3-bromo-2-ethyl-8-methoxy-4H-pyrido[1,2-a]pyrimidin-4-one (Intermediate 1-T), [6-(2,2,2-trifluoroethoxy)pyridin-3-yl]boronic acid (Combi-Blocks Inc.) |
| 1-61 | 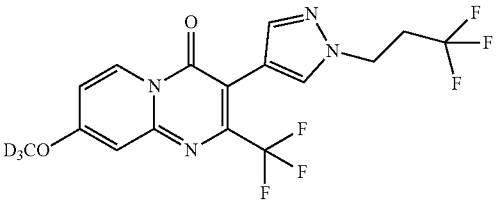 | 8-(methyloxy-$d_3$)-2-(trifluoromethyl)-3-(1-(3,3,3-trifluoropropyl)-1H-pyrazol-4-yl)-4H-pyrido[1,2-a]pyrimidin-4-one | Intermediates 1-N, 2-D |
| 1-62 | 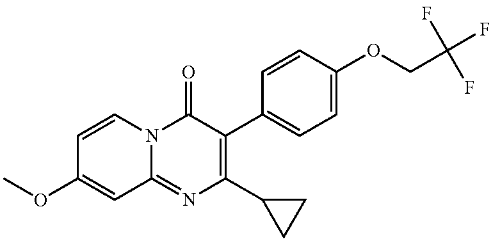 [SMILES: COc1ccn2c(=O)c(-c3ccc(OCC(F)(F)F)cc3)c(C3CC3)nc2c1] | 2-cyclopropyl-8-methoxy-3-(4-(2,2,2-trifluoroethoxy)phenyl)-4H-pyrido[1,2-a]pyrimidin-4-one | 3-bromo-2-cyclopropyl-8-methoxy-4H-pyrido[1,2-a]pyrimidin-4-one (Intermediate 1-U), 4-(2,2,2-trifluoroethoxy)benzene-boronic acid (Combi-Blocks Inc.) |
| 1-63 | 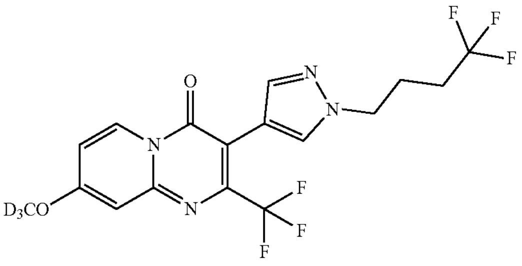 | 8-(methyloxy-$d_3$)-3-(1-(4,4,4-trifluorobutyl)-1H-pyrazol-4-yl)-2-(trifluoromethyl)-4H-pyrido[1,2-a]pyrimidin-4-one | Intermediates 1-N, 2-E |
| 1-64 | 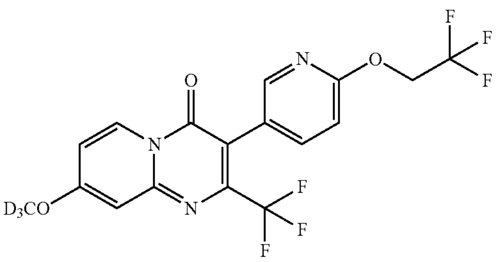 | 8-(methyloxy-$d_3$)-3-(6-(2,2,2-trifluoroethoxy)-3-pyridinyl)-2-(trifluoromethyl)-4H-pyrido[1,2-a]pyrimidin-4-one | Intermediate 1-N, [6-(2,2,2-trifluoroethoxy)pyridin-3-yl]boronic acid (Combi-Blocks Inc.) |

TABLE 4-continued

| Ex. # | Chemical Structure | Name | Reagent and Method Changes |
|---|---|---|---|
| 1-65 | 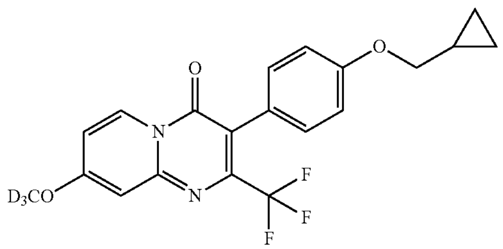 | 3-(4-(cyclopropylmethoxy)phenyl)-8-(methyloxy-$d_3$)-2-(trifluoromethyl)-4H-pyrido[1,2-a]pyrimidin-4-one | Intermediate 1-N, [4-(cyclopropylmethoxy)phenyl]boranediol (Combi-Blocks Inc.) |
| 1-66 | 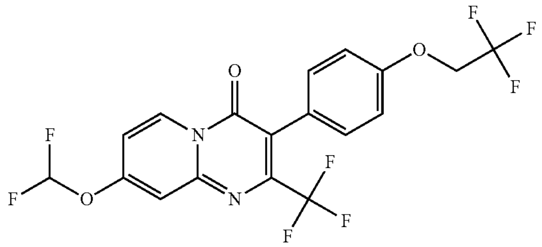 [SMILES: O=c1c(-c2ccc(OCC(F)(F)F)cc2)c(C(F)(F)F)nc2cc(OC(F)F)ccn12] | 8-(difluoromethoxy)-3-(4-(2,2,2-trifluoroethoxy)phenyl)-2-(trifluoromethyl)-4H-pyrido[1,2-a]pyrimidin-4-one | 3-bromo-8-(difluoromethoxy)-2-(trifluoromethyl)-4H-pyrido[1,2-a]pyrimidin-4-one (Intermediate 1-V), 4-(2,2,2-trifluoroethoxy)benzeneboronic acid (Combi-Blocks Inc.) |
| 1-67 | 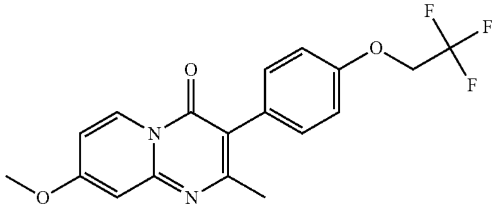 [SMILES: COc1ccn2c(=O)c(-c3ccc(OCC(F)(F)F)cc3)c(C)nc2c1] | 8-methoxy-2-methyl-3-(4-(2,2,2-trifluoroethoxy)phenyl)-4H-pyrido[1,2-a]pyrimidin-4-one | 3-bromo-8-methoxy-2-methyl-4H-pyrido[1,2-a]pyrimidin-4-one (Intermediate 1-W), 4-(2,2,2-trifluoroethoxy)benzeneboronic acid (Combi-Blocks Inc.) |
| 1-68 | 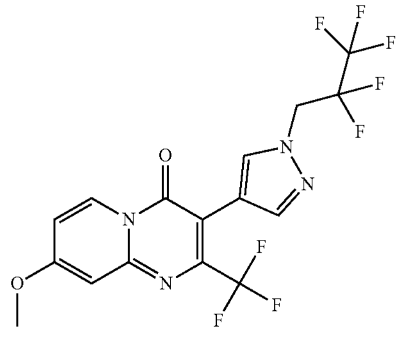 [SMILES: COc1ccn2c(=O)c(-c3cnn(CC(F)(F)C(F)(F)F)c3)c(C(F)(F)F)nc2c1] | 8-methoxy-3-(1-(2,2,3,3,3-pentafluoropropyl)-1H-pyrazol-4-yl)-2-(trifluoromethyl)-4H-pyrido[1,2-a]pyrimidin-4-one | Intermediates 1-A, 2-G |
| 1-69 | 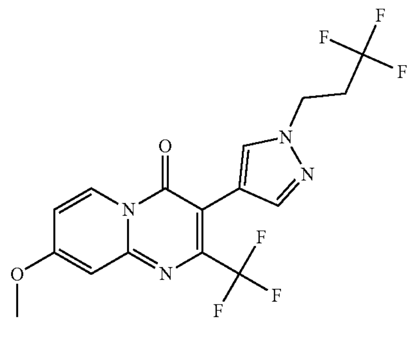 [SMILES: COc1ccn2c(=O)c(-c3cnn(CCC(F)(F)F)c3)c(C(F)(F)F)nc2c1] | 8-methoxy-2-(trifluoromethyl)-3-(1-(3,3,3-trifluoropropyl)-1H-pyrazol-4-yl)-4H-pyrido[1,2-a]pyrimidin-4-one | Intermediates 1-A, 2-D |

TABLE 4-continued

| Ex. # | Chemical Structure | Name | Reagent and Method Changes |
|---|---|---|---|
| 1-70 | 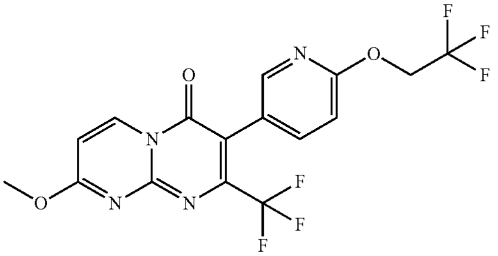 [SMILES: COc1ccn2c(=O)c(-c3ccc(OCC(F)(F)F)nc3)c(C(F)(F)F)nc2n1] | 8-methoxy-3-(6-(2,2,2-trifluoroethoxy)-3-pyridinyl)-2-(trifluoromethyl)-4H-pyrimido[1,2-a]pyrimidin-4-one | Intermediates 1-O, [6-(2,2,2-trifluoroethoxy)pyridin-3-yl]boronic acid (Combi-Blocks Inc.) |
| 1-71 | 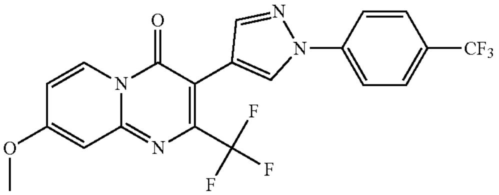 [SMILES: COc1ccn2c(=O)c(-c3cnn(-c4ccc(C(F)(F)F)cc4)c3)c(C(F)(F)F)nc2c1] | 8-methoxy-2-(trifluoromethyl)-3-(1-(4-(trifluoromethyl)phenyl)-1H-pyrazol-4-yl)-4H-pyrido[1,2-a]pyrimidin-4-one | Intermediate 1-A), 1-(4-trifluoromethylphenyl)-1h-pyrazole-4-boronic acid pinacol ester (CombiPhos) |
| 1-72 | 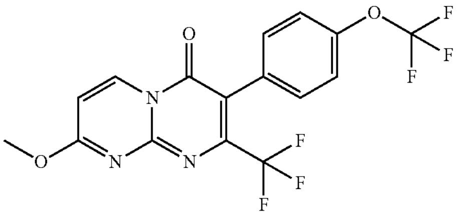 | 8-methoxy-3-(4-(trifluoromethoxy)phenyl)-2-(trifluoromethyl)-4H-pyrimido[1,2-a]pyrimidin-4-one | Intermediate 1-O, 4-(trifluoromethoxy)benzene-boronic acid (Oakwood chemicals) |
| 1-73 | 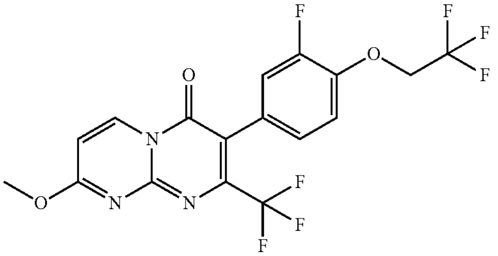 [SMILES: COc1ccn2c(=O)c(-c3ccc(OCC(F)(F)F)c(F)c3)c(C(F)(F)F)nc2n1] | 3-(3-fluoro-4-(2,2,2-trifluoroethoxy)phenyl)-8-methoxy-2-(trifluoromethyl)-4H-pyrimido[1,2-a]pyrimidin-4-one | Intermediate 1-O, 3-fluoro-4-(2,2,2-trifluoroethoxy)benzeneboronic acid (Combi-Blocks Inc.) |
| 1-74 | 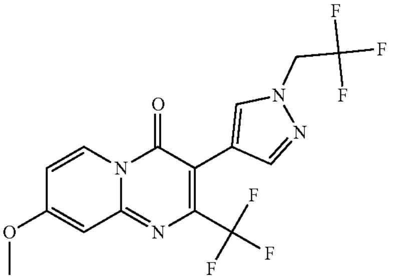 [SMILES: COc1ccn2c(=O)c(-c3cnn(CC(F)(F)F)c3)c(C(F)(F)F)nc2c1] | 8-methoxy-3-(1-(2,2,2-trifluoroethyl)-1H-pyrazol-4-yl)-2-(trifluoromethyl)-4H-pyrido[1,2-a]pyrimidin-4-one | Intermediate 1-A, 4-(4,4,5,5-tetramethyl-1,3,2-dioxaborolan-2-yl)-1-(2,2,2-trifluoroethyl)-1H-pyrazole (Intermediate 2-M) |
| 1-75 | 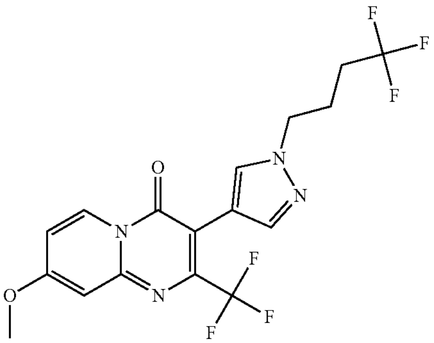 [SMILES: COc1ccn2c(=O)c(-c3cnn(CCCC(F)(F)F)c3)c(C(F)(F)F)nc2c1] | 8-methoxy-3-(1-(4,4,4-trifluorobutyl)-1H-pyrazol-4-yl)-2-(trifluoromethyl)-4H-pyrido[1,2-a]pyrimidin-4-one | Intermediates 1-A, 2-E |

TABLE 4-continued

| Ex. # | Chemical Structure | Name | Reagent and Method Changes |
|---|---|---|---|
| 1-76 | 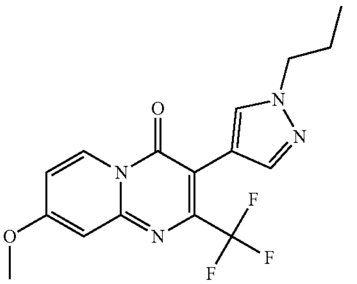 [SMILES: CCCn1cc(-c2c(C(F)(F)F)nc3cc(OC)ccn3c2=O)cn1] | 8-methoxy-3-(1-propyl-1H-pyrazol-4-yl)-2-(trifluoromethyl)-4H-pyrido[1,2-a]pyrimidin-4-one | Intermediate 1-A, 1-propyl-4-(4,4,5,5,5-tetramethyl-1,3,2-dioxaborolan-2-yl)-1H-pyrazole (Ark Pharm) |
| 1-77 | 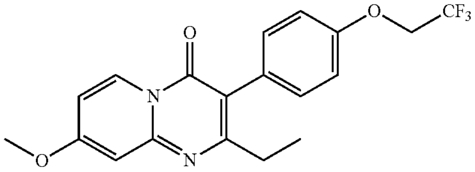 [SMILES: CCc1nc2cc(OC)ccn2c(=O)c1-c1ccc(OCC(F)(F)F)cc1] | 2-ethyl-8-methoxy-3-(4-(2,2,2-trifluoroethoxy)phenyl)-4H-pyrido[1,2-a]pyrimidin-4-one | 3-bromo-2-ethyl-8-methoxy-4H-pyrido[1,2-a]pyrimidin-4-one (Intermediate 1-T); 4-(2,2,2-trifluoroethoxy)benzeneboronic acid (Combi-Blocks Inc.) |
| 1-78 | 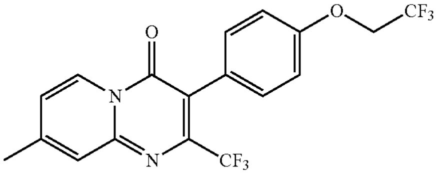 [SMILES: Cc1ccn2c(=O)c(-c3ccc(OCC(F)(F)F)cc3)c(C(F)(F)F)nc2c1] | 8-methyl-3-(4-(2,2,2-trifluoroethoxy)phenyl)-2-(trifluoromethyl)-4H-pyrido[1,2-a]pyrimidin-4-one | 3-bromo-8-methyl-2-(trifluoromethyl)-4H-pyrido[1,2-a]pyrimidin-4-one (Intermediate 2-V); 4-(2,2,2-trifluoroethoxy)benzeneboronic acid (Combi-Blocks Inc.) |
| 1-79 | 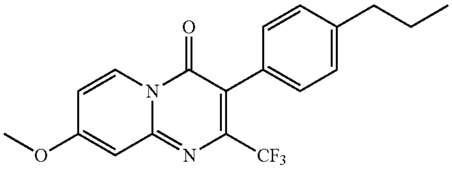 [SMILES: CCCc1ccc(-c2c(C(F)(F)F)nc3cc(OC)ccn3c2=O)cc1] | 8-methoxy-3-(4-propylphenyl)-2-(trifluoromethyl)-4H-pyrido[1,2-a]pyrimidin-4-one | Intermediate 1-A, 4-propylphenylboronic acid |
| 1-80 | 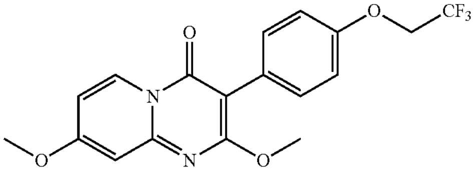 [SMILES: COc1ccn2c(=O)c(-c3ccc(OCC(F)(F)F)cc3)c(OC)nc2c1] | 2,8-dimethoxy-3-(4-(2,2,2-trifluoroethoxy)phenyl)-4H-pyrido[1,2-a]pyrimidin-4-one | 3-iodo-2,8-dimethoxy-4H-pyrido[1,2-a]pyrimidin-4-one (Intermediate 2-W), 4-(2,2,2-trifluoroethoxy)benzeneboronic acid (Combi-Blocks Inc.); $K_3PO_4$ and toluene replacing $Cs_2CO_3$ and dioxane |
| 1-81 | 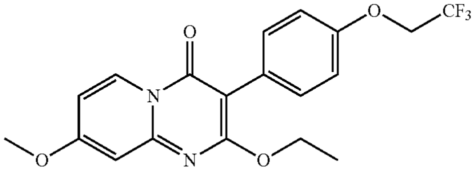 [SMILES: CCOc1nc2cc(OC)ccn2c(=O)c1-c1ccc(OCC(F)(F)F)cc1] | 2-ethoxy-8-methoxy-3-(4-(2,2,2-trifluoroethoxy)phenyl)-4H-pyrido[1,2-a]pyrimidin-4-one | 2-ethoxy-3-iodo-8-methoxy-4H-pyrido[1,2-a]pyrimidin-4-one (Intermediate 2-X), 4-(2,2,2-trifluoroethoxy)benzeneboronic acid (Combi-Blocks Inc.); $K_3PO_4$ and toluene replacing $Cs_2CO_3$ and dioxane |
| 1-82 | 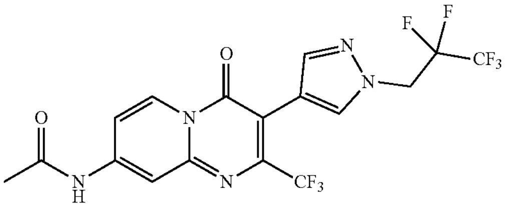 [SMILES: CC(=O)Nc1ccn2c(=O)c(-c3cnn(CC(F)(F)C(F)(F)F)c3)c(C(F)(F)F)nc2c1] | N-(4-oxo-3-(1-(2,2,3,3,3-pentafluoropropyl)-1H-pyrazol-4-yl)-2-(trifluoromethyl)-4H-pyrido[1,2-a]pyrimidin-8-yl)acetamide | Intermediates 1-L, 2-G |

TABLE 4-continued

| Ex. # | Chemical Structure | Name | Reagent and Method Changes |
|---|---|---|---|
| 1-85 | 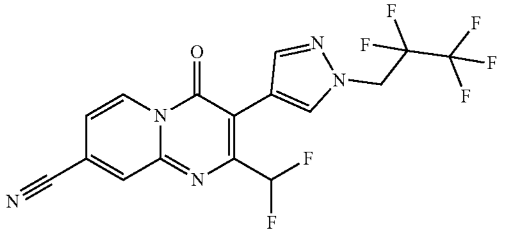 [SMILES: N#Cc1ccn2c(=O)c(-c3cnn(CC(F)(F)C(F)(F)F)c3)c(C(F)F)nc2c1] | 2-(difluoromethyl)-4-oxo-3-(1-(2,2,3,3,3-pentafluoropropyl)-1H-pyrazol-4-yl)-4H-pyrido[1,2-a]pyrimidine-8-carbonitrile | 2-(Difluoromethyl)-3-iodo-4-oxo-4H-pyrido[1,2-a]pyrimidine-8-carbonitrile (Intermediate 1-J), Intermediate 2-G |
| 1-86 | 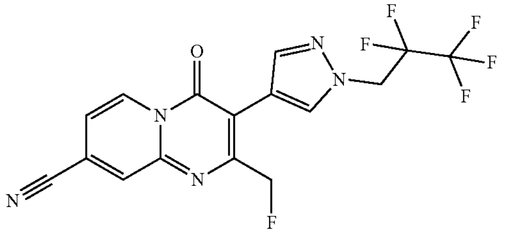 [SMILES: N#Cc1ccn2c(=O)c(-c3cnn(CC(F)(F)C(F)(F)F)c3)c(CF)nc2c1] | 2-(fluoromethyl)-4-oxo-3-(1-(2,2,3,3,3-pentafluoropropyl)-1H-pyrazol-4-yl)-4H-pyrido[1,2-a]pyrimidine-8-carbonitrile | 2-(Fluoromethyl)-3-iodo-4-oxo-4H-pyrido[1,2-a]pyrimidine-8-carbonitrile (Intermediate 2-K), Intermediate 2-G |
| 1-87 | 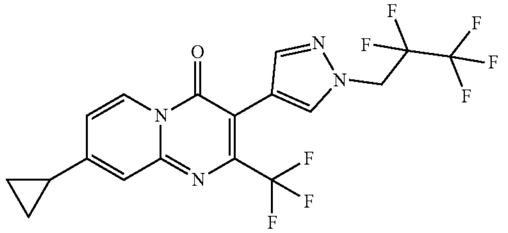 [SMILES: O=c1c(-c2cnn(CC(F)(F)C(F)(F)F)c2)c(C(F)(F)F)nc2cc(C3CC3)ccn12] | 8-cyclopropyl-3-(1-(2,2,3,3,3-pentafluoropropyl)-1H-pyrazol-4-yl)-2-(trifluoromethyl)-4H-pyrido[1,2-a]pyrimidin-4-one | 8-Cyclopropyl-3-iodo-2-(trifluoromethyl)-4H-pyrido[1,2-a]pyrimidin-4-one (Intermediate 3-D), Intermediate 2-G |
| 1-88 | 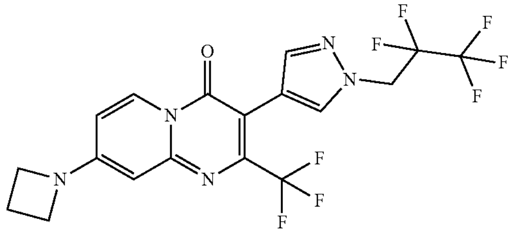 [SMILES: O=c1c(-c2cnn(CC(F)(F)C(F)(F)F)c2)c(C(F)(F)F)nc2cc(N3CCC3)ccn12] | 8-(1-azetidinyl)-3-(1-(2,2,3,3,3-pentafluoropropyl)-1H-pyrazol-4-yl)-2-(trifluoromethyl)-4H-pyrido[1,2-a]pyrimidin-4-one | 8-(azetidin-1-yl)-3-iodo-2-(trifluoromethyl)-4H-pyrido[1,2-a]pyrimidin-4-one (Intermediate 3-E), Intermediate 2-G |

Method 2

Example 2-1: 8-Ethyl-3-(4-(2,2,2-trifluoroethoxy)phenyl)-2-(trifluoromethyl)-4H-pyrido[1,2-a]pyrimidin-4-one

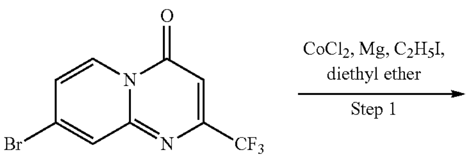

Intermediate-3C

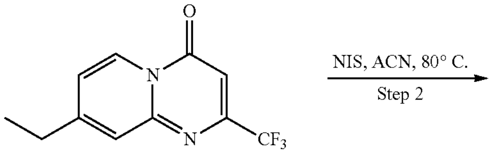

-continued

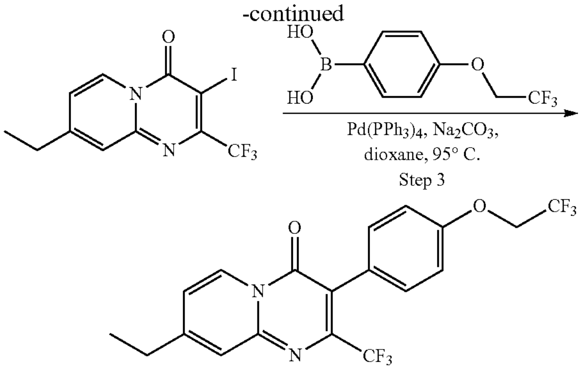

Step 1: 8-Ethyl-2-(trifluoromethyl)-4H-pyrido[1,2-a]pyrimidin-4-one

Cobalt(II) chloride (0.400 g, 3.07 mmol) and a freshly prepared Grignard solution-prepared from magnesium turnings (0.67 g, 27 mmol) and iodoethane (0.56 ml, 6.8 mmol) in anhydrous diethyl ether (10 mL)—were added to a solution of 8-bromo-2-(trifluoromethyl)-4H-pyrido[1,2-a] pyrimidin-4-one (Intermediate 3-C, 2.0 g, 6.83 mmol) in benzene (15.0 mL) at rt under nitrogen environment. The reaction mixture was heated to 75° C. for 2 h. The reaction mixture was quenched with aqueous HCl solution (1.5 N, 10 mL). After 10 minutes, the pH of the reaction mixture was adjusted to pH 8 by the addition of aq. $NaHCO_3$. The reaction mixture was extracted with ethyl acetate (2×25 mL). The combined organic layers were dried over anhydrous $Na_2SO_4$ and concentrated under reduced pressure. The crude product was purified by silica gel chromatography (eluent: 0-40% EtOAc/hexane) to afford 8-ethyl-2-(trifluoromethyl)-4H-pyrido[1,2-a]pyrimidin-4-one (0.4 g, 24% yield) as a pale yellow solid. LC/MS ($ESI^+$) m/z=243.1 $[M+H]^+$. $^1H$ NMR (400 MHz, DMSO-$d_6$) δ 8.96 (d, J=7.3 Hz, 1H), 7.74-7.67 (m, 1H), 7.45 (dd, J=7.2, 2.0 Hz, 1H), 6.76 (s, 1H), 2.83 (q, J=7.5 Hz, 2H), 1.27 (q, J=7.5 Hz, 3H).

Step 2: 8-Ethyl-3-iodo-2-(trifluoromethyl)-4H-pyrido[1,2-a]pyrimidin-4-one

NIS (0.84 g, 3.72 mmol, 3.0 eq.) was added to a solution of 8-ethyl-2-(trifluoromethyl)-4H-pyrido[1,2-a]pyrimidin-4-one (0.3 g, 1.239 mmol) in acetonitrile (6.0 mL). The reaction mixture was heated to 80° C. for 48 h and then concentrated under reduced pressure. The crude residue was purified by silica gel chromatography (eluent: 0-20% of ethyl acetate/hexane) to afford compound 8-ethyl-3-iodo-2-(trifluoromethyl)-4H-pyrido[1,2-a]pyrimidin-4-one (0.4 g, 88% yield) as yellow solid. LC/MS ($ESI^+$) m/z=369.0 $[M+H]^+$. $^1H$ NMR (400 MHz, DMSO-$d_6$) δ 8.95 (d, J=7.20 Hz, 1H), 7.73 (s, 1H), 7.50 (dd, J=2.00, 7.40 Hz, 1H), 2.82 (q, J=7.20 Hz, 2H), 1.27 (t, J=7.60 Hz, 3H).

Step 3: 8-ethyl-3-(4-(2,2,2-trifluoroethoxy)phenyl)-2-(trifluoromethyl)-4H-pyrido[1,2-a]pyrimidin-4-one A resealable vial with was charged with 8-ethyl-3-iodo-2-(trifluoromethyl)-4H-pyrido[1,2-a]pyrimidin-4-one (0.45 g, 1.2 mmol), 1,4-dixoane (5.0 mL), (4-(2,2,2-trifluoroethoxy)phenyl)boronic acid (0.325 g, 1.46 mmol, Combi-Blocks Inc.) and aqueous sodium carbonate solution (1.0 M, 2.5 mL, 2.445 mmol) at ambient temperature under nitrogen environment. The reaction mixture was purged with nitrogen for 15 minutes, followed by addition of $Pd(PPh_3)_4$(0.140 g, 0.122 mmol, Hindustan Platinum). The reaction mixture was stirred heated to 95° C. for 16 h. The reaction mixture was concentrated under reduced pressure and the crude residue was purified by silica gel chromatography (eluent: 0-5% methanol in dichloromethane) to afford 8-ethyl-3-(4-(2,2,2-trifluoroethoxy)phenyl)-2-(trifluoromethyl)-4H-pyrido[1,2-a]pyrimidin-4-one (0.17 g, 32% yield) as a pale yellow solid. LC/MS ($ESI^+$) m/z=417.0 $[M+H]^+$. $^1H$ NMR (400 MHz, DMSO-$d_6$) δ 8.93 (d, J=7.3 Hz, 1H), 7.72 (s, 1H), 7.44 (dd, J=7.3, 2.0 Hz, 1H), 7.28 (d, J=8.5 Hz, 2H), 7.16-7.08 (m, 2H), 4.84 (q, J=8.8 Hz, 2H), 2.84 (q, J=7.5 Hz, 2H), 1.29 (t, J=7.5 Hz, 3H).

Examples 2-2 to 2-9 listed in Table 5 were prepared following the procedure described in Method 2, Step 3, above as follows.

TABLE 5

| Ex. # | Chemical Structure | Name | Reagent |
|---|---|---|---|
| 2-2 | 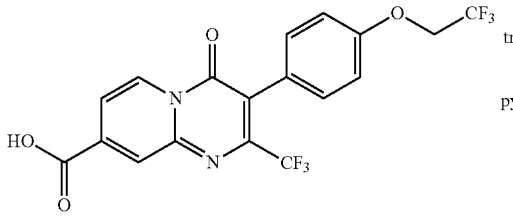 | 4-oxo-3-(4-(2,2,2-trifluoroethoxy)phenyl)-2-(trifluoromethyl)-4H-pyrido[1,2-a]pyrimidine-8-carboxylic acid | methyl 3-iodo-4-oxo-2-(trifluoromethyl)-4H-pyrido[1,2-a]pyrimidine-8-carboxylate (Intermediate 1-D) |
| 2-3 | 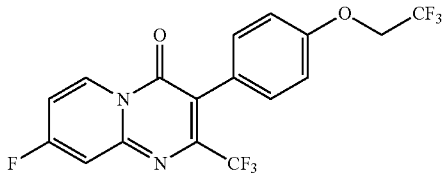 [SMILES: O=c1c(-c2ccc(OCC(F)(F)F)cc2)c(C(F)(F)F)nc2cc(F)ccn12] | 8-fluoro-3-(4-(2,2,2-trifluoroethoxy)phenyl)-2-(trifluoromethyl)-4H-pyrido[1,2-a]pyrimidin-4-one | 8-fluoro-3-iodo-2-(trifluoromethyl)-4H-pyrido[1,2-a]pyrimidin-4-one (Intermediate 1-Y) |
| 2-4 | 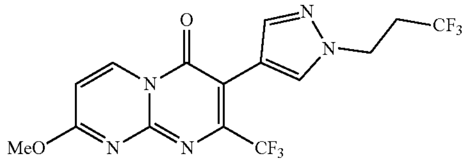 [SMILES: COc1ccn2c(=O)c(-c3cnn(CCC(F)(F)F)c3)c(C(F)(F)F)nc2n1] | 8-methoxy-2-(trifluoromethyl)-3-(1-(3,3,3-trifluoropropyl)-1H-pyrazol-4-yl)-4H-pyrimido[1,2-a]pyrimidin-4-one | 3-bromo-8-methoxy-2-(trifluoromethyl)pyrimido[1,2-a]pyrimidin-4-one (Intermediate 1-O), 4-(4,4,5,5-tetramethyl-1,3,2-dioxaborolan-2-yl)-1-(3,3,3-trifluoropropyl)pyrazole (Intermediate 2-D) |

TABLE 5-continued

| Ex. # | Chemical Structure | Name | Reagent |
|---|---|---|---|
| 2-5 | 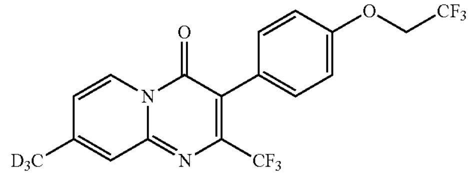 | 8-(methyl-$d_3$)-3-(4-(2,2,2-trifluoroethoxy)phenyl)-2-(trifluoromethyl)-4H-pyrido[1,2-a]pyrimidin-4-one | 3-iodo-8-(methyl-$d_3$)-2-(trifluoromethyl)-4H-pyrido[1,2-a]pyrimidin-4-one (Intermediate 1-Z) |
| 2-6 | 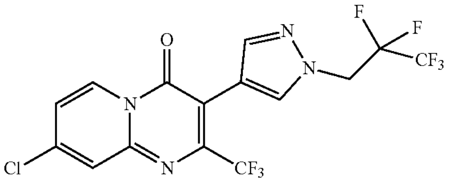 [SMILES: O=c1c(-c2cnn(CC(F)(F)C(F)(F)F)c2)c(C(F)(F)F)nc2cc(Cl)ccn12] | 8-chloro-3-(1-(2,2,3,3,3-pentafluoropropyl)-1H-pyrazol-4-yl)-2-(trifluoromethyl)-4H-pyrido[1,2-a]pyrimidin-4-one | 8-chloro-3-iodo-2-(trifluoromethyl)-4H-pyrido[1,2-a]pyrimidin-4-one (Intermediate 2-T), 1-(2,2,3,3,3-pentafluoropropyl)-4-(4,4,5,5-tetramethyl-1,3,2-dioxaborolan-2-yl)-1H-pyrazole (Intermediate 2-G) |
| 2-7 | 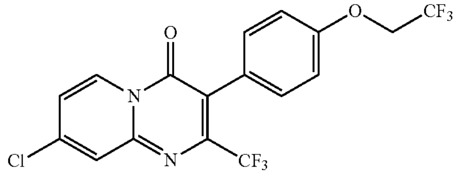 [SMILES: O=c1c(-c2ccc(OCC(F)(F)F)cc2)c(C(F)(F)F)nc2cc(Cl)ccn12] | 8-chloro-3-(4-(2,2,2-trifluoroethoxy)phenyl)-2-(trifluoromethyl)-4H-pyrido[1,2-a]pyrimidin-4-one | 8-chloro-3-iodo-2-(trifluoromethyl)-4H-pyrido[1,2-a]pyrimidin-4-one (Intermediate 2-T) |
| 2-8 | 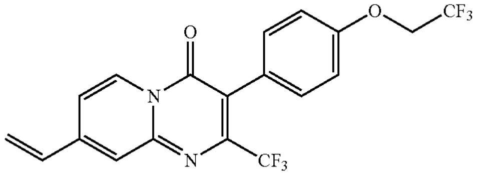 [SMILES: C=Cc1ccn2c(=O)c(-c3ccc(OCC(F)(F)F)cc3)c(C(F)(F)F)nc2c1] | 8-ethenyl-3-(4-(2,2,2-trifluoroethoxy)phenyl)-2-(trifluoromethyl)-4H-pyrido[1,2-a]pyrimidin-4-one | 3-iodo-2-(trifluoromethyl)-8-vinyl-pyrido[1,2-a]pyrimidin-4-one (Intermediate 2-U) |
| 2-9 | 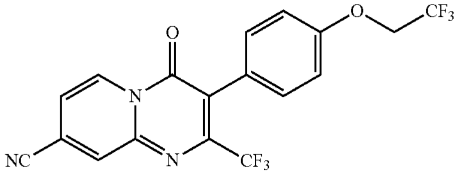 [SMILES: N#Cc1ccn2c(=O)c(-c3ccc(OCC(F)(F)F)cc3)c(C(F)(F)F)nc2c1] | 4-oxo-3-(4-(2,2,2-trifluoroethoxy)phenyl)-2-(trifluoromethyl)-4H-pyrido[1,2-a]pyrimidine-8-carbonitrile | 3-iodo-4-oxo-2-(trifluoromethyl)pyrido[1,2-a]pyrimidine-8-carbonitrile (Intermediate 1-H) |

Method 3

Example 3-1: 2-Ethyl-8-methoxy-3-(1-(2,2,3,3,3-pentafluoropropyl)-1H-pyrazol-4-yl)-4H-pyrido[1,2-a]pyrimidin-4-one

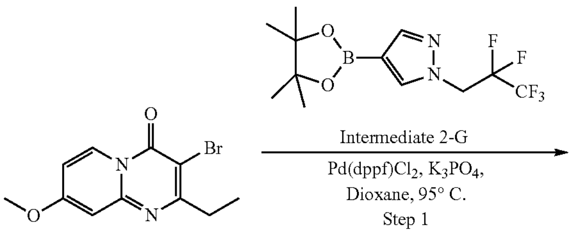

Intermediate 1-T

-continued

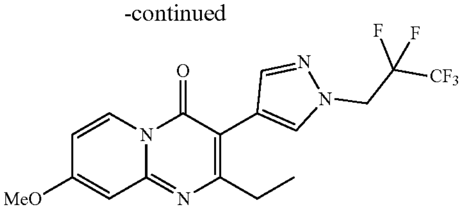

Step 1: 2-Ethyl-8-methoxy-3-(1-(2,2,3,3,3-pentafluoropropyl)-1H-pyrazol-4-yl)-4H-pyrido[1,2-a]pyrimidin-4-one A resealable vial with was charged with 3-bromo-2-ethyl-8-methoxy-4H-pyrido[1,2-a]pyrimidin-4-one (9.0 g, 31.8 mmol, Intermediate 1-T), (1-(2,2,3,3,3-pentafluoropropyl)-1H-pyrazol-4-yl)boronic acid (9.3 g, 38 mmol, Intermediate 2-G), potassium phosphate (10 g, 48 mmol) and 1,4-dioxane (70 mL). The reaction mixture was purged with nitrogen for 10 minutes, followed by addition of $Pd(dppf)Cl_2$ (2.3 g, 3.2 mmol). The reaction mixture was heated to 95° C. for 16 h. The reaction mixture was allowed to cool to room temperature and filtered through a pad of celite. The celite was rinsed with ethyl acetate (2×250 mL) and the filtrate was concentrated under reduced pressure. The crude residue was adsorbed onto a plug of silica gel and purified by silica gel chromatography (eluent: 0-35% ethyl acetate/hexane, to provide 2-ethyl-8-methoxy-3-(1-(2,2,3,3,3-pentafluoropropyl)-1H-pyrazol-4-yl)-4H-pyrido[1,2-a]pyrimidin-4-one (7.9 g, 19.6 mmol, 62% yield) as a light orange solid. LC/MS ($ESI^+$) m/z=403.1 $[M+H]^+$. $^1H$ NMR (300 MHz, DMSO-$d_6$) δ 8.89-8.74 (m, 1H), 8.10 (s, 1H), 7.78 (s, 1H), 7.07-6.92 (m, 2H), 5.26 (t, J=15.2 Hz, 2H), 3.99 (s, 3H), 2.71 (q, J=7.5 Hz, 2H), 1.21 (t, J=7.5 Hz, 3H).

Example 3-2 listed in Table 6 was prepared following the procedure described in Method 3, Step 1, above as follows.

TABLE 6

| Ex. # | Chemical Structure | Name | Reagent |
|---|---|---|---|
| 3-2 | 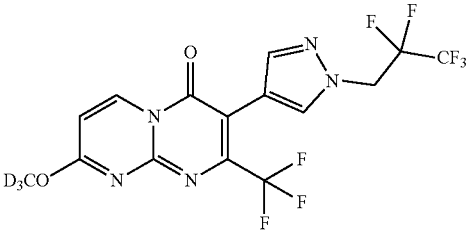 | 8-(methyloxy-$d_3$)-3-(1-(2,2,3,3,3-pentafluoropropyl)-1H-pyrazol-4-yl)-2-(trifluoromethyl)-4H-pyrimido[1,2-a]pyrimidin-4-one | 3-Bromo-8-(methoxy-$d_3$)-2-(trifluoromethyl)-4H-pyrimido[1,2-a]pyrimidin-4-one (Intermediate 1-R) |

Method 4

Example 4-1: 3-(4-(2,2,2-Trifluoroethoxy)phenyl)-2,8-bis(trifluoromethyl)-4H-pyrido[1,2-a]pyrimidin-4-one

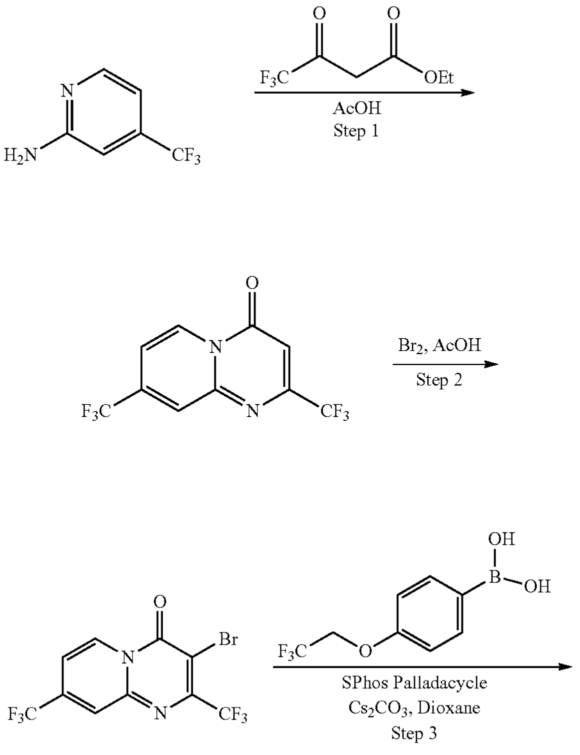

-continued

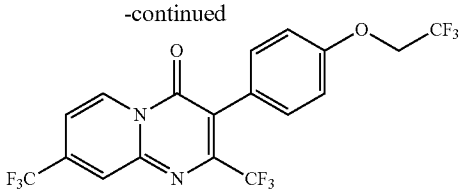

Step 1: 2,8-Bis(trifluoromethyl)-4H-pyrido[1,2-a]pyrimidin-4-one

A solution 4-(trifluoromethyl)pyridin-2-amine (2.5 g, 15.4 mmol, ArkPharm) and 4,4,4-trifluoroacetoacetic acid ethyl ester (3.4 ml, 23 mmol) in acetic acid (6 ml) was heated to 110° C. for 20 hours. The reaction mixture was cooled to rt and neutralized with saturated bicarbonate solution. The reaction mixture was partitioned with EtOAc and the aqueous layer was backextracted with EtOAc. The combined organic phases were dried over $MgSO_4$, filtered, concentrated and adsorbed onto a pad of silica gel. The crude residue was purified by silica gel chromatography (eluent: 0-10% (3:1 EtOAc in Ethanol)/heptane) to provide 2,8-bis(trifluoromethyl)-4H-pyrido[1,2-a]pyrimidin-4-one (0.27 g, 0.97 mmol, 6% yield) as a white solid. LC/MS ($ESI^+$) m/z=283.0 $[M+H]^+$.

Step 2: 3-Bromo-2,8-bis(trifluoromethyl)-4H-pyrido[1,2-a]pyrimidin-4-one

A solution of bromine (0.25 ml, 4.8 mmol) in acetic acid (1.382 ml) was added dropwise to a solution of 2,8-bis(trifluoromethyl)-4H-pyrido[1,2-a]pyrimidin-4-one (0.27 g, 0.97 mmol) in acetic acid (3.5 ml) at rt. After 24 h, the reaction mixture was cooled to 0° C. and quenched via dropwise addition of a saturated thiosulfate solution (5 mL). The reaction mixture was partitioned between EtOAc and brine and the aqueous layer was back extracted 3x with EtOAc. The combined organic layers were dried over $MgSO_4$, filtered and concentrated in vacuo. The resultant solid was triturated with $Et_2O$ to provide 3-bromo-2,8-bis(trifluoromethyl)-4H-pyrido[1,2-a]pyrimidin-4-one (0.35 g, 0.97 mmol, 99% yield) as a white solid. The product was taken onto the next step without further purification. LC/MS ($ESI^+$) m/z=361.0 $[M+H]^+$. 1H NMR (400 MHz, $CDCl_3$) δ 9.17 (d, J=7.5 Hz, 1H), 8.10 (s, 1H), 7.41 (d, J=7.3 Hz, 1H).

Step 3: 3-(4-(2,2,2-Trifluoroethoxy)phenyl)-2,8-bis(trifluoromethyl)-4H-pyrido[1,2-a]pyrimidin-4-one A resealable vial was charged with SPhos Palladacycle (0.012 ml, 0.017 mmol, Strem Chemicals, Inc.), cesium carbonate (0.173 g, 0.532 mmol, Strem Chemicals, Inc.), 3-bromo-2,8-bis(trifluoromethyl)-4H-pyrido[1,2-a]pyrimidin-4-one (0.12 g, 0.332 mmol) and (4-(2,2,2-trifluoroethoxy)phenyl)boronic acid (0.110 g, 0.499 mmol, Combi-Blocks Inc.).

The vial was evacuated and backfilled with nitrogen. This procedure was repeated 3 times, followed by the addition of 1,4-dioxane (1.6 mL). The reaction mixture was heated to 40° C.

After 2 h, the reaction mixture was partitioned between water and EtOAc. The organic phase was separated, washed with brine, dried over magnesium sulfate, filtered, and adsorbed onto a pad of silica gel. The crude product was purified by silica gel chromatography (eluent: 0-10% (3:1 EtOAc in Ethanol)/heptane) to yield 3-(4-(2,2,2-trifluoroethoxy)phenyl)-2,8-bis(trifluoromethyl)-4H-pyrido[1,2-a]pyrimidin-4-one (45 mg, 0.1 mmol, 30% yield) was obtained as an off-white solid. LC/MS ($ESI^+$) m/z=457.0 $[M+H]^+$. $^1H$ NMR (DMSO-$d_6$, 500 MHz) δ 9.08 (d, J=7.5 Hz, 1H), 8.36 (s, 1H), 7.67 (dd, J=7.5, 1.9 Hz, 1H), 7.28-7.31 (m, J=8.7 Hz, 2H), 7.14-7.17 (m, 2H), 4.84 (q, J=8.8 Hz, 2H).

Examples 4-2 to 4-3 listed in Table 7 were prepared following the procedure described in Method 4, Step 1, above as follows.

TABLE 7

| Ex. # | Chemical Structure | Name | Reagent |
| --- | --- | --- | --- |
| 4-2 | 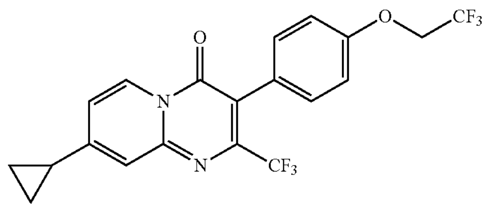 [SMILES: O=c1c(-c2ccc(OCC(F)(F)F)cc2)c(C(F)(F)F)nc2cc(C3CC3)ccn12] | 8-cyclopropyl-3-(4-(2,2,2-trifluoroethoxy)phenyl)-2-(trifluoromethyl)-4H-pyrido[1,2-a]pyrimidin-4-one | 3-bromo-8-cyclopropyl-2-(trifluoromethyl)-4H-pyrido[1,2-a]pyrimidin-4-one (Intermediate 1-X) |
| 4-3 | 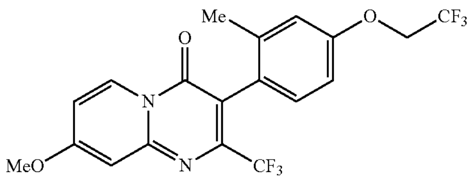 | 8-methoxy-3-(2-methyl-4-(2,2,2-trifluoroethoxy)phenyl)-2-(trifluoromethyl)-4H-pyrido[1,2-a]pyrimidin-4-one | Intermediate 1A, (2-methyl-4-(2,2,2-trifluoroethoxy)phenyl)boronic acid (Intermediate 2-S) |

Method 5

Example 5-1: 3-(2-Fluoro-4-(2,2,2-trifluoroethoxy)phenyl)-2-(trifluoromethyl)-4H-pyrido[1,2-a]pyrimidin-4-one

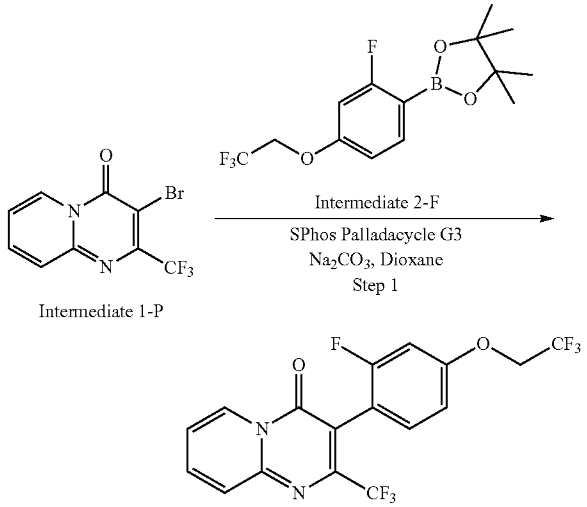

Step 1: 3-(2-Fluoro-4-(2,2,2-trifluoroethoxy)phenyl)-2-(trifluoromethyl)-4H-pyrido[1,2-a]pyrimidin-4-one A resealable vial was charged with, 2-(2-fluoro-4-(2,2,2-trifluoroethoxy)phenyl)-4,4,5,5-tetramethyl-1,3,2-dioxaborolane (218 mg, 0.68 mmol, Intermediate 2-F), Sphos Palladacycle G3 (27 mg, 0.034 mmol, Strem), 3-bromo-2-(trifluoromethyl)-4H-pyrido[1,2-a]pyrimidin-4-one (100 mg, 0.34 mmol, Intermediate 1-P), and sodium carbonate (72 mg, 0.68 mmol). The vial was evacuated and backfilled with nitrogen. This procedure was repeated 3 times, followed by the addition of 1,4-dioxane (800 μL) and water (200 μL). The reaction mixture was heated to 85° C. After 2 h, the reaction mixture was partitioned between water and EtOAc and filtered through a pad of silica gel. The filtrate was sequentially washed with 1 N HCl (50 mL), sat. aq. sodium bicarbonate (50 mL), and brine (50 mL). The organic phase was dried over magnesium sulfate, filtered, and concentrated. The crude residue was purified by SFC ((IC, 150×21 mm, 5 μm), 10% (20 mM $NH_3$ in MeOH)/$CO_2$, 80 g/min, 100 bar) to obtain 3-(2-fluoro-4-(2,2,2-trifluoroethoxy)phenyl)-2-(trifluoromethyl)-4H-pyrido[1,2-a]pyrimidin-4-one (32 mg, 0.08 mmol, 23% yield) was obtained as a white solid. LC/MS ($ESI^+$) m/z=407.6 $[M+H]^+$. $^1H$ NMR (400 MHz, $CD_2Cl_2$) δ 4.45 (q, J=8.02 Hz, 2H) 6.82 (dd, J=10.76, 2.54 Hz, 1H) 6.86 (dd, J=8.41, 2.54 Hz, 1H) 7.27 (t, J=8.41 Hz, 1H) 7.31-7.38 (m, 1H) 7.83 (d, J=8.80 Hz, 1H) 7.89-8.03 (m, 1H) 9.07 (d, J=7.24 Hz, 1H).

Examples 5-2 to 5-4 listed in Table 8 were prepared following the procedure described in Method 5, Step 1, above as follows.

TABLE 8

| Ex. # | Chemical Structure | Name | Reagent |
|---|---|---|---|
| 5-2 | 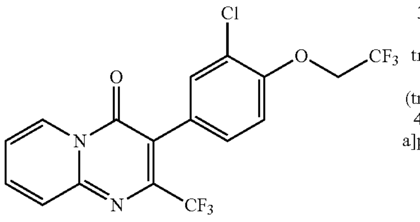 | 3-(3-chloro-4-(2,2,2-trifluoroethoxy)phenyl)-2-(trifluoromethyl)-4H-pyrido[1,2-a]pyrimidin-4-one | 2-(3-chloro-4-(2,2,2-trifluoroethoxy)phenyl)-4,4,5,5-tetramethyl-1,3,2-dioxaborolane (Intermediate 2-N) |
| 5-3 | 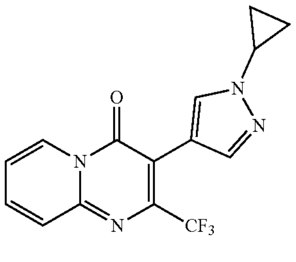 [SMILES: O=c1c(-c2cnn(C3CC3)c2)c(C(F)(F)F)nc2ccccn12] | 3-(1-cyclopropyl-1H-pyrazol-4-yl)-2-(trifluoromethyl)-4H-pyrido[1,2-a]pyrimidin-4-one | 1-cyclopropyl-4-(4,4,5,5-tetramethyl-1,3,2-dioxaborolan-2-yl)-1h (Synthonix Corp.) |

TABLE 8-continued

| Ex. # | Chemical Structure | Name | Reagent |
|---|---|---|---|
| 5-4 | 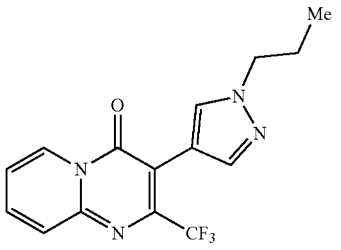 [SMILES: CCCn1cc(-c2c(C(F)(F)F)nc3ccccn3c2=O)cn1] | 3-(1-propyl-1H-pyrazol-4-yl)-2-(trifluoromethyl)-4H-pyrido[1,2-a]pyrimidin-4-one | 1-propyl-4-(4,4,5,5-tetramethyl-1,3,2-dioxaborolan-2-yl)-1H-pyrazole (ArkPharm) |

Method 6

Example 6-1: 8-Amino-3-(1-(2,2,3,3,3-pentafluoropropyl)-1H-pyrazol-4-yl)-2-(trifluoromethyl)-4H-pyrido[1,2-a]pyrimidin-4-one

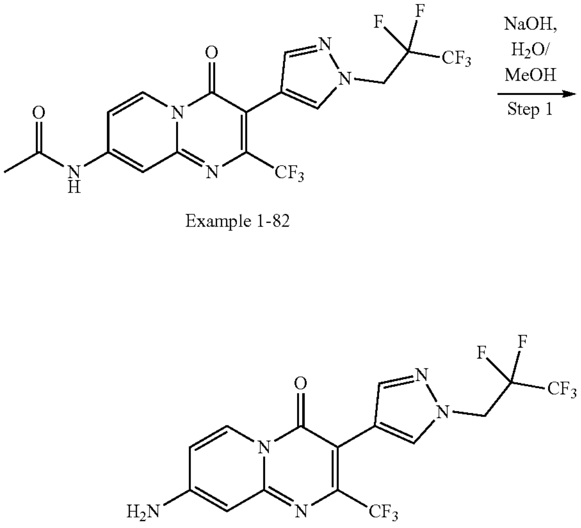

Example 1-82

Step 1: 8-Amino-3-(1-(2,2,3,3,3-pentafluoropropyl)-1H-pyrazol-4-yl)-2-(trifluoromethyl)-4H-pyrido[1,2-a]pyrimidin-4-one A solution of 10% aqueous sodium hydroxide solution (0.8 mL, 1.92 mmol) was added to a solution of N-(4-oxo-3-(1-(2,2,3,3,3-pentafluoropropyl)-1H-pyrazol-4-yl)-2-(trifluoromethyl)-4H-pyrido[1,2-a]pyrimidin-8-yl)acetamide (0.3 g, 0.64 mmol, Example 1-82) in methanol (10.0 mL) at rt. After 15 min, the reaction mixture was concentrated under reduced pressure, the residue was dissolved in 5% methanol in DCM solution (50 mL) and washed with water (2×20 mL). The organic layer was dried over sodium sulfate, filtered and concentrated under reduced pressure. The crude material was purified by silica gel chromatography (eluent: 0-65% EtOA/hexane) to afford 8-amino-3-(1-(2,2,3,3,3-pentafluoropropyl)-1H-pyrazol-4-yl)-2-(trifluoromethyl)-4H-pyrido[1,2-a]pyrimidin-4-one (0.165 g, 0.39 mmol, 60% yield) as a pale yellow solid. LC/MS ($ESI^+$) m/z=428.0 $[M+H]^+$. $^1H$ NMR (400 MHz, DMSO-$d_6$) δ 8.72 (dd, J=7.8, 1.5 Hz, 1H), 7.88 (s, 1H), 7.57 (s, 1H), 7.39 (s, 2H), 6.88 (dt, J=7.9, 2.0 Hz, 1H), 6.53 (t, J=2.0 Hz, 1H), 5.23 (t, J=15.0 Hz, 2H).

Example 6-2 listed in Table 9 was prepared following the procedure described in Method 6, Step 1, above as follows.

TABLE 9

| Ex. # | Chemical Structure | Name | Reagent |
|---|---|---|---|
| 6-2 | 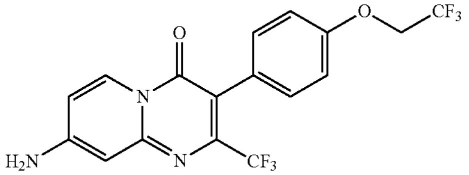 [SMILES: Nc1ccn2c(=O)c(-c3ccc(OCC(F)(F)F)cc3)c(C(F)(F)F)nc2c1] | 8-amino-3-(4-(2,2,2-trifluoroethoxy)phenyl)-2-(trifluoromethyl)-4H-pyrido[1,2-a]pyrimidin-4-one | Example 1-31 |

Method 7

Example 7-1: 3-(2-Fluoro-6-(2,2,2-trifluoroethoxy)-3-pyridinyl)-8-methoxy-2-(trifluoromethyl)-4H-pyrido[1,2-a]pyrimidin-4-one

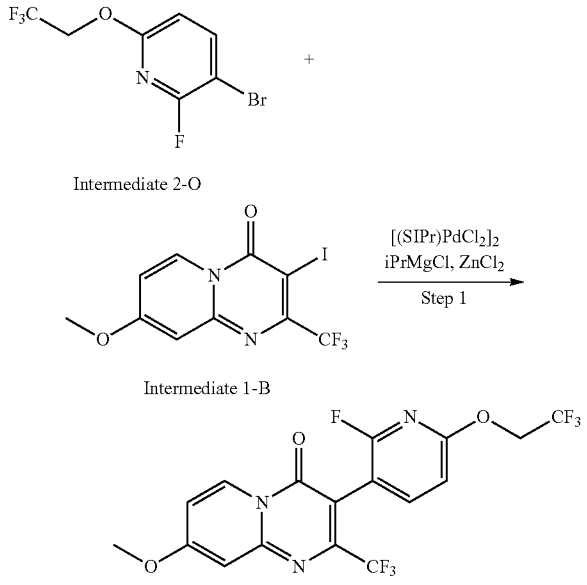

Intermediate 2-O

Intermediate 1-B

Step 1: 3-(2-fluoro-6-(2,2,2-trifluoroethoxy)-3-pyridinyl)-8-methoxy-2-(trifluoromethyl)-4H-pyrido[1,2-a]pyrimidin-4-one A solution of isopropyl magnesium chloride (2M in THF, 0.5 ml, 1.1 mmol, Acros Organics, Geel, Belgium) was added dropwise to a solution of 3-iodo-8-methoxy-2-(trifluoromethyl)-4H-pyrido[1,2-a]pyrimidin-4-one (Intermediate 1-B, 0.367 g, 0.992 mmol) in THF (1 mL) at 0° C. under nitrogen atmosphere. The reaction mixture was stirred for 15 minutes at 0° C., followed by dropwise addition of $ZnCl_2$ (0.5M in THF, 2.2 ml, 1.1 mmol). The reaction mixture was allowed to warm to rt over 1 h and subsequently added to a 20 min aged solution of $[(SIPr)PdCl_2]_2$(47 mg, 0.04 mmol, Umicore Ag & Co.Kg., Rodenbacher, Germany) and 3-bromo-2-fluoro-6-(2,2,2-trifluoroethoxy)pyridine (Intermediate 2-0, 0.23 g, 0.83 mmol) in THF (1 mL). The reaction mixture was then heated to 70° C. for 12 h. The reaction was cooled to rt, filtered through a pad of celite, concentrated and adsorbed onto a pad of silica gel. The crude residue was purified by silica gel chromatography (eluent: 0-40% (3:1 EtOAc/EtOH)/heptane) to obtain 3-(2-fluoro-6-(2,2,2-trifluoroethoxy)-3-pyridinyl)-8-methoxy-2-(trifluoromethyl)-4H-pyrido[1,2-a]pyrimidin-4-one (0.17 g, 0.38 mmol, 46% yield) as a light yellow solid. MS ($ESI^+$) m/z=438.1 $[M+H]^+$. $^{19}F$ NMR (376 MHz, $CDCl_3$) δ −73.81 (s, 1 F) −69.99 (br d, J=1.74 Hz, 1 F) −65.15 (d, J=2.60 Hz, 1 F). $^1H$ NMR (400 MHz, $CDCl_3$) δ 3.90-4.13 (m, 3H) 4.60-4.83 (m, 2H) 6.72-6.89 (m, 1H) 6.91-7.04 (m, 1H) 7.04-7.17 (m, 1H) 7.57-7.73 (m, 1H) 8.88-9.06 (m, 1H).

Examples 7-2 to 7-6 listed in Table 10 were prepared following the procedure described in Method 7, Step 1, above as follows.

TABLE 10

| Ex. # | Chemical Structure | Name | Reagent |
|---|---|---|---|
| 7-2 | 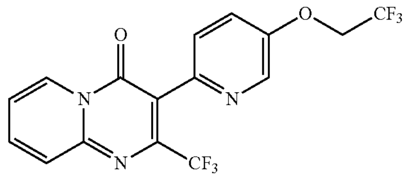 [SMILES: O=c1c(-c2ccc(OCC(F)(F)F)cn2)c(C(F)(F)F)nc2ccccn12] | 3-(5-(2,2,2-trifluoroethoxy)-2-pyridinyl)-2-(trifluoromethyl)-4H-pyrido[1,2-a]pyrimidin-4-one | Intermediate 1P, 2-bromo-5-(2,2,2-trifluoroethoxy) pyridine (Intermediate 2-P) |
| 7-3 | 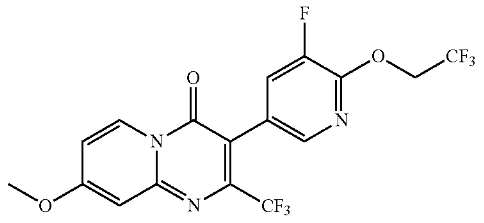 [SMILES: COc1ccn2c(=O)c(-c3cnc(OCC(F)(F)F)c(F)c3)c(C(F)(F)F)nc2c1] | 3-(5-fluoro-6-(2,2,2-trifluoroethoxy)-3-pyridinyl)-8-methoxy-2-(trifluoromethyl)-4H-pyrido[1,2-a]pyrimidin-4-one | 5-bromo-3-fluoro-2-(2,2,2-trifluoroethoxy) pyridine (Intermediate 2-Q) |
| 7-4 | 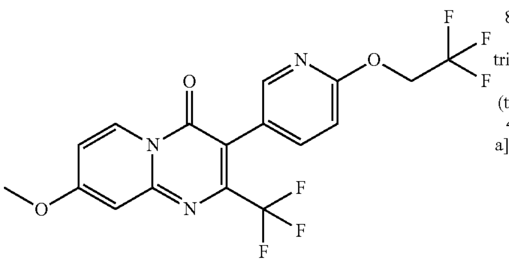 | 8-methoxy-3-6-(2,2,2-trifluoroethoxy)-3-pyridinyl)-2-(trifluoromethyl)-4H-pyrido[1,2-a]pyrimidin-4-one | 5-bromo-2-(2,2,2-trifluoroethoxy) pyridine (Intermediate 2-R) |

TABLE 10-continued

| Ex. # | Chemical Structure | Name | Reagent |
|---|---|---|---|
| 7-5 | 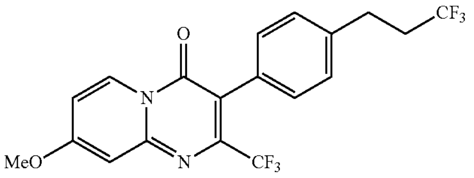 [SMILES: COc1ccn2c(=O)c(-c3ccc(CCC(F)(F)F)cc3)c(C(F)(F)F)nc2c1] | 8-methoxy-2-(trifluoromethyl)-3-(4-(3,3,3-trifluoropropyl)phenyl)-4H-pyrido[1,2-a]pyrimidin-4-one | 1-bromo-4-(3,3,3-trifluoropropyl)benzene (Oakwood Products) |
| 7-6 | 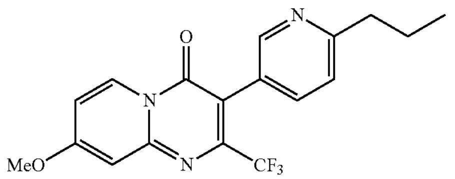 [SMILES: CCCc1ccc(-c2c(C(F)(F)F)nc3cc(OC)ccn3c2=O)cn1] | 8-methoxy-3-(6-propyl-3-pyridinyl)-2-(trifluoromethyl)-4H-pyrido[1,2-a]pyrimidin-4-one | 3-bromo-6-(n-propyl)pyridine (CombiPhos Catalysts, Inc.) |

Method 8

Example 8-1: 3-(4-(Cyclopropylmethoxy)-2-fluorophenyl)-8-methoxy-2-(trifluoromethyl)-4H-pyrido[1,2-a]pyrimidin-4-one

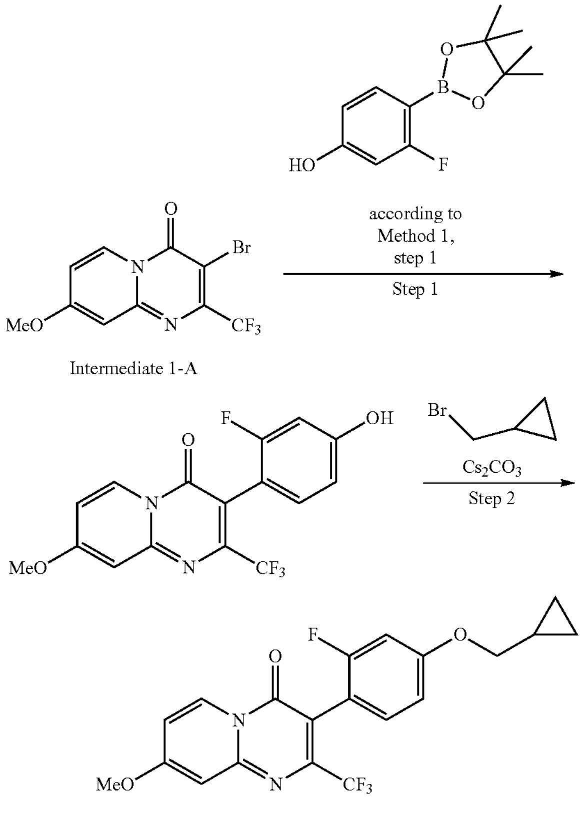

Step 1: 3-(2-Fluoro-4-hydroxyphenyl)-8-methoxy-2-(trifluoromethyl)-4H-pyrido[1,2-a]pyrimidin-4-one The title compound was prepared using the procedure described in Method 1, Step 1 with the following modifications: Step 1 performed with 2-fluoro-4-hydroxybenzeneboronic acid pinacol ester (Combi-Blocks Inc.). MS ($ESI^+$) m/z=355.0 $[M+H]^+$.

Step 2: 3-(4-(Cyclopropylmethoxy)-2-fluorophenyl)-8-methoxy-2-(trifluoromethyl)-4H-pyrido[1,2-a]pyrimidin-4-one A resealable vial was charged with 3-(2-fluoro-4-hydroxyphenyl)-8-methoxy-2-(trifluoromethyl)-4H-pyrido[1,2-a]pyrimidin-4-one (309 mg, 0.87 mmol) and cesium carbonate (1.3 g, 3.9 mmol). The vial was evacuated and backfilled with nitrogen. This procedure was repeated 3 times, followed by the addition of DMF (4 mL) and (bromomethyl)cyclopropane (0.127 mL, 1.308 mmol). The reaction mixture was heated to 80° C. for 12 h. The reaction mixture was cooled to rt and filtered through a plug of Celite. The filtrate was extracted with EtOAc (100 mL) and the organic phase was washed sequentially with water (100 mL) and 1 M LiCl (100 mL). The organic phase was dried over anhydrous magnesium sulfate, filtered through Celite, and concentrated under reduced pressure. The crude residue was adsorbed onto a plug of silica gel and purified by silica gel chromatography (eluent: 0-40% EtOAc/heptane) to obtain 3-(4-(cyclopropylmethoxy)-2-fluorophenyl)-8-methoxy-2-(trifluoromethyl)-4H-pyrido[1,2-a]pyrimidin-4-one (184 mg, 0.45 mmol, 52% yield) as a light-yellow solid. MS ($ESI^+$) m/z=409.0 $[M+H]^+$. $^1H$ NMR (400 MHz, $CD_2Cl_2$) δ 0.33-0.41 (m, 2H) 0.61-0.71 (m, 2H) 1.23-1.39 (m, 1H) 3.85 (d, J=7.05 Hz, 2H) 4.02 (s, 3H) 6.72 (dd, J=11.61, 2.28 Hz, 1H) 6.78 (dd, J=8.50, 2.28 Hz, 1H) 6.95 (dd, J=7.88, 2.70 Hz, 1H) 7.06 (d, J=2.49 Hz, 1H) 7.16 (t, J=8.50 Hz, 1H) 8.92 (d, J=7.88 Hz, 1H).

Examples 8-2 to 8-5 listed in Table 11 were prepared following the procedure described in Method 8, Step 2, above as follows.

TABLE 11

| Ex. # | Chemical Structure | Name | Method Changes | Reagent |
|---|---|---|---|---|
| 8-2 | 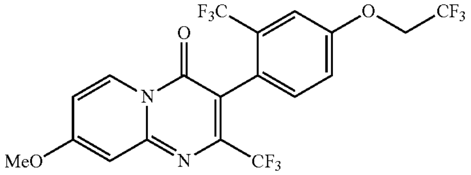 | 8-methoxy-3-(4-(2,2,2-trifluoroethoxy)-2-(trifluoromethyl)phenyl)-2-(trifluoromethyl)-4H-pyrido[1,2-a]pyrimidin-4-one | | 3-(4-hydroxy-2-(trifluoromethyl)phenyl)-8-methoxy-2-(trifluoromethyl)-4H-pyrido[1,2-a]pyrimidin-4-one (Intermediate 2-Y), 1,1,1-trifluoro-2-iodoethane (Oakwood Products Inc.) |
| 8-3 | 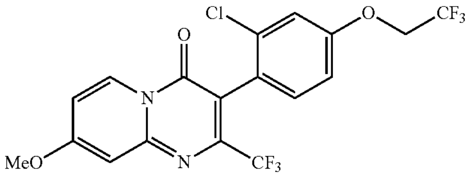 [SMILES: COc1ccn2c(=O)c(-c3ccc(OCC(F)(F)F)cc3Cl)c(C(F)(F)F)nc2c1] | 3-(2-chloro-4-(2,2,2-trifluoroethoxy)phenyl)-8-methoxy-2-(trifluoromethyl)-4H-pyrido[1,2-a]pyrimidin-4-one | | 3-(2-chloro-4-hydroxyphenyl)-8-methoxy-2-(trifluoromethyl)-4H-pyrido[1,2-a]pyrimidin-4-one (Intermediate 2-Z), 1,1,1-trifluoro-2-iodoethane (Oakwood Products Inc.) |
| 8-4 | 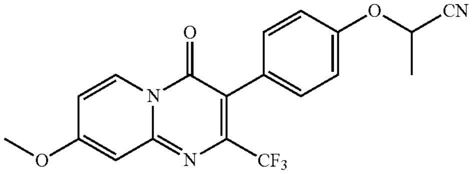 | 2-(4-(8-methoxy-4-oxo-2-(trifluoromethyl)-4H-pyrido[1,2-a]pyrimidin-3-yl)phenoxy)propanenitrile | Step 2: $K_2CO_3$, acetone, rt | 3-(4-hydroxyphenyl)-8-methoxy-2-(trifluoromethyl)-4H-pyrido[1,2-a]pyrimidin-4-one (Intermediate 3-A), 2-bromopropanenitrile |
| 8-5 | 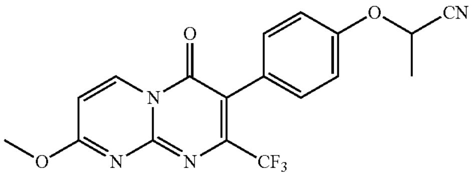 [SMILES: COc1ccn2c(=O)c(-c3ccc(OC(C)C#N)cc3)c(C(F)(F)F)nc2n1] | 2-(4-(8-methoxy-4-oxo-2-(trifluoromethyl)-4H-pyrimido[1,2-a]pyrimidin-3-yl)phenoxy)propanenitrile | Step 2: $K_2CO_3$, acetone, 70° C. | 3-(4-hydroxyphenyl)-8-methoxy-2-(trifluoromethyl)-4H-pyrimido[1,2-a]pyrimidin-4-one (Intermediate 3-B), 2-bromopropanenitrile |

Method 9

Example 9-1: 8-Methoxy-3-(4-(2,2,3,3-tetrafluoropropoxy)phenyl)-2-(trifluoromethyl)-4H-pyrido[1,2-a]pyrimidin-4-one

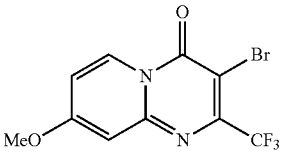

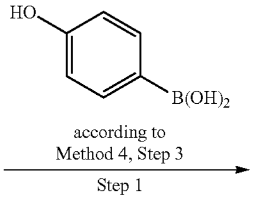

Intermediate 1-A

-continued

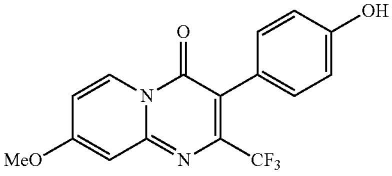

Intermediate 3-A

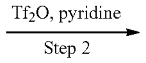

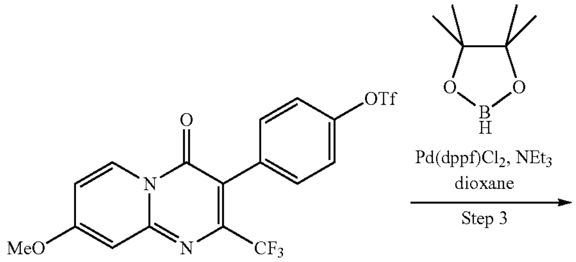

-continued

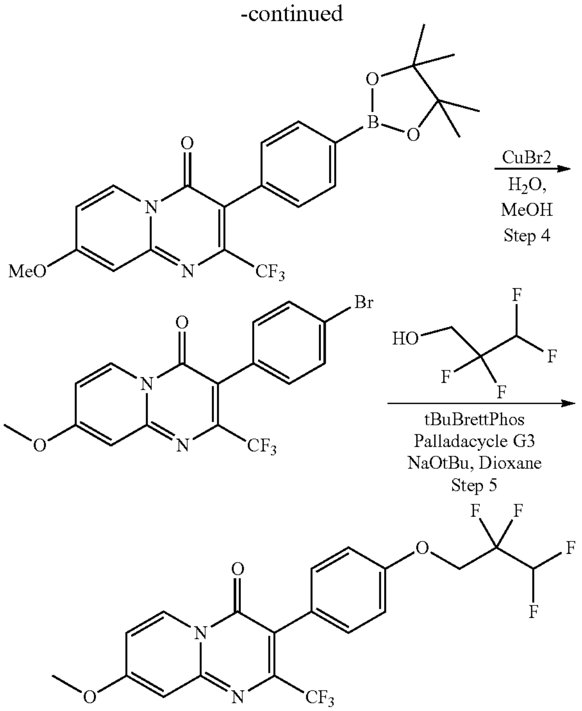

Step 1: 3-(4-Hydroxyphenyl)-8-methoxy-2-(trifluoromethyl)-4H-pyrido[1,2-a]pyrimidin-4-one The title compound was prepared using the procedure described in Method 1, Step with the following modifications: Step 1 performed with 2-fluoro-4-hydroxybenzeneboronic acid pinacol ester (Combi-Blocks Inc.). MS ($ESI^+$) m/z=337.0 $[M+H]^+$.

Step 2: 4-(8-Methoxy-4-oxo-2-(trifluoromethyl)-4H-pyrido[1,2-a]pyrimidin-3-yl)phenyl trifluoromethanesulfonate A reaction mixture of 3-(4-hydroxyphenyl)-8-methoxy-2-(trifluoromethyl)-4H-pyrido[1,2-a]pyrimidin-4-one (0.5 g, 1.5 mmol), pyridine (0.25 ml, 3.0 mmol), and dichloromethane (7 ml) was cooled to 0° C., followed by the addition of trifluoromethanesulfonic anhydride (0.3 ml, 1.8 mmol). The reaction mixture was allowed to warm to rt and then stirred for additional 2 h. The crude material was adsorbed onto silica gel and purified by silica gel chromatography (eluent: 0-30% (3:1 EtOAc/EtOH)/heptane) to obtain 4-(8-methoxy-4-oxo-2-(trifluoromethyl)-4H-pyrido[1,2-a]pyrimidin-3-yl) phenyl trifluoromethanesulfonate (0.64 g, 1.36 mmol, 91% yield) as a white solid. MS ($ESI^+$) m/z=469.0 $[M+H]^+$.

Step 3: 8-Methoxy-3-(4-(4,4,5,5-tetramethyl-1,3,2-dioxaborolan-2-yl)phenyl)-2-(trifluoromethyl)-4H-pyrido[1,2-a]pyrimidin-4-one A vial was charged with Pd(dppf)$Cl_2$ (0.100 g, 0.136 mmol) and 4-(8-methoxy-4-oxo-2-(trifluoromethyl)-4H-pyrido[1,2-a]pyrimidin-3-yl)phenyl trifluoromethanesulfonate (0.64 g, 1.4 mmol). The vial was evacuated and backfilled with nitrogen. This procedure was repeated 3 times, followed by the addition of 1,4-dioxane (6.80 ml), and triethylamine (0.57 ml, 4.1 mmol). The reaction mixture was heated to 80° C. for 6 h. The reaction mixture was cooled to rt, filtered through a pad of celite, adsorbed onto a pad of silica gel and purified by silica gel chromatography (eluent: 0-30% (3:1 EtOAc/EtOH)/heptane) to obtain 8-methoxy-3-(4-(4,4,5,5-tetramethyl-1,3,2-dioxaborolan-2-yl)phenyl)-2-(trifluoromethyl)-4H-pyrido[1,2-a]pyrimidin-4-one (0.8 g, 1.8 mmol, 75% purity). The product was taken onto the next step without additional purification. MS ($ESI^+$) m/z=447.0 $[M+H]^+$.

Step 4: 3-(4-Bromophenyl)-8-methoxy-2-(trifluoromethyl)-4H-pyrido[1,2-a]pyrimidin-4-one A reaction mixture of 8-methoxy-3-(4-(4,4,5,5-tetramethyl-1,3,2-dioxaborolan-2-yl)phenyl)-2-(trifluoromethyl)-4H-pyrido[1,2-a]pyrimidin-4-one (0.61 g, 1.36 mmol), copper(II) bromide (0.9 g, 4.1 mmol), water (1 ml), and methanol (6 mL) was heated to 90° C. for 5 h. The reaction mixture was cooled to rt, partitioned between EtOAc and water. The organic phase was washed with water and brine and adsorbed onto a pad of silica gel. The crude product was purified by silica gel chromatography (eluent: 10-30% 3:1 EtOAc/EtOH in heptane to provide 3-(4-bromophenyl)-8-methoxy-2-(trifluoromethyl)-4H-pyrido[1,2-a]pyrimidin-4-one (0.34 g, 0.86 mmol, 90% purity). The product was taken onto the next step without additional purification. MS ($ESI^+$) m/z=398.9 $[M+H]^+$.

Step 5: 8-Methoxy-3-(4-(2,2,3,3-tetrafluoropropoxy)phenyl)-2-(trifluoromethyl)-4H-pyrido[1,2-a]pyrimidin-4-one A resealable vial was charged with 3-(4-bromophenyl)-8-methoxy-2-(trifluoromethyl)-4H-pyrido[1,2-a]pyrimidin-4-one (50 mg, 0.125 mmol), sodium tert-butoxide (17 mg, 0.175 mmol), and tBuBrettPhos Palladacycle G3 (6 mg, 7.5 µmol). The vial was evacuated and backfilled with nitrogen. This procedure was repeated 3 times, followed by the addition of 1,4-dioxane (835 µl) and 2,2,3,3-tetrafluoro-1-propanol (33 µl, 0.38 mmol). The reaction mixture was heated to 60° C. for 2 h, filtered through a pad of silica gel and extracted with EtOAc (60 mL). The organic phase was sequentially washed with sat. aq. sodium bicarbonate (60 mL) and brine (60 mL). The organic phase was dried over magnesium sulfate, filtered, and concentrated under reduced pressure. The crude residue was adsorbed onto a plug of silica gel and purified by silica gel chromatography (eluent: 0-50% EtOAc/heptane) to obtain 8-methoxy-3-(4-(2,2,3,3-tetrafluoropropoxy)phenyl)-2-(trifluoromethyl)-4H-pyrido[1,2-a]pyrimidin-4-one (23 mg, 0.05 mmol, 41% yield) as a light-orange solid. MS ($ESI^+$) m/z=451.0 $[M+H]^+$. $^1H$ NMR (400 MHz, $CD_2Cl_2$) δ 4.03 (s, 3H) 4.43 (t, J=11.92 Hz, 2H) 5.99-6.31 (m, 1H) 6.94 (dd, J=7.88, 2.70 Hz, 1H) 6.99-7.04 (m, 2H) 7.05 (d, J=2.49 Hz, 1H) 7.29 (d, J=8.50 Hz, 2H) 8.91 (d, J=7.88 Hz, 1H).

Example 9-2 listed in Table 12 was prepared following the procedure described in Method 9, Step 5, above as follows.

TABLE 12

| Ex. # | Chemical Structure | Name | Reagent |
|---|---|---|---|
| 9-2 | 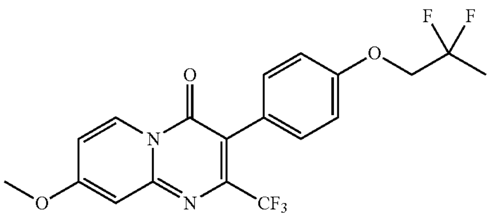 [SMILES: COc1ccn2c(=O)c(-c3ccc(OCC(C)(F)F)cc3)c(C(F)(F)F)nc2c1] | 3-(4-(2,2-difluoropropoxy)phenyl)-8-methoxy-2-(trifluoromethyl)-4H-pyrido[1,2-a]pyrimidin-4-one | 2,2-difluoro-1-hydroxypropane (Oakwood Products) |

Method 10

Example 10-1: 3-(4-(2,2,2-Trifluoroethoxy)phenyl)-2-(trifluoromethyl)-4H-pyrido[1,2-a]pyrimidine-4,8(1H)-dione

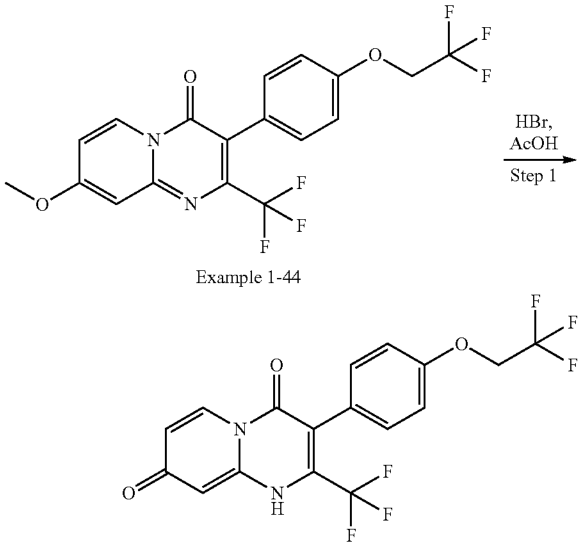

Step 1: 3-(4-(2,2,2-Trifluoroethoxy)phenyl)-2-(trifluoromethyl)-4H-pyrido[1,2-a]pyrimidine-4,8(1H)-dione A solution of 8-methoxy-3-(4-(2,2,2-trifluoroethoxy)phenyl)-2-(trifluoromethyl)-4H-pyrido[1,2-a]pyrimidin-4-one (1 g, 2.4 mmol, Example 1-44) in HBr (33% in acetic acid, 1.3 ml, 7.2 mmol) was heated to 110° C. for 2 days. The reaction mixture was cooled to rt, partitioned between EtOAc and water and the aqueous layer was backextracted with EtOAc (2×). The combined organic layers were dried over MgSO4, filtered, and concentrated in vacuo to provide a residue which was triturated with $Et_2O$ (20 mL). The solid was filtered off and dried to provide 3-(4-(2,2,2-trifluoroethoxy)phenyl)-2-(trifluoromethyl)-4H-pyrido[1,2-a]pyrimidine-4,8(1H)-dione (0.92 g, 2.3 mmol, 95% yield) as a white solid. MS (ESI) m/z=404.9 $[M+H]^+$. $^1H$ NMR (DMSO-$d_6$, 400 MHz) δ 12.25 (br s, 1H), 8.87 (br d, J=6.8 Hz, 1H), 7.23 (br d, J=8.3 Hz, 2H), 7.08 (br d, J=8.7 Hz, 3H), 6.88 (br s, 1H), 4.80 (q, J=8.8 Hz, 2H).

Examples 10-2 to 10-4 listed in Table 13 were prepared following the procedure described in Method 10, Step 1, above as follows.

TABLE 13

| Ex. # | Chemical Structure | Name | Reagent |
|---|---|---|---|
| 10-2 | 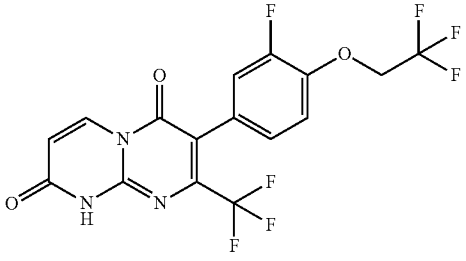 [SMILES: O=c1ccn2c(=O)c(-c3ccc(OCC(F)(F)F)c(F)c3)c(C(F)(F)F)nc2[nH]1] | 7-(3-fluoro-4-(2,2,2-trifluoroethoxy)phenyl)-8-(trifluoromethyl)-2H-pyrimido[1,2-a]pyrimidine-2,6(1H)-dione | 3-(3-fluoro-4-(2,2,2-trifluoroethoxy)phenyl)-8-methoxy-2-(trifluoromethyl)-4H-pyrimido[1,2-a]pyrimidin-4-one (Example 1-73) |

TABLE 13-continued

| Ex. # | Chemical Structure | Name | Reagent |
| --- | --- | --- | --- |
| 10-3 | 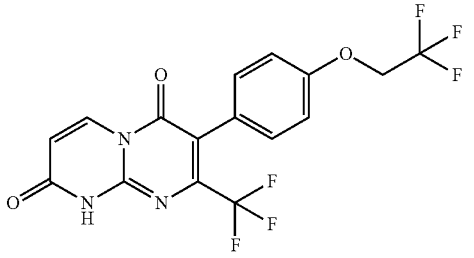 [SMILES: O=c1ccn2c(=O)c(-c3ccc(OCC(F)(F)F)cc3)c(C(F)(F)F)nc2[nH]1] | 7-(4-(2,2,2-trifluoroethoxy)phenyl)-8-(trifluoromethyl)-2H-pyrimido[1,2-a]pyrimidine-2,6(1H)-dione | 8-methoxy-3-[4-(2,2,2-trifluoroethoxy)phenyl]-2-(trifluoromethyl)pyrimido[1,2-a]pyrimidin-4-one (Example 1-50) |
| 10-4 | 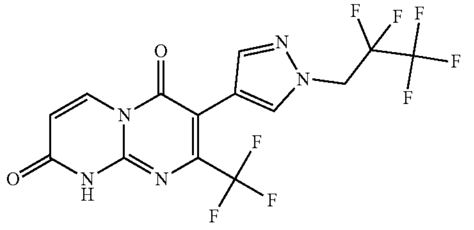 [SMILES: O=c1ccn2c(=O)c(-c3cnn(CC(F)(F)C(F)(F)F)c3)c(C(F)(F)F)nc2[nH]1] | 7-(1-(2,2,3,3,3-pentafluoropropyl)-1H-pyrazol-4-yl)-8-(trifluoromethyl)-2H-pyrimido[1,2-a]pyrimidine-2,6(1H)-dione | 8-methoxy-3-[1-(2,2,3,3,3-pentafluoropropyl)pyrazol-4-yl]-2-(trifluoromethyl)pyrimido[1,2-a]pyrimidin-4-one (Example 1-34) |

Method 11

Example 11-1: 1-(Methyl-$d_3$)-7-(4-(2,2,2-trifluoroethoxy)phenyl)-8-(trifluoromethyl)-2H-pyrimido[1,2-a]pyrimidine-2,6(1H)-dione

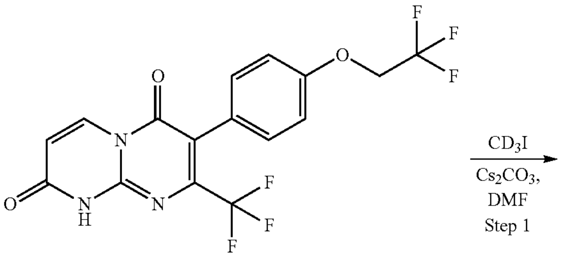

Example 10-3

-continued

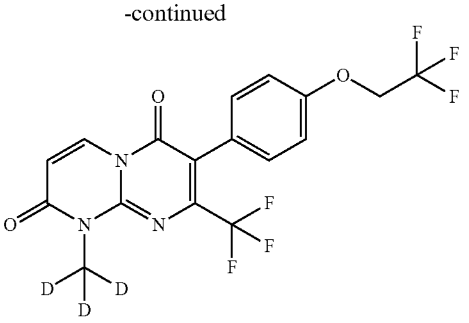

Step 1: 1-(Methyl-$d_3$)-7-(4-(2,2,2-trifluoroethoxy)phenyl)-8-(trifluoromethyl)-2H-pyrimido[1,2-a]pyrimidine-2,6(1H)-dione Deuterated iodomethane (0.07 mL, 1.1 mmol) was added to a suspension of 7-(4-(2,2,2-trifluoroethoxy)phenyl)-8-(trifluoromethyl)-2H-pyrimido[1,2-a]pyrimidine-2,6(1H)-dione (Example 10-3, 7.0 mg, 0.20 mmol) and cesium carbonate (0.12 g, 0.36 mmol) in DMF (2 mL). The reaction mixture was stirred at rt for 3 h, subsequently diluted with water and extracted with EtOAc. The organic phase was separated, concentrated under reduced pressure and purified by silica gel chromatography (eluent: 0-30% EtOAc/heptane) to obtain 1-(methyl-$d_3$)-7-(4-(2,2,2-trifluoroethoxy)phenyl)-8-(trifluoromethyl)-2H-pyrimido[1,2-a]pyrimidine-2,6(1H)-dione (5 mg, 0.12 mmol, 67% yield). MS ($ESI^+$) m/z=423.2 $[M+H]^+$. $^1H$ NMR (400 MHz, DMSO-$d_6$) δ 8.58 (d, J=8.29 Hz, 1H), 7.20-7.27 (m, J=8.71 Hz, 2H), 7.11-7.17 (m, J=8.71 Hz, 2H), 6.55 (d, J=8.29 Hz, 1H), 4.83 (q, J=8.91 Hz, 2H).

Examples 11-2 to 11-3 listed in Table 14 were prepared following the procedure described in Method 11, Step 1, above as follows.

TABLE 14

| Ex. # | Chemical Structure | Name | Reagent |
| --- | --- | --- | --- |
| 11-2 | 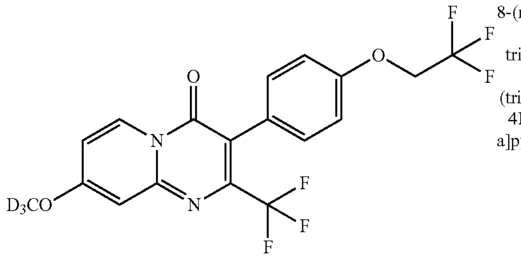 | 8-(methyloxy-$d_3$)-3-(4-(2,2,2-trifluoroethoxy) phenyl)-2-(trifluoromethyl)-4H-pyrido[1,2-a]pyrimidin-4-one | Example 10-1 |
| 11-3 | 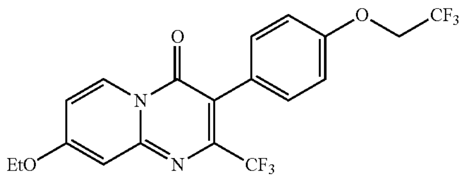 | 8-ethoxy-3-(4-(2,2,2-trifluoroethoxy) phenyl)-2-(trifluoromethyl)-4H-pyrido[1,2-a]pyrimidin-4-one | Example 10-1, ethyl iodide (Acros Organics) |

Method 12

Example 12-1: N-Methyl-4-oxo-3-(4-(2,2,2-trifluoroethoxy)phenyl)-2-(trifluoromethyl)-4H-pyrido[1,2-a]pyrimidine-8-carboxamide

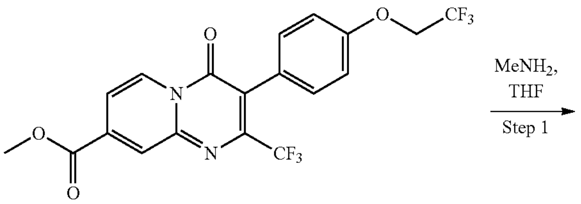

Example 1-36

-continued

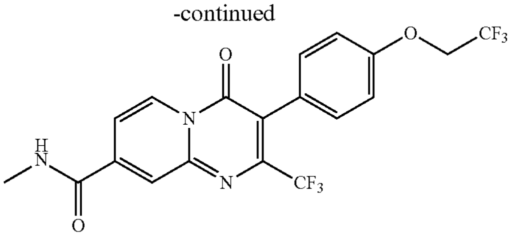

A solution of methyl 4-oxo-3-(4-(2,2,2-trifluoroethoxy) phenyl)-2-(trifluoromethyl)-4H-pyrido[1,2-a]pyrimidine-8-carboxylate (Example 1-36, 0.25 g, 0.56 mmol) in methylamine (2 M in THF, 2.5 mL, Spectrochem) was stirred for 1 h at 0° C. The reaction mixture was concentrated under reduced and the crude residue was treated with diethyl ether (15 mL) for 30 minutes. The solid was filtered off and dried to obtain N-methyl-4-oxo-3-(4-(2,2,2-trifluoroethoxy)phenyl)-2-(trifluoromethyl)-4H-pyrido[1,2-a]pyrimidine-8-carboxamide (0.22 g, 88% yield) as off white solid. LC/MS (ESI) m/z=446.1 $[M+H]^+$. $^1H$ NMR (400 MHz, DMSO-$d_6$) δ 9.05 (dd, J=13.4, 6.0 Hz, 2H), 8.29 (d, J=1.8 Hz, 1H), 7.75 (dd, J=7.4, 1.9 Hz, 1H), 7.35-7.27 (m, 2H), 7.19-7.08 (m, 2H), 4.84 (q, J=8.9 Hz, 2H), 2.86 (d, J=4.4 Hz, 3H).

Examples 12-2 to 12-5 listed in Table 15 were prepared following the procedure described in Method 12, Step 1, above as follows.

TABLE 15

| Ex. # | Chemical Structure | Name | Reagent |
| --- | --- | --- | --- |
| 12-2 | 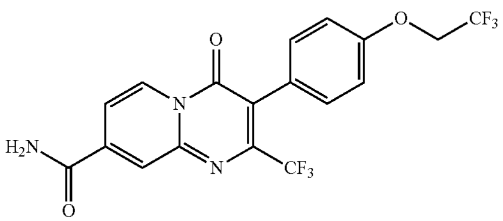 [SMILES: NC(=O)c1ccn2c(=O)c(-c3ccc(OCC(F)(F)F)cc3)c(C(F)(F)F)nc2c1] | 4-oxo-3-(4-(2,2,2-trifluoroethoxy) phenyl)-2-(trifluoromethyl)-4H-pyrido[1,2-a]pyrimidine-8-carboxamide | 2M $NH_3$ in methanol |

TABLE 15-continued

| Ex. # | Chemical Structure | Name | Reagent |
|---|---|---|---|
| 12-3 | 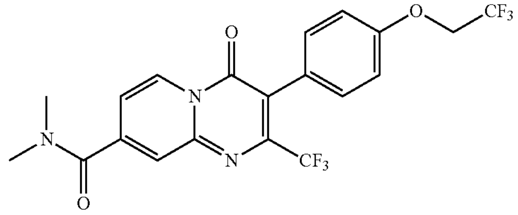 [SMILES: CN(C)C(=O)c1ccn2c(=O)c(-c3ccc(OCC(F)(F)F)cc3)c(C(F)(F)F)nc2c1] | N,N-dimethyl-4-oxo-3-(4-(2,2,2-trifluoroethoxy) phenyl)-2-(trifluoromethyl)-4H-pyrido[1,2-a]pyrimidine-8-carboxamide | 40% solution of dimethyl amine in THF (Spectrochem) |
| 12-4 | 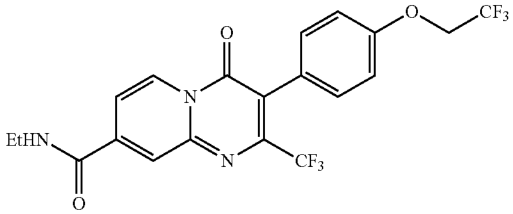 | N-ethyl-4-oxo-3-(4-(2,2,2-trifluoroethoxy) phenyl)-2-(trifluoromethyl)-4H-pyrido[1,2-a]pyrimidine-8-carboxamide | 2M ethylamine solution in THF (Spectrochem) |
| 12-5 | 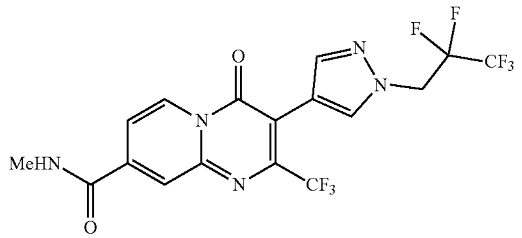 [SMILES: CNC(=O)c1ccn2c(=O)c(-c3cnn(CC(F)(F)C(F)(F)F)c3)c(C(F)(F)F)nc2c1] | N-methyl-4-oxo-3-(1-(2,2,3,3,3-pentafluoropropyl)-1H-pyrazol-4-yl)-2-(trifluoromethyl)-4H-pyrido[1,2-a]pyrimidine-8-carboxamide | methyl 4-oxo-3-(1-(2,2,3,3,3-pentafluoropropyl)-1H-pyrazol-4-yl)-2-(trifluoromethyl)-4H-pyrido[1,2-a]pyrimidine-8-carboxylate (Intermediate 3-F), 33 wt. % methyl amine in ethanol (Spectrochem) |

Method 13

Examples 13-1 and 13-2: 8-(Hydroxymethyl)-3-(1-(2,2,3,3,3-pentafluoropropyl)-1H-pyrazol-4-yl)-2-(trifluoromethyl)-4H-pyrido[1,2-a]pyrimidin-4-one and 8-(fluoromethyl)-3-(1-(2,2,3,3,3-pentafluoropropyl)-1H-pyrazol-4-yl)-2-(trifluoromethyl)-4H-pyrido[1,2-a]pyrimidin-4-one

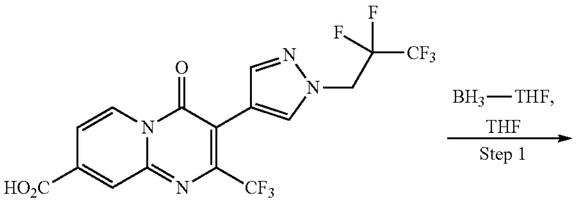

Example 1-21

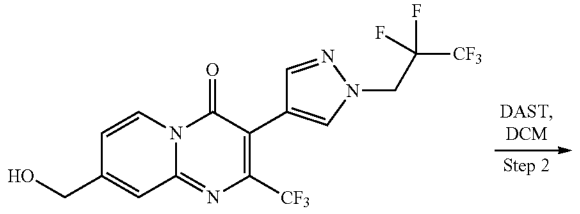

Example 13-1

-continued

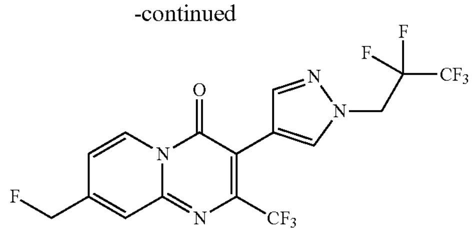

Example 13-2

Step 1: 8-(Hydroxymethyl)-3-(1-(2,2,3,3,3-pentafluoropropyl)-1H-pyrazol-4-yl)-2-(trifluoromethyl)-4H-pyrido[1,2-a]pyrimidin-4-one Solution of borane (1.0 M in THF, 5.5 mL, 5.5 mmol) was added dropwise to a solution of 4-oxo-3-(1-(2,2,3,3,3-pentafluoropropyl)-1H-pyrazol-4-yl)-2-(trifluoromethyl)-4H-pyrido[1,2-a]pyrimidine-8-carboxylic acid (Example 1-21, 0.5 g, 1.1 mmol) in THF (5.0 mL) at 0° C. under nitrogen atmosphere. After 10 min, the reaction mixture was allowed to warm to rt and stirred for additional 5 h. The reaction mixture was cooled to 0° C. and quenched by addition of methanol (2 mL). The resulting solution was concentrated under reduced pressure, diluted with water (5 mL) and extracted with ethyl acetate (3×5 mL). The combined organic layer was washed with brine solution (5 mL), dried over anhydrous $Na_2SO_4$ and concentrated under reduced pressure. The crude material was purified by silica gel chromatography (eluent: 0-55% EtOAc/hexane) to afford 8-(hydroxymethyl)-3-(1-(2,2,3,3,3-pentafluoropropyl)-1H-pyrazol-4-yl)-2-(trifluoromethyl)-4H-pyrido[1,2-a]pyrimidin-4-one (0.35 g, 72% yield) as yellow solid. MS ($ESI^+$) m/z=443.1 $[M+H]^+$. $^1H$ NMR (400 MHz, DMSO-$d_6$) δ 8.97 (d, J=7.3 Hz, 1H), 8.05 (s, 1H), 7.69 (s, 2H), 7.43 (dd, J=7.5, 1.8 Hz, 1H), 5.78 (t, J=5.7 Hz, 1H), 5.29 (t, J=14.9 Hz, 2H), 4.71 (d, J=5.4 Hz, 2H).

Step 2: 8-(Fluoromethyl)-3-(1-(2,2,3,3,3-pentafluoropropyl)-1H-pyrazol-4-yl)-2-(trifluoromethyl)-4H-pyrido[1,2-a]pyrimidin-4-one DAST (0.1 mL, 0.75 mL) was added dropwise to a solution of 8-(hydroxymethyl)-3-(1-(2,2,3,3,3-pentafluoropropyl)-1H-pyrazol-4-yl)-2-(trifluoromethyl)-4H-pyrido[1,2-a]pyrimidin-4-one (Example 13-1, 0.17 g, 0.37 mmol) in DCM (3.0 mL) at 0° C. under nitrogen atmosphere. The reaction mixture was allowed to warm to rt and stirred for 1 h. The reaction mixture was cooled to 0° C., quenched by addition of aqueous 10% $NaHCO_3$ solution (3 mL) and extracted with DCM (3×5 mL). The combined organic layer was washed with brine (5 mL), dried over anhydrous $Na_2SO_4$, filtered and concentrated under reduced pressure. The crude residue was purified by silica gel chromatography (eluent: 0-35% EtOAc/hexane) to obtain 8-(fluoromethyl)-3-(1-(2,2,3,3,3-pentafluoropropyl)-1H-pyrazol-4-yl)-2-(trifluoromethyl)-4H-pyrido[1,2-a]pyrimidin-4-one (0.12 g, 0.26 mmol, 70% yield) as yellow solid. MS ($ESI^+$) m/z=445.1 $[M+H]^+$. $^1H$ NMR (400 MHz, DMSO-$d_6$) δ 9.03 (d, J=7.3 Hz, 1H), 8.08 (s, 1H), 7.78 (s, 1H), 7.72 (s, 1H), 7.46 (dd, J=7.4, 1.8 Hz, 1H), 5.71 (dd, J=46.0 Hz, 1.3 Hz, 2H), 5.31 (t, J=15.0 Hz, 2H).

Examples 13-3 and 13-4 listed in Table 16 were prepared following the procedure described in Method 13, Steps 1 and 2, above as follows.

TABLE 16

| Ex. # | Chemical Structure | Name | Reagent |
|---|---|---|---|
| 13-3 | 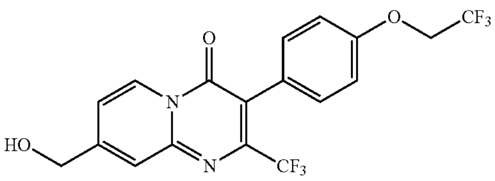 [SMILES: O=c1c(-c2ccc(OCC(F)(F)F)cc2)c(C(F)(F)F)nc2cc(CO)ccn12] | 8-(hydroxymethyl)-3-(4-(2,2,2-trifluoroethoxy)phenyl)-2-(trifluoromethyl)-4H-pyrido[1,2-a]pyrimidin-4-one | Step 1: Example 1-36. Step 2: $NaBH_4$ |
| 13-4 | 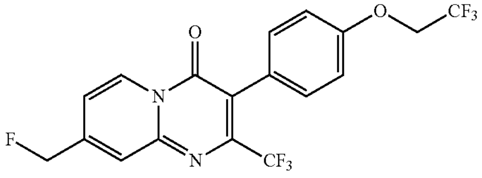 [SMILES: O=c1c(-c2ccc(OCC(F)(F)F)cc2)c(C(F)(F)F)nc2cc(CF)ccn12] | 8-(fluoromethyl)-3-(4-(2,2,2-trifluoroethoxy)phenyl)-2-(trifluoromethyl)-4H-pyrido[1,2-a]pyrimidin-4-one | Step 2: Example 13-2 |

Method 14

Example 14-1: 8-(Methylamino)-3-(4-(2,2,2-trifluoroethoxy)phenyl)-2-(trifluoromethyl)-4H-pyrimido[1,2-a]pyrimidin-4-one

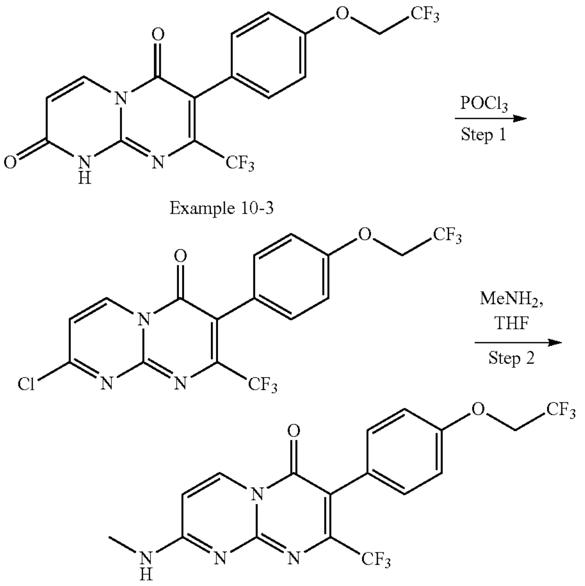

Step 1: 8-Chloro-3-(4-(2,2,2-trifluoroethoxy)phenyl)-2-(trifluoromethyl)-4H-pyrimido[1,2-a]pyrimidin-4-one 7-(4-(2,2,2-Trifluoroethoxy)phenyl)-8-(trifluoromethyl)-2H-pyrimido[1,2-a]pyrimidine-2,6(1H)-dione (0.43 g, 1.1 mmol, Example 10-3) was suspended in phosphorous oxychloride (5.0 mL) under nitrogen atmosphere and the resulting reaction mixture was heated to 110° C. for 16 h. The reaction mixture was cooled to room temperature and concentrated under reduced pressure. The residual $POCl_3$ was removed by azeotropic distillation with toluene (3×5 mL) to yield 8-chloro-3-(4-(2,2,2-trifluoroethoxy)phenyl)-2-(trifluoromethyl)-4H-pyrimido[1,2-a]pyrimidin-4-one as a solid. The product was taken onto the next step without further purification. MS ($ESI^+$) m/z=424.0 $[M+H]^+$.

Step 2: 8-(Methylamino)-3-(4-(2,2,2-trifluoroethoxy)phenyl)-2-(trifluoromethyl)-4H-pyrimido[1,2-a]pyrimidin-4-one Methyl amine (2.0 M in THF, 5.3 mL, 10.6 mmol) was added dropwise to a solution of 8-chloro-3-(4-(2,2,2-trifluoroethoxy)phenyl)-2-(trifluoromethyl)-4H-pyrimido[1,2-a]pyrimidin-4-one (0.45 g, 1.1 mmol) in anhydrous THF (4.5 mL) at 0° C. over a period of 10 min. The reaction mixture was allowed to warm to room temperature and stirred for 1 h. The reaction mixture was diluted with water (5 mL) and extracted with a mixture of methanol in DCM (ratio 1:9; 3×5 mL). The combined organic layer was dried over anhydrous $Na_2SO_4$, filtered and concentrated under reduced pressure. The crude residue was purified by silica gel chromatography (eluent: 100% (1.5% methanol in dichloromethane)) to afford 8-(methylamino)-3-(4-(2,2,2-trifluoroethoxy)phenyl)-2-(trifluoromethyl)-4H-pyrimido[1,2-a]pyrimidin-4-one (0.36 g) as an off white solid. MS ($ESI^+$) m/z=419.1 $[M+H]^+$. $^1H$ NMR (400 MHz, DMSO-$d_6$) δ 8.81 (t, J=4.8 Hz, 1H), 8.67 (dd, J=7.8, 2.7 Hz, 1H), 7.21 (dd, J=9.1, 2.6 Hz, 2H), 7.15-7.05 (m, 2H), 6.69 (dd, J=7.8, 2.6 Hz, 1H), 4.82 (qd, J=9.0, 2.7 Hz, 2H), 2.98 (dd, J=4.9, 2.6 Hz, 3H).

Example 14-2 listed in Table 17 was prepared following the procedure described in Method 14, Step 2, above as follows.

TABLE 17

| Ex. # | Chemical Structure | Name | Reagent |
|---|---|---|---|
| 14-2 | 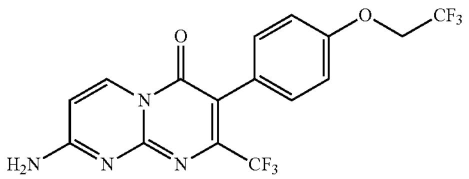 [SMILES: Nc1ccn2c(=O)c(-c3ccc(OCC(F)(F)F)cc3)c(C(F)(F)F)nc2n1] | 8-amino-3-(4-(2,2,2-trifluoroethoxy)phenyl)-2-(trifluoromethyl)-4H-pyrimido[1,2-a]pyrimidin-4-one | $NH_3$ (gas) in THF |

Method 15

Example 15-1: 8-(Methylsulfinyl)-3-(4-(2,2,2-trifluoroethoxy)phenyl)-2-(trifluoromethyl)-4H-pyrido[1,2-a]pyrimidin-4-one

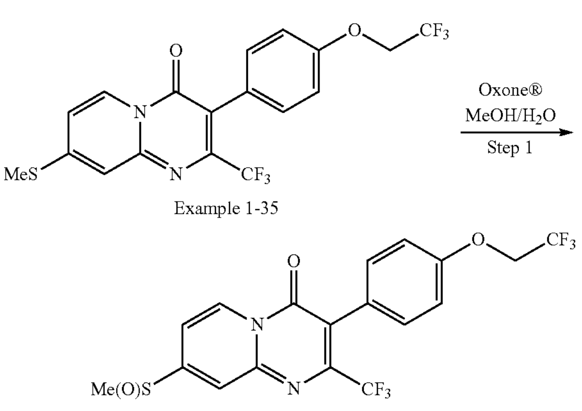

Example 1-35

Step 1: 8-(Methylsulfinyl)-3-(4-(2,2,2-trifluoroethoxy)phenyl)-2-(trifluoromethyl)-4H-pyrido[1,2-a]pyrimidin-4-one Oxone* (3.3 g, 5.3 mmol) was added to a solution of 8-(methylsulfanyl)-3-(4-(2,2,2-trifluoroethoxy)phenyl)-2-(trifluoromethyl)-4H-pyrido[1,2-a]pyrimidin-4-one (2.3 g, 5.3 mmol, Example 1-35) in methanol (46 mL) and water (23 mL) at room temperature. The reaction mixture was stirred at room temperature for 18 h. The solvent were partially removed under reduced pressure, the pH of the crude residue was adjusted to ~7 by addition of saturated $NaHCO_3$ solution (50 mL) and the reaction mixture was extracted with ethyl acetate (3x100 mL). The combined organic layer was dried over sodium sulfate, filtered and concentrated under reduced pressure. The crude material was purified by silica gel chromatography (eluent: 0-90% EtOAc/hexane) to obtain 8-(methylsulfinyl)-3-(4-(2,2,2-trifluoroethoxy)phenyl)-2-(trifluoromethyl)-4H-pyrido[1,2-a]pyrimidin-4-one (0.90 g, 2.0 mmol, 38% yield). MS ($ESI^+$) m/z=451.0 $[M+H]^+$. $^1H$ NMR (400 MHz, DMSO-$d_6$) δ 9.09 (d, J=7.4 Hz, 1H), 8.05 (d, J=1.7 Hz, 1H), 7.72 (dd, J=7.4, 1.9 Hz, 1H), 7.33-7.25 (m, 2H), 7.20-7.12 (m, 2H), 4.85 (q, J=8.8 Hz, 2H), 2.97 (s, 3H).

Examples 15-4 and 15-7 listed in Table 18 were prepared following the procedure described in Method 15, Step 1, above as follows.

TABLE 18

| Ex. # | Chemical Structure | Name | Reagent |
|---|---|---|---|
| 15-4 | 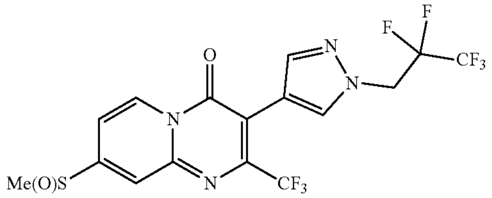 | 8-(methylsulfinyl)-3-(1-(2,2,3,3,3-pentafluoropropyl)-1H-pyrazol-4-yl)-2-(trifluoromethyl)-4H-pyrido[1,2-a]pyrimidin-4-one | Example 1-30 |
| 15-7 | 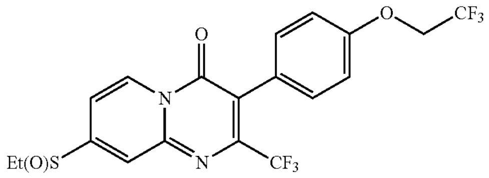 | 8-(ethylsulfinyl)-3-(4-(2,2,2-trifluoroethoxy) phenyl)-2-(trifluoromethyl)-4H-pyrido[1,2-a]pyrimidin-4-one | 8-(ethylthio)-3-(4-(2,2,2-trifluoroethoxy) pheny])-2-(trifluoromethyl)-4H-pyrido[1,2-a]pyrimidin-4-one (Intermediate 3-G) |

Method 16

Example 16-1: (4-Oxo-3-(1-(2,2,3,3,3-pentafluoropropyl)-1H-pyrazol-4-yl)-2-(trifluoromethyl)-4H-pyrido[1,2-a]pyrimidin-8-yl)acetonitrile

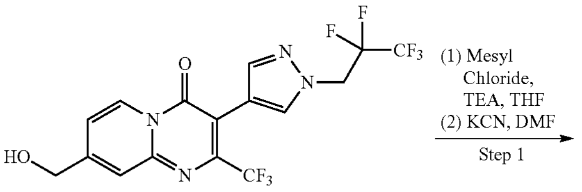

Example 13-1

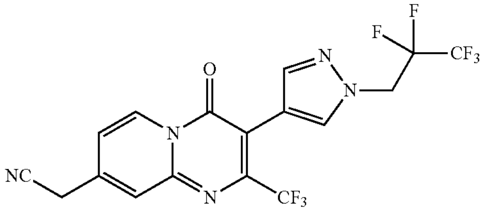

Step 1-1: (4-Oxo-3-(1-(2,2,3,3,3-pentafluoropropyl)-1H-pyrazol-4-yl)-2-(trifluoromethyl)-4H-pyrido[1,2-a]pyrimidin-8-yl)methyl methanesulfonate Triethylamine (0.3 mL, 2.4 mmol) was added to a solution of 8-(hydroxymethyl)-3-(1-(2,2,3,3,3-pentafluoropropyl)-1H-pyrazol-4-yl)-2-(trifluoromethyl)-4H-pyrido[1,2-a]pyrimidin-4-one (700 mg, 1.6 mmol, Example 13-1) in THF (7.0 mL) at 0° C., followed by addition of mesyl chloride (160 μL, 2.1 mmol). The reaction mixture was allowed to warm to rt. After 1 h, the reaction mixture was cooled to 0° C., quenched with water (30 mL) and extracted with ethyl acetate (2x30 mL). The combined organic layers were dried over potassium carbonate, filtered and concentrated under reduced pressure to get the crude product (700 mg) which was used in the next step without further purification.

Step 1-2: (4-Oxo-3-(1-(2,2,3,3,3-pentafluoropropyl)-1H-pyrazol-4-yl)-2-(trifluoromethyl)-4H-pyrido[1,2-a]pyrimidin-8-yl)acetonitrile Potassium cyanide (186 mg, 2.9 mmol) was added to a solution of the crude product obtained in Step 1-1 (700 mg) in DMF (7.0 mL) at rt. After 1 h, the reaction mixture was quenched with water (30 mL) and extracted with ethyl acetate (3x30 mL). The combined organic layers were dried over sodium sulfate, filtered and concentrated under reduced pressure. The crude material was purified by RP HPLC (Gemini NX C18, 250x19 mm, 5p, Mobile Phase A: 10 mM Ammonium acetate in water, Mobile Phase B: Acetonitrile, Flow Rate: 15 ml/min) to get (4-oxo-3-(1-(2,2,3,3,3-pentafluoropropyl)-1H-pyrazol-4-yl)-2-(trifluoromethyl)-4H-pyrido[1,2-a]pyrimidin-8-yl)acetonitrile (55 mg) as a solid. LC/MS (ESI$^+$) m/z=452.0 [M+H]$^+$. $^1$H NMR (400 MHz, $CDCl_3$) δ 9.10 (d, J=7.4 Hz, 1H), 7.93 (s, 1H), 7.86 (d, J=11.4 Hz, 2H), 7.22 (dd, J=7.4, 1.9 Hz, 1H), 4.85 (t, J=13.8 Hz, 2H), 3.96 (d, J=1.3 Hz, 2H).

Example 16-2 listed in Table 19 was prepared following the procedure described in Method 16, Step 1, above as follows.

TABLE 19

| Ex. # | Chemical Structure | Name | Reagent |
|---|---|---|---|
| 16-2 | 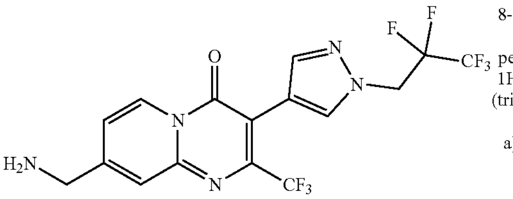 | 8-(aminomethyl)-3-(1-(2,2,3,3,3-pentafluoropropyl)-1H-pyrazol-4-yl)-2-(trifluoromethyl)-4H-pyrido[1,2-a]pyrimidin-4-one | Step 1-2: $NH_3$ (2.0M in EtOH) |

Method 17

Examples 17-1 and 17-2: 8-((Methylsulfanyl) methoxy)-3-(4-(2,2,2-trifluoroethoxy)phenyl)-2-(trifluoromethyl)-4H-pyrido[1,2-a]pyrimidin-4-one and 8-(fluoromethoxy)-3-(4-(2,2,2-trifluoroethoxy) phenyl)-2-(trifluoromethyl)-4H-pyrido[1,2-a]pyrimidin-4-one

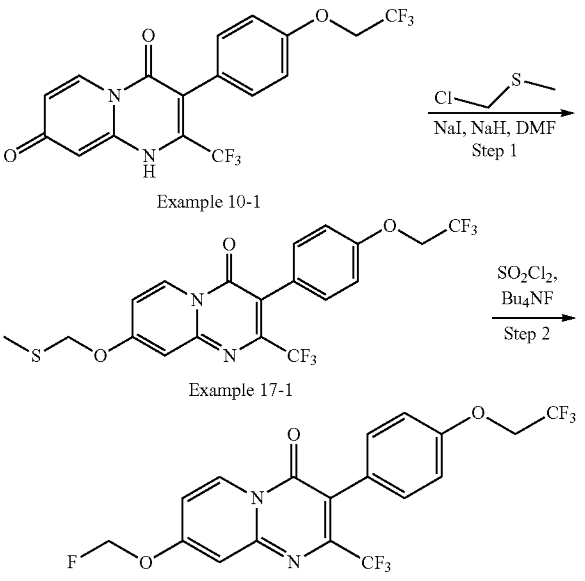

Example 10-1

Example 17-1

Example 17-2

Step 1: 8-((Methylsulfanyl)methoxy)-3-(4-(2,2,2-trifluoroethoxy)phenyl)-2-(trifluoromethyl)-4H-pyrido[1,2-a]pyrimidin-4-one A resealable vial was charged with 3-(4-(2,2,2-trifluoroethoxy)phenyl)-2-(trifluoromethyl)-4H-pyrido[1,2-a]pyrimidine-4,8(1H)-dione (Example 10-1, 0.15 g, 0.37 mmol), sodium iodide (5 mg, 0.37 mmol), and DMF (1.0 mL). The reaction mixture was cooled to 0° C. and sodium hydride (8 mg, 0.34 mmol) was added. The reaction mixture was stirred at 0° C. for 30 min, followed by the addition of chloromethyl methyl sulfide (65 mg, 0.68 mmol). The reaction was warmed to rt and stirring was continued for 24 h. The reaction mixture was quenched with MeOH, and the directly adsorbed onto a plug of silica gel. Purification of the crude material by silica gel chromatography (eluent: 0-30% (3:1 EtOAc in EtOH)/heptane) provided 8-((methylsulfanyl) methoxy)-3-(4-(2,2,2-trifluoroethoxy)phenyl)-2-(trifluoromethyl)-4H-pyrido[1,2-a]pyrimidin-4-one (Example 17-1, 74 mg, 0.16 mmol, 47% yield) as a white solid. LC/MS ($ESI^+$) m/z=464.9 $[M+H]^+$. $^1H$ NMR ($CDCl_3$, 400 MHz) δ 8.95 (d, J=7.9 Hz, 1H), 7.28-7.30 (m, 1H), 7.08 (d, J=2.5 Hz, 1H), 6.91-7.03 (m, 3H), 5.29 (s, 2H), 4.34-4.42 (m, 1H), 4.38 (d, J=8.1 Hz, 1H), 2.30 (s, 3H). 19F NMR ($CDCl_3$, 376 MHz) δ −63.10 (s, 3F), −73.94 (s, 3F).

Step 2: 8-(Fluoromethoxy)-3-(4-(2,2,2-trifluoroethoxy)phenyl)-2-(trifluoromethyl)-4H-pyrido[1,2-a] pyrimidin-4-one Sulfuryl chloride solution (1M in DCM, 43 μl, 0.43 mmol) was added to a solution of 8-((methylsulfanyl) methoxy)-3-(4-(2,2,2-trifluoroethoxy)phenyl)-2-(trifluoromethyl)-4H-pyrido[1,2-a]pyrimidin-4-one (Example 17-1, 67 mg, 0.14 mmol) in dichloromethane (0.7 ml). The reaction mixture was stirred for 15 min and then concentrated under reduced pressure. The crude residue was dissolved in DCM (1 mL) followed by addition of tetrabutylammonium fluoride (1M in THF, 0.3 ml, 0.23 mmol). The reaction mixture was stirred at rt for 16 h. The reaction mixture was partitioned between EtOAc and water. The organic phase was washed with water and brine, and was subsequently dried over $MgSO_4$. The filtrate was concentrated in vacuo and the residue was purified by RP HPLC (Xbridge Column, 100×19 mm, 10 μM, Mobile Phase A: 0.1% $NH_4OH$ in water, Mobile Phase B: Acetonitrile) to provide 8-(fluoromethoxy)-3-(4-(2,2,2-trifluoroethoxy)phenyl)-2-(trifluoromethyl)-4H-pyrido[1,2-a]pyrimidin-4-one (Example 17-2, 15 mg, 0.034 mmol, 24% yield) as a white solid. LC/MS ($ESI^+$) m/z=437.1 $[M+H]^+$. $^1H$ NMR (DMSO-$d_6$, 500 MHz) δ 8.97-8.92 (m, 1H), 7.50-7.45 (m, 1H), 7.24-7.34 (m, 3H), 7.11-7.15 (m, 2H), 6.23-6.03 (m, 2H), 4.83 (q, J=9.0 Hz, 2H). $^{19}F$ NMR ($CDCl_3$, 376 MHz) δ −63.11 (s, 3F), −73.94 (s, 3F), −154.87 (s, 1F).

Example 17-3 in Table 20 was prepared following the procedure described in Method 17, Steps 1 and 2, above as follows

TABLE 20

| Ex. # | Chemical Structure | Name | Reagent |
|---|---|---|---|
| 17-3 | 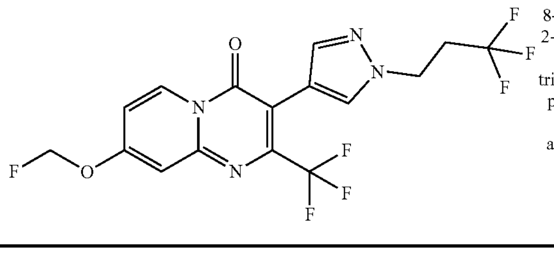 | 8-(fluoromethoxy)-2-(trifluoromethyl)-3-(1-(3,3,3-trifluoropropyl)-1H-pyrazol-4-yl)-4H-pyrido[1,2-a]pyrimidin-4-one | 8-Hydroxy-2-(trifluoromethyl)-3-(1-(3,3,3-trifluoropropyl)-1H-pyrazol-4-yl)-4H-pyrido[1,2-a]pyrimidin-4-one (Intermediate 3-J) |

Method 18

Examples 1-83 and 1-84: 3-(4-(((1R)-2,2-Difluorocyclopropyl)methoxy)phenyl)-8-methoxy-2-(trifluoromethyl)-4H-pyrido[1,2-a]pyrimidin-4-one and 3-(4-(((1S)-2,2-difluorocyclopropyl)methoxy)phenyl)-8-methoxy-2-(trifluoromethyl)-4H-pyrido[1,2-a]pyrimidin-4-one

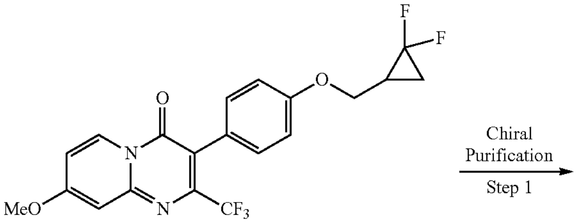

Example 1-4

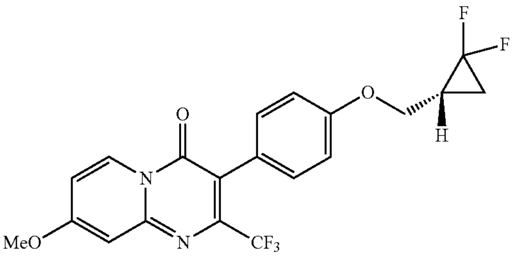

$1^{st}$-eluting isomer

-continued

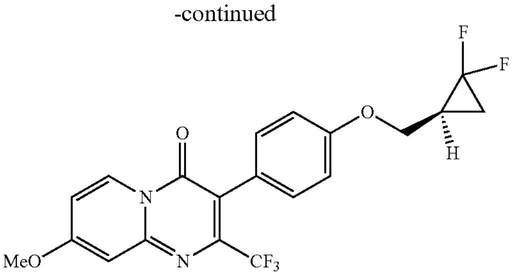

$2^{nd}$-eluting isomer

Step 1: 3-(4-(((1R)-2,2-Difluorocyclopropyl)methoxy)phenyl)-8-methoxy-2-(trifluoromethyl)-4H-pyrido[1,2-a]pyrimidin-4-one and 3-(4-(((1S)-2,2-difluorocyclopropyl)methoxy)phenyl)-8-methoxy-2-(trifluoromethyl)-4H-pyrido[1,2-a]pyrimidin-4-one The racemic mixture of 3-(4-((2,2-difluorocyclopropyl)methoxy)phenyl)-8-methoxy-2-(trifluoromethyl)-4H-pyrido[1,2-a]pyrimidin-4-one (Example 1-4, 0.090 g, 0.21 mmol) was purified by SFC ((OJ-H, 250×20 mm, 5 μm), 35% $MeOH/CO_2$, 60 m/min, 100 bar) to obtain two peaks: 1S eluting isomer (0.038 g, 0.09 mmol, 92% ee) and $2^{nd}$ eluting isomer (0.033 g, 0.08 mmol, 96% ee). The stereochemistry of the isomers was assigned arbitrarily to be 3-(4-(((1R)-2,2-difluorocyclopropyl)methoxy)phenyl)-8-methoxy-2-(trifluoromethyl)-4H-pyrido[1,2-a]pyrimidin-4-one as $1^{st}$ eluting isomer and 3-(4-(((1S)-2,2-difluorocyclopropyl)methoxy)phenyl)-8-methoxy-2-(trifluoromethyl)-4H-pyrido[1,2-a]pyrimidin-4-one as $2^{nd}$ eluting isomer. $1^{st}$ Eluting isomer: LC/MS ($ESI^+$) m/z=427.1 $[M+H]^+$; $^1H$ NMR (400 MHz, DMSO-$d_6$) δ 1.47-1.55 (m, 1H) 1.75 (tdd, J=12.15, 12.15, 7.72, 4.87 Hz, 1H) 2.20-2.31 (m, 1H) 4.04 (s, 4H) 4.20 (br s, 1H) 6.99-7.05 (m, 2H) 7.15-7.28 (m, 4H) 8.87 (d, J=7.88 Hz, 1H). $2^{nd}$ Eluting isomer: LC/MS ($ESI^+$) m/z=427.1 $[M+H]^+$; $^1H$ NMR (400 MHz, DMSO-$d_6$) δ 1.46-1.55 (m, 1H) 1.74 (tdd, J=11.97, 11.97, 7.57, 4.77 Hz, 1H) 2.21-2.30 (m, 1H) 4.03 (s, 4H) 4.16-4.23 (m, 1H) 7.01 (d, J=8.71 Hz, 2H) 7.14-7.28 (m, 4H) 8.87 (d, J=7.88 Hz, 1H).

The examples listed in Table 21 were obtained following the procedure described in Method 18, Step 1 above as follows.

TABLE 21

| Ex. # | Chemical Structure | Name | Racemic separation conditions |
|---|---|---|---|
| 8-6 | 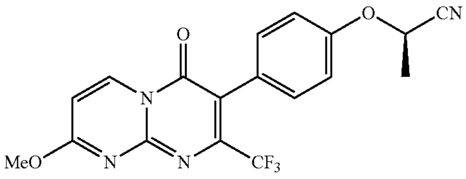 [SMILES: COc1ccn2c(=O)c(-c3ccc(O[C@H](C)C#N)cc3)c(C(F)(F)F)nc2n1] $1^{st}$-eluting isomer | (2R)-2-(4-(8-methoxy-4-oxo-2-(trifluoromethyl)-4H-pyrimido[1,2-a]pyrimidin-3-yl)phenoxy)propanenitrile | Example 8-5/Lux C3(250-50 mm, 5 μm), 50% $MeOH/CO_2$, 150 ml/min, 100 bar |

TABLE 21-continued

| Ex. # | Chemical Structure | Name | Racemic separation conditions |
|---|---|---|---|
| 8-7 | 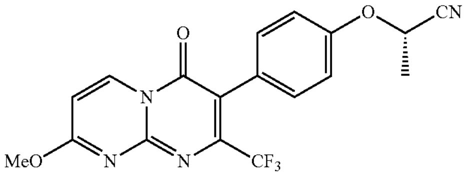 [SMILES: COc1ccn2c(=O)c(-c3ccc(O[C@@H](C)C#N)cc3)c(C(F)(F)F)nc2n1] 2$^{nd}$-eluting isomer | (2S)-2-(4-(8-methoxy-4-oxo-2-(trifluoromethyl)-4H-pyrimido[1,2-a]pyrimidin-3-yl)phenoxy) propanenitrile | Example 8-5/Lux C3(250-50 mm, 5 μm), 50% MeOH/$CO_2$, 150 ml/min, 100 bar |
| 8-8 | 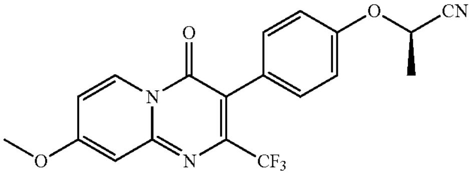 1$^{st}$-eluting isomer | (2R)-2-(4-(8-methoxy-4-oxo-2-(trifluoromethyl)-4H-pyrido[1,2-a]pyrimidin-3-yl)phenoxy) propanenitrile | Example 8-4/Lux C3(250-50 mm, 5 μm), 50% MeOH/$CO_2$, 100 ml/min, 100 bar |
| 8-9 | 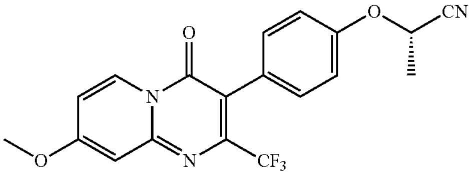 2$^{nd}$-eluting isomer | (2S)-2-(4-(8-methoxy-4-oxo-2-(trifluoromethyl)-4H-pyrido[1,2-a]pyrimidin-3-yl)phenoxy) propanenitrile | Example 8-4/Lux C3(250-50 mm, 5 μm), 50% MeOH/$CO_2$, 100 ml/min, 100 bar |
| 15-5 | 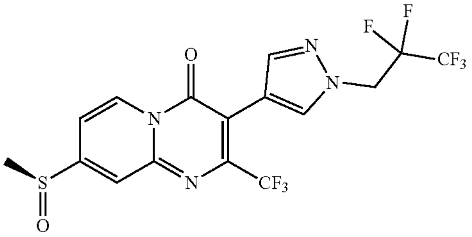 [SMILES: C[S@](=O)c1ccn2c(=O)c(-c3cnn(CC(F)(F)C(F)(F)F)c3)c(C(F)(F)F)nc2c1] 2$^{nd}$-eluting isomer | 8-((S)-methylsulfinyl)-3-(1-(2,2,3,3,3-pentafluoropropyl)-1H-pyrazol-4-yl)-2-(trifluoromethyl)-4H-pyrido[1,2-a]pyrimidin-4-one | Example 15-4/(S,S) Whelk-01 (250 × 30 mm, 5 μm), 30% $CH_3CN/CO_2$, 80 ml/min, 100 bar |
| 15-6 | 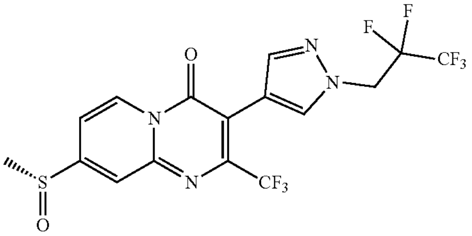 [SMILES: C[S@@](=O)c1ccn2c(=O)c(-c3cnn(CC(F)(F)C(F)(F)F)c3)c(C(F)(F)F)nc2c1] 1$^{st}$-eluting isomer | 8-((R)-methylsulfinyl)-3-(1-(2,2,3,3,3-pentafluoropropyl)-1H-pyrazol-4-yl)-2-(trifluoromethyl)-4H-pyrido[1,2-a]pyrimidin-4-one | Example 15-4/(S,S) Whelk-01 (250 × 30 mm, 5 μm), 30% $CH_3CN/CO_2$, 80 ml/min, 100 bar |
| 15-8 | 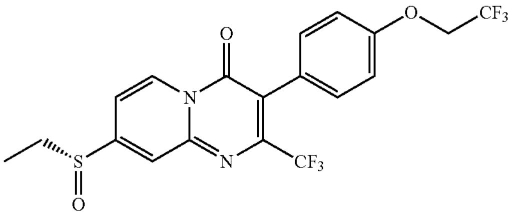 [SMILES: CC[S@@](=O)c1ccn2c(=O)c(-c3ccc(OCC(F)(F)F)cc3)c(C(F)(F)F)nc2c1] 2$^{nd}$-eluting isomer | 8-((R)-ethylsulfinyl)-3-(4-(2,2,2-trifluoroethoxy) phenyl)-2-(trifluoromethyl)-4H-pyrido[1,2-a]pyrimidin-4-one | Example 15-7/ Chiralpak IC (250 × 30 mm, 5 μm), 50% MeOH/$CO_2$, 100 ml/min, 100 bar |

TABLE 21-continued

| Ex. # | Chemical Structure | Name | Racemic separation conditions |
|---|---|---|---|
| 15-9 | 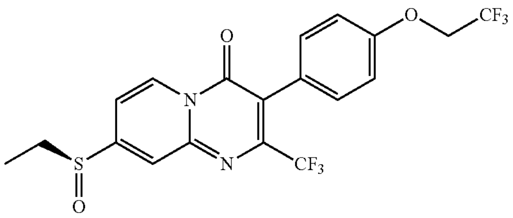 [SMILES: CC[S@](=O)c1ccn2c(=O)c(-c3ccc(OCC(F)(F)F)cc3)c(C(F)(F)F)nc2c1] 1st-eluting isomer | 8-((S)-ethylsulfinyl)-3-(4-(2,2,2-trifluoroethoxy) phenyl)-2-(trifluoromethyl)-4H-pyrido[1,2-a]pyrimidin-4-one | Example 15-7/ Chiralpak IC (250 × 30 mm, 5 μm), 50% MeOH/$CO_2$, 100 ml/min, 100 bar |
| 15-2 | 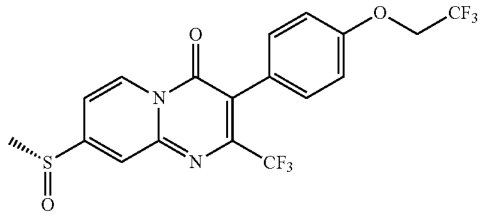 [SMILES: C[S@@](=O)c1ccn2c(=O)c(-c3ccc(OCC(F)(F)F)cc3)c(C(F)(F)F)nc2c1] 1st-eluting isomer | 8-((R)-methylsulfinyl)-3-(4-(2,2,2-trifluoroethoxy) phenyl)-2-(trifluoromethyl)-4H-pyrido[1,2-a]pyrimidin-4-one | Example 15-1/ Chiralpak IC (250 × 30 mm, 5 μm), 40% MeOH/$CO_2$, 120 ml/min, 100 bar |
| 15-3 | 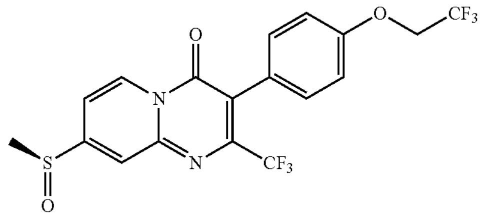 [SMILES: C[S@](=O)c1ccn2c(=O)c(-c3ccc(OCC(F)(F)F)cc3)c(C(F)(F)F)nc2c1] 2nd-eluting isomer | 8-((S)-methylsulfinyl)-3-(4-(2,2,2-trifluoroethoxy) phenyl)-2-(trifluoromethyl)-4H-pyrido[1,2-a]pyrimidin-4-one | Example 15-1/ Chiralpak IC (250 × 30 mm, 5 μm), 40% MeOH/$CO_2$, 120 ml/min, 100 bar |
| 30-1 | 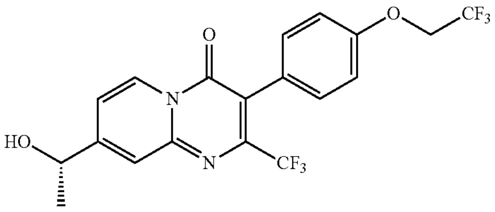 [SMILES: C[C@H](O)c1ccn2c(=O)c(-c3ccc(OCC(F)(F)F)cc3)c(C(F)(F)F)nc2c1] 1st-eluting isomer | 8-((1S)-1-hydroxyethyl)-3-(4-(2,2,2-trifluoroethoxy) phenyl)-2-(trifluoromethyl)-4H-pyrido[1,2-a]pyrimidin-4-one | Example 30/YMC Amylose SA (250 × 30 mm, 5 μm), 20% EtOH/$CO_2$, 70 ml/min, 100 bar |
| 30-2 | 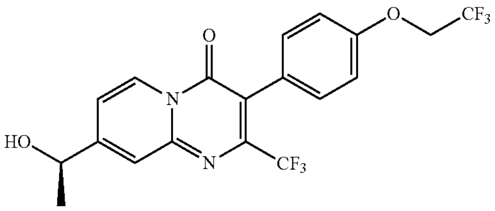 [SMILES: C[C@@H](O)c1ccn2c(=O)c(-c3ccc(OCC(F)(F)F)cc3)c(C(F)(F)F)nc2c1] 2nd-eluting isomer | 8-((1R)-1-hydroxyethyl)-3-(4-(2,2,2-trifluoroethoxy) phenyl)-2-(trifluoromethyl)-4H-pyrido[1,2-a]pyrimidin-4-one | Example 30/YMC Amylose SA (250 × 30 mm, 5 μm), 20% EtOH/$CO_2$, 70 ml/min, 100 bar |
| 31-1 | 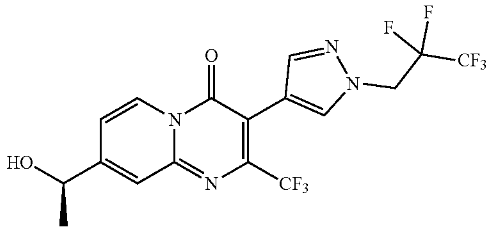 [SMILES: C[C@@H](O)c1ccn2c(=O)c(-c3cnn(CC(F)(F)C(F)(F)F)c3)c(C(F)(F)F)nc2c1] 1st-eluting isomer | 8-((1R)-1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one | Example 31/Lux C3(250-50 mm, 5 μm), 30% MeOH/$CO_2$, 100 ml/min, 100 bar |

TABLE 21-continued

| Ex. # | Chemical Structure | Name | Racemic separation conditions |
|---|---|---|---|
| 31-2 | 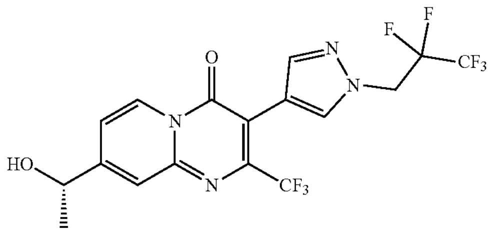 [SMILES: C[C@H](O)c1ccn2c(=O)c(-c3cnn(CC(F)(F)C(F)(F)F)c3)c(C(F)(F)F)nc2c1] $2^{nd}$-eluting isomer | 8-((1S)-1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one | Example 31/Lux C3(250-50 mm, 5 μm), 30% $MeOH/CO_2$, 100 ml/min, 100 bar |

Example 18

3-(1-(2,2,3,3,3-Pentafluoropropyl)-1H-Pyrazol-4-yl)-2-(trifluoromethyl)-4H-pyrido[1,2-a]pyrimidine-4,8(1H)-dione

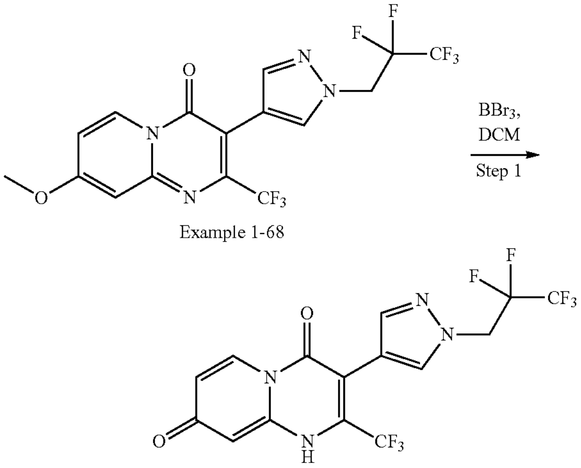

Step 1: 3-(1-(2,2,3,3,3-pentafluoropropyl)-1H-Pyrazol-4-yl)-2-(trifluoromethyl)-4H-pyrido[1,2-a]pyrimidine-4,8(1H)-dione Boron tribromide (2.2 mL, 24 mmol) was added to a solution of 8-methoxy-3-(1-(2,2,3,3,3-pentafluoropropyl)-1H-pyrazol-4-yl)-2-(trifluoromethyl)-4H-pyrido[1,2-a]pyrimidin-4-one (0.70 g, 1.6 mmol, Example 1-68) in dichloromethane (10 mL) at 0° C. under nitrogen atmosphere. The reaction mixture was allowed to warm to room temperature and heated to 50° C. for 48 h. The reaction mixture was cooled to room temperature and concentrated under reduced pressure. The crude residue was purified by silica gel chromatography (eluent: 0-40% EtOAc/hexane) to afford 3-(1-(2,2,3,3,3-pentafluoropropyl)-1H-pyrazol-4-yl)-2-(trifluoromethyl)-4H-pyrido[1,2-a]pyrimidine-4,8(1H)-dione (0.18 g, 27% yield) as a white solid. LC/MS ($ESI^+$) m/z=429.0 $[M+H]^+$. $^1H$ NMR (400 MHz, DMSO-$d_6$) δ 12.29 (s, 1H), 8.92 (d, J=7.9 Hz, 1H), 7.97 (s, 1H), 7.64 (s, 1H), 7.11 (dd, J=7.8, 2.6 Hz, 1H), 6.93 (d, J=2.6 Hz, 1H), 5.27 (t, J=15.0 Hz, 2H).

Example 19

8-(Methylsulfonyl)-3-(4-(2,2,2-trifluoroethoxy)phenyl)-2-(trifluoromethyl)-4H-pyrido[1,2-a]pyrimidin-4-one

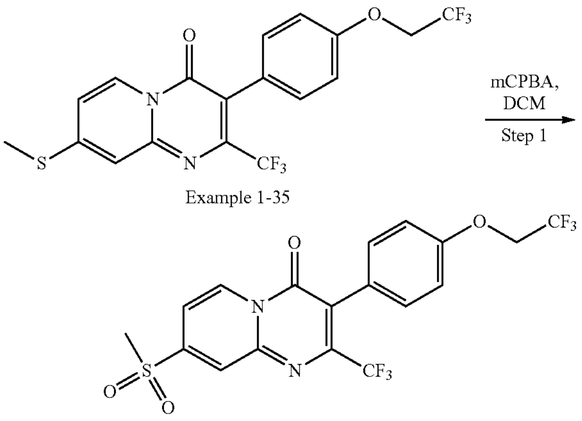

Step 1: 8-(Methylsulfonyl)-3-(4-(2,2,2-trifluoroethoxy)phenyl)-2-(trifluoromethyl)-4H-pyrido[1,2-a]pyrimidin-4-one mCPBA (0.25 g, 1.0 mmol) was added to a solution of 8-(methylsulfanyl)-3-(4-(2,2,2-trifluoroethoxy)phenyl)-2-(trifluoromethyl)-4H-pyrido[1,2-a]pyrimidin-4-one (0.2 g, 0.46 mmol, Example 1-35) in dichloromethane (4 mL) at 0° C. The reaction mixture stirred at 0° C. for 30 min and then allowed to warm to rt. After 3 h, the reaction mixture was diluted with dichloromethane (25 mL) and washed with saturated aqueous sodium bicarbonate (3×50 mL). The organic layer was separated, dried over sodium sulfate, filtered and concentrated under reduced pressure. The crude residue was suspended in diethyl ether. The solid was filtered off and dried to obtain 8-(methylsulfonyl)-3-(4-(2,2,2-trifluoroethoxy)phenyl)-2-(trifluoromethyl)-4H-pyrido[1,2-a]pyrimidin-4-one (0.10 g, 47% yield) as yellow solid. LC/MS ($ESI^+$) m/z=467.0 $[M+H]^+$. $^1H$ NMR (400 MHz, DMSO-$d_6$) δ 9.12 (d, J=7.5 Hz, 1H), 8.32 (d, J=1.8 Hz, 1H), 7.77 (dd, J=7.5, 2.0 Hz, 1H), 7.35-7.28 (m, 2H), 7.21-7.12 (m, 2H), 4.85 (q, J=8.8 Hz, 2H), 3.52 (s, 3H).

Example 20

3-(6-(2,2,2-Trifluoroethoxy)-3-pyridinyl)-2-(trifluoromethyl)-4H-pyrido[1,2-a]pyrimidin-4-one

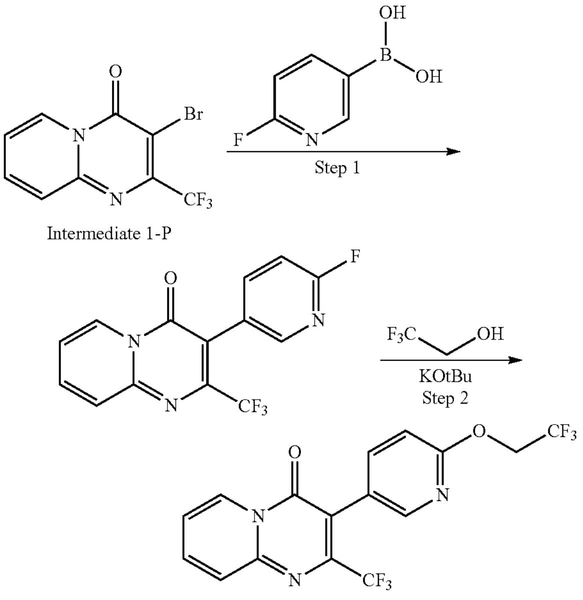

Step 1: 3-(6-Fluoropyridin-3-yl)-2-(trifluoromethyl)-4H-pyrido[1,2-a]pyrimidin-4-one The title compound was prepared using the procedure described in Method 1, Step 1 with the following modification: Step 1 was performed with 3-bromo-2-(trifluoromethyl)-4H-pyrido[1,2-a]pyrimidin-4-one (Intermediate 1-P) and 2-fluoropyridine-5-boronic acid (0.1 g, 0.8 mmol) (Frontier Scientific, Logan, UT, USA). LC/MS ($ESI^+$) m/z=310.1 $[M+H]^+$.

Step 2: 3-(6-(2,2,2-Trifluoroethoxy)-3-pyridinyl)-2-(trifluoromethyl)-4H-pyrido[1,2-a]pyrimidin-4-one A resealable vial was charged with 2,2,2-trifluoroethanol (17 μl, 0.23 mmol), 2-methyl-2-propano potassium salt (0.23 ml, 0.23 mmol), 3-(6-fluoropyridin-3-yl)-2-(trifluoromethyl)-4H-pyrido[1,2-a]pyrimidin-4-one (7.0 mg, 0.20 mmol) and tetrahydrofuran (1.0 mL). The reaction mixture was heated to 70° C. for 2 h. The reaction mixture was cooled to rt, and partitioned between EtOAc and water. The organic phase was separated and dried over $MgSO_4$. The filtrate was concentrated under reduced pressure and the crude residue was purified via silica gel chromatography (eluent: 0-40% EtOAc/heptane) to obtain 3-(6-(2,2,2-trifluoroethoxy)-3-pyridinyl)-2-(trifluoromethyl)-4H-pyrido[1,2-a]pyrimidin-4-one (41 mg, 0.1 mmol, 50% yield) as an off-white solid. LC/MS ($ESI^+$) m/z=390.1 $[M+H]^+$. $^1H$ NMR (400 MHz, $CDCl_3$) δ 4.74-4.88 (m, 2H) 6.94-7.03 (m, 1H) 7.30-7.40 (m, 1H) 7.63-7.73 (m, 1H) 7.83-7.98 (m, 2H) 8.09-8.18 (m, 1H) 9.02-9.17 (m, 1H). $^{19}F$ NMR (376 MHz, $CDCl_3$) δ −73.78 (s, 1 F) −62.82 (s, 1 F).

Example 21

(4-(8-Methoxy-4-oxo-2-(trifluoromethyl)-4H-pyrido[1,2-a]pyrimidin-3-yl)phenoxy)acetonitrile

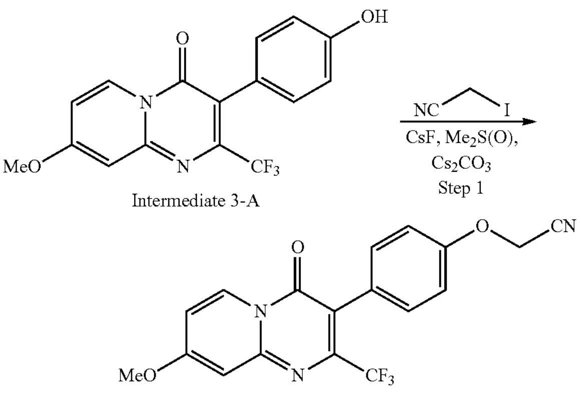

Step 1: (4-(8-Methoxy-4-oxo-2-(trifluoromethyl)-4H-pyrido[1,2-a]pyrimidin-3-yl)phenoxy)acetonitrile A resealable vial was charged with 3-(4-hydroxyphenyl)-8-methoxy-2-(trifluoromethyl)-4H-pyrido[1,2-a]pyrimidin-4-one (Intermediate 3-A, 85 mg, 0.25 mmol), cesium carbonate (124 mg, 0.38 mmol), cesium fluoride (57 mg, 0.38 mmol), 2-iodoacetonitrile (37 μl, 0.51 mmol), and dimethyl sulfoxide (1.3 mL). The reaction mixture was heated to 70° C. for 48 h. The reaction mixture cooled to rt, diluted with EtOAc (50 mL) and water (50 mL). The organic phase was separated, washed with water (50 mL) and brine (50 mL). The combined aqueous extracts were extracted with EtOAc (3×20 mL). The combined organic extracts were dried over magnesium sulfate, filtered, and concentrated under reduced pressure. The crude residue was purified by RP HPLC (XSelect Column, 100×19 mm, 10 μm, Mobile Phase A: 0.1% formic acid in water, Mobile Phase B: acetonitrile). to obtain (4-(8-methoxy-4-oxo-2-(trifluoromethyl)-4H-pyrido[1,2-a]pyrimidin-3-yl)phenoxy)acetonitrile (26 mg, 0.07 mmol, 27% yield) was obtained as a solid. LC/MS ($ESI^+$) m/z=376.0 $[M+H]^+$. $^1H$ NMR (400 MHz, DMSO-$d_6$) δ 4.04 (s, 3H) 5.22 (s, 2H) 7.07-7.15 (m, 2H) 7.18 (dd, J=7.88, 2.70 Hz, 1H) 7.25-7.34 (m, 3H) 8.88 (d, J=7.88 Hz, 1H).

Example 22

8-Methoxy-3-(4-(2,2,3,3,3-pentafluoropropoxy)phenyl)-2-(trifluoromethyl)-4H-pyrido[1,2-a]pyrimidin-4-one

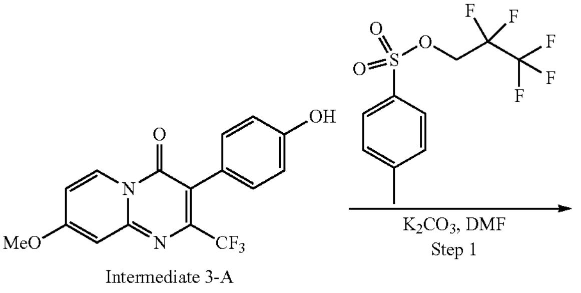

-continued

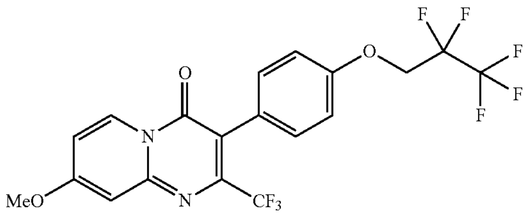

Step 1: 8-Methoxy-3-(4-(2,2,3,3,3-pentafluoropropoxy)phenyl)-2-(trifluoromethyl)-4H-pyrido[1,2-a]pyrimidin-4-one A resealable vial was charged with, 3-(4-hydroxyphenyl)-8-methoxy-2-(trifluoromethyl)-4H-pyrido[1,2-a]pyrimidin-4-one (Intermediate 3-A, 66 mg, 0.2 mmol), potassium carbonate (49 mg, 0.36 mmol), and DMF (400 μL). The reaction mixture was stirred at rt for 1 h, and then added to 2,2,3,3,3-pentafluoropropyl 4-methylbenzenesulfonate (60 mg, 0.2 mmol; synthesized according to the procedure described in US20070155726). The reaction mixture was heated to 90° C. for 12 h. Additional potassium carbonate (49 mg, 0.36 mmol) was added and the reaction mixture was heated to 120° C. for 12 h. The reaction mixture was cooled to rt and diluted with EtOAc (20 mL) and water (20 mL). The organic phase was separated, extracted with water (20 mL) and brine (20 mL), dried over magnesium sulfate, filtered, and concentrated under reduced pressure. Purification of the crude residue purification by SFC (OD column, 150×21 mm, 5 μm, 35% (20 mM $NH_3$ in MeOH)/$CO_2$, flow rate 50 g/min, 100 bar) gave 8-methoxy-3-(4-(2,2,3,3,3-pentafluoropropoxy)phenyl)-2-(trifluoromethyl)-4H-pyrido[1,2-a]pyrimidin-4-one (11 mg, 0.024 mmol, 12% yield) as a solid. LC/MS ($ESI^+$) m/z=469.0 $[M+H]^+$. $^1H$ NMR (400 MHz, $CD_2Cl_2$) δ 1.56 (br s, 2H) 3.42 (s, 1H) 4.03 (s, 3H) 4.52 (td, J=12.44, 0.83 Hz, 2H) 6.94 (dd, J=7.98, 2.80 Hz, 1H) 7.00-7.03 (m, 1H) 7.03-7.07 (m, 2H) 7.30 (d, J=8.71 Hz, 2H) 8.91 (d, J=7.88 Hz, 1H).

Example 23

Ethyl(4-oxo-3-(1-(2,2,3,3,3-pentafluoropropyl)-1H-pyrazol-4-yl)-2-(trifluoromethyl)-4H-pyrido[1,2-a]pyrimidin-8-yl)carbamyl fluoride

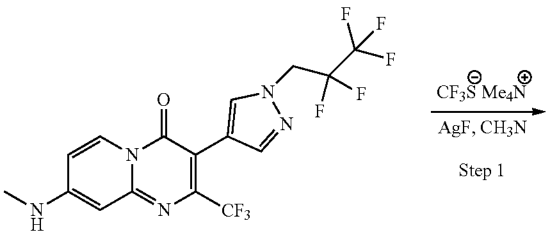

Example 1-23

-continued

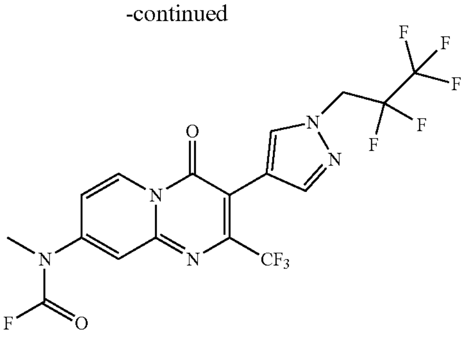

Step 1: Methyl(4-oxo-3-(1-(2,2,3,3,3-pentafluoropropyl)-1H-pyrazol-4-yl)-2-(trifluoromethyl)-4H-pyrido[1,2-a]pyrimidin-8-yl)carbamyl fluoride A resealable vial was charged with 8-(methylamino)-3-(1-(2,2,3,3,3-pentafluoropropyl)-1H-pyrazol-4-yl)-2-(trifluoromethyl)-4H-pyrido[1,2-a]pyrimidin-4-one (Example 1-23, 100 mg, 0.23 mmol), tetramethylammonium trifluoromethanethiolate (51 mg, 0.3 mmol, synthesized as described in Scattolin T et al., Angew. Chem. Int. Ed. Engl. 56(1):221-224 (2017)) and a mixture of DCM:acetonitrile (1:1, 3 mL). The reaction mixture was stirred for 1.5 h at rt and additional tetramethylammonium trifluoromethanethiolate (52 mg, 0.3 mmol) was added. Stirring was continued for 36 h. Silver(I) fluoride (172 mg, 1.36 mmol) was added and the mixture was stirred for 40 min. The reaction mixture was filtered through pad of celite and concentrated under reduced pressure. The residue was purified by silica gel chromatography (eluent: 10-80% EtOAc/heptane) to afford methyl(4-oxo-3-(1-(2,2,3,3,3-pentafluoropropyl)-1H-pyrazol-4-yl)-2-(trifluoromethyl)-4H-pyrido[1,2-a]pyrimidin-8-yl)carbamyl fluoride (33 mg, 0.07 mmol, 30% yield). LC/MS ($ESI^+$) m/z=488.0 $[M+H]^+$. $^1H$ NMR (500 MHz, DMSO-$d_6$) δ 1.17 (s, 1H) 3.32 (s, 10H) 3.48 (s, 9H) 5.29 (t, J=14.92 Hz, 6H) 7.70 (s, 3H) 7.74 (br s, 2H) 7.83 (d, J=2.21 Hz, 3H) 8.06 (s, 3H) 8.99 (d, J=7.92 Hz, 3H).

Example 24

2-(4-(8-Methoxy-4-oxo-2-(trifluoromethyl)-4H-pyrido[1,2-a]pyrimidin-3-yl)phenoxy)-2-methylpropanenitrile

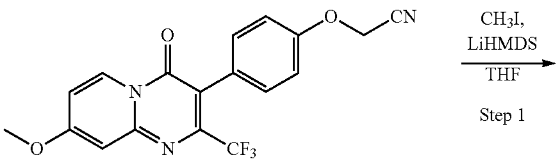

Example 21

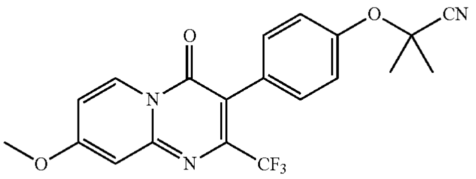

Step 1: 2-(4-(8-Methoxy-4-oxo-2-(trifluoromethyl)-4H-pyrido[1,2-a]pyrimidin-3-yl)phenoxy)-2-methylpropanenitrile Iodomethane (4.5 g, 32 mmol) was added to a solution of (4-(8-methoxy-4-oxo-2-(trifluoromethyl)-4H-pyrido[1,2-a]pyrimidin-3-yl)phenoxy)acetonitrile (Example 21, 2.0 g, 5.3 mmol) in THF (12 mL), followed by dropwise addition of LiHMDS (1 M in THF, 16 mL) at −78° C. The reaction mixture was stirred at −78° C. for 2 h. The reaction mixture was quenched with saturated ammonium chloride solution and partitioned between EtOAc (20 mL) and water (20 mL). The aqueous layer was back-extracted with ethyl acetate (2×20 mL). The combined organic layers were washed with brine (20 mL), dried over $Na_2SO_4$, filtered and concentrated under reduced pressure. The crude residue was purified by RP HPLC (XBridge C18 OBD, 150×19 mm, 5 μm, Mobile Phase A: 10 mM ammonium acetate in water, Mobile Phase B: acetonitrile, Flow rate: 15.0 mL/min) to afford 2-(4-(8-methoxy-4-oxo-2-(trifluoromethyl)-4H-pyrido[1,2-a]pyrimidin-3-yl)phenoxy)-2-methylpropanenitrile (98 mg, 4% yield). LC/MS ($ESI^+$) m/z=404.1 $[M+H]^+$. $^1H$ NMR (400 MHz, $CDCl_3$) δ 8.97 (d, J=8.0 Hz, 1H), 7.39-7.32 (m, 2H), 7.27-7.25 (m, 2H), 7.09 (d, J=2.7 Hz, 1H), 6.96 (dd, J=7.9, 2.7 Hz, 1H), 4.04 (s, 3H), 1.78 (s, 6H).

Example 25

8-Methoxy-2-(trifluoromethyl)-3-(1-(3,3,3-trifluoropropyl)-1H-imidazol-4-yl)-4H-pyrido[1,2-a]pyrimidin-4-one

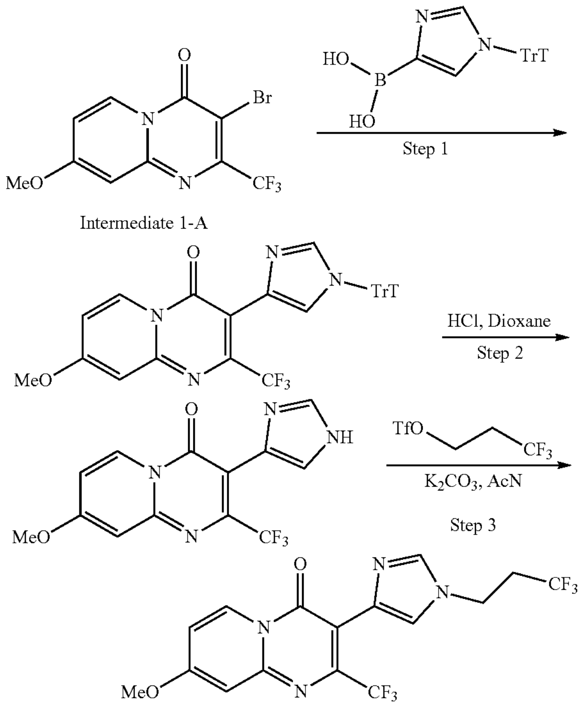

Step 1: 8-Methoxy-2-(trifluoromethyl)-3-(1-trityl-1H-imidazol-4-yl)-4H-pyrido[1,2-a]pyrimidin-4-one The title compound was prepared using the procedure described in Method 1, Step 1 with the following modification: Step 1 was performed with 3-bromo-8-methoxy-2-(trifluoromethyl)pyrido[1,2-a]pyrimidin-4-one (Intermediate 1-A) and (1-trityl-1H-imidazol-4-yl)boronic acid (0.11 g, 0.8 mmol, synthesized following procedure described in PCT Int. Appl., 2016055786). LC/MS ($ESI^+$) m/z=553.2 $[M+H]^+$.

Step 2: 3-(1H-Imidazol-4-yl)-8-methoxy-2-(trifluoromethyl)-4H-pyrido[1,2-a]pyrimidin-4-one A reaction mixture of 8-methoxy-2-(trifluoromethyl)-3-(1-trityl-1H-imidazol-4-yl)-4H-pyrido[1,2-a]pyrimidin-4-one (0.62 g, 1.1 mmol) and HCl (2M in dioxane, 0.7 mL) was stirred at ambient temperature for 16 h and then concentrated under reduced pressure. The crude material was washed with ethyl acetate (3×5 mL) and suspended in a solution of aqueous 10% $NaHCO_3$ (6 mL) to get a yellow precipitate. The yellow solid was collected by filtration, washed with water (3×5 mL) and dried in vacuo to get 3-(1H-imidazol-4-yl)-8-methoxy-2-(trifluoromethyl)-4H-pyrido[1,2-a]pyrimidin-4-one (0.26 g, 75% yield) as yellow solid. LC/MS ($ESI^+$) m/z=311.1 $[M+H]^+$.

Step 3: 8-Methoxy-2-(trifluoromethyl)-3-(1-(3,3,3-trifluoropropyl)-1H-imidazol-4-yl)-4H-pyrido[1,2-a]pyrimidin-4-one Potassium carbonate (0.4 g, 2.9 mmol) was added to the solution of 3-(1H-imidazol-4-yl)-8-methoxy-2-(trifluoromethyl)-4H-pyrido[1,2-a]pyrimidin-4-one (0.18 g, 0.58 mmol) in anhydrous acetonitrile (8 mL) at 0° C. A solution of 3,3,3-trifluoropropyl trifluoromethanesulfonate (0.143 g, 0.058 mmol) in acetonitrile (2.0 mL) was added dropwise to the above reaction mixture and stirring was continued for 2 h at rt. The reaction mixture was concentrated under reduced pressure and the crude residue was purified by SFC (*Viridis* Silica (150×50 mm, 5 μm), 30% $MeOH/CO_2$, Flow rate: 80 mL/min) to yield 8-methoxy-2-(trifluoromethyl)-3-(1-(3,3,3-trifluoropropyl)-1H-imidazol-4-yl)-4H-pyrido[1,2-a]pyrimidin-4-one (5.0 mg, 2% yield) as a yellow solid. LC/MS ($ESI^+$) m/z=407.1 $[M+H]^+$. $^1H$ NMR (400 MHz, $CDCl_3$) δ 8.98 (d, J=7.9 Hz, 1H), 7.69-7.62 (m, 1H), 7.27 (s, 1H), 7.06 (d, J=2.7 Hz, 1H), 6.94 (dd, J=7.9, 2.7 Hz, 1H), 4.34-4.26 (m, 2H), 4.03 (s, 3H), 2.77-2.63 (m, 2H).

Example 26

8-((Dimethylamino)methyl)-3-(1-(2,2,3,3,3-pentafluoropropyl)-1H-pyrazol-4-yl)-2-(trifluoromethyl)-4H-pyrido[1,2-a]pyrimidin-4-one

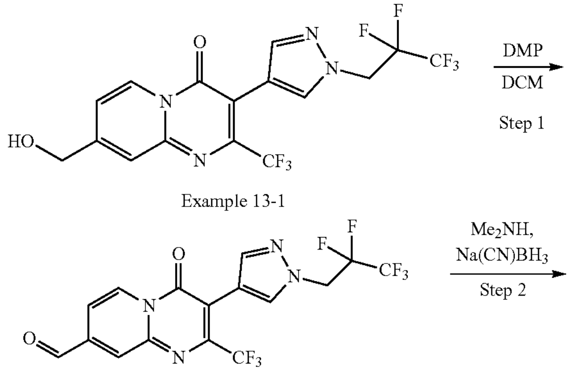

-continued

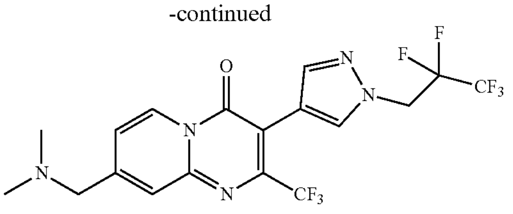

Step 1: 4-Oxo-3-(1-(2,2,3,3,3-pentafluoropropyl)-1H-pyrazol-4-yl)-2-(trifluoromethyl)-4H-pyrido[1,2-a]pyrimidine-8-carbaldehyde Dess-Martin periodinane (2.5 g, 5.9 mmol) was added to a solution of 8-(hydroxymethyl)-3-(1-(2,2,3,3,3-pentafluoropropyl)-1H-pyrazol-4-yl)-2-(trifluoromethyl)-4H-pyrido[1,2-a]pyrimidin-4-one (1.3 g, 2.9 mmol, Example 13-1) in anhydrous DCM (26 mL) at 0° C. under nitrogen atmosphere. The reaction mixture was allowed to warm to rt. After 1 h, the reaction mixture was filtered through a pad of celite using 10% methanol in DCM (3×5 mL). The filtrate was washed with aqueous 10% $NaHCO_3$ (2×10 mL), dried over anhydrous $Na_2SO_4$, filtered and concentrated under reduced pressure. The crude material was purified by silica gel chromatography (eluent: 20-35% ethyl acetate/hexane) to afford 4-oxo-3-(1-(2,2,3,3,3-pentafluoropropyl)-1H-pyrazol-4-yl)-2-(trifluoromethyl)-4H-pyrido[1,2-a]pyrimidine-8-carbaldehyde (0.8 g, 18 mmol, 62% yield) as yellow solid. LC/MS ($ESI^+$) m/z=441.0 $[M+H]^+$.

Step 2: 8-((Dimethylamino)methyl)-3-(1-(2,2,3,3,3-pentafluoropropyl)-1H-pyrazol-4-yl)-2-(trifluoromethyl)-4H-pyrido[1,2-a]pyrimidin-4-one Dimethyl amine (2M in THF, 7.8 mL, 15.6 mmol), acetic acid (0.47 mL, 7.8 mmol) and sodium acetate (0.26 g, 3.1 mmol) were added to a solution of 4-oxo-3-(1-(2,2,3,3,3-pentafluoropropyl)-1H-pyrazol-4-yl)-2-(trifluoromethyl)-4H-pyrido[1,2-a]pyrimidine-8-carbaldehyde (0.68 g, 1.56 mmol) in methanol (7 mL) under nitrogen atmosphere. The reaction mixture was stirred for 30 min at rt. The reaction mass was cooled to 0° C. and sodium cyanoboronhdyride (0.49 g, 7.8 mmol) was added. The reaction mixture was allowed to warm to rt. After 1 h, the reaction mixture was quenched by the addition of ice (2 g) and concentrated under reduce pressure. The crude residue was dissolved in water (10 mL) and extracted with diethyl ether (3×10 mL). The combined organic layers were washed with aqueous 1.5 N HCl solution (3×10 mL). The pH of the combined aqueous layers was adjusted to pH=8 with saturated aqueous $NaHCO_3$ solution and extracted with ethyl acetate (3×10 mL). The combined organic layers were washed with brine (10 mL), dried over $Na_2SO_4$, filtered and concentrated under reduced pressure. The crude material was purified by RP HPLC (Gemini NX C18 (250×21 mm, 5 μm), Mobile Phase A: 10 mM ammonium acetate in water, Mobile Phase B: acetonitrile) to yield 8-((dimethylamino)methyl)-3-(1-(2,2,3,3,3-pentafluoropropyl)-1H-pyrazol-4-yl)-2-(trifluoromethyl)-4H-pyrido[1,2-a]pyrimidin-4-one (0.11 g, 0.23 mmol, 15% yield) as a solid. LC/MS ($ESI^+$) m/z=470.1 $[M+H]^+$. $^1H$ NMR (400 MHz, DMSO-$d_6$) δ 8.98 (dd, J=7.3, 2.5 Hz, 1H), 8.06 (d, J=2.4 Hz, 1H), 7.74 (d, J=2.2 Hz, 1H), 7.70 (d, J=2.5 Hz, 1H), 7.48 (dt, J=7.5, 2.2 Hz, 1H), 5.37-5.25 (m, 2H), 3.61 (s, 2H), 2.24 (d, J=2.6 Hz, 6H).

Example 27

8-(2-Methyl-2-oxetanyl)-3-(4-(2,2,2-trifluoroethoxy)phenyl)-2-(trifluoromethyl)-4H-pyrido[1,2-a]pyrimidin-4-one

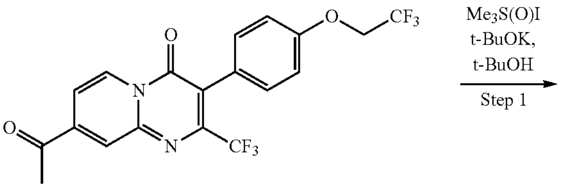

Example 1-25

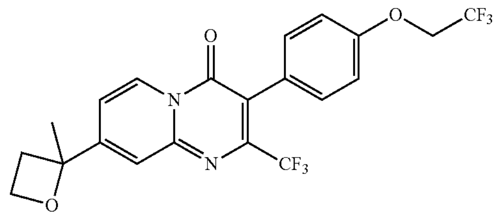

Step 1: 8-(2-Methyl-2-oxetanyl)-3-(4-(2,2,2-trifluoroethoxy)phenyl)-2-(trifluoromethyl)-4H-pyrido[1,2-a]pyrimidin-4-one Potassium tert-butoxide (170 mg, 1.5 mmol) was added portion wise to a mixture of trimethylsulfoxonium iodide (340 mg, 1.5 mmol) in tert-butanol (1 mL) at 50° C. After 30 min, a solution of 8-acetyl-3-(4-(2,2,2-trifluoroethoxy)phenyl)-2-(trifluoromethyl)-4H-pyrido[1,2-a]pyrimidin-4-one (300 mg, 0.70 mmol, Example 1-25) in t-BuOH (0.5 mL) was added dropwise to the reaction mixture. The resulting reaction mixture was stirred at 50° C. for 16 h. The reaction mixture was allowed to cool to rt and filtered through a celite pad. The filtrate was concentrated under reduced pressure. The residue was partitioned between EtOAc (20 mL) and water (20 mL). The aqueous layer was back extracted with EtOAc (2×30 mL). The combined organic layers were dried over $Na_2SO_4$, filtered and concentrated in vacuo. The crude material was adsorbed onto a plug of silica gel and purified by silica gel chromatography (eluent: 0-15% EtOAc/hexane) to give 8-(2-methyl-2-oxetanyl)-3-(4-(2,2,2-trifluoroethoxy)phenyl)-2-(trifluoromethyl)-4H-pyrido[1,2-a]pyrimidin-4-one (120 mg, 38% yield) as yellow solid. LC/MS ($ESI^+$) m/z=459.1 $[M+H]^+$. $^1H$ NMR (400 MHz, DMSO-$d_6$) δ 7.36-7.06 (m, 6H), 6.36 (dd, J=26.5, 8.3 Hz, 1H), 4.82 (qd, J=8.8, 2.5 Hz, 2H), 2.80-2.74 (m, 1H), 2.64 (t, J=5.4 Hz, 1H), 1.91-1.74 (m, 1H), 1.42 (dd, J=47.4, 2.4 Hz, 3H), 0.61 (dt, J=49.8, 4.6 Hz, 1H).

Example 28

8-(3-Azetidinyl)-3-(4-(2,2,2-trifluoroethoxy)phenyl)-2-(trifluoromethyl)-4H-pyrido[1,2-a]pyrimidin-4-one

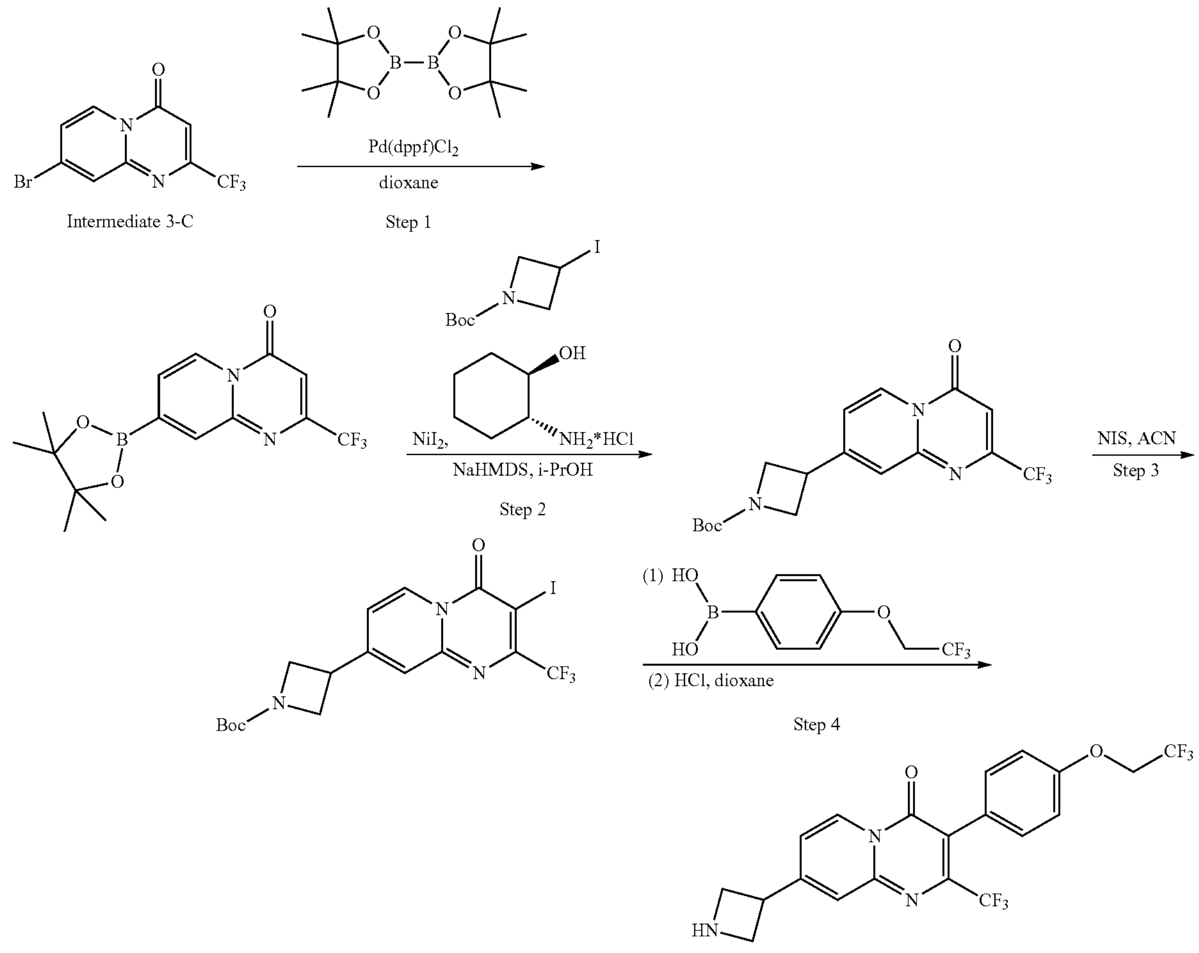

Step 1: 8-(4,4,5,5-Tetramethyl-1,3,2-dioxaborolan-2-yl)-2-(trifluoromethyl)-4H-pyrido[1,2-a]pyrimidin-4-one A resealable tube was charged with 8-bromo-2-(trifluoromethyl)-4H-pyrido[1,2-a]pyrimidin-4-one (5.0 g, 17.0 mmol, Intermediate 3-C), bis(pinacolato)diboron (4.3 g, 17 mmol), potassium acetate (5 g, 51 mmol) and 1,4-dioxane (50 mL). The reaction mixture was purged with nitrogen for 10 min, followed by the addition of $Pd(dppf)Cl_2$ (1.25 g, 1.7 mmol). The reaction mixture was stirred at 80° C. for 10 min. The reaction mixture was cooled to room temperature, diluted with water (50 mL) and extracted with ethyl acetate (2×100 mL). The combined organic layers were dried over sodium sulfate, filtered and concentrated under reduced pressure. The crude material was purified by RP HPLC (Reveleris Grace, C18, 120 G, 40 μm, Mobile Phase: 0-18% acetonitrile/water) to afford 8-(4,4,5,5-tetramethyl-1,3,2-dioxaborolan-2-yl)-2-(trifluoromethyl)-4H-pyrido[1,2-a]pyrimidin-4-one (2.5 g, 7.4 mmol, 43% yield) as an off-white solid. LC/MS ($ESI^+$) m/z=341.2 $[M+H]^+$. $^1H$ NMR (400 MHz, DMSO-$d_6$) δ 8.96 (d, J=7.1 Hz, 1H), 7.92 (d, J=21.9 Hz, 1H), 7.54 (dd, J=7.0, 1.3 Hz, 1H), 6.85 (s, 1H), 1.17 (d, J=3.3 Hz, 12H).

Step 2: tert-Butyl 3-(4-oxo-2-(trifluoromethyl)-4H-pyrido [1,2-a]pyrimidin-8-yl)azetidine-1-carboxylate A resealable vial was charged with 8-(4,4,5,5-tetramethyl-1,3,2-dioxaborolan-2-yl)-2-(trifluoromethyl)-4H-pyrido[1,2-a]pyrimidin-4-one (4.8 g, 14. mmol), nickel(II) iodide (0.13 g, 0.42 mmol), trans-2-aminocyclohexanol hydrochloride (64 mg, 0.42 mmol), isopropanol (40 mL) and sodium hexamethyldisilazane (2M in THF, 7 mL, 14 mmol). The reaction mixture was stirred for 10 minutes at rt, followed by addition of a solution of tert-butyl 3-iodoazetidine-1-carboxylate (2.0 g, 7.1 mmol) in isopropyl alcohol (2 mL). The resulting reaction mixture was heated to 80° C. for 30 minutes in the microwave (Biotage Initiator). The reaction mixture was cooled to room temperature, diluted with ethanol (100 mL), and filtered. The filtrate was concentrated under reduced pressure. The residue was purified by RP HPLC (Reveleris Grace, C18, 120 G, 40 μm, Mobile Phase:

0-40% acetonitrile/water) to obtain tert-butyl 3-(4-oxo-2-(trifluoromethyl)-4H-pyrido [1,2-a]pyrimidin-8-yl)azetidine-1-carboxylate (0.45 g, 0.77 mmol, 11% yield) as yellow solid. LC/MS ($ESI^+$) m/z=370.1 $[M+H]^+$.

Step 3: tert-Butyl 3-(3-iodo-4-oxo-2-(trifluoromethyl)-4H-pyrido[1,2-a]pyrimidin-8-yl)azetidine-1-carboxylate N-iodosuccinimide (0.59 g, 2.6 mmol) was added to a solution of tert-butyl 3-(4-oxo-2-(trifluoromethyl)-4H-pyrido [1,2-a]pyrimidin-8-yl)azetidine-1-carboxylate (0.5 g, 0.87 mmol) in acetonitrile (15 mL). The reaction mixture was heated to 80° C. for 48 hours. The reaction mixture was concentrated in vacuo and the crude residue was purified by RP HPLC (Reveleris Grace, C18, 120 G, 40 μm, Mobile Phase: 0-50% acetonitrile/water) to get tert-butyl 3-(3-iodo-4-oxo-2-(trifluoromethyl)-4H-pyrido[1,2-a]pyrimidin-8-yl) azetidine-1-carboxylate (0.38 g, 0.78 mmol, 89% yield). LC/MS ($ESI^+$) m/z=496.1 $[M+H]^+$. $^1H$ NMR (400 MHz, DMSO-$d_6$) δ 9.41-8.79 (m, 1H), 7.86 (d, J=14.4 Hz, 1H), 7.57 (d, J=8.3 Hz, 1H), 4.29 (s, 2H), 4.08-3.94 (m, 3H), 1.40 (s, 9H).

Step 4-1: tert-Butyl 3-(3-iodo-4-oxo-2-(trifluoromethyl)-4H-pyrido[1,2-a]pyrimidin-8-yl)azetidine-1-carboxylate The title compound was prepared using the procedure described in Method 1, Step 1 with the following modification: Step 1 was performed with tert-butyl 3-(3-iodo-4-oxo-2-(trifluoromethyl)-4H-pyrido[1,2-a]pyrimidin-8-yl) azetidine-1-carboxylate (0.5 g, 1.0 mmol) and (4-(2,2,2-trifluoroethoxy)phenyl)boronic acid (0.27 g, 1.2 mmol). The product was used in the next step without purification.

Step 4-2: 8-(3-Azetidinyl)-3-(4-(2,2,2-trifluoroethoxy)phenyl)-2-(trifluoromethyl)-4H-pyrido[1,2-a]pyrimidin-4-one The crude material from Step 4-1 was taken up in methanol (10 mL) and hydrochloric acid (37%, 0.31 mL, 10 mmol) was added slowly. The resulting solution was stirred at rt for 6 h. The reaction mixture was concentrated under reduced pressure and the crude residue was purified by RP HPLC (Gemini NX C18, 250×21.2 mm, 5 μm, Mobile Phase A: 10 mM ammonium acetate/water, Mobile Phase B: acetonitrile, flow rate: 15 ml/min) to get 8-(3-azetidinyl)-3-(4-(2,2,2-trifluoroethoxy)phenyl)-2-(trifluoromethyl)-4H-pyrido[1,2-a]pyrimidin-4-one (40 mg, 0.090 mmol, 9% yield) as an off-white solid. LC/MS ($ESI^+$) m/z=444.4 $[M+H]^+$. $^1H$ NMR (400 MHz, DMSO-$d_6$) δ 8.98 (d, J=7.3 Hz, 1H), 7.80 (s, 1H), 7.60 (dd, J=7.4, 1.9 Hz, 1H), 7.29 (d, J=8.4 Hz, 2H), 7.13 (d, J=8.6 Hz, 2H), 4.84 (q, J=8.8 Hz, 2H), 4.05 (p, J=7.2 Hz, 1H), 3.90 (t, J=7.8 Hz, 211), 3.62 (t, J=6.9 Hz, 2H).

Example 29

8-(1,3-Oxazol-2-yl)-3-(4-(2,2,2-trifluoroethoxy)phenyl)-2-(trifluoromethyl)-4H-pyrido[1,2-a]pyrimidin-4-one

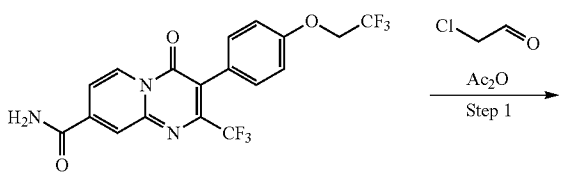

Example 12-2

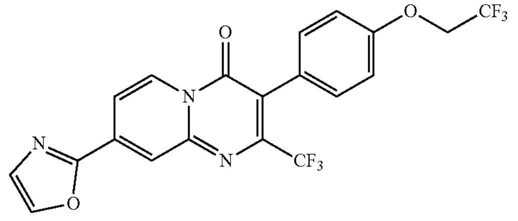

Step 1: 8-(1,3-Oxazol-2-yl)-3-(4-(2,2,2-trifluoroethoxy)phenyl)-2-(trifluoromethyl)-4H-pyrido[1,2-a]pyrimidin-4-one 2-Chloroacetaldehyde (0.95 mL, 8.1 mmol) was added dropwise to a suspension of 4-oxo-3-(4-(2,2,2-trifluoroethoxy)phenyl)-2-(trifluoromethyl)-4H-pyrido[1,2-a]pyrimidine-8-carboxamide (Example 12-2, 0.35 g, 0.81 mmol) in acetic anhydride (3.5 mL) at rt under nitrogen atmosphere. The reaction mixture was heated to 70° C. for 15 minutes and to 135° C. for 10 h. The reaction mixture was cooled to rt and concentrated under reduced pressure. The residue was dissolved in ethyl acetate (25 mL) and successively washed with water (25 mL), aqueous 10% $NaHCO_3$ solution (25 mL) and brine (10 mL). The organic phase was dried over $Na_sSO_4$, filtered and concentrated under reduced pressure. The crude residue was purified by silica gel chromatography (eluent: 20-25% of ethyl acetate/hexane) to afford 8-(1,3-oxazol-2-yl)-3-(4-(2,2,2-trifluoroethoxy)phenyl)-2-(trifluoromethyl)-4H-pyrido[1,2-a]pyrimidin-4-one (0.20 g, 0.44 mmol, 54% yield) as yellow solid. LC/MS ($ESI^+$) m/z=456.0 $[M+H]^+$. $^1H$ NMR (400 MHz, DMSO-$d_6$) δ 9.07 (d, J=7.4 Hz, 1H), 8.54 (d, J=5.3 Hz, 1H), 8.22 (d, J=5.2 Hz, 1H), 7.93 (dd, J=7.6, 2.1 Hz, 1H), 7.68 (d, J=5.0 Hz, 1H), 7.32 (d, J=8.1 Hz, 2H), 7.16 (d, J=8.1 Hz, 2H), 4.85 (q, J=8.8 Hz, 2H).

Example 30

8-(1-Hydroxyethyl)-3-(4-(2,2,2-trifluoroethoxy)phenyl)-2-(trifluoromethyl)-4H-pyrido[1,2-a]pyrimidin-4-one

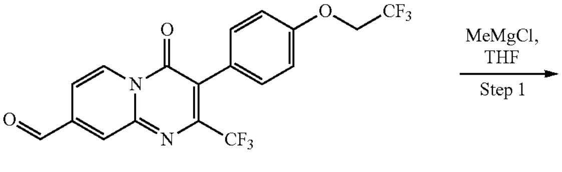

Intermediate 3-H

-continued

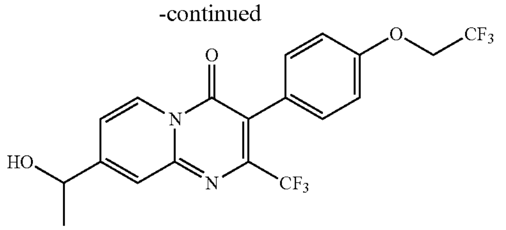

Step 1: 8-(1-Hydroxyethyl)-3-(4-(2,2,2-trifluoroethoxy)phenyl)-2-(trifluoromethyl)-4H-pyrido[1,2-a]pyrimidin-4-one Methyl magnesium chloride (3 M in $Et_2O$, 3.4 mL, 10.21 mmol) was added dropwise to a solution of 4-oxo-3-(4-(2,2,2-trifluoroethoxy)phenyl)-2-(trifluoromethyl)-4H-pyrido[1,2-a]pyrimidine-8-carbaldehyde (0.85 g, 2.0 mmol, Intermediate 3-H) in THF (17 mL) at −20° C. The reaction mixture was allowed to warm to rt and stirred for 5 h. Saturated, aqueous ammonium chloride solution (20 mL) was added and the reaction mixture was extracted with ethyl acetate (2×100 mL). The combined organic layers were dried over sodium sulfate, filtered and concentrated under reduced pressure. The crude material was purified by RP HPLC (Gemini NX C18 250×21.2 mm, 5 μm, Mobile Phase A: 10 mM ammonium acetate in water, Mobile Phase B: acetonitrile, flow rate: 15 ml/min) to get 8-(1-hydroxyethyl)-3-(4-(2,2,2-trifluoroethoxy)phenyl)-2-(trifluoromethyl)-4H-pyrido[1,2-a]pyrimidin-4-one (200 mg, 0.46 mmol, 23% yield) as an off-white solid. LC/MS ($ESI^+$) m/z=433.2 $[M+H]^+$. $^1H$ NMR (400 MHz, DMSO-$d_6$) δ 9.16-8.81 (m, 1H), 7.75 (s, L H), 7.51 (dt, J=7.5, 1.7 Hz, 1H), 7.28 (d, J=8.4 Hz, 2H), 7.16-7.06 (m, 2H), 5.76 (dd, J=4.8, 1.5 Hz, 1H), 4.93 (p, J=6.1 Hz, 1H), 4.83 (q, J=8.5 Hz, 2H), 1.41 (dd, J=6.6, 1.6 Hz, 3H).

Example 31

8-(1-Hydroxyethyl)-3-(1-(2,2,3,3,3-pentafluoropropyl)-1H-pyrazol-4-yl)-2-(trifluoromethyl)-4H-pyrido[1,2-a]pyrimidin-4-one

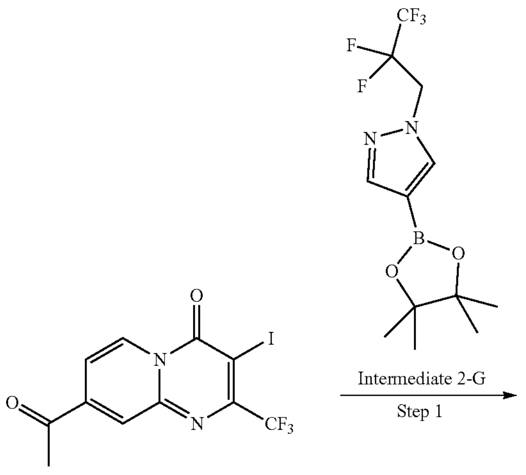

Intermediate 1-G

-continued

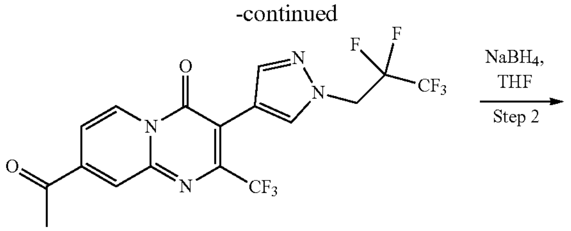

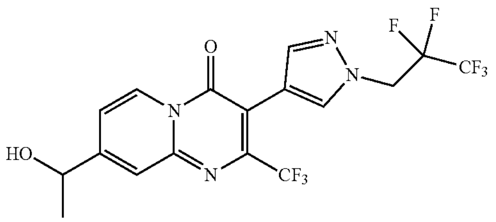

Step 1: 8-Acetyl-3-(1-(2,2,3,3,3-pentafluoropropyl)-1H-pyrazol-4-yl)-2-(trifluoromethyl)-4H-pyrido[1,2-a]pyrimidin-4-one The title compound was prepared using the procedure described in Method 1, Step 1 with the following modification: Step 1 was performed with 8-acetyl-3-iodo-2-(trifluoromethyl)-4H-pyrido[1,2-a]pyrimidin-4-one (650 mg, 1.7 mmol, Intermediate 1-G) and 1-(2,2,3,3,3-pentafluoropropyl)-4-(4,4,5,5-tetramethyl-1,3,2-dioxaborolan-2-yl)-1H-pyrazole (555 mg, 1.7 mmol, Intermediate 2-G). LC/MS ($ESI^+$) m/z=455.0 $[M+H]^+$.

Step 2: 8-(1-Hydroxyethyl)-3-(1-(2,2,3,3,3-pentafluoropropyl)-1H-pyrazol-4-yl)-2-(trifluoromethyl)-4H-pyrido[1,2-a]pyrimidin-4-one Sodium borohydride (60 mg, 1.54 mmol) was added to a solution of 8-acetyl-3-(1-(2,2,3,3,3-pentafluoropropyl)-1H-pyrazol-4-yl)-2-(trifluoromethyl)-4H-pyrido[1,2-a]pyrimidin-4-one (700 mg, 1.54 mmol) in THF (7 mL) at 0° C. under nitrogen atmosphere. The reaction mixture was allowed to warm to rt and stir for 1 h. The reaction mixture was cooled to 0° C. and quenched with the addition of ice water (20 mL). The mixture was extracted with ethyl acetate (2×30 mL) and the combined organic layers were dried over $Na_2SO_4$, filtered and concentrated under reduced pressure. The crude material was purified by silica gel chromatography (eluent: 0-70% EtOAc/hexane) to afford 8-(1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one (400 mg, 0.88 mmol, 57% yield) as yellow solid. LC/MS ($ESI^+$) m/z=457.0 $[M+H]^+$. $^1H$ NMR (400 MHz, DMSO-$d_6$) δ 8.99 (dd, J=7.4, 1.8 Hz, 1H), 8.05 (s, 1H), 7.72 (d, J=15.6 Hz, 2H), 7.52 (dt, J=7.4, 1.9 Hz, 1H), 5.76 (dd, J=4.7, 1.8 Hz, 1H), 5.30 (t, J=15.1 Hz, 2H), 4.97-4.90 (m, 1H), 1.42 (dd, J=6.5, 1.7 Hz, 3H).

Example 32

8-(Difluoromethyl)-3-(4-(2,2,2-trifluoroethoxy)phenyl)-2-(trifluoromethyl)-4H-pyrido[1,2-a]pyrimidin-4-one

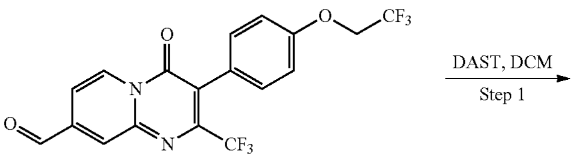

Intermediate 3-H

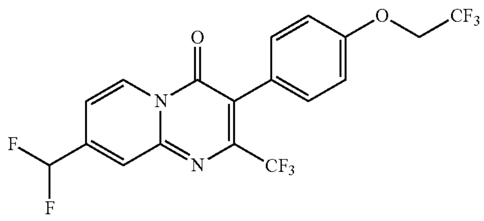

Step 1: 8-(Difluoromethyl)-3-(4-(2,2,2-trifluoroethoxy)phenyl)-2-(trifluoromethyl)-4H-pyrido[1,2-a]pyrimidin-4-one DAST (0.32 mL, 2.4 mmol) was added to a solution of 4-oxo-3-(4-(2,2,2-trifluoroethoxy)phenyl)-2-(trifluoromethyl)-4H-pyrido[1,2-a]pyrimidine-8-carbaldehyde (0.5 g, 1.2 mmol, Intermediate 3-H) in DCM (12.5 mL) at −10° C. The reaction mixture was quenched by the addition of saturated sodium bicarbonate solution (20 mL) and extracted with DCM (2×50 mL). The combined organic layers were dried over sodium sulfate, filtered and concentrated under reduced pressure. The crude material was purified by silica gel chromatography (eluent: 2% MeOH in DCM) to get 8-(difluoromethyl)-3-(4-(2,2,2-trifluoroethoxy)phenyl)-2-(trifluoromethyl)-4H-pyrido[1,2-a]pyrimidin-4-one (0.10 g, 0.23 mmol, 19% yield) as off-white solid. LC/MS ($ESI^+$) m/z=438.1 $[M+H]^+$. $^1H$ NMR (400 MHz, DMSO-$d_6$) δ 9.06 (d, J=7.4 Hz, 1H), 8.07 (dd, J=2.6, 1.4 Hz, 1H), 7.57 (dd, J=7.5, 1.9 Hz, 1H), 7.29 (dd, J=10.1, 8.2 Hz, 3H), 7.20-7.03 (m, 2H), 4.84 (q, J=8.8 Hz, 2H).

Example 33

7-Fluoro-8-methoxy-3-[1-(2,2,3,3,3-pentafluoropropyl)-1H-pyrazol-4-yl]-2-(trifluoromethyl)-4H-pyrido[1,2-a]pyrimidin-4-one

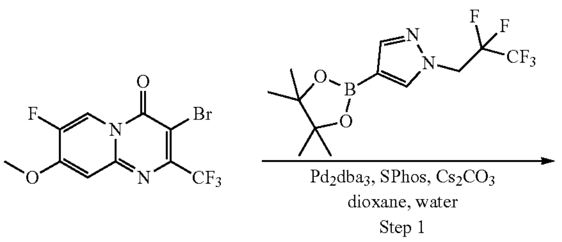

-continued

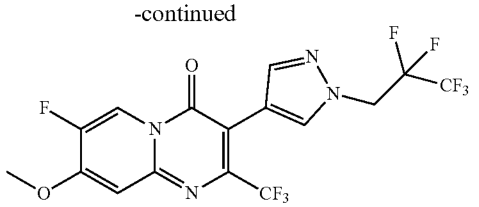

Step 1: 7-fluoro-8-methoxy-3-[1-(2,2,3,3,3-pentafluoropropyl)-1H-pyrazol-4-yl]-2-(trifluoromethyl)-4H-pyrido[1,2-a]pyrimidin-4-one A mixture of 1-(2,2,3,3,3-pentafluoropropyl)-4-(4,4,5,5-tetramethyl-1,3,2-dioxaborolan-2-yl)pyrazole (Intermediate 2-G, 2.83 g, 8.67 mmol), cesium carbonate (6.06 g, 18.47 mmol), tris(dibenzylideneacetone)dipalladium(0) (0.68 g, 0.740 mmol) and 2-dicyclohexylphosphino-2',6'-dimethoxybiphenyl (0.76 g, 1.85 mmol) in 1,4-dioxane (26 mL) and water (2.6 mL) was degassed for 15 minutes with a flow of nitrogen and then 3-bromo-8-methoxy-6-methyl-2-(trifluoromethyl)pyrido[1,2-a]pyrimidin-4-one (Intermediate 3-L, 2.52 g, 7.39 mmol) was added and the mixture was stirred under nitrogen at 90° C. for 4 h. The mixture was partioned between water and EtOAc. The organic phase was dried over sodium sulfate, filtered and concentrated under vacuum. The resulting crude product was suspended in DCM and the solid collected by filtration. The resulting solid was resuspended in DCM:MeOH in ratio 9:1, the collected by filtration and freeze dried from acetonitrile/water to give 7-fluoro-8-methoxy-3-[1-(2,2,3,3,3-pentafluoropropyl)-1H-pyrazol-4-yl]-2-(trifluoromethyl)-4H-pyrido[1,2-a]pyrimidin-4-one as an off-white solid (1.38 g, 2.99 mmol, 41% yield).

LC/MS ($ESI^+$) m/z=461.3 $[M+H]^+$. $^1H$ NMR (400 MHz, DMSO-d6) δ 9.05 (d, J=6.80 Hz, 1H), 8.02 (s, 1H), 7.67 (s, 1H), 7.50 (d, J=7.89 Hz, 1H), 5.28 (t, J=14.91 Hz, 2H), 4.12 (s, 3H).

Example 34

8-Methoxy-3-[1-(2,2,3,3,3-pentafluoropropyl)-1H-pyrazol-4-yl]-2-(trifluoromethyl)-4H-pyrimido[1,2-b]pyridazin-4-one

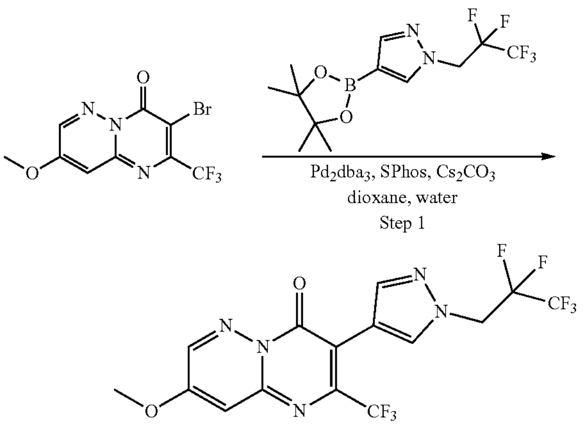

Step 1: 8-methoxy-3-[1-(2,2,3,3,3-pentafluoropropyl)-1H-pyrazol-4-yl]-2-(trifluoromethyl)-4H-pyrimido[1,2-b]pyridazin-4-one A screw-capped vial was charged with 3-bromo-8-methoxy-2-(trifluoromethyl)pyrimido[1,2-b]pyridazin-4-one (Intermediate 3-M, 60.0 mg, 0.19 mmol), 1,4-dioxane (5.5 mL), water (0.5 mL), cesium carbonate (152 mg, 0.46 mmol), 1-(2,2,3,3,3-pentafluoropropyl)-4-(4,4,5,5-tetramethyl-1,3,2-dioxaborolan-2-yl)pyrazole (Intermediate 2-G, 78 mg, 0.24 mmol), 2-dicyclohexylphosphino-2',6'-dimethoxybiphenyl (15 mg, 0.04 mmol) and tris(dibenzylideneacetone)dipalladium(0) (17 mg, 0.02 mmol). The mixture was degassed with a flow of nitrogen for 10 min then stirred at 90° C. for 2 h. The mixture was concentrated under vacuum and the crude product was purified by reverse phase flash chromatography (C18, $H_2O$+1% HCOOH:MeCN as eluant, from 90:10 to 100% MeCN) to obtain 8-methoxy-3-[1-(2,2,3,3,3-pentafluoropropyl)-1H-pyrazol-4-yl]-2-(trifluoromethyl)-4H-pyrimido[1,2-b]pyridazin-4-one as a white solid (14 mg, 0.032 mmol, 17% yield). LC/MS ($ESI^+$) m/z=444.3 $[M+H]^+$. $^1H$ NMR (500 MHz, DMSO-$d_6$) δ 4.05 (s, 3H), 5.29 (t, J=14.96 Hz, 2H), 7.55 (d, J=2.88 Hz, 1H), 7.68 (s, 1H), 8.06 (s, 1H), 8.81 (d, J=2.88 Hz, 1H).

Example 35

7-Chloro-3-[1-(2,2,3,3,3-pentafluoropropyl)-1H-pyrazol-4-yl]-2-(trifluoromethyl)-4H-pyrido[1,2-a]pyrimidin-4-one

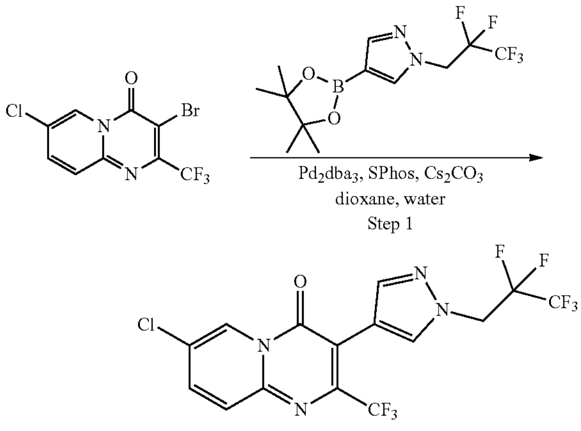

Step 1: 7-chloro-3-[1-(2,2,3,3,3-pentafluoropropyl)-1H-pyrazol-4-yl]-2-(trifluoromethyl)-4H-pyrido[1,2-a]pyrimidin-4-one A screw-capped vial was charged with 3-bromo-7-chloro-2-(trifluoromethyl)-4H-pyrido[1,2-a]pyrimidin-4-one (Intermediate 3-Q, 500 mg, 1.51 mmol), 1,4-dioxane (10 mL), water (1 mL), cesium carbonate (1.24 g, 3.78 mmol), 1-(2,2,3,3,3-pentafluoropropyl)-4-(4,4,5,5-tetramethyl-1,3,2-dioxaborolan-2-yl)pyrazole (Intermediate 2-G, 641 mg, 1.96 mmol), 2-dicyclohexylphosphino-2',6'-dimethoxybiphenyl (124 mg, 0.30 mmol) and tris(dibenzylideneacetone)dipalladium(0) (138 mg, 0.15 mmol). The mixture was degassed with a flow nitrogen for 10 min then stirred at 90° C. for 1 h. The mixture was partioned between water and EtOAc and the aqueous phase extracted with EtOAc. The combined organic phase was dried over sodium sulfate, filtered and concentrated under vacuum. The crude product was purified by Reverse phase flash chromatography (C18, $H_2O$+1% HCOOH/MeCN as eluant, from 90:10 to 100% MeCN) followed by flash chromatography (SiO2, cyclohexane/EtOAc from 95:5 to 20:80 EtOAc) to obtain 7-chloro-3-[1-(2,2,3,3,3-pentafluoropropyl)-1H-pyrazol-4-yl]-2-(trifluoromethyl)-4H-pyrido[1,2-a]pyrimidin-4-one as a yellow solid (260 mg, 0.58 mmol, 39% yield). LC/MS ($ESI^+$) m/z=447.1/449.1 $[M+H]^+$. $^1H$ NMR (500 MHz, DMSO-$d_6$) δ 5.31 (t, J=14.96 Hz, 2H), 7.72 (s, 1H), 7.90 (d, J=9.33 Hz, 1H), 8.10 (s, 1H), 8.14 (dd, J=9.47, 1.51 Hz, 1H), 9.02 (d, J=2.20 Hz, 11H).

Example 36

8-(Methoxymethyl)-3-[1-(2,2,3,3,3-pentafluoropropyl)-1H-pyrazol-4-yl]-2-(trifluoromethyl)-4H-pyrido[1,2-a]pyrimidin-4-one

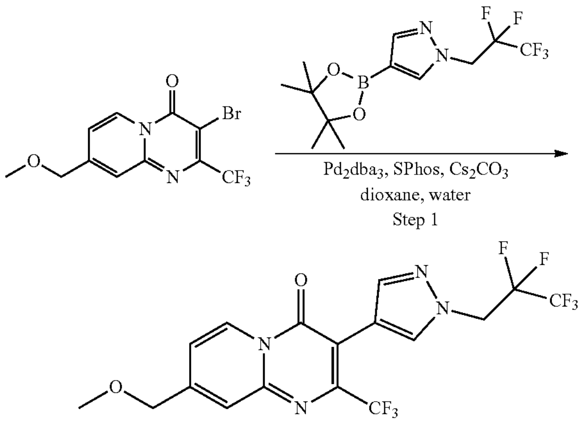

Step 1: 8-(methoxymethyl)-3-[1-(2,2,3,3,3-pentafluoropropyl)-1H-pyrazol-4-yl]-2-(trifluoromethyl)-4H-pyrido[1,2-a]pyrimidin-4-one A screw-capped vial was charged with 3-bromo-8-(methoxymethyl)-2-(trifluoromethyl)-4H-pyrido[1,2-a]pyrimidin-4-one (Intermediate 3-R, 40 mg, 0.12 mmol), 1,4-dioxane (2.5 mL), water (0.5 mL), cesium carbonate (97 mg, 0.30 mmol), 1-(2,2,3,3,3-pentafluoropropyl)-4-(4,4,5,5-tetramethyl-1,3,2-dioxaborolan-2-yl)pyrazole (Intermediate 2-G, 77 mg, 0.24 mmol), 2-dicyclohexylphosphino-2',6'-dimethoxybiphenyl (10 mg, 0.02 mmol). The mixture was degassed with a flow nitrogen for 10 min then tris(dibenzylideneacetone)dipalladium(0) (11 mg, 0.01 mmol) was added and the mixture was stirred at 95° C. for 1 h. The mixture was partioned between water and EtOAc and the aqueous phase extracted with EtOAc. The combined organic phase was dried over sodium sulfate, filtered and concentrated under vacuum. The crude product was purified by flash chromatography (SiO2, cyclohexane/EtOAc from 100:0 to 20:80 EtOAc) to obtain 8-(methoxymethyl)-3-[1-(2,2,3,3,3-pentafluoropropyl)-1H-pyrazol-4-yl]-2-(trifluoromethyl)-4H-pyrido[1,2-a]pyrimidin-4-one (26 mg, 0.057 mmol, 48% yield). LC/MS ($ESI^+$) m/z=457.4 $[M+H]^+$. $^1H$ NMR (500 MHz, $CDCl_3$) δ 3.52 (s, 3H), 4.61 (s, 2H), 4.83

(t, J=13.94 Hz, 2H), 7.25 (d, J=7.34 Hz, 1H), 7.77 (s, 1H), 7.84 (s, 1H), 7.89 (s, 1H), 9.05 (d, J=7.34 Hz, 1H).

Example 37

8-Methoxy-3-[2-(2,2,2-trifluoroethoxy)pyrimidin-5-yl]-2-(trifluoromethyl)-4H-pyrido[1,2-a]pyrimidin-4-one

Step 1: 8-methoxy-3-[2-(2,2,2-trifluoroethoxy)pyrimidin-5-yl]-2-(trifluoromethyl)-4H-pyrido[1,2-a]pyrimidin-4-one A screw-capped vial was charged with 3-bromo-8-methoxy-2-(trifluoromethyl)pyrido[1,2-a]pyrimidin-4-one (Intermediate 1-A, 500 mg, 1.54 mmol), 1,4-dioxane (10 mL), water (1 mL), cesium carbonate (1.26 g, 3.86 mmol), [2-(2,2,2-trifluoroethoxy)pyrimidin-5-yl]boronic acid (Intermediate 4-Q, 514 mg, 2.32 mmol), 2-dicyclohexylphosphino-2',6'-dimethoxybiphenyl (234 mg, 0.57 mmol) and tris(dibenzylideneacetone)dipalladium(0) (141 mg, 0.15 mmol). The mixture was degassed with a flow nitrogen for 10 min then stirred at 90° C. for 2 h. The mixture was concentrated under vacuum then purified by flash chromatography (SiO2, cyclohexane/EtOAc from 100:0 to 20:80 EtOAc) to obtain 8-methoxy-3-[2-(2,2,2-trifluoroethoxy)pyrimidin-5-yl]-2-(trifluoromethyl)-4H-pyrido[1,2-a]pyrimidin-4-one (548 mg, 1.30 mmol, 84% yield). LC/MS ($ESI^+$) m/z=421.3 $[M+H]^+$. $^1H$ NMR (500 MHz, DMSO-$d_6$) δ 4.06 (s, 3H), 5.12 (q, J=9.06 Hz, 2H), 7.26 (dd, J=7.82, 2.88 Hz, 1H), 7.37 (d, J=2.74 Hz, 1H), 8.65 (s, 2H), 8.88-8.97 (m, 1H).

Example 38

8-Methoxy-3-[2-(2,2,2-trifluoroethoxy)pyrimidin-5-yl]-2-(trifluoromethyl)-4H-pyrimido[1,2-b]pyridazin-4-one

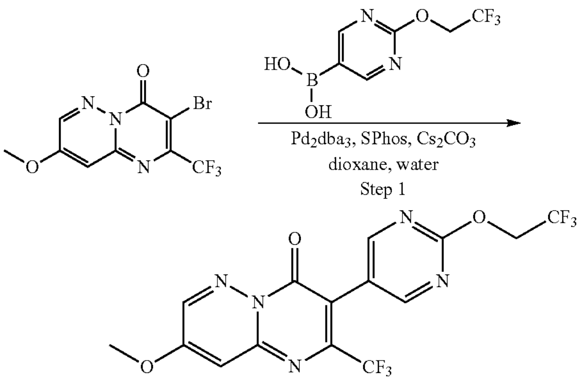

Step 1: 8-methoxy-3-[2-(2,2,2-trifluoroethoxy)pyrimidin-5-yl]-2-(trifluoromethyl)-4H-pyrimido[1,2-b]pyridazin-4-one A screw-capped vial was charged with 3-bromo-8-methoxy-2-(trifluoromethyl)pyrimido[1,2-b]pyridazin-4-one (Intermediate 3-M, 50 mg, 1.540.15 mmol), 1,4-dioxane (4 mL), water (0.4 mL), cesium carbonate (126 g, 0.39 mmol), [2-(2,2,2-trifluoroethoxy)pyrimidin-5-yl]boronic acid (Intermediate 4-Q, 52 mg, 0.23 mmol), 2-dicyclohexylphosphino-2',6'-dimethoxybiphenyl (13 mg, 0.03 mmol) and tris(dibenzylideneacetone)dipalladium(0) (14 mg, 0.015 mmol). The mixture was degassed with a flow nitrogen for 10 min then stirred at 90° C. for 2 h. The mixture was partioned between water and EtOAc and the aqueous phase extracted with EtOAc. The combined organic phase was dried over sodium sulfate, filtered and concentrated under vacuum. The crude product was purified by reverse phase flash chromatography (C18, $H_2O$+1% HCOOH/MeCN as eluant, from 90:10 to 100% MeCN) followed by flash chromatography (SiO2, DCM/MeOH from 99:1 to 95:5) to obtain 8-methoxy-3-[2-(2,2,2-trifluoroethoxy)pyrimidin-5-yl]-2-(trifluoromethyl)-4H-pyrimido[1,2-b]pyridazin-4-one. (23 mg, 0.055 mmol, 35% yield). LC/MS ($ESI^+$) m/z=422.1 $[M+H]^+$. $^1H$ NMR (500 MHz, DMSO-$d_6$) δ 4.08 (s, 3H), 5.13 (q, J=9.06 Hz, 2H), 7.66 (d, J=2.74 Hz, 1H), 8.67 (s, 2H), 8.88 (d, J=2.74 Hz, 1H).

Method 39

Example 39-1: 8-Methoxy-3-[1-(2,2,3,3,3-pentafluoropropyl)-1H-pyrazol-3-yl]-2-(trifluoromethyl)-4H-pyrido[1,2-a]pyrimidin-4-one

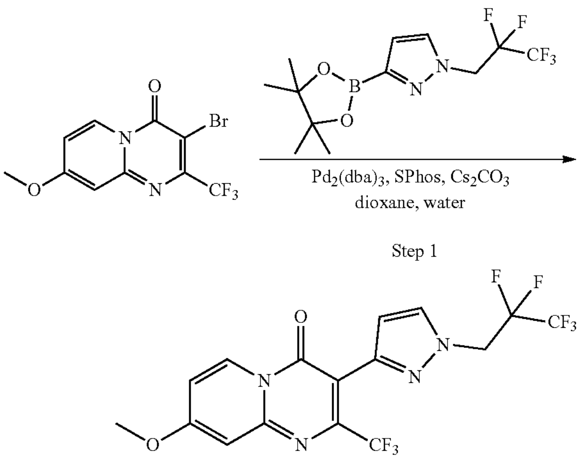

Step 1: 8-methoxy-3-[1-(2,2,3,3,3-pentafluoropropyl)-1H-pyrazol-3-yl]-2-(trifluoromethyl)-4H-pyrido[1,2-a]pyrimidin-4-one A screw-capped vial was charged with 3-bromo-8-methoxy-2-(trifluoromethyl)pyrido[1,2-a]pyrimidin-4-one (Intermediate 1-A, 70 mg, 0.22 mmol), 1,4-dioxane (3.7 mL), water (0.4 mL), cesium carbonate (213 mg, 0.65 mmol), 1-(2,2,3,3,3-pentafluoropropyl)-3-(4,4,5,5-tetramethyl-1,3,2-dioxaborolan-2-yl)pyrazole (Intermediate 4-Y, 106 mg, 0.33 mmol), 2-dicyclohexylphosphino-2',6'-dimethoxybiphenyl (27 mg, 0.065 mmol) and tris(dibenzylideneacetone)dipalladium(0) (24 mg, 0.026 mmol). The mixture was degassed with a flow nitrogen for several minutes with a flow of nitrogen then stirred at 90° C. for 2 h. The mixture was partioned between water and EtOAc and the aqueous phase extracted with EtOAc. The combined organic phase was dried over sodium sulfate, filtered and concentrated under vacuum. The crude product was purified by flash chromatography (SiO2, cyclohexane/EtOAc from 100:0 to 20:80 EtOAc) to obtain 8-methoxy-3-[1-(2,2,3,3,3-pentafluoropropyl)-1H-pyrazol-3-yl]-2-(trifluoromethyl)-4H-pyrido[1,2-a]pyrimidin-4-one as a white solid (68 mg, 0.015 mmol, 71% yield).

LC/MS (ESI$^+$) m/z=443.1 [M+H]$^+$. $^1$H NMR (400 MHz, DMSO-$d_6$) δ 4.04 (s, 3H), 5.21 (t, J=14.9 Hz, 2H), 6.47 (d, J=2.4 Hz, 1H), 7.21 (dd, J=7.8, 2.7 Hz, 1H), 7.29 (d, J=2.9 Hz, 1H), 7.92 (d, J=2.4 Hz, 1H), 8.90 (d, J=7.9 Hz, 1H).

Examples 39-2 to 39-59 listed in Table 22 were prepared following the procedure described in Method 39, Step 1, above as follows.

TABLE 22

| Ex. # | Chemical Structure | Name | Method Changes | Reagents |
|---|---|---|---|---|
| 39-2 | 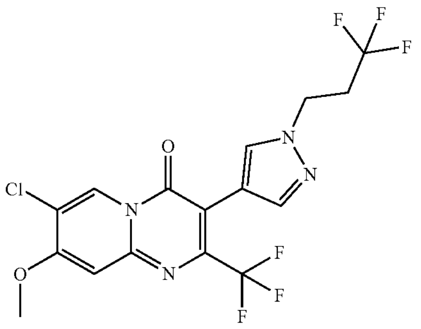 [SMILES: COc1cc2nc(C(F)(F)F)c(-c3cnn(CCC(F)(F)F)c3)c(=O)n2cc1Cl] | 7-chloro-8-methoxy-2-(trifluoromethyl)-3-[1-(3,3,3-trifluoropropyl)-1H-pyrazol-4-yl]-4H-pyrido[1,2-a]pyrimidin-4-one | Heated at 90° C. for 10 h | 7-chloro-3-iodo-8-methoxy-2-(trifluoromethyl)pyrido[1,2-a]pyrimidin-4-one (Intermediate 1-I) and 4-(4,4,5,5-tetramethyl-1,3,2-dioxaborolan-2-yl)-3-(3,3,3-trifluoropropyl)pyrazole (Intermediate 2-D) |
| 39-3 | 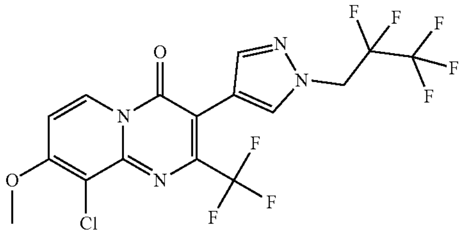 [SMILES: COc1ccn2c(=O)c(-c3cnn(CC(F)(F)C(F)(F)F)c3)c(C(F)(F)F)nc2c1Cl] | 9-chloro-8-methoxy-3-[1-(2,2,3,3,3-pentafluoropropyl)-1H-pyrazol-4-yl]-2-(trifluoromethyl)-4H-pyrido[1,2-a]pyrimidin-4-one | Heated at 90° C. for 10 h. Product further purified by RP chromatography (C18, $H_2O$/MeCN as eluant, from 100:0 to 40:60) | 9-chloro-3-iodo-8-methoxy-2-(trifluoromethyl)pyrido[1,2-a]pyrimidin-4-one (Intermediate 4-Z) and 1-(2,2,3,3,3-pentafluoropropyl)-4-(4,4,5,5-tetramethyl-1,3,2-dioxaborolan-2-yl)pyrazole (Intermediate 2-G) |
| 39-4 | 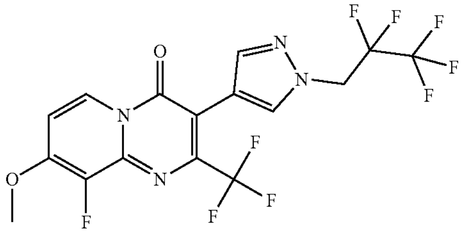 [SMILES: COc1ccn2c(=O)c(-c3cnn(CC(F)(F)C(F)(F)F)c3)c(C(F)(F)F)nc2c1F] | 9-fluoro-8-methoxy-3-[1-(2,2,3,3,3-pentafluoropropyl)-1H-pyrazol-4-yl]-2-(trifluoromethyl)-4H-pyrido[1,2-a]pyrimidin-4-one | | 9-fluoro-3-iodo-8-methoxy-2-(trifluoromethyl)pyrido[1,2-a]pyrimidin-4-one (Intermediate 3-K) and 1-(2,2,3,3,3-pentafluoropropyl)-4-(4,4,5,5-tetramethyl-1,3,2-dioxaborolan-2-yl)pyrazole (Intermediate 2-G) |
| 39-5 | 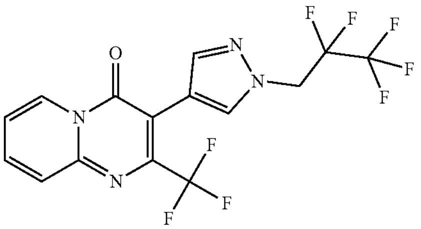 [SMILES: O=c1c(-c2cnn(CC(F)(F)C(F)(F)F)c2)c(C(F)(F)F)nc2ccccn12] | 3-[1-(2,2,3,3,3-pentafluoropropyl)-1H-pyrazol-4-yl]-2-(trifluoromethyl)-4H-pyrido[1,2-a]pyrimidin-4-one | Heated at 90° C. for 16 h | 3-iodo-2-(trifluoromethyl)pyrido[1,2-a]pyrimidin-4-one (Intermediate 3-N) and 1-(2,2,3,3,3-pentafluoropropyl)-4-(4,4,5,5-tetramethyl- |

TABLE 22-continued

| Ex. # | Chemical Structure | Name | Method Changes | Reagents |
|---|---|---|---|---|
| | | | | 1,3,2-dioxaborolan-2-yl)pyrazole (Intermediate 2-G) |
| 39-6 | 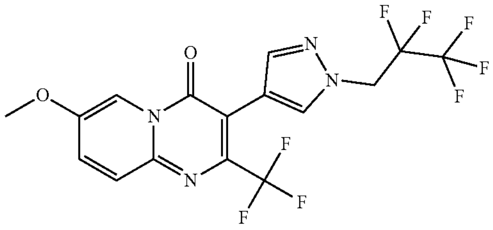 [SMILES: COc1ccc2nc(C(F)(F)F)c(-c3cnn(CC(F)(F)C(F)(F)F)c3)c(=O)n2c1] | 7-methoxy-3-[1-(2,2,3,3,3-pentafluoropropyl)-1H-pyrazol-4-yl]-2-(trifluoromethyl)-4H-pyrido[1,2-a]pyrimidin-4-one | Heated at 90° C. for 1.5 h. Product repurified by flash chromagraphy (NH-silica, eluted with cyclohexane/DCM/EtOAc 5:4:1) | 3-bromo-7-methoxy-2-(trifluoromethyl)pyrido[1,2-a]pyrimidin-4-one (Intermediate 3-O) and 1-(2,2,3,3,3-pentafluoropropyl)-4-(4,4,5,5-tetramethyl-1,3,2-dioxaborolan-2-yl)pyrazole (Intermediate 2-G) |
| 39-7 | 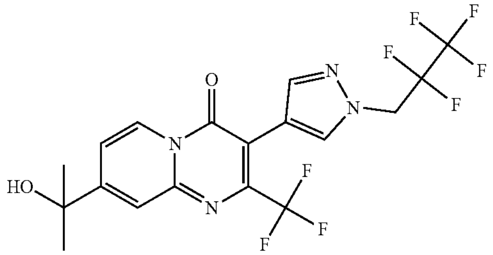 [SMILES: CC(C)(O)c1ccn2c(=O)c(-c3cnn(CC(F)(F)C(F)(F)F)c3)c(C(F)(F)F)nc2c1] | 8-(2-hydroxypropan-2-yl)-3-[1-(2,2,3,3,3-pentafluoropropyl)-1H-pyrazol-4-yl]-2-(trifluoromethyl)-4H-pyrido[1,2-a]pyrimidin-4-one | | 3-bromo-8-(2-hydroxypropan-2-yl)-2-(trifluoromethyl)pyrido[1,2-a]pyrimidin-4-one (Intermediate 3-P) and 1-(2,2,3,3,3-pentafluoropropyl)-4-(4,4,5,5-tetramethyl-1,3,2-dioxaborolan-2-yl)pyrazole (Intermediate 2-G) |
| 39-8 | 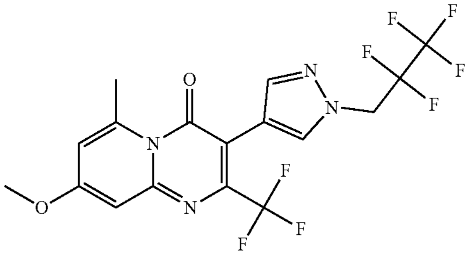 [SMILES: COc1cc(C)n2c(=O)c(-c3cnn(CC(F)(F)C(F)(F)F)c3)c(C(F)(F)F)nc2c1] | 8-methoxy-6-methyl-3-[1-(2,2,3,3,3-pentafluoropropyl)-1H-pyrazol-4-yl]-2-(trifluoromethyl)-4H-pyrido[1,2-a]pyrimidin-4-one | Product further purified by RP chromatography (C18, 0.1% HCOOH in water/MeCN as eluant, from 80:20 to 40:60) | 3-bromo-8-methoxy-6-methyl-2-(trifluoromethyl)pyrido[1,2-a]pyrimidin-4-one (Intermediate 3-S) and 1-(2,2,3,3,3-pentafluoropropyl)-4-(4,4,5,5-tetramethyl-1,3,2-dioxaborolan-2-yl)pyrazole (Intermediate 2-G) |
| 39-9 | 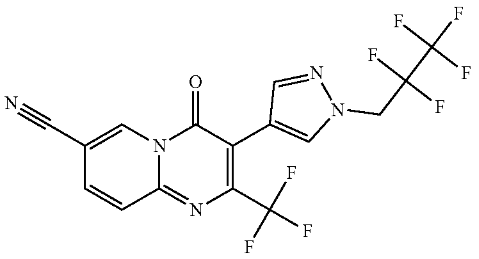 [SMILES: N#Cc1ccc2nc(C(F)(F)F)c(-c3cnn(CC(F)(F)C(F)(F)F)c3)c(=O)n2c1] | 4-oxo-3-[1-(2,2,3,3,3-pentafluoropropyl)-1H-pyrazol-4-yl]-2-(trifluoromethyl)-4H-pyrido[1,2-a]pyrimidine-7-carbonitrile | Heated at 90° C. for 16 h. Product purified by reverse phase flash chromatography (C18, 0.1% HCOOH in water/MeCN as eluant, | 3-bromo-4-oxo-2-(trifluoromethyl)pyrido[1,2-a]pyrimidine-7-carbonitrile (Intermediate 3-T) and 1-(2,2,3,3,3-pentafluoropropyl)-4-(4,4,5,5-tetramethyl-1,3,2-dioxaborolan-2-yl)pyrazole |

TABLE 22-continued

| Ex. # | Chemical Structure | Name | Method Changes | Reagents |
|---|---|---|---|---|
| | | | 50:50) followed by flash chroma-tography ($SiO_2$, EtOAc/DCM, 50:50) | (Intermediate 2-G) |
| 39-10 | 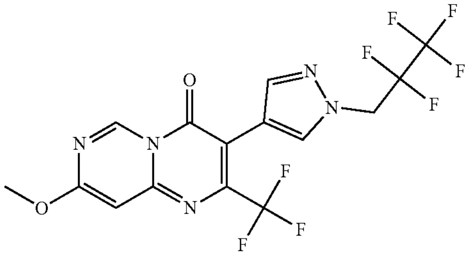 [SMILES: COc1cc2nc(C(F)(F)F)c(-c3cnn(CC(F)(F)C(F)(F)F)c3)c(=O)n2cn1] | 8-methoxy-3-[1-(2,2,3,3,3-pentafluoropropyl)-1H-pyrazol-4-yl]-2-(trifluoromethyl)-4H-[1,3]diazino[1,6-a]pyrimidin-4-one | Heated at 73° C. for 45 min. Product repurified by flash chroma-tography ($SiO_2$, DCM/EtOAc, 100:0 to 80:20) | 3-bromo-8-methoxy-2-(trifluoromethyl)pyrimido[1,6-a]pyrimidin-4-one (Intermediate 4-A)and 1-(2,2,3,3,3-pentafluoropropyl)-4-(4,4,5,5-tetramethyl-1,3,2-dioxaborolan-2-yl)pyrazole (Intermediate 2-G) |
| 39-11 | 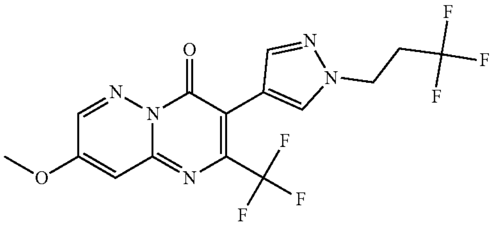 [SMILES: COc1cnn2c(=O)c(-c3cnn(CCC(F)(F)F)c3)c(C(F)(F)F)nc2c1] | 8-methoxy-2-(trifluoromethyl)-3-[1-(3,3,3-trifluoropropyl)-1H-pyrazol-4-yl]-4H-pyrimido[1,2-b]pyridazin-4-one | Product purified by reverse phase flash chroma-tography (C18, 0.1% HCOOH in water/MeCN as eluant, from 95:5 to 20:80) | 3-bromo-8-methoxy-2-(trifluoromethyl)pyrimido[1,2-b]pyridazin-4-one (Intermediate 3-M) and 4-(4,4,5,5-tetramethyl-1,3,2-dioxaborolan-2-yl)-1-(3,3,3-trifluoropropyl)pyrazole (Intermediate 2-D) |
| 39-12 | 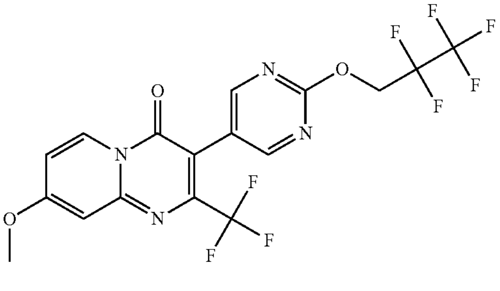 [SMILES: COc1ccn2c(=O)c(-c3cnc(OCC(F)(F)C(F)(F)F)nc3)c(C(F)(F)F)nc2c1] | 8-methoxy-3-[2-(2,2,3,3,3-pentafluoropropoxy)pyrimidin-5-yl]-2-(trifluoromethyl)-4H-pyrido[1,2-a]pyrimidin-4-one | Heated at 90° C. for 3 h. | 3-bromo-8-methoxy-2-(trifluoromethyl)pyrido[1,2-a]pyridazin-4-one (Intermediate 1-A) and [2-(2,2,3,3,3-pentafluoropropoxy)pyrimidin-5-yl]boronic acid (Intermediate 4-R) |
| 39-13 | 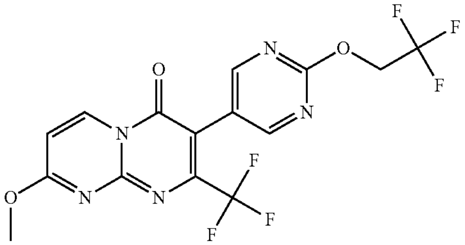 [SMILES: COc1ccn2c(=O)c(-c3cnc(OCC(F)(F)F)nc3)c(C(F)(F)F)nc2n1] | 8-methoxy-3-[2-(2,2,2-trifluoroethoxy)pyrimidin-5-yl]-2-(trifluoromethyl)-4H-[1,3]diazino[1,2-a]pyrimidin-4-one | Heated at 90° C. for 4 h. | 3-bromo-8-methoxy-2-(trifluoromethyl)pyrimido[1,2-a]pyrimidin-4-one (Intermediate 1-O) and [2-(2,2,2-trifluoroethoxy)pyrimidin-5-yl]boronic acid (Intermediate 4-Q) |

TABLE 22-continued

| Ex. # | Chemical Structure | Name | Method Changes | Reagents |
| --- | --- | --- | --- | --- |
| 39-14 | 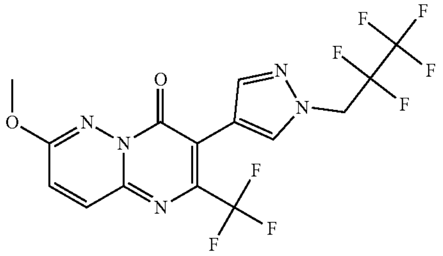 [SMILES: COc1ccc2nc(C(F)(F)F)c(-c3cnn(CC(F)(F)C(F)(F)F)c3)c(=O)n2n1] | 7-methoxy-3-[1-(2,2,3,3,3-pentafluoropropyl)-1H-pyrazol-4-yl]-2-(trifluoromethyl)-4H-pyrimido[1,2-b]pyridazin-4-one | Heated at 70° C. for 2 h. Product purified by reverse phase flash chroma-tography (C18, 0.1% HCOOH in water/ MeCN as eluant, from 95:5 to 20:80) | 3-bromo-7-methoxy-2-(trifluoromethyl) pyrimido[1,2-b]pyridazin-4-one (Intermediate 3-U)and 1-(2,2,3,3,3-pentafluoropropyl)-4-(4,4,5,5-tetramethyl-1,3,2-dioxaborolan-2-yl)pyrazole (Intermediate 2-G) |
| 39-15 | 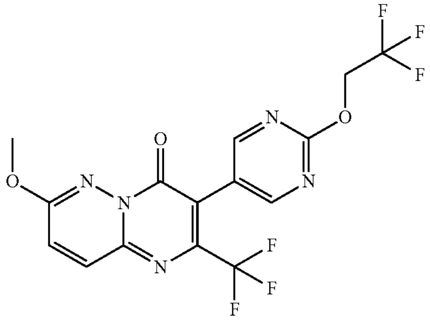 [SMILES: COc1ccc2nc(C(F)(F)F)c(-c3cnc(OCC(F)(F)F)nc3)c(=O)n2n1] | 7-methoxy-3-[2-(2,2,2-trifluoroethoxy) pyrimidin-5-yl]-2-(trifluoromethyl)-4H-pyrimido[1,2-b]pyridazin-4-one | Heated at 70° C. for 4 h. Product purified by reverse phase flash chroma-tography (C18, 0.1% HCOOH in water/ MeCN as eluant, from 95:5 to 20:80) followed by flash chroma-tography ($SiO_2$, cyclohexane/ EtOAc from 80:20 to 50:50) | 3-bromo-7-methoxy-2-(trifluoromethyl) pyrimido[1,2-b]pyridazin-4-one (Intermediate 3-U) and [2-(2,2,2-trifluoroethoxy) pyrimidin-5-yl]boronic acid (Intermediate 4-Q) |
| 39-16 | 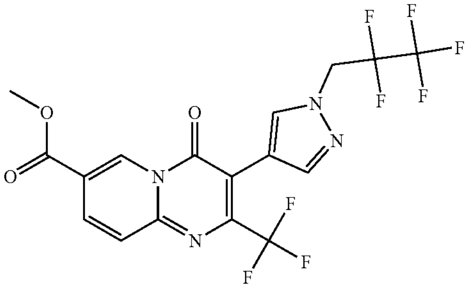 [SMILES: COC(=O)c1ccc2nc(C(F)(F)F)c(-c3cnn(CC(F)(F)C(F)(F)F)c3)c(=O)n2c1] | methyl 4-oxo-3-[1-(2,2,3,3,3-pentafluoropropyl)-1H-pyrazol-4-yl]-2-(trifluoromethyl)-4H-pyrido[1,2-a]pyrimidine-7-carboxylate | Heated at 90° C. for 16 h. | methyl 3-bromo-4-oxo-2-(trifluoromethyl) pyrido[1,2-a]pyrimidine-7-carboxylate (Intermediate 3-B) and 1-(2,2,3,3,3-pentafluoropropyl)-4-(4,4,5,5-tetramethyl-1,3,2-dioxaborolan-2-yl)pyrazole (Intermediate 2-G) |
| 39-17 | 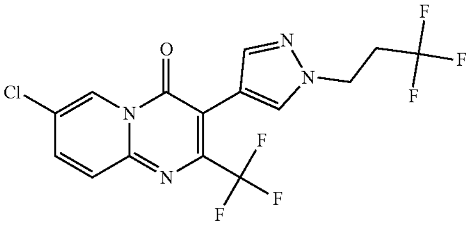 [SMILES: O=c1c(-c2cnn(CCC(F)(F)F)c2)c(C(F)(F)F)nc2ccc(Cl)cn12] | 7-chloro-2-(trifluoromethyl)-3-[1-(3,3,3-trifluoropropyl)-1H-pyrazol-4-yl]-4H-pyrido[1,2-a]pyrimidin-4-one | Heated at 90° C. for 1 h. | 3-bromo-7-chloro-2-(trifluoromethyl) pyrido[1,2-a]pyrimidin-4-one (Intermediate 3-Q) and 4-(4,4,5,5-tetramethyl-1,3,2-dioxaborolan-2-yl)-1-(3,3,3- |

TABLE 22-continued

| Ex. # | Chemical Structure | Name | Method Changes | Reagents |
|---|---|---|---|---|
| | | | | trifluoropropyl) pyrazole (Intermediate 2-D) |
| 39-18 | 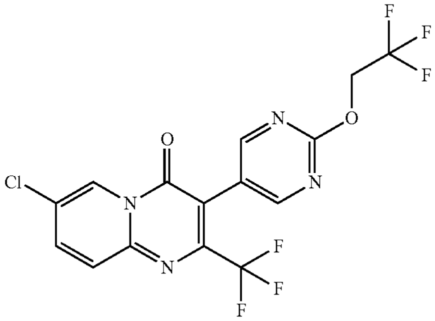 [SMILES: O=c1c(-c2cnc(OCC(F)(F)F)nc2)c(C(F)(F)F)nc2ccc(Cl)cn12] | 7-chloro-3-[2-(2,2,2-trifluoroethoxy) pyrimidin-5-yl]-2-(trifluoromethyl)-4H-pyrido[1,2-a]pyrimidin-4-one | Heated at 90° C. for 1 h. Product purified by reverse phase flash chromatography (C18, 0.1% HCOOH in water/ MeCN as eluant, from 90:10 to 0:100) followed by flash chromatography ($SiO_2$, cyclohexane/ EtOAc from 90:10 to 60:40) | 3-bromo-7-chloro-2-(trifluoromethyl) pyrido[1,2-a]pyrimidin-4-one (Intermediate 3-Q) and [2-(2,2,2-trifluoroethoxy) pyrimidin-5-yl]boronic acid (Intermediate 4-Q) |
| 39-19 | 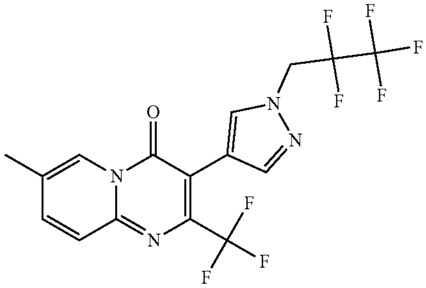 [SMILES: Cc1ccc2nc(C(F)(F)F)c(-c3cnn(CC(F)(F)C(F)(F)F)c3)c(=O)n2c1] | 7-methyl-3-[1-(2,2,3,3,3-pentafluoropropyl)-1H-pyrazol-4-yl]-2-(trifluoromethyl)-4H-pyrido[1,2-a]pyrimidin-4-one | Heated at 85° C. for 3 h. | 3-bromo-7-methyl-2-(trifluoromethyl) pyrido[1,2-a]pyrimidin-4-one (Intermediate 3-X) and 1-(2,2,3,3,3-pentafluoropropyl)-4-(4,4,5,5-tetramethyl-1,3,2-dioxaborolan-2-yl)pyrazole (Intermediate 2-G) |
| 39-20 | 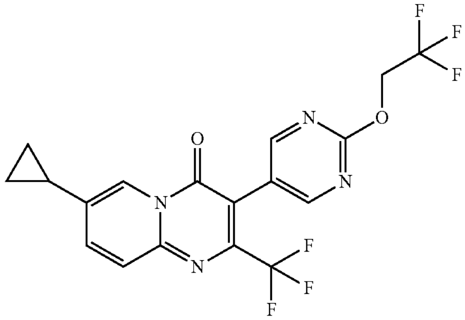 [SMILES: O=c1c(-c2cnc(OCC(F)(F)F)nc2)c(C(F)(F)F)nc2ccc(C3CC3)cn12] | 7-cyclopropyl-3-[2-(2,2,2-trifluoroethoxy) pyrimidin-5-yl]-2-(trifluoromethyl)-4H-pyrido[1,2-a]pyrimidin-4-one | Product further purified by RP chromatography (C18, $H_2O$/ MeCN as eluant, from 97:3 to 40:60) | 3-bromo-7-cyclopropyl-2-(trifluoromethyl) pyrido[1,2-a]pyrimidin-4-one (Intermediate 4-J) and [2-(2,2,2-trifluoroethoxy) pyrimidin-5-yl]boronic acid (Intermediate 4-Q) |
| 39-21 | 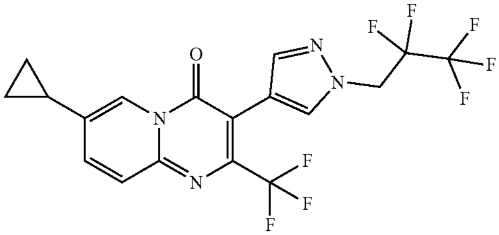 [SMILES: O=c1c(-c2cnn(CC(F)(F)C(F)(F)F)c2)c(C(F)(F)F)nc2ccc(C3CC3)cn12] | 7-cyclopropyl-3-[1-(2,2,3,3,3-pentafluoropropyl)-1H-pyrazol-4-yl]-2-(trifluoromethyl)-4H-pyrido[1,2-a]pyrimidin-4-one | Product further purified by RP chromatography (C18, $H_2O$/ MeCN as eluant, from 97:3 to 40:60) | 3-bromo-7-cyclopropyl-2-(trifluoromethyl) pyrido(1,2-a]pyrimidin-4-one (Intermediate 4-J) and 1-(2,2,3,3,3-pentafluoropropyl)-4-(4,4,5,5- |

TABLE 22-continued

| Ex. # | Chemical Structure | Name | Method Changes | Reagents |
| --- | --- | --- | --- | --- |
| | | | | tetramethyl-1,3,2-dioxaborolan-2-yl)pyrazole (Intermediate 2-G) |
| 39-22 | 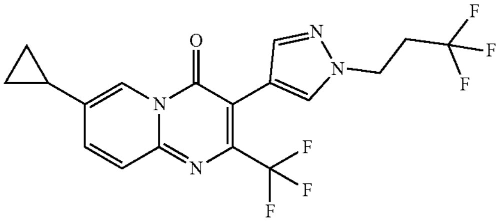 [SMILES: O=c1c(-c2cnn(CCC(F)(F)F)c2)c(C(F)(F)F)nc2ccc(C3CC3)cn12] | 7-cyclopropyl-2-(trifluoromethyl)-3-[1-(3,3,3-trifluoropropyl)-1H-pyrazol-4-yl]-4H-pyrido[1,2-a]pyrimidin-4-one | Product further purified by RP chroma-tography (C18, $H_2O$/MeCN as eluant, from 97:3 to 40:60) | 3-bromo-7-cyclopropyl-2-(trifluoromethyl)pyrido[1,2-a]pyrimidin-4-one (Intermediate 4-J) and 4-(4,4,5,5-tetramethyl-1,3,2-dioxaborolan-2-yl)-1-(3,3,3-trifluoropropyl)pyrazole (Intermediate 2-D) |
| 39-23 | 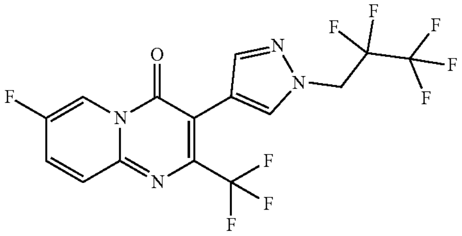 [SMILES: O=c1c(-c2cnn(CC(F)(F)C(F)(F)F)c2)c(C(F)(F)F)nc2ccc(F)cn12] | 7-fluoro-3-[1-(2,2,3,3,3-pentafluoropropyl)-1H-pyrazol-4-yl]-2-(trifluoromethyl)-4H-pyrido[1,2-a]pyrimidin-4-one | Heated at 90° C. for 1 h. | 3-bromo-7-fluoro-2-(trifluoromethyl)pyrido[1,2-a]pyrimidin-4-one (Intermediate 3-Y) and 1-(2,2,3,3,3-pentafluoropropyl)-4-(4,4,5,5-tetramethyl-1,3,2-dioxaborolan-2-yl)pyrazole (Intermediate 2-G) |
| 39-24 | 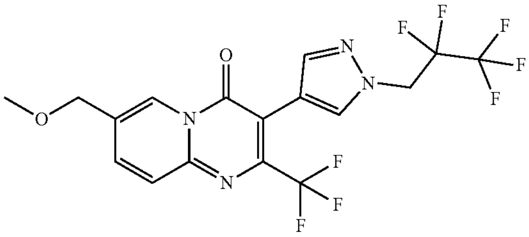 [SMILES: COCc1ccc2nc(C(F)(F)F)c(-c3cnn(CC(F)(F)C(F)(F)F)c3)c(=O)n2c1] | 7-(methoxymethyl)-3-[1-(2,2,3,3,3-pentafluoropropyl)-1H-pyrazol-4-yl]-2-(trifluoromethyl)-4H-pyrido[1,2-a]pyrimidin-4-one | Heated at 80° C. for 2 h. | 3-bromo-7-(methoxymethyl)-2-(trifluoromethyl)pyrido[1,2-a]pyrimidin-4-one (Intermediate 4-L) and 1-(2,2,3,3,3-pentafluoropropyl)-4-(4,4,5,5-tetramethyl-1,3,2-dioxaborolan-2-yl)pyrazole (Intermediate 2-G) |
| 39-25 | 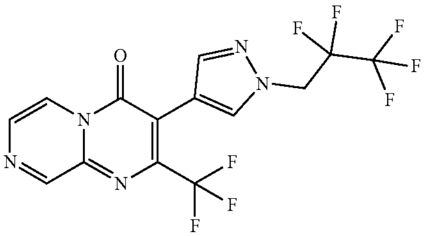 [SMILES: O=c1c(-c2cnn(CC(F)(F)C(F)(F)F)c2)c(C(F)(F)F)nc2cnccn12] | 3-[1-(2,2,3,3,3-pentafluoropropyl)-1H-pyrazol-4-yl]-2-(trifluoromethyl)-4H-pyrazino[1,2-a]pyrimidin-4-one | Heated at 92° C. for 7 h Product further purified by RP chroma-tography (C18, $H_2O$/MeCN as | 3-bromo-2-(trifluoromethyl)pyrazino[1,2-a]pyrimidin-4-one (Intermediate 4-C) and 1-(2,2,3,3,3-pentafluoropropyl)-4-(4,4,5,5-tetramethyl- |

TABLE 22-continued

| Ex. # | Chemical Structure | Name | Method Changes | Reagents |
|---|---|---|---|---|
| | | | eluant, from 100:0 to 33:67) | 1,3,2-dioxaborolan-2-yl)pyrazole (Intermediate 2-G) |
| 39-26 | 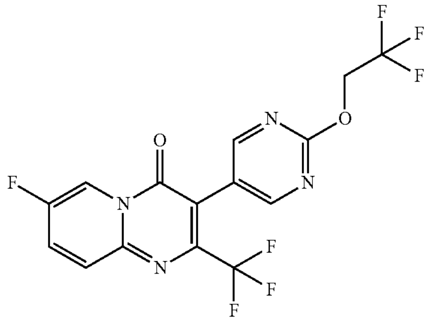 [SMILES: O=c1c(-c2cnc(OCC(F)(F)F)nc2)c(C(F)(F)F)nc2ccc(F)cn12] | 7-fluoro-3-[2-(2,2,2-trifluoroethoxy) pyrimidin-5-yl]-2-(trifluoromethyl)-4H-pyrido[1,2-a]pyrimidin-4-one | Heated at 90° C. for 3 h | 3-bromo-7-fluoro-2-(trifluoromethyl) pyrido[1,2-a]pyrimidin-4-one (Intermediate 3-Y) and [2-(2,2,2-trifluoroethoxy) pyrimidin-5-yl]boronic acid (Intermediate 4-Q) |
| 39-27 | 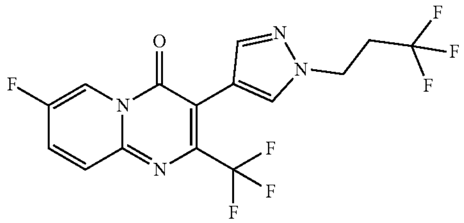 [SMILES: O=c1c(-c2cnn(CCC(F)(F)F)c2)c(C(F)(F)F)nc2ccc(F)cn12] | 7-fluoro-2-(trifluoromethyl)-3-[1-(3,3,3-trifluoropropyl)-1H-pyrazol-4-yl]-4H-pyrido[1,2-a]pyrimidin-4-one | Heated at 90° C. for 1 h | 3-bromo-7-fluoro-2-(trifluoromethyl) pyrido[1,2-a]pyrimidin-4-one (Intermediate 3-Y) and 4-(4,4,5,5-tetramethyl-1,3,2-dioxaborolan-2-yl)-1-(3,3,3-trifluoropropyl) pyrazole (Intermediate 2-D) |
| 39-28 | 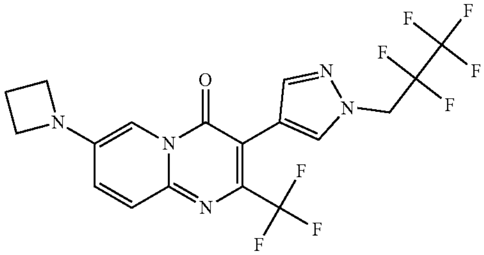 [SMILES: O=c1c(-c2cnn(CC(F)(F)C(F)(F)F)c2)c(C(F)(F)F)nc2ccc(N3CCC3)cn12] | 7-(azetidin-1-yl)-3-[1-(2,2,3,3,3-pentafluoropropyl)-1H-pyrazol-4-yl]-2-(trifluoromethyl)-4H-pyrido[1,2-a]pyrimidin-4-one | Heated at 90° C. for 90 min Product further purified by RP chromatography (C18, $H_2O$/MeCN as eluant, from 97:3 to 40:60) | 7-(azetidin-1-yl)-3-bromo-2-(trifluoromethyl) pyrido[1,2-a]pyrimidin-4-one (Intermediate 4-K) and 1-(2,2,3,3,3-pentafluoropropyl)-4-(4,4,5,5-tetramethyl-1,3,2-dioxaborolan-2-yl)pyrazole (Intermediate 2-G) |
| 39-29 | 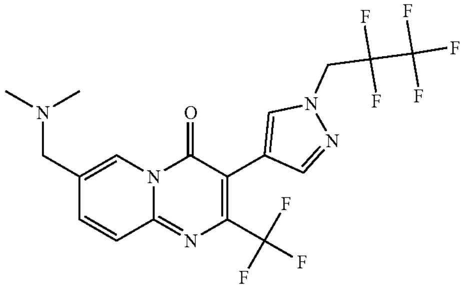 [SMILES: CN(C)Cc1ccc2nc(C(F)(F)F)c(-c3cnn(CC(F)(F)C(F)(F)F)c3)c(=O)n2c1] | 7-[(dimethylamino) methyl]-3-[1-(2,2,3,3,3-pentafluoropropyl)-1H-pyrazol-4-yl]-2-(trifluoromethyl)-4H-pyrido[1,2-a]pyrimidin-4-one | Heated at 80° C. for 3 hours | 3-bromo-7-[(dimethylamino) methyl]-2-(trifluoromethyl) pyrido[1,2-a]pyrimidin-4-on (Intermediate 4-M) and 1-(2,2,3,3,3-pentafluoropropyl)-4-(4,4,5,5-tetramethyl-1,3,2-dioxaborolan-2-yl)pyrazole (Intermediate 2-G) |

TABLE 22-continued

| Ex. # | Chemical Structure | Name | Method Changes | Reagents |
|---|---|---|---|---|
| 39-30 | 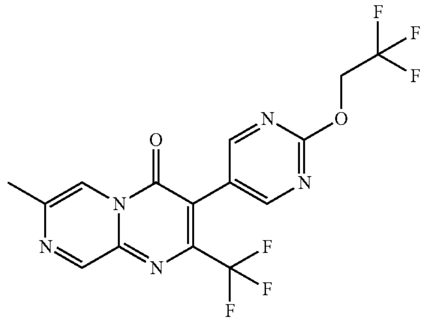 [SMILES: Cc1cn2c(=O)c(-c3cnc(OCC(F)(F)F)nc3)c(C(F)(F)F)nc2cn1] | 7-methyl-3-[2-(2,2,2-trifluoroethoxy) pyrimidin-5-yl]-2-(trifluoromethyl)-4H-pyrazino[1,2-a]pyrimidin-4-one | Product further purified by RP chroma-tography (C18, $H_2O$/MeCN as eluant, from 100:0 to 40:60) | 3-bromo-7-fluoro-2-(trifluoromethyl) pyrido[1,2-a]pyrimidin-4-one (Intermediate 4-D) and [2-(2,2,2-trifluoroethoxy) pyrimidin-5-yl]boronic acid (Intermediate 4-Q) |
| 39-31 | 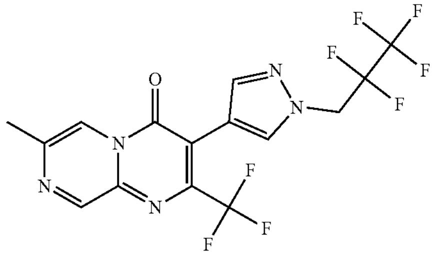 [SMILES: Cc1cn2c(=O)c(-c3cnn(CC(F)(F)C(F)(F)F)c3)c(C(F)(F)F)nc2cn1] | 7-methyl-3-[1-(2,2,3,3,3-pentafluoropropyl)-1H-pyrazol-4-yl]-2-(trifluoromethyl)-4H-pyrazino[1,2-a]pyrimidin-4-one | Heated at 90° C. for 7 h Product further purified by RP chroma-tography (C18, $H_2O$/MeCN as eluant, from 100:0 to 50:50) | 3-bromo-7-fluoro-2-(trifluoromethyl) pyrido[1,2-a]pyrimidin-4-one (Intermediate 4-D) and 1-(2,2,3,3,3-pentafluoropropyl)-4-(4,4,5,5-tetramethyl-1,3,2-dioxaborolan-2-yl)pyrazole (Intermediate 2-G) |
| 39-32 | 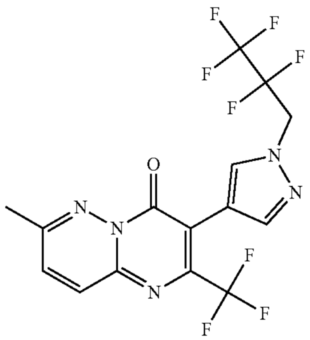 [SMILES: Cc1ccc2nc(C(F)(F)F)c(-c3cnn(CC(F)(F)C(F)(F)F)c3)c(=O)n2n1] | 7-methyl-3-[1-(2,2,3,3,3-pentafluoropropyl)-1H-pyrazol-4-yl]-2-(trifluoromethyl)-4H-pyrimido[1,2-b]pyridazin-4-one | Product further purified by RP chroma-tography (C18, $H_2O$/MeCN as eluant, from 95:5 to 20:80) | 3-bromo-7-methyl-2-(trifluoromethyl) pyrimido[1,2-b]pyridazin-4-one (Intermediate 3-Z) and 1-(2,2,3,3,3-pentafluoropropyl)-4-(4,4,5,5-tetramethyl-1,3,2-dioxaborolan-2-yl)pyrazole (Intermediate 2-G) |
| 39-33 | 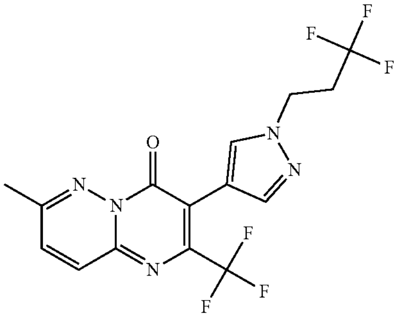 [SMILES: Cc1ccc2nc(C(F)(F)F)c(-c3cnn(CCC(F)(F)F)c3)c(=O)n2n1] | 7-methyl-2-(trifluoromethyl)-3-[1-(3,3,3-trifluoropropyl)-1H-pyrazol-4-yl]-4H-pyrimido[1,2-b]pyridazin-4-one | Product purified by reverse phase flash chroma-tography (C18, 0.1% HCOOH in water/MeCN as eluant, from 95:5 to 20:80) followed by flash chroma-tography ($SiO_2$, cyclohexane/EtOAc from 20:80 to 0:100) | 3-bromo-7-methyl-2-(trifluoromethyl) pyrimido[1,2-b]pyridazin-4-one (Intermediate 3-Z) and 4-(4,4,5,5-tetramethyl-1,3,2-dioxaborolan-2-yl)-1-(3,3,3-trifluoropropyl) pyrazole (Intermediate 2-D) |

TABLE 22-continued

| Ex. # | Chemical Structure | Name | Method Changes | Reagents |
|---|---|---|---|---|
| 39-34 | 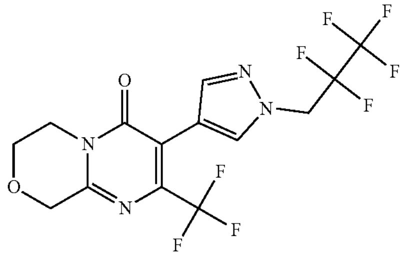 [SMILES: O=c1c(-c2cnn(CC(F)(F)C(F)(F)F)c2)c(C(F)(F)F)nc2n1CCOC2] | 3-[1-(2,2,3,3,3-pentafluoropropyl)-1H-pyrazol-4-yl]-2-(trifluoromethyl)-4H,6R,7H,9H-pyrimido[2,1-c][1,4]oxazin-4-one | Heated at 90° C. for 3 h Product purified by reverse phase flash chromatography (C18, 0.1% HCOOH in water/MeCN as eluant, from 95:5 to 30:70) followed by flash chromatography ($SiO_2$, cyclohexane/EtOAc from 100:0 to 60:40) | 3-bromo-2-(trifluoromethyl)-7,9-dihydro-6H-pyrimido[2,1-c][1,4]oxazin-4-one (Intermediate 3-AA) and 1-(2,2,3,3,3-pentafluoropropyl)-4-(4,4,5,5-tetramethyl-1,3,2-dioxaborolan-2-yl)pyrazole (Intermediate 2-G) |
| 39-35 | 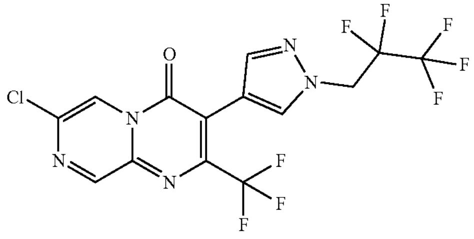 [SMILES: O=c1c(-c2cnn(CC(F)(F)C(F)(F)F)c2)c(C(F)(F)F)nc2cnc(Cl)cn12] | 7-chloro-3-[1-(2,2,3,3,3-pentafluoropropyl)-1H-pyrazol-4-yl]-2-(trifluoromethyl)-4H-pyrazino[1,2-a]pyrimidin-4-one | Heated at 90° C. for 3 h | 3-bromo-7-chloro-2-(trifluoromethyl)-4H-pyrazino[1,2-a]pyrimidin-4-one (Intermediate 4-E) and 1-(2,2,3,3,3-pentafluoropropyl)-4-(4,4,5,5-tetramethyl-1,3,2-dioxaborolan-2-yl)pyrazole (Intermediate 2-G) |
| 39-36 | 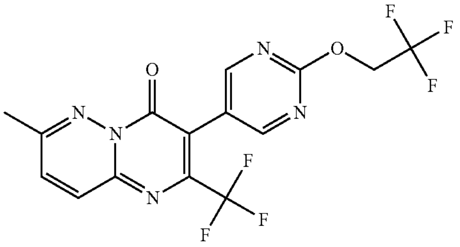 [SMILES: Cc1ccc2nc(C(F)(F)F)c(-c3cnc(OCC(F)(F)F)nc3)c(=O)n2n1] | 7-methyl-3-[2-(2,2,2-trifluoroethoxy)pyrimidin-5-yl]-2-(trifluoromethyl)-4H-pyrimido[1,2-b]pyridazin-4-one | Product further purified by RP chromatography (C18, $H_2O$/MeCN as eluant, from 95:5 to 20:80) | 3-bromo-7-methyl-2-(trifluoromethyl)pyrimido[1,2-b]pyridazin-4-one (Intermediate 3-Z) and [2-(2,2,2-trifluoroethoxy)pyrimidin-5-yl]boronic acid (Intermediate 4-Q) |
| 39-37 | 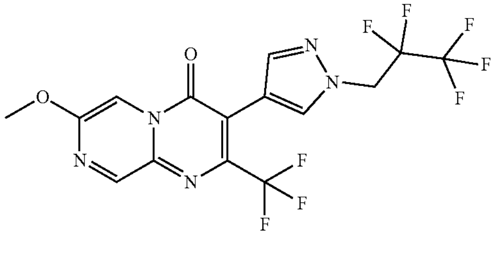 [SMILES: COc1cn2c(=O)c(-c3cnn(CC(F)(F)C(F)(F)F)c3)c(C(F)(F)F)nc2cn1] | 7-methoxy-3-[1-(2,2,3,3,3-pentafluoropropyl)-1H-pyrazol-4-yl]-2-(trifluoromethyl)-4H-pyrazino[1,2-a]pyrimidin-4-one | Heated at 90° C. for 3 h Following purification the product was triturated with diethyl | 3-bromo-7-methoxy-2-(trifluoromethyl)pyrazino[1,2-a]pyrimidin-4-one (Intermediate 4-F) and 1-(2,2,3,3,3-pentafluoropropyl)-4-(4,4,5,5- |

TABLE 22-continued

| Ex. # | Chemical Structure | Name | Method Changes | Reagents |
|---|---|---|---|---|
| | | | ether | tetramethyl-1,3,2-dioxaborolan-2-yl)pyrazole (Intermediate 2-G) |
| 39-38 | 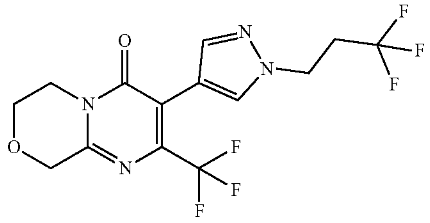 [SMILES: O=c1c(-c2cnn(CCC(F)(F)F)c2)c(C(F)(F)F)nc2n1CCOC2] | 2-(trifluoromethyl)-3-[1-(3,3,3-trifluoropropyl)-1H-pyrazol-4-yl]-4H,6H,7H,9H-pyrimido[2,1-c][1,4]oxazin-4-one | Heated at 90° C. for 16 h Product purified by reverse phase flash chromatography (C18, 0.1% HCOOH in water/MeCN as eluant, from 95:5 to 30:70) followed by flash chromatography ($SiO_2$, cyclohexane/EtOAc from 100:0 to 60:40) | 3-bromo-2-(trifluoromethyl)-7,9-dihydro-6H-pyrimido[2,1-c][1,4]oxazin-4-one (Intermediate 3-AA) and 4-(4,4,5,5-tetramethyl-1,3,2-dioxaborolan-2-yl)-1-(3,3,3-trifluoropropyl) pyrazole (Intermediate 2-D) |
| 39-39 | 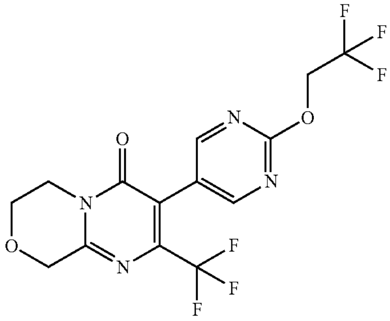 [SMILES: O=c1c(-c2cnc(OCC(F)(F)F)nc2)c(C(F)(F)F)nc2n1CCOC2] | 3-[2-(2,2,2-trifluoroethoxy) pyrimidin-5-yl]-2-(trifluoromethyl)-4H,6H,7H,9H-pyrimido[2,1-c][1,4]oxazin-4-one | Heated at 90° C. for 16 h Product purified by reverse phase flash chromatography (C18, 0.1% HCOOH in water/MeCN as eluant, from 95:5 to 50:50) followed by flash chromatography ($SiO_2$, cyclohexane/EtOAc from 100:0 to 40:60) | 3-bromo-2-(trifluoromethyl)-7,9-dihydro-6H-pyrimido[2,1-c][1,4]oxazin-4-one (Intermediate 3-AA) and [2-(2,2,2-trifluoroethoxy) pyrimidin-5-yl]boronic acid (Intermediate 4-Q) |
| 39-40 | 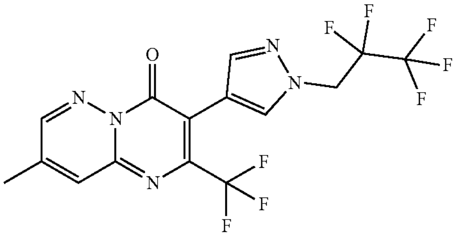 [SMILES: Cc1cnn2c(=O)c(-c3cnn(CC(F)(F)C(F)(F)F)c3)c(C(F)(F)F)nc2c1] | 8-methyl-3-[1-(2,2,3,3,3-pentafluoropropyl)-1H-pyrazol-4-yl]-2-(trifluoromethyl)-4H-pyrimido[1,2-b]pyridazin-4-one | Product purified by reverse phase flash chromatography (C18, 0.1% HCOOH in water/MeCN as eluant, from 95:5 | 3-bromo-8-methyl-2-(trifluoromethyl) pyrimido[1,2-b]pyridazin-4-one (Intermediate 3-AB) and 1-(2,2,3,3,3-pentafluoropropyl)-4-(4,4,5,5-tetramethyl-1,3,2- |

TABLE 22-continued

| Ex. # | Chemical Structure | Name | Method Changes | Reagents |
|---|---|---|---|---|
| | | | to 20:80) | dioxaborolan-2-yl)pyrazole (Intermediate 2-C) |
| 39-41 | 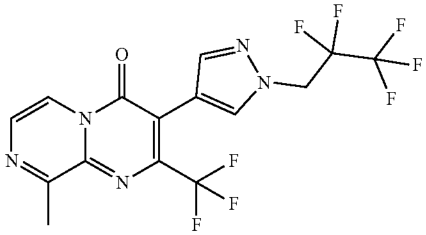 [SMILES: Cc1nccn2c(=O)c(-c3cnn(CC(F)(F)C(F)(F)F)c3)c(C(F)(F)F)nc12] | 9-methyl-3-[1-(2,2,3,3,3-pentafluoropropyl)-1H-pyrazol-4-yl]-2-(trifluoromethyl)-4H-pyrazino[1,2-a]pyrimidin-4-one | Product further purified by RP chroma-tography (C18, $H_2O$/MeCN as eluant, from 100:0 to 30:70) | 3-bromo-9-methyl-2-(trifluoromethyl) pyrazino[1,2-a]pyrimidin-4-one (Intermediate 4-H) and 1-(2,2,3,3,3-pentafluoropropyl)-4-(4,4,5,5-tetramethyl-1,3,2-dioxaborolan-2-yl)pyrazole (Intermediate 2-G) |
| 39-42 | 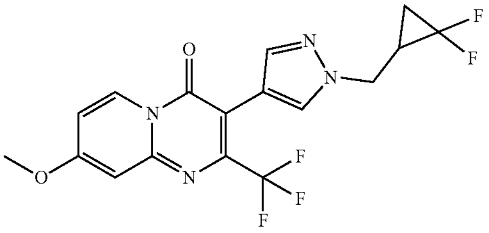 [SMILES: COc1ccn2c(=O)c(-c3cnn(CC4CC4(F)F)c3)c(C(F)(F)F)nc2c1] | 3-1-[(2,2-difluorocyclopropyl) methyl]-1H-pyrazol-4-yl}-8-methoxy-2-(trifluoromethyl)-4H-pyrido[1,2-a]pyrimidin-4-one | Heated at 90° C. for 4 h | 3-bromo-8-methoxy-2-(trifluoromethyl) pyrido[1,2-a]pyrimidin-4-one (Intermediate I-A) and 1-[(2,2-difluorocyclopropyl) methyl]-4-(4,4,5,5-tetramethyl-1,3,2-dioxaborolan-2-yl)pyrazole (Intermediate 4-T) |
| 39-43 | 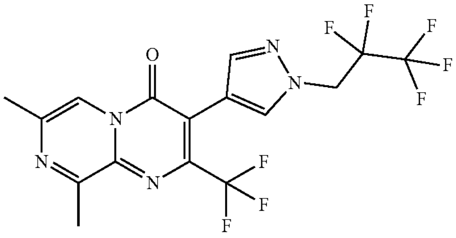 [SMILES: Cc1cn2c(=O)c(-c3cnn(CC(F)(F)C(F)(F)F)c3)c(C(F)(F)F)nc2c(C)n1] | 7,9-dimethyl-3-[1-(2,2,3,3,3-pentafluoropropyl)-1H-pyrazol-4-yl]-2-(trifluoromethyl)-4H-pyrazino[1,2-a]pyrimidin-4-one | Product further purified by RP chroma-tography (C18, $H_2O$/MeCN as eluant, from 100:0 to 30:70) | 3-bromo-7,9-dimethyl-2-(trifluoromethyl) pyrazino[1,2-a]pyrimidin-4-one (Intermediate 4-I) and 1-(2,2,3,3,3-pentafluoropropyl)-4-(4,4,5,5-tetramethyl-1,3,2-dioxaborolan-2-yl)pyrazole (Intermediate 2-G) |
| 39-44 | 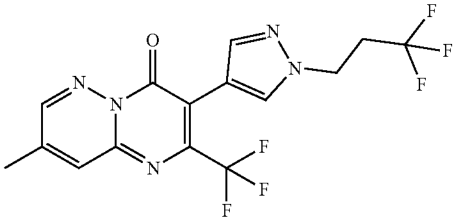 [SMILES: Cc1cnn2c(=O)c(-c3cnn(CCC(F)(F)F)c3)c(C(F)(F)F)nc2c1] | 8-methyl-2-(trifluoromethyl)-3-[1-(3,3,3-trifluoropropyl)-1H-pyrazol-4-yl]-4H-pyrimido[1,2-b)pyridazin-4-one | Heated at 90° C. for 1 h Product purified by reverse phase flash chroma-tography (C18, 0.1% HCOOH in water/MeCN as eluant, from 95:5 | 3-bromo-8-methyl-2-(trifluoromethyl) pyrimido[1,2-b]pyridazin-4-one (Intermediate 3-AB) and 4-(4,4,5,5-tetramethyl-1,3,2-dioxaborolan-2-yl)-1-(3,3,3-trifluoropropyl) pyrazole (Intermediate |

TABLE 22-continued

| Ex. # | Chemical Structure | Name | Method Changes | Reagents |
|---|---|---|---|---|
| | | | to 20:80) followed by flash chroma-tography ($SiO_2$, EtOAc) | 2-D) |
| 39-45 | 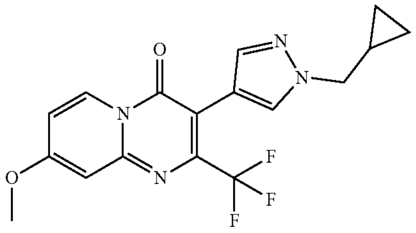 [SMILES: COc1ccn2c(=O)c(-c3cnn(CC4CC4)c3)c(C(F)(F)F)nc2c1] | 3-[1-(cyclopropylmethyl)-1H-pyrazol-4-yl]-8-methoxy-2-(trifluoromethyl)-4H-pyrido[1,2-a]pyrimidin-4-one | | 3-bromo-8-methoxy-2-(trifluoromethyl) pyrido[1,2-a]pyrimidin-4-one (Intermediate 1-A) and 1-(cyclopropylmethyl)-4-(4,4,5,5-tetramethyl-1,3,2-dioxaborolan-2-yl)pyrazole (Intermediate 4-U) |
| 39-46 | 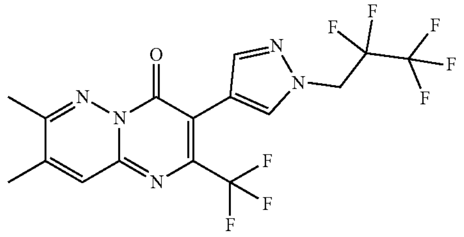 [SMILES: Cc1cc2nc(C(F)(F)F)c(-c3cnn(CC(F)(F)C(F)(F)F)c3)c(=O)n2nc1C] | 7,8-dimethyl-3-[1-(2,2,3,3,3-pentafluoropropyl)-1H-pyrazol-4-yl]-2-(trifluoromethyl)-4H-pyrimido[1,2-b]pyridazin-4-one | Heated at 90° C. for 3 h Product purified by reverse phase flash chroma-tography (C18, 0.1% HCOOH in water/ MeCN as eluant, from 95:5 to 20:80) | 3-bromo-7,8-dimethyl-2-(trifluoromethyl) pyrimido[1,2-b]pyridazin-4-one (Intermediate 3-AD) and 1-(2,2,3,3,3-pentafluoropropyl)-4-(4,4,5,5-tetramethyl-1,3,2-dioxaborolan-2-yl)pyrazole (Intermediate 2-G) |
| 39-47 | 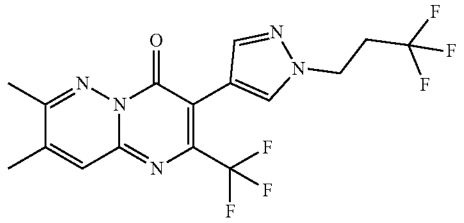 [SMILES: Cc1cc2nc(C(F)(F)F)c(-c3cnn(CCC(F)(F)F)c3)c(=O)n2nc1C] | 7,8-dimethyl-2-(trifluoromethyl)-3-[1-(3,3,3-trifluoropropyl)-1H-pyrazol-4-yl]-4H-pyrimido[1,2-b]pyridazin-4-one | Heated at 90° C. for 3 h Product purified by reverse phase flash chroma-tography (C18, 0.1% HCOOH in water/ MeCN as eluant, from 95:5 to 20:80) followed by flash chroma-tography ($SiO_2$, cyclohexane/ EtOAc from 50:50 to 0:100) | 3-bromo-7,8-dimethyl-2-(trifluoromethyl) pyrimido[1,2-b]pyridazin-4-one (Intermediate 3-AD) and 4-(4,4,5,5-tetramethyl-1,3,2-dioxaborolan-2-yl)-1-(3,3,3-trifluoropropyl) pyrazole (Intermediate 2-D) |

TABLE 22-continued

| Ex. # | Chemical Structure | Name | Method Changes | Reagents |
|---|---|---|---|---|
| 39-48 | 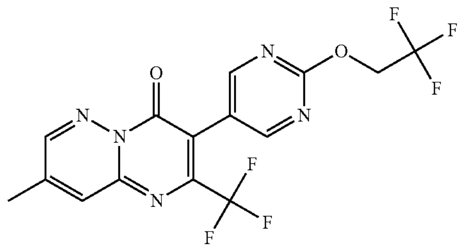 [SMILES: Cc1cnn2c(=O)c(-c3cnc(OCC(F)(F)F)nc3)c(C(F)(F)F)nc2c1] | 8-methyl-3-[2-(2,2,2-trifluoroethoxy)pyrimidin-5-yl]-2-(trifluoromethyl)-4H-pyrimido[1,2-b]pyridazin-4-one | Product purified by reverse phase flash chromatography (C18, 0.1% HCOOH in water/MeCN as eluant, from 95:5 to 20:80) followed by flash chromatography ($SiO_2$, EtOAc) | 3-bromo-8-methyl-2-(trifluoromethyl)pyrimido[1,2-b]pyridazin-4-one (Intermediate 3-AB) and [2-(2,2,2-trifluoroethoxy)pyrimidin-5-yl]boronic acid (Intermediate 4-Q) |
| 39-49 | 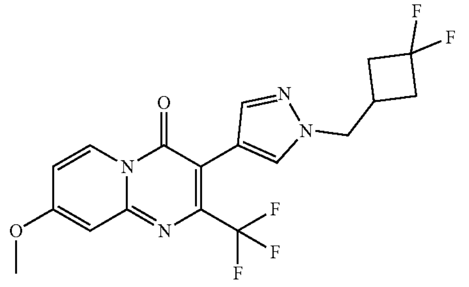 [SMILES: COc1ccn2c(=O)c(-c3cnn(CC4CC(F)(F)C4)c3)c(C(F)(F)F)nc2c1] | 3-{1-[(3,3-difluorocyclobutyl)methyl]-1H-pyrazol-4-yl}-8-methoxy-2-(trifluoromethyl)-4H-pyrido[1,2-a]pyrimidin-4-one | Heated at 90° C. for 36 h Product repurified by reverse phase HPLC | 3-bromo-8-methoxy-2-(trifluoromethyl)pyrido[1,2-a]pyrimidin-4-one (Intermediate 1-A) and 1-[(3,3-difluorocyclobutyl)methyl]-4-(4,4,5,5-tetramethyl-1,3,2-dioxaborolan-2-yl)pyrazole (Intermediate 4-V) |
| 39-50 | 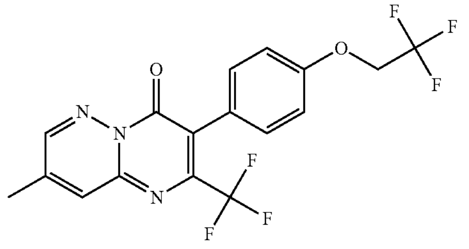 [SMILES: Cc1cnn2c(=O)c(-c3ccc(OCC(F)(F)F)cc3)c(C(F)(F)F)nc2c1] | 8-methyl-3-[4-(2,2,2-trifluoroethoxy)phenyl]-2-(trifluoromethyl)-4H-pyrimido[1,2-b]pyridazin-4-one | Product purified by reverse phase flash chromatography (C18, 0.1% HCOOH in water/MeCN as eluant, from 90:10 to 20:80) followed by flash chromatography ($SiO_2$, cyclohexane/EtOAc from 50:50 to 0:100) | 3-bromo-8-methyl-2-(trifluoromethyl)pyrimido[1,2-b]pyridazin-4-one (Intermediate 3-AB) and 4,4,5,5-tetramethyl-2-[4-(2,2,2-trifluoroethoxy)phenyl]-1,3,2-dioxaborolane (Intermediate 4-W) |

TABLE 22-continued

| Ex. # | Chemical Structure | Name | Method Changes | Reagents |
|---|---|---|---|---|
| 39-51 | 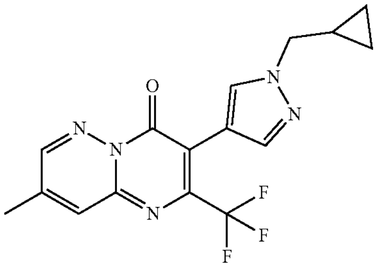 [SMILES: Cc1cnn2c(=O)c(-c3cnn(CC4CC4)c3)c(C(F)(F)F)nc2c1] | 3-[1-(cyclopropylmethyl)-1H-pyrazol-4-yl]-8-methyl-2-(trifluoromethyl)-4H-pyrimido[1,2-b]pyridazin-4-one | Product purified by reverse phase flash chroma-tography (C18, 0.1% HCOOH in water/MeCN as eluant, from 95:5 to 20:80) followed by flash chroma-tography ($SiO_2$, cyclohexane/EtOAc 20:80) | 3-bromo-8-methyl-2-(trifluoromethyl)pyrimido[1,2-b]pyridazin-4-one (Intermediate 3-AB) and 1-(cyclopropylmethyl)-4-(4,4,5,5-tetramethyl-1,3,2-dioxaborolan-2-yl)pyrazole (Intermediate 4-U) |
| 39-52 | 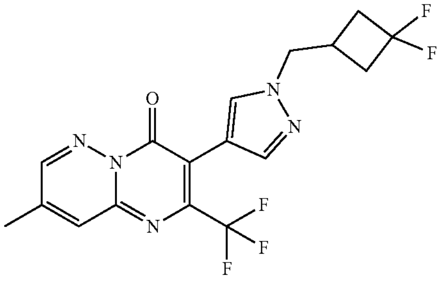 [SMILES: Cc1cnn2c(=O)c(-c3cnn(CC4CC(F)(F)C4)c3)c(C(F)(F)F)nc2c1] | 3-{1-[(3,3-difluorocyclobutyl)methyl]-1H-pyrazol-4-yl)-8-methyl-2-(trifluoromethyl)-4H-pyrimido[1,2-b]pyridazin-4-one | Heated at 90° C. for 20 h Product purified by reverse phase flash chroma-tography (C18, 0.1% HCOOH in water/MeCN as eluant, from 95:5 to 20:80) followed by flash chroma-tography ($SiO_2$, cyclohexane/EtOAc 20:80) | 3-bromo-8-methyl-2-(trifluoromethyl)pyrimido[1,2-b]pyridazin-4-one (Intermediate 3-AB) and 1-[(3,3-difluorocyclobutyl)methyl]-4-(4,4,5,5-tetramethyl-1,3,2-dioxaborolan-2-yl)pyrazole (Intermediate 4-V) |
| 39-53 | 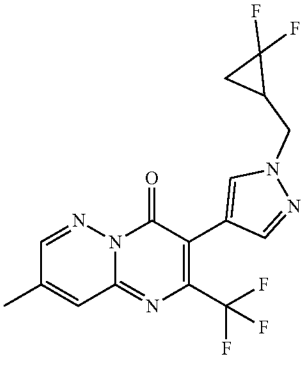 [SMILES: Cc1cnn2c(=O)c(-c3cnn(CC4CC4(F)F)c3)c(C(F)(F)F)nc2c1] | 3-{1-[(2,2-difluorocyclopropyl)methyl]-1H-pyrazol-4-yl}-8-methyl-2-(trifluoromethyl)-4H-pyrimido[1,2-b]pyridazin-4-one | Heated at 90° C. for 18 h Product purified by reverse phase flash chroma-tography (C18, 0.1% HCOOH in water/MeCN as eluant, from 95:5 to 20:80) followed by flash chroma-tography ($SiO_2$, cyclohexane/EtOAc from 50:50 to 0:100) | 3-bromo-8-methyl-2-(trifluoromethyl)pyrimido[1,2-b]pyridazin-4-one (Intermediate 3-AB) and 1-[(2,2-difluorocyclopropyl)methyl]-4-(4,4,5,5-tetramethyl-1,3,2-dioxaborolan-2-yl)pyrazole (Intermediate 4-T) |

TABLE 22-continued

| Ex. # | Chemical Structure | Name | Method Changes | Reagents |
|---|---|---|---|---|
| 39-54 | 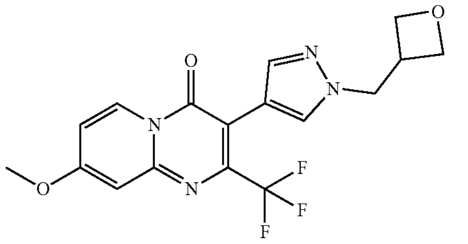 [SMILES: COc1ccn2c(=O)c(-c3cnn(CC4COC4)c3)c(C(F)(F)F)nc2c1] | 8-methoxy-3-{1-[(oxetan-3-yl)methyl]-1H-pyrazol-4-yl}-2-(trifluoromethyl)-4H-pyrido[1,2-a]pyrimidin-4-one | Heated at 90° C. for 3 h Product repurified by reverse phase flash chromatography (C18, 0.1% HCOOH in water/MeCN as eluant, from 95:5 to 40:60) | 3-bromo-8-methoxy-2-(trifluoromethyl)pyrido[1,2-a]pyrimidin-4-one (Intermediate 1-A) and1-(oxetan-3-ylmethyl)-4-(4,4,5,5-tetramethyl-1,3,2-dioxaborolan-2-yl)pyrazole (Intermediate 4-X) |
| 39-55 | 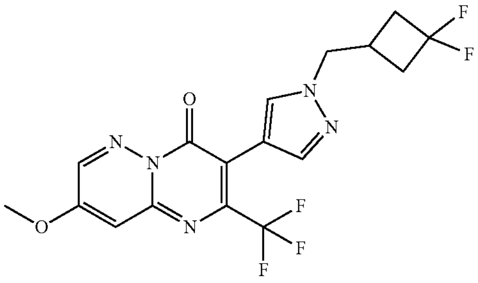 [SMILES: COc1cnn2c(=O)c(-c3cnn(CC4CC(F)(F)C4)c3)c(C(F)(F)F)nc2c1] | 3-{1-[(3,3-difluorocyclobutyl)methyl)-1H-pyrazol-4-yl}-8-methoxy-2-(trifluoromethyl)-4H-pyrimido[1,2-b]pyridazin-4-one | Product triturated with EtOAc/MeOH 3:2 | 3-bromo-8-methoxy-2-(trifluoromethyl)pyrimido[1,2-b]pyridazin-4-one (Intermediate 3-M) and 1-[(3,3-difluorocyclobutyl)methyl]-4-(4,4,5,5-tetramethyl-1,3,2-dioxaborolan-2-yl)pyrazole (Intermediate 4-V) |
| 39-56 | 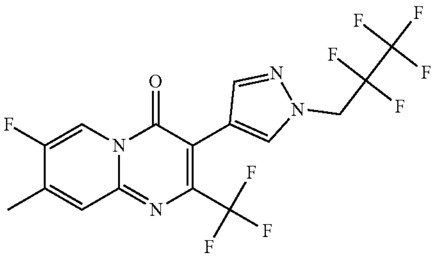 [SMILES: Cc1cc2nc(C(F)(F)F)c(-c3cnn(CC(F)(F)C(F)(F)F)c3)c(=O)n2cc1F] | 7-fluoro-8-methyl-3-[1-(2,2,3,3,3-pentafluoropropyl)-1H-pyrazol-4-yl]-2-(trifluoromethyl)-4H-pyrido[1,2-a]pyrimidin-4-one | Heated at 90° C. for 4 h Product repurified by reverse phase flash chromatography (C18, water/MeCN as eluant, from 80:20 to 20:80) | 3-bromo-7-fluoro-8-methyl-2-(trifluoromethyl)pyrido[1,2-a]pyrimidin-4-one (Intermediate 3-AF) and 1-(2,2,3,3,3-pentafluoropropyl)-4-(4,4,5,5-tetramethyl-1,3,2-dioxaborolan-2-yl)pyrazole (Intermediate 2-G) |
| 39-57 | 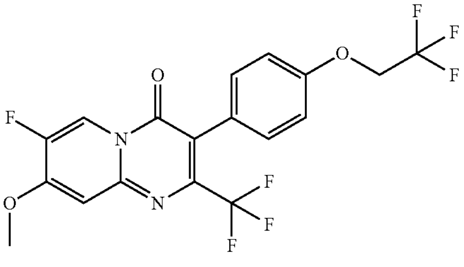 [SMILES: COc1cc2nc(C(F)(F)F)c(-c3ccc(OCC(F)(F)F)cc3)c(=O)n2cc1F] | 7-fluoro-8-methoxy-3-[4-(2,2,2-trifluoroethoxy)phenyl]-2-(trifluoromethyl)-4H-pyrido[1,2-a]pyrimidin-4-one | Product repurified by reverse phase flash chromatography (C18, 0.1% HCOOH in water/MeCN as eluant, from 100:0 to 34:66) | 3-bromo-7-fluoro-8-methoxy-2-(trifluoromethyl)-4H-pyrido[1,2-a]pyrimidin-4-one (Intermediate 3-L) and 4,4,5,5-tetramethyl-2-[4-(2,2,2-trifluoroethoxy)phenyl]-1,3,2-dioxaborolane (Intermediate 4-W) |

TABLE 22-continued

| Ex. # | Chemical Structure | Name | Method Changes | Reagents |
|---|---|---|---|---|
| 39-58 | 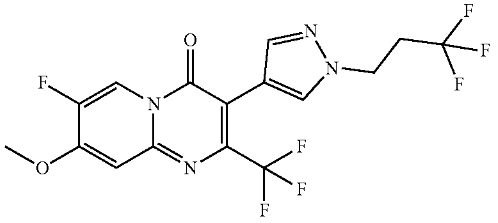 [SMILES: COc1cc2nc(C(F)(F)F)c(-c3cnn(CCC(F)(F)F)c3)c(=O)n2cc1F] | 7-fluoro-8-methoxy-2-(trifluoromethyl)-3-[1-(3,3,3-trifluoropropyl)-1H-pyrazol-4-yl]-4H-pyrido[1,2-a]pyrimidin-4-one | Heated at 90° C. for 3 h Product repurified by reverse phase flash chromatography (C18, 0.1% HCOOH in water/MeCN as eluant, from 100:0 to 43:57) | 3-bromo-7-fluoro-S-methoxy-2-(trifluoromethyl)-4H-pyrido[1,2-a]pyrimidin-4-one (Intermediate 3-L) and 4-(4,4,5,5-tetramethyl-1,3,2-dioxaborolan-2-yl)-1-(3,3,3-trifluoropropyl) pyrazole (Intermediate 2-D) |
| 39-59 | 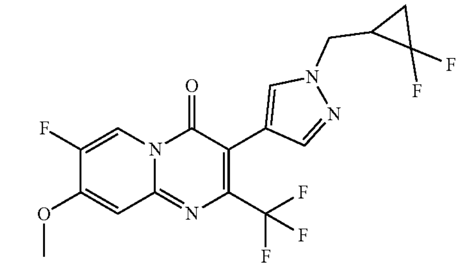 [SMILES: COc1cc2nc(C(F)(F)F)c(-c3cnn(CC4CC4(F)F)c3)c(=O)n2cc1F] | 3-{1-[(2,2-difluorocyclopropyl) methyl]-1H-pyrazol-4-yl}-7-fluoro-8-methoxy-2-(trifluoromethyl)-4H-pyrido[1,2-a]pyrimidin-4-one | Heated at 100° C. for 5 h Product repurified by reverse phase flash chromatography (C18, 0.1% HCOOH in water/MeCN as eluant, from 100:0 to 50:50) | 3-bromo-7-fluoro-8-methoxy-2-(trifluoromethyl)-4H-pyrido[1,2-a]pyrimidin-4-one (Intermediate 3-L) and 1-[(2,2-difluorocyclopropyl) methyl]-4-(4,4,5,5-tetramethyl-1,3,2-dioxaborolan-2-yl)pyrazole (Intermediate 4-T) |

Method 40

Example 40-1: 7-Methoxy-3-[1-(2,2,3,3,3-pentafluoropropyl)-1H-pyrazol-4-yl]-2-(trifluoromethyl)-4H-[1,3]diazino[1,2-a]pyrimidin-4-one

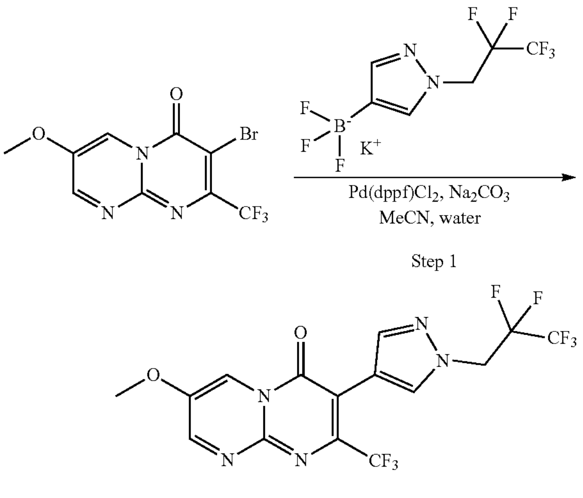

Step 1: 7-methoxy-3-[1-(2,2,3,3,3-pentafluoropropyl)-1H-pyrazol-4-yl]-2-(trifluoromethyl)-4H-[1,3]diazino[1,2-a]pyrimidin-4-one A microwave reactor vial was charged with 3-bromo-7-methoxy-2-(trifluoromethyl)pyrimido[1,2-a]pyrimidin-4-one (Intermediate 4-B, 100 mg, 0.31 mmol), potassium trifluoro-[1-(2,2,3,3,3-pentafluoropropyl)pyrazol-4-yl]boranuide (Intermediate 4-S, 142 mg, 0.460 mmol) in MeCN (3 mL) and sodium carbonate (82 mg, 0.770 mmol) in water (0.700 mL) was added. The mixture was degassed with nitrogen for 5 min then [1,1'-bis(diphenylphosphino)ferrocene]dichloropalladium(II) (23 mg, 0.030 mmol) was added and the mixture was heated under microwave irradiation at 120° C. for 30 minutes. The mixture was partioned between water and EtOAc and the aqueous phase extracted with EtOAc. The combined organic phase was dried over sodium sulfate, filtered and concentrated under vacuum. The crude product was purified by flash chromatography ($SiO_2$, cyclohexane/EtOAc from 95:5 to 10:90 EtOAc) followed by reverse phase flash chromatography (C18, 0.1% HCOOH in water/MeCN as eluant, from 100:0 to 0:100) to obtain 7-methoxy-3-[1-(2,2,3,3,3-pentafluoropropyl)-1H-pyrazol-4-yl]-2-(trifluoromethyl)-4H-[1,3]diazino[1,2-a]pyrimidin-4-one as a yellow solid (17 mg, 0.039 mmol, 13% yield). LC/MS (ESI$^+$) m/z=444.3 $[M+H]^+$. $^1H$ NMR (500 MHz, DMSO-$d_6$) δ 4.01 (s, 3H), 5.31 (t, J=14.96 Hz, 2H), 7.73 (s, 1H), 8.10 (s, 1H), 8.72 (d, J=3.29 Hz, 1H), 9.22 (d, J=3.29 Hz, 1H).

Example 40-2 listed in Table 23 was prepared following the procedure described in Method 40, Step 1, above as follows.

TABLE 23

| Ex. # | Chemical Structure | Name | Method Changes | Reagents |
|---|---|---|---|---|
| 40-2 | 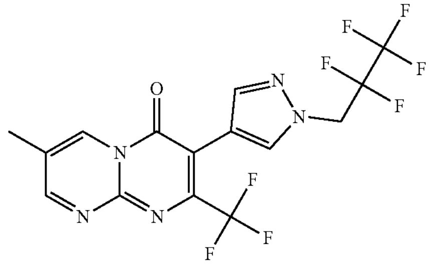 [SMILES: Cc1cnc2nc(C(F)(F)F)c(-c3cnn(CC(F)(F)C(F)(F)F)c3)c(=O)n2c1] | 7-methyl-3-[1-(2,2,3,3,3-pentafluoropropyl)-1H-pyrazol-4-yl]-2-(trifluoromethyl)-4H-[1,3]diazino[1,2-a]pyrimidin-4-one | Product purified by reverse phase flash chromatography (C18, 0.1% HCOOH in water/MeCN as eluant, from 95:5 to 20:80) followed by flash chromatography ($SiO_2$, DCM/MeOH from 99:1 to 95:5) | 3-bromo-7-methyl-2-(trifluoromethyl)pyrimido[1,2-a]pyrimidin-4-one (Intermediate 4-G) and potassium trifluoro-[1-(2,2,3,3,3-pentafluoropropyl)pyrazol-4-yl]boranuide (Intermediate 4-S) |

Method 41

Example 41-1: 7-Chloro-8-methyl-3-[1-(2,2,3,3,3-pentafluoropropyl)-1H-pyrazol-4-yl]-2-(trifluoromethyl)-4H-pyrido[1,2-a]pyrimidin-4-one

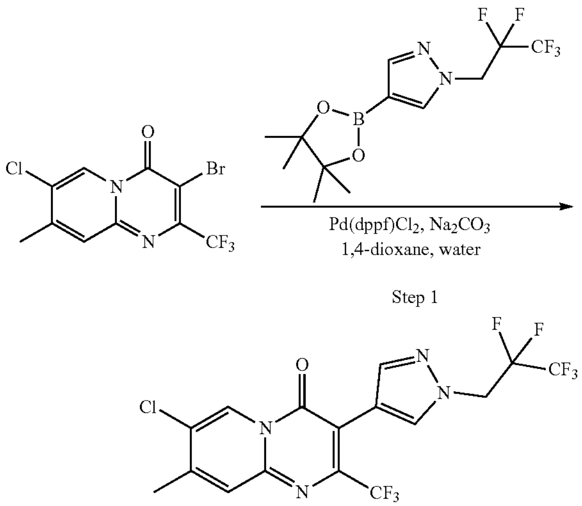

Step 1: 7-chloro-8-methyl-3-[1-(2,2,3,3,3-pentafluoropropyl)-1H-pyrazol-4-yl]-2-(trifluoromethyl)-4H-pyrido[1,2-a]pyrimidin-4-one A screw-capped vial was charged with 3-bromo-7-chloro-8-methyl-2-(trifluoromethyl)pyrido[1,2-a]pyrimidin-4-one (Intermediate 3-AE, 50 mg, 0.15 mmol), 1,4-Dioxane (2.4 mL), water (0.4 mL), [1,1'-Bis(diphenylphosphino)ferrocene]dichloropalladium(II) (11 mg, 0.01 mmol), 1-(2,2,3,3,3-pentafluoropropyl)-4-(4,4,5,5-tetramethyl-1,3,2-dioxaborolan-2-yl)pyrazole (Intermediate 2-G, 53 mg, 0.16 mmol), and sodium carbonate (39 mg, 0.37 mmol). The mixture was degassed with nitrogen for 10 min then it was stirred at 70° C. for 4 h. The reaction mixture was partitioned between water and EtOAc and extracted twice with EtOAc. The combined organic phase was dried over Na2SO4, filtered and concentrated under vacuum. The resulting crude material was purified by flash chromatography ($SiO_2$, eluant cyclohexane/EtOAc from 90:10 to 60:40) followed by reverse phase flash chromatography (C18, Eluant $H_2O$+HCOOH 0.1%/MeCN from 80:20 to 0:100) to give 7-chloro-8-methyl-3-[o-(2,2,3,3,3-pentafluoropropyl)pyrazol-4-yl]-2-(trifluoromethyl)pyrido[1,2-a]pyrimidin-4-one as a white solid (29 mg, 0.063 mmol, 43% yield). LC/MS ($ESI^+$) m/z=461.0/462.9 $[M+H]^+$. $^1H$ NMR (500 MHz, DMSO-$d_6$) δ 2.53 (s, 3H), 5.30 (t, J=15.0 Hz, 2H), 7.70 (s, 1H), 7.95 (s, 1H), 8.07 (s, 1H), 9.00 (s, 1H).

Examples 41-2 to 41-4 listed in Table 24 were prepared following the procedure described in Method 41, Step 1, above as follows.

TABLE 24

| Ex. # | Chemical Structure | Name | Method Changes | Reagents |
|---|---|---|---|---|
| 41-2 | 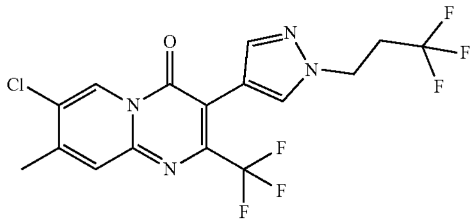 [SMILES: Cc1cc2nc(C(F)(F)F)c(-c3cnn(CCC(F)(F)F)c3)c(=O)n2cc1Cl] | 7-chloro-8-methyl-2-(trifluoromethyl)-3-[1-(3,3,3-trifluoropropyl)-1H-pyrazol-4-yl]-4H-pyrido[1,2-a]pyrimidin-4-one | Purified by flash chromatography ($SiO_2$, cyclohexane/EtOAc 80:20 to 50:50) | 3-bromo-7-chloro-8-methyl-2-(trifluoromethyl)pyrido[1,2-a]pyrimidin-4-one (Intermediate 3-AE) and 4-(4,4,5,5-tetramethyl-1,3,2-dioxaborolan-2-yl)-1-(3,3,3-trifluoropropyl)pyrazole (Intermediate 2-D) |

TABLE 24-continued

| Ex. # | Chemical Structure | Name | Method Changes | Reagents |
|---|---|---|---|---|
| 41-3 | 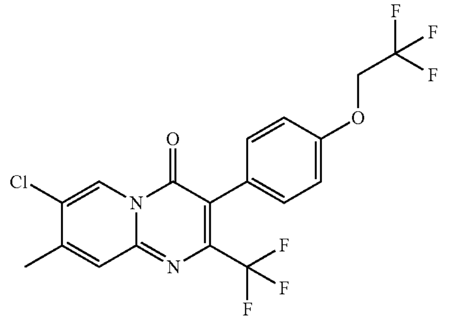 [SMILES: Cc1cc2nc(C(F)(F)F)c(-c3ccc(OCC(F)(F)F)cc3)c(=O)n2cc1Cl] | 7-chloro-8-methyl-3-[4-(2,2,2-trifluoroethoxy)phenyl]-2-(trifluoromethyl)-4H-pyrido[1,2-a]pyrimidin-4-one | Purified by flash chromatography ($SiO_2$, cyclohexane/EtOAc 90:10 to 60:40) | 3-bromo-7-chloro-8-methyl-2-(trifluoromethyl)pyrido[1,2-a]pyrimidin-4-one (Intermediate 3-AE) and 4,4,5,5-tetramethyl-2-[4-(2,2,2-trifluoroethoxy)phenyl]-1,3,2-dioxaborolane (Intermediate 4-W) |
| 41-4 | 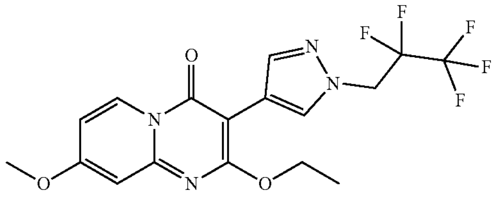 [SMILES: CCOc1nc2cc(OC)ccn2c(=O)c1-c1cnn(CC(F)(F)C(F)(F)F)c1] | 2-ethoxy-8-methoxy-3-[1-(2,2,3,3,3-pentafluoropropyl)-1H-pyrazol-4-yl]-4H-pyrido[1,2-a]pyrimidin-4-one | Heated at 100° C. for 45 min Product repurified by reverse phase flash chromatography (C18, 0.1% HCOOH in water/MeCN as eluant, from 100:0 to 50:50) | 3-bromo-2-ethoxy-8-methoxy-4H-pyrido[1,2-a]pyrimidin-4-one (Intermediate-4-O) and 1-(2,2,3,3,3-pentafluoropropyl)-4-(4,4,5,5-tetramethyl-1,3,2-dioxaborolan-2-yl)pyrazole (Intermediate 2-G) |

Example 42

7-Fluoro-8-methoxy-3-[1-(2,2,3,3,3-pentafluoropropyl)-1H-pyrazol-4-yl]-2-(trifluoromethyl)-4H-[1,3]diazino[1,2-a]pyrimidin-4-one

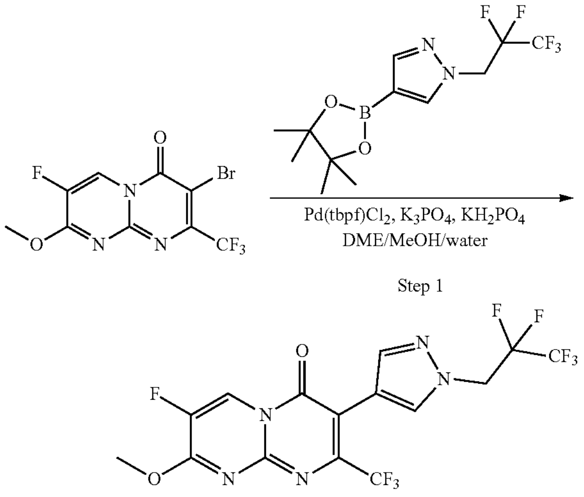

Step 1: 7-fluoro-8-methoxy-3-[1-(2,2,3,3,3-pentafluoropropyl)-1H-pyrazol-4-yl]-2-(trifluoromethyl)-4H-[1,3]diazino[1,2-a]pyrimidin-4-one A mixture of 1,2-dimethoxyethane (9 mL), methanol (5.5 mL) and water (1.9 mL) was degassed for 10 minutes then 7-bromo-3-fluoro-2-methoxy-8-(trifluoromethyl)pyrimido[1,2-a]pyrimidin-6-one (Intermediate 3-AC, 96 mg, 0.27 mmol), 1-(2,2,3,3,3-pentafluoropropyl)-4-(4,4,5,5-tetramethyl-1,3,2-dioxaborolan-2-yl)pyrazole (Intermediate 2-G, 174 mg, 0.53 mmol), [1,1'-Bis(di-tert-butylphosphino)ferrocene]dichloropalladium(II) (17 mg, 0.03 mmol), potassium dihydrogen phosphate (38 mg, 0.27 mmol) and potassium tripotassium phosphate (59 mg, 0.27 mmol) were added. The mixture was degassed for 10 minutes, then it was left stirring at room temperature overnight. Further 1-(2,2,3,3,3-pentafluoropropyl)-4-(4,4,5,5-tetramethyl-1,3,2-dioxaborolan-2-yl)pyrazole (Intermediate 2-G, 174 mg, 0.53 mmol) and [1,1'-Bis(di-tert-butylphosphino)ferrocene]dichloropalladium(II) (17 mg, 0.03 mmol) were added and the mixture was stirred for a further 48 hr at room temperature. EtOAc and $H_2O$ were added, phases were separated and organic phase was dried over Na2SO4, filtered and concentrated. The obtained crude was purified twice by flash-chromatography ($SiO_2$, cyclohexane/EtOAc from 100:0 to 20:80, then DCM/MeCN 100:0 to 40:60) to give 3-fluoro-2-methoxy-7-[1-(2,2,3,3,3-pentafluoropropyl)pyrazol-4-yl]-8-(trifluoromethyl)pyrimido[1,2-a]pyrimidin-6-one as a white solid. (34 mg, 0.074 mmol, 28% yield). LC/MS ($ESI^+$) m/z=462 $[M+H]^+$. $^1$H NMR (I H NMR (500 MHz, DMSO-$d_6$) δ 4.20 (s, 3H), 5.29 (t, J=15.0 Hz, 2H), 7.69 (s, 1H), 8.06 (s, 1H), 9.29 (d, J=5.2 Hz, 1H).

Example 43

7-Fluoro-8-hydroxy-3-[1-(2,2,3,3,3-pentafluoropropyl)-1H-pyrazol-4-yl]-2-(trifluoromethyl)-4H-pyrido[1,2-a]pyrimidin-4-one

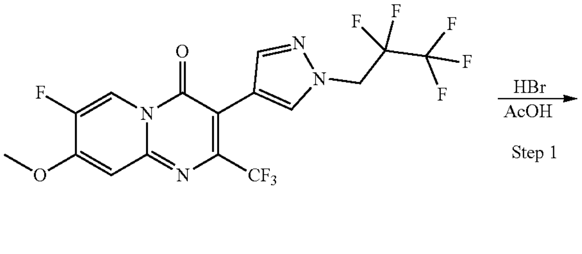

-continued

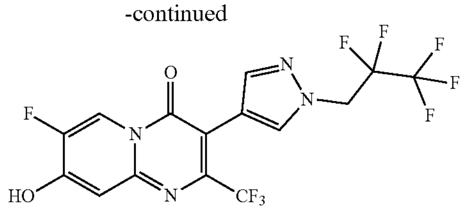

Step 1: 7-fluoro-8-hydroxy-3-[1-(2,2,3,3,3-pentafluoropropyl)-1H-pyrazol-4-yl]-2-(trifluoromethyl)-4H-pyrido[1,2-a]pyrimidin-4-one A mixture of 7-fluoro-8-methoxy-3-[1-(2,2,3,3,3-pentafluoropropyl)pyrazol-4-yl]-2-(trifluoromethyl)pyrido[1,2-a]pyrimidin-4-one (Example 33, 31 mg, 0.070 mmol) and 33% hydrogen bromide in acetic acid (0.1 mL) was stirred at 90° C. for 2 h. The mixture was partioned between water and EtOAc. The organic phase was dried over $Na_2SO_4$, filtered and concentrated under vacuum. The crude material was triturated in DCM then purified by flash chromatography ($SiO_2$, DCM/MeOH as eluant, from 100:0 to 50:50). The resulting product was tritured in EtOAc, filtered and the solid collected to afforded 7-fluoro-8-hydroxy-3-[1-(2,2,3,3,3-pentafluoropropyl)-1H-pyrazol-4-yl]-2-(trifluoromethyl)-4H-pyrido[1,2-a]pyrimidin-4-one as a pale yellow solid (6.5 mg, 0.015 mmol, 22% yield). LC/MS ($ESI^+$) m/z=447.3 $[M+H]^+$. $^1H$ NMR (500 MHz, DMSO-$d_6$) δ 5.19 (t, J=14.96 Hz, 2H), 6.12 (d, J=8.78 Hz, 1H), 7.50 (s, 1H), 7.78 (s, 1H), 8.52 (d, J=7.96 Hz, 1H).

Example 44

8-Hydroxy-3-[1-(2,2,3,3,3-pentafluoropropyl)-1H-pyrazol-4-yl]-2-(trifluoromethyl)-4H-pyrimido[1,2-b]pyridazin-4-one

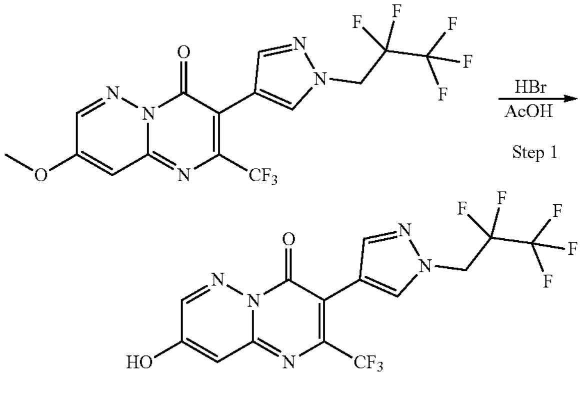

Step 1: 8-hydroxy-3-[1-(2,2,3,3,3-pentafluoropropyl)-1H-pyrazol-4-yl]-2-(trifluoromethyl)-4H-pyrimido[1,2-b]pyridazin-4-one A mixture of 8-methoxy-3-[1-(2,2,3,3,3-pentafluoropropyl)-1H-pyrazol-4-yl]-2-(trifluoromethyl)-4H-pyrimido[1,2-b]pyridazin-4-one (Example 34, 63 mg, 0.070 mmol) and 33% hydrogen bromide in acetic acid (0.5 mL) was stirred at 90° C. for 5 h. The mixture was partioned between water and EtOAc. The organic phase was dried over Na2SO4, filtered and concentrated under vacuum to give 8-hydroxy-3-[1-(2,2,3,3,3-pentafluoropropyl)-1H-pyrazol-4-yl]-2-(trifluoromethyl)-4H-pyrimido[1,2-b]pyridazin-4-one (48 mg, 0.11 mmol, 83% yield). LC/MS ($ESI^+$) m/z=430.0 $[M+H]^+$. $^1H$ NMR (500 MHz, DMSO-$d_6$) δ 5.27 (t, J=15.0 Hz, 2H), 7.03 (d, J=2.7 Hz, 1H), 7.65 (s, 1H), 8.01 (s, 1H), 8.68 (d, J=2.7 Hz, 1H), 11.55-13.07 (m, 1H).

Examples 45 and 46

Example 45: 8-(Fluoromethoxy)-3-[1-(2,2,3,3,3-pentafluoropropyl)-1H-pyrazol-4-yl]-2-(trifluoromethyl)-4H-pyrido[1,2-a]pyrimidin-4-one and Example 46: 8-(Chloromethoxy)-3-[1-(2,2,3,3,3-pentafluoropropyl)-1H-pyrazol-4-yl]-2-(trifluoromethyl)-4H-pyrido[1,2-a]pyrimidin-4-one

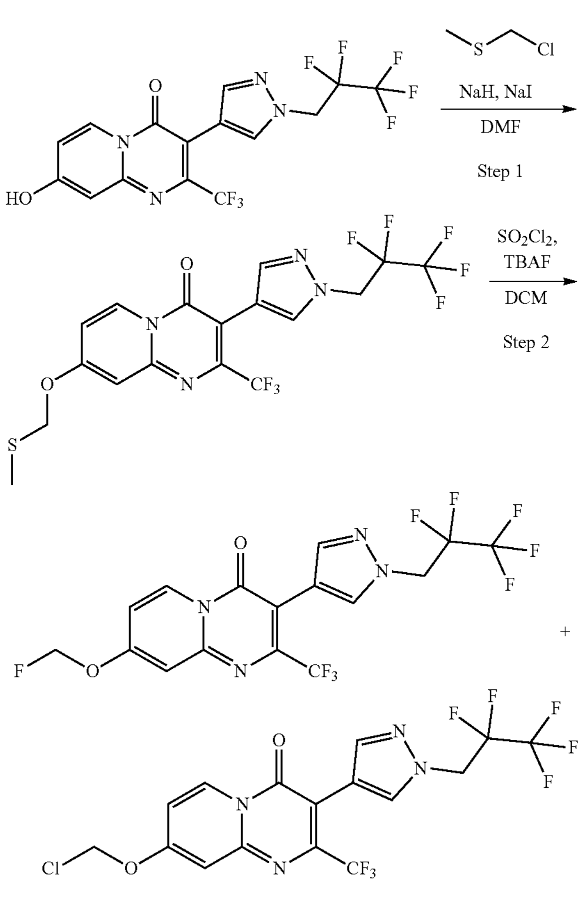

Step 1: 8-(methylsulfanylmethoxy)-3-[1-(2,2,3,3,3-pentafluoropropyl)-1H-pyrazol-4-yl]-2-(trifluoromethyl)-4H-pyrido[1,2-a]pyrimidin-4-one To a solution of 8-hydroxy-3-[1-(2,2,3,3,3-pentafluoropropyl)-1H-pyrazol-4-yl]-2-(trifluoromethyl)-4H-pyrido[1,2-a]pyrimidin-4-one (Example 18, 1.78 g, 4.15 mmol) in DMF (15 mL) sodium iodide (621.62 mg, 4.15 mmol) and sodium hydride (166.0 mg, 4.15 mmol) were added at 0° C. The mixture was stirred at 0° C. for 40 minutes then chloro-(methylthio)methane (0.63 mL, 7.46 mmol) was added. The reaction was left to reach room temperature and it was stirred overnight. The reaction was quenched with a few drops of EtOH then purified by flash-chromatography ($SiO_2$, Cyclohexane/EtOAc, from 95:5 to 2:8) to give 8-(methylsulfanylmethoxy)-3-[1-(2,2,3,3,3-pentafluoropropyl)pyrazol-4-yl]-2-(trifluoromethyl)pyrido[1,2-a]pyrimidin-4-one (958 mg, 1.962 mmol, 47% yield) as a white-off solid. LC/MS ($ESI^+$) m/z=489.2 $[M+H]^+$.

Step 2: 8-(fluoromethoxy)-3-[1-(2,2,3,3,3-pentafluoropropyl)-1H-pyrazol-4-yl]-2-(trifluoromethyl)-4H-pyrido[1,2-a]pyrimidin-4-one and 8-(chloromethoxy)-3-[1-(2,2,3,3,3-pentafluoropropyl)-1H-pyrazol-4-yl]-2-(trifluoromethyl)-4H-pyrido[1,2-a]pyrimidin-4-one To a solution of 8-(methylsulfanylmethoxy)-3-[1-(2,2,3,3,3-pentafluoropropyl)-1H-pyrazol-4-yl]-2-(trifluoromethyl)-4H-pyrido[1,2-a]pyrimidin-4-one (958 mg, 1.96 mmol) in DCM (10 mL) a solution of sulfuryl dichloride (0.47 mL, 5.76 mmol) in DCM (4 mL) was added. The mixture was stirred at room temperature for 15 minutes. Volatiles were removed and the crude was redissolved in DCM (10 mL). 1M tetrabutylammonium fluoride (3.93 mL, 3.93 mmol) in THF was added and the mixture was left stirring at room temperature for 3 days. Further TBAF (2 mL) was added and the mixture was left stirring at room temperature for an additional 4 days. The mixture was partitioned between EtOAc and brine and the phases were separated. The organic phase was washed with brine (×2), dried over $Na_2SO_4$, filtered and concentrated. The crude product was purified by reverse phase flash-chromatography (C18, $H_2O$+0.1% HCOOH/$CH_3CN$ from 95:5 to 2:8) followed by flash chromatography (SiO2, Cyclohexane/EtOAc from 9:1 to 2:8) to give 8-(fluoromethoxy)-3-[1-(2,2,3,3,3-pentafluoropropyl)-1H-pyrazol-4-yl]-2-(trifluoromethyl)-4H-pyrido[1,2-a]pyrimidin-4-one as a white solid (161 mg, 0.350 mmol, 18% yield). LC/MS ($ESI^+$) m/z=461.1 $[M+H]^+$. $^1H$ NMR (400 MHz, DMSO-$d_6$) δ 8.99 (d, J=7.89 Hz, 1H), 8.03 (s, 1H), 7.68 (s, 1H), 7.46 (d, J=2.41 Hz, 1H), 7.33 (dd, J=7.89, 2.63 Hz, 1H), 6.16 (d, J=51.30 Hz, 2H), 5.28 (t, J=14.91 Hz, 2H).

The product 8-(chloromethoxy)-3-[1-(2,2,3,3,3-pentafluoropropyl)-1H-pyrazol-4-yl]-2-(trifluoromethyl)-4H-pyrido[1,2-a]pyrimidin-4-one was isolated as a byproduct in step 2. The compound was obtained as a white solid (140 mg, 0.294 mmol, 15% yield). LC/MS ($ESI^+$) m/z=477.1/479.0 $[M+H]^+$. $^1H$ NMR (500 MHz, DMSO-$d_6$) δ 5.27 (t, J=14.96 Hz, 2H), 6.40 (s, 2H), 7.29 (dd, J=7.68, 2.74 Hz, 1H), 7.53 (d, J=2.74 Hz, 1H), 7.66 (s, 1H), 8.01 (s, 1H), 8.94 (d, J=7.70 Hz, 1H).

Examples 47 and 48

Example 47: 8-(Fluoromethoxy)-3-[1-(2,2,3,3,3-pentafluoropropyl)-1H-pyrazol-4-yl]-2-(trifluoromethyl)-4H-pyrimido[1,2-b]pyridazin-4-one and Example 48: 8-(Chloromethoxy)-3-[1-(2,2,3,3,3-pentafluoropropyl)-1H-pyrazol-4-yl]-2-(trifluoromethyl)-4H-pyrimido[1,2-b]pyridazin-4-one

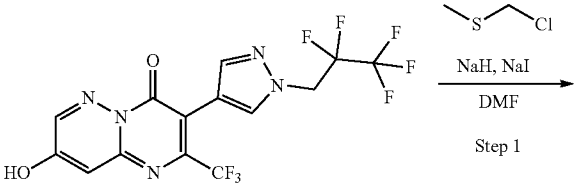

-continued

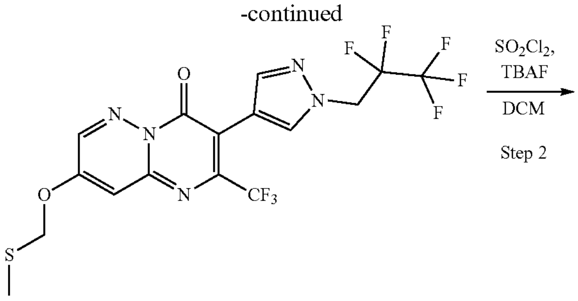

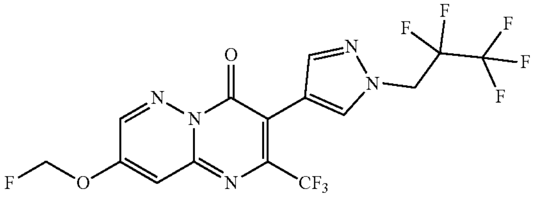

+

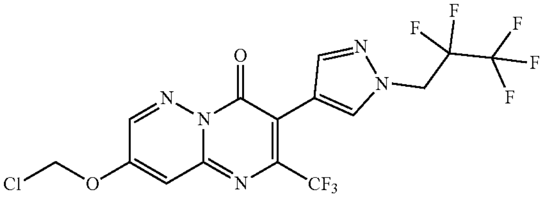

8-(fluoromethoxy)-3-[1-(2,2,3,3,3-pentafluoropropyl)-1H-pyrazol-4-yl]-2-(trifluoromethyl)-4H-pyrimido[1,2-b]pyridazin-4-one The title compound was prepared from 8-hydroxy-3-[1-(2,2,3,3,3-pentafluoropropyl)-1H-pyrazol-4-yl]-2-(trifluoromethyl)-4H-pyrimido[1,2-b]pyridazin-4-one (Example 44) following the procedures described for Examples 45 and 46, Steps 1 and 2, to give impure 8-(fluoromethoxy)-3-[1-(2,2,3,3,3-pentafluoropropyl)-1H-pyrazol-4-yl]-2-(trifluoromethyl)-4H-pyrimido[1,2-b]pyridazin-4-one. LC/MS ($ESI^+$) m/z=462.0 $[M+H]^+$.

8-(chloromethoxy)-3-[1-(2,2,3,3,3-pentafluoropropyl)-1H-pyrazol-4-yl]-2-(trifluoromethyl)-4H-pyrimido[1,2-b]pyridazin-4-one The title compound was prepared from 8-hydroxy-3-[1-(2,2,3,3,3-pentafluoropropyl)-1H-pyrazol-4-yl]-2-(trifluoromethyl)-4H-pyrimido[1,2-b]pyridazin-4-one (Example 44) following the procedures described for Examples 45 and 46, Steps 1 and 2, to give 8-(chloromethoxy)-3-[-(2,2,3,3,3-pentafluoropropyl)-1H-pyrazol-4-yl]-2-(trifluoromethyl)-4H-pyrimido[1,2-b]pyridazin-4-one. LC/MS ($ESI^+$) m/z=478.0/479.9 $[M+H]^+$. $^1H$ NMR (400 MHz, DMSO-$d_6$) δ 5.30 (t, J=15.0 Hz, 2H), 6.43 (s, 2H), 7.70 (s, 1H), 7.84 (d, J=2.9 Hz, 1H), 8.09 (s, 1H), 8.90 (d, J=2.8 Hz, 1H).

Example 49

3-(1-Cyclopropyl-1H-pyrazol-4-yl)-8-methoxy-2-(trifluoromethyl)-4H-pyrido[1,2-a]pyrimidin-4-one

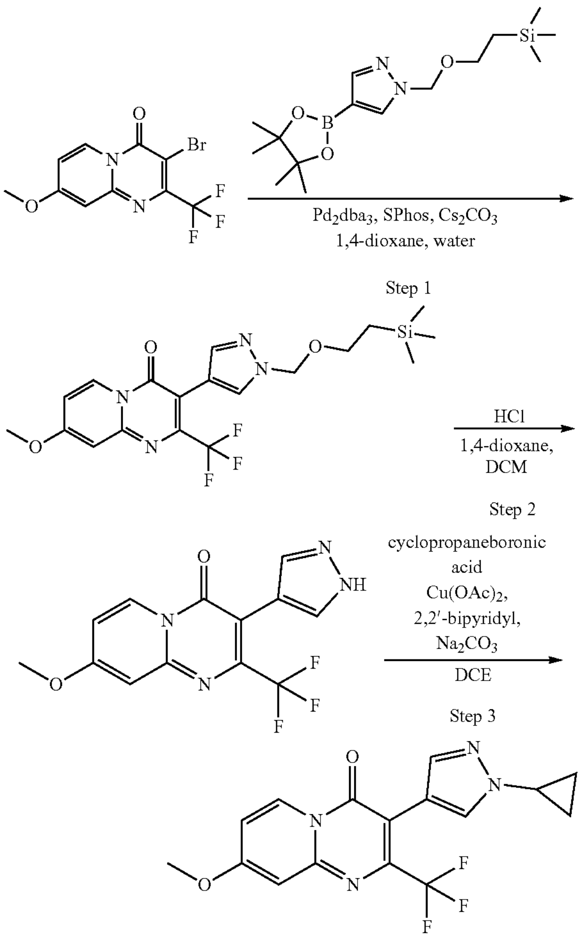

Step 1: 8-methoxy-2-(trifluoromethyl)-3-[1-(2-trimethylsilylethoxymethyl)-1H-pyrazol-4-yl]-4H-pyrido[1,2-a]pyrimidin-4-one A suspension of 3-bromo-8-methoxy-2-(trifluoromethyl)pyrido[1,2-a]pyrimidin-4-one (Intermediate 1-A, 280 mg, 0.87 mmol), 4-(4,4,5,5-Tetramethyl-1,3,2-dioxaborolan-2-yl)-1-((2-(trimethylsilyl)ethoxy)methyl)-1H-pyrazole (675 mg, 1.04 mmol, CAS 894807-98-8, ABCR GmbH), cesium carbonate (710 mg, 2.17 mmol) and 2-dicyclohexylphosphino-2',6'-dimethoxybiphenyl (71 mg, 0.170 mmol) in 1,4-dioxane (7 mL)/water (0.700 mL) was degassed for 10 min with a flow of nitrogen. Tris(dibenzylideneacetone)dipalladium(0) (79.36 mg, 0.090 mmol) was added and degassing was continued for 5 min and the mixture was warmed to 95° C. and stirred at that temperature for 3 h. After cooling, the mixture was diluted with EtOAc and washed with water. Organic phase was dried and evaporated and crude was purified by flash chromatography ($SiO_2$, Cy/EtOAc from 100:0 to 50:50) affording: 8-methoxy-2-(trifluoromethyl)-3-[1-(2-trimethylsilylethoxymethyl)-1H-pyrazol-4-yl]-4H-pyrido[1,2-a]pyrimidin-4-one as a yellow solid (344 mg, 0.781 mmol, 90% yield). LC/MS ($ESI^+$) m/z=441.3 $[M+H]^+$.

Step 2: 8-methoxy-3-(1H-pyrazol-4-yl)-2-(trifluoromethyl)pyrido[1,2-a]pyrimidin-4-one To a solution of 8-methoxy-2-(trifluoromethyl)-3-[1-(2-trimethylsilylethoxymethyl)-1H-pyrazol-4-yl]-4H-pyrido[1,2-a]pyrimidin-4-one (340 mg, 0.70 mmol) in DCM (5 mL) was added hydrogen chloride (4M in dioxane, 0.96 mL, 3.86 mmol). The mixture was stirred at rt overnight. A white precipitate was formed which was collected and dried under vacuum, to give crude 8-methoxy-3-(1H-pyrazol-4-yl)-2-(trifluoromethyl)pyrido[1,2-a]pyrimidin-4-one as a white solid (310 mg), which was used for next step without further purification. LC/MS ($ESI^+$) m/z=311.2 $[M+H]^+$.

Step 3: 3-(1-cyclopropyl-1H-pyrazol-4-yl)-8-methoxy-2-(trifluoromethyl)-4H-pyrido[1,2-a]pyrimidin-4-one A mixture of 8-methoxy-3-(1H-pyrazol-4-yl)-2-(trifluoromethyl)pyrido[1,2-a]pyrimidin-4-one (25 mg, 0.080 mmol), cyclopropylboronic acid (14 mg, 0.160 mmol), 2-(2-pyridinyl)pyridine (13 mg, 0.080 mmol) and sodium carbonate (17 mg, 0.160 mmol) in 1,2-dichloroethane (3 mL) was degassed under nitrogen for 5 min, then copper diacetate (15 mg, 0.080 mmol) was added and mixture was shaken at 70° C. overnight. The mixture was concentrated and crude was purified by flash chromatography ($SiO_2$, Cy/EtOAc from 100:0 to 0:100) affording 3-(1-cyclopropylpyrazol-4-yl)-8-methoxy-2-(trifluoromethyl)pyrido[1,2-a]pyrimidin-4-one as a white solid (9 mg, 0.026 mmol, 32% yield). LC/MS ($ESI^+$) m/z=441.3 $[M+H]^+$. $^1H$ NMR (500 MHz, $CDCl_3$) δ 1.00-1.11 (m, 2H), 1.15-1.26 (m, 2H), 1.56 (s, 10H), 3.67 (dt, J=7.3, 3.6 Hz, 1H), 4.01 (s, 3H), 6.92 (dd, J=7.8, 2.6 Hz, 1H), 7.02 (d, J=2.7 Hz, 1H), 7.68 (s, 1H), 7.78 (s, 1H), 8.95 (d, J=7.7 Hz, 1H).

Example 50

8-Methyl-2-(trifluoromethyl)-3-[5-(3,3,3-trifluoropropyl)-1,2,4-oxadiazol-3-yl]-4H-pyrido[1,2-a]pyrimidin-4-one

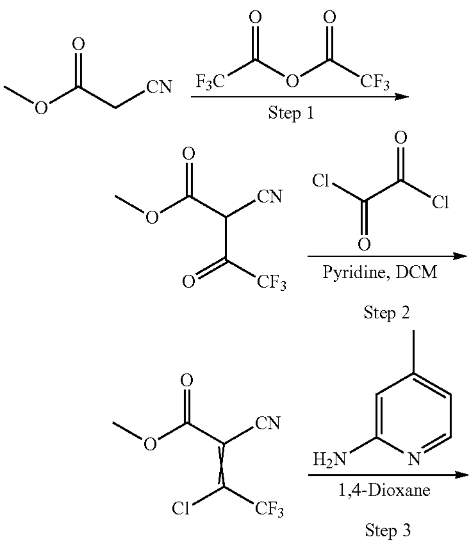

-continued

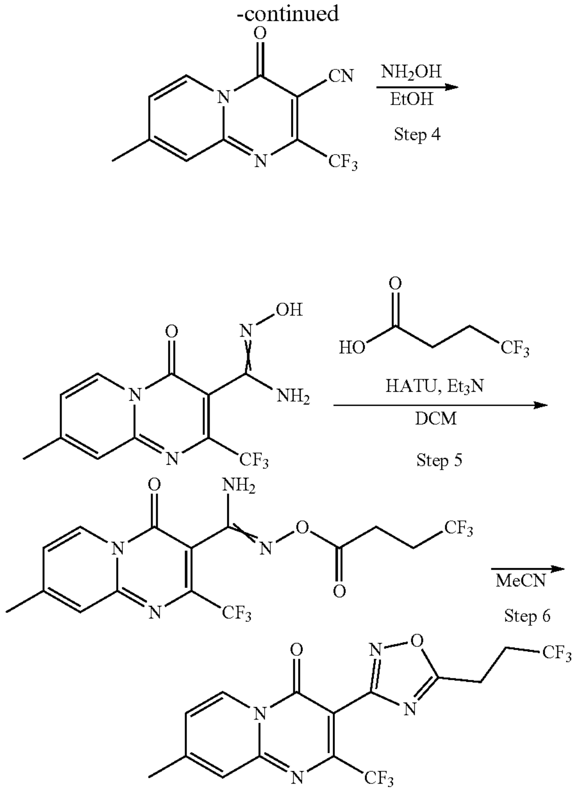

Step 1: methyl 2-cyano-4,4,4-trifluoro-3-oxobutanoate

2-Cyanoacetic acid methyl ester (5.0 g, 50.5 mmol) and trifluoroacetic anhydride (8.5 mL, 60.6 mmol) were dissolved in anhydrous DCM (50 mL) and cooled to 0° C. under nitrogen atmosphere. Triethylamine (17.5 mL, 126.2 mmol) was added dropwise with cooling and the mixture stirred for 30 minutes. It was then allowed to warm to room temperature and stirred for 1 hour. The solution was diluted with DCM, washed three times with water, dried and the solvent removed. The product methyl 2-cyano-4,4,4-trifluoro-3-oxobutanoate was used as crude for the next reaction.

Step 2: methyl 3-chloro-2-cyano-4,4,4-trifluorobut-2-enoate

Methyl 2-cyano-4,4,4-trifluoro-3-oxobutanoate, obtained as crude from Step 1, was dissolved in dry DCM (150 mL). Oxalyl chloride (16 mL, 186 mmol) was added dropwise and the mixture stirred until gas evolution ceased. Pyridine (a few drops) was added and the reaction heated to reflux for 1 hour, then stirred overnight at room temperature. The mixture was poured into water, shaken and the phases separated. The organic phase was then washed with water, dried and removed to give the crude product methyl 3-chloro-2-cyano-4,4,4-trifluorobut-2-enoate which was used directly in the next step.

Step 3: 8-methyl-4-oxo-2-(trifluoromethyl)-4H-pyrido[1,2-a]pyrimidine-3-carbonitrile Methyl 3-chloro-2-cyano-4,4,4-trifluorobut-2-enoate, obtained as crude from Step 2, was dissolved in dry 1,4-dioxane (40 mL) and 4-methyl-2-pyridinamine (1.50 g, 14.1 mmol) was added. The mixture was stirred at room temperature for 2 hours, then diluted with EtOAc, washed with water, saturated $NaHCO_3$ solution and brine, dried and finally evaporated. The residue was purified by flash chromatography ($SiO_2$, DCM/MeOH from 100:0 to 95:5) to give 8-methyl-4-oxo-2-(trifluoromethyl)pyrido[1,2-a]pyrimidine-3-carbonitrile (413 mg, 1.63 mmol, 17% yield). LC/MS ($ESI^4$) m/z=254.3 $[M+H]^+$.

Step 4: N'-hydroxy-8-methyl-4-oxo-2-(trifluoromethyl)-4H-pyrido[1,2-a]pyrimidine-3-carboximidamide 8-Methyl-4-oxo-2-(trifluoromethyl)-4H-pyrido[1,2-a]pyrimidine-3-carbonitrile (50.0 mg, 0.20 mmol) was suspended in ethanol (2.0 mL) in a pressure resistant tube and hydroxylamine (50% in water) (36.3 uL, 0.60 mmol) was added. The tube was sealed and the mixture stirred for 4 hours at 120° C. The mixture was allowed to cool to room temperature and the mother liquor evaporated to give the crude N'-hydroxy-8-methyl-4-oxo-2-(trifluoromethyl)pyrido[1,2-a]pyrimidine-3-carboximidamide (35.0 mg, 0.12 mmol, 62% yield). LC/MS ($ESI^+$) m/z=287.1 $[M+H]^+$.

Step 5: [[amino-[8-methyl-4-oxo-2-(trifluoromethyl)-4H-pyrido[1,2-a]pyrimidin-3-yl]methylidene]amino]4,4,4-trifluorobutanoate N'-hydroxy-8-methyl-4-oxo-2-(trifluoromethyl)pyrido[1,2-a]pyrimidine-3-carboximidamide (35.0 mg, 0.12 mmol), HATU (70.0 mg, 0.18 mmol), 4,4,4-trifluorobutanoic acid (21.0 mg, 0.15 mmol) and triethylamine (0.05 mL, 0.37 mmol) were dissolved in DCM (10.0 mL) and the mixture was stirred overnight at room temperature. The reaction was diluted with DCM, washed with water, the organic phase dried and removed. The crude was then purified by flash chromatography ($SiO_2$, Cyclohxane:EtOAc) to give [[amino-[8-methyl-4-oxo-2-(trifluoromethyl)-4H-pyrido[1,2-a]pyrimidin-3-yl]methylidene]amino]4,4,4-trifluorobutanoate (13.0 mg, 0.03 mmol, 26% yield).

$^1H$ NMR (400 MHz, Acetone-$d_6$) 2.62 (s, 5H) 2.61-2.64 (m, 4H) 2.73 (s, 8H) 2.78-2.84 (m, 3H) 6.37-6.51 (m, 2H) 7.42-7.53 (m, 1H) 7.67-7.72.

Step 6: 8-methyl-2-(trifluoromethyl)-3-[5-(3,3,3-trifluoropropyl)-1,2,4-oxadiazol-3-yl]pyrido[1,2-a]pyrimidin-4-one

[[Amino-[8-methyl-4-oxo-2-(trifluoromethyl)pyrido[1,2-a]pyrimidin-3-yl]methylidene]amino]4,4,4-trifluoro butanoate (13.0 mg, 0.03 mmol) was dissolved in MeCN (2.0 mL) and heated under microwave irradiation at 110° C. for 3 hours. The solvent was evaporated and the residue purified by flash chromatography ($SiO_2$, cyclohexane:EtOAc) to give 8-methyl-2-(trifluoromethyl)-3-[5-(3,3,3-trifluoropropyl)-1,2,4-oxadiazol-3-yl]-4H-pyrido[1,2-a]pyrimidin-4-one (3.0 mg, 0.01 mmol, 24% yield). LC/MS ($ESI^+$) m/z=393.3 $[M+H]^+$. $^1H$ NMR (500 MHz, Acetone-$d_6$) δ 2.66 (d, J=1.10 Hz, 3H), 2.86-3.00 (m, 2H), 3.39 (t, J=7.70 Hz, 2H), 7.55 (dd, J=7.27, 1.78 Hz, 1H), 7.75-7.81 (m, 1H), 9.06 (d, J=7.14 Hz, 1H).

Example 51

8-Methoxy-3-[4-(2,2,2-trifluoroethoxy)-1,3-thiazol-2-yl]-2-(trifluoromethyl)-4H-pyrido[1,2-a]pyrimidin-4-one

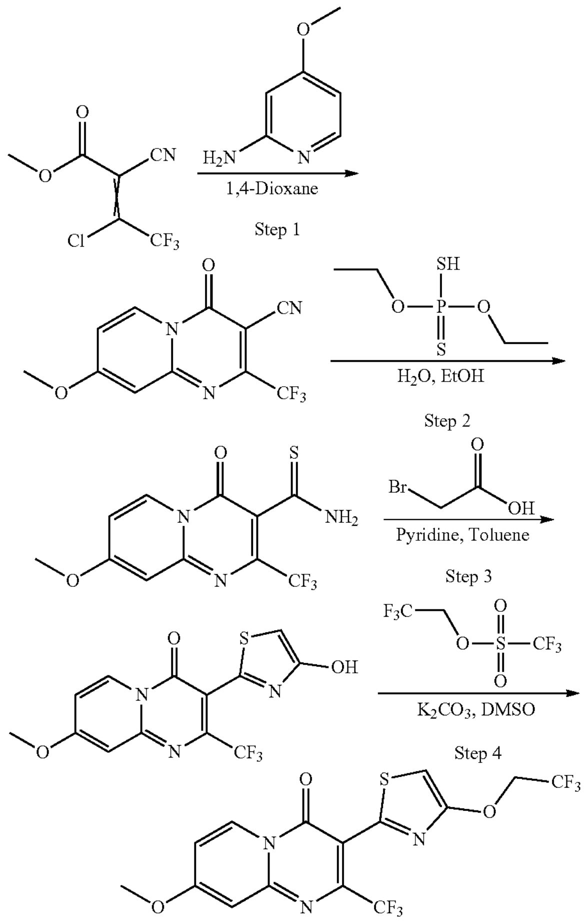

Step 1: 8-methoxy-4-oxo-2-(trifluoromethyl)pyrido[1,2-a]-4H-pyrimidine-3-carbonitrile Methyl 3-chloro-2-cyano-4,4,4-trifluorobut-2-enoate (Example 50, Step 2, 3.5 g, 16.3 mmol) and 4-methoxypyridin-2-amine (3.0 g, 24.4 mmol) were dissolved in 1,4-dioxane (75 mL) and stirred at room temperature for 2 hours. The mixture was diluted with EtOAc (200 mL) and washed with water, saturated $NaHCO_3$ solution and brine, dried and the solvent removed. The residue was purified by flash chromatography ($SiO_2$, MeOH in DCM) to give the product 8-methoxy-4-oxo-2-(trifluoromethyl)-4H-pyrido[1,2-a]pyrimidine-3-carbonitrile (815 mg, 3.03 mmol, 19% yield). LC/MS ($ESI^+$) m/z=270.1 $[M+H]^+$.

Step 2: 8-methoxy-4-oxo-2-(trifluoromethyl)pyrido[1,2-a]pyrimidine-3-carbothioamide 8-Methoxy-4-oxo-2-(trifluoromethyl)pyrido[1,2-a]pyrimidine-3-carbonitrile (100 mg, 0.40 mmol) was diluted in ethanol (3.0 mL) and diethoxy-mercapto-sulfanylidenephosphorane (0.20 mL, 1.10 mmol) was added, followed by water (0.10 mL). The mixture was stirred at 80° C. overnight. After this time, it was quenched with a saturated $NaHCO_3$ solution and extracted with EtOAc. The organic layer was dried, filtered and concentrated. The crude was purified by flash chromatography ($SiO_2$, cyclohexane:EtOAc) to give 8-methoxy-4-oxo-2-(trifluoromethyl)-4H-pyrido[1,2-a]pyrimidine-3-carbothioamide (25 mg, 0.08 mmol, 22% yield). LC/MS ($ESI^+$) m/z=304.2 $[M+H]^+$.

Step 3: 3-(4-hydroxy-1,3-thiazol-2-yl)-8-methoxy-2-(trifluoromethyl)-4H-pyrido[1,2-a]pyrimidin-4-one A mixture of 8-methoxy-4-oxo-2-(trifluoromethyl)-4H-pyrido[1,2-a]pyrimidine-3-carbothioamide (25 mg, 0.08 mmol), 2-bromoacetic acid (14 mg, 0.10 mmol) and pyridine (13 uL, 0.16 mmol) in toluene (1.0 mL) was stirred at 110° C. for 1 hour. The reaction mixture was rinsed with DCM and concentrated under reduced pressure to afford the crude product, which was purified by flash chromatography ($SiO_2$, cyclohexane:EtOAc) to give 3-(4-hydroxy-1,3-thiazol-2-yl)-8-methoxy-2-(trifluoromethyl)pyrido[1,2-a]pyrimidin-4-one (24 mg, 0.07 mmol, 85% yield). LC/MS ($ESI^+$) m/z=344.2 $[M+H]^+$.

Step 4: 8-methoxy-3-[4-(2,2,2-trifluoroethoxy)-1,3-thiazol-2-yl]-2-(trifluoromethyl)-4H-pyrido[1,2-a]pyrimidin-4-one 3-(4-Hydroxy-1,3-thiazol-2-yl)-8-methoxy-2-(trifluoromethyl)-4H-pyrido[1,2-a]pyrimidin-4-one (24 mg, 0.07 mmol) was diluted in DMF (1.0 mL) and potassium carbonate (12 mg, 0.08 mmol) was added, followed by trifluoromethanesulfonic acid 2,2,2-trifluoroethyl ester (15 uL, 0.10 mmol). The resulting solution was stirred at room temperature for 5 hours. Water was added and the mixture was extracted with EtOAc. The organic layer was then dried, filtered and evaporated. The residue was purified by flash chromatography ($SiO_2$, cyclohexane:EtOAc) to afford 8-methoxy-3-[4-(2,2,2-trifluoroethoxy)-1,3-thiazol-2-yl]-2-(trifluoromethyl)-4H-pyrido[1,2-a]pyrimidin-4-one (12 mg, 0.03 mmol, 39% yield). LC/MS ($ESI^+$) m/z=426.1 $[M+H]^+$. $^1H$ NMR (400 MHz, DMSO-$d_6$) δ 4.08 (s, 3H), 4.95 (q, J=8.99 Hz, 2H), 6.98 (s, 1H), 7.33 (dd, J=7.78, 2.74 Hz, 1H), 7.42 (d, J=2.63 Hz, 1H), 9.04 (d, J=7.89 Hz, 1H).

Example 52

3-[5-Iodo-1-(2,2,3,3,3-pentafluoropropyl)-1H-1,2,3-triazol-4-yl]-8-methoxy-2-(trifluoromethyl)-4H-pyrido[1,2-a]pyrimidin-4-one

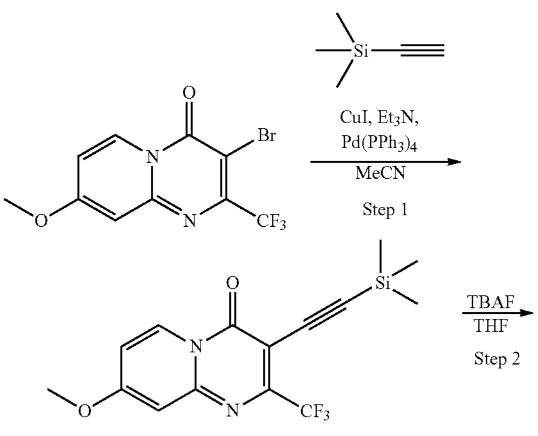

-continued

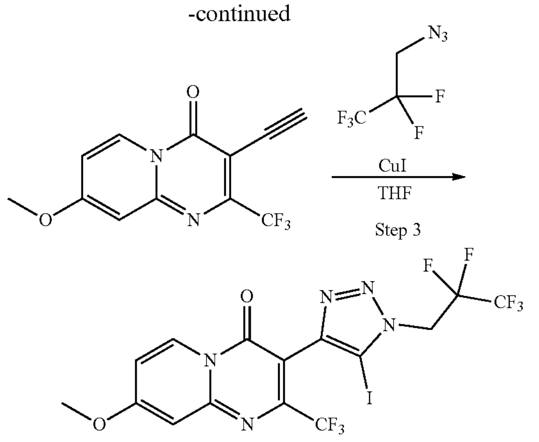

Step 1: 8-methoxy-2-(trifluoromethyl)-3-(2-trimethylsilylethynyl)-4H-pyrido[1,2-a]pyrimidin-4-one 3-Bromo-8-methoxy-2-(trifluoromethyl)-4H-pyrido[1,2-a]pyrimidin-4-one (Intermediate 1-A, 100 mg, 0.31 mmol) copper (I) iodide (3.0 mg, 0.02 mmol) and triethylamine (0.13 mL, 0.93 mmol) were dissolved in dry MeCN (4.0 mL) in a sealed vial. The mixture was degassed, then palladium triphenylphosphine (3.6 mg, 0.01 mmol) was added, followed by ethynyl(trimethyl)silane (46 mg, 0.46 mmol). The reaction was stirred at 100° C. overnight, then copper (I) iodide (3.0 mg), palladium tetrakistriphenylphosphine (3.0 mg) and ethynyl(trimethyl)silane (0.10 mL) were added and the mixture was stirred under microwave irradiation (100° C./1 hour; 130° C./2 hours; 140° C./2 hours). The crude was then filtered and the solvent evaporated. The product was purified by reverse phase chromatography (C18, $H_2O$: MeCN) to give 8-methoxy-2-(trifluoromethyl)-3-(2-trimethylsilylethynyl)-4H-pyrido[1,2-a]pyrimidin-4-one (15.0 mg, 0.04 mmol, 14% yield). LC/MS ($ESI^+$) m/z=341.3 $[M+H]^+$.

Step 2: 8-methoxy-2-(trifluoromethyl)-3-(2-trimethylsilylethynyl)-4H-pyrido[1,2-a]pyrimidin-4-one Tetrabutylammonium fluoride (0.09 mL, 0.09 mmol) was added to a solution of 8-methoxy-2-(trifluoromethyl)-3-(2-trimethylsilylethynyl)-4H-pyrido[1,2-a]pyrimidin-4-one (15.0 mg, 0.04 mmol) in THF (2.0 mL). The mixture was then diluted with EtOAc and washed with water. The organic phase was dried and evaporated to give 3-ethynyl-8-methoxy-2-(trifluoromethyl)-4H-pyrido[1,2-a]pyrimidin-4-one (12.0 mg, 0.06 mmol, 99% yield). LC/MS ($ESI^+$) m/z=269.2 $[M+H]^+$.

Step 3: 3-[5-iodo-1-(2,2,3,3,3-pentafluoropropyl)-1H-1,2,3-triazol-4-yl]-8-methoxy-2-(trifluoromethyl)-4H-pyrido[1,2-a]pyrimidin-4-one 3-Azido-1,1,1,2,2-pentafluoropropane (10.0 mg, 0.06 mmol, Enamine Ltd) was added to a suspension of 3-ethynyl-8-methoxy-2-(trifluoromethyl)-4H-pyrido[1,2-a]pyrimidin-4-one (15.0 mg, 0.06 mmol) and copper (I) iodide (10.7 mg, 0.06 mmol) in THF (2.0 mL), and the mixture was stirred at 60° C. for 2 hours. After this time, it was allowed to reach room temperature and the reaction was diluted with EtOAc, washed with saturated $NH_4Cl$ and water. The organic phase was dried and removed. The resulting crude was purified by flash chromatography ($SiO_2$, cyclohexane; EtOAc) to give 3-[5-iodo-1-(2,2,3,3,3-pentafluoropropyl)-1H-1,2,3-triazol-4-yl]-8-methoxy-2-(trifluoromethyl)-4H-pyrido[1,2-a]pyrimidin-4-one (5.0 mg, 0.01 mmol, 16% yield). LC/MS ($ESI^+$) m/z=570.1 $[M+H]^+$. $^1H$ NMR (500 MHz, $CDCl_3$) δ 4.06 (s, 3H), 5.11 (t, J=12.90 Hz, 2H), 7.02 (dd, J=7.82, 2.61 Hz, 1H), 7.16 (d, J=2.74 Hz, 1H), 9.01 (d, J=7.68 Hz, 1H).

Example 53

8-Methoxy-3-[1-(2,2,3,3,3-pentafluoropropyl)-1H-1,2,3-triazol-4-yl]-2-(trifluoromethyl)-4H-pyrido[1,2-a]pyrimidin-4-one

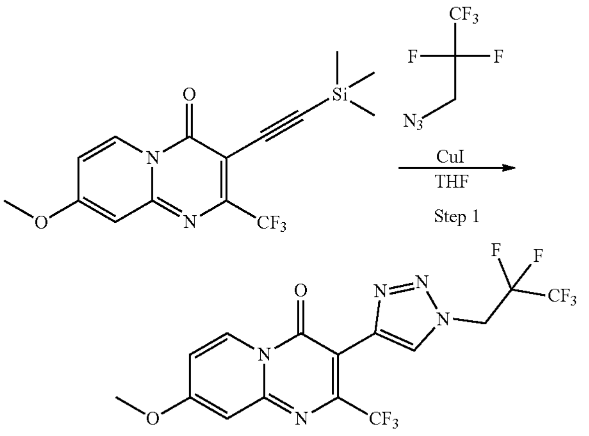

Step 1: 8-methoxy-3-[1-(2,2,3,3,3-pentafluoropropyl)triazol-4-yl]-2-(trifluoromethyl)-4H-pyrido[1,2-a]pyrimidin-4-one 3-Azido-1,1,1,2,2-pentafluoropropane (0.75 mL, 0.30 mmol, Enamine Ltd) was added to a suspension of 8-methoxy-2-(trifluoromethyl)-3-(2-trimethylsylilethynyl)-4H-pyrido[1,2-a]pyrimidin-4-one (Example 52, Step 1, 100 mg, 0.29 mmol) and copper (I) iodide (56.0 mg, 0.29 mmol) in MeOH (3.0 mL), and the mixture was stirred at 60° C. for 2 hours. After this time, it was allowed to cool to room temperature and EtOAc was added. The organic phase was washed with saturated $NH_4Cl$ and water, dried and evaporated. The crude was purified by flash chromatography ($SiO_2$, cyclohexane:EtOAc) and preparative HPLC to give 8-methoxy-3-[1-(2,2,3,3,3-pentafluoropropyl)triazol-4-yl]-2-(trifluoromethyl)-4H-pyrido[1,2-a]pyrimidin-4-one (19.5 mg, 0.04 mmol, 14% yield). LC/MS (ESI) m/z=444.4 $[M+H]^+$. $^1H$ NMR (400 MHz, $CDCl_3$) δ 4.04 (s, 3H), 5.11 (t, J=13.81 Hz, 2H), 6.99 (dd, J=7.89, 2.63 Hz, 1H), 7.12 (d, J=2.63 Hz, 1H), 8.04 (s, 1H), 9.00 (d, J=7.67 Hz, 1H).

Example 54

8-Methoxy-3-[1-(2,2,3,3,3-pentafluoropropyl)-1H-1,2,4-triazol-3-yl]-2-(trifluoromethyl)-4H-pyrido[1,2-a]pyrimidin-4-one

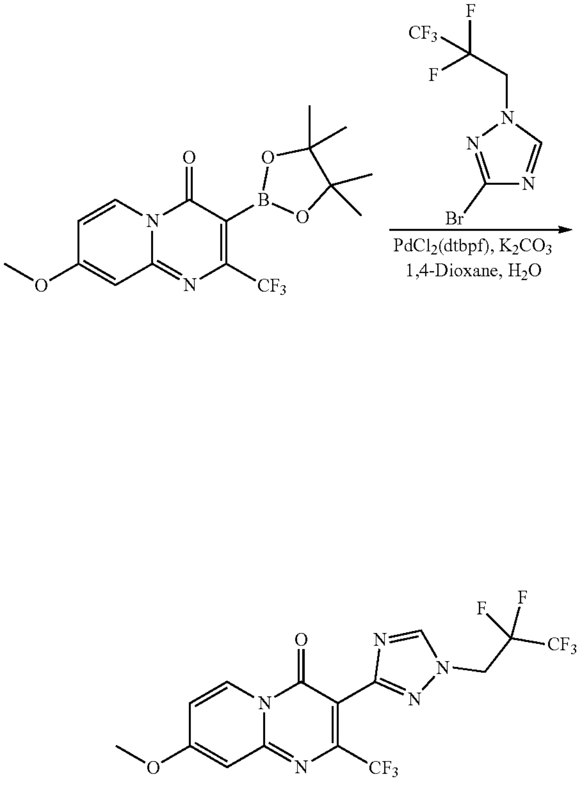

Step 1: 8-methoxy-3-[1-(2,2,3,3,3-pentafluoropropyl)-1H-1,2,4-triazol-3-yl]-2-(trifluoromethyl)-4H-pyrido[1,2-a]pyrimidin-4-one 8-Methoxy-3-(4,4,5,5-tetramethyl-1,3,2-dioxaborolan-2-yl)-2-(trifluoromethyl)-4H-pyrido[1,2-a]pyrimidin-4-one (Intermediate 4-N, 29.0 mg, 0.08 mmol) and potassium carbonate (32.5 mg, 0.24 mmol) were dissolved in a mixture of 1,4-dioxane (4.0 mL) and water (0.5 mL) in a Schlenk tube and the mixture was degassed. 3-Bromo-1-(2,2,3,3,3-pentafluoropropyl)-1,2,4-triazole (Intermediate 4-P, 33.0 mg, 0.12 mmol) was added, followed by [1,1'-bis(di-tert-butylphosphino)ferrocene]dichloropalladium(II) (5.1 mg, 0.01 mmol). The mixture was degassed again and stirred for 1 hour at 90° C. After this time, the reaction was allowed to cool to room temperature, poured into EtOAc and washed with water and brine. The organic phase was dried and the solvent removed. The crude material was purified by flash chromatography ($SiO_2$, cyclohexane:EtOAc) to give 8-methoxy-3-[1-(2,2,3,3,3-pentafluoropropyl)-1,2,4-triazol-3-yl]-2-(trifluoromethyl)-4H-pyrido[1,2-a]pyrimidin-4-one (2.0 mg, 0.01 mmol, 6% yield). LC/MS ($ESI^+$) m/z=444.2 $[M+H]^+$. $^1$H NMR (400 MHz, $CDCl_3$) δ 4.05 (s, 3H) 4.90 (t, J=13.5 Hz, 2H) 6.99 (dd, J=7.80, 2.60 Hz, 1H) 7.12 (d, J=2.60 Hz, 1H) 8.35 (s, 1H) 9.01 (d, J=7.80 Hz, 1H).

Example 55

8-Methoxy-2-(trifluoromethyl)-3-[3-(3,3,3-trifluoropropyl)-1,2-oxazol-5-yl]-4H-pyrido[1,2-a]pyrimidin-4-one

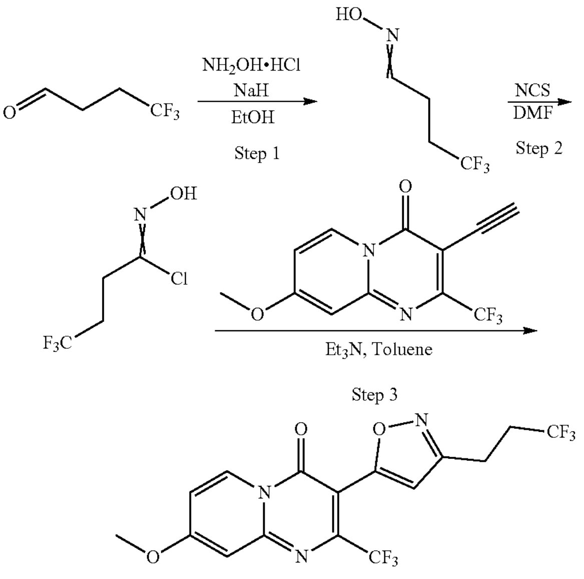

Step 1: N-(4,4,4-trifluorobutylidene)hydroxylamine

NaOH (50% solution in water, 0.2 mL) was added dropwise to a stirred solution of 4,4,4-trifluorobutyraldehyde (200 mg, 1.60 mmol) and hydroxylamine hydrochloride (132 mg, 1.90 mmol) in ethanol (1.0 mL) and water (2.0 mL) at 0° C. The mixture was allowed to reach room temperature and was left stirring overnight. After this time, volatiles were evaporated, the mixture was acidified to pH 7 with HCl (6N) and extracted with EtOAc. The organic phase was dried and evaporated to afford the product N-(4,4,4-trifluorobutylidene)hydroxylamine (130 mg, 0.9 mmol, 58% yield). LC/MS ($ESI^+$) m/z=142.1 $[M+H]^+$.

Step 2: 4,4,4-trifluoro-N-hydroxybutanimidoyl chloride

N-Chlorosuccinimide (135 mg, 1.0 mmol) was added to a stirred solution of N-(4,4,4-trifluorobutylidene)hydroxylamine (130 mg, 0.90 mmol) in DMF (3.0 mL), and the mixture was left stirring at room temperature for 24 hours. After this time, it was diluted with water and extracted with EtOAc. The organic phase was dried and evaporated to afford crude 4,4,4-trifluoro-N-hydroxybutanimidoyl chloride, which was used directly in the next reaction.

Step 3: 8-Methoxy-2-(trifluoromethyl)-3-[3-(3,3,3-trifluoropropyl)-1,2-oxazol-5-yl]-4H-pyrido[1,2-a]pyrimidin-4-one 4,4,4-Trifluoro-N-hydroxybutanimidoyl chloride, obtained as crude in the previous step, was added to a stirred solution of 3-ethynyl-8-methoxy-2-(trifluoromethyl)pyrido[1,2-a]pyrimidin-4-one (Example 52, Step 2, 20 mg, 0.07 mmol) in toluene (3.0 mL) at 80° C.

Then, triethylamine (0.01 mL, 0.09 mmol) was added and the mixture was left stirring at the same temperature for 24 hours. After this time, the solvent was evaporated and the crude was purified by flash chromatography ($SiO_2$, cyclohexane:EtOAc), then reverse phase chromatography (C18, $H_2O$:MeCN) to give 8-methoxy-2-(trifluoromethyl)-3-[3-(3,3,3-trifluoropropyl)-1,2-oxazol-5-yl]-4H-pyrido[1,2-a]pyrimidin-4-one (5.5 mg, 0.01 mmol, 18% yield). LC/MS ($ESI^+$) m/z=408.3 $[M+H]^+$. $^1H$ NMR (400 MHz, DMSO-$d_6$) δ 2.69-2.83 (m, 2H), 2.94-3.02 (m, 2H), 4.07 (s, 3H), 6.80 (s, 1H), 7.30 (dd, J=7.78, 2.74 Hz, 1H), 7.41 (d, J=2.63 Hz, 1H), 8.98 (d, J=7.89 Hz, 1H).

Example 56

8-Methoxy-3-[2-(2,2,2-trifluoroethoxy)-1,3-thiazol-5-yl]-2-(trifluoromethyl)-4H-pyrido[1,2-a]pyrimidin-4-one

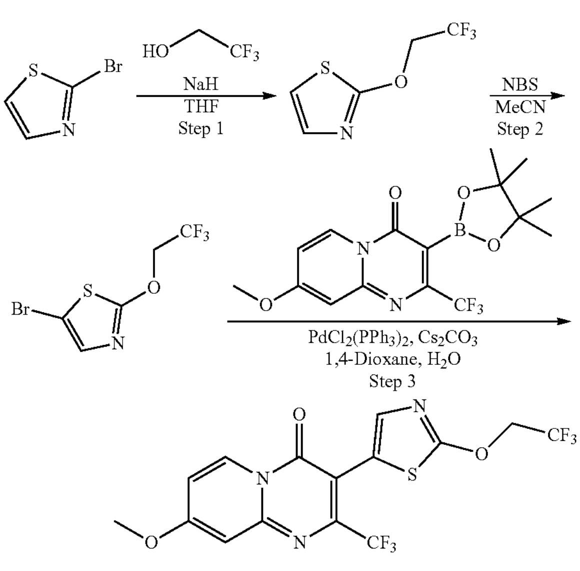

Step 1: 2-(2,2,2-trifluoroethoxy)-1,3-thiazole 2,2,2-Trifluorooethanol (0.70 g, 7.30 mmol) was dissolved in THF (15.0 mL) and sodium hydride (366 mg, 9.10 mmol) was slowly added at 0° C. The mixture was left stirring at room temperature for 15 minutes. Then, 2-bromothiazole (0.50 mL, 6.10 mmol) was added and the reaction was heated to reflux for 3 days. After this time, it was allowed to reach room temperature, it was diluted with water and extracted with DCM. The organic layer was washed with brine, dried and eliminated. The crude was purified by reverse phase chromatography (C18, $H_2O$:MeCN) to give 2-(2,2,2-trifluoroethoxy)-1,3-thiazole (300 mg, 1.10 mmol, 27% yield). LC/MS ($ESI^+$) m/z=184.1 [M+H]~.

Step 2: 5-bromo-2-(2,2,2-trifluoroethoxy)-1,3-thiazole

N-bromosuccinimide (266 mg, 1.50 mmol) was added to a stirred solution of 2-(2,2,2-trifluoroethoxy)-1,3-thiazole (300 mg, 1.10 mmol) in MeCN (7.0 mL) and the mixture was stirred at room temperature for 7 hours. After this time, the solvent was removed and the crude was purified by flash chromatography ($SiO_2$, cyclohexane:EtOAc) to give 5-bromo-2-(2,2,2-trifluoroethoxy)-1,3-thiazole (147 mg, 0.56 mmol, 49% yield). $^1H$ NMR (400 MHz, $CDCl_3$) δ 4.78 (q, J=8.19 Hz, 2H), 7.07 (s, 1H).

Step 3: 8-methoxy-3-[2-(2,2,2-trifluoroethoxy)-1,3-thiazol-5-yl]-2-(trifluoromethyl)-4H-pyrido[1,2-a]pyrimidin-4-one 8-Methoxy-3-(4,4,5,5-tetramethyl-1,3,2-dioxaborolan-2-yl)-2-(trifluoromethyl)pyrido[1,2-a]pyrimidin-4-one (Intermediate 4-N, 100 mg, 0.27 mmol), 5-bromo-2-(2,2,2-trifluoroethoxy)-1,3-thiazole (71 mg, 0.27 mmol) and cesium carbonate (117 mg, 0.54 mmol) were suspended in 1,4-dioxane (3.0 mL) and water (0.3 mL) in a screw capped vial. The mixture was degassed, then palladium (II) triphenylphosphine dichloride (19.0 mg, 0.03 mmol) was added and the mixture was stirred at 80° C. for 2 hours. After this time, the reaction was allowed to reach room temperature, EtOAc was added and washed with water. The organic phase was dried and evaporated and the resulting crude was purified by reverse chromatography (C18, $H_2O$:MeCN) to give 8-methoxy-3-[2-(2,2,2-trifluoroethoxy)-1,3-thiazol-5-yl]-2-(trifluoromethyl)-4H-pyrido[1,2-a]pyrimidin-4-one (4.7 mg, 0.01 mmol, 4% yield). LC/MS ($ESI^+$) m/z=426.0 $[M+H]^+$. $^1H$ NMR (400 MHz, $CDCl_3$) δ 4.05 (s, 3H), 4.86 (q, J=8.26 Hz, 2H), 6.99 (dd, J=7.89, 2.63 Hz, 1H), 7.10 (d, J=2.63 Hz, 1H), 7.14 (s, 1H), 8.97 (d, J=7.90 Hz, 1H).

Example 57

8-Methoxy-3-[5-(2,2,2-trifluoroethoxy)-1,3-thiazol-2-yl]-2-(trifluoromethyl)-4H-pyrido[1,2-a]pyrimidin-4-one

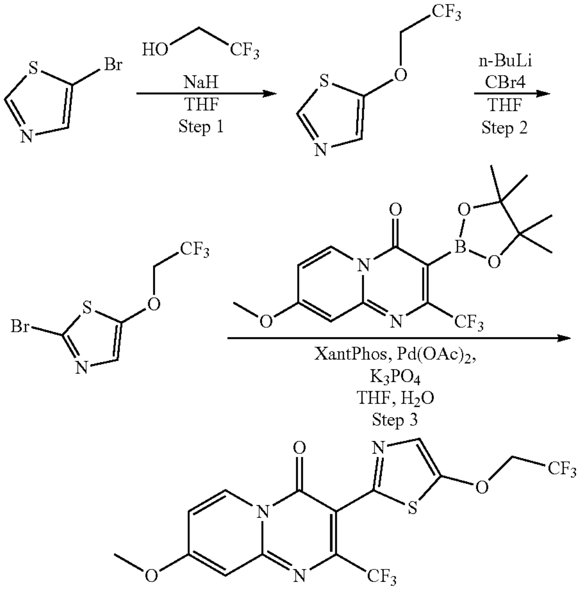

Step 1: 5-(2,2,2-trifluoroethoxy)-1,3-thiazole 2,2,2-Trifluoroethanol (0.53 mL, 7.32 mmol) was dissolved in THF (15.0 mL) and sodium hydride (366 mg, 9.15 mmol) was slowly added at 0° C. The mixture was left to react at room temperature for 15 min. Then, 5-bromothiazole (0.54 mL, 6.10 mmol) was added and the reaction was heated to reflux for 24 hours. It was allowed to reach room temperature, diluted with water and extracted with EtOAc. The organic layer was washed with brine, dried and eliminated to give a crude material that was purified with flash chromatography ($SiO_2$, cyclohexane:EtOAc) to give 5-(2,2,2-trifluoroethoxy)-1,3-thiazole (480 mg, 2.62 mmol, 43% yield). $^1H$ NMR (400 MHz, DMSO-$d_6$) δ 8.57 (d, J=0.9 Hz, 1H), 7.50 (d, J=0.9 Hz, 1H), 4.90 (q, J=8.8 Hz, 2H).

Step 2: 2-bromo-5-(2,2,2-trifluoroethoxy)-1,3-thiazole n-Butyllithium (2.5 M in hexanes, 1.0 mL, 2.54 mmol) was added to 5-(2,2,2-trifluoroethoxy)-1,3-thiazole (465 mg, 2.54 mmol) in THF (9.3 mL) at −78° C. and the mixture was stirred at the same temperature for 30 min. A solution of tetrabromomethane (842 mg, 2.54 mmol) in THF (3.7 mL) was then added maintaining the temperature lower than −70° C. during the addition. The mixture was left stirring under these conditions for 3 hours. After this time, the reaction was quenched by cautious addition of water and allowed to warm to room temperature over 1 hour. The mixture was extracted with EtOAc, dried and evaporated. The obtained crude was purified by flash chromatography ($SiO_2$, cyclohexane:EtOAc) to give 2-bromo-5-(2,2,2-trifluoroethoxy)-1,3-thiazole (190 mg, 0.73 mmol, 28% yield). LC/MS ($ESI^+$) m/z=264.0/265.0 $[M+H]^+$.

Step 3: 8-methoxy-3-[5-(2,2,2-trifluoroethoxy)-1,3-thiazol-2-yl]-2-(trifluoromethyl)-4H-pyrido[1,2-a]pyrimidin-4-one A mixture of 2-bromo-5-(2,2,2-trifluoroethoxy)-1,3-thiazole (186 mg, 0.71 mmol), 8-methoxy-3-(4,4,5,5-tetramethyl-1,3,2-dioxaborolan-2-yl)-2-(trifluoromethyl)pyrido[1,2-a]pyrimidin-4-one (Intermediate 4-N, 105 mg, 0.28 mmol), potassium phosphate (183 mg, 0.85 mmol), (5-diphenylphosphino-9,9-dimethyl-4-xanthenyl)-diphenylphosphine (32.8 mg, 0.06 mmol) and palladium (II) diacetate (6.4 mg, 0.03 mmol) in THF (3.0 mL) and water (0.14 mL) was degassed and heated at 60° C. for 2 hours. The solution was then diluted with water, extracted with EtOAc, dried and the solvent evaporated. The obtained crude was purified by flash chromatography ($SiO_2$, cyclohexane:EtOAc) followed by reverse phase chromatography (C18, $H_2O$:MeCN) to afford 8-methoxy-3-[5-(2,2,2-trifluoroethoxy)-1,3-thiazol-2-yl]-2-(trifluoromethyl)-4H-pyrido[1,2-a]pyrimidin-4-one (16.0 mg, 0.04 mmol, 13% yield). LC/MS ($ESI^+$) m/z=426.0 $[M+H]^+$. $^1H$ NMR (400 MHz, DMSO-$d_6$) δ 4.07 (s, 3H), 4.97 (q, J=8.8 Hz, 2H), 7.29 (dd, J=7.9, 2.9 Hz, 1H), 7.38 (d, J=2.6 Hz, 1H), 7.53 (s, 1H), 8.99 (d, J=7.9 Hz, 1H).

Example 58

8-Methoxy-2-(trifluoromethyl)-3-[5-(3,3,3-trifluoropropyl)-1,3-thiazol-2-yl]-4H-pyrido[1,2-a]pyrimidin-4-one

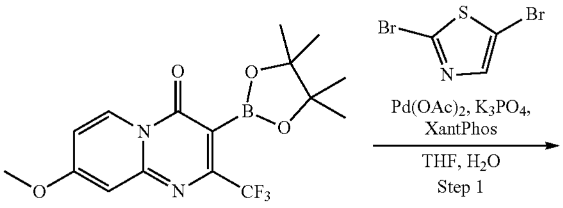

-continued

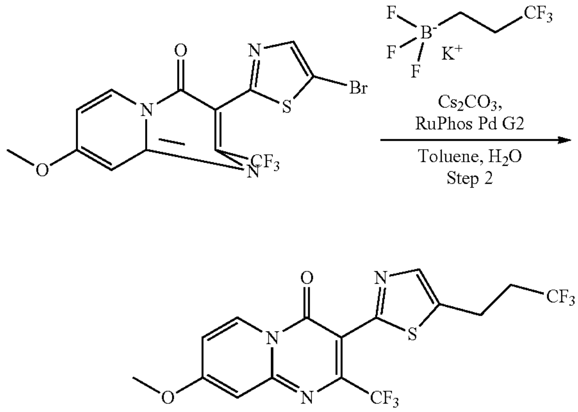

Step 1: 3-(5-bromo-1,3-thiazol-2-yl)-8-methoxy-2-(trifluoromethyl)-4H-pyrido[1,2-a]pyrimidin-4-one A mixture of 2,5-dibromothiazole (492 mg, 2.03 mmol), 8-methoxy-3-(4,4,5,5-tetramethyl-1,3,2-dioxaborolan-2-yl)-2-(trifluoromethyl)pyrido[1,2-a]pyrimidin-4-one (Intermediate 4-N, 300 mg, 0.81 mmol), tripotassium phosphate (523 mg, 2.43 mmol), (5-diphenylphosphino-9,9-dimethyl-4-xanthenyl)-diphenylphosphine (93.8 mg, 0.16 mmol) and palladium (II) diacetate (18.4 mg, 0.08 mmol) in THF (10.0 mL) and water (0.40 mL) was degassed and heated at 60° C. for 3 hours. After this time, it was diluted with water and extracted with EtOAc. The organic phase was dried and evaporated. The crude was purified by reverse phase chromatography (C18, $H_2O$:MeCN) and flash chromatography ($SiO_2$, cyclohexane:EtOAc) to give 3-(5-bromo-1,3-thiazol-2-yl)-8-methoxy-2-(trifluoromethyl)-4H-pyrido[1,2-a]pyrimidin-4-one (15.0 mg, 0.04 mmol, 4% yield). LC/MS ($ESI^+$) m/z=407.9/409.0 $[M+H]^+$.

Step 2: 8-methoxy-2-(trifluoromethyl)-3-[5-(3,3,3-trifluoropropyl)-1,3-thiazol-2-yl]-4H-pyrido[1,2-a]pyrimidin-4-one A mixture 3-(5-bromo-1,3-thiazol-2-yl)-8-methoxy-2-(trifluoromethyl)-4H-pyrido[1,2-a]pyrimidin-4-one (25 mg, 0.05 mmol), potassium trifluoro(3,3,3-trifluoropropyl)boranuide (21.0 mg, 0.10 mmol, Combi-Blocks Inc), cesium carbonate (53.3 mg, 0.16 mmol), chloro(2-dicyclohexylphosphino-2',6'-diisopropoxy-1,1'-biphenyl)[2-(2'-amino-1,1'-biphenyl)]palladium (II) (4.2 mg, 0.01 mmol) in toluene (0.90 mL) and water (0.09 mL) was degassed and stirred at 100° C. for 4 hours. Then it was diluted with water and extracted with EtOAc. The organic phase was washed with brine, dried and concentrated to obtain a crude material that was purified by flash chromatography ($SiO_2$, cyclohexane: EtOAc) and reverse phase chromatography (C18, $H_2O$+0.1% HCOOH:MeCN) to give 8-methoxy-2-(trifluoromethyl)-3-[5-(3,3,3-trifluoropropyl)-1,3-thiazol-2-yl]-4H-pyrido[1,2-a]pyrimidin-4-one (11.0 mg, 0.03 mmol, 48% yield). LC/MS ($ESI^+$) m/z=424.0 $[M+H]^+$. $^1H$ NMR (400 MHz, DMSO-$d_6$) δ 2.67-2.80 (m, 2H), 3.12-3.20 (m, 2H), 4.07 (s, 3H), 7.29 (dd, J=7.8, 2.7 Hz, 1H), 7.38 (d, J=2.7 Hz, 111), 7.77 (s, 1H), 8.98 (d, J=7.8 Hz, 1H).

Example 59

8-Methoxy-2-(trifluoromethyl)-3-[4-(3,3,3-trifluoropropyl)-1H-imidazol-1-yl]-4H-pyrido[1,2-a]pyrimidin-4-one

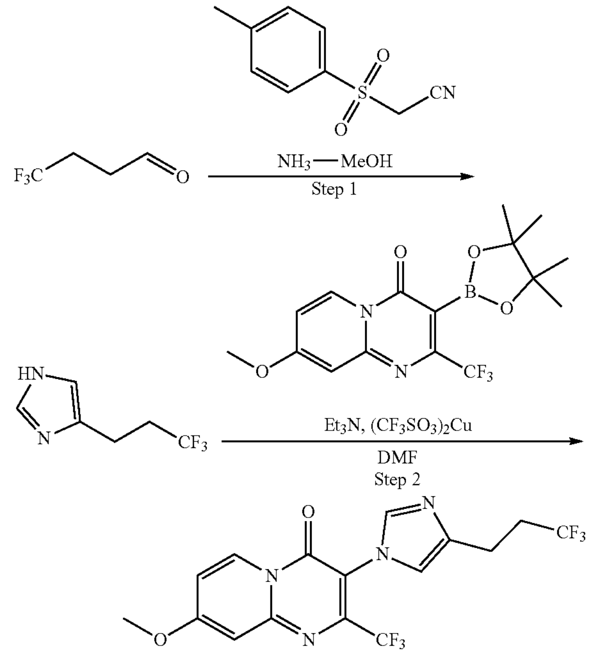

Step 1: 4-(3,3,3-trifluoropropyl)-1H-imidazole 4,4,4-Trifluorobutyraldehyde (3.0 g, 23.8 mmol) was added to 7N ammonia in methanol solution (34.0 mL, 238 mmol) and the mixture was left stirring at room temperature for 2 hours. 1-(Isocyanomethylsulfonyl)-4-methylbenzene (7.0 g, 35.7 mmol) was then added and the mixture was heated to 60° C. overnight. After this time, the reaction was allowed to cool to room temperature and it was poured into HCl 6N and extracted with $Et_2O$. The aqueous phase was basified and extracted with EtOAc, dried and evaporated. The crude was purified by flash chromatography ($SiO_2$, DCM:MeOH) to afford 4-(3,3,3-trifluoropropyl)-1H-imidazole (160 mg, 0.97 mmol, 4% yield). LC/MS ($ESI^+$) m/z=165.0 $[M+H]^+$.

Step 2: 8-methoxy-2-(trifluoromethyl)-3-[4-(3,3,3-trifluoropropyl)-1H-imidazol-1-yl]-4H-pyrido[1,2-a]pyrimidin-4-one Triethylamine (0.17 mL, 1.19 mmol) was added to a stirred solution of 4-(3,3,3-trifluoropropyl)-1H-imidazole (107 mg, 0.65 mmol), 8-methoxy-3-(4,4,5,5-tetramethyl-1,3,2-dioxaborolan-2-yl)-2-(trifluoromethyl)pyrido[1,2-a]pyrimidin-4-one (Intermediate 4-N, 200 mg, 0.54 mmol), and copper trifluoromethanesulfonate (195 mg, 0.54 mmol) in DMF (3.0 mL). The mixture was stirred at room temperature under oxygen atmosphere for 1 hour. Then it was diluted with EtOAc, filtered, washed with water, 10% $NH_4OH$ aqueous solution, brine, dried and removed. The residue was purified by reverse phase chromatography (C18, $H_2O$:MeCN) and preparative HPLC to give 8-methoxy-2-(trifluoromethyl)-3-[4-(3,3,3-trifluoropropyl)-1H-imidazol-1-yl]-4H-pyrido[1,2-a]pyrimidin-4-one (10.0 mg, 0.03 mmol, 4% yield). LC/MS ($ESI^+$) m/z=407.0 $[M+H]^+$. $^1H$ NMR (500 MHz, $CDCl_3$) δ 2.51-2.62 (m, 2H), 2.89-2.95 (m, 2H), 4.08 (s, 3H), 6.81 (s, 1H), 7.06 (dd, J=7.7, 2.7 Hz, 1H), 7.17 (d, J=2.5 Hz, 1H), 7.49 (s, 1H), 8.99 (d, J=8.0 Hz, 1H).

Example 60

8-Methoxy-3-[3-(2,2,3,3,3-pentafluoropropyl)-1,2-oxazol-5-yl]-2-(trifluoromethyl)-4H-pyrido[1,2-a]pyrimidin-4-one

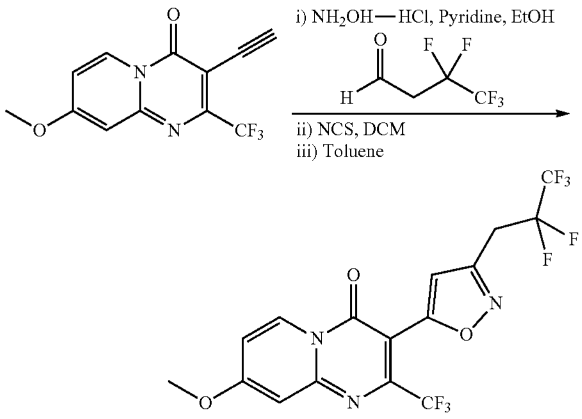

A solution of 3,3,4,4,4-pentafluorobutanal (50.0 mg, 0.31 mmol), hydroxylamine hydrochloride (64.3 mg, 0.93 mmol) and pyridine (0.15 mL, 1.85 mmol) in ethanol (2.0 mL) was stirred at room temperature overnight. Volatiles were evaporated and the crude was dissolved in dry DCM (2.0 mL), N-chlorosuccinimide (40 mg, 0.30 mmol) was added, and the mixture was stirred at room temperature overnight. After this time, the solvent was evaporated and resulting crude was dissolved in toluene (2.0 mL) and added to a solution of 3-ethynyl-8-methoxy-2-(trifluoromethyl)-4H-pyrido[1,2-a]pyrimidin-4-one (Example 52, Step 2, 21.7 mg, 0.07 mmol) and triethylamine (0.04 mL, 0.31 mmol) in toluene (2.0 mL). The resulting mixture was shaken at 80° C. overnight. Then, EtOAc was added and washed with water. The organic phase was dried and removed to give a crude material that was purified by reverse phase chromatography ($H_2O$:MeCN) to finally afford 8-methoxy-3-[3-(2,2,3,3,3-pentafluoropropyl)-1,2-oxazol-5-yl]-2-(trifluoromethyl)-4H-pyrido[1,2-a]pyrimidin-4-one (1.5 mg, 0.003 mmol, 1% yield). LC/MS ($ESI^+$) m/z=444.0 $[M+H]^+$. $^1H$ NMR (400 MHz, $CDCl_3$) δ 3.59 (t, J=17.3 Hz, 2H), 4.07 (s, 3H), 6.75 (s, 1H), 7.05 (dd, J=7.9, 2.9 Hz, 1H), 7.16 (d, J=2.6 Hz, 1H), 9.05 (d, J=7.9 Hz, 1H).

Example 61

8-Methoxy-3-(5-propyl-1,2-oxazol-3-yl)-2-(trifluoromethyl)-4H-pyrido[1,2-a]pyrimidin-4-one

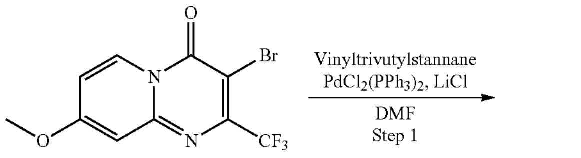

-continued

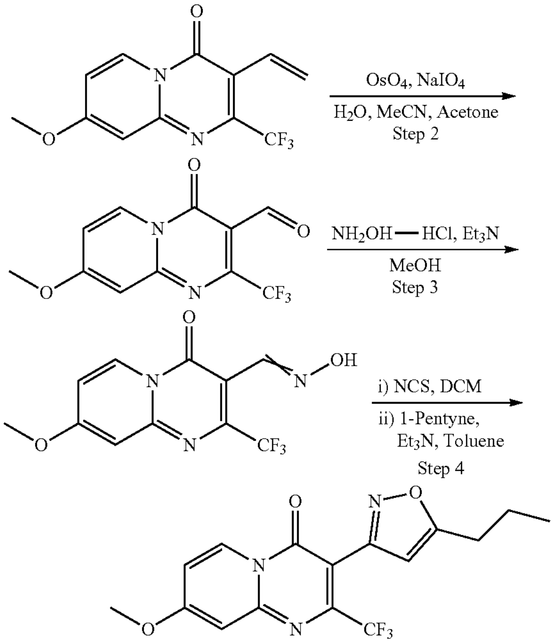

Step 1: 3-ethenyl-8-methoxy-2-(trifluoromethyl)-4H-pyrido[1,2-a]pyrimidin-4-one

A suspension of 3-bromo-8-methoxy-2-(trifluoromethyl)-4H-pyrido[1,2-a]pyrimidin-4-one (Intermediate 1-A, 1.0 g, 3.10 mmol), lithium chloride (403 mg, 9.29 mmol) and tributyl(ethenyl)stannane (1.18 mL, 4.02 mmol) in DMF (20.0 mL) was degassed before palladium (II) triphenylphosphine dichloride (436 mg, 0.62 mmol) was added and the resulting mixture was stirred at 90° C. for 24 hours. Then, it was diluted with EtOAc, washed with water and brine, dried and finally evaporated to obtain a crude material that was purified by flash chromatography ($SiO_2$, cyclohexane:EtOAc) to afford 3-ethenyl-8-methoxy-2-(trifluoromethyl)-4H-pyrido[1,2-a]pyrimidin-4-one (160 mg, 0.59 mmol, 19% yield). LC/MS ($ESI^+$) m/z=271.0 $[M+H]^+$.

Step 2: 8-methoxy-4-oxo-2-(trifluoromethyl)-4H-pyrido[1,2-a]pyrimidine-3-carbaldehyde Sodium periodate (380 mg, 0.59 mmol) was added to a solution of 3-ethenyl-8-methoxy-2-(trifluoromethyl)-4H-pyrido[1,2-a]pyrimidin-4-one (160 mg, 0.59 mmol) in water (2.0 mL), MeCN (2.0 mL), and acetone (2.0 mL), followed by osmium tetraoxide (0.74 mL, 0.12 mmol). The resulting mixture was stirred at room temperature for 2 hours. Then it was filtered, the filtrate was diluted with EtOAc and washed with HCl 1N, $NaHCO_3$ saturated aqueous solution and brine. The organic phase was dried and evaporated to give a crude that was purified by flash chromatography ($SiO_2$, cyclohexane:EtOAc) to afford 8-methoxy-4-oxo-2-(trifluoromethyl)-4H-pyrido[1,2-a]pyrimidine-3-carbaldehyde (89.0 mg, 0.33 mmol, 55% yield). LC/MS ($ESI^+$) m/z=273.0 $[M+H]^+$.

Step 3: 3-(hydroxyiminomethyl)-8-methoxy-2-(trifluoromethyl)-4H-pyrido[1,2-a]pyrimidin-4-one A mixture of 8-methoxy-4-oxo-2-(trifluoromethyl)-4H-pyrido[1,2-a]pyrimidine-3-carbaldehyde (89.0 mg, 0.30 mmol), hydroxylamine hydrochloride (27.5 mg, 0.40 mmol) and triethylamine (0.06 mL, 0.46 mmol) in methanol (3.0 mL) was stirred at room temperature for 17 hours. After this time, volatiles were evaporated, DCM was added and washed with water and brine, dried and evaporated, affording 3-(hydroxyiminomethyl)-8-methoxy-2-(trifluoromethyl)-4H-pyrido[1,2-a]pyrimidin-4-one (50.0 mg, 0.17 mmol, 57% yield).

LC/MS ($ESI^+$) m/z=288.1 $[M+H]^+$.

Step 4: 8-methoxy-3-(5-propyl-1,2-oxazol-3-yl)-2-(trifluoromethyl)-4H-pyrido[1,2-a]pyrimidin-4-one A suspension of 3-(hydroxyiminomethyl)-8-methoxy-2-(trifluoromethyl)-4H-pyrido[1,2-a]pyrimidin-4-one (50.0 mg, 0.17 mmol) and N-chlorosuccinimide (27.9 mg, 0.21 mmol) in DCM (3.0 mL) was stirred at room temperature overnight. After this time, additional DCM was added and the organic phase was washed with water, dried and evaporated. The resulting crude was dissolved in toluene (1.0 mL), and triethylamine (0.05 mL, 0.35 mmol) was added followed by 1-pentyne (11.8 mg, 0.17 mmol). The mixture was left stirring at 70° C. for 1 hour. Then volatiles were evaporated and the crude was purified by flash chromatography ($SiO_2$, cyclohexane:EtOAc) to afford 8-methoxy-3-(5-propyl-1,2-oxazol-3-yl)-2-(trifluoromethyl)-4H-pyrido[1,2-a]pyrimidin-4-one (7.6 mg, 0.02 mmol, 12% yield). LC/MS ($ESI^+$) m/z=354.1 $[M+H]^+$. $^1H$ NMR (500 MHz, DMSO-$d_6$) δ 0.95 (t, J=7.4 Hz, 3H), 1.70 (sxt, J=7.4 Hz, 2H), 2.81 (t, J=7.3 Hz, 2H), 4.06 (s, 3H), 6.38 (s, 1H), 7.27 (dd, J=8.0, 2.7 Hz, 1H), 7.37 (d, J=2.5 Hz, 1H), 8.93 (d, J=7.7 Hz, 1H).

Example 62

8-Methoxy-3-[3-(2,2,2-trifluoroethoxy)phenyl]-2-(trifluoromethyl)-4H-pyrido[1,2-a]pyrimidin-4-one

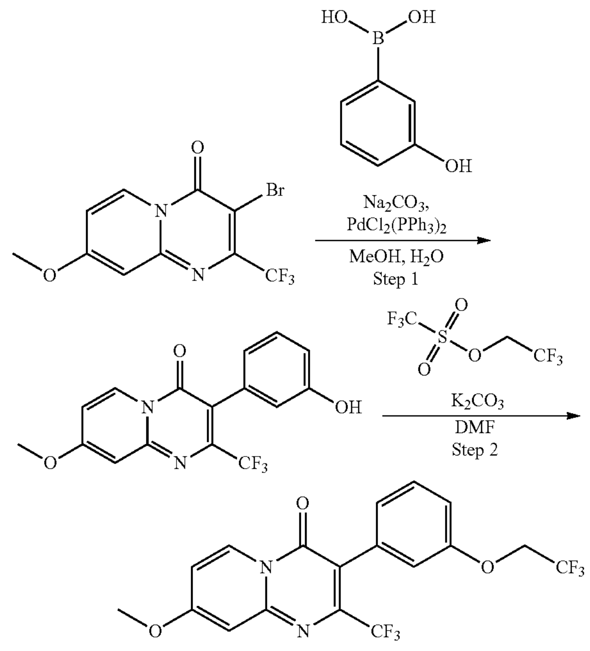

Step 1: 3-(3-hydroxyphenyl)-8-methoxy-2-(trifluoromethyl)-4H-pyrido[1,2-a]pyrimidin-4-one A screw-capped vial was charged with (3-hydroxyphenyl) boronic acid (0.51 g, 3.71 mmol), 3-bromo-8-methoxy-2-(trifluoromethyl)pyrido[1,2-a]pyrimidin-4-one (Intermediate 1-A, 1.0 g, 3.1 mmol), palladium (II) triphenylphosphine chloride (21.8 mg, 0.03 mmol) and sodium carbonate (656 mg, 6.19 mmol). The reactants were dissolved in methanol (14.0 mL) and Water (14.0 mL) and the mixture was degassed for 20 minutes with nitrogen and was left to react at reflux for 5 hours. The reaction mixture was cooled to room temperature and filtered, the solvent eliminated and the residue was dissolved with EtOAc and washed with water and brine. The organic layer was dried with $Na_2SO_4$ and concentrated to afford a crude product, which was purified by flash chromatography ($SiO_2$, cyclohexanes:EtOAc) to give 3-(3-hydroxyphenyl)-8-methoxy-2-(trifluoromethyl)pyrido[1,2-a]pyrimidin-4-one (145 mg, 0.43 mmol, 14% yield). LC/MS (ESI$^+$) m/z=337.3 [M+H]$^+$.

Step 2: 8-methoxy-3-[3-(2,2,2-trifluoroethoxy)phenyl]-2-(trifluoromethyl)-4H-pyrido[1,2-a]pyrimidin-4-one 3-(3-Hydroxyphenyl)-8-methoxy-2-(trifluoromethyl)-4H-pyrido[1,2-a]pyrimidin-4-one (125 mg, 0.37 mmol) was dissolved in DMF (3.71 mL), then potassium carbonate (61.6 mg, 0.45 mmol) and trifluoromethanesulfonic acid 2,2,2-trifluoroethyl ester (80.3 μL, 0.56 mmol) were added to the reaction. The mixture was left to react at 85° C. for 24 hours. Water was added to the reaction mixture and the solution was extracted with EtOAc. The organic phase was washed with water, brine, dried over $Na_2SO_4$ and removed. The crude was purified by flash chromatography ($SiO_2$, Cyclohexanes:EtOAc) to afford 8-methoxy-3-[3-(2,2,2-trifluoroethoxy)phenyl]-2-(trifluoromethyl)-4H-pyrido[1,2-a]pyrimidin-4-one (99.0 mg, 0.24 mmol, 63% yield). LC/MS (ESI$^+$) m/z=419.1 [M+H]$^+$. $^1$H NMR (500 MHz, DMSO-$d_6$) δ 8.87 (d, J=7.95 Hz, 1H), 7.38 (t, J=7.95 Hz, 1H), 7.28 (d, J=2.69 Hz, 1H), 7.18 (dd, J=7.89, 2.75 Hz, 1H), 7.09 (dd, J=8.07, 2.32 Hz, 1H), 6.98 (d, J=2.32 Hz, 1H), 6.95 (d, J=7.58 Hz, 1H), 4.75 (q, J=8.80 Hz, 2H), 4.02 (s, 3H).

Example 63

3-Fluoro-1-methyl-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione

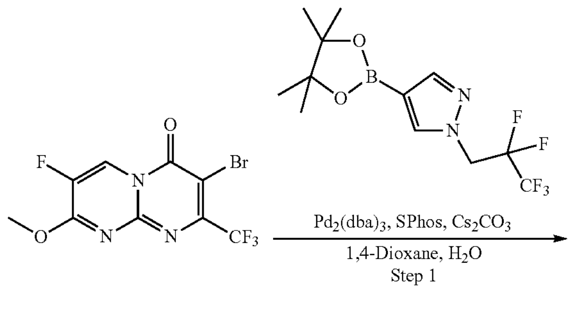

-continued

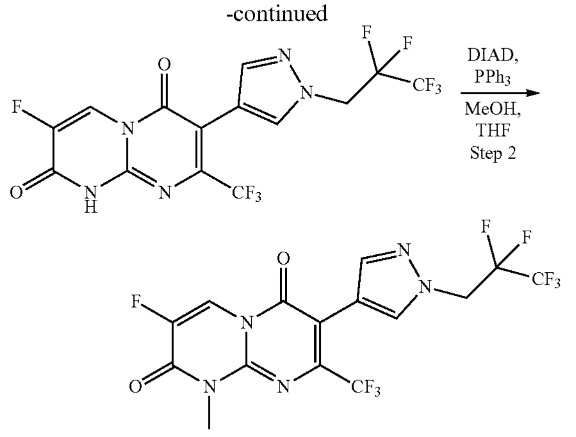

Step 1: 3-fluoro-7-[1-(2,2,3,3,3-pentafluoropropyl)-1H-pyrazol-4-yl]-8-(trifluoromethyl)-1H,2H,6H-pyrimido[1,2-a][1,3]diazine-2,6-dione A mixture of cesium carbonate (92.2 mg, 0.28 mmol), (1E,4E)-1,5-diphenyl-3-penta-1,4-dienone palladium (10.3 mg, 0.01 mmol), dicyclohexyl-[2-(2,6-dimethoxyphenyl) phenyl]phosphine (11.5 mg, 0.03 mmol) and 1-(2,2,3,3,3-pentafluoropropyl)-4-(4,4,5,5-tetramethyl-1,3,2-dioxaborolan-2-yl)pyrazole (Intermediate 2-G, 40.4 mg, 0.12 mmol) in 1,4-dioxane (2.0 mL) and water (0.20 mL) was degassed for 15 minutes, then 3-bromo-7-fluoro-8-methoxy-2-(trifluoromethyl)-4H-pyrimido[1,2-a]pyrimidin-4-one (Intermediate 3-AC, 50.0 mg, 0.11 mmol) was added and the reaction was stirred at 90° C. for 1 hour. The mixture was partitioned between water and EtOAc. The organic phase was washed with brine, dried over $Na_2SO_4$, filtered and concentrated under vacuum. The crude material was purified by flash chromatography ($SiO_2$, cyclohexane:EtOAc) to obtain 3-fluoro-7-[1-(2,2,3,3,3-pentafluoropropyl)-1H-pyrazol-4-yl]-8-(trifluoromethyl)-1H,2H,6H-pyrimido[1,2-a][1,3]diazine-2,6-dione (28 mg, 0.06 mmol, 56% yield). LC/MS (ESI$^+$) m/z=448.2 [M+H]$^+$.

Step 2: 3-Fluoro-1-methyl-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione To a solution of 3-fluoro-7-[1-(2,2,3,3,3-pentafluoropropyl)-1H-pyrazol-4-yl]-8-(trifluoromethyl)-1H,2H,6H-[1,3] diazino[1,2-a]pyrimidine-2,6-dione (21.0 mg, 0.05 mmol) in methanol (3.0 μL, 0.07 mmol) and THF (2.0 mL), triphenylphosphine (18.5 mg, 0.07 mmol) was added followed by diisopropyl azodicarboxylate (0.01 mL, 0.07 mmol) and the reaction was stirred at room temperature overnight. The mixture was concentrated and portioned between water and EtOAc. The organic phase was dried over $Na_2SO_4$, filtered and concentrated under vacuum. The resulting crude material was purified by flash chromatography ($SiO_2$, cyclohexane:EtOAc) and reverse phase chromatography (C18 $H_2O$+0.1% HCOOH/MeCN) to obtain 3-fluoro-1-methyl-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione (2.8 mg, 0.006 mmol, 13% yield). LC/MS (ESI$^+$) m/z=462.2 [M+H]$^+$. $^1$H NMR (500 MHz, DMSO-$d_6$) δ 3.56 (s, 3H), 5.29 (t, J=14.96 Hz, 2H), 7.67 (s, 1H), 8.06 (s, 1H), 8.86-9.07 (m, 1H).

Example 64

8-Methyl-3-[1-(2,2,3,3,3-pentafluoropropyl)-1H-pyrazol-4-yl]-2-(trifluoromethyl)-4H,6H,7H,8H,9H-pyrimido[1,2-a]pyrazin-4-one

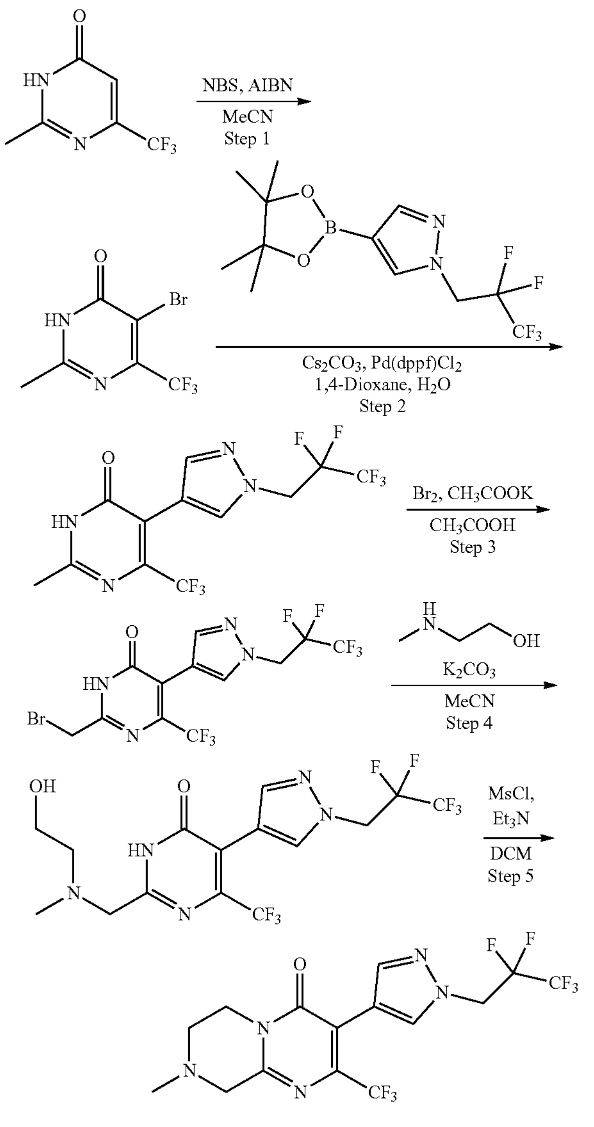

Step 1: 5-bromo-2-methyl-4-(trifluoromethyl)-1H-pyrimidin-6-one

2-Methyl-4-(trifluoromethyl)-1H-pyrimidin-6-one (3.0 g, 16.8 mmol) was added to a mixture of N-bromosuccinimide (3.15 g, 17.8 mmol) and 2,2'-azobis(2-methylpropionitrile) (0.28 g, 1.68 mmol) in MeCN (75 mL) and the reaction was heated at 80° C. for 2 hours. The mixture was then cooled to room temperature, diluted with EtOAc and washed with saturated aqueous $NaHCO_3$, brine, dried over anhydrous $Na_2SO_4$, and evaporated. The crude was purified by reverse phase chromatography (C18, $H_2O$+01% HCOOH:MeCN) to give 5-bromo-2-methyl-4-(trifluoromethyl)-1H-pyrimidin-6-one (2.25 g, 8.75 mmol, 53% yield). LC/MS ($ESI^+$)

m/z=259.1/260.1 $[M+H]^+$. $^1H$ NMR (400 MHz, DMSO-$d_6$) δ 2.34 (s, 3H) 13.44 (br s, 1H)

Step 2: 2-methyl-5-[1-(2,2,3,3,3-pentafluoropropyl)pyrazol-4-yl]-4-(trifluoromethyl)-1H-pyrimidin-6-one 5-Bromo-2-methyl-4-(trifluoromethyl)-1H-pyrimidin-6-one (1.65 g, 6.42 mmol) and 1-(2,2,3,3,3-pentafluoropropyl)-4-(4,4,5,5-tetramethyl-1,3,2-dioxaborolan-2-yl)pyrazole (Intermediate 2-G, 4.19 g, 12.8 mmol) were dissolved in 1,4-dioxane (18.5 mL) and water (3.72 mL). Cesium carbonate (6.28 g, 19.3 mmol) and [1,1'-bis(diphenylphosphino)ferrocene]dichloropalladium (II) (4.7 g, 0.64 mmol) were added and the resulting suspension was degassed under nitrogen and heated at 100° C. for 1 hour. After cooling to room temperature, the solid was filtered off and washed with EtOAc. Water was added and the pH was adjusted to pH 5 using HCl 1N. The aqueous phase was extracted with EtOAc and the combined organic layers were dried over anhydrous $Na_2SO_4$, filtered and concentrated under vacuum. The resulting crude was purified by flash chromatography (DCM:EtOH) to afford 2-methyl-5-[1-(2,2,3,3,3-pentafluoropropyl)pyrazol-4-yl]-4-(trifluoromethyl)-1H-pyrimidin-6-one (2.0 g, 5.32 mmol, 83% yield). LC/MS ($ESI^+$) m/z=377.0 $[M+H]^+$.

Step 3: 2-(bromomethyl)-5-[1-(2,2,3,3,3-pentafluoropropyl)pyrazol-4-yl]-4-(trifluoromethyl)-1H-pyrimidin-6-one A mixture of 2-methyl-5-[1-(2,2,3,3,3-pentafluoropropyl)pyrazol-4-yl]-4-(trifluoromethyl)-1H-pyrimidin-6-one (1.84 g, 4.90 mmol), potassium acetate (721 mg, 7.35 mmol) and molecular bromine (0.38 mL, 7.35 mmol) in acetic acid (92.1 mL) was stirred at 50° C. overnight. The reaction was treated with solid $NaHCO_3$ until pH 5-6. DCM and water were added and the organic layer was separated, washed with 10% sodium thiosulphate, brine and dried over anhydrous $Na_2SO_4$. Removal of the solvent gave crude mixture that was purified by flash chromatography ($SiO_2$, DCM:EtOH) to give 2-(bromomethyl)-5-[1-(2,2,3,3,3-pentafluoropropyl)pyrazol-4-yl]-4-(trifluoromethyl)-1H-pyrimidin-6-one (764 mg, 1.68 mmol, 34% yield). LC/MS ($ESI^+$) m/z=456.9/458.0 $[M+H]^+$.

Step 4: 2-[[2-hydroxyethyl(methyl)amino]methyl]-5-[1-(2,2,3,3,3-pentafluoropropyl)pyrazol-4-yl]-4-(trifluoromethyl)-1H-pyrimidin-6-one 2-(bromomethyl)-5-[1-(2,2,3,3,3-pentafluoropropyl)pyrazol-4-yl]-4-(trifluoromethyl)-1H-pyrimidin-6-one (300.0 mg, 0.66 mmol) was dissolved in MeCN (3.0 mL). 2-(Methylamino)ethanol (105.9 uL, 1.32 mmol) and potassium carbonate (273 mg, 1.98 mmol) were added and the mixture was stirred at 80° C. for 2.5 hours, then at room temperature overnight. After this time, DCM was added (10 mL) and the suspension was filtered. The organic phase was evaporated and the crude 2-[[2-hydroxyethyl(methyl)amino]methyl]-5-[1-(2,2,3,3,3-pentafluoropropyl)pyrazol-4-yl]-4-(trifluoromethyl)-1H-pyrimidin-6-one was used in the following step without any further purification.

Step 5: 8-methyl-3-[1-(2,2,3,3,3-pentafluoropropyl)-1H-pyrazol-4-yl]-2-(trifluoromethyl)-4H,6H,7H,8H,9H-pyrimido[1,2-a]pyrazin-4-one 2-[[2-Hydroxyethyl(methyl)amino]methyl]-5-[1-(2,2,3,3,3-pentafluoropropyl)pyrazol-4-yl]-4-(trifluoromethyl)-1H-pyrimidin-6-one obtained as crude in the previous step, was dissolved in DCM (1.5 mL), and triethylamine (0.23 mL, 1.67 mmol) was added. The reaction was cooled to 0° C. and methanesulfonyl chloride (0.06 mL, 0.74 mmol) was added dropwise. The reaction was kept at 0° C. for 1 hour and stirred at room temperature for 20 hours. The reaction mixture was evaporated under reduced pressure and the crude purified by flash chromatography ($SiO_2$, DCM: MeCN) to afford 8-methyl-3-[1-(2,2,3,3,3-pentafluoropropyl)-1H-pyrazol-4-yl]-2-(trifluoromethyl)-4H,6H,7H,8H,9H-pyrimido[1,2-a]pyrazin-4-one (8.5 mg, 0.02 mmol, 6% yield). LC/MS ($ESI^+$) m/z=432.1 $[M+H]^+$. $^1H$ NMR (400 MHz, DMSO-$d_6$) δ 1.68 (s, 3H), 2.11 (t, J=5.7 Hz, 2H), 2.90 (s, 2H), 3.17 (t, J=5.7 Hz, 2H), 4.26 (t, J=14.6 Hz, 2H), 6.90 (s, 1H), 7.18 (s, 1H).

Example 65

1-(Chloromethyl)-7-[1-(2,2,3,3,3-pentafluoropropyl)-1H-pyrazol-4-yl]-8-(trifluoromethyl)-1H,2H,6H-pyrimido[1,2-a][1,3]diazine-2,6-dione

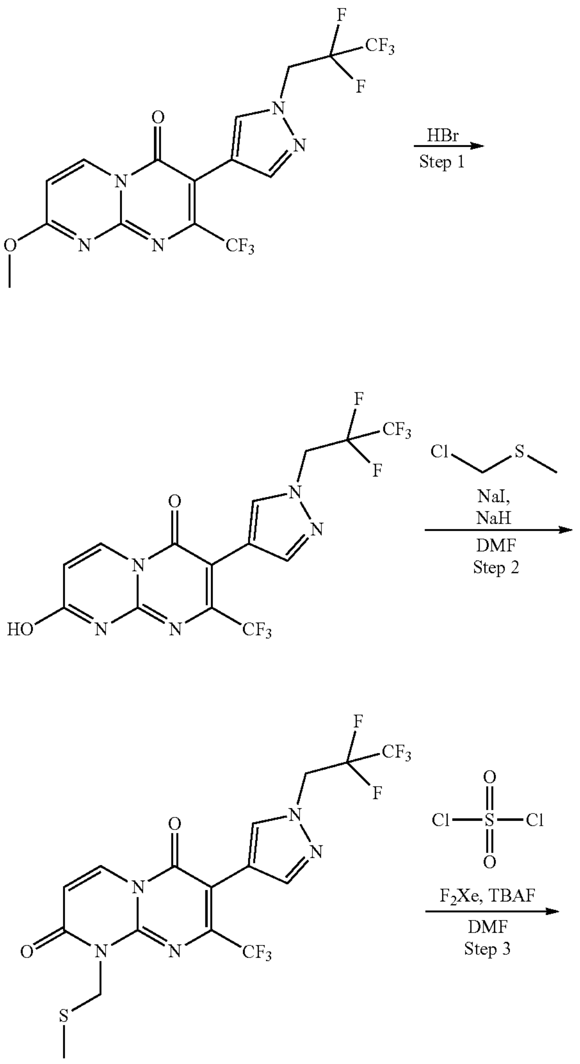

-continued

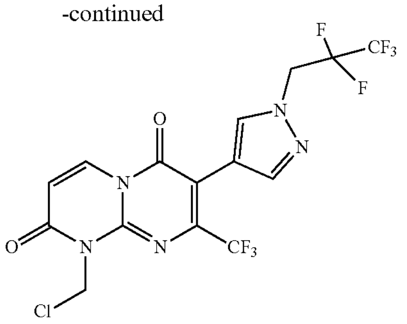

Step 2: 9-(methylsulfanylmethyl)-3-[1-(2,2,3,3,3-pentafluoropropyl)pyrazol-4-yl]-2-(trifluoromethyl)pyrimido[1,2-a]pyrimidine-4,8-dione Sodium iodide (40.5 mg, 0.27 mmol) and sodium hydride (10.8 mg, 0.27 mmol) were added to a solution of 7-(1-(2,2,3,3,3-pentafluoropropyl)-1H-pyrazol-4-yl)-8-(trifluoromethyl)-2H-pyrimido[1,2-a]pyrimidine-2,6(1H)-dione (Example 10-4, 116 mg, 0.27 mmol) in DMF (2.0 mL) at 0° C. The mixture was stirred at this temperature for 40 minutes then chloro-(methylthio)methane (0.04 mL, 0.49 mmol) was added. The reaction was left to reach room temperature and it was stirred overnight. It was then quenched with EtOH and purified by flash chromatography ($SiO_2$, cyclohexane: EtOAc) to give 9-(methylsulfanylmethyl)-3-[1-(2,2,3,3,3-pentafluoropropyl)pyrazol-4-yl]-2-(trifluoromethyl)pyrimido[1,2-a]pyrimidine-4,8-dione (121 mg, 0.25 mmol, 92% yield). LC/MS ($ESI^+$) m/z=490.1 $[M+H]^+$.

Step 3: 1-(chloromethyl)-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione A solution of sulfuryl chloride (0.06 mL, 0.73 mmol) in DCM (0.5 mL) was added to a solution of 9-(methylsulfanylmethyl)-3-[1-(2,2,3,3,3-pentafluoropropyl)pyrazol-4-yl]-2-(trifluoromethyl)pyrimido[1,2-a]pyrimidine-4,8-dione (121 mg, 0.25 mmol) in DCM (0.5 mL). The mixture was stirred at room temperature for 15 minutes, then volatiles were removed. The crude was dissolved in DCM (1.0 mL) and tetrabutylammonium fluoride (0.5 mL, 0.50 mmol) was added. The mixture was stirred at room temperature for 3 days. Difluoroxenon (41.9 mg, 0.25 mmol) was added and the reaction was stirred for 24 hr. EtOAc and brine were added, the phases were separated and the organic one was dried over $Na_2SO_4$, filtered and concentrated. The obtained crude was purified by flash-chromatography ($SiO_2$, cyclohexane:EtOAc) to give 1-(chloromethyl)-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione (47 mg, 0.10 mmol, 40% yield). LC/MS ($ESI^+$) m/z=478.3/480.3 $[M+H]^+$. $^1H$ NMR (500 MHz, DMSO-$d_6$) δ 8.61 (d, J=8.20 Hz, 1H), 8.07 (s, 1H), 7.68 (s, 1H), 6.59 (d, J=8.23 Hz, 1H), 5.98 (s, 2H), 5.30 (t, J=14.96 Hz, 2H).

Example 66

7-Chloro-8-methoxy-3-[1-(2,2,3,3,3-pentafluoropropyl)-1H-pyrazol-4-yl]-2-(trifluoromethyl)-4H-[1,3]diazino[1,2-a]pyrimidin-4-one

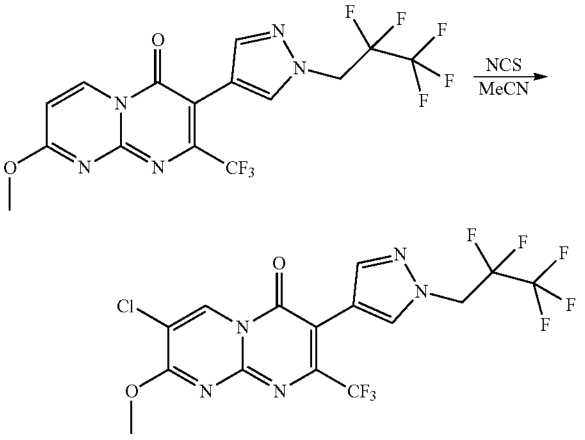

A mixture of 8-methoxy-3-(1-(2,2,3,3,3-pentafluoropropyl)-1H-pyrazol-4-yl)-2-(trifluoromethyl)-4H-pyrimido[1,2-a]pyrimidin-4-one (Example 1-34, 2.07 g, 4.67 mmol) and N-chlorosuccinimide (2.76 g, 20.7 mmol) in MeCN (30 mL)was stirred at 80° C. for three days. The mixture was portioned between water and EtOAc. The organic phase was washed with $NaHCO_3$ and $Na_2SO_3$ saturated solutions, dried over $Na_2SO_4$ filtered and concentrated. The resulting crude material was purified by flash chromatography ($SiO_2$, cyclohexane:EtOAc) and reverse phase chromatography (C18, $H_2O$+0.1% HCOOH:MeCN) to afford 7-chloro-8-methoxy-3-[1-(2,2,3,3,3-pentafluoropropyl)-1H-pyrazol-4-yl]-2-(trifluoromethyl)-4H-[1,3]diazino[1,2-a]pyrimidin-4-one (247 mg, 0.52 mmol, 11% yield). LC/MS ($ESI^+$) m/z=478.2/480.2 $[M+H]^+$. $^{1}H$ NMR (500 MHz, DMSO-$d_6$) δ 4.19 (s, 3H), 5.30 (t, J=14.96 Hz, 2H), 7.68 (s, 1H), 8.06 (s, 1H), 9.24 (s, 1H).

Example 67

1-Methyl-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione

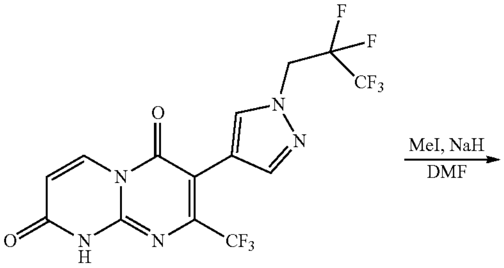

-continued

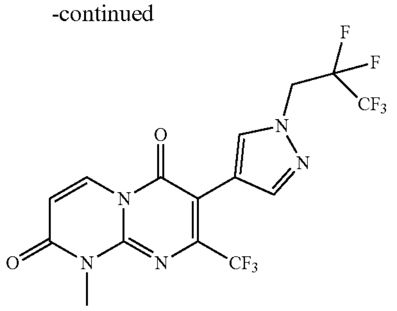

Sodium hydride (5.13 mg, 0.13 mmol) was added to a solution of 7-(1-(2,2,3,3,3-pentafluoropropyl)-1H-pyrazol-4-yl)-8-(trifluoromethyl)-2H-pyrimido[1,2-a]pyrimidine-2,6(1H)-dione (Example 10-4, 50.0 mg, 0.12 mmol) in DMF (1.0 mL) at 0° C. The reaction was stirred at this temperature for 40 minutes then iodomethane (10.9 uL, 0.17 mmol) was added. The reaction was left to reach room temperature and was stirred overnight. It was quenched with EtOH and was purified by flash-chromatography ($SiO_2$, cyclohexane:EtOAc) to give 1-methyl-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione (21 mg, 0.05 mmol, 41% yield). LC/MS ($ESI^+$) m/z=444.3 $[M+H]^+$. $^{1}H$ NMR (400 MHz, DMSO-$d_6$) δ 3.50 (s, 3H), 5.28 (t, J=15.02 Hz, 2H), 6.55 (d, J=8.33 Hz, 1H), 7.65 (s, 1H), 8.04 (s, 1H), 8.60 (d, J=8.33 Hz, 1H).

Example 68

1-(Fluoromethyl)-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione

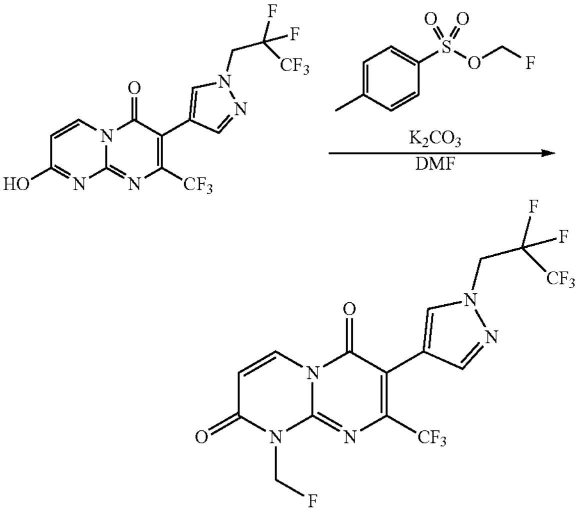

Potassium carbonate (32.2 mg, 0.23 mmol) and fluoromethyl 4-methylbenzenesulfonate (47.6 mg, 0.23 mmol, Fluorochem Ltd) were added to a solution of 7-(1-(2,2,3,3,3-pentafluoropropyl)-1H-pyrazol-4-yl)-8-(trifluoromethyl)-2H-pyrimido[1,2-a]pyrimidine-2,6(1H)-dione (Example 10-4, 50.0 mg, 0.12 mmol) in DMF (1.0 mL). The reaction was stirred at room temperature overnight then it was purified by flash-chromatography ($SiO_2$, cyclohexane:E-tOAc) to give 1-(fluoromethyl)-7-[1-(2,2,3,3,3-pentafluoropropyl)-1H-pyrazol-4-yl]-8-(trifluoromethyl)-1H,2H,6H-[1,3]diazino[1,2-a]pyrimidine-2,6-dione (23 mg, 0.05 mmol, 43% yield). LC/MS ($ESI^+$) m/z=462.1 $[M+H]^+$. $^1H$ NMR (500 MHz, DMSO-$d_6$) δ 5.30 (t, J=14.96 Hz, 2H), 6.12-6.37 (m, 2H), 6.58 (d, J=8.23 Hz, 1H), 7.68 (s, 1H), 8.07 (s, 1H), 8.61 (d, J=8.23 Hz, 1H).

Examples 69 and 70

Examples 69: 3-(1-{[(1R)-2,2-Difluorocyclopropyl]methyl}-1H-pyrazol-4-yl)-8-methoxy-2-(trifluoromethyl)-4H-pyrido[1,2-a]pyrimidin-4-one and

Example 70: 3-(1-{[(1S)-2,2-Difluorocyclopropyl]methyl}-1H-pyrazol-4-yl)-8-methoxy-2-(trifluoromethyl)-4H-pyrido[1,2-a]pyrimidin-4-one

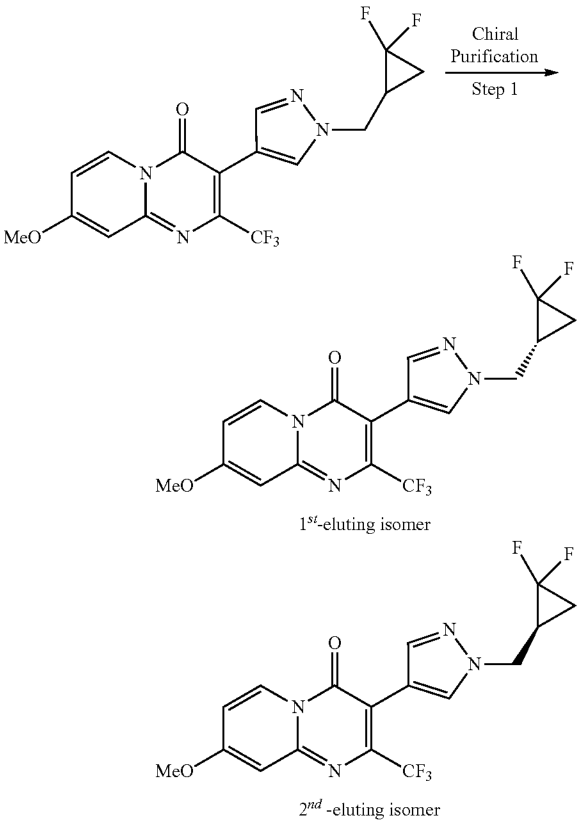

$1^{st}$-eluting isomer $2^{nd}$-eluting isomer

Step 1: 3-(1-{[(1R)-2,2-difluorocyclopropyl]methyl}-1H-pyrazol-4-yl)-8-methoxy-2-(trifluoromethyl)-4H-pyrido[1,2-a]pyrimidin-4-one and 3-(1-{[(1S)-2,2-difluorocyclopropyl]methyl}-1H-pyrazol-4-yl)-8-methoxy-2-(trifluoromethyl)-4H-pyrido[1,2-a]pyrimidin-4-one The racemic mixture of 3-{1-[(2,2-difluorocyclopropyl)methyl]-1H-pyrazol-4-yl}-8-methoxy-2-(trifluoromethyl)-4H-pyrido[1,2-a]pyrimidin-4-one (Example 39-42, 25 mg, 0.062 mmol) was purified by Chiral HPLC (Chiralcel OD-H (25×0.46 cm)) eluting with n-Hexane/(ethanol+0.1% isopropylamine) 50/50% to obtain two peaks: $1^{st}$ eluting isomer (9 mg, 0.023 mmol, >99% ee) and $2^{nd}$ eluting isomer 9 mg, 0.023 mmol, >99% ee). The stereochemistry of the isomers was assigned arbitrarily to be 3-(1-{[(1R)-2,2-difluorocyclopropyl]methyl}-1H-pyrazol-4-yl)-8-methoxy-2-(trifluoromethyl)-4H-pyrido[1,2-a]pyrimidin-4-one as $1^{st}$ eluting isomer and 3-(1-{[(1S)-2,2-difluorocyclopropyl]methyl}-1H-pyrazol-4-yl)-8-methoxy-2-(trifluoromethyl)-4H-pyrido[1,2-a]pyrimidin-4-one as $2^{nd}$ eluting isomer.

$1^{st}$ Eluting isomer: $^1H$ NMR (400 MHz, $CDCl_3$) δ 1.26-1.37 (m, 1H), 1.56-1.66 (m, 1H), 2.09-2.32 (m, 1H), 4.00 (s, 3H), 4.23-4.43 (m, 2H), 6.91 (dd, J=7.9, 2.6 Hz, 1H), 7.02 (d, J=2.6 Hz, 1H), 7.66-7.79 (m, 2H), 8.95 (d, J=7.9 Hz, 1H).

$2^{nd}$ Eluting isomer: $^1H$ NMR (400 MHz, $CDCl_3$) δ 1.26-1.37 (m, 1H), 1.56-1.66 (m, 1H), 2.09-2.32 (m, 1H), 4.00 (s, 3H), 4.23-4.43 (m, 2H), 6.91 (dd, J=7.9, 2.6 Hz, 1H), 7.02 (d, J=2.6 Hz, 1H), 7.66-7.79 (m, 2H), 8.95 (d, J=7.9 Hz, 1H).

Examples 71 and 72

Examples 71: 3-(1-(((1R)-2,2-difluorocyclopropyl)methyl)-1H-pyrazol-4-yl)-7-fluoro-8-methoxy-2-(trifluoromethyl)-4H-pyrido[1,2-a]pyrimidin-4-one and

Example 72: 3-(1-(((1S)-2,2-difluorocyclopropyl)methyl)-1H-pyrazol-4-yl)-7-fluoro-8-methoxy-2-(trifluoromethyl)-4H-pyrido[1,2-a]pyrimidin-4-one

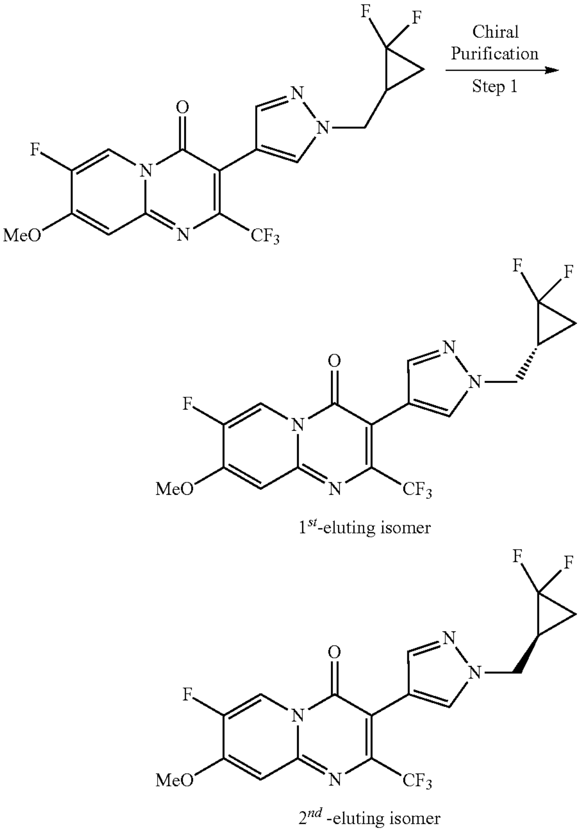

$1^{st}$-eluting isomer $2^{nd}$-eluting isomer

Step 1: 3-(1-(((1R)-2,2-difluorocyclopropyl) methyl)-1H-pyrazol-4-yl)-7-fluoro-8-methoxy-2-(trifluoromethyl)-4H-pyrido[1,2-a]pyrimidin-4-one and 3-(1-(((1S)-2,2-difluorocyclopropyl)methyl)-1H-pyrazol-4-yl)-7-fluoro-8-methoxy-2-(trifluoromethyl)-4H-pyrido[1,2-a]pyrimidin-4-one The racemic mixture of 3-{1-[(2,2-difluorocyclopropyl) methyl]-1H-pyrazol-4-yl}-7-fluoro-8-methoxy-2-(trifluoromethyl)-4H-pyrido[1,2-a]pyrimidin-4-one (Example 39-59, 20 mg, 0.05 mmol) was purified by Chiral HPLC (Chiralpak AD-H (25×2.0 cm)) eluting with n-hexane/ethanol 55/45% to obtain two peaks: 1$^{st}$ eluting isomer (8 mg, 0.02 mmol, >99% ee) and 2$^{nd}$ eluting isomer (8 mg, 0.02 mmol, >99% ee). The stereochemistry of the isomers was assigned arbitrarily to be -(1-(((1R)-2,2-difluorocyclopropyl)methyl)-1H-pyrazol-4-yl)-7-fluoro-8-methoxy-2-(trifluoromethyl)-4H-pyrido[1,2-a]pyrimidin-4-one as 1$^{4}$ eluting isomer and 3-(1-(((1S)-2,2-difluorocyclopropyl) methyl)-1H-pyrazol-4-yl)-7-fluoro-8-methoxy-2-(trifluoromethyl)-4H-pyrido[1,2-a]pyrimidin-4-one as 2$^{nd}$ eluting isomer.

1$^{st}$ Eluting isomer: $^1$H NMR (400 MHz, DMSO-d$_6$) δ 1.44-1.55 (m, 1H), 1.69 (tdd, J=12.0, 12.0, 7.7, 4.8 Hz, 1H), 2.19-2.34 (m, 1H), 4.12 (s, 3H), 4.32 (d, J=7.5 Hz, 2H), 7.48 (d, J=7.9 Hz, 1H), 7.58 (s, 1H), 7.95 (s, 1H), 9.03 (d, J=6.8 Hz, 1H).

2$^{nd}$ Eluting isomer: $^1$H NMR (400 MHz, DMSO-d$_6$) δ 1.44-1.55 (m, 1H), 1.69 (tdd, J=12.0, 12.0, 7.7, 4.8 Hz, 1H), 2.19-2.34 (m, 1H), 4.12 (s, 3H), 4.32 (d, J=7.5 Hz, 2H), 7.48 (d, J=7.9 Hz, 1H), 7.58 (s, 1H), 7.95 (s, 1H), 9.03 (d, J=6.8 Hz, 1H).

Analytical Data

Table 25 provides analytical data for compounds presented herein.

TABLE 25

| Ex. | LRMS: m/z (ESI, +ve ion): (M + H)$^+$ | NMR |
|---|---|---|
| 1-2 | 360.0 | $^1$H NMR (400 MHz, CD$_2$Cl$_2$) δ 3.84 (s, 2H) 4.03 (s, 3H) 6.95 (dd, J = 7.88, 2.70 Hz, 1H) 7.06 (d, J = 2.70 Hz, 1H) 7.31-7.40 (m, 2H) 7.40-7.49 (m, 2H) 8.92 (d, J = 7.88 Hz, 1H). |
| 1-3 | 387.1 | $^1$H NMR (400 MHz, DMSO-d$_6$) δ 8.95 (d, J = 7.8 Hz, 1H), 8.60 (d, J = 2.6 Hz, 1H), 7.87 (d, J = 7.9 Hz, 2H), 7.53 (t, J = 7.9 Hz, 2H), 7.37-7.28 (m, 2H), 7.24 (dd, J = 7.9, 2.8 Hz, 1H), 6.69 (d, J = 2.6 Hz, 1H), 4.07 (s, 3H). |
| 1-4 | 427.1 | $^1$H NMR (400 MHz, DMSO-d$_6$) δ 8.88 (d, J = 7.9 Hz, 1H), 7.28 (d, J = 2.8 Hz, 1H), 7.24-7.16 (m, 3H), 7.04-6.98 (m, 2H), 4.21 (ddd, J = 10.0, 6.5, 3.1 Hz, 1H), 4.04 (s, 4H), 2.25 (dq, J = 14.2, 7.5, 6.9 Hz, 1H), 1.76 (tdd, J = 12.1, 7.9, 4.8 Hz, 1H), 1.52 (dtd, J = 12.3, 7.9, 4.2 Hz, 1H). |
| 1-5 | 388.1 | $^1$H NMR (400 MHz, DMSO-d$_6$) δ 9.02 (d, J = 7.8 Hz, 1H), 8.01-7.93 (m, 2H), 7.60-7.52 (m, 3H), 7.45 (d, J = 2.8 Hz, 1H), 7.38-7.30 (m, 2H), 4.09 (s, 3H). |
| 1-6 | 388.1 | $^1$H NMR (400 MHz, DMSO-d$_6$) δ 9.01 (d, J = 7.8 Hz, 1H), 8.02-7.97 (m, 2H), 7.71 (s, 1H), 7.61-7.55 (m, 3H), 7.39 (d, J = 2.8 Hz, 1H), 7.31-7.28 (m, 1H), 4.07 (s, 3H). |
| 1-7 | 361.0 | $^1$H NMR (400 MHz, CD$_2$Cl$_2$) δ 4.05 (s, 3H) 7.01 (dd, J = 7.88, 2.70 Hz, 1H) 7.08-7.17 (m, 2H) 7.23-7.30 (m, 1H) 7.31-7.38 (m, 1H) 7.52 (d, J = 8.09 Hz, 1H) 7 65 (d, J = 7.46 Hz, 1H) 9.01 (d, J = 7.88 Hz, 1H). |
| 1-8 | 391.1 | $^1$H NMR (400 MHz, CD$_2$Cl$_2$) δ 0.32-0.40 (m, 2H) 0.60-0.70 (m, 2H) 1.23-1.36 (m, 1H) 3.85 (d, J = 6.84 Hz, 2H) 4.02 (s, 3H) 6.90-6.93 (m, 1H) 6.95 (d, J = 8.91 Hz, 2H) 7.03 (d, J = 2.49 Hz, 1H) 7.22 (d, J = 8.50 Hz, 2H) 8.90 (d, J = 7.88 Hz, 1H). |
| 1-9 | 122.9 | $^1$H NMR (400 MHz, CD$_2$Cl$_2$) δ 4.04 (s, 3H) 6.99 (dd, J = 7.88, 2.70 Hz, 1H) 7.06-7.11 (m, 2H) 7.14 (br d, J = 9.33 Hz, 1H) 7.35 (t, J = 8.19 Hz, 1H) 8.91 (d, J = 1.04 Hz, 1H) 8.94 (d, J = 7.88 Hz, 1H). |
| 1-10 | 401.0 | $^1$H NMR (400 MHz, CD$_2$Cl$_2$) δ 4.02 (s, 3H) 4.26 (td, J = 13.37, 3.94 Hz, 2H) 5.97-6.31 (m, 1H) 6.94 (dd, J = 7.88, 2.49 Hz, 1H) 7.00 (d, J = 8.71 Hz, 2H) 7.04 (d, J = 2.49 Hz, 1H) 7.27 (d, J = 8.50 Hz, 2H) 8.91 (d, J = 7.88 Hz, 1H). |
| 1-11 | 383.0 | H NMR (400 MHz, CDCl$_3$) δ 8.94 (d, J = 7.88 Hz, 1H) 7.27-7.31 (m, 2H) 7.04 (d, J = 2.49 Hz, 1H) 7.00 (d, J = 8.71 Hz, 2H) 6.91 (dd, J = 7.77, 2.59 Hz, 1H) 4.81-4.87 (m, 1H) 4.69-4.76 (m, 1H) 4.27-4.33 (m, 1H) 4.20-4.25 (m, 1H) 4.01 (s, 3H). |
| 1-12 | 419.1 | $^1$H NMR (400 MHz, CDCl$_3$) δ 8.96 (1H, d, J = 7.88 Hz), 7.14 (2H, d, J = 4.15 Hz), 7.10 (1H, d, J = 2.49 Hz), 6.92 (1H, dd, J = 7.88, 2.70 Hz), 6.25-6.56 (1H, m), 4.49 (2H, q, J = 8.09 Hz), 4.02 (3H, s) |
| 1-13 | 402.0 | $^1$H NMR (400 MHz, CDCl$_3$) δ 8.95 (1H, d, J = 7.88 Hz), 8.16 (1H, d, J = 2.28 Hz), 7.74 (1H, dd, J = 8.50, 2.49 Hz), 7.09 (1H, d, J = 2.49 Hz), 6.99 (1H, d, J = 8.29 Hz), 6.92 (1H, dd, J = 7.88, 2.70 Hz), 6.22-6.59 (1H, m), 4.81 (2H, q, J = 8.50 Hz), 4.02 (3H, s). |
| 1-14 | 389.1 | $^1$H NMR (400 MHz, CDCl$_3$) δ 8.94 (1H, d, J = 7.88 Hz), 7.85 (1H, s), 7.78 (1H, s), 7.05 (1H, d, J = 2.49 Hz), 6.88 (1H, dd, J = 7.88, 2.49 Hz), 6.54-6.70 (1H, m), 4.44 (2H, t, J = 7.26 Hz), 3.99 (3H, s), 2.82 (2H, br t, J = 7.05 Hz) |
| 1-15 | 401.0 | $^1$H NMR (400 MHz, CDCl$_3$) δ 8.95 (1H, d, J = 7.88 Hz), 7.38 (2H, d, J = 8.71 Hz), 7.01-7.12 (3H, m), 6.88 (1H, dd, J = 7.88, 2.70 Hz), 6.22-6.58 (1H, m), 4.41 (2H, q, J = 8.09 Hz), 4.00 (3H, s) |
| 1-16 | 403.1 | $^1$H NMR (400 MHz, CDCl$_3$) δ 8.94 (1H, d, J = 7.88 Hz), 7.85 (1H, s), 7.77 (1H, s), 7.05 (1H, d, J = 2.70 Hz), 6.88 (1H, dd, J = 7.88, 2.70 Hz), 6.47-6.82 (1H, m), 4.27 (2H, t, J = 6.53 Hz), 3.99 (3H, s), 2.10-2.30 (4 H, m). |

TABLE 25-continued

| Ex. | LRMS: m/z (ESI, +ve ion): $(M + H)^+$ | NMR |
|---|---|---|
| 1-17 | 405.0 | $^1$H NMR (400 MHz, $CD_2Cl_2$) δ 4.03 (s, 3H) 6.96 (br d, J = 7.24 Hz, 1H) 7.0.5 (br s, 1H) 7.19 (br t, J = 7.92 Hz, 2H) 7.74 (br s, 2H) 7.85 (br s, 1H) 8.19 (s, 1H) 8.95 (br d, J = 7.63 Hz, 1H). |
| 1-18 | 405.0 | $^1$H NMR (400 MHz, DMSO-$d_6$) δ 4.05 (s, 3H) 7.13-7.20 (m, 1H) 7.22 (dd, J = 7.92, 2.64 Hz, 1H) 7.30 (d, J = 2.54 Hz, 1H) 7.52-7.61 (m, 1H) 7.75-7.81 (m, 2H) 7.83 (s, 1H) 8.68 (s, 1H) 8.93 (d, J = 7.83 Hz, 1H). |
| 1-19 | 427.0 | $^1$H NMR (400 MHz, DMSO-$d_6$) δ 4.05 (s, 3H) 7.23 (dd, J = 7.92, 2.64 Hz, 1H) 7.31 (d, J = 2.54 Hz, 1H) 7.66-7.73 (m, 1H) 7.73-7.82 (m, 1H) 7.86 (s, 1H) 8.23 (s, 1H) 8.25 (s, 1H) 8.83 (s, 1H) 8.93 (d, J = 8.02 Hz, 1H). |
| 1-20 | 437.0 | $^1$H NMR (400 MHz, $CD_2Cl_2$) δ 4.03 (s, 3H) 4.44 (q, J = 8.15 Hz, 2H) 6.75-6.89 (m, 2H) 6.97 (dd, J = 7.82, 2.74 Hz, 1H) 7.09 (d, J = 2.54 Hz, 1H) 7.25 (t, J = 8.41 Hz, 1H) 8.93 (d, J = 7.83 Hz, 1H). |
| 1-21 | 457.0 | $^1$H NMR (400 MHz, DMSO-$d_6$) δ 14.27 (s, 1H), 9.05 (d, J = 7.2 Hz, 1H), 8.14 (d, J = 6.0 Hz, 2H), 7.79-7.69 (m, 2H), 5.32 (t, J = 15.0 Hz, 2H). |
| 1-22 | 456.2 | $^1$H NMR (400 MHz, DMSO-$d_6$) δ 8.74 (dd, J = 8.2, 1.3 Hz, 1H), 7.90 (s, 1H), 7.59 (s, 1H), 7.20 (dt, J = 8.2, 2.0 Hz, 1H), 6.63 (d, J = 2.8 Hz, 1H), 5.23 (t, J = 15.0 Hz, 2H), 3.18 (s, 6H). |
| 1-23 | 442.0 | $^1$H NMR (400 MHz, $CDCl_3$) δ 8.68 (d, J = 7.7 Hz, 1H), 7.92 (d, J = 11.2 Hz, 2H), 7.59 (s, 1H), 6.93-6.85 (m, 1H), 6.46 (s, 1H), 5.24 (t, J = 15.0 Hz, 2H), 2.88 (d, J = 4.8 Hz, 3H). |
| 1-24 | 364.1 | $^1$H NMR (400 MHz, DMSO-$d_6$) δ 8.89 (d, J = 7.9 Hz, 1H), 7.99 (s, 1H), 7.61 (s, 1H), 7.25 (d, J = 2.7 Hz, 1H), 7.19 (dd, J = 7.9, 2.7 Hz, 1H), 4.47 (t, J = 6.4 Hz, 2H), 4.03 (s, 3H), 3.09 (q, J = 6.1 Hz, 2H). |
| 1-25 | 431.0 | $^1$H NMR (400 MHz, DMSO-$d_6$) δ 9.00 (d, J = 7.4 Hz, 1H), 8.47 (d, J = 1.9 Hz, 1H), 7.68 (dd, J = 7.4, 1.9 Hz, 1H), 7.34-7.29 (m, 2H), 7.19-7.13 (m, 2H), 4.85 (q, J = 8.9 Hz, 2H), 2.77 (s, 3H). |
| 1-26 | 350.1 | $^1$H NMR (400 MHz, DMSO-$d_6$) δ 8.90 (d, J = 7.9 Hz, 1H), 8.03 (d, J = 7.2 Hz, 1H), 7.67 (d, J = 7.2 Hz, 1H), 7.28 (t, J = 4.2 Hz, 1H), 7.20 (dt, J = 7.9, 3.3 Hz, 1H), 5.60 (d, J = 8.5 Hz, 2H), 4.05 (d, J = 8.0 Hz, 3H). |
| 1-27 | 438.1 | $^1$H NMR (400 MHz, $CDCl_3$) δ 9.10 (dd, J = 7 4, 0.9 Hz, 1H), 8.14-8.10 (m, 1H), 8.00 (s, 1H), 7.91 (s, 1H), 7.29 (d, J = 1.8 Hz, 1H), 4.85 (t, J = 13.8 Hz, 2H). |
| 1-28 | 432.1 | $^1$H NMR (400 MHz, DMSO-$d_6$) δ 8.73 (d, J = 8.1 Hz, 1H), 7.22 (t J = 7.0 Hz, 3H), 7.08 (d, J = 8.4 Hz, 2H) 6.66 (d, J = 2.7 Hz, 1H), 4.80 (t, J = 8.9 Hz, 2H), 3.19 (s, 6H). |
| 1-29 | 418.0 | $^1$H NMR (400 MHz, DMSO-$d_6$) δ 8.66 (d, J = 7.7 Hz, 1H), 7.91 (q, J = 5.0, 4.4 Hz, 1H), 7.22 (d, J = 8.3 Hz, 2H), 7.13-7.06 (m, 2H), 6.88 (d, J = 7.5 Hz, 1H), 6.48 (s, 1H), 4.81 (q, J = 8.8 Hz, 2H), 2.89 (d, J = 4.8 Hz, 3H). |
| 1-30 | 459.1 | $^1$H NMR (400 MHz, $CDCl_3$) δ 8.87 (d, J = 7.6 Hz, 1H), 7.84 (d, J = 14.0 Hz, 2H), 7.35 (d, J = 2.1 Hz, 1H), 7.07 (dd, J = 7.6, 2.1 Hz, 1H), 4.83 (t, J = 13.8 Hz, 2H), 2.64 (s, 3H). |
| 1-31 | 446.1 | $^1$H NMR (400 MHz, DMSO-$d_6$) δ 10.95 (s, 1H), 8.95 (d, J = 7.8 Hz, 1H), 8.18 (d, J = 2.3 Hz, 1H), 7.45 (dd, J = 7.8, 2.4 Hz, 1H), 7.33-7.22 (m, 2H), 7.18-7.09 (m, 2H), 4.83 (q, J = 8.9 Hz, 2H), 2.21 (s, 3H). |
| 1-32 | 431.0 | $^1$H NMR (400 MHz, DMSO-$d_6$) δ 8.93 (dd, J = 7.4, 2.5 Hz, 1H), 7.71 (d, J = 1.9 Hz, 1H), 7.50 (dt, J = 7.6, 1.6 Hz, 1H), 7.28 (d, J = 8.3 Hz, 2H), 7.17-7.10 (m, 2H), 4.83 (q, J = 8.9 Hz, 2H), 3.14 (p, J = 6 9 Hz, 1H), 1.31 (dd, J = 7.0, 1.2 Hz, 6H). |
| 1-33 | 446.2 | $^1$H NMR (400 MHz, DMSO-$d_6$) δ 8.91 (dd, J = 7.9, 1.8 Hz, 1H), 8.01 (s, 1H), 7.67 (d, J = 1.7 Hz, 1H), 7.27 (t, J = 2.3 Hz, 1H), 7.20 (dd, J = 7.9, 2.6 Hz, 1H), 5.29 (t, J = 15.0 Hz, 2H). |
| 1-34 | 444.0 | $^1$H NMR (400 MHz, DMSO-$d_6$) δ 9.05 (dd, J = 7.6, 2.0 Hz, 1H), 8.05 (d, J = 1.9 Hz, 1H), 7.68 (d, J = 1.9 Hz, 1H), 7.07 (dd, J = 7.7, 2.0 Hz, 1H), 5.30 (t, J = 15.0 Hz, 2H), 4.11 (d, J = 2.0 Hz, 3H). |
| 1-35 | 444.0 | $^1$H NMR (400 MHz, DMSO-$d_6$) δ 8.77 (d, J = 7.6 Hz, 1H), 7.48 (d, J = 2.0 Hz, 1H), 7.41-7.35 (m, 1H), 7.27 (d, J = 8.4 Hz, 2H), 7.12 (d, J = 8.4 Hz, 2H), 4.83 (q, J = 8.9 Hz, 2H), 2.70 (s, 3H). |
| 1-36 | 446.0 | $^1$H NMR (400 MHz, DMSO-$d_6$) δ 9.10-9.00 (m, 1H), 8.27-8.19 (m, 1H), 7.73 (qt, J = 5.4, 2.6 Hz, 1H), 7.36-7.26 (m, 2H), 7.16 (dq, J = 6.3, 3.0, 2.2 Hz, 2H), 4.85 (dtd J = 13.6, 7.6, 6.1, 3.3 Hz, 2H), 4.03-3.91 (m, 3H). |
| 1-37 | 329.0 | H NMR (400 MHz, $CD_2C1_2$) δ 0.30-0.44 (m, 2H) 0.59-0.69 (m, 2H) 1.22-1.39 (m, 1H) 3.85 (d, J = 6.84 Hz, 2H) 4.20 (s, 3H) 6.76 (d, J = 7.67 Hz, 1H) 6.93-6.99 (m, 2H) 7.21 (d, J = 8.50 Hz, 2H) 9.01 (d, J = 7.67 Hz, 1H). |
| 1-38 | 422.0 | $^1$H NMR (500 MHz, DMSO-$d_6$) δ 1.95-2.09 (m, 2H) 2.10-2.27 (m, 2H) 4.09 (s, 3H) 4.27 (t, J = 6.75 Hz, 2H) 7.04 (d, J = 7.66 Hz, 1H) 7.56 (s, 1H) 7.95 (s, 1H) 9.03 (d, J = 7.66 Hz, 1H). |
| 1-39 | 389.0 | $^1$H NMR (400 MHz, $CD_2Cl_2$) δ 1.59 (t, J = 18.87 Hz, 3H) 4.02 (s, 3H) 4.52 (t, J = 12.23 Hz, 2H) 6.93 (dd, J = 7.88, 2.70 Hz, 1H) 7.02 (d, J = 2.49 Hz, 1H) 7.68 (s, 1H) 7.76 (s, 1H) 8.92 (d, J = 7.88 Hz, 1H). |
| 1-40 | 377.0 | $^1$H NMR (400 MHz, $CDCl_3$) δ 4.24 (s, 3H) 4.81 (s, 2H) 6.77 (d, J = 7.67 Hz, 1H) 7.04-7.09 (m, 2H) 7.32 (d, J = 8.50 Hz, 2H) 9.05 (d, J = 7.67 Hz, 1H). |

TABLE 25-continued

| Ex. | LRMS: m/z (ESI, +ve ion): $(M + H)^+$ | NMR |
|---|---|---|
| 1-41 | 419.0 | $^1$H NMR (400 MHz, $CD_2Cl_2$) δ 4.03 (s, 3H) 4.2.5 (td, J = 13.27, 3.94 Hz, 2H) 5.97-6.32 (m, 1H) 6.74-6.86 (m, 2H) 6.96 (dd, J = 7.88, 2.70 Hz, 1H) 7.07 (d, J = 2.49 Hz, 1H) 7.23 (t, J = 8.40 Hz, 1H) 8.92, (d, J = 7.88 Hz, 1H |
| 1-42 | 389.0 | $^1$H NMR (400 MHz, DMSO-$d_6$) δ 4.83 (q, J = 9.00 Hz, 2H) 7.14 (d, J = 8.61 Hz, 2H) 7.29 (d, J = 8.61 Hz, 2H) 7.51 (t, J = 6.85 Hz, 1H) 7.82-7.96 (m, 1H) 8.06-8.17 (m, 1H) 9.01 (d, J = 6.85 Hz, 1H). |
| 1-43 | 357.0 | $^1$H NMR (400 MHz, DMSO-$d_6$) δ 7.32-7.39 (m, 1H) 7.51-7.58 (m, 3H) 7.84-7.94 (m, 4H) 8.13 (ddd, J = 8.75, 6.90, 1.37 Hz, 1H) 8.65 (s, 1H) 9.06 (d, J = 6.46 Hz, 1H). |
| 1-44 | 419.0 | $^1$H NMR (400 MHz, DMSO-$d_6$) δ 4.04 (s, 3H) 4.83 (q, J = 8.74 Hz, 2H) 7.04-7.15 (m, 2H) 7.16-7.22 (m, 1H) 7.24-7.32 (m, 3H) 8.88 (br d, J = 8.02 Hz, 1H). |
| 1-45 | 477.0 | $^1$H NMR (500 MHz, DMSO-$d_6$) δ 9.02 (s, 1H), 8.02 (s, 1H), 7.67 (s, 1H), 7.42 (s, 1H), 5.28 (t, J = 14.96 Hz, 2H), 4.13 (s, 3H) |
| 1-46 | 375.0 | $^1$H NMR (400 MHz, DMSO-$d_6$) δ 7.38 (t, J = 8.80 Hz, 2H) 7.54 (t, J = 6.94 Hz, 1H) 7.84 (s, 1H) 7.87-7.93 (m, 2H) 7.93-7.98 (m, 1H) 8.07-8.17 (m, 1H) 8.64 (s, 1H) 9.05 (d, J = 6.65 Hz, 1H). |
| 1-47 | 387.0 | $^1$H NMR (400 MHz, DMSO-$d_6$) δ 4.05 (s, 3H) 7.22 (dd, J = 7.83, 2.74 Hz, 1H) 7.30 (d, J = 2.74 Hz, 1H) 7.32-7 37 (m, 1H) 7.53 (t, J = 7.92 Hz, 2H) 7.80 (s, 1H) 7.89 (d, J = 8.02 Hz, 2H) 8.60 (s, 1H) 8.93 (d, J = 8.02 Hz, 1H). |
| 1-48 | 437.0 | $^1$H NMR (400 MHz, DMSO-$d_6$) δ 8.89 (1H, d, J = 7.8 Hz), 7.17-7.39 (4 H, m), 7.10 (1H, br d, J = 8.4 Hz), 4.92 (2H, q, J = 8.8 Hz), 4.04 (3H, s) |
| 1-49 | 405.1 | $^1$H NMR (400 MHz, DMSO-$d_6$) δ 8.89 (d, J = 7.82 Hz, 1H), 7.44 (s, 4H), 7.31 (d, J = 2.54 Hz, 1H), 7.21 (dd, J = 2.64, 7.92 Hz, 1H), 4.04 (s, 3H). |
| 1-50 | 420.1 | $^1$H NMR (400 MHz, $CDCl_3$) δ 9.06 (d, J = 7.63 Hz, 1H), 7.28-7.32 (m, J = 8.61 Hz, 2H), 7.00-7.07 (m, J = 8.61 Hz, 2H), 6.77 (d, J = 7.63 Hz, 1H), 4.41 (q, J = 8.15 Hz, 2H), 4.24 (s, 3H). |
| 1-51 | 386.0 | H NMR (400 MHz, $CDCl_3$) δ 4.21-4.25 (m, 1H) 4.28-4.32 (m, 1H) 4.70-4.74 (m, 1H) 4.82-4.86 (m, 1H) 6.91 (dd, J = 7.88, 2.70 Hz, 1H) 6.98-7.02 (m, 2H) 7.04 (d, J = 2.70 Hz, 1H) 7.26-7.29 (m, 2H) 8.94 (d, J = 7.88 Hz, 1H). |
| 1-52 | 404.0 | $^1$H NMR (400 MHz, $CDCl_3$) δ 4.23 (td, J = 13.06, 4.15 Hz, 2H) 5.92-6.32 (m, 1H) 6.92 (dd, J = 7.88, 2.70 Hz, 1H) 6.97-7.02 (m, 2H) 7.04 (d, J = 2.70 Hz, 1H) 7.29 (d, J = 8.71 Hz, 2H) 8.94 (d, J = 7.88 Hz, 1H). |
| 1-53 | 438.0 | $^1$H NMR (400 MHz, $CDCl_3$) δ 9.06 (d, J = 7.67 Hz, 1H) 7.23 (t, J = 8.40 Hz, 1H) 6.76-6.86 (m, 3H) 4.39 (q, J = 8.02 Hz, 2H) 4.24 (s, 3H) |
| 1-54 | 386.9 | $^1$H NMR (400 MHz, $CD_2C1_2$) δ 4.03 (s, 3H) 6.41-6.85 (m, 1H) 6.96 (dd, J = 7.88, 2.49 Hz, 1H) 7.06 (d, J = 2.70 Hz, 1H) 7.19 (d, J = 8.50 Hz, 2H) 7.34 (d, J = 8.50 Hz, 2H) 8.92 (d, J = 8.09 Hz, 1H). |
| 1-55 | 387.0 | $^1$H NMR (400 MHz, $CDCl_3$) δ 4.19-4.26 (m, 1H) 4.27-4.33 (m, 1H) 4.68-4.76 (m, 1H) 4.80-4.87 (m, 1H) 6.75 (d, J = 7.67 Hz, 1H) 7.01 (d, J = 8.71 Hz, 2H) 7.26 (s, 2H) 9.05 (d, J = 7.67 Hz, 1H). |
| 1-56 | 370.1 | $^1$H NMR (400 MHz, $CDCl_3$) δ 2.42-3.33 (m, 1H) 4.20-4.24 (m, 1H) 4.27-4.31 (m, 1H) 4.68-4.77 (m, 1H) 4.79-4.87 (m, 1H) 6.42 (d, J = 8.09 Hz, 1H) 6.94-7.04 (m, 2H) 7.21 (d, J = 8.71 Hz, 2H) 8.61 (d, J = 8.29 Hz, 1H). |
| 1-57 | 384.0 | $^1$H NMR (400 MHz, $CDCl_3$) δ 4.21-4.25 (m, 4H) 4.27-4.33 (m, 1H) 4.69-4.76 (m, 1H) 4.81-4.87 (m, 1H) 6.75 (d, J = 7.67 Hz, 1H) 6.96-7.06 (m, 2H) 7.22-7.33 (m, 2H) 9.04 (d, J = 7.46 Hz, 1H). |
| 1-58 | 383.0 | $^1$H NMR (400 MHz, $CDCl_3$) δ 8.88 (d, J = 7.88 Hz, 1H), 7.27 (d, J = 8.50 Hz, 2H), 7.02 (br s, 1H), 6.96 (d, J = 8.71 Hz, 2H), 6.79 (dd, J = 2.28, 7.46 Hz, 1H), 5.15 (d, J = 47.27 Hz, 2H), 4.33 (q, J = 24.30 Hz, 2H), 3.93 (s, 3H) |
| 1-59 | 423.2 | $^1$H NMR (400 MHz, $CDCl_3$) δ 9.04 (d, J = 7.67 Hz, 1H), 7.29 (d, J = 8.50 Hz, 2H), 7.01 (d, J = 8.50 Hz, 2H), 6.75 (d, J = 7.46 Hz, 1H), 4.39 (q, J = 8.09 Hz, 2H). |
| 1-60 | 380.1 | $^1$H NMR (400 MHz, DMSO-$d_6$) δ 8.81 (d, J = 7.46 Hz, 1H), 8.14 (d, J = 1.66 Hz, 1H), 7.77 (dd, J = 2.28, 8.50 Hz, 1H), 7.01-7.10 (m, 3H), 5.04 (q, J = 27.40 Hz, 2H), 3.98-4.01 (m, 3H), 2.44-2.49 (m, 2H), 1.14 (t, J = 14.90 Hz, 3H) |
| 1-61 | 410.0 | $^1$H NMR (400 MHz, $CDCl_3$) δ 8.98 (d, J = 7.88 Hz, 1H), 7.77 (d, J = 14.98 Hz, 2H), 7.06 (d, J = 2.49 Hz, 1H), 6.95 (dd, J = 2.49, 7.88 Hz, 1H), 4.46 (t, J = 7.26 Hz, 2H), 2.77-2.92 (m, 2H). |
| 1-62 | 391.0 | 1H NMR (400 MHz, $CDCl_3$) δ 8.88 (d, J = 7.67 Hz, 1H), 7.43 (d, J = 8.50 Hz, 2H), 7.03 (d, J = 8.71 Hz, 2H), 6.68-6.73 (m 2H), 4.39 (q, J = 24.50 Hz, 2H), 3.94-3.98 (m, 3H), 1.86-1.95 (m, 1H), 1.20-1.28 (m, 2H), 0.84-0.93 |
| 1-63 | 424.0 | $^1$H NMR (400 MHz, $CDCl_3$) δ 8.95 (d, J = 7.88 Hz, 1H), 7.74 (s, 1H), 7.70 (s, 1H), 7.02 (d, J = 2.49 Hz, 1H), 6.92 (dd, J = 2.70, 7.88 Hz, 1H), 4.26 (t, J = 6.53 Hz, 2H), 2.17-2.26 (m, 2H), 2.04-2.17 (m, 2H). |
| 1-64 | 423.0 | $^1$H NMR (400 MHz, $CDCl_3$) δ 8.95 (d, J = 7.67 Hz, 1H), 8.08-8.13 (m, 1H), 7.65 (dd, J = 2.18, 8.60 Hz, 1H), 7.08 (d, J = 2.49 Hz, 1H), 6.96 (d, J = 8.50 Hz, 2H), 4.80 (q, J = 8.64 Hz, 2H). |

TABLE 25-continued

| Ex. | LRMS: m/z (ESI, +ve ion): $(M + H)^+$ | NMR |
|---|---|---|
| 1-65 | 394.0 | $^1H$ NMR (400 MHz, $CDCl_3$) δ 8.95 (d, J = 7.88 Hz, 1H), 7.25 (d, J = 8.50 Hz, 2H), 7.05 (d, J = 2.70 Hz, 1H), 6.98 (d, J = 8.71 Hz, 2H), 6.91 (dd, J = 2.70, 7.88 Hz, 1H), 3.85 (d, J = 6.84 Hz, 2H), 1.26-1.36 (m, 1H), 0.62-0.71 (m, 2H), 0.34-0.42 (m, 2H). |
| 1-66 | 455.0 | $^1H$ NMR (400 MHz, $CDCl_3$) δ 8.87-9.04 (m, 1H) 7.63-7.77 (m, 1H) 7.30-7.40 (m, 2H) 7.11-7.56 (m, 1H) 6.96-7.09 (m, 2H) |
| 1-67 | 365.1 | $^1H$ NMR (400 MHz, $CDCl_3$) δ 8.87 (1H, J = 7.88 Hz), 7.28 (2H, d, J = 8.71 Hz), 6.99 (2H, d, J = 8.71 Hz), 6.81 (1H, d, J = 2.70 Hz), 6.75 (1H, br d, J = 2.70 Hz), 6.73 (1H, d, J = 2.70 Hz), 4.36 (2H, q, J = 8.09 Hz), 3.93 (3H, s), 2.29 (3H, s). |
| 1-68 | 443.0 | $^1H$ NMR (400 MHz, ($CD_2Cl_2$) δ 4.02, (s, 3H) 4.83 (t, J = 13.99 Hz, 2H) 6.95 (dd, J = 7.88, 2.70 Hz, 1H) 7.04 (d, J = 2.49 Hz, 1H) 7.73 (s, 1H) 7.80 (s, 1H) 8.93 (d, J = 7.88 Hz, 1H). |
| 1-69 | 407.0 | H NMR (400 MHz, $CD_2Cl_2$) δ 2.82, (qt, J = 10.56, 7.18 Hz, 2H) 4.01 (s, 3H) 4.42 (t, J = 7.15 Hz, 2H) 6.93 (dd, J = 7.98, 2.59 Hz, 1H) 7.02 (d, J = 2.49 Hz, 1H) 7.67 (s, 1H) 7.72 (s, 1H) 8.91 (d, J = 7.88 Hz, 1H). |
| 1-70 | 422.1 | $^1H$ NMR (400 MHz, $CDCl_3$) δ 9.06 (d, J = 7.46 Hz, 1H), 8.10 (s, 1H), 7.63 (dd, J = 2.28, 8.50 Hz, 1H), 6.97 (d, J = 8.50 Hz, 1H), 6.80 (d, J = 7.67 Hz, 1H), 4.80 (q, J = 8.50 Hz, 2H), 4.25 (s, 3H). |
| 1-71 | 455.0 | $^1H$ NMR (400 MHz, DMSO-$d_6$) δ 4.05 (s, 3H) 7.23 (dd, J = 7.92, 2.64 Hz, 1H) 7.31 (d, J = 2.54 Hz, 1H) 7.84-7.95 (m, 3H) 8.14 (d, J = 8.61 Hz, 2H) 8.77 (s, 1H) 8.93 (d, J = 7.82 Hz, 1H). |
| 1-72 | 406.1 | $^1H$ NMR (400 MHz, $CDCl_3$,) δ 9.04 (d, J = 7.63 Hz, 1H), 7.32-7.37 (m, 2H), 7.26-7.31 (m, 2H), 6.77 (d, J = 7.63 Hz, 1H), 4.23 (s, 3H). |
| 1-73 | 438.1 | $^1H$ NMR (400 MHz, $CDCl_3$) δ 9.06 (d, J = 7.43 Hz, 1H), 6.97-7.21 (m, 3H), 6.79 (d, J = 7.63 Hz, 1H), 4.48 (q, J = 8.02 Hz, 2H), 4.25 (s, 3H). |
| 1-74 | 393.1 | $^1H$ NMR (400 MHz, DMSO-$d_6$) δ 8.89 (d, J = 8.0 Hz, 1H), 8.00 (s, 1H), 7.65 (s, 1H), 7.26 (d, J = 2.5 Hz, 1H), 7.19 (dd, J = 2.7, 7.8 Hz, 1H), 5.21 (q, J = 9.1 Hz, 2H), 4.03 (s, 3H). |
| 1-75 | 421.1 | $^1H$ NMR (400 MeOH-$d_4$) δ 2.05-2.27 (m, 6H) 4.22 (br t, J = 6.26 Hz, 1H) 4.29 (br t, J = 5.77 Hz, 2H) 4.84 (s, 2H) 7.05-7.10 (m, 1H) 7.13 (br s, 1H) 7.60-7.69 (m, 1H) 7.78-7.86 (m, 1H) 8.92 (dd, J = 7.73, 3.23 Hz, 1H). |
| 1-76 | 353.0 | $^1H$ NMR (400 MHz, DMSO-$d_6$) δ 8.88 (d, J = 7.8 Hz, 1H), 7.85 (s, 1H), 7.50 (s, 1H), 7.23 (d, J = 2.7 Hz, 1H), 7.17 (dd, J = 2.7, 8.0 Hz, 1H), 4.12 (t, J = 6.8 Hz, 2H), 4.02, (s, 3H), 1.80 (sxt, J = 7.1 Hz, 2H), 0.83 (t, J = 7.3 Hz, 3H). |
| 1-77 | 379.1 | $^1H$ NMR (400 MHz, DMSO-$d_6$) δ 8.80 (d, J = 7.67 Hz, 1H), 7.26 (d, J = 8.71 Hz, 2H), 7.11 (d, J = 8.71 Hz, 2H), 6.96-7.04 (m, 2H), 4.81 (q, J = 26.50 Hz, 2H), 3.97-4.01 (m, 3H), 2.42-2.49 (m, 2H), 1.12 (t, J = 14.90 Hz, 3H) |
| 1-78 | 403.0 | $^1H$ NMR (400 MHz, $CDCl_3$) δ 8.94 (d, J = 7.3 Hz, 1H), 7.59 (s, 1H), 7.31-7.28 (m, 1H), 7.08 (br d, J = 7.3 Hz, 1H), 6.99 (br d, J = 8.5 Hz, 2H), 4.37 (q, J = 8.1 Hz, 2H), 2.52 (s, 3H) |
| 1-79 | 363.1 | $^1H$ NMR (400 MHz, DMSO-$d_6$) δ 8.87 (d, J = 7.88 Hz, 1H), 7.16-7.29 (m, 6H), 4.03 (s, 3H), 2.58-2.63 (m, 2H), 1.57-1.69 (m, 2H), 0.86-0.96 (m, 3H) |
| 1-80 | 381.0 | $^1H$ NMR (400 MHz, $CDCl_3$) δ 9.00 (d, J = 7.88 Hz, 1H), 7.54 (d, J = 8.91 Hz, 2H), 6.94-7.07 (m, 3H), 6.81 (dd, J = 2.70, 7.88 Hz, 1H), 4.38 (q, J = 8.09 Hz, 2H), 4.05 (s, 3H), 4.02 (s, 3H). |
| 1-81 | 395.1 | $^1H$ NMR (400 MHz, $CDCl_3$) δ 9.00 (d, J = 7.88 Hz, 1H), 7.58 (d, J = 8.71 Hz, 2H), 6.91-7.04 (m, 3H), 6.80 (dd, J = 2.59, 7.77 Hz, 1H), 4.53 (q, J = 6.98 Hz, 2H), 4.39 (q, J = 8.09 Hz, 2H), 4.02 (s, 3H), 1.37-1.43 (t, J = 4.0 Hz, 3H). |
| 1-82 | 470.1 | $^1H$ NMR (400 MHz, DMSO-$d_6$) δ 10.95 (s, 1H), 8.97 (d, J = 7.8 Hz, 1H), 8.16 (d, J = 2.2 Hz, 1H), 8.01 (s, 1H), 7.67 (s, 1H), 7.45 (dd, J = 7.9, 2.3 Hz, 1H), 5.28 (t, J = 15.0 Hz, 2H), 2.21 (s, 3H). |
| 1-85 | 420.1 | $^1H$ NMR (500 MHz, DMSO-$d_6$) δ 9.01 (dd, J = 7.34, 0.73 Hz, 1H), 8.54 (d, J = 0.98 Hz, 1H), 8.30 (s, 1H), 7.87 (s, 1H), 7.60 (dd, J = 7.46, 1.83 Hz, 1H), 6.95 (t, J = 53.70 Hz, 1H), 5.34 (t, J = 15.28 Hz, 2H) |
| 1-86 | 402.1 | $^1H$ NMR (400 MHz, DMSO-$d_6$) δ 9.02 (dd, J = 7.45, 0.66 Hz, 1H), 8.47 (dd, J = 1.64, 0.77 Hz, 1H), 8.37 (s, 1H), 7.95 (s, 1H), 7.57 (dd, J = 7.45, 1.97 Hz, 1H), 5.51 (d, J = 47.10 Hz, 2H), 5.33 (t, J = 15.13 Hz, 2H) |
| 1-87 | 453.1 | $^1H$ NMR (500 MHz, $CDCl_3$) δ 0.98-1.06 (m, 2H), 1.27-1.37 (m, 2H), 2.00-2.12 (m, 1H), 4.82 (t, J = 13.72 Hz, 2H), 6.98 (dd, J = 7.4, 1.92 Hz, 1H), 7.43 (d, J = 1.65 Hz, 1H), 7.82 (s, 1H), 7.85 (s, 1H), 8.97 (d, J = 7.41 Hz, 1H) |
| 1-88 | 468.1 | $^1H$ NMR (500 MHz, $CDCl_3$) δ 8.86 (d, J = 7.96 Hz, 1H), 7.75 (s, 1H), 7.74 (s, 1H), 6.47 (dd, J = 7.96, 2.47 Hz, 1H), 6.35 (d, J = 2.47 Hz, 1H), 4.80 (t, J = 13.86 Hz, 2H), 4.21 (br s, 4H), 2.51-2.65 (m, 2H) |
| 2-2 | 433.1 | $^1H$ NMR (400 MHz, DMSO-$d_6$) δ 14.28 (s, 1H), 9.03 (d, 1H), 8.17 (d, J = 5.8 Hz, 1H), 7.72 (dd, 1H), 7.31 (dt, J = 8.3, 3.6 Hz, 2H), 7.16 (dd, J = 8.2, 5.0 Hz, 2H), 4.95-4.76 (m, 2H). |
| 2-3 | 407.1 | $^1H$ NMR (400 MHz, DMSO-$d_6$) δ 9.07 (dd, J = 8.0, 6.2 Hz, 1H), 7.83 (dd, J = 9.3, 2.8 Hz, 1H), 7.58-7.52 (m, 1H), 7.33-7.25 (m, 2H), 7.18-7.10 (m, 2H), 4.84 (q, J = 8.9 Hz, 2H). |

TABLE 25-continued

| Ex. | LRMS: m/z (ESI, +ve ion): $(M + H)^+$ | NMR |
|---|---|---|
| 2-4 | 408.1 | $^1$H NMR (400 MHz, DMSO-$d_6$) δ 9.03 (d, J = 7.6 Hz, 1H), 8.00 (s, 1H), 7.58 (s, 1H), 7.05 (d, J = 7.7 Hz, 1H), 4.47 (t, J = 6.7 Hz, 2H), 4.10 (s, 3H), 2.95-2.87 (m, 2H). |
| 2-5 | 406.1 | $^1$H NMR (400 MHz, DMSO-$d_6$) δ 8.91 (dd, J = 7.1, 1.6 Hz, 1H), 7.74 (d, J = 1.9 Hz, 1H), 7.39 (dt, J = 7.3, 1.8 Hz, 1H), 7.35-7.22 (m, 2H), 7.16-7.05 (m, 2H), 4.93-4.75 (m, 2H). |
| 2-6 | 447.0 | $^1$H NMR (DMSO-$d_6$) δ 8.95 (d, J = 7.7 Hz, 1H), 8.08 (s, 2H), 7.70 (s, 1H), 7.54 (dd, J = 7.7, 2.1 Hz, 1H), 5.29 (t, J = 14.9 Hz, 2H) |
| 2-7 | 423.0 | $^1$H NMR (400 MHz, DMSO-$d_6$) δ 8.95 (dd, J = 7.7, 4.9 Hz, 1H), 8.15-8.09 (m, 1H), 7.59-7.52 (m, 1H), 7.29 (dd, J = 8.5, 4.9 Hz, 2H), 7.14 (dd, J = 8.5, 5.1 Hz, 2H), 4.84 (qd, J = 8.7, 4.6 Hz, 2H). |
| 2-8 | 415.1 | $^1$H NMR (400 MHz, DMSO-$d_6$) δ 9.21-8.75 (m, 1H), 7.91 (q, J = 2.0 Hz, 1H), 7.75 (dt, J = 7.2, 2.3 Hz, 1H), 7.46-7.20 (m, 2H), 7.18-7.08 (m, 2H), 7.06-6.90 (m, 1H), 6.48-6.28 (m, 1H), 5.93-5.63 (m, 2H), 4.99-4.65 (m, 2H). |
| 2-9 | 414.2 | $^1$H NMR (400 MHz, DMSO-$d_6$) δ 9.01 (d, J = 7.4 Hz, 1H), 8.67-8.58 (m, 1H), 7.67 (dd, J = 7.6, 1.6 Hz, 1H), 7.35-7.26 (m, 2H), 7.20-7.12 (m, 2H), 4.85 (q, J = 8.8 Hz, 2H). |
| 3-2 | 447.0 | $^1$H NMR (400 MHz, DMSO-$d_6$) δ 9.05 (d, J = 7.6 Hz, 1H), 8.04 (s, 1H), 7.68 (s, 1H), 7.06 (d, J = 7.6 Hz, 1H), 5.30 (t, J = 15.0 Hz, 2H). |
| 4-2 | 429.0 | $^1$H NMR (DMSO-$d_6$, 500 MHz) δ 8.85 (d, J = 7.4 Hz, 1H), 7.64 (s, 1H), 7.21-7.28 (m, 3H), 7.11 (d, J = 8.2 Hz, 2H), 4.82 (q, J = 8.8 Hz, 2H), 2.19-2.25 (m, 1H), 1.19-1.28 (m, 2H), 1.01-1.11 (m, 2H) |
| 4-3 | 433.0 | $^1$H NMR ($CDCl_3$, 400 MHz) δ 8.95 (d, J = 7.9 Hz, 1H), 7.09 (d, J = 7.7 Hz, 2H), 6.93 (d, J = 8.5 Hz, 1H), 6.90 (s, 1H), 6.81 (dd, J = 8.5, 2.7 Hz, 1H), 4.38 (q, J = 8.2 Hz, 2H), 4.02 (s, 3H), 2.14 (s, 3H) |
| 5-2 | 422.9 | H NMR (400 MHz, DMSO-$d_6$) δ 4.95 (q, J = 8.74 Hz, 2H) 7.25-7.32 (m, 1H) 7.33-7.38 (m, 1H) 7.46 (d, J = 1.96 Hz, 1H) 7.50-7.57 (m, 1H) 7.91 (d, J = 8.80 Hz, 1H) 8.14 (ddd, J = 8.75, 6.99, 1.47 Hz, 1H) 9.02 (d, J = 6.65 Hz, 1H). |
| 5-3 | 321.0 | $^1$H NMR (400 MHz, $CD_2Cl_2$) δ 0.98-1.07 (m, 2H) 1.13-1.22 (m, 2H) 3.66 (tt, J = 7.34, 3.81 Hz, 1H) 7.23-7.33 (m, 1H) 7.64 (s, 1H) 7.72-7.78 (m, 1H) 7.79-7.89 (m, 2H) 9.04 (d, J = 7.24 Hz, 1H). |
| 5-4 | 323.0 | H NMR (400 MHz, $CD_2Cl_2$) δ 0.93 (t, J = 7.43 Hz, 3H) 1.92 (sxt, J = 7.24 Hz, 2H) 4.13 (t, J = 7.04 Hz, 2H) 7.22-7.30 (m, 1H) 7.68 (s, 1H) 7.72-7.78 (m, 2H) 7.79-7.89 (m, 1H) 9.04 (d, J = 6.85 Hz, 1H). |
| 6-2 | 439.3 | $^1$H NMR (400 MHz, DMSO-$d_6$) δ 8.71 (d, J = 7.8 Hz, 1H), 7.39 (s, 2H), 7.24-7.18 (m, 2H), 7.10-7.05 (m, 2H), 6.89 (dd, J = 7.8, 2.4 Hz, 1H), 6.55 (d, J = 2.5 Hz, 1H), 4.81 (q, J = 8.9 Hz, 2H). |
| 7-2 | 390.1 | $^1$H NMR (400 MHz, $CDCl_3$) δ 4.37-4.50 (m, 2H) 7.26-7.33 (m, 1H) 7.33-7.39 (m, 1H) 7.41-7.48 (m, 1H) 7.80-7.92 (m, 2H) 8.40-8.49 (m, 1H) 9.02-9.13 (m, 1H). |
| 7-3 | 438.1 | $^1$H NMR (400 MHz, $CDCl_3$) δ 3.98-4.09 (m, 3H) 4.61-4.76 (m, 2H) 6.94-7.04 (m, 1H) 7.07-7.14 (m, 2H) 7.16-7.23 (m, 1H) 8.89-9.04 (m, 1H). |
| 7-4 | 420.1 | $^1$H NMR (400 MHz, $CDCl_3$) δ 8.96 (d, J = 8.02 Hz, 1H), 8.08-8.13 (m, 1H), 7.65 (dd, J = 2.25, 8.51 Hz, 1H), 7.08 (d, J = 2.54 Hz, 1H), 6.92-6 99 (m, 2H), 4.81 (q, J = 8.54 Hz, 2H), 4.03 (s, 3H). |
| 7-5 | 416.9 | $^1$H NMR (400 MHz, MeOH-$d_4$) δ 8.86 (d, J = 7.88 Hz, 1H), 7.15-7.26 (m, 4H), 7.10 (d, J = 2.70 Hz, 1H), 7.03 (dd, J = 2.59, 7.77 Hz, 1H), 3.97 (s, 3H), 2.82-2.87 (m, 2H), 2.37-2.49 (m, 2H) |
| 7-6 | 364.0 | $^1$H NMR (400 MHz, MeOH-$d_4$) δ 8.95 (d, J = 7.88 Hz, 1H), 8.34 (s, 1H), 7.70 (d, J = 7.63 Hz, 1H), 7.36 (d, J = 8.09 Hz, 1H), 7.19 (d, J = 2.49 Hz, 1H), 7.12 (dd, J = 2.70, 7.88 Hz, 1H), 4.05 (s, 3H), 2.80 (t, J = 7.57 Hz, 2H), 1.71-1.82 (m, 2H), 0.97 (t, J = 7.36 Hz, 3H) |
| 8-2 | 487.0 | $^1$H NMR (DMSO-$d_6$, 500 MHz) δ 8.89 (d, J = 7.9 Hz, 1H), 7.41-7.50 (m, 3H), 7.34 (d, J = 2.7 Hz, 1H), 7.22 (dd, J = 7.8, 2.7 Hz, 1H), 4.98 (q, J = 8.8 Hz, 2H), 4.05 (s, 3H) |
| 8-3 | 452.9 | $^1$H NMR (DMSO-$d_6$, 500 MHz) δ 8.91 (d, J = 7.9 Hz, 1H), 7.31-7.35 (m, 3H), 7.23 (dd, J = 7.8, 2.8 Hz, 1H), 7.11 (dd, J = 8.7, 2.7 Hz, 1H), 4.84-4.94 (m, 2H), 4.05 (s, 3H) |
| 8-4 | 390.0 | $^1$H NMR (400 MHz, DMSO-$d_6$) δ 8.97 (d, J = 8.0 Hz, 1H), 7.37-7.32 (m, 2H), 7.10 (dd, J = 8.7, 1.9 Hz, 3H), 6.95 (dd, J = 7.9, 2.5 Hz, 1H), 4.96 (q, J = 6.8 Hz, 1H), 4.04 (s, 3H), 1.85 (d, J = 6.8 Hz, 3H) |
| 8-5 | 391.1 | not available |
| 8-6 | 391.1 | $^1$H NMR (400 MHz, DMSO-$d_6$) δ 9.03 (d, J = 7.6 Hz, 1H), 7.29 (d, J = 8.8 Hz, 2H), 7.21-7.11 (m, 2H), 7.06 (d, J = 7.6 Hz, 1H), 5.52 (q, J = 6.7 Hz, 1H), 4.11 (s, 3H), 1.73 (d, J = 6.7 Hz, 3H) |
| 8-7 | 391.1 | $^1$H NMR (400 MHz, DMSO-$d_6$) δ 9.03 (d, J = 7.6 Hz, 1H), 7.29 (d, J = 8.8 Hz, 2H), 7.2.1-7.11 (m, 2H), 7.06 (d, J = 7.6 Hz, 1H), 5.52 (q, J = 6.7 Hz, 1H), 4.11 (s, 3H), 1.73 (d, J = 6.7 Hz, 3H) |
| 8-8 | 390.0 | $^1$H NMR (400 MHz, DMSO-$d_6$) δ 8.97 (d, J = 8.0 Hz, 1H), 7.37-7.32 (m, 2H), 7.10 (dd, J = 8.7, 1.9 Hz, 3H), 6.95 (dd, J = 7.9, 2.5 Hz, 1H), 4.96 (q, J = 6.8 Hz, 1H), 4.04 (s, 3H), 1.85 (d, J = 6.8 Hz, 3H) |

TABLE 25-continued

| Ex. | LRMS: m/z (ESI, +ve ion): $(M + H)^+$ | NMR |
|---|---|---|
| 8-9 | 390.0 | $^1H$ NMR (400 MHz, DMSO-$d_6$) δ 8.97 (d, J = 8.0 Hz, 1H), 7.37-7.32 (m, 2H), 7.10 (dd, J = 8.7, 1.9 Hz, 3H), 6.95 (dd, J = 7.9, 2.5 Hz, 1H), 4.96 (q, J = 6.8 Hz, 1H), 4.04 (s, 3H), 1.85 (d, J = 6.8 Hz, 3H) |
| 9-2 | 415.0 | $^1H$ NMR (500 MHz, DMSO-$d_6$) δ 1.77 (t, J = 19.27 Hz, 3H) 4.03 (s, 3H) 4.34 (t, J = 12.59 Hz, 2H) 7.06 (d, J = 8.56 Hz, 2H) 7.18 (dd, J = 7.91, 1.95 Hz, 1H) 7.23 (d, J = 8.43 Hz, 2H) 7.27 (d, J = 1.69 Hz, 1H) 8.87 (d, J = 7.92 Hz, 1H). |
| 10-2 | 424.0 | $^1H$ NMR (400 MHz, DMSO-$d_6$) δ 13.15 (br s, 1H), 8.51 (d, J = 8.02 Hz, 1H), 7.35 (t, J = 8.71 Hz, 1H), 7.15-7.21 (m, 1H), 7.05 (br d, J = 8.22 Hz, 1H), 6.42 (d, J = 8.22 Hz, 1H), 4.92 (q, J = 8.80 Hz, 2H) |
| 10-3 | 406.2 | $^1H$ NMR (400 MHz, $CDCl_3$) δ 9.24 (br s, 1H), 8.58-8.62 (m, J = 8.22 Hz, 1H), 7.24-7.27 (d, J = 8.80 Hz, 2H), 7.02 (d, J = 8.80 Hz, 2H), 6.41-6.44 (m, J = 8.22 Hz, 1H), 4.40 (q, J = 8.15 Hz, 2H) |
| 10-4 | 430.1 | $^1H$ NMR (400 MHz, DMSO-$d_6$) δ 13.05 (s, 1H), 8.52 (d, J = 8.29 Hz, 1H), 7.98 (s, 1H), 7.61 (s, 1H), 6.39 (d, J = 8.09 Hz, 1H), 5.27 (t, J = 14.93 Hz, 2H) |
| 11-2 | 422.2 | $^1H$ NMR (400 MHz, $CDCl_3$) δ 8.94 (d, J = 7.88 Hz, 1H), 7.30 (d, J = 7.95 Hz, 2H), 7.09 (d, J = 2.49 Hz, 1H), 7.02 (d, J = 8.71 Hz, 2H), 6.93 (dd, J = 2.49, 7.88 Hz, 1H), 4.40 (q, J = 8.09 Hz, 2H) |
| 11-3 | 433.0 | $^1H$ NMR ($CDCl_3$, 400 MHz) δ 8.94 (d, J = 7.9 Hz, 1H), 7.30 (d, J = 7.9 Hz, 2H), 6.99-7.05 (m, 3H), 6.91 (dd, J = 7.9, 2.7 Hz, 1H), 4.39 (q, J = 8.1 Hz, 2H), 4.24 (q, J = 7.0 Hz, 2H), 1.53 (t, J = 6.9 Hz, 3H) |
| 12-2 | 432.0 | $^1H$ NMR (400 MHz, DMSO-$d_6$) δ 9.02 (d, J = 7.4 Hz, 1H), 8.52 (s, 1H), 8.36 (d, J = 1.8 Hz, 1H), 8.04 (s, 1H), 7.76 (dd, J = 7.5, 1.9 Hz, 1H), 7.31 (d, J = 8.3 Hz, 2H), 7.20-7.10 (m, 2H), 4.84 (q, J = 8.9 Hz, 2H) |
| 12-3 | 460.3 | $^1H$ NMR (400 MHz, DMSO-$d_6$) δ 9.01 (dd, J = 7.3, 1.9 Hz, 1H), 7.89 (d, J = 1.8 Hz, 1H), 7.45 (dt, J = 7.3, 1.8 Hz, 1H), 7.42-7.18 (m, 2H), 7.22-6.88 (m, 2H), 4.85 (q, J = 8.9 Hz, 2H), 3.05 (d, J = 1.8 Hz, 3H), 2.98 (d, J = 1.8 Hz, 3H) |
| 12-4 | 460.1 | $^1H$ NMR (400 MHz, DMSO-$d_6$) δ 9.24-8.86 (m, 2H), 8.33 (d, J = 1.8 Hz, 1H), 7.76 (dd, J = 7.4, 1.9 Hz, 1H), 7.38-7.24 (m, 2H), 7.20-7.06 (m, 2H), 4.84 (q, J = 8.9 Hz, 2H), 3.34 (s, 2H), 1.18 (t, J = 7.2 Hz, 3H) |
| 12-5 | 470.1 | $^1H$ NMR (400 MHz, DMSO-d) δ 9.11-9.01 (m, 2H), 8.26 (dd, J = 1.9, 0.8 Hz, 1H), 8.11 (s, 1H), 7.81-7.71 (m, 2H), 5.32 (t, J = 15.0 Hz, 2H), 2.86 (d, J = 4.5 Hz, 3H) |
| 13-3 | 419.1 | $^1H$ NMR (400 MHz, DMSO-$d_6$) δ 8.97 (dd, J = 7.4, 1.9 Hz, 1H), 7.72 (d, J = 1.8 Hz, 1H), 7.44 (dd, J = 7.4, 1.9 Hz, 1H), 7.29 (dd, J = 8.9, 2.2 Hz, 2H), 7.19-7.09 (m, 2H), 5.81 (td, J = 5.7, 2.1 Hz, 1H), 4.90-4.79 (m, 2H), 4.73 (dd, J = 5.7, 1.5 Hz, 2H) |
| 13-4 | 421.2 | $^1H$ NMR (400 MHz, DMSO-$d_6$) δ 9.02 (dd, J = 7.4, 3.5 Hz, 1H), 7.80 (s, 1H), 7.46 (dd, J = 7.3, 1.9 Hz, 1H), 7.30 (dd, J = 9.6, 2.8 Hz, 2H), 7.23-7.05 (m, 2H), 5.87-5.62 (m, 2H), 4.85 (qd, J = 8.9, 3.5 Hz, 2H) |
| 14-2 | 405.1 | $^1H$ NMR (400 MHz, DMSO-$d_6$) δ 8.77-8.67 (m, 1H), 8.27 (d, J = 6.6 Hz, 2H), 7.20 (d, J = 8.0 Hz, 2H), 7.07 (dd, J = 8.8, 2.5 Hz, 2H), 6.67 (dd, J = 7.8, 2.4 Hz, 1H), 4.93-4.70 (m, 2H) |
| 15-2 | 451.0 | $^1H$ NMR (400 MHz, DMSO-$d_6$) δ 9.09 (d, J = 7.4 Hz, 1H), 8.05 (d, J = 1.7 Hz, 1H), 7.73 (dd, J = 7.4, 1.9 Hz, 1H), 7.35-7.25 (m, 2H), 7.20-7.12 (m, 2H), 4.85 (q, J = 8.8 Hz, 2H), 2.97 (s, 3H) |
| 15-3 | 451.0 | $^1H$ NMR (400 MHz, DMSO-$d_6$) δ 9.09 (d, J = 7.4 Hz, 1H), 8.05 (d, J = 1.7 Hz, 1H), 7.73 (dd, J = 7.4, 1.9 Hz, 1H), 7.35-7.25 (m 2H), 7.20-7.12 (m, 2H), 4.85 (q, J = 8.8 Hz, 2H), 2.97 (s, 3H) |
| 15-4 | 475.1 | $^1H$ NMR (400 MHz, DMSO-d) δ 9.11 (dd, J = 7.5, 2.2 Hz, 1H), 8.12 (d, J = 2.1 Hz, 1H), 8.02 (q, J = 1.6 Hz, 1H), 7.77-7.70 (m, 2H), 5.32 (t, J = 15.0 Hz, 2H), 2.97 (t, J = 1.7 Hz, 3H) |
| 15-5 | 475.1 | $^1H$ NMR (400 MHz, DMSO-d) δ 9.11 (dd, J = 7.5, 2.2 Hz, 1H), 8.12 (d, J = 2.1 Hz, 1H), 8.02 (q, J = 1.6 Hz, 1H), 7.77-7.70 (m 2H), 5.32 (t, J = 15.0 Hz, 2H), 2.97 (1, J = 1.7 Hz, 3H) |
| 15-6 | 475.1 | $^1H$ NMR (400 MHz, DMSO-d) δ 9.11 (dd, J = 7.5, 2.2 Hz, 1H), 8.12 (d, J = 2.1 Hz, 1H), 8.02 (q, J = 1.6 Hz, 1H), 7.77-7.70 (m 2H), 5.32 (t, J = 15.0 Hz, 2H), 2.97 (t, J = 1.7 Hz, 3H) |
| 15-7 | 465.0 | $^1H$ NMR (400 MHz, DMSO-d J = δ 9.07 (dd, J = 7.3, 2.8 Hz, 1H), 7.97 (s, 1H), 7.66 (dd, J = 7.5, 2.0 Hz, 1H), 7.33-7.25 (m, 2H), 7.20-7.12 (m, 2H), 4.92-4.76 (m, 2H), 3.27 (s, 1H), 3.03 (dq, J = 14.3, 7.2 Hz, 1H), 1.08 (td, J = 7.4, 2.7 Hz, 3H) |
| 15-8 | 465.0 | $^1H$ NMR (400 MHz, DMSO-$d_6$) δ 9.07 (dd, J = 7.3, 2.8 Hz, 1H), 7.97 (s, 1H), 7.66 (dd, J = 7.5, 2.0 Hz, 1H), 7.31-7.24 (m, 2H), 7.20-7.12 (m, 2H), 4.95-4.78 (m, 2H), 3.2.7 (s, 1H), 3.03 (dq, J = 14.3, 7.2 Hz, 1H), 1.09 (td, J = 7.4, 2.7 Hz, 3H) |
| 15-9 | 465.0 | $^1H$ NMR (400 MHz, DMSO-$d_6$) δ 9.07 (dd, J = 7.3, 2.8 Hz, 1H), 7.98 (s, 1H), 7.66 (dd, J = 7.5, 2.0 Hz, 1H), 7.33-7.27 (m, 2H), 7.21-7.10 (m, 2H), 4.92-4.76 (m, 2H), 3.27 (s, 1H), 3.03 (dq, J = 14.3, 7.2 Hz, 1H), 1.08 (td, J = 7.4, 2.7 Hz, 3H) |
| 16-2 | 442.1 | $^1H$ NMR (400 MHz, DMSO-$d_6$) δ 8.96 (d, J = 7.3 Hz, 1H), 8.05 (s, 1H), 7.80 (d, J = 1.8 Hz, 1H), 7.70 (s, 1H), 7.48 (dd, J = 7.3, 1.8 Hz, 1H), 5.30 (t, J = 14.9 Hz, 2H), 3.93 (s, 2H); Note: $NH_2$ protons are not observed |

TABLE 25-continued

| Ex. | LRMS: m/z (ESI, +ve ion): $(M + H)^+$ | NMR |
|---|---|---|
| 17-3 | 475.3 | H NMR (500 MHz, $CDCl_3$) δ 2.82 (qt, J = 10.38, 7.34 Hz, 2H), 4.35-4.53 (m, 2H), 5.89 (d, J = 52.10 Hz, 2H), 7.03 (dd, J = 7.82, 2.61 Hz, 1H), 7.32 (d, J = 2.47 Hz, 1H), 7.67-7.87 (m, 2H), 9.04 (d, J = 7.96 Hz, 1H) |
| 30-1 | 433.2 | $^1$H NMR (400 MHz, DMSO-$d_6$) δ 9.16-8.81 (m 1H), 7.75 (s, 1H), 7.51 (dt, J = 7.5, 1.7 Hz, 1H), 7.28 (d, J = 8.4 Hz, 2H), 7.16-7.06 (m, 2H), 5.76 (dd, J = 4.8, 1.5 Hz, 1H), 4.93 (p, J = 6.1 Hz, 1H), 4.83 (q, J = 8.5 Hz, 2H), 1.41 (dd, J = 6.6, 1.6 Hz, 3H) |
| 30-2 | 433.2 | $^1$H NMR (400 MHz, DMSO-$d_6$) δ 8.97 (d, J = 7.3 Hz, 1H), 7.76 (d, J = 1.6 Hz, 1H), 7.52 (dd, J = 7.4, 1.8 Hz, 1H), 7.36-7.20 (m, 2H), 7.17-7.04 (m, 2H), 5.77 (d, J = 4.6 Hz, 1H), 4.93 (q, J = 6.1 Hz, 1H), 4.84 (q, J = 8.8 Hz, 2H), 1.42 (d, J = 6.5 Hz, 3H) |
| 31-1 | 457.0 | $^1$H NMR (400 MHz, DMSO-$d_6$) δ 8.99 (dd, J = 7.4, 1.8 Hz, 1H), 8.05 (s, 1H), 7.72 (d, J = 15.6 Hz, 2H), 7.52 (dt, J = 7.4, 1.9 Hz, 1H), 5.76 (dd, J = 4.7, 1.8 Hz, 1H), 5.30 (t, J = 15.1 Hz, 2H), 4.97-4.90 (m, 1H), 1.42 (dd, J = 6.5, 1.7 Hz, 3H) |
| 31-2 | 457.0 | $^1$H NMR (400 MHz, DMSO-$d_6$) δ 8.99 (dd, J = 7.4, 1.8 Hz, 1H), 8.05 (s, 1H), 7.72 (d, J = 15.6 Hz, 2H), 7.52 (dt, J = 7.4, 1.9 Hz, 1H), 5.76 (dd, J = 4.7, 1.8 Hz, 1H), 5.30 (t, J = 15.1 Hz, 2H), 4.97-4.90 (m, 1H), 1.42 (dd, J = 6.5, 1.7 Hz, 3H) |
| 39-2 | 441.1/443.1 | $^1$H NMR (400 MHz, DMSO-$d_6$) δ 9.00 (s, 1H), 7.98 (s, 1H), 7.57 (s, 1H), 7.40 (s, 1H), 4.46 (t, J = 6.80 Hz, 2H), 4.12 (s, 3H), 2.80-3.01 (m, 2H) |
| 39-3 | 477.2/479.2 | $^1$H NMR (500 MHz, DMSO-$d_6$) δ 9.03 (d, J = 8.07 Hz, 1H), 8.03 (s, 1H), 7.67 (s, 1H), 7.64 (d, J = 8.31 Hz, 1H), 5.29 (t, J = 14.92 Hz, 2H), 4.18 (s, 3H) |
| 39-4 | 461.3 | $^1$H NMR (500 MHz, DMSO-$d_6$) δ 4.16 (s, 3H), 5.28 (t, J = 14.96 Hz, 2H), 7.64-7.70 (m, 2H), 8.02 (s, 1H), 8.90 (dd, J = 8.10, 1.51 Hz, 1H) |
| 39-5 | 413.3 | $^1$H NMR (500 MHz, DMSO-$d_6$) δ 5.30 (t, J = 14.96 Hz, 2H), 7.51 (td, J = 7.00, 1.37 Hz, 1H), 7.71 (s, 1H), 7.87 (dt, J = 8.85, 1.06 Hz, 1H), 8.06 (s, 1H), 8.09 (ddd, J = 8.85, 6.93, 1.51 Hz, 1H), 9.02 (dt, J = 7.14, 0.82 Hz, 1H) |
| 39-6 | 443.1 | $^1$H NMR (500 MHz, DMSO-$d_6$) δ 3.96 (s, 3H), 5.30 (t, J = 14.82 Hz, 2H), 7.71 (s, 1H), 7.85-7.90 (m, 1H), 7.91-7.97 (m, 1H), 8.06 (s, 1H), 8.52 (d, J = 2.74 Hz, 1H) |
| 39-7 | 471.1 | $^1$H NMR (500 MHz, DMSO-$d_6$) δ 1.51 (s, 6H), 4.94-6.18 (m, 1H), 5.29 (t, J = 14.92 Hz, 2H), 7.64 (dd, J = 7.58, 1.96 Hz, 1H), 7.69 (s, 1H), 7.80 (d, J = 1.71 Hz, 1H), 8.05 (s, 1H), 8.92-9.00 (m, 1H) |
| 39-8 | 457.2 | $^1$H NMR (500 MHz, DMSO-$d_6$) δ 2.87 (s, 3H), 3.96 (s, 3H), 5.25 (t, J = 15.09 Hz, 2H), 6.87 (d, J = 2.20 Hz, 1H), 6.97 (d, J = 2.74 Hz, 1H), 7.61 (s, 1H), 7.96 (s, 1H) |
| 39-9 | 438.1 | $^1$H NMR (400 MHz, DMSO-$d_6$) δ 5.32 (t, J = 14.87 Hz, 2H), 7.73 (s, 1H), 7.90 (d, J = 9.39 Hz, 1H), 8.12 (s, 1H), 8.22 (dd, J = 9.19, 1.76 Hz, 1H), 9.55 (d, J = 1.96 Hz, 1H) |
| 39-10 | 444.3 | $^1$H NMR (500 MHz, DMSO-$d_6$) δ 4.05 (s, 3H), 5.29 (t, J = 14.96 Hz, 2H), 7.05 (s, 1H), 7.66 (s, 1H), 8.02 (s, 1H), 9.55 (s, 1H) |
| 39-11 | 408.1 | $^1$H NMR (500 MHz, DMSO-$d_6$) δ 2.90 (qt, J = 11.21, 6.79 Hz, 2H), 4.04 (s, 3H), 4.47 (t, J = 6.72 Hz, 2H), 7.53 (d, J = 2.74 Hz, 1H), 7.59 (s, 1H), 8.02 (s, 1H), 8.79 (d, J = 3.02 Hz, 1H) |
| 39-12 | 471.2 | $^1$H NMR (500 MHz, DMSO-$d_6$) δ 4.06 (s, 3H), 5.22 (t, J = 13.72 Hz, 2H), 7.26 (dd, J = 7.96, 2.74 Hz, 1H), 7.37 (d, J = 2.74 Hz, 1H), 8.66 (s, 2H), 8.93 (d, J = 7.96 Hz, 1H) |
| 39-13 | 422.1 | $^1$H NMR (400 MHz, DMSO-$d_6$) δ 4.13 (s, 3H), 5.13 (q, J = 8.99 Hz, 2H), 7.13 (d, J = 7.67 Hz, 1H), 8.64 (s, 2H), 9.08 (d, J = 7.67 Hz, 1H) |
| 39-14 | 444.1 | $^1$H NMR (400 MHz, DMSO-$d_6$) δ 4.05 (s, 3H), 5.31 (t, J = 15.02 Hz, 2H), 7.60 (d, J = 9.65 Hz, 1H), 7.74 (s, 1H), 8.08 (d, J = 9.65 Hz, 1H), 8.11 (s, 1H) |
| 39-15 | 422.1 | $^1$H NMR (500 MHz, DMSO-$d_6$) δ 4.05 (s, 3H), 5.14 (q, J = 8.97 Hz, 2H), 7.72 (d, J = 9.78 Hz, 1H), 8.19 (d, J = 9.29 Hz, 1H), 8.68 (s, 2H) |
| 39-16 | 471.1 | $^1$H NMR (400 MHz, $CDCl_3$) δ 9.73 (s, 1H), 8.31 (d, 1H), 7.94 (s, 1H), 7.87 (s, 1H), 7.81 (d, 1H), 4.92-4.79 (t, 2H), 4.04 (s, 3H) |
| 39-17 | 411.3/413.3 | $^1$H NMR (500 MHz, DMSO-$d_6$) δ 2.83-2.99 (m, 2H), 4.48 (t, J = 6.72 Hz, 2H), 7.62 (s, 1H), 7.88 (dd, J = 9.47, 0.69 Hz, 1H), 8.05 (s, 1H), 8.07-8.17 (m, 1H), 8.99 (dd, J = 2.33, 0.69 Hz, 1H) |
| 39-18 | 425.0/427.0 | $^1$H NMR (500 MHz, DMSO-$d_6$) δ 5.13 (q, J = 8.60 Hz, 211), 8.01 (d, J = 9.61 Hz, 1H), 8.27 (dd, J = 9.47, 2.33 Hz, 1H), 8.67 (s, 211), 9.08 (d, J = 2.20 Hz, 1H) |
| 39-19 | 427.1 | $^1$H NMR (500 MHz, DMSO-$d_6$) δ 2.46 (d, J = 0.82 Hz, 3H), 5.29 (t, J = 14.96 Hz, 2H), 7.70 (s, 1H), 7.82 (d, J = 9.06 Hz, 1H), 7.99 (dd, J = 8.92, 2.06 Hz, 1H), 8.05 (s, 1H), 8.85-8.89 (m, 1H) |
| 39-20 | 431.2 | $^1$H NMR (500 MHz, DMSO-$d_6$) δ 0.84-0.94 (m, 2H), 1.06-1.16 (m, 2H), 2.30 (tt, J = 8.40, 5.04 Hz, 1H), 5.13 (q, J = 9.06 Hz, 2H), 7.86-7.93 (m, 2H), 8.67 (s, 2H), 8.90 (br s, 1H) |
| 39-21 | 453.1 | $^1$H NMR (500 MHz, DMSO-$d_6$) δ 0.81-0.92 (m, 2H), 1.02-1.15 (m, 2H), 2.26 (tt, J = 8.44, 5.01 Hz, 1H), 5.29 (t, J = 14.96 Hz, 2H), 7.70 (s, 1H), 7.75-7.82 (m, 2H), 8.05 (s, 1H), 8.86 (s, 1H) |

TABLE 25-continued

| Ex. | LRMS: m/z (ESI, +ve ion): $(M + H)^+$ | NMR |
|---|---|---|
| 39-22 | 417.1 | $^1$H NMR (500 MHz, DMSO-$d_6$) δ 0.81-0.91 (m 2H), 1.03-1.14 (m, 2H), 2.20-2.29 (m, 1H), 2.83-2.96 (m, 2H), 4.47 (t, J = 6.72 Hz, 2H), 7.60 (s, 1H), 7.73-7.81 (m, 2H), 8.01 (s, 1H), 8.84 (d, J = 1.65 Hz, 1H) |
| 39-23 | 431.1 | $^1$H NMR (500 MHz, DMSO-$d_6$) δ 5.31 (t, J = 15.10 Hz, 2H), 7.72 (s, 1H), 8.00 (dd, J = 9.61, 5.21 Hz, 1H), 8.09 (s, 1H), 8.23 (ddd, J = 9.47, 7.00, 2.74 Hz, 1H), 9.04 (dd, J = 4.39, 2.74 Hz, 1H) |
| 39-24 | 457.1 | $^1$H NMR (500 MHz, $CDCl_3$) δ 3.48 (s, 3H), 4.57 (s, 2H), 4.83 (t, J = 13.7 Hz, 2H), 7.79-7.83 (m, 1H), 7.84-7.89 (m, 2H), 7.90 (s, 1H), 9.04 (d, J = 0.8 Hz, 1H) |
| 39-25 | 414.1 | $^1$H NMR (400 MHz, DMSO-$d_6$) δ 5.33 (1, J = 14.9 Hz, 2H), 7.77 (s, 1H), 8.18 (s, 1H), 8.34 (d, J = 4.8 Hz, 1H), 8.72 (dd, J = 4.7, 1.2 Hz, 1H), 9.29 (d, J = 1.1 Hz, 1H) |
| 39-26 | 409.1 | $^1$H NMR (400 MHz, DMSO-$d_6$) δ 5.10 (q, J = 8.9 Hz, 2H), 8.07 (dd, J = 9.6, 5.3 Hz, 1H), 8.32 (ddd, J = 9.8, 7.1, 2.8 Hz, 1H), 8.64 (s, 2H), 9.04-9.11 (m, 1H) |
| 39-27 | 395.1 | $^1$H NMR (400 MHz, DMSO-$d_6$) δ 2.83-2.99 (m, 2H), 4.48 (t, J = 6.8 Hz, 2H), 7.63 (s, 1H), 7.97 (dd, J = 9.8, 5.4 Hz, 1H), 8.05 (s, 1H), 8.21 (ddd, J = 9.8, 7.1, 2.9 Hz, 1H), 8.97-9.05 (m, 1H) |
| 39-28 | 468.2 | $^1$H NMR (500 MHz, $CDCl_3$) δ 2.53 (quin, J = 7.3 Hz, 2H), 4.07 (t, J = 7.3 Hz, 4.H), 4.82 (t, J = 13.9 Hz, 2H), 7.31 (dd, J = 9.5, 2.6 Hz, 1H), 7.75 (d, J = 9.3 Hz, 1H), 7.85 (s, 1H), 7.88 (s, 1H), 8.10 (d, J = 2.7 Hz, 1H) |
| 39-29 | 470.4 | $^1$H NMR (500 MHz, $CDCl_3$) δ 2.30 (s, 6H), 3.54 (s, 2H), 4.83 (t, J = 13.7 Hz, 2H), 7.80 (d, J = 9.1 Hz, 1H), 7.85 (s, 1H), 7.89 (s, 1H), 7.96 (dd, J = 9.1, 1.9 Hz, 1H), 8.88-9.03 (m, 1H) |
| 39-30 | 406.1 | $^1$H NMR (400 MHz, DMSO-$d_6$) δ 2.63 (s, 3H), 5.14 (q, J = 8.8 Hz, 2H), 8.68 (s, 2H), 8.73 (s, 1H), 9.38 (s, 1H) |
| 39-31 | 428.3 | $^1$H NMR (400 MHz, DMSO-$d_6$) δ 2.59 (s, 3H), 5.32 (t, J = 15.1 Hz, 2H), 7.76 (s, 1H), 8.16 (s, 1H), 8.65 (t, J = 1.0 Hz, 1H), 9.26 (d, J = 0.8 Hz, 1H) |
| 39-32 | 428.1 | $^1$H NMR (500 MHz, DMSO-$d_6$) δ 2.63 (s, 3H), 5.31 (t, J = 15.0 Hz, 2H), 7.72 (s, 1H), 7.78 (d, J = 9.3 Hz, 1H), 8.07-8.11 (m, 2H) |
| 39-33 | 392.1 | $^1$H NMR (400 MHz, DMSO-$d_6$) δ 2.62 (s, 3H), 2.91 (qt, J = 11.2, 6.7 Hz, 2H), 4.48 (t, J = 6.7 Hz, 2H), 7.63 (s, 1H), 7.76 (d, J = 9.2 Hz, 1H), 8.02-8.12 (m, 2H) |
| 39-34 | 419.3 | $^1$H NMR (400 MHz, DMSO-$d_6$) δ 3.85 (t, J = 5.2 Hz, 2H), 4.07 (t, J = 5.3 Hz, 2H), 4.71 (s, 2H), 5.28 (t, J = 15.0 Hz, 2H), 7.67 (s, 1H), 8.07 (s, 1H) |
| 39-35 | 448.0/450.0 | $^1$H NMR (400 MHz, DMSO-$d_6$) δ 5.33 (t, J = 15.0 Hz, 2H), 7.79 (s, 1H), 8.22 (s, 1H), 8.87 (d, 11.0 Hz, 1H), 9.25 (d, J = 1.0 Hz, 1H) |
| 39-36 | 406.0 | $^1$H NMR (500 MHz, DMSO-$d_6$) δ 2.66 (s, 3H), 5.13 (q, J = 9.0 Hz, 2H), 7.89 (d, J = 9.3 Hz, 1H), 8.19 (d, J = 9.3 Hz, 1H), 8.68 (s, 2H) |
| 39-37 | 444.0 | $^1$H NMR (500 MHz, $CDCl_3$) δ 4.12 (s, 3H), 4.83 (td, J = 13.7, 11.1 Hz, 2H), 7.91 (s, 1H), 8.00 (s, 1H), 8.39 (d, J = 1.4 Hz, 1H), 9.13 (s, 1H) |
| 39-38 | 383.1 | $^1$H NMR (500 MHz, DMSO-$d_6$) δ 2.88 (qt, J = 11.2, 6.7 Hz, 2H), 3.84 (t, J = 5.2 Hz, 2H), 4.07 (t, J = 5.4 Hz, 2H), 4.46 (t, J = 6.7 Hz, 2H), 4.70 (s, 2H), 7.57 (s, 1H), 8.03 (s, 1H) |
| 39-39 | 397.0 | $^1$H NMR (500 MHz, DMSO-$d_6$) δ 3.87 (t, J = 5.2 Hz, 2H), 4.10 (t, J = 5.2 Hz, 2H), 4.79 (s, 2H), 5.12 (q, J = 8.9 Hz, 2H), 8.61 (s, 2H) |
| 39-40 | 428.0 | $^1$H NMR (400 MHz, DMSO-$d_6$) δ 2.47 (d, J = 1.3 Hz, 3H), 5.30 (t, J = 15.0 Hz, 2H), 7.71 (s, 1H), 8.00 (dd, J = 2.0, 1.3 Hz, 1H), 8.10 (s, 1H), 8.84 (d, J = 2.2 Hz, 1H) |
| 39-41 | 428.1 | $^1$H NMR (500 MHz, DMSO-$d_6$) δ 2.81 (s, 3H), 5.32 (t J = 15.0 Hz, 2H), 7.77 (s, 1H), 8.17 (s, 1H), 8.19 (d, J = 4.9 Hz, 1H), 8.62 (d, J = 4.7 Hz, 1H) |
| 39-42 | 401.0 | $^1$H NMR (400 MHz, $CDCl_3$) δ 1.26-1.37 (m, 1H), 1.56-1.66 (m, 1H), 2.09-2.32 (m, 1H), 4.00 (s, 3H), 4.23-4.43 (m, 2H), 6.91 (dd, J = 7.9, 2.6 Hz, 1H), 7.02 (d, J = 2.6 Hz, 1H), 7.66-7.79 (m, 2H), 8.95 (d, J = 7.9 Hz, 1H) |
| 39-43 | 442.1 | $^1$H NMR (400 MHz, DMSO-$d_6$) δ 2.54 (s, 3H), 2.80 (s, 3H), 5.32 (t, J = 15.0 Hz, 2H), 7.76 (s, 1H), 8.15 (s, 1H), 8.54 (s, 1H) |
| 39-44 | 392.0 | $^1$H NMR (500 MHz, DMSO-$d_6$) δ 2.46 (s, 3H), 2.85-2.98 (m, 2H), 4.48 (t, J = 6.7 Hz, 2H), 7.62 (s, 1H), 7.98 (s, 1H), 8.06 (s, 1H), 8.82 (d, J = 1.9 Hz, 1H) |
| 39-45 | 365.1 | $^1$H NMR (400 MHz, $CDCl_3$) δ 0.42 (q, J = 5.0 Hz, 2H), 0.60-0.76 (m, 2H), 1.28-1.43 (m, 1H), 4.01 (s, 3H), 4.06 (d, J = 7.0 Hz, 2H), 6.91 (dd, J = 7.9, 2.6 Hz, 1H), 7.02 (d, J = 2.6 Hz, 1H), 7.73 (s, 1H), 7.83 (s, 1H), 8.95 (d, J = 7.9 Hz, 1H) |
| 39-46 | 442.0 | $^1$H NMR (500 MHz, DMSO-$d_6$) δ 2.44 (d, J = 1.1 Hz, 3H), 2.60 (s, 3H), 5.30 (t, J = 15.0 Hz, 2H), 7.70 (s, 1H), 7.97 (d, J = 1.1 Hz, 1H), 8.07 (s, 1H) |
| 39-47 | 406.0 | $^1$H NMR (500 MHz, DMSO-$d_6$) δ 2.43 (d, J = 0.8 Hz, 3H), 2.59 (s, 3H), 2.84-3.00 (m, 2H), 4.48 (t, J = 6.7 Hz, 2H), 7.6.1 (s, 1H), 7.95 (d, J = 1.1 Hz, 1H), 8.03 (s, 1H) |
| 39-48 | 406.0 | $^1$H NMR (500 MHz, DMSO-$d_6$) δ 2.51 (brs, 3H), 5.13 (q, J = 9.1 Hz, 2H), 8.11 (dd, J = 2.1, 1.2 Hz, 1H), 8.68 (s, 2H), 8.92 (d, J = 1.9 Hz, 1H) |

TABLE 25-continued

| Ex. | LRMS: m/z (ESI, +ve ion): $(M + H)^+$ | NMR |
|---|---|---|
| 39-49 | 415.1 | $^1$H NMR (500 MHz, DMSO-$d_6$) δ 2.37-2.49 (m, 2H), 2.55-2.70 (m, 3H), 4.02 (s, 3H), 4.30 (d, J = 5.8 Hz, 2H), 7.18 (dd, J = 8.0, 2.7 Hz, 1H), 7.24 (d, J = 2.7 Hz, 1H), 7.54 (s, 1H), 7.93 (s, 1H), 8.88 (d, J = 7.7 Hz, 1H) |
| 39-50 | 404.0 | $^1$H NMR (500 MHz, DMSO-$d_6$) δ 2.48 (d, J = 1.1 Hz, 3H), 4.83 (q, J = 8.9 Hz, 2H), 7.10-7.17 (m, 2H), 7.25-7.32 (m, 2H), 7.99-8.05 (m, 1H), 8.84 (d, J = 2.2 Hz, 1H) |
| 39-51 | 350.4 | $^1$H NMR (500 MHz, DMSO-$d_6$) δ 0.33-0.44 (m, 2H), 0.50-0.59 (m, 2H), 1.22-1.33 (m, 1H), 2.46 (d, J = 1.1 Hz, 3H), 4.05 (d, J = 7.1 Hz, 2H), 7.58 (s, 1H), 7.98 (t, J = 1.5 Hz, 1H), 8.01 (s, 1H), 8.82 (d, J = 2.2 Hz, 1H) |
| 39-52 | 400.1 | $^1$H NMR (500 MHz, DMSO-$d_6$) δ 2.39-2.46 (m, 2H), 2.46 (d, J = 1.1 Hz, 3H), 2.56-2.71 (m, 3H), 4.33 (d, J = 5.8 Hz, 2H), 7.60 (s, 1H), 7.97-8.00 (m, 1H), 8.03 (s, 1H), 8.82 (d, J = 2.2 Hz, 1H) |
| 39-53 | 386.1 | $^1$H NMR (500 MHz, DMSO-$d_6$) δ 1.51 (dtd, J = 13.7, 7.7, 7.7, 4.1 Hz, 1H), 1.70 (tdd, J = 12.0, 12.0, 7.8, 4.7 Hz, 1H), 2.27 (ddq, J = 13.3, 11.5, 7.5, 7.5, 7.5 Hz, 1H), 2.46 (d, J = 1.1 Hz, 3H), 4.33 (d, J = 7.4 Hz, 2H), 7.63 (s, 1H), 7.98 (dd, J = 2.2, 1.4 Hz, 1H), 8.02 (s, 1H), 8.83 (d, J = 1.9 Hz, 1H) |
| 39-54 | 381.1 | $^1$H NMR (400 MHz, DMSO-$d_6$) δ 3.37-3.51 (m, 1H), 4.02 (s, 3H), 4.43 (t, J = 6.1 Hz, 2H), 4.47 (d, J = 7.2 Hz, 2H), 4.64 (dd, J = 7.8, 6.1 Hz, 2H), 7.17 (dd, J = 7.9, 2.7 Hz, 1H), 7.23 (d, J = 2.6 Hz, 1H), 7.52 (s, 1H), 7.92 (s, 1H), 8.88 (d, J = 7.9 Hz, 1H) |
| 39-55 | 416.1 | $^1$H NMR (500 MHz, DMSO-$d_6$ δ 2.38-2.48 (m, 2H), 2.56-2.69 (m, 3H), 4.04 (s, 3H), 4.32 (d, J = 5.8 Hz, 2H), 7.53 (d, J = 2.7 Hz, 1H), 7.57 (s, 1H), 7.99 (s, 1H), 8.79 (d, J = 2.7 Hz, 1H) |
| 39-56 | 445.1 | $^1$H NMR (500 MHz, DMSO-$d_6$ δ 2.49 (br s, 3H), 5.29 (t, J = 15.0 Hz, 2H), 7.70 (s, 1H), 7.93 (d, J = 7.1 Hz, 1H), 8.07 (s, 1H), 8.98 (d, J = 5.2 Hz, 1H) |
| 39-57 | 437.1 | $^1$H NMR (400 MHz, DMSO-$d_6$) δ 4.14 (s, 3H), 4.82 (q, J = 8.8 Hz, 2H), 7.12 (d, J = 8.8 Hz, 2H), 7.26 (d, J = 8.8 Hz, 2H), 7.52 (d, J = 7.9 Hz, 1H), 9.02 (d, J = 6.8 Hz, 1H) |
| 39-58 | 425.1 | $^1$H NMR (400 MHz, DMSO-$d_6$) δ 2.90 (qt, J = 11.2, 6.6 Hz, 2H), 4.12 (s, 3H), 4.46 (t, J = 6.8 Hz, 2H), 7.48 (d, J = 8.1 Hz, 1H) 7.57 (s, 1H), 7.98 (s, 1H), 9.03 (d, J = 6.8 Hz, 1H) |
| 39-59 | 419.1 | $^1$H NMR (400 MHz, DMSO-$d_6$) δ 1.44-1.55 (m, 1H), 1.69 (tdd, J = 12.0, 12.0, 7.7, 4.8 Hz, 1H), 2.19-2.34 (m, 1H), 4.12 (s, 3H), 4.32 (d, J = 7.5 Hz, 2H), 7.48 (d, J = 7.9 Hz, 1H), 7.58 (s, 1H), 7.95 (s, 1H), 9.03 (d, J = 6.8 Hz, 1H) |
| 40-2 | 428.0 | $^1$H NMR(400 MHz, DMSO-$d_6$) δ 2.45 (d, J = 0.7 Hz, 3H), 5.30 (t, J = 15.0 Hz, 2H), 7.71 (s, 1H), 8.08 (s, 1H), 9.05-9.24 (m, 2H) |
| 41-2 | 425.0/427.1 | $^1$H NMR (400 MHz, DMSO-$d_6$) δ 2.52 (d, J = 0.7 Hz, 3H), 2.75-3.01 (m, 2H), 4.47 (t, J = 6.8 Hz, 2H), 7.60 (s, 1H), 7.92 (s, 1H), 8.02 (s, 1H), 8.98 (s, 1H) |
| 41-3 | 437.0/439.0 | $^1$H NMR (400 MHz, DMSO-$d_6$) δ 2.54 (s, 3H), 4.83 (q, J = 8.9 Hz, 2H), 7.10-7.17 (m, 2H), 7.22-7.31 (m, 2H), 7.96 (s, 1H), 8.97 (s, 1H) |
| 41-4 | 419.0 | $^1$H NMR (500 MHz, DMSO-$d_6$) δ 1.46 (t, J = 7.0 Hz, 3H), 4.00 (s, 3H), 4.57 (q, J = 7.1 Hz, 2H), 5.26 (t, J = 15.2 Hz, 2H), 6.95 (d, J = 2.7 Hz, 1H), 7.05 (dd, J = 7.7, 2.7 Hz, 1H), 8.28 (s, 1H), 8.53 (s, 1H), 8.94 (d, J = 8.0 Hz, 1H) |

Biological Evaluation

Provided in this section is the biological evaluation of the specific examples provided herein. See Tables 26-28.

In vitro Measurement of Delta-5-Desaturase Inhibitory Activity using DGLA-CoA and Arachidonyl-CoA Mass Spectrometric Assays Membrane preparations of D5D-overexpressing HEK293 6E cells were prepared in which the total protein concentration was 5.6 mg/mL. Stock D5D membrane preparations were diluted in D5D assay buffer (25 mM 2-amino-2-(hydroxymethyl)-1,3-propanediol, pH 7.5 containing 10 mM $MgCl_2$, 1 mM octyl glucoside (SigmaAldrich 0-8001), 1 mM tris(2-carboxyethyl)phosphine hydrochloride (SigmaAldrich 646547)) to a final D5D membrane concentration of 10 μg/mL in an assay plate containing serially diluted test compounds. To 15 μL of this D5D preparation was added 15 μL of a substrate solution (0.25 mM NADH (nicotinamide adenine dinucleotide, Roche Diag. 10107735001), 0.25 mM adenosine triphosphate (SigmaAldrich A-3377), 0.05 mM coenzyme A hydrate (SigmaAldrich C-4282), and 0.01 mM DGLA (dihomo-g-linolenic acid, Sigma E-4504) in the same D5D assay buffer. After one-hour incubation at ambient temperature acetonitrile (30 μL) was added to quench the reaction and plates were centrifuged for 10 min @3,000 rpm. Mass spectrometric analysis involved a Rapidfire 360 SPE system coupled to an ABSciex API4000 Triple Quadrupole mass spectrometer using a C18 SPE cartridge (G9203-80105) with ionization in negative mode (solvent A=100% water; solvent B=100% acetonitrile, each solvent containing 5 mM ammonium acetate). DGLA-CoA and Arachidonyl-CoA were detected by multiple reaction monitoring (MRM) of the doubly charged parent ions at m/z 526.6 and 525.6, respectively.

The % of inhibition was expressed as percentage of the maximal inhibition value obtained in the absence of enzyme according to the formula: % inhibition=100−(100*(Sx−Sc)/(So−Sc)). Sx is value from unknown sample, So is value from DMSO alone and Sc is value from no enzyme well. For CRC analysis, the % of inhibitions were analyzed with 4 Parameter Logistic Model or Sigmoidal Dose-Response Model using XLfit (IDBS, Guilford, UK). The potency of the test item was expressed as IC50 nM, corresponding to the test item concentration able to inhibit the 50% of the enzyme maximal response. $IC_{50}$ values were averaged values determined by at least two independent runs.

The results presented in Table 26 have been generated with the in vitro assay described above. This assay may be used to test any of the compounds described herein to assess and characterize a compound's ability to inhibit D5D.

TABLE 26

| Example Number | D5D IC50 (μM) |
|---|---|
| 1-42 | 0.0104 |
| 1-43 | 0.0456 |
| 1-44 | 0.0034 |
| 20 | 0.109 |
| 5-4 | 0.198 |
| 5-3 | 5.19 |
| 5-2 | 0.157 |
| 5-1 | 0.0125 |
| 1-46 | 0.0364 |
| 7-2 | 5.23 |
| 1-47 | 0.0054 |
| 1-48 | 0.0051 |
| 1-49 | 0.0054 |
| 1-50 | 0.0168 |
| 1-76 | 0.0176 |
| 7-4 | 0.027 |
| 1-75 | 0.0296 |
| 7-3 | 4.05 |
| 1-74 | 0.0276 |
| 1-17 | 0.0139 |
| 1-20 | 0.0089 |
| 1-19 | 0.345 |
| 1-18 | 0.0252 |
| 1-73 | 0.022 |
| 10-2 | 0.328 |
| 1-72 | 0.0572 |
| 1-71 | 4.88 |
| 10-1 | 0.0438 |
| 10-3 | 0.9 |
| 1-70 | 0.262 |
| 1-79 | 0.0036 |
| 1-77 | 0.0066 |
| 1-69 | 0.0152 |
| 1-68 | 0.0116 |
| 11-1 | 0.0482 |
| 1-67 | 0.0342 |
| 11-2 | 0.004 |
| 1-15 | 0.0124 |
| 1-16 | 0.383 |
| 1-8 | 0.0051 |
| 1-7 | 0.0852 |
| 7-1 | 0.125 |
| 1-66 | 0.0791 |
| 7-5 | 0.0119 |
| 1-65 | 0.0032 |
| 1-13 | 0.0342 |
| 1-12 | 0.0099 |
| 1-14 | 0.0229 |
| 7-6 | 0.302 |
| 1-64 | 0.0215 |
| 1-63 | 0.0281 |
| 1-62 | 0.0109 |
| 1-61 | 0.0114 |
| 1-60 | 0.0378 |
| 1-78 | 0.0027 |
| 1-59 | 0.0145 |
| 1-58 | 0.0661 |
| 1-81 | 0.0129 |
| 1-80 | 0.0125 |
| 1-11 | 0.0261 |
| 1-57 | 0.226 |
| 1-56 | 9.28 |

TABLE 26-continued

| Example Number | D5D IC50 (μM) |
|---|---|
| 1-55 | 0.112 |
| 1-10 | 0.0079 |
| 1-54 | 0.0066 |
| 1-53 | 0.0085 |
| 1-52 | 0.0056 |
| 1-51 | 0.0266 |
| 1-41 | 0.0249 |
| 1-9 | 0.0059 |
| 1-40 | 0.0186 |
| 21 | 0.0058 |
| 1-1 | 0.197 |
| 4-1 | 5.22 |
| 1-2 | 0.305 |
| 1-39 | 0.0422 |
| 1-38 | 0.18 |
| 4-2 | 0.111 |
| 11-3 | 0.0275 |
| 22 | 0.0040 |
| 17-1 | 0.317 |
| 8-3 | 0.0225 |
| 8-2 | 0.605 |
| 17-2 | 0.0486 |
| 1-37 | 0.0131 |
| 9-1 | 0.0111 |
| 1-36 | 0.199 |
| 4-3 | 0.022 |
| 24 | 0.0289 |
| 9-2 | 0.0113 |
| 2-9 | 0.44 |
| 8-4 | 0.0162 |
| 8-1 | 0.0122 |
| 15-3 | 0.235 |
| 15-2 | 0.562 |
| 2-8 | 0.0254 |
| 2-7 | 0.0041 |
| 2-3 | 0.0884 |
| 1-35 | 0.0104 |
| 2-2 | 0.646 |
| 2-4 | 0.0574 |
| 1-34 | 0.0307 |
| 2-1 | 0.0226 |
| 2-5 | 0.0039 |
| 19 | 10.1 |
| 12-1 | 0.12 |
| 13-3 | 0.0056 |
| 1-3 | 0.371 |
| 1-5 | 0.046 |
| 1-33 | 0.0173 |
| 13-4 | 0.0094 |
| 1-4 | 0.0066 |
| 32 | 0.141 |
| 30-1 | 0.0742 |
| 30-2 | 0.111 |
| 12-4 | 0.685 |
| 1-32 | 0.421 |
| 1-6 | 0.11 |
| 12-3 | 2.54 |
| 15-1 | 0.441 |
| 8-8 | 0.566 |
| 8-9 | 0.0116 |
| 1-31 | 1.72 |
| 1-30 | 0.0188 |
| 6-2 | 0.0068 |
| 1-29 | 0.0070 |
| 1-28 | 0.0435 |
| 1-27 | 0.0187 |
| 15-4 | 0.712 |
| 15-9 | 0.191 |
| 15-8 | 0.185 |
| 12-5 | 0.313 |
| 15-6 | 0.173 |
| 15-5 | 0.159 |
| 25 | 0.0662 |
| 29 | 0.0971 |
| 1-26 | 0.278 |
| 28 | 2.94 |
| 27 | 0.553 |

TABLE 26-continued

| Example Number | D5D IC50 (μM) |
|---|---|
| 12-2 | 0.0052 |
| 1-25 | 0.0064 |
| 1-83 | 0.0057 |
| 1-84 | 0.0027 |
| 1-24 | 0.833 |
| 8-7 | 4.91 |
| 8-6 | 0.0235 |
| 6-1 | 0.0148 |
| 1-23 | 0.0199 |
| 1-22 | 0.121 |
| 13-1 | 0.0239 |
| 13-2 | 0.0205 |
| 1-21 | 3.39 |
| 31-2 | 0.16 |
| 31-1 | 0.164 |
| 18 | 0.132 |
| 3-1 | 0.0539 |
| 26 | 0.128 |
| 16-1 | 0.0524 |
| 14-2 | 0.0357 |
| 14-1 | 0.0409 |
| 16-2 | 0.137 |
| 10-4 | 0.0684 |
| 1-82 | 0.056 |
| 23 | 0.0016 |
| 2-6 | 0.0082 |
| 3-2 | 0.0342 |
| 45 | 0.0101 |
| 1-88 | 2.35 |
| 1-87 | 0.0859 |
| 1-86 | 0.134 |
| 1-85 | 0.148 |
| 1-45 | 0.0861 |
| 17-3 | 0.0296 |
| 39-2 | 0.113 |
| 39-3 | 0.188 |
| 33 | 0.0209 |
| 39-4 | 0.0464 |
| 65 | 0.0905 |
| 67 | 0.0325 |
| 46 | 0.0166 |
| 43 | 0.742 |
| 34 | 0.118 |
| 39-6 | 0.115 |
| 50 | 5.38 |
| 66 | 0.111 |
| 39-7 | 1.43 |
| 37 | 0.0876 |
| 39-5 | 0.0089 |
| 62 | >67 |
| 68 | 0.0807 |
| 35 | 0.0038 |
| 51 | 2.98 |
| 52 | 0.158 |
| 39-8 | 1.35 |
| 53 | 0.0447 |
| 39-9 | 0.0473 |
| 36 | 0.162 |
| 39-10 | 0.0063 |
| 39-11 | 0.0069 |
| 38 | 0.0992 |
| 39-12 | 0.0537 |
| 54 | >67 |
| 55 | 0.0087 |
| 39-13 | 0.248 |
| 63 | 0.0436 |
| 39-14 | 44.36 |
| 39-15 | >67 |
| 56 | 0.0215 |
| 40-1 | 0.153 |
| 39-17 | 0.0024 |
| 39-16 | 35.1 |
| 39-18 | >67 |
| 39-19 | 0.0017 |
| 39-20 | >67 |
| 39-21 | 0.110 |
| 39-22 | 2.95 |

TABLE 26-continued

| Example Number | D5D IC50 (μM) |
|---|---|
| 39-23 | 0.0021 |
| 39-24 | 1.52 |
| 39-25 | 0.0037 |
| 39-26 | >67 |
| 39-27 | 0.0011 |
| 39-28 | >67 |
| 39-29 | >67 |
| 57 | 1.15 |
| 39-30 | >67 |
| 39-31 | 0.028 |
| 39-32 | 0.154 |
| 39-33 | 0.0199 |
| 58 | 0.594 |
| 39-34 | 0.0302 |
| 39-35 | 0.0134 |
| 39-36 | >67.0 |
| 39-37 | 0.061 |
| 59 | 0.365 |
| 39-38 | 1.07 |
| 39-39 | >67 |
| 39-40 | 0.067 |
| 49 | 0.104 |
| 40-2 | 0.0518 |
| 42 | 0.168 |
| 39-41 | 0.0651 |
| 60 | 0.0749 |
| 61 | 0.0469 |
| 39-42 | 0.0114 |
| 39-43 | 0.179 |
| 69 | 0.0182 |
| 70 | 0.0105 |
| 39-44 | 0.241 |
| 39-45 | 0.0474 |
| 39-46 | 6.77 |
| 41-4 | 0.0223 |
| 39-47 | 0.0656 |
| 39-48 | 0.518 |
| 39-49 | 0.0046 |
| 39-50 | 0.105 |
| 39-51 | 0.0743 |
| 39-52 | 0.420 |
| 39-53 | 0.369 |
| 39-54 | 0.207 |
| 44 | 1.81 |
| 39-55 | 0.748 |
| 48 | 0.119 |
| 41-1 | 0.0012 |
| 47 | 0.0335 |
| 64 | 0.540 |
| 41-2 | 0.0511 |
| 41-3 | 0.241 |
| 39-56 | 0.0191 |
| 39-57 | 0.0041 |
| 39-58 | 0.0204 |
| 39-59 | 0.005 |
| 39-1 | 0.085 |
| 71 | 0.0317 |
| 72 | 0.0549 |

In vivo Measurement of Delta-5-Desaturase Inhibitory Activity

Diet-induced obese (DIO; Jackson Laboratories strain #3800050) mice were used to screen for pharmacodynamic (PD) activity of test compounds. Generally, 14 to 24 week old DIO mice, were administered test compounds formulated in the vehicle of 2% hydroxypropyl methylcellulose (HPMC) and 1% Tween80. Animals were dosed on body weight by oral gavage with a single dose (30 mg/kg) for PD studies. Necropsy included plasma collection for PUFA analysis. 10 μl of plasma or standards diluted in surrogate matrix (65 g/l bovine serum albumin in Dulbecco's phosphate-buffered saline) were mixed with 10 μl of an internal standard (100 μM alpha-linolenic acid-$d_{14}$ (ALA-$d_{14}$, Cayman Chemical)) in a 96 well plate. 100 μl of 2N NAOH was added to the mixture for subsequent saponification at 65° C. for 1 hour. The mixture was then acidified with 50 μl of formic acid followed by two consecutive hexane extractions. Hexane (500 μl) was added and the mixture thoroughly mixed by vortexing, followed by centrifugation at 4,000 rpm for 15 min. The hexane phase was transferred to a new 1 ml 96 well plate and the remaining aqueous layer was extracted with hexane. The organic extracts were combined and the solvent was removed by placing the plate under nitrogen gas at 55° C. 250 μl of 90% methanol was added to the plate followed by vortexing for 2 minutes. 200 μl of the samples were transferred to a new 96 well polypropylene plate. The samples were analyzed on a LC-MS/MS for the following PUFAs: arachidonic acid (AA), dihomo-gamma-linolenic acid (DGLA), with ALA-$d_{14}$ as the internal standard. Description of the LC-MS/MS method: 5 μl of sample was injected onto a Poroshell 120 EC-C18 3.0×50 mm, 1.9 μm id column. Mobile phases were 20% acetonitrile containing 5 mM ammonium acetate for mobile phase A and 99.8% acetonitrile containing 2 mM ammonium acetate for mobile phase B. The LC gradient was a 11.30 min long method at a flow rate of 0.5 mL/minute consisting of 0% B to 45% B from 0 to 2.25 min, followed by a 45% B to 71% B from 6.0 to 9.5 min, followed by a 71% B to 95% B from 9.5 to 9.6 min; the system was then maintained at 95% B from 9.6 min to 10.10 min and returned to 0% B from 10.20 min to 11.30 min at the end of the method. The PUFA peak areas were quantified by using the SCIEX Analyst software. To determine the degree of D5D inhibition, the product/substrate ratio, AA/DGLA ratio was calculated by dividing the AA content (retention time 8.25 min) by the DGLA content (retention time 9.31 min). The relative decrease of the AA/DGLA ratio of the test compound administered group relative to the vehicle administered group was calculated and used as an index for the degree of D5D inhibition.

This procedure was used to show that the compounds provided herein inhibited in vivo D5D enzyme activity with changes in polyunsaturated fatty acids (PUFAs).

The results presented in Table 27 were obtained using certain compounds described herein in the in vivo protocol described above.

TABLE 27

| Example Number | Average % D5D Inhibition expressed as Plasma Endogenous AA/DGLA Ratio | Additional Information |
|---|---|---|
| 10-1 | 74 | |
| 10-4 | 52 | |
| 1-10 | 75 | |
| 11-2 | 79 | |
| 11-3 | 37 | |
| 1-15 | 70 | |
| 1-20 | 78 | Average of two independent experiments |
| 1-22 | 59 | |
| 1-23 | 57 | Average of two independent experiments |
| 1-27 | 78 | Average of two independent experiments |
| 1-29 | 77 | |
| 13-1 | 52 | |
| 13-3 | 77 | |
| 1-33 | 84 | Averagee of three independent experiments |
| 13-4 | 75 | |
| 1-34 | 66 | Average of two independent experiments |
| 1-39 | 62 | |
| 1-4 | 60 | |

TABLE 27-continued

| Example Number | Average % D5D Inhibition expressed as Plasma Endogenous AA/DGLA Ratio | Additional Information |
|---|---|---|
| 1-41 | 63 | |
| 14-2 | 73 | |
| 1-42 | 64 | |
| 1-44 | 76 | Average of four independent experiments |
| 1-48 | 66 | |
| 1-50 | 73 | |
| 1-58 | 74 | |
| 1-59 | 73 | |
| 1-62 | 56 | |
| 1-68 | 80 | Average of five independent experiments |
| 1-69 | 71 | |
| 1-72 | 54 | |
| 1-73 | 72 | |
| 1-75 | 77 | |
| 1-77 | 75 | Average of two independent experiments |
| 1-8 | 62 | |
| 1-80 | 57 | |
| 1-81 | 44 | |
| 1-9 | 35 | |
| 24 | 70 | |
| 3-2 | 67 | |
| 4-3 | 60 | |
| 6-1 | 51 | |
| 6-2 | 66 | Average of two independent experiments |
| 7-4 | 60 | |
| 8-9 | 79 | |
| 9-2 | 67 | |
| 35 | 75 | |
| 33 | 71 | |
| 45 | 62 | |

Assessment of D5D) Inhibitor in Diet-Induced Obese (DIO) Mice

Thirty-six male C57BL/6J DIO mice (Jackson Laboratories, stock No.: 380050) fed high-fat diet (Research Diets, Inc., D12492) for 14 weeks. All animals were given free access to water and chow. Animals were acclimated to per os dosing for 3 days prior to the start of the experiment. Animals were randomized on body weight, fat mass, lean mass, and blood glucose concentrations in to 4 groups of 8 animals per group. Animals were daily dosed per os with either: vehicle (2% hydroxypropyl methyl cellulose, 1% Tween 80 in water), Example 1-68 at 30 mg/kg, Example 1-34 at 10 mg/kg, and Example 1-27 at 10 mg/kg, all compounds were formulated in 2% hydroxypropyl methylcellulose, 1% Tween 80 in water. Three-day average food consumption was measured on day 0 through day 2, and day 49 through day 51. On day 52, a 4-hour fasted blood collection was performed, blood glucose was immediately measured, and plasma samples were created from the remaining blood and used to measure cholesterol, triglycerides, LDL cholesterol, and insulin. On day 54, body composition (EchoMRI) was determined. On day 56 the animals were sacrificed, and plasma was collected for measurement of DGLA and AA concentrations. Liver, epididymal white adipose tissue and inguinal white adipose tissue weights were recorded. Data was analyzed using GraphPad Prism v. 7.04. All data are presented in Table 28.

All compounds led to weight loss over the course of the experiment (Table 28) compared to vehicle controls. Consistently fat and lean mass was reduced, along with lower inguinal and epididymal white adipose tissue (WAT) weights at necropsy. Blood glucose and plasma insulin levels were both reduced by the FADS1 inhibitors, along with reductions in plasma cholesterol, LDL cholesterol and triglycerides. Evidence of target engagement was established by observing increases in plasma DGLA and decreases in plasma AA.

TABLE 28

| measurement | day | Vehicle | Example 1-68 | Example 1-34 | Example 1-27 |
|---|---|---|---|---|---|
| | | | Dose (mg/kg) | | |
| | | | 30 | 10 | 10 |
| Body weight (g) | 56 | 54.9 ± 1.0 | 40.7 ± 1.5* | 34.7 ± 1.6* | 45.7 ± 1.1* |
| Blood glucose (mg/dL) | 52 | 200.8 ± 10.9 | 146.6 ± 7.1* | 150.5 ± 8.3* | 178.8 ± 7.5 |
| Insulin (ng/mL) | 52 | 17.6 ± 2.5 | 1.1 ± 0.2* | 0.6 ± 0.2* | 3.3 ± 1.2* |
| Cholesterol (mg/dL) | 52 | 228.3 ± 14.0 | 166.2 ± 7.8* | 177.1 ± 12.6* | 191.3 ± 14.5 |
| LDL cholesterol (mg/dL) | 52 | 150.8 ± 12.6 | 86.5 ± 12.5* | 88.6 ± 9.2* | 104.6 ± 9.1* |
| Triglycerides (mg/dL) | 52 | 32.0 ± 2.0 | 14.5 ± 1.0* | 15.6 ± 2.3* | 24.1 ± 1.2* |
| Fat mass (g) | 54 | 22.7 ± 0.4 | 13.3 ± 1.0* | 7.4 ± 0.9* | 16.9 ± 0.5* |
| Lean mass (g) | 54 | 31.2 ± 0.7 | 26.7 ± 0.5* | 26.6 ± 0.7* | 28.1 ± 0.5* |
| Food consumption(g/day) | 0-2 | 2.9 ± 0.2 | 2.7 ± 0.1 | 2.2 ± 0.1* | 2.5 ± 0.1 |
| Food consumption(g/day) | 50-52 | 3.0 ± 0.1 | 2.6 ± 0.1* | 3.0 ± 0.1 | 3.1 ± 0.1 |
| Liver weights (g) | 56 | 3.2 ± 0.2 | 2.9 ± 0.2 | 2.9 ± 0.3 | 2.8 ± 0.2 |
| inguinal WAT (g) | 56 | 2.3 ± 0.1 | 1.6 ± 0.2* | 0.8 ± 0.1* | 1.9 ± 0.1 |
| epididymal WAT (g) | 56 | 1.5 ± 0.1 | 1.6 ± 0.1 | 0.9 ± 0.1* | 1.8 ± 0.1 |
| DGLA (μg/mL) | 56 | 58.5 ± 4.3 | 258.4 ± 8.5* | 161.4 ± 8.5* | 310.3 ± 13.7* |
| AA (μg/mL) | 56 | 367.0 ± 16.2 | 38.0 ± 1.6* | 29.4 ± 0.9* | 60.8 ± 1.9* |

*P < 0.05 vs. vehicle, one-way ANOVA with Dunnett's posthoc test

REFERENCES

Baugh S D et al., Design, synthesis, and in vivo activity of novel inhibitors of delta-5 desaturase for the treatment of metabolic syndrome, *Bioorg. Med. Chem. Lett.* 25(18): 3836-3839 (2015).

Chopra M et al., A global response to a global problem: the epidemic of overnutrition, *Bull. World Health Organ.* 80:952-958 (2002).

Di Marzo V and Matias I, Endocannabinoid control of food intake and energy balance, *Nat. Neurosci.* 8(5):585-589 (2005).

Dupuis J, New genetic loci implicated in fasting glucose homeostasis and their impact on type 2 diabetes risk, *Nat. Genet.* 42(2):105-116 (2010).

Fumagalli M et al., Greenlandic Inuit show genetic signatures of diet and climate adaptation, *Science* 349(6254): 1343-1347 (2015).

Haidar Y M and Cosman B C, Obesity epidemiology, *Clin. Colon Rectal Surg.* 24:205-210 (2011).

Harizi H et al., Arachidonic-acid-derived eicosanoids: roles in biology and immunopathology, *Trends Mol. Med.* 14(10):461-469 (2008).

Kroeger J and Schulze M B, Recent insights into the relation of delta5 desaturase and delta6 desaturase activity to the development of type 2 diabetes, *Curr. Opin. Lipidol.* 23(1):4-10 (2012).

Mendis S et al., World Health Organization (WHO) and International Society of Hypertension (ISH) risk prediction charts: assessment of cardiovascular risk for prevention and control of cardiovascular disease in low and middle-income countries, *J. Hypertens.* 25:1578-1582 (2007).

Merino D M et al., Genetic variation in lipid desaturases and its impact on the development of human disease, *Lipids Health Dis.* 9:63 (2010).

Merino D M et al., Polymorphisms in FADS1 and FADS2 alter desaturase activity in young Caucasian and Asian adults, *Mol. Genet. Metab.* 103(2):171-178 (2011).

Miyahisa I et al., T-3364366 Targets the Desaturase Domain of Delta-5 Desaturase with Nanomolar Potency and a Multihour Residence Time, *ACS Med. Chem. Lett.* 7(9): 868-872 (2016).

Monteiro C A et al., Socioeconomic status and obesity in adult populations of developing countries: a review. *Bull. World Health Organ.* 82:940-946 (2004).

Obukowicz M G et al., Novel, selective delta6 or delta5 fatty acid desaturase inhibitors as antiinflammatory agents in mice, *J. Pharmacol. Exp. Ther.* 287(1):157-166 (1998).

Powell D R et al., Fatty acid desaturase 1 knockout mice are lean with improved glycemic control and decreased development of atheromatous plaque, *Diabetes Metab. Syndr.*

Obes. 9:185-199 (2016).

Tosi F et al., Delta-5 and delta-6 desaturases: crucial enzymes in polyunsaturated fatty acid-related pathways with pleiotropic influences in health and disease, *Adv. Exp. Med. Biol.* 824:61-81 (2014).

Willer C J et al., Discovery and refinement of loci associated with lipid levels, *Nat. Genet.* 45(11):1274-1283 (2013).

Yashiro H et al., A Novel Selective Inhibitor of Delta-5 Desaturase Lowers Insulin Resistance and Reduces Body Weight in Diet-Induced Obese C57BL/6J Mice, PLoS One 11(11):e0166198 (2016).

The foregoing description is merely illustrative and is not intended to limit the disclosure to the described compounds, compositions and methods. Variations and changes, which are obvious to one skilled in the art, are intended to be within the scope and nature of the invention, as defined in the appended claims.

All references, for example, a scientific publication or patent application publication, cited herein are incorporated herein by reference in their entirety and for all purposes to the same extent as if each reference was specifically and individually indicated to be incorporated by reference in its entirety for all purposes.

What is claimed is:

1. A compound of Formula I

I

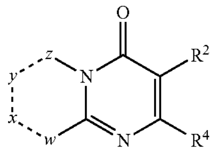

or a tautomer thereof, or a pharmaceutically acceptable salt of said compound or said tautomer, wherein

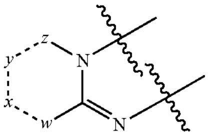

is

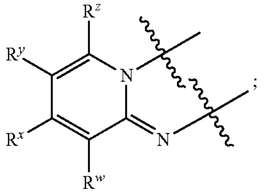

;

wherein $R^w$ is H, F, Cl, —CN, —COMe, —SMe, —$CONH_2$, —$NH_2$, —NHMe, —$N(CH_3)_2$, —$NH(COCH_3)$, —$N(CH_3)C(=O)F$, methyl, ethyl, —$CD_3$, cyclopropyl, —$CH=CH_2$, —$OCD_3$, or 1,3-oxazol-2-yl; wherein the methyl group is optionally substituted with 1 to 3 substituents independently selected from F, Cl, —OH, —CN, methoxy, —$NH_2$, and —$N(CH_3)_2$;

$R^y$ is H, F, Cl, —OH, —CN, —$CONH_2$, —$NH_2$, $C_{1-4}$alkylamino, di$C_{1-4}$alkylamino, $C_{1-4}$alkoxy, or $C_{1-4}$deuteroalkoxyl: wherein the $C_{1-4}$alkoxy is optionally substituted with 1 to 4 substituents independently selected from halogen, —OH, $C_{1-4}$alkoxy, —$NH_2$, and di$C_{1-4}$ alkylamino;

$R^x$ and $R^z$ are independently H, halogen, —OH, —CN, —$CONH_2$, —NI-2, $C_{1-4}$alkylamino, di$C_{1-4}$alkylamino, $C_{1-4}$alkoxy, or $C_{1-4}$deuteroalkoxyl; wherein the $C_{1-4}$alkoxy is optionally substituted with 1 to 4 substituents independently selected from halogen, —OH, $C_{1-4}$alkoxy, —$NH_2$, and di$C_{1-4}$alkylamino;

$R^2$ is

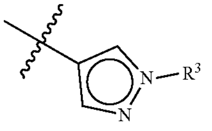

or

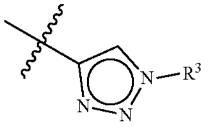

$R^3$ is $C_{2-6}$alkyl or $C_{1-3}$alkoxy; wherein the $C_{2-6}$alkyl and $C_{1-3}$alkoxy groups are optionally substituted with 3-5 halogen atoms;

$R^4$ is $C_{1-3}$alkyl, $C_{1-4}$haloalkyl, $C_{1-4}$alkoxy, $C_{1-4}$haloalkoxy, $C_{3-5}$cycloalkyl, or $C_{3-5}$cyclohaloalkyl;

n is 0, 1, or 2.

2. A compound, or a tautomer thereof, or a pharmaceutically acceptable salt of said compound or said tautomer, wherein the compound is (2R)-2-(4-(8-methoxy-4-oxo-2-(trifluoromethyl)-4H-pyrido[1,2-a]pyrimidin-3-yl)phenoxy)propanenitrile;

(2S)-2-(4-(8-methoxy-4-oxo-2-(trifluoromethyl)-4H-pyrido[1,2-a]pyrimidin-3-yl)phenoxy)propanenitrile;

(4-(8-methoxy-4-oxo-2-(trifluoromethyl)-4H-pyrido[1,2-a]pyrimidin-3-yl)-1H-pyrazol-1-yl)acetonitrile;

(4-(8-methoxy-4-oxo-2-(trifluoromethyl)-4H-pyrido[1,2-a]pyrimidin-3-yl)phenoxy)acetonitrile;

(4-(8-methoxy-4-oxo-2-(trifluoromethyl)-4H-pyrido[1,2-a]pyrimidin-3-yl)phenyl)acetonitrile;

(4-oxo-3-(1-(2,2,3,3,3-pentafluoropropyl)-1H-pyrazol-4-yl)-2-(trifluoromethyl)-4H-pyrido[1,2-a]pyrimidin-8-yl)acetonitrile;

2-(4-(8-methoxy-4-oxo-2-trifluoromethyl)-4H-pyrido[1,2-a]pyrimidin-3-yl)phenoxy)-2-methylpropanenitrile;

2-(4-(8-methoxy-4-oxo-2-(trifluoromethyl)-4H-pyrido[1,2-a]pyrimidin-3-yl)phenoxy)propanenitrile;

2-(difluoromethyl)-3-(3-fluoro-4-(2,2,2-trifluoroethoxy)phenyl)-8-methoxy-4H-pyrido[1,2-a]pyrimidin-4-one;

2-(difluoromethyl)-4-oxo-3-(1-(2,2,3,3,3-pentafluoropropyl)-1H-pyrazol-4-yl)-4H-pyrido[1,2-a]pyrimidine-8-carbonitrile;

2-(difluoromethyl)-8-methoxy-3-(1-(3,3,3-trifluoropropyl)-1H-pyrazol-4-yl)-4H-pyrido[1,2-a]pyrimidin-4-one;

2-(difluoromethyl)-8-methoxy-3-(1-(4,4,4-trifluorobutyl)-1H-pyrazol-4-yl)-4H-pyrido[1,2-a]pyrimidin-4-one;

2-(difluoromethyl)-8-methoxy-3-(4-(2,2,2-trifluoroethoxy)phenyl)-4H-pyrido[1,2-a]pyrimidin-4-one;

2-(difluoromethyl)-8-methoxy-3-(6-(2,2,2-trifluoroethoxy)-3-pyridinyl)-4H-pyrido[1,2-a]pyrimidin-4-one;

2-(fluoromethyl)-4-oxo-3-(1-(2,2,3,3,3-pentafluoropropyl)-1H-pyrazol-4-yl)-4H-pyrido[1,2-a]pyrimidine-8-carbonitrile;

2-(fluoromethyl)-8-methoxy-3-(4-(2,2,2-trifluoroethoxy)phenyl)-4H-pyrido[1,2-a]pyrimidin-4-one;

2,8-dimethoxy-3-(4-(2,2,2-trifluoroethoxy)phenyl)-4H-pyrido[1,2-a]pyrimidin-4-one;

2-cyclopropyl-8-methoxy-3-(4-(2,2,2-trifluoroethoxy)phenyl)-4H-pyrido[1,2-a]pyrimidin-4-one;

2-ethoxy-8-methoxy-3-(4-(2,2,2-trifluoroethoxy)phenyl)-4H-pyrido[1,2-a]pyrimidin-4-one;

2-ethoxy-8-methoxy-3-[1-(2,2,3,3,3-pentafluoropropyl)-1H-pyrazol-4-yl]-4H-pyrido[1,2-a]pyrimidin-4-one;

2-ethyl-8-methoxy-3-(1-(2,2,3,3,3-pentafluoropropyl)-1H-pyrazol-4-yl)-4H-pyrido[1,2-a]pyrimidin-4-one;

2-ethyl-8-methoxy-3-(4-(2,2,2-trifluoroethoxy)phenyl)-4H-pyrido[1,2-a]pyrimidin-4-one;

2-ethyl-8-methoxy-3-(6-(2,2,2-trifluoroethoxy)-3-pyridinyl)-4H-pyrido[1,2-a]pyrimidin-4-one;

3-(1-(2,2,3,3,3-pentafluoropropyl)-1H-pyrazol-4-yl)-2-(trifluoromethyl)-4H-pyrido[1,2-a]pyrimidine-4,8(1H)-dione;

3-(1-(2,2-difluoropropyl)-1H-pyrazol-4-yl)-8-methoxy-2-(trifluoromethyl)-4H-pyrido[1,2-a]pyrimidin-4-one;

3-(1-(3-fluorophenyl)-1H-pyrazol-4-yl)-8-methoxy-2-(trifluoromethyl)-4H-pyrido[1,2-a]pyrimidin-4-one;

3-(1-(4-fluorophenyl)-1H-pyrazol-4-yl)-2-(trifluoromethyl)-4H-pyrido[1,2-a]pyrimidin-4-one;

3-(1-(4-fluorophenyl)-1H-pyrazol-4-yl)-8-methoxy-2-(trifluoromethyl)-4H-pyrido[1,2-a]pyrimidin-4-one;

3-(1-{[(1R)-2,2-difluorocyclopropyl]methyl}-1H-pyrazol-4-yl)-8-methoxy-2-(trifluoromethyl)-4H-pyrido[1,2-a]pyrimidin-4-one;

3-(1-{[(1S)-2,2-difluorocyclopropyl]methyl}-1H-pyrazol-4-yl)-8-methoxy-2-(trifluoromethyl)-4H-pyrido[1,2-a]pyrimidin-4-one;

3-(1-benzofuran-2-yl)-8-methoxy-2-(trifluoromethyl)-4H-pyrido[1,2-a]pyrimidin-4-one;

3-(1-cyclopropyl-1H-pyrazol-4-yl)-2-(trifluoromethyl)-4H-pyrido[1,2-a]pyrimidin-4-one;
3-(1-cyclopropyl-1H-pyrazol-4-yl)-8-methoxy-2-(trifluoromethyl)-4H-pyrido[1,2-a]pyrimidin-4-one;
3-(1-phenyl-1H-pyrazol-4-yl)-2-(trifluoromethyl)-4H-pyrido[1,2-a]pyrimidin-4-one;
3-(1-propyl-1H-pyrazol-4-yl)-2-(trifluoromethyl)-4H-pyrido[1,2-a]pyrimidin-4-one;
3-(2-chloro-4-(2,2,2-trifluoroethoxy)phenyl)-8-methoxy-2-(trifluoromethyl)-4H-pyrido[1,2-a]pyrimidin-4-one;
3-(2-fluoro-4-(2,2,2-trifluoroethoxy)phenyl)-2-(trifluoromethyl)-4H-pyrido[1,2-a]pyrimidin-4-one;
3-(2-fluoro-4-(2,2,2-trifluoroethoxy)phenyl)-8-methoxy-2-(trifluoromethyl)-4H-pyrido[1,2-a]pyrimidin-4-one;
3-(2-fluoro-4-(trifluoromethoxy)phenyl)-8-methoxy-2-(trifluoromethyl)-4H-pyrido[1,2-a]pyrimidin-4-one;
3-(2-fluoro-6-(2,2,2-trifluoroethoxy)-3-pyridinyl)-8-methoxy-2-(trifluoromethyl)-4H-pyrido[1,2-a]pyrimidin-4-one;
3-(3-chloro-4-(2,2,2-trifluoroethoxy)phenyl)-2-(trifluoromethyl)-4H-pyrido[1,2-a]pyrimidin-4-one;
3-(3-fluoro-4-(2,2,2-trifluoroethoxy)phenyl)-8-methoxy-2-(trifluoromethyl)-4H-pyrido[1,2-a]pyrimidin-4-one;
3-(4-(((1R)-2,2-difluorocyclopropyl)methoxy)phenyl)-8-methoxy-2-(trifluoromethyl)-4H-pyrido[1,2-a]pyrimidin-4-one;
3-(4-(((1S)-2,2-difluorocyclopropyl)methoxy)phenyl)-8-methoxy-2-(trifluoromethyl)-4H-pyrido[1,2-a]pyrimidin-4-one;
3-(4-((2,2-difluorocyclopropyl)methoxy)phenyl)-8-methoxy-2-(trifluoromethyl)-4H-pyrido[1,2-a]pyrimidin-4-one;
3-(4-(2,2,2-trifluoroethoxy)phenyl)-2-(trifluoromethyl)-4H-pyrido[1,2-a]pyrimidin-4-one;
3-(4-(2,2,2-trifluoroethoxy)phenyl)-2-(trifluoromethyl)-4H-pyrido[1,2-a]pyrimidine-4,8(1H)-dione;
3-(4-(2,2,2-trifluoroethoxy)phenyl)-2,8-bis(trifluoromethyl)-4H-pyrido[1,2-a]pyrimidin-4-one;
3-(4-(2,2-difluoroethoxy)-2-fluorophenyl)-8-methoxy-2-(trifluoromethyl)-4H-pyrido[1,2-a]pyrimidin-4-one;
3-(4-(2,2-difluoroethoxy)phenyl)-8-(methyloxy-d3)-2-(trifluoromethyl)-4H-pyrido[1,2-a]pyrimidin-4-one;
3-(4-(2,2-difluoroethoxy)phenyl)-8-methoxy-2-(trifluoromethyl)-4H-pyrido[1,2-a]pyrimidin-4-one;
3-(4-(2,2-difluoropropoxy)phenyl)-8-methoxy-2-(trifluoromethyl)-4H-pyrido[1,2-a]pyrimidin-4-one;
3-(4-(2-fluoroethoxy)phenyl)-8-(methyloxy-d3)-2-(trifluoromethyl)-4H-pyrido[1,2-a]pyrimidin-4-one;
3-(4-(2-fluoroethoxy)phenyl)-8-methoxy-2-(trifluoromethyl)-4H-pyrido[1,2-a]pyrimidin-4-one;
3-(4-(8-methoxy-4-oxo-2-(trifluoromethyl)-4H-pyrido[1,2-a]pyrimidin-3-yl)-1H-pyrazol-1-yl)propanenitrile;
3-(4-(8-methoxy-4-oxo-2-(trifluoromethyl)-4H-pyrido[1,2-a]pyrimidin-3-yl)phenyl)propanenitrile;
3-(4-(cyclopropylmethoxy)-2-fluorophenyl)-8-methoxy-2-(trifluoromethyl)-4H-pyrido[1,2-a]pyrimidin-4-one;
3-(4-(cyclopropylmethoxy)phenyl)-8-(methyloxy-d3)-2-(trifluoromethyl)-4H-pyrido[1,2-a]pyrimidin-4-one;
3-(4-(cyclopropylmethoxy)phenyl)-8-methoxy-2-(trifluoromethyl)-4H-pyrido[1,2-a]pyrimidin-4-one;
3-(4-(difluoromethoxy)phenyl)-8-methoxy-2-(trifluoromethyl)-4H-pyrido[1,2-a]pyrimidin-4-one;
3-(5-(2,2,2-trifluoroethoxy)-2-pyridinyl)-2-(trifluoromethyl)-4H-pyrido[1,2-a]pyrimidin-4-one;
3-(5-fluoro-6-(2,2,2-trifluoroethoxy)-3-pyridinyl)-8-methoxy-2-(trifluoromethyl)-4H-pyrido[1,2-a]pyrimidin-4-one;
3-(6-(2,2,2-trifluoroethoxy)-3-pyridinyl)-2-(trifluoromethyl)-4H-pyrido[1,2-a]pyrimidin-4-one;
3-[1-(2,2,3,3,3-pentafluoropropyl)-1H-pyrazol-4-yl]-2-(trifluoromethyl)-4H-pyrido[1,2-a]pyrimidin-4-one;
3-[1-(cyclopropylmethyl)-1H-pyrazol-4-yl]-8-methoxy-2-(trifluoromethyl)-4H-pyrido[1,2-a]pyrimidin-4-one;
3-[5-iodo-1-(2,2,3,3,3-pentafluoropropyl)-1H-1,2,3-triazol-4-yl]-8-methoxy-2-(trifluoromethyl)-4H-pyrido[1,2-a]pyrimidin-4-one;
3-{1-[(2,2-difluorocyclopropyl)methyl]-1H-pyrazol-4-yl}-7-fluoro-8-methoxy-2-(trifluoromethyl)-4H-pyrido[1,2-a]pyrimidin-4-one;
3-{1-[(2,2-difluorocyclopropyl)methyl]-1H-pyrazol-4-yl}-8-methoxy-2-(trifluoromethyl)-4H-pyrido[1,2-a]pyrimidin-4-one;
3-{1-[(3,3-difluorocyclobutyl)methyl]-1H-pyrazol-4-yl}-8-methoxy-2-(trifluoromethyl)-4H-pyrido[1,2-a]pyrimidin-4-one;
4-oxo-3-(1-(2,2,3,3,3-pentafluoropropyl)-1H-pyrazol-4-yl)-2-(trifluoromethyl)-4H-pyrido[1,2-a]pyrimidine-8-carbonitrile;
4-oxo-3-(1-(2,2,3,3,3-pentafluoropropyl)-1H-pyrazol-4-yl)-2-(trifluoromethyl)-4H-pyrido[1,2-a]pyrimidine-8-carboxylic acid;
4-oxo-3-(4-(2,2,2-trifluoroethoxy)phenyl)-2-(trifluoromethyl)-4H-pyrido[1,2-a]pyrimidine-8-carbonitrile;
4-oxo-3-(4-(2,2,2-trifluoroethoxy)phenyl)-2-(trifluoromethyl)-4H-pyrido[1,2-a]pyrimidine-8-carboxamide;
4-oxo-3-(4-(2,2,2-trifluoroethoxy)phenyl)-2-(trifluoromethyl)-4H-pyrido[1,2-a]pyrimidine-8-carboxylic acid;
4-oxo-3-[1-(2,2,3,3,3-pentafluoropropyl)-1H-pyrazol-4-yl]-2-(trifluoromethyl)-4H-pyrido[1,2-a]pyrimidine-7-carbonitrile;
7-(methoxymethyl)-3-[1-(2,2,3,3,3-pentafluoropropyl)-1H-pyrazol-4-yl]-2-(trifluoromethyl)-4H-pyrido[1,2-a]pyrimidin-4-one;
7-chloro-2-(trifluoromethyl)-3-[1-(3,3,3-trifluoropropyl)-1H-pyrazol-4-yl]-4H-pyrido[1,2-a]pyrimidin-4-one;
7-chloro-3-[1-(2,2,3,3,3-pentafluoropropyl)-1H-pyrazol-4-yl]-2-(trifluoromethyl)-4H-pyrido[1,2-a]pyrimidin-4-one;
7-chloro-8-methoxy-2-(trifluoromethyl)-3-[1-(3,3,3-trifluoropropyl)-1H-pyrazol-4-yl]-4H-pyrido[1,2-a]pyrimidin-4-one;
7-chloro-8-methoxy-3-[1-(2,2,3,3,3-pentafluoropropyl)-1H-pyrazol-4-yl]-2-(trifluoromethyl)-4H-pyrido[1,2-a]pyrimidin-4-one;
7-chloro-8-methyl-2-(trifluoromethyl)-3-[1-(3,3,3-trifluoropropyl)-1H-pyrazol-4-yl]-4H-pyrido[1,2-a]pyrimidin-4-one;
7-chloro-8-methyl-3-[1-(2,2,3,3,3-pentafluoropropyl)-1H-pyrazol-4-yl]-2-(trifluoromethyl)-4H-pyrido[1,2-a]pyrimidin-4-one;
7-chloro-8-methyl-3-[4-(2,2,2-trifluoroethoxy)phenyl]-2-(trifluoromethyl)-4H-pyrido[1,2-a]pyrimidin-4-one;
7-cyclopropyl-2-(trifluoromethyl)-3-[1-(3,3,3-trifluoropropyl)-1H-pyrazol-4-yl]-4H-pyrido[1,2-a]pyrimidin-4-one;
7-cyclopropyl-3-[1-(2,2,3,3,3-pentafluoropropyl)-1H-pyrazol-4-yl]-2-(trifluoromethyl)-4H-pyrido[1,2-a]pyrimidin-4-one;
7-fluoro-2-(trifluoromethyl)-3-[1-(3,3,3-trifluoropropyl)-1H-pyrazol-4-yl]-4H-pyrido[1,2-a]pyrimidin-4-one;
7-fluoro-3-[1-(2,2,3,3,3-pentafluoropropyl)-1H-pyrazol-4-yl]-2-(trifluoromethyl)-4H-pyrido[1,2-a]pyrimidin-4-one;

7-fluoro-8-hydroxy-3-[1-(2,2,3,3,3-pentafluoropropyl)-1H-pyrazol-4-yl]-2-(trifluoromethyl)-4H-pyrido[1,2-a]pyrimidin-4-one;

7-fluoro-8-methoxy-2-(trifluoromethyl)-3-[1-(3,3,3-trifluoropropyl)-1H-pyrazol-4-yl]-4H-pyrido[1,2-a]pyrimidin-4-one;

7-fluoro-8-methoxy-3-[1-(2,2,3,3,3-pentafluoropropyl)-1H-pyrazol-4-yl]-2-(trifluoromethyl)-4H-pyrido[1,2-a]pyrimidin-4-one;

7-fluoro-8-methoxy-3-[4-(2,2,2-trifluoroethoxy)phenyl]-2-(trifluoromethyl)-4H-pyrido[1,2-a]pyrimidin-4-one;

7-fluoro-8-methyl-3-[1-(2,2,3,3,3-pentafluoropropyl)-1H-pyrazol-4-yl]-2-(trifluoromethyl)-4H-pyrido[1,2-a]pyrimidin-4-one;

7-methoxy-3-[1-(2,2,3,3,3-pentafluoropropyl)-1H-pyrazol-4-yl]-2-(trifluoromethyl)-4H-pyrido[1,2-a]pyrimidin-4-one;

7-methyl-3-[1-(2,2,3,3,3-pentafluoropropyl)-1H-pyrazol-4-yl]-2-(trifluoromethyl)-4H-pyrido[1,2-a]pyrimidin-4-one;

8-((1R)-1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one;

8-((1R)-1-hydroxyethyl)-3-(4-(2,2,2-trifluoroethoxy)phenyl)-2-(trifluoromethyl)-4H-pyrido[1,2-a]pyrimidin-4-one;

8-((1S)-1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one;

8-((1S)-1-hydroxyethyl)-3-(4-(2,2,2-trifluoroethoxy)phenyl)-2-(trifluoromethyl)-4H-pyrido[1,2-a]pyrimidin-4-one;

8-((dimethylamino)methyl)-3-(1-(2,2,3,3,3-pentafluoropropyl)-1H-pyrazol-4-yl)-2-(trifluoromethyl)-4H-pyrido[1,2-a]pyrimidin-4-one;

8-(methyloxy-d3)-2-(trifluoromethyl)-3-(1-(3,3,3-trifluoropropyl)-1H-pyrazol-4-yl)-4H-pyrido[1,2-a]pyrimidin-4-one;

8-((methylsulfanyl)methoxy)-3-(4-(2,2,2-trifluoroethoxy)phenyl)-2-(trifluoromethyl)-4H-pyrido[1,2-a]pyrimidin-4-one;

8-((R)-ethylsulfinyl)-3-(4-(2,2,2-trifluoroethoxy)phenyl)-2-(trifluoromethyl)-4H-pyrido[1,2-a]pyrimidin-4-one;

8-((R)-methylsulfinyl)-3-(1-(2,2,3,3,3-pentafluoropropyl)-1H-pyrazol-4-yl)-2-(trifluoromethyl)-4H-pyrido[1,2-a]pyrimidin-4-one;

8-((R)-methylsulfinyl)-3-(4-(2,2,2-trifluoroethoxy)phenyl)-2-(trifluoromethyl)-4H-pyrido[1,2-a]pyrimidin-4-one;

8-((S)-ethylsulfinyl)-3-(4-(2,2,2-trifluoroethoxy)phenyl)-2-(trifluoromethyl)-4H-pyrido[1,2-a]pyrimidin-4-one;

8-((S)-methylsulfinyl)-3-(1-(2,2,3,3,3-pentafluoropropyl)-1H-pyrazol-4-yl)-2-(trifluoromethyl)-4H-pyrido[1,2-a]pyrimidin-4-one;

8-((S)-methylsulfinyl)-3-(4-(2,2,2-trifluoroethoxy)phenyl)-2-(trifluoromethyl)-4H-pyrido[1,2-a]pyrimidin-4-one;

8-(1,3-oxazol-2-yl)-3-(4-(2,2,2-trifluoroethoxy)phenyl)-2-(trifluoromethyl)-4H-pyrido[1,2-a]pyrimidin-4-one;

8-(1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one;

8-(1-hydroxyethyl)-3-(4-(2,2,2-trifluoroethoxy)phenyl)-2-(trifluoromethyl)-4H-pyrido[1,2-a]pyrimidin-4-one;

8-(2-hydroxypropan-2-yl)-3-[1-(2,2,3,3,3-pentafluoropropyl)-1H-pyrazol-4-yl]-2-(trifluoromethyl)-4H-pyrido[1,2-a]pyrimidin-4-one;

8-(2-methyl-2-oxetanyl)-3-(4-(2,2,2-trifluoroethoxy)phenyl)-2-(trifluoromethyl)-4H-pyrido[1,2-a]pyrimidin-4-one;

8-(2-propanyl)-3-(4-(2,2,2-trifluoroethoxy)phenyl)-2-(trifluoromethyl)-4H-pyrido[1,2-a]pyrimidin-4-one;

8-(3-azetidinyl)-3-(4-(2,2,2-trifluoroethoxy)phenyl)-2-(trifluoromethyl)-4H-pyrido[1,2-a]pyrimidin-4-one;

8-(aminomethyl)-3-(1-(2,2,3,3,3-pentafluoropropyl)-1H-pyrazol-4-yl)-2-(trifluoromethyl)-4H-pyrido[1,2-a]pyrimidin-4-one;

8-(1-azetidinyl)-3-(1-(2,2,3,3,3-pentafluoropropyl)-1H-pyrazol-4-yl)-2-(trifluoromethyl)-4H-pyrido[1,2-a]pyrimidin-4-one;

8-(chloromethoxy)-3-[1-(2,2,3,3,3-pentafluoropropyl)-1H-pyrazol-4-yl]-2-(trifluoromethyl)-4H-pyrido[1,2-a]pyrimidin-4-one;

8-(difluoromethoxy)-3-(4-(2,2,2-trifluoroethoxy)phenyl)-2-(trifluoromethyl)-4H-pyrido[1,2-a]pyrimidin-4-one;

8-(difluoromethyl)-3-(4-(2,2,2-trifluoroethoxy)phenyl)-2-(trifluoromethyl)-4H-pyrido[1,2-a]pyrimidin-4-one;

8-(dimethylamino)-3-(1-(2,2,3,3,3-pentafluoropropyl)-1H-pyrazol-4-yl)-2-(trifluoromethyl)-4H-pyrido[1,2-a]pyrimidin-4-one;

8-(dimethylamino)-3-(4-(2,2,2-trifluoroethoxy)phenyl)-2-(trifluoromethyl)-4H-pyrido[1,2-a]pyrimidin-4-one;

8-(ethylsulfinyl)-3-(4-(2,2,2-trifluoroethoxy)phenyl)-2-(trifluoromethyl)-4H-pyrido[1,2-a]pyrimidin-4-one;

8-(fluoromethoxy)-2-(trifluoromethyl)-3-(1-(3,3,3-trifluoropropyl)-1H-pyrazol-4-yl)-4H-pyrido[1,2-a]pyrimidin-4-one;

8-(fluoromethoxy)-3-(4-(2,2,2-trifluoroethoxy)phenyl)-2-(trifluoromethyl)-4H-pyrido[1,2-a]pyrimidin-4-one;

8-(fluoromethoxy)-3-[1-(2,2,3,3,3-pentafluoropropyl)-1H-pyrazol-4-yl]-2-(trifluoromethyl)-4H-pyrido[1,2-a]pyrimidin-4-one;

8-(fluoromethyl)-3-(1-(2,2,3,3,3-pentafluoropropyl)-1H-pyrazol-4-yl)-2-(trifluoromethyl)-4H-pyrido[1,2-a]pyrimidin-4-one;

8-(fluoromethyl)-3-(4-(2,2,2-trifluoroethoxy)phenyl)-2-(trifluoromethyl)-4H-pyrido[1,2-a]pyrimidin-4-one;

8-(hydroxymethyl)-3-(1-(2,2,3,3,3-pentafluoropropyl)-1H-pyrazol-4-yl)-2-(trifluoromethyl)-4H-pyrido[1,2-a]pyrimidin-4-one;

8-(hydroxymethyl)-3-(4-(2,2,2-trifluoroethoxy)phenyl)-2-(trifluoromethyl)-4H-pyrido[1,2-a]pyrimidin-4-one;

8-(methoxymethyl)-3-[1-(2,2,3,3,3-pentafluoropropyl)-1H-pyrazol-4-yl]-2-(trifluoromethyl)-4H-pyrido[1,2-a]pyrimidin-4-one;

8-(methylamino)-3-(1-(2,2,3,3,3-pentafluoropropyl)-1H-pyrazol-4-yl)-2-(trifluoromethyl)-4H-pyrido[1,2-a]pyrimidin-4-one;

8-(methylamino)-3-(4-(2,2,2-trifluoroethoxy)phenyl)-2-(trifluoromethyl)-4H-pyrido[1,2-a]pyrimidin-4-one;

8-(methyl-d3)-3-(4-(2,2,2-trifluoroethoxy)phenyl)-2-(trifluoromethyl)-4H-pyrido[1,2-a]pyrimidin-4-one;

8-(methyloxy-d3)-3-(1-(2,2,3,3,3-pentafluoropropyl)-1H-pyrazol-4-yl)-2-(trifluoromethyl)-4H-pyrido[1,2-a]pyrimidin-4-one;

8-(methyloxy-d3)-3-(1-(4,4,4-trifluorobutyl)-1H-pyrazol-4-yl)-2-(trifluoromethyl)-4H-pyrido[1,2-a]pyrimidin-4-one;

8-(methyloxy-d3)-3-(4-(2,2,2-trifluoroethoxy)phenyl)-2-(trifluoromethyl)-4H-pyrido[1,2-a]pyrimidin-4-one;

8-(methyloxy-d3)-3-(6-(2,2,2-trifluoroethoxy)-3-pyridinyl)-2-(trifluoromethyl)-4H-pyrido[1,2-a]pyrimidin-4-one;

8-(methylsulfanyl)-3-(1-(2,2,3,3,3-pentafluoropropyl)-1H-pyrazol-4-yl)-2-(trifluoromethyl)-4H-pyrido[1,2-a]pyrimidin-4-one;
8-(methylsulfanyl)-3-(4-(2,2,2-trifluoroethoxy)phenyl)-2-(trifluoromethyl)-4H-pyrido[1,2-a]pyrimidin-4-one;
8-(methylsulfinyl)-3-(1-(2,2,3,3,3-pentafluoropropyl)-1H-pyrazol-4-yl)-2-(trifluoromethyl)-4H-pyrido[1,2-a]pyrimidin-4-one;
8-(methylsulfinyl)-3-(4-(2,2,2-trifluoroethoxy)phenyl)-2-(trifluoromethyl)-4H-pyrido[1,2-a]pyrimidin-4-one;
8-(methylsulfonyl)-3-(4-(2,2,2-trifluoroethoxy)phenyl)-2-(trifluoromethyl)-4H-pyrido[1,2-a]pyrimidin-4-one;
8-acetyl-3-(4-(2,2,2-trifluoroethoxy)phenyl)-2-(trifluoromethyl)-4H-pyrido[1,2-a]pyrimidin-4-one;
8-amino-3-(1-(2,2,3,3,3-pentafluoropropyl)-1H-pyrazol-4-yl)-2-(trifluoromethyl)-4H-pyrido[1,2-a]pyrimidin-4-one;
8-amino-3-(4-(2,2,2-trifluoroethoxy)phenyl)-2-(trifluoromethyl)-4H-pyrido[1,2-a]pyrimidin-4-one;
8-chloro-3-(1-(2,2,3,3,3-pentafluoropropyl)-1H-pyrazol-4-yl)-2-(trifluoromethyl)-4H-pyrido[1,2-a]pyrimidin-4-one;
8-chloro-3-(4-(2,2,2-trifluoroethoxy)phenyl)-2-(trifluoromethyl)-4H-pyrido[1,2-a]pyrimidin-4-one;
8-cyclopropyl-3-(4-(2,2,2-trifluoroethoxy)phenyl)-2-(trifluoromethyl)-4H-pyrido[1,2-a]pyrimidin-4-one;
8-cyclopropyl-3-(1-(2,2,3,3,3-pentafluoropropyl)-1H-pyrazol-4-yl)-2-(trifluoromethyl)-4H-pyrido[1,2-a]pyrimidin-4-one;
8-ethenyl-3-(4-(2,2,2-trifluoroethoxy)phenyl)-2-(trifluoromethyl)-4H-pyrido[1,2-a]pyrimidin-4-one;
8-ethoxy-3-(4-(2,2,2-trifluoroethoxy)phenyl)-2-(trifluoromethyl)-4H-pyrido[1,2-a]pyrimidin-4-one;
8-ethyl-3-(4-(2,2,2-trifluoroethoxy)phenyl)-2-(trifluoromethyl)-4H-pyrido[1,2-a]pyrimidin-4-one;
8-fluoro-3-(4-(2,2,2-trifluoroethoxy)phenyl)-2-(trifluoromethyl)-4H-pyrido[1,2-a]pyrimidin-4-one;
8-methoxy-2-(trifluoromethyl)-3-(1-(3-(trifluoromethyl)phenyl)-1H-pyrazol-4-yl)-4H-pyrido[1,2-a]pyrimidin-4-one;
8-methoxy-2-(trifluoromethyl)-3-(1-(3,3,3-trifluoropropyl)-1H-imidazol-4-yl)-4H-pyrido[1,2-a]pyrimidin-4-one;
8-methoxy-2-(trifluoromethyl)-3-(1-(3,3,3-trifluoropropyl)-1H-pyrazol-4-yl)-4H-pyrido[1,2-a]pyrimidin-4-one;
8-methoxy-2-(trifluoromethyl)-3-(1-(4-(trifluoromethyl)phenyl)-1H-pyrazol-4-yl)-4H-pyrido[1,2-a]pyrimidin-4-one;
8-methoxy-2-(trifluoromethyl)-3-(4-(3,3,3-trifluoropropyl)phenyl)-4H-pyrido[1,2-a]pyrimidin-4-one;
8-methoxy-2-(trifluoromethyl)-3-[3-(3,3,3-trifluoropropyl)-1,2-oxazol-5-yl]-4H-pyrido[1,2-a]pyrimidin-4-one;
8-methoxy-2-(trifluoromethyl)-3-[4-(3,3,3-trifluoropropyl)-1H-imidazol-1-yl]-4H-pyrido[1,2-a]pyrimidin-4-one;
8-methoxy-2-(trifluoromethyl)-3-[5-(3,3,3-trifluoropropyl)-1,3-thiazol-2-yl]-4H-pyrido[1,2-a]pyrimidin-4-one;
8-methoxy-2-methyl-3-(4-(2,2,2-trifluoroethoxy)phenyl)-4H-pyrido[1,2-a]pyrimidin-4-one;
8-methoxy-3-(1-(2,2,2-trifluoroethyl)-1H-pyrazol-4-yl)-2-(trifluoromethyl)-4H-pyrido[1,2-a]pyrimidin-4-one;
8-methoxy-3-(1-(2,2,3,3,3-pentafluoropropyl)-1H-pyrazol-4-yl)-2-(trifluoromethyl)-4H-pyrido[1,2-a]pyrimidin-4-one;
8-methoxy-3-(1-(4,4,4-trifluorobutyl)-1H-pyrazol-4-yl)-2-(trifluoromethyl)-4H-pyrido[1,2-a]pyrimidin-4-one;
8-methoxy-3-(1-phenyl-1H-pyrazol-3-yl)-2-(trifluoromethyl)-4H-pyrido[1,2-a]pyrimidin-4-one;
8-methoxy-3-(1-phenyl-1H-pyrazol-4-yl)-2-(trifluoromethyl)-4H-pyrido[1,2-a]pyrimidin-4-one;
8-methoxy-3-(1-propyl-1H-pyrazol-4-yl)-2-(trifluoromethyl)-4H-pyrido[1,2-a]pyrimidin-4-one;
8-methoxy-3-(2-methyl-4-(2,2,2-trifluoroethoxy)phenyl)-2-(trifluoromethyl)-4H-pyrido[1,2-a]pyrimidin-4-one;
8-methoxy-3-(2-phenyl-1,3-oxazol-5-yl)-2-(trifluoromethyl)-4H-pyrido[1,2-a]pyrimidin-4-one;
8-methoxy-3-(3-phenyl-1,2-oxazol-5-yl)-2-(trifluoromethyl)-4H-pyrido[1,2-a]pyrimidin-4-one;
8-methoxy-3-(4-(2,2,2-trifluoroethoxy)-2-(trifluoromethyl)phenyl)-2-(trifluoromethyl)-4H-pyrido[1,2-a]pyrimidin-4-one;
8-methoxy-3-(4-(2,2,2-trifluoroethoxy)phenyl)-2-(trifluoromethyl)-4H-pyrido[1,2-a]pyrimidin-4-one;
8-methoxy-3-(4-(2,2,3,3,3-pentafluoropropoxy)phenyl)-2-(trifluoromethyl)-4H-pyrido[1,2-a]pyrimidin-4-one;
8-methoxy-3-(4-(2,2,3,3-tetrafluoropropoxy)phenyl)-2-(trifluoromethyl)-4H-pyrido[1,2-a]pyrimidin-4-one;
8-methoxy-3-(4-(trifluoromethoxy)phenyl)-2-(trifluoromethyl)-4H-pyrido[1,2-a]pyrimidin-4-one;
8-methoxy-3-(4-propylphenyl)-2-(trifluoromethyl)-4H-pyrido[1,2-a]pyrimidin-4-one;
8-methoxy-3-(5-propyl-1,2-oxazol-3-yl)-2-(trifluoromethyl)-4H-pyrido[1,2-a]pyrimidin-4-one;
8-methoxy-3-(6-(2,2,2-trifluoroethoxy)-3-pyridinyl)-2-(trifluoromethyl)-4H-pyrido[1,2-a]pyrimidin-4-one;
8-methoxy-3-(6-propyl-3-pyridinyl)-2-(trifluoromethyl)-4H-pyrido[1,2-a]pyrimidin-4-one;
8-methoxy-3-[1-(2,2,3,3,3-pentafluoropropyl)-1H-1,2,3-triazol-4-yl]-2-(trifluoromethyl)-4H-pyrido[1,2-a]pyrimidin-4-one;
8-methoxy-3-[1-(2,2,3,3,3-pentafluoropropyl)-1H-pyrazol-3-yl]-2-(trifluoromethyl)-4H-pyrido[1,2-a]pyrimidin-4-one;
8-methoxy-3-[2-(2,2,2-trifluoroethoxy)-1,3-thiazol-5-yl]-2-(trifluoromethyl)-4H-pyrido[1,2-a]pyrimidin-4-one;
8-methoxy-3-[2-(2,2,2-trifluoroethoxy)pyrimidin-5-yl]-2-(trifluoromethyl)-4H-pyrido[1,2-a]pyrimidin-4-one;
8-methoxy-3-[2-(2,2,3,3,3-pentafluoropropoxy)pyrimidin-5-yl]-2-(trifluoromethyl)-4H-pyrido[1,2-a]pyrimidin-4-one;
8-methoxy-3-[3-(2,2,3,3,3-pentafluoropropyl)-1,2-oxazol-5-yl]-2-(trifluoromethyl)-4H-pyrido[1,2-a]pyrimidin-4-one;
8-methoxy-3-[4-(2,2,2-trifluoroethoxy)-1,3-thiazol-2-yl]-2-(trifluoromethyl)-4H-pyrido[1,2-a]pyrimidin-4-one;
8-methoxy-3-[5-(2,2,2-trifluoroethoxy)-1,3-thiazol-2-yl]-2-(trifluoromethyl)-4H-pyrido[1,2-a]pyrimidin-4-one;
8-methoxy-3-{1-[(oxetan-3-yl)methyl]-1H-pyrazol-4-yl}-2-(trifluoromethyl)-4H-pyrido[1,2-a]pyrimidin-4-one;
8-methoxy-6-methyl-3-[1-(2,2,3,3,3-pentafluoropropyl)-1H-pyrazol-4-yl]-2-(trifluoromethyl)-4H-pyrido[1,2-a]pyrimidin-4-one;
8-methyl-2-(trifluoromethyl)-3-[5-(3,3,3-trifluoropropyl)-1,2,4-oxadiazol-3-yl]-4H-pyrido[1,2-a]pyrimidin-4-one;
8-methyl-3-(4-(2,2,2-trifluoroethoxy)phenyl)-2-(trifluoromethyl)-4H-pyrido[1,2-a]pyrimidin-4-one;

9-chloro-8-methoxy-3-[1-(2,2,3,3,3-pentafluoropropyl)-1H-pyrazol-4-yl]-2-(trifluoromethyl)-4H-pyrido[1,2-a]pyrimidin-4-one;

9-fluoro-8-methoxy-3-[1-(2,2,3,3,3-pentafluoropropyl)-1H-pyrazol-4-yl]-2-(trifluoromethyl)-4H-pyrido[1,2-a]pyrimidin-4-one;

methyl 4-oxo-3-(4-(2,2,2-trifluoroethoxy)phenyl)-2-(trifluoromethyl)-4H-pyrido[1,2-a]pyrimidine-8-carboxylate;

methyl(4-oxo-3-(1-(2,2,3,3,3-pentafluoropropyl)-1H-pyrazol-4-yl)-2-(trifluoromethyl)-4H-pyrido[1,2-a]pyrimidin-8-yl)carbamyl fluoride;

N-(4-oxo-3-(1-(2,2,3,3,3-pentafluoropropyl)-1H-pyrazol-4-yl)-2-(trifluoromethyl)-4H-pyrido[1,2-a]pyrimidin-8-yl)acetamide;

N-(4-oxo-3-(4-(2,2,2-trifluoroethoxy)phenyl)-2-(trifluoromethyl)-4H-pyrido[1,2-a]pyrimidin-8-yl)acetamide;

N,N-dimethyl-4-oxo-3-(4-(2,2,2-trifluoroethoxy)phenyl)-2-(trifluoromethyl)-4H-pyrido[1,2-a]pyrimidine-8-carboxamide;

N-ethyl-4-oxo-3-(4-(2,2,2-trifluoroethoxy)phenyl)-2-(trifluoromethyl)-4H-pyrido[1,2-a]pyrimidine-8-carboxamide;

N-methyl-4-oxo-3-(1-(2,2,3,3,3-pentafluoropropyl)-1H-pyrazol-4-yl)-2-(trifluoromethyl)-4H-pyrido[1,2-a]pyrimidine-8-carboxamide; or N-methyl-4-oxo-3-(4-(2,2,2-trifluoroethoxy)phenyl)-2-(trifluoromethyl)-4H-pyrido[1,2-a]pyrimidine-8-carboxamide.

3. A compound, or a tautomer thereof, or a pharmaceutically acceptable salt of said compound or said tautomer, wherein the compound is (2S)-2-(4-(8-methoxy-4-oxo-2-(trifluoromethyl)-4H-pyrido[1,2-a]pyrimidin-3-yl)phenoxy)propanenitrile;

2-(4-(8-methoxy-4-oxo-2-(trifluoromethyl)-4H-pyrido[1,2-a]pyrimidin-3-yl)phenoxy)-2-methylpropanenitrile;

2-(difluoromethyl)-8-methoxy-3-(4-(2,2,2-trifluoroethoxy)phenyl)-4H-pyrido[1,2-a]pyrimidin-4-one;

2-(fluoromethyl)-8-methoxy-3-(4-(2,2,2-trifluoroethoxy)phenyl)-4H-pyrido[1,2-a]pyrimidin-4-one;

2,8-dimethoxy-3-(4-(2,2,2-trifluoroethoxy)phenyl)-4H-pyrido[1,2-a]pyrimidin-4-one;

2-cyclopropyl-8-methoxy-3-(4-(2,2,2-trifluoroethoxy)phenyl)-4H-pyrido[1,2-a]pyrimidin-4-one;

2-ethoxy-8-methoxy-3-(4-(2,2,2-trifluoroethoxy)phenyl)-4H-pyrido[1,2-a]pyrimidin-4-one;

2-ethyl-8-methoxy-3-(4-(2,2,2-trifluoroethoxy)phenyl)-4H-pyrido[1,2-a]pyrimidin-4-one;

3-(1-(2,2,3,3,3-pentafluoropropyl)-1H-pyrazol-4-yl)-2-(trifluoromethyl)-4H-pyrido[1,2-a]pyrimidine-4,8(1H)-dione;

3-(1-(2,2-difluoropropyl)-1H-pyrazol-4-yl)-8-methoxy-2-(trifluoromethyl)-4H-pyrido[1,2-a]pyrimidin-4-one;

3-(2-fluoro-4-(2,2,2-trifluoroethoxy)phenyl)-8-methoxy-2-(trifluoromethyl)-4H-pyrido[1,2-a]pyrimidin-4-one;

3-(2-fluoro-4-(trifluoromethoxy)phenyl)-8-methoxy-2-(trifluoromethyl)-4H-pyrido[1,2-a]pyrimidin-4-one;

3-(3-fluoro-4-(2,2,2-trifluoroethoxy)phenyl)-8-methoxy-2-(trifluoromethyl)-4H-pyrido[1,2-a]pyrimidin-4-one;

3-(4-((2,2-difluorocyclopropyl)methoxy)phenyl)-8-methoxy-2-(trifluoromethyl)-4H-pyrido[1,2-a]pyrimidin-4-one;

3-(4-(2,2,2-trifluoroethoxy)phenyl)-2-(trifluoromethyl)-4H-pyrido[1,2-a]pyrimidin-4-one;

3-(4-(2,2,2-trifluoroethoxy)phenyl)-2-(trifluoromethyl)-4H-pyrido[1,2-a]pyrimidine-4,8(1H)-dione;

3-(4-(2,2-difluoroethoxy)-2-fluorophenyl)-8-methoxy-2-(trifluoromethyl)-4H-pyrido[1,2-a]pyrimidin-4-one;

3-(4-(2,2-difluoroethoxy)phenyl)-8-methoxy-2-(trifluoromethyl)-4H-pyrido[1,2-a]pyrimidin-4-one;

3-(4-(2,2-difluoropropoxy)phenyl)-8-methoxy-2-(trifluoromethyl)-4H-pyrido[1,2-a]pyrimidin-4-one;

3-(4-(2-fluoroethoxy)phenyl)-8-methoxy-2-(trifluoromethyl)-4H-pyrido[1,2-a]pyrimidin-4-one;

3-(4-(cyclopropylmethoxy)phenyl)-8-methoxy-2-(trifluoromethyl)-4H-pyrido[1,2-a]pyrimidin-4-one;

4-oxo-3-(1-(2,2,3,3,3-pentafluoropropyl)-1H-pyrazol-4-yl)-2-(trifluoromethyl)-4H-pyrido[1,2-a]pyrimidine-8-carbonitrile;

4-oxo-3-(4-(2,2,2-trifluoroethoxy)phenyl)-2-(trifluoromethyl)-4H-pyrido[1,2-a]pyrimidine-8-carboxamide;

7-chloro-3-[1-(2,2,3,3,3-pentafluoropropyl)-1H-pyrazol-4-yl]-2-(trifluoromethyl)-4H-pyrido[1,2-a]pyrimidin-4-one;

7-fluoro-8-methoxy-3-[1-(2,2,3,3,3-pentafluoropropyl)-1H-pyrazol-4-yl]-2-(trifluoromethyl)-4H-pyrido[1,2-a]pyrimidin-4-one;

8-((1R)-1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one;

8-((1S)-1-hydroxyethyl)-3-(1-(2,2,3,3,3-pentafluoropropyl)-1H-pyrazol-4-yl)-2-(trifluoromethyl)-4H-pyrido[1,2-a]pyrimidin-4-one;

8-((dimethylamino)methyl)-3-(1-(2,2,3,3,3-pentafluoropropyl)-1H-pyrazol-4-yl)-2-(trifluoromethyl)-4H-pyrido[1,2-a]pyrimidin-4-one;

8-(aminomethyl)-3-(1-(2,2,3,3,3-pentafluoropropyl)-1H-pyrazol-4-yl)-2-(trifluoromethyl)-4H-pyrido[1,2-a]pyrimidin-4-one;

8-(dimethylamino)-3-(1-(2,2,3,3,3-pentafluoropropyl)-1H-pyrazol-4-yl)-2-(trifluoromethyl)-4H-pyrido[1,2-a]pyrimidin-4-one;

8-(fluoromethoxy)-3-[1-(2,2,3,3,3-pentafluoropropyl)-1H-pyrazol-4-yl]-2-(trifluoromethyl)-4H-pyrido[1,2-a]pyrimidin-4-one;

8-(fluoromethyl)-3-(4-(2,2,2-trifluoroethoxy)phenyl)-2-(trifluoromethyl)-4H-pyrido[1,2-a]pyrimidin-4-one;

8-(hydroxymethyl)-3-(1-(2,2,3,3,3-pentafluoropropyl)-1H-pyrazol-4-yl)-2-(trifluoromethyl)-4H-pyrido[1,2-a]pyrimidin-4-one;

8-(hydroxymethyl)-3-(4-(2,2,2-trifluoroethoxy)phenyl)-2-(trifluoromethyl)-4H-pyrido[1,2-a]pyrimidin-4-one;

8-(methoxymethyl)-3-[1-(2,2,3,3,3-pentafluoropropyl)-1H-pyrazol-4-yl]-2-(trifluoromethyl)-4H-pyrido[1,2-a]pyrimidin-4-one;

8-(methylamino)-3-(1-(2,2,3,3,3-pentafluoropropyl)-1H-pyrazol-4-yl)-2-(trifluoromethyl)-4H-pyrido[1,2-a]pyrimidin-4-one;

8-(methylamino)-3-(4-(2,2,2-trifluoroethoxy)phenyl)-2-(trifluoromethyl)-4H-pyrido[1,2-a]pyrimidin-4-one;

8-(methyloxy-d3)-3-(1-(2,2,3,3,3-pentafluoropropyl)-1H-pyrazol-4-yl)-2-(trifluoromethyl)-4H-pyrido[1,2-a]pyrimidin-4-one;

8-(methyloxy-d3)-3-(4-(2,2,2-trifluoroethoxy)phenyl)-2-(trifluoromethyl)-4H-pyrido[1,2-a]pyrimidin-4-one;

8-amino-3-(1-(2,2,3,3,3-pentafluoropropyl)-1H-pyrazol-4-yl)-2-(trifluoromethyl)-4H-pyrido[1,2-a]pyrimidin-4-one;

8-amino-3-(4-(2,2,2-trifluoroethoxy)phenyl)-2-(trifluoromethyl)-4H-pyrido[1,2-a]pyrimidin-4-one;

8-chloro-3-(1-(2,2,3,3,3-pentafluoropropyl)-1H-pyrazol-4-yl)-2-(trifluoromethyl)-4H-pyrido[1,2-a]pyrimidin-4-one;

8-ethoxy-3-(4-(2,2,2-trifluoroethoxy)phenyl)-2-(trifluoromethyl)-4H-pyrido[1,2-a]pyrimidin-4-one;

8-methoxy-2-(trifluoromethyl)-3-(1-(3,3,3-trifluoropropyl)-1H-pyrazol-4-yl)-4H-pyrido[1,2-a]pyrimidin-4-one;

8-methoxy-3-(1-(2,2,3,3,3-pentafluoropropyl)-1H-pyrazol-4-yl)-2-(trifluoromethyl)-4H-pyrido[1,2-a]pyrimidin-4-one;

8-methoxy-3-(1-(4,4,4-trifluorobutyl)-1H-pyrazol-4-yl)-2-(trifluoromethyl)-4H-pyrido[1,2-a]pyrimidin-4-one;

8-methoxy-3-(2-methyl-4-(2,2,2-trifluoroethoxy)phenyl)-2-(trifluoromethyl)-4H-pyrido[1,2-a]pyrimidin-4-one;

8-methoxy-3-(4-(2,2,2-trifluoroethoxy)phenyl)-2-(trifluoromethyl)-4H-pyrido[1,2-a]pyrimidin-4-one;

8-methoxy-3-(6-(2,2,2-trifluoroethoxy)-3-pyridinyl)-2-(trifluoromethyl)-4H-pyrido[1,2-a]pyrimidin-4-one;

8-methoxy-3-[1-(2,2,3,3,3-pentafluoropropyl)-1H-1,2,3-triazol-4-yl]-2-(trifluoromethyl)-4H-pyrido[1,2-a]pyrimidin-4-one; or 8-methoxy-3-[2-(2,2,2-trifluoroethoxy)pyrimidin-5-yl]-2-(trifluoromethyl)-4H-pyrido[1,2-a]pyrimidin-4-one.

4. The compound according to claim 2, or a tautomer thereof, or a pharmaceutically acceptable salt of said compound or said tautomer, wherein the compound is 4-oxo-3-(1-(2,2,3,3,3-pentafluoropropyl)-1H-pyrazol-4-yl)-2-(trifluoromethyl)-4H-pyrido[1,2-a]pyrimidine-8-carbonitrile;

8-(methyloxy-d3)-3-(1-(2,2,3,3,3-pentafluoropropyl)-1H-pyrazol-4-yl)-2-(trifluoromethyl)-4H-pyrido[1,2-a]pyrimidin-4-one;

8-amino-3-(4-(2,2,2-trifluoroethoxy)phenyl)-2-(trifluoromethyl)-4H-pyrido[1,2-a]pyrimidin-4-one;

8-methoxy-3-(1-(2,2,3,3,3-pentafluoropropyl)-1H-pyrazol-4-yl)-2-(trifluoromethyl)-4H-pyrido[1,2-a]pyrimidin-4-one; or 8-methoxy-3-(4-(2,2,2-trifluoroethoxy)phenyl)-2-(trifluoromethyl)-4H-pyrido[1,2-a]pyrimidin-4-one.

5. The compound according to claim 2, or a pharmaceutically acceptable salt thereof, wherein the compound is

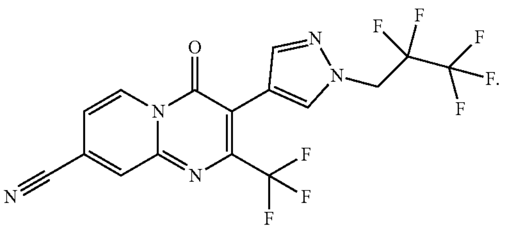 [SMILES: N#Cc1ccn2c(=O)c(-c3cnn(CC(F)(F)C(F)(F)F)c3)c(C(F)(F)F)nc2c1]

6. The compound according to claim 2, or a tautomer thereof, or a pharmaceutically acceptable salt of said compound or said tautomer, wherein the compound is

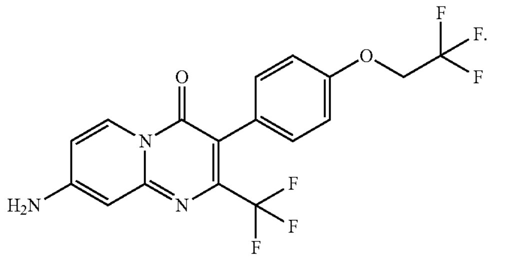 [SMILES: Nc1ccn2c(=O)c(-c3ccc(OCC(F)(F)F)cc3)c(C(F)(F)F)nc2c1]

7. The compound according to claim 2, or a pharmaceutically acceptable salt thereof, wherein the compound is

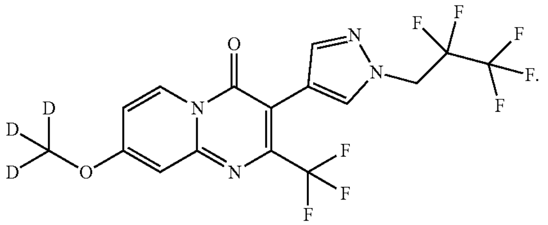 [SMILES: [2H]C([2H])([2H])Oc1ccn2c(=O)c(-c3cnn(CC(F)(F)C(F)(F)F)c3)c(C(F)(F)F)nc2c1]

8. The compound according to claim 2, or a pharmaceutically acceptable salt thereof, wherein the compound is

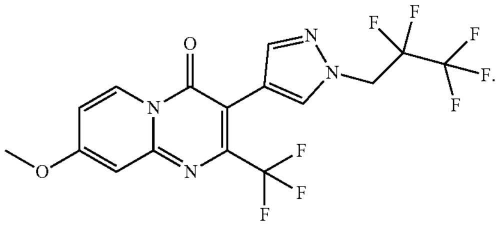 [SMILES: COc1ccn2c(=O)c(-c3cnn(CC(F)(F)C(F)(F)F)c3)c(C(F)(F)F)nc2c1]

9. The compound according to claim 2, or a pharmaceutically acceptable salt thereof, wherein the compound is

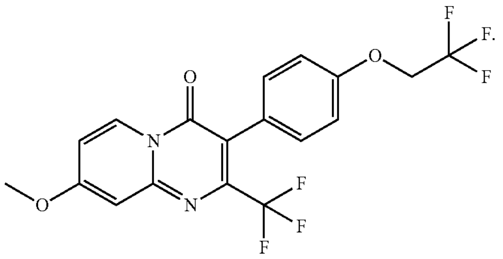 [SMILES: COc1ccn2c(=O)c(-c3ccc(OCC(F)(F)F)cc3)c(C(F)(F)F)nc2c1]

10. A pharmaceutical composition comprising the compound according to claim 1, or a tautomer thereof, or a pharmaceutically acceptable salt of said compound or said tautomer, and a pharmaceutically acceptable excipient.

* * * * *